(12) United States Patent
Ast et al.

(10) Patent No.: US 10,184,009 B2
(45) Date of Patent: *Jan. 22, 2019

(54) MUTANT INTERLEUKIN-2 POLYPEPTIDES

(71) Applicant: Roche Glycart AG, Schlieren (CH)

(72) Inventors: Oliver Ast, Bassersdorf (CH); Peter Bruenker, Hittnau (CH); Anne Freimoser-Grundschober, Zurich (CH); Sylvia Herter, Regensdorf (CH); Thomas U. Hofer, Zurich (CH); Ralf Hosse, Cham (CH); Christian Klein, Bonstetten (CH); Ekkehard Moessner, Kreuzlingen (CH); Valeria G. Nicolini, Erlenbach/ZH (CH); Pablo Umana, Wollerau (CH)

(73) Assignee: ROCHE GLYCART AG, Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/849,501

(22) Filed: Dec. 20, 2017

(65) Prior Publication Data

US 2018/0142037 A1 May 24, 2018

Related U.S. Application Data

(60) Division of application No. 14/996,789, filed on Jan. 15, 2016, which is a continuation of application No. 13/367,843, filed on Feb. 7, 2012, now Pat. No. 9,266,938.

(30) Foreign Application Priority Data

Feb. 10, 2011 (EP) ..................................... 11153964
Apr. 29, 2011 (EP) ..................................... 11164237

(51) Int. Cl.
| | | |
|---|---|---|
| *C07K 14/55* | (2006.01) | |
| *A61K 38/20* | (2006.01) | |
| *C07K 16/40* | (2006.01) | |
| *C07K 16/30* | (2006.01) | |
| *C07K 16/28* | (2006.01) | |
| *A61K 39/395* | (2006.01) | |
| *A61K 47/68* | (2017.01) | |
| *A61K 39/00* | (2006.01) | |

(52) U.S. Cl.
CPC .......... *C07K 16/40* (2013.01); *A61K 38/2013* (2013.01); *A61K 39/39558* (2013.01); *A61K 47/6813* (2017.08); *A61K 47/6849* (2017.08); *A61K 47/6871* (2017.08); *A61K 47/6891* (2017.08); *C07K 14/55* (2013.01); *C07K 16/28* (2013.01); *C07K 16/30* (2013.01); *A61K 2039/505* (2013.01); *C07K 2319/00* (2013.01)

(58) Field of Classification Search
None
See application file for complete search history.

(56) References Cited

U.S. PATENT DOCUMENTS

| | | |
|---|---|---|
| 5,731,168 A | 3/1998 | Carter et al. |
| 6,545,462 B2 | 4/2003 | Schott et al. |
| 6,602,684 B1 | 8/2003 | Umana et al. |
| 6,635,241 B1 | 10/2003 | Rose et al. |
| 7,371,371 B2 | 5/2008 | Epstein et al. |
| 7,396,917 B2 | 7/2008 | Bowdish et al. |
| 7,404,956 B2 | 7/2008 | Peters et al. |
| 7,767,405 B2 | 8/2010 | Gillies et al. |
| 8,568,727 B2 | 10/2013 | Adolf et al. |
| 8,945,571 B2 | 2/2015 | Moessner et al. |
| 8,969,526 B2 | 3/2015 | Baehner et al. |
| 9,011,847 B2 | 4/2015 | Bacac et al. |
| 9,206,243 B2 | 12/2015 | Monzón et al. |
| 9,266,938 B2 | 2/2016 | Ast et al. |
| 9,346,872 B2 | 5/2016 | Duerner et al. |
| 9,447,159 B2 | 9/2016 | Ast et al. |
| 9,526,797 B2 | 12/2016 | Gerdes et al. |
| 2003/0124678 A1 | 3/2003 | Epstein et al. |
| 2003/0166163 A1 | 4/2003 | Gillies |
| 2003/0143229 A1 | 7/2003 | Park et al. |
| 2003/0175884 A1 | 9/2003 | Umana et al. |
| 2004/0241817 A1 | 2/2004 | Umana et al. |
| 2004/0081651 A1 | 4/2004 | Karpusas et al. |
| 2004/0132066 A1 | 8/2004 | Balint et al. |

(Continued)

FOREIGN PATENT DOCUMENTS

| | | |
|---|---|---|
| EP | 2085095 A1 | 8/2009 |
| EP | 1071700 A1 | 2/2010 |

(Continued)

OTHER PUBLICATIONS

Rao et al., Protein Eng., 2003, vol. 16(12):1080-1087.*
Buchli et al., Arch. Biochem. Biophys., 1993, vol. 307(2):411-415 (abstract).*
Baum et al., "Single-chain Fv immunoliposomes for the targeting of fibroblast activation protein-expressing tumor stromal cells" Journal of Drug Targeting 15(6):399-406 (2007).
Buchli et al., "Structural and Biologic Properties of a Human Aspartic Acid-126 Interleukin-2 Analog" Archives of Biochemistry and Biophysics 307(2):411-415 (1993).

(Continued)

*Primary Examiner* — Xiaozhen Xie

(57) ABSTRACT

The present invention generally relates to mutant interleukin-2 polypeptides that exhibit reduced affinity to the α-subunit of the IL-2 receptor, for use as immunotherapeutic agents. In addition, the invention relates to immunoconjugates comprising said mutant IL-2 polypeptides, polynucleotide molecules encoding the mutant IL-2 polypeptides or immunoconjugates, and vectors and host cells comprising such polynucleotide molecules. The invention further relates to methods for producing the mutant IL-2 polypeptides or immunoconjugates, pharmaceutical compositions comprising the same, and uses thereof.

30 Claims, 51 Drawing Sheets

Figure 1:
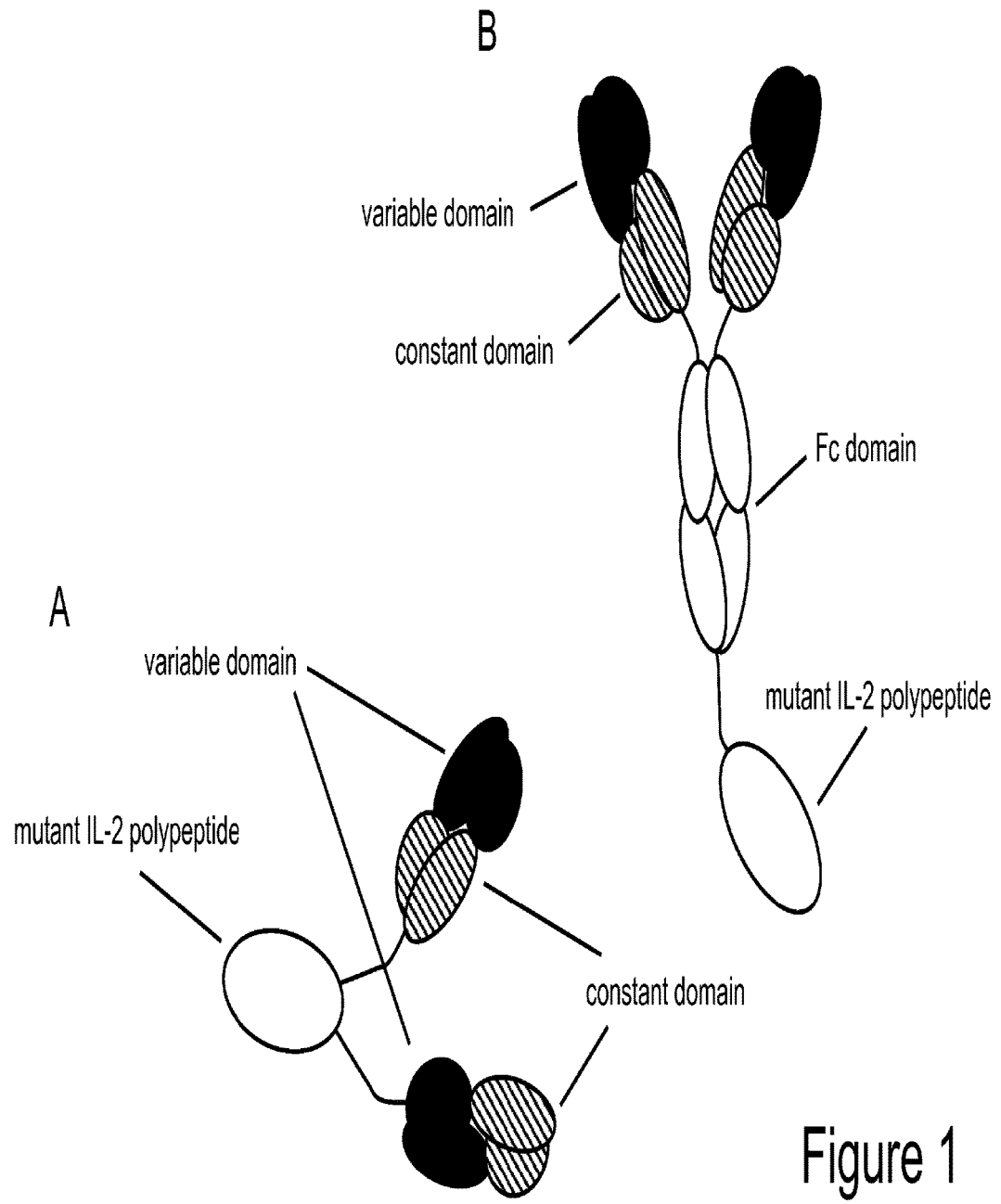

Specification includes a Sequence Listing.

(56) References Cited

U.S. PATENT DOCUMENTS

| | | |
|---|---|---|
| 2004/0175357 A1 | 9/2004 | Shanafelt et al. |
| 2006/0269515 A1 | 11/2006 | Denis-Mize et al. |
| 2008/0025947 A1 | 1/2008 | Gillies et al. |
| 2009/0238789 A1 | 9/2009 | Guyon et al. |
| 2009/0304718 A1 | 10/2009 | Adolf et al. |
| 2010/0021477 A1 | 1/2010 | Tsui et al. |
| 2010/0260765 A1 | 10/2010 | Barry et al. |
| 2011/0064751 A1 | 3/2011 | Mossner et al. |
| 2012/0184718 A1 | 7/2012 | Bruenker et al. |
| 2012/0244112 A1 | 9/2012 | Ast et al. |
| 2014/0370019 A1 | 12/2014 | Bruenker et al. |
| 2015/0239981 A1 | 8/2015 | Baehner et al. |
| 2016/0060356 A1 | 3/2016 | Bacac et al. |
| 2016/0060357 A1 | 3/2016 | Bacac et al. |
| 2016/0159917 A1 | 6/2016 | Bruenker et al. |
| 2016/0175397 A1 | 6/2016 | Umana et al. |
| 2016/0208017 A1 | 7/2016 | Ast et al. |
| 2016/0263240 A1 | 9/2016 | Ast et al. |
| 2017/0056522 A1 | 3/2017 | Gerdes et al. |
| 2017/0088631 A1 | 3/2017 | Ast et al. |
| 2017/0137530 A1 | 5/2017 | Baehner et al. |

FOREIGN PATENT DOCUMENTS

| | | |
|---|---|---|
| EP | 1587921 B1 | 7/2010 |
| EP | 11160251.2 | 3/2011 |
| WO | 88/07089 A1 | 9/1988 |
| WO | 98/17797 A1 | 4/1998 |
| WO | 99/51642 A1 | 10/1999 |
| WO | 99/54342 A1 | 10/1999 |
| WO | 1999/057151 A2 | 11/1999 |
| WO | 1999/060128 A1 | 11/1999 |
| WO | 00/477228 A1 | 8/2000 |
| WO | 01/68708 | 9/2001 |
| WO | 03/011878 A2 | 2/2003 |
| WO | 2003/048334 A2 | 6/2003 |
| WO | 04/065540 A2 | 8/2004 |
| WO | 2005/001025 A2 | 1/2005 |
| WO | 2005/062929 A2 | 7/2005 |
| WO | 2005/086751 | 9/2005 |
| WO | 2005/086798 A3 | 9/2005 |
| WO | 2006/119897 A2 | 11/2006 |
| WO | 2007/077173 A1 | 7/2007 |
| WO | 2007/128563 A1 | 11/2007 |
| WO | 2008/003473 A2 | 1/2008 |
| WO | 2008/017963 | 2/2008 |
| WO | 2008/143954 A2 | 11/2008 |
| WO | 2009/085462 A1 | 7/2009 |
| WO | 2009/126558 A1 | 10/2009 |
| WO | 2009/138396 A2 | 11/2009 |
| WO | 2010/085495 A1 | 7/2010 |
| WO | 2010/088444 A1 | 8/2010 |
| WO | 2010/111282 A1 | 9/2010 |
| WO | 2010/117448 A2 | 10/2010 |
| WO | 2011/001276 A1 | 1/2011 |
| WO | 2011/020783 A2 | 2/2011 |
| WO | 2011/023787 A1 | 3/2011 |
| WO | 2012/020006 A2 | 2/2012 |
| WO | 2012/107417 A1 | 8/2012 |
| WO | 2012/117002 A1 | 9/2012 |
| WO | 2012/130831 A1 | 10/2012 |
| WO | 2012/146628 A1 | 11/2012 |
| WO | 2014023752 A1 | 2/2014 |

OTHER PUBLICATIONS

Casset et al., "A peptide mimetic of an anti-CD4 monoclonal antibody by rational design" Biochem Bioph Res Co(307):198-205 (2003).
Chen et al., "Selection and analysis of an optimized anti-VEGF antibody: Crystal structure of an affinity-matured Fab in complex with antigen" J Mol Biol 293:865-881 (1999).
De Jong et al., "Interaction of IL-15 with the Shared IL-2 Receptor β and γc subunits" J. Immunol. 156(4):1339-1348 (1996).
De Pascalis et al., "Grafting of 'abbreviated' complementarity-determining containing specificity-determining residues essential for ligand contact to engineer a less immunogenic humanized monoclonal antibody" J Immunol 169:3076-3084 (2002).
Ferrara et al., "Modulation of therapeutic antibody effector functions by glycosylation engineering: influence of Golgi enzyme localization domain and co-expression of heterologous beta 1, 4-N-acetylglucosaminyltransferase III and Golgi alpha-monnosidase II" Biotechnology and Bioengineering 93(5):851-861 (2006).
Fingl et al. Basis of Therapeutics, "Ch. 1—General Principles" Fifth edition, New York:Macmillan Publishing Co., Inc.,:1-46 (1975).
Heaton et al., "Chracterization of Lymphokine-Activated Killing by Human Periperal Blood Mononuclear Cells Stimulated with Interleukin 2 (IL-2) Analogs Specific for the Intermediate Affinity IL-2 Receptor" Cellular Immunology 147:167-179 (1993).
Hezareh et al., "Effector function activities of a panel of mutants of a broadly neutralizing antibody against human immunodeficiency virus type 1." J Virol 75(24):12161-12168 (2001).
International Preliminary Report on Patentability dated Feb. 19, 2013 for PCT/EP2011/063648 filed on Aug. 9, 2011, twelve pages.
Lamminmak et al., "Crystal structure of a recombinant anti-estradiol Fab fragment in complex with 17β-estradiol" Journal of Biological Chemistry 276(39):36687-36694 (2001).
Little, "Recombinant Antibodies for Immunotherapy," Cambridge University Press: 144-153 (2009).
MacCallum et al., "Antibody-antigen interactions: contact analysis and binding site topography" J Mol Biol 262(5):732-745 (1996).
Mersmann, "Human Antibody Derivatives Against the Fibroblast Protein for Tumor Stroma Targeting of Carcinomas" International Journal of Cancer 92(2):240-248 (2001).
Mott et al., "The Solution Structure of the F42A Mutant of Human Interleukin 2" J. Mol. Biol. 247:99-994 (1995).
Ortiz-Sanchez et al., "Antibody-cytokine fusion proteins: applications in cancer therapy" Expert Opin. Biol. Ther. 5(8):609-632 (2008).
Padlan et al., "Structure of an antibody-antigen complex: Crystal structure of the HyHEL-10 Fab-lysozyme complex" Proc. Natl. Acad. Sci. USA 86:5938-5942, (1989).
International Search Report dated Feb. 14, 2012, for PCT Patent Application No. PCT/EP2011/063648 filed on Aug. 9, 2011, seven pages.
International Search Report dated Aug. 20, 2012 for PCT Patent Application No. PCT/EP2012/051990 filed on Feb. 7, 2012, six pages.
Rao et al., "Interleukin-2 mutants with enhanced α-receptor subunit binding affinity" Protein Engineering 16(12):1081-1087 (2003).
Remington Remington's Pharmaceutical Sciences 18th edition,Mack Publishing,:1289-1329 (1990).
Ricart et al., "Technology Insight: cytotoxic drug immunoconjugates for cancer therapy" Nature Clinical Practice Oncology 4(4):245-255 (2007).
Rudikoff et al., "Single amino acid substitution altering antigen-binding specificity," Proc. Nat. Acad. Sci. USA, vol. 79, pp. 1979-1983, Mar. 1982.
Sauve et al., "Localization in human interleukin 2 of the binding site to the alpha chain (p55) of the interleukin 2 receptor" Proc Natl Acad Sci U S A. 88(11):4636-40 (1991).
Schliemann et al., "Complete eradication of human B-cell lymphoma xenografts using rituximab in combination with the immunocytokine L19-IL2" Blood 113(10):2275-83 (2009).
Shanafelt et al., "A T-Cell-Selective Interleukin 2 Mutein Exhibits Potent Antitumor Activity and is Well Tolerated in Vivo" Nature Biotechnology 18(11):1197-1202 (2000).
Shields et al. et al., "High resolution mapping of the binding site on human IgG1 for Fc gamma RI, Fc gamma RII, Fc gamma RIII, and FcRn and design of IgG1 variants with improved binding to the Fc gamma R" J Biol Chem 276(9):6591-6604 (2001).
Shields et al., "Lack of Fucose on Human IgG1 N-Linked Oligosaccharide Improves Binding to Human Fcgamma RIII and Antibody-dependent Cellular Toxicity" The Journal of Biological Chemistry 277(30):26733-26740 (2002).

(56) References Cited

OTHER PUBLICATIONS

Umana et al., "Engineered glycoforms of an antineuroblastoma IgG1 with optimized antibody-dependent cellular cytotoxic activity" Nat Biotechnol 17:176-180 (1999).
Vajdos et al. et al., "Comprehensive functional maps of the antigen-binding site of an anti-ErbB2 antibody obtained with shotgun scanning mutagenesis" J Mol Biol 320(2):415-428 (2002).
Written Opinion dated Feb. 13, 2013 for PCT Patent Application No. PCT/EP2011/063648 filed on Aug. 9, 2011, eleven pages.
Wu et al., "Humanization of a murine monoclonal antibody by simultaneous optimization of framework and CDR residues" J Mol Biol 294(1):151-162 (1999).

* cited by examiner

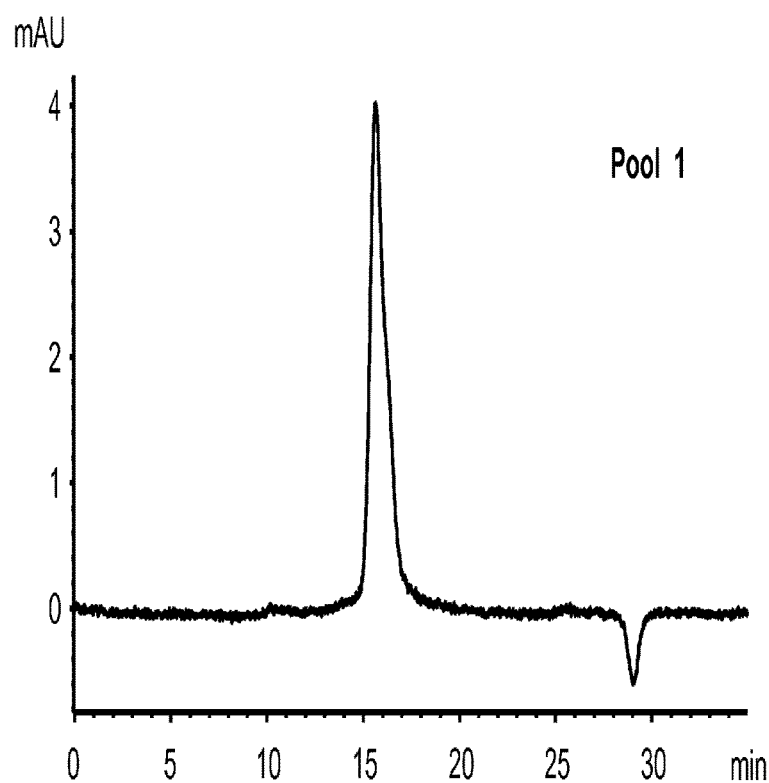
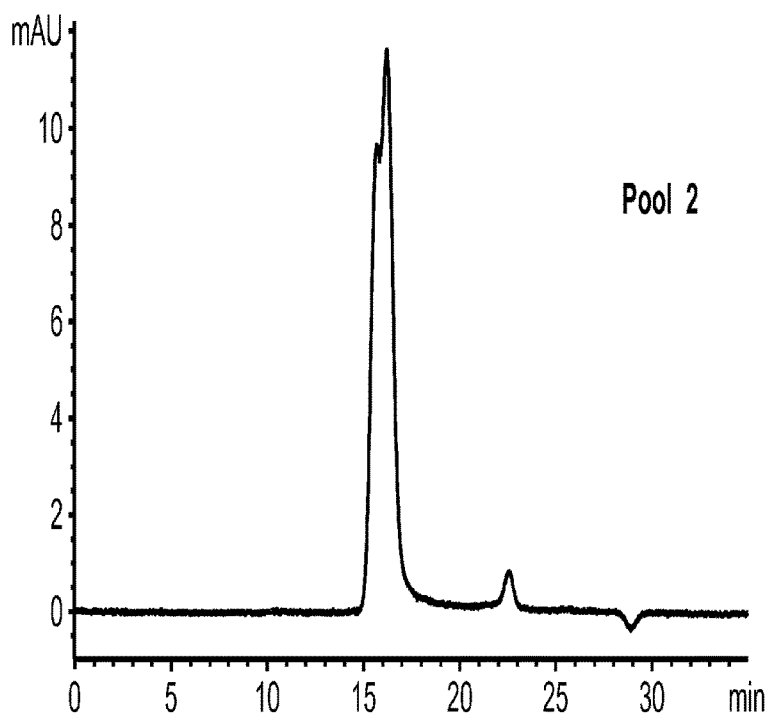
Figure 4

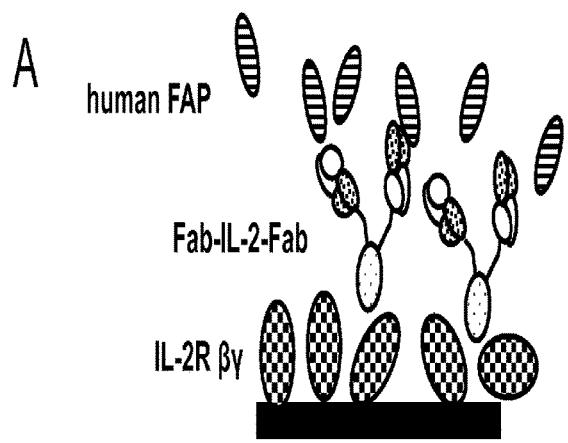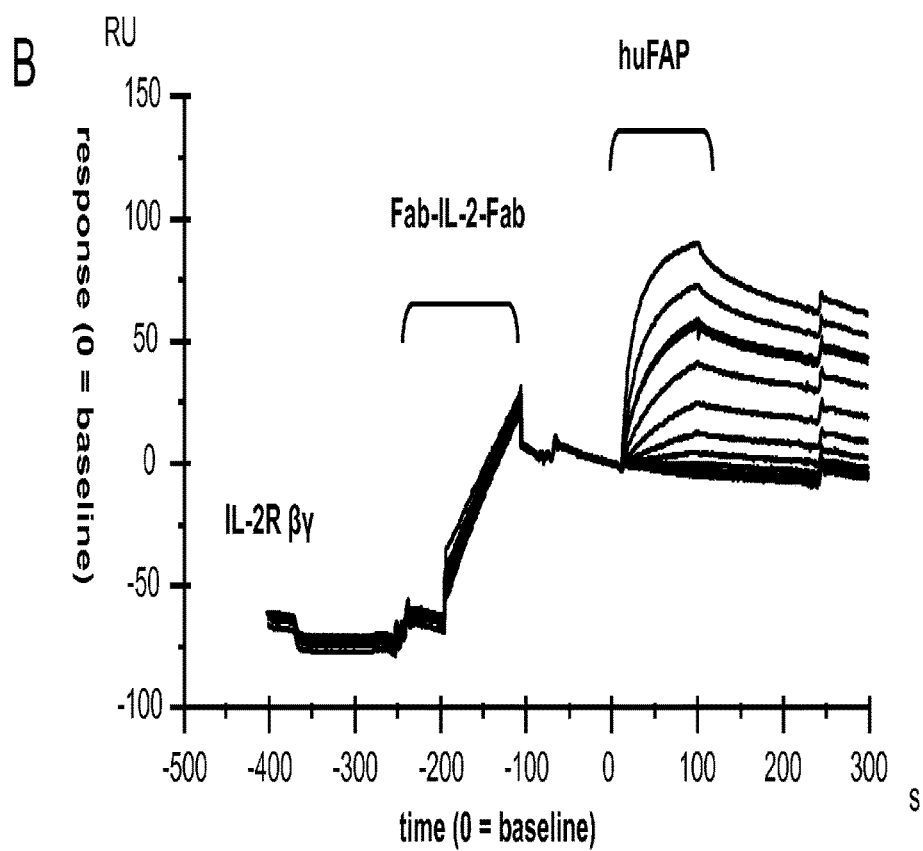
Figure 8

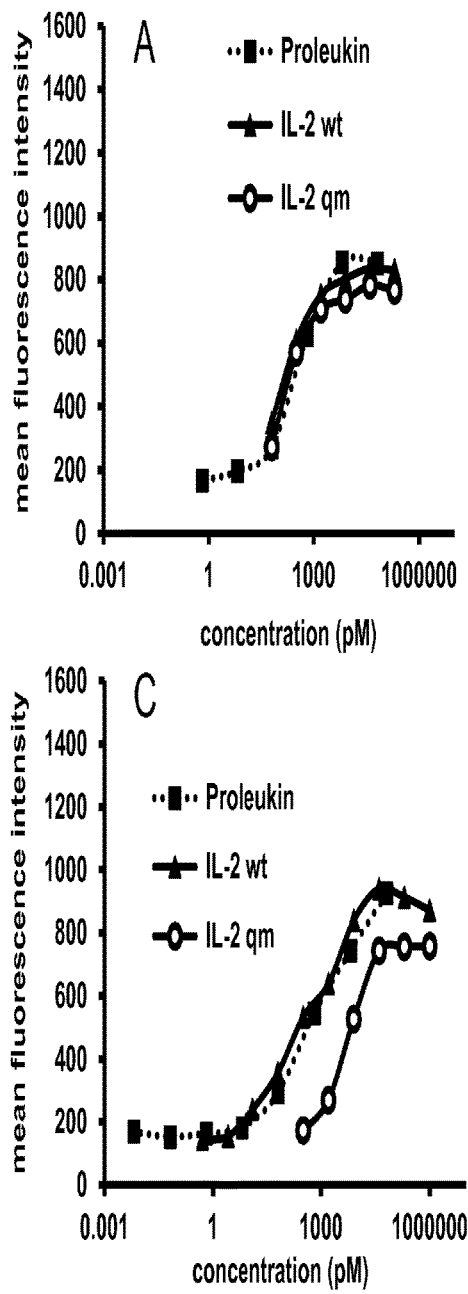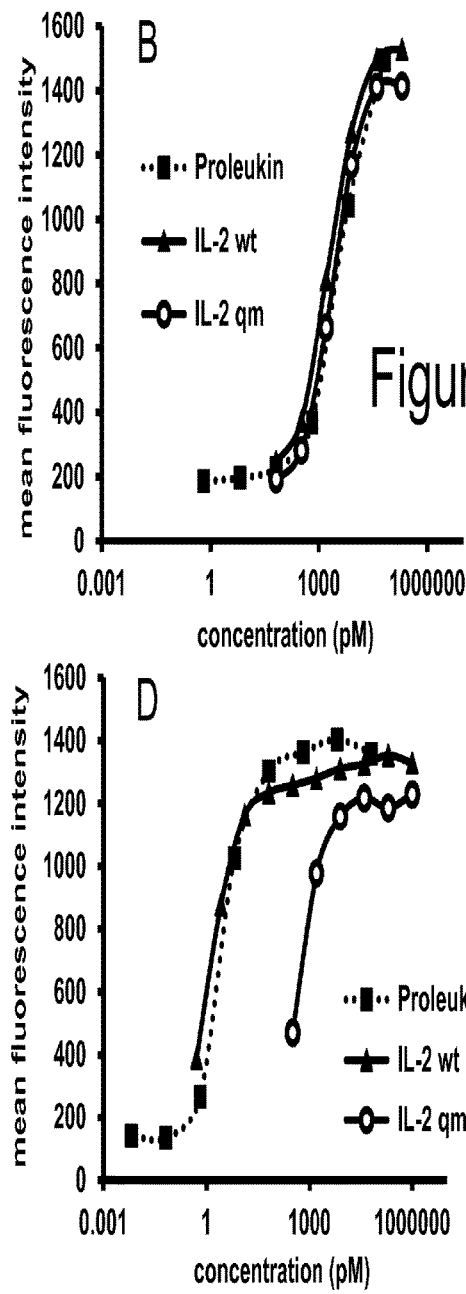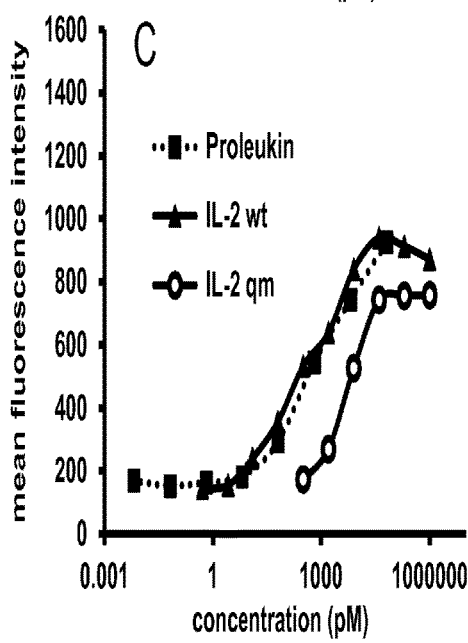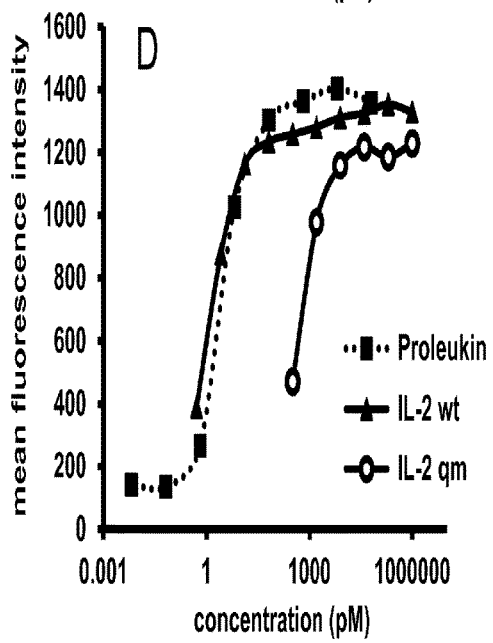
Figure 38

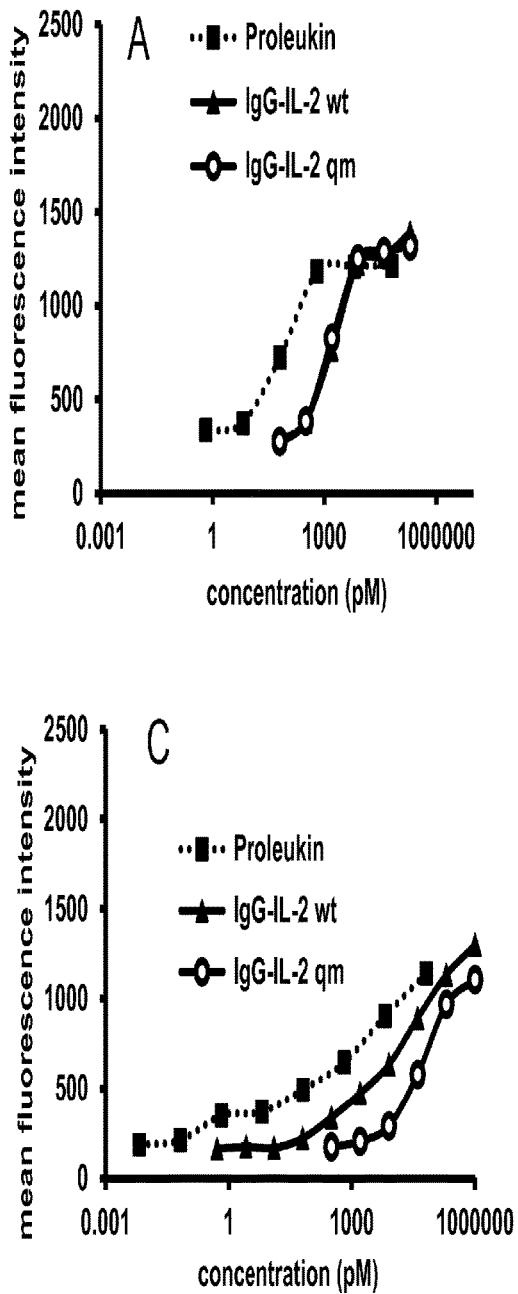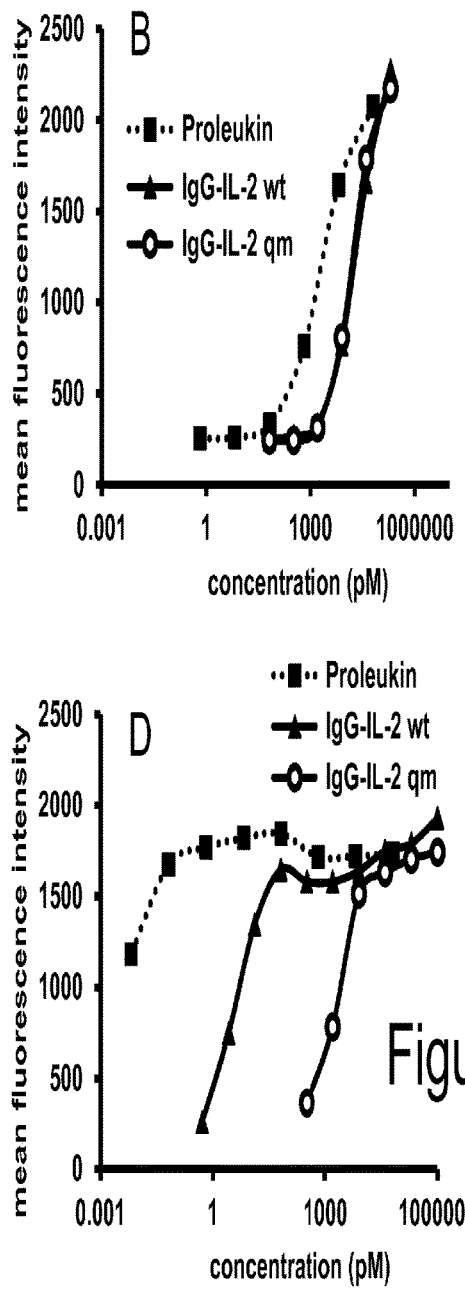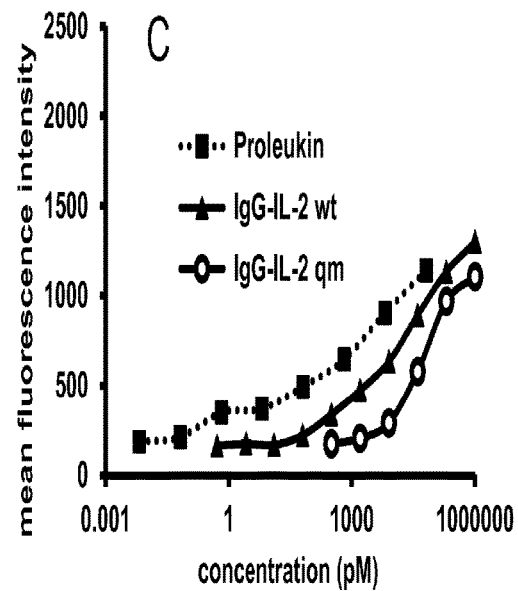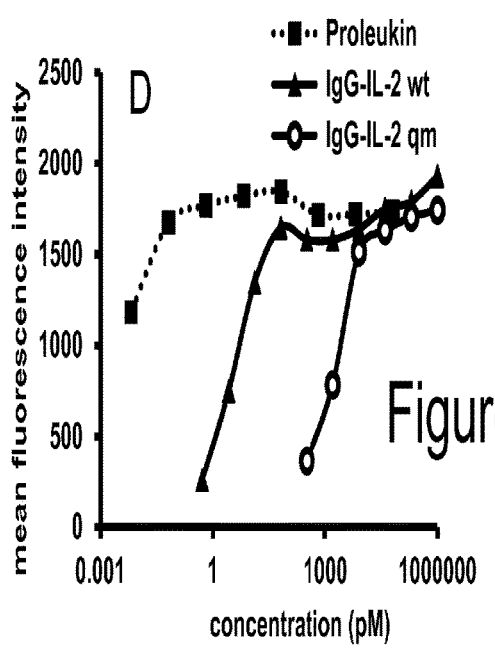
Figure 39

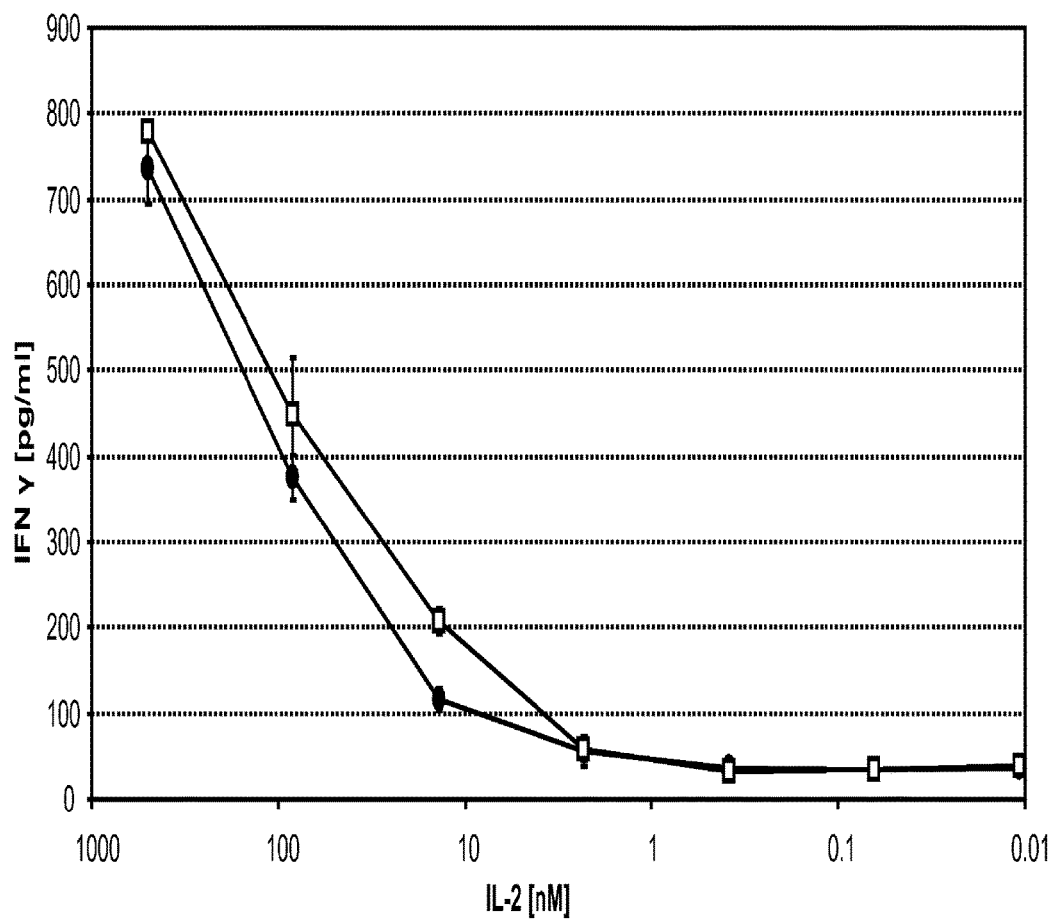

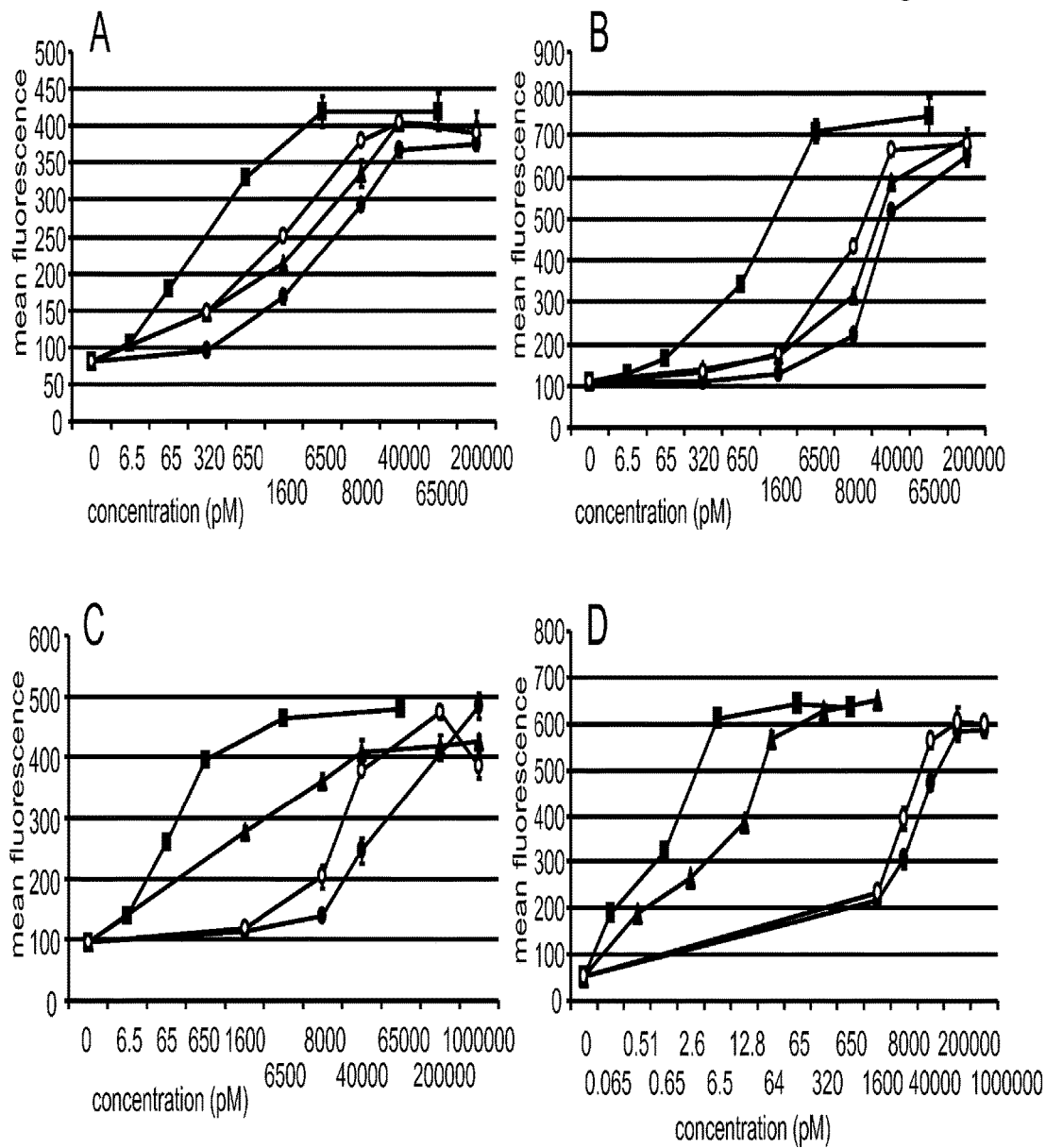

MUTANT INTERLEUKIN-2 POLYPEPTIDES

CROSS-REFERENCE TO RELATED APPLICATIONS

This application is a divisional of U.S. application Ser. No. 14/996,789, filed Jan. 15, 2016, which is a continuation of U.S. application Ser. No. 13/367,843, filed Feb. 7, 2012, now U.S. Pat. No. 9,266,938, issued Feb. 23, 2016, which claims benefit under 35 U.S.C. § 119 to European Patent Application No. 11153964.9, filed Feb. 10, 2011, and European Patent Application No. 11164237.7, filed Apr. 29, 2011. Each of the foregoing applications is herein incorporated by reference in its entirety.

SEQUENCE LISTING

The present application contains a Sequence Listing which has been submitted electronically as a text file in ASCII format and is hereby incorporated by reference in its entirety. Said text file, created on Dec. 14, 2017, is named P27307-US-5_seqlist.txt and is 483,328 bytes in size.

FIELD OF THE INVENTION

The present invention generally relates to mutant interleukin-2 polypeptides. More particularly, the inventions concerns mutant IL-2 polypeptides that exhibit improved properties for use as immunotherapeutic agents. In addition, the invention relates to immunoconjugates comprising said mutant IL-2 polypeptides, polynucleotide molecules encoding the mutant IL-2 polypeptides or immunoconjugates, and vectors and host cells comprising such polynucleotide molecules. The invention further relates to methods for producing the mutant IL-2 polypeptides or immunoconjugates, pharmaceutical compositions comprising the same, and uses thereof.

BACKGROUND

Interleukin-2 (IL-2), also known as T cell growth factor (TCGF), is a 15.5 kDa globular glycoprotein playing a central role in lymphocyte generation, survival and homeostasis. It has a length of 133 amino acids and consists of four antiparallel, amphiphatic α-helices that form a quaternary structure indispensable of its function (Smith, Science 240, 1169-76 (1988); Bazan, Science 257, 410-413 (1992)). Sequences of IL-2 from different species are found under NCBI RefSeq Nos, NP000577 (human), NP032392 (mouse), NP446288 (rat) or NP517425 (chimpanzee).

IL-2 mediates its action by binding to IL-2 receptors (IL-2R), which consist of up to three individual subunits, the different association of which can produce receptor forms that differ in their affinity to IL-2. Association of the α (CD25), β (CD122), and γ ($\gamma_c$, CD132) subunits results in a trimeric, high-affinity receptor for IL-2. Dimeric IL-2 receptor consisting of the β and γ subunits is termed intermediate-affinity IL-2R. The a subunit forms the monomeric low affinity IL-2 receptor. Although the dimeric intermediate-affinity IL-2 receptor binds IL-2 with approximately 100-fold lower affinity than the trimeric high-affinity receptor, both the dimeric and the trimeric IL-2 receptor variants are able to transmit signal upon IL-2 binding (Minami et al., Annu Rev Immunol 11, 245-268 (1993)). Hence, the α-subunit, CD25, is not essential for IL-2 signalling. It confers high-affinity binding to its receptor, whereas the β subunit, CD122, and the γ-subunit are crucial for signal transduction (Krieg et al., Proc Natl Acad Sci 107, 11906-11 (2010)). Trimeric IL-2 receptors including CD25 are expressed by (resting) CD4$^+$ forkhead box P3 (FoxP3)$^+$ regulatory T ($T_{reg}$) cells. They are also transiently induced on conventional activated T cells, whereas in the resting state these cells express only dimeric IL-2 receptors. $T_{reg}$ cells consistently express the highest level of CD25 in vivo (Fontenot et al., Nature Immunol 6, 1142-51 (2005)).

IL-2 is synthesized mainly by activated T-cells, in particular CD4$^+$ helper T cells. It stimulates the proliferation and differentiation of T cells, induces the generation of cytotoxic T lymphocytes (CTLs) and the differentiation of peripheral blood lymphocytes to cytotoxic cells and lymphokine-activated killer (LAK) cells, promotes cytokine and cytolytic molecule expression by T cells, facilitates the proliferation and differentiation of B-cells and the synthesis of immunoglobulin by B-cells, and stimulates the generation, proliferation and activation of natural killer (NK) cells (reviewed e.g. in Waldmann, Nat Rev Immunol 6, 595-601 (2009); Olejniczak and Kasprzak, Med Sci Monit 14, RA179-89 (2008); Malek, Annu Rev Immunol 26, 453-79 (2008)).

Its ability to expand lymphocyte populations in vivo and to increase the effector functions of these cells confers antitumor effects to IL-2, making IL-2 immunotherapy an attractive treatment option for certain metastatic cancers. Consequently, high-dose IL-2 treatment has been approved for use in patients with metastatic renal-cell carcinoma and malignant melanoma.

However, IL-2 has a dual function in the immune response in that it not only mediates expansion and activity of effector cells, but also is crucially involved in maintaining peripheral immune tolerance.

A major mechanism underlying peripheral self-tolerance is IL-2 induced activation-induced cell death (AICD) in T cells. AICD is a process by which fully activated T cells undergo programmed cell death through engagement of cell surface-expressed death receptors such as CD95 (also known as Fas) or the TNF receptor. When antigen-activated T cells expressing a high-affinity IL-2 receptor (after previous exposure to IL-2) during proliferation are re-stimulated with antigen via the T cell receptor (TCR)/CD3 complex, the expression of Fas ligand (FasL) and/or tumor necrosis factor (TNF) is induced, making the cells susceptible for Fas-mediated apoptosis. This process is IL-2 dependent (Lenardo, Nature 353, 858-61 (1991)) and mediated via STAT5. By the process of AICD in T lymphocytes tolerance can not only be established to self-antigens, but also to persistent antigens that are clearly not part of the host's makeup, such as tumor antigens.

Moreover, IL-2 is also involved in the maintenance of peripheral CD4$^+$ CD25$^+$ regulatory T ($T_{reg}$) cells (Fontenot et al., Nature Immunol 6, 1142-51 (2005); D'Cruz and Klein, Nature Immunol 6, 1152-59 (2005); Maloy and Powrie, Nature Immunol 6, 1171-72 (2005), which are also known as suppressor T cells. They suppress effector T cells from destroying their (self-)target, either through cell-cell contact by inhibiting T cell help and activation, or through release of immunosuppressive cytokines such as IL-10 or TGF-β. Depletion of $T_{reg}$ cells was shown to enhance IL-2 induced anti-tumor immunity (Imai et al., Cancer Sci 98, 416-23 (2007)).

Therefore, IL-2 is not optimal for inhibiting tumor growth, because in the presence of IL-2 either the CTLs generated might recognize the tumor as self and undergo AICD or the immune response might be inhibited by IL-2 dependent $T_{reg}$ cells.

A further concern in relation to IL-2 immunotherapy are the side effects produced by recombinant human IL-2 treatment. Patients receiving high-dose IL-2 treatment frequently experience severe cardiovascular, pulmonary, renal, hepatic, gastrointestinal, neurological, cutaneous, haematological and systemic adverse events, which require intensive monitoring and in-patient management. The majority of these side effects can be explained by the development of so-called vascular (or capillary) leak syndrome (VLS), a pathological increase in vascular permeability leading to fluid extravasation in multiple organs (causing e.g. pulmonary and cutaneous edema and liver cell damage) and intravascular fluid depletion (causing a drop in blood pressure and compensatory increase in heart rate). There is no treatment of VLS other than withdrawal of IL-2. Low-dose IL-2 regimens have been tested in patients to avoid VLS, however, at the expense of suboptimal therapeutic results. VLS was believed to be caused by the release of proinflammatory cytokines, such as tumor necrosis factor (TNF)-α from IL-2-activated NK cells, however it has recently been shown that IL-2-induced pulmonary edema resulted from direct binding of IL-2 to lung endothelial cells, which expressed low to intermediate levels of functional αβγ IL-2 receptors (Krieg et al., Proc Nat Acad Sci USA 107, 11906-11 (2010)).

Several approaches have been taken to overcome these problems associated with IL-2 immunotherapy. For example, it has been found that the combination of IL-2 with certain anti-IL-2 monoclonal antibodies enhances treatment effects of IL-2 in vivo (Kamimura et al., J Immunol 177, 306-14 (2006); Boyman et al., Science 311, 1924-27 (2006)). In an alternative approach, IL-2 has been mutated in various ways to reduce its toxicity and/or increase its efficacy. Hu et al. (Blood 101, 4853-4861 (2003), US Pat. Publ. No. 2003/0124678) have substituted the arginine residue in position 38 of IL-2 by tryptophan to eliminate IL-2's vasopermeability activity. Shanafelt et al. (Nature Biotechnol 18, 1197-1202 (2000)) have mutated asparagine 88 to arginine to enhance selectivity for T cells over NK cells. Heaton et al. (Cancer Res 53, 2597-602 (1993); U.S. Pat. No. 5,229,109) have introduced two mutations, Arg38Ala and Phe42Lys, to reduce the secretion of proinflammatory cytokines from NK cells. Gillies et al. (US Pat. Publ. No. 2007/0036752) have substituted three residues of IL-2 (Asp20Thr, Asn88Arg, and Gln126Asp) that contribute to affinity for the intermediate-affinity IL-2 receptor to reduce VLS. Gillies et al. (WO 2008/0034473) have also mutated the interface of IL-2 with CD25 by amino acid substitution Arg38Trp and Phe42Lys to reduce interaction with CD25 and activation of $T_{reg}$ cells for enhancing efficacy. To the same aim, Wittrup et al. (WO 2009/061853) have produced IL-2 mutants that have enhanced affinity to CD25, but do not activate the receptor, thus act as antagonists. The mutations introduced were aimed at disrupting the interaction with the β- and/or γ-subunit of the receptor.

However, none of the known IL-2 mutants was shown to overcome all of the above-mentioned problems associated with IL-2 immunotherapy, namely toxicity caused by the induction of VLS, tumor tolerance caused by the induction of AICD, and immunosuppression caused by activation of $T_{reg}$ cells. Thus there remains a need in the art to further enhance the therapeutic usefulness of IL-2 proteins.

SUMMARY OF THE INVENTION

The present invention is based, in part, on the recognition that the interaction of IL-2 with the α-subunit of the trimeric, high-affinity IL-2 receptor is responsible for the problems associated with IL-2 immunotherapy.

Accordingly, in a first aspect the invention provides a mutant interleukin-2 (IL-2) polypeptide comprising a first amino acid mutation that abolishes or reduces affinity of the mutant IL-2 polypeptide to the high-affinity IL-2 receptor and preserves affinity of the mutant IL-2 polypeptide to the intermediate-affinity IL-2 receptor, each compared to a wild-type IL-2 polypeptide. In one embodiment said first amino acid mutation is at a position corresponding to residue 72 of human IL-2 (SEQ ID NO:1). In one embodiment said first amino acid mutation is an amino acid substitution, selected from the group of L72G, L72A, L72S, L72T, L72Q, L72E, L72N, L72D, L72R, and L72K. In a more specific embodiment said first amino acid mutation is the amino acid substitution L72G. In certain embodiments the mutant IL-2 polypeptide comprises a second amino acid mutation that abolishes or reduces affinity of the mutant IL-2 polypeptide to the high-affinity IL-2 receptor and preserves affinity of the mutant IL-2 polypeptide to the intermediate-affinity IL-2 receptor, each compared to a wild-type IL-2 polypeptide. In one embodiment said second amino acid mutation is at a position selected from the positions corresponding to residue 35, 38, 42, 43, and 45 of human IL-2 (SEQ ID NO:1). In a specific embodiment said second amino acid mutation is at a position corresponding to residue 42 of human IL-2 (SEQ ID NO:1). In a more specific embodiment said second amino acid mutation is an amino acid substitution, selected from the group of F42A, F42G, F42S, F42T, F42Q, F42E, F42N, F42D, F42R, and F42K. In an even more specific embodiment said second amino acid mutation is the amino acid substitution F42A. In certain embodiments the mutant interleukin-2 polypeptide comprises a third amino acid mutation that abolishes or reduces affinity of the mutant IL-2 polypeptide to the high-affinity IL-2 receptor and preserves affinity of the mutant IL-2 polypeptide to the intermediate-affinity IL-2 receptor, each compared to a wild-type IL-2 polypeptide. In a particular embodiment, the mutant interleukin-2 polypeptide comprises three amino acid mutations that abolish or reduce affinity of the mutant IL-2 polypeptide to the high-affinity IL-2 receptor and preserve affinity of the mutant IL-2 polypeptide to the intermediate-affinity IL-2 receptor, each compared to a wild-type IL-2 polypeptide, wherein said three amino acid mutations are at positions corresponding to residue 42, 45, and 72 of human IL-2 (SEQ ID NO:1). In one embodiment said three amino acid mutations are amino acid substitutions selected from the group of F42A, F42G, F42S, F42T, F42Q, F42E, F42N, F42D, F42R, F42K, Y45A, Y45G, Y45S, Y45T, Y45Q, Y45E, Y45N, Y45D, Y45R, Y45K, L72G, L72A, L72S, L72T, L72Q, L72E, L72N, L72D, L72R, and L72K. In a specific embodiment said three amino acid mutations are the amino acid substitutions F42A, Y45A and L72G. In certain embodiments the mutant interleukin-2 polypeptide further comprises an amino acid mutation which eliminates the O-glycosylation site of IL-2 at a position corresponding to residue 3 of human IL-2 (SEQ ID NO:1). In one embodiment said amino acid mutation which eliminates the O-glycosylation site of IL-2 at a position corresponding to residue 3 of human IL-2 is an amino acid substitution selected from the group of T3A, T3G, T3Q, T3E, T3N, T3D, T3R, T3K, and T3P. In a specific embodiment the amino acid mutation which eliminates the O-glycosylation site of IL-2 at a position corresponding to residue 3 of human IL-2 is T3A. In certain embodiments the mutant IL-2 polypeptide is essentially a full-length IL-2 molecule, particularly a human full-length IL-2 molecule.

The invention further provides for a mutant interleukin-2 polypeptide linked to a non-IL-2 moiety. In certain embodiments said non-IL-2 moiety is a targeting moiety. In certain embodiments said non-IL-2 moiety is an antigen binding moiety. In one embodiment said antigen binding moiety is an antibody. In another embodiment said antigen binding moiety is an antibody fragment. In a more specific embodiment said antigen binding moiety is selected from a Fab molecule and a scFv molecule. In a particular embodiment said antigen binding moiety is a Fab molecule. In another embodiment said antigen binding moiety is a scFv molecule. In particular embodiments the mutant IL-2 polypeptide is linked to a first and a second non-IL-2 moiety. In one such embodiment the mutant interleukin-2 polypeptide shares a carboxy-terminal peptide bond with said first non-IL-2 moiety and an amino-terminal peptide bond with said second non-IL-2 moiety. In one embodiment said antigen binding moiety is an immunoglobulin molecule. In a more specific embodiment said antigen binding moiety is an IgG class, particularly an IgG$_1$ subclass, immunoglobulin molecule. In certain embodiments said antigen binding moiety is directed to an antigen presented on a tumor cell or in a tumor cell environment, particularly an antigen selected from the group of Fibroblast Activation Protein (FAP), the A1 domain of Tenascin-C (TNC A1), the A2 domain of Tenascin-C (TNC A2), the Extra Domain B of Fibronectin (EDB), Carcinoembryonic Antigen (CEA) and the Melanoma-associated Chondroitin Sulfate Proteoglycan (MCSP).

Also provided by the invention is an immunoconjugate comprising a mutant IL-2 polypeptide as described herein, and an antigen binding moiety. In one embodiment of the immunoconjugate according to the invention the mutant IL-2 polypeptide shares an amino- or carboxy-terminal peptide-bond with said antigen binding moiety. In particular embodiments the immunoconjugate comprises as first and a second antigen binding moiety. In one such embodiment the mutant IL-2 polypeptide comprised in the immunoconjugate according to the invention shares an amino- or carboxy-terminal peptide bond with a first antigen binding moiety and a second antigen binding moiety shares an amino- or carboxy-terminal peptide bond with either i) the mutant IL-2 polypeptide or ii) said first antigen binding moiety. In one embodiment the antigen binding moiety comprised in the immunoconjugate according to the invention is an antibody, in another embodiment said antigen binding moiety is an antibody fragment. In a specific embodiment said antigen binding moiety is selected from a Fab molecule and a scFv molecule. In a particular embodiment said antigen binding moiety is a Fab molecule. In another particular embodiment said antigen binding moiety is an immunoglobulin molecule. In a more specific embodiment said antigen binding moiety is an IgG class, particularly an IgG$_1$ subclass, immunoglobulin molecule. In certain embodiments said antigen binding moiety is directed to an antigen presented on a tumor cell or in a tumor cell environment, particularly an antigen selected from the group of Fibroblast Activation Protein (FAP), the A1 domain of Tenascin-C (TNC A1), the A2 domain of Tenascin-C (TNC A2), the Extra Domain B of Fibronectin (EDB), Carcinoembryonic Antigen (CEA) and the Melanoma-associated Chondroitin Sulfate Proteoglycan (MCSP).

The invention further provides isolated polynucleotides encoding a mutant IL-2 polypeptide or an immunoconjugate as described herein, expression vectors comprising said polynucleotides, and host cells comprising the polynucleotides or the expression vectors.

Also provided is a method of producing a mutant IL-2 polypeptide or an immunoconjugate as described herein; comprising culturing the host cell described herein under conditions suitable for the expression of the mutant IL-2 polypeptide or immunoconjugate as described herein and isolating the mutant IL-2 polypeptide or immunoconjugate as described herein; a mutant IL-2 polypeptide or an immunoconjugate produced by the method described herein, a pharmaceutical composition comprising a mutant IL-2 polypeptide or an immunoconjugate as described herein and a pharmaceutically acceptable carrier, and methods of using a mutant IL-2 polypeptide or an immunoconjugate as described herein.

In particular, the invention encompasses a mutant IL-2 polypeptide or an immunoconjugate as described herein for use in the treatment of a disease in an individual in need thereof. In a particular embodiment said disease is cancer. In a particular embodiment the individual is a human.

Also encompassed by the invention is the use of the mutant IL-2 polypeptide or immunoconjugate as described herein for the manufacture of a medicament for treating a disease in an individual in need thereof.

Further provided is a method of treating disease in an individual, comprising administering to said individual a therapeutically effective amount of a composition comprising a mutant IL-2 polypeptide or an immunoconjugate as described herein. Said disease preferably is cancer.

Also provided is a method of stimulating the immune system of an individual, comprising administering to said individual an effective amount of a composition comprising the mutant IL-2 polypeptide or immunoconjugate described herein in a pharmaceutically acceptable form.

DETAILED DESCRIPTION OF THE INVENTION

Definitions

Terms are used herein as generally used in the art, unless otherwise defined in the following.

The term "interleukin-2" or "IL-2" as used herein, refers to any native IL-2 from any vertebrate source, including mammals such as primates (e.g. humans) and rodents (e.g., mice and rats), unless otherwise indicated. The term encompasses unprocessed IL-2 as well as any form of IL-2 that results from processing in the cell. The term also encompasses naturally occurring variants of IL-2, e.g. splice variants or allelic variants. The amino acid sequence of an exemplary human IL-2 is shown in SEQ ID NO: 1. Unprocessed human IL-2 additionally comprises an N-terminal 20 amino acid signal peptide having the sequence of SEQ ID NO: 272, which is absent in the mature IL-2 molecule.

The term "IL-2 mutant" or "mutant IL-2 polypeptide" as used herein is intended to encompass any mutant forms of various forms of the IL-2 molecule including full-length IL-2, truncated forms of IL-2 and forms where IL-2 is linked to another molecule such as by fusion or chemical conjugation. "Full-length" when used in reference to IL-2 is intended to mean the mature, natural length IL-2 molecule. For example, full-length human IL-2 refers to a molecule that has 133 amino acids (see e.g. SEQ ID NO: 1). The various forms of IL-2 mutants are characterized in having a at least one amino acid mutation affecting the interaction of IL-2 with CD25. This mutation may involve substitution, deletion, truncation or modification of the wild-type amino acid residue normally located at that position. Mutants obtained by amino acid substitution are preferred. Unless otherwise indicated, an IL-2 mutant may be referred to herein as an IL-2 mutant peptide sequence, an IL-2 mutant polypeptide, IL-2 mutant protein or IL-2 mutant analog.

Designation of various forms of IL-2 is herein made with respect to the sequence shown in SEQ ID NO: 1. Various designations may be used herein to indicate the same mutation. For example a mutation from phenylalanine at position 42 to alanine can be indicated as 42A, A42, $A_{42}$, F42A, or Phe42Ala.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to CD25. Amino acid sequence deletions and insertions include amino- and/or carboxy-terminal deletions and insertions of amino acids. An example of a terminal deletion is the deletion of the alanine residue in position 1 of full-length human IL-2. Preferred amino acid mutations are amino acid substitutions. For the purpose of altering e.g. the binding characteristics of an IL-2 polypeptide, non-conservative amino acid substitutions, i.e. replacing one amino acid with another amino acid having different structural and/or chemical properties, are particularly preferred. Preferred amino acid substitutions include replacing a hydrophobic by a hydrophilic amino acid. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful.

As used herein, a "wild-type" form of IL-2 is a form of IL-2 that is otherwise the same as the mutant IL-2 polypeptide except that the wild-type form has a wild-type amino acid at each amino acid position of the mutant IL-2 polypeptide. For example, if the IL-2 mutant is the full-length IL-2 (i.e. IL-2 not fused or conjugated to any other molecule), the wild-type form of this mutant is full-length native IL-2. If the IL-2 mutant is a fusion between IL-2 and another polypeptide encoded downstream of IL-2 (e.g. an antibody chain) the wild-type form of this IL-2 mutant is IL-2 with a wild-type amino acid sequence fused to the same downstream polypeptide. Furthermore, if the IL-2 mutant is a truncated form of IL-2 (the mutated or modified sequence within the non-truncated portion of IL-2) then the wild-type form of this IL-2 mutant is a similarly truncated IL-2 that has a wild-type sequence. For the purpose of comparing IL-2 receptor binding affinity or biological activity of various forms of IL-2 mutants to the corresponding wild-type form of IL-2, the term wild-type encompasses forms of IL-2 comprising one or more amino acid mutation that does not affect IL-2 receptor binding compared to the naturally occurring, native IL-2, such as e.g. a substitution of cysteine at a position corresponding to residue 125 of human IL-2 to alanine. In some embodiments wild-type IL-2 for the purpose of the present invention comprises the amino acid substitution C125A (see SEQ ID NO: 3). In certain embodiments according to the invention the wild-type IL-2 polypeptide to which the mutant IL-2 polypeptide is compared comprises the amino acid sequence of SEQ ID NO: 1. In other embodiments the wild-type IL-2 polypeptide to which the mutant IL-2 polypeptide is compared comprises the amino acid sequence of SEQ ID NO: 3.

The term "CD25" or "α-subunit of the IL-2 receptor" as used herein, refers to any native CD25 from any vertebrate source, including mammals such as primates (e.g. humans) and rodents (e.g., mice and rats), unless otherwise indicated. The term encompasses "full-length", unprocessed CD25 as well as any form of CD25 that results from processing in the cell. The term also encompasses naturally occurring variants of CD25, e.g. splice variants or allelic variants. In certain embodiments CD25 is human CD25. The amino acid sequence of an exemplary human CD25 (with signal sequence, Avi-tag and His-tag) is shown in SEQ ID NO: 278.

The term "high-affinity IL-2 receptor" as used herein refers to the heterotrimeric form of the IL-2 receptor, consisting of the receptor γ-subunit (also known as common cytokine receptor γ-subunit$_2$ $γ_c$, or CD132), the receptor β-subunit (also known as CD122 or p70) and the receptor α-subunit (also known as CD25 or p55). The term "intermediate-affinity IL-2 receptor" by contrast refers to the IL-2 receptor including only the γ-subunit and the β-subunit, without the α-subunit (for a review see e.g. Olejniczak and Kasprzak, Med Sci Monit 14, RA179-189 (2008)).

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., receptor and a ligand). The affinity of a molecule-X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well established methods known in the art, including those described herein.

The affinity of the mutant or wild-type IL-2 polypeptide for various forms of the IL-2 receptor can be determined in accordance with the method set forth in the Examples by surface plasmon resonance (SPR), using standard instrumentation such as a BIAcore instrument (GE Healthcare) and receptor subunits such as may be obtained by recombinant expression (see e.g. Shanafelt et al., Nature Biotechnol 18, 1197-1202 (2000)). Alternatively, binding affinity of 11-2 mutants for different forms of the IL-2 receptor may be evaluated using cell lines known to express one or the other such form of the receptor. Specific illustrative and exemplary embodiments for measuring binding affinity are described hereinafter.

By "regulatory T cell" or "$T_{reg}$ cell" is meant a specialized type of CD4$^+$ T cell that can suppress the responses of other T cells. $T_{reg}$ cells are characterized by expression of the α-subunit of the IL-2 receptor (CD25) and the transcription factor forkhead box P3 (FOXP3) (Sakaguchi, Annu Rev Immunol 22, 531-62 (2004)) and play a critical role in the induction and maintenance of peripheral self-tolerance to antigens, including those expressed by tumors. $T_{reg}$ cells require IL-2 for their function and development and induction of their suppressive characteristics.

As used herein, the term "effector cells" refers to a population of lymphocytes that mediate the cytotoxic effects of IL-2. Effector cells include effector T cells such as CD8$^+$ cytotoxic T cells, NK cells, lymphokine-activated killer (LAK) cells and macrophages/monocytes.

As used herein, the term "antigen binding moiety" refers to a polypeptide molecule that specifically binds to an antigenic determinant. In one embodiment, an antigen binding moiety is able to direct the entity to which it is attached (e.g. a cytokine or a second antigen binding moiety) to a target site, for example to a specific type of tumor cell or tumor stroma bearing the antigenic determinant. Antigen binding moieties include antibodies and fragments thereof as further defined herein. Preferred antigen binding moieties include an antigen binding domain of an antibody, comprising an antibody heavy chain variable region and an antibody light chain variable region. In certain embodiments, the antigen binding moieties may include antibody constant regions as further defined herein and known in the art. Useful heavy chain constant regions include any of the five isotypes: α, δ, ε, γ, or μ. Useful light chain constant regions include any of the two isotypes: κ and λ.

By "specifically binds" is meant that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g. surface plasmon resonance technique (analyzed on a BIAcore instrument) (Liljeblad et al., Glyco J 17, 323-329 (2000)), and traditional binding assays (Heeley, Endocr Res 28, 217-229 (2002)).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding-moiety binds, forming an antigen binding moiety-antigen complex. Useful antigenic determinants can be found, for example, on the surfaces of tumor cells, on the surfaces of virus-infected cells, on the surfaces of other diseased cells, free in blood serum, and/or in the extracellular matrix (ECM).

As used herein, term "polypeptide" refers to a molecule composed of monomers (amino acids) linearly linked by amide bonds (also known as peptide bonds). The term "polypeptide" refers to any chain of two or more amino acids, and does not refer to a specific length of the product. Thus, peptides, dipeptides, tripeptides, oligopeptides, "protein," "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

By an "isolated" polypeptide or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a therapeutic polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extra-chromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode mutant IL-2 polypeptides or immunoconjugates of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as: well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode mutant IL-2 polypeptides or immunoconjugates of the invention or fragments thereof.

The term "artificial" refers to a synthetic, or non-host cell derived composition, e.g. a chemically-synthesized oligonucleotide.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen binding activity.

The terms "full length antibody," "intact antibody," and "whole antibody" are used herein interchangeably to refer to an antibody having a structure substantially similar to a native antibody structure or having heavy chains that contain an Fc region as defined herein.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$, diabodies, linear antibodies, single-chain antibody molecules (e.g. scFv), and multispecific antibodies formed from antibody fragments. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and $F(ab')_2$ fragments comprising salvage receptor binding epitope residues and having increased in vivo half-life, see U.S. Pat. No. 5,869,046. Diabodies are antibody fragments with two antigen binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Antibody fragments can be made by various techniques, including but not limited to proteolytic digestion of an intact antibody as well as production by recombinant host cells (e.g. *E. coli* or phage), as described herein.

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five classes, called α (IgA), δ (IgD), ε (IgE), γ (IgG), or μ (IgM), some of which may be further divided into subclasses, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\alpha_2$ (IgA$_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The term "antigen binding domain" refers to the part of an antibody that comprises the area which specifically binds to and is complementary to part or all of an antigen. An antigen binding domain may be provided by, for example, one or more antibody variable domains (also called antibody variable regions). Preferably, an antigen binding domain comprises an antibody light chain variable region (VL) and an antibody heavy chain variable region (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6$^{th}$ ed., W.H. Freeman and Co., page 91 (2007). A single VH or VL domain may be sufficient to confer antigen binding specificity.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

| CDR Definitions[1] | | | |
|---|---|---|---|
| CDR | Kabat | Chothia | AbM[2] |
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table 1 is according to the numbering conventions set forth by Kabat et al. (see below).
[2]"AbM" with a lowercase "b" as used in Table 1 refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

The polypeptide sequences of the sequence listing (i.e., SEQ ID NOs: 23, 25, 27, 29, 31, 33, etc.) are not numbered according to the Kabat numbering system. However, it is well within the ordinary skill of one in the art to convert the numbering of the sequences of the Sequence Listing to Kabat numbering.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or -VL): FR1-H1(L1)-FR2-H2(L2)-FR3-H3(L3)-FR4.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present.

A "modification promoting heterodimerization" is a manipulation of the peptide backbone or the post-translational modifications of a polypeptide, e.g. an immunoglobulin heavy chain, that reduces or prevents the association of the polypeptide with an identical polypeptide to form a homodimer. A modification promoting heterodimerization as used herein particularly includes separate modifications made to each of two polypeptides desired to form a dimer, wherein the modifications are complementary to each other so as to promote association of the two polypeptides. For example, a modification promoting heterodimerization may alter the structure or charge of one or both of the polypeptides desired to form a dimer so as to make their association sterically or electrostatically favorable, respectively. Heterodimerization occurs between two non-identical polypeptides, such as two immunoglobulin heavy chains wherein further immunoconjugate components fused to each of the heavy chains (e.g. IL-2 polypeptide) are not the same. In the immunoconjugates of the present invention, the modification promoting heterodimerization is in the heavy chain(s), specifically in the Fc domain, of an immunoglobulin molecule. In some embodiments the modification promoting heterodimerziation comprises an amino acid mutation, specifically an amino acid substitution. In a particular embodiment, the modification promoting heterodimerization comprises a separate amino acid mutation, specifically an amino acid substitution, in each of the two immunoglobulin heavy chains.

The term "effector functions" when used in reference to antibodies refer to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, down regulation of cell surface receptors (e.g. B cell receptor), and B cell activation.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89).

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

As used herein, the term "immunoconjugate" refers to a polypeptide molecule that includes at least one IL-2 moiety and at least one antigen binding moiety. In certain embodiments, the immunoconjugate comprises at least one IL-2 moiety, and at least two antigen binding moieties. Particular immunoconjugates according to the invention essentially consist of one IL-2 moiety and two antigen binding moieties joined by one or more linker sequences. The antigen binding moiety can be joined to the IL-2 moiety by a variety of interactions and in a variety of configurations as described herein.

As used herein, the term "control antigen binding moiety" refers to an antigen binding moiety as it would exist free of other antigen binding moieties and effector moieties. For example, when comparing an Fab-IL2-Fab immunoconjugate of the invention with a control antigen binding moiety, the control antigen binding moiety is free Fab, wherein the Fab-IL2-Fab immunoconjugate and the free Fab molecule can both specifically bind to the same antigen determinant.

As used herein, the terms "first" and "second" with respect to antigen binding moieties etc., are used for convenience of distinguishing when there is more than one of each type of moiety. Use of these terms is not intended to confer a specific order or orientation of the immunoconjugate unless explicitly so stated.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Preferably, the individual or subject is a human.

The term "pharmaceutical composition" refers to a preparation which is in such form as to permit the biological activity of an active ingredient contained therein to be effective, and which contains no additional components which are unacceptably toxic to a subject to which the composition would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

DETAILED DESCRIPTION OF THE EMBODIMENTS

The present invention aims at providing a mutant IL-2 polypeptide having improved properties for immunotherapy. In particular the invention aims at eliminating pharmacological properties of IL-2 that contribute to toxicity but are not essential for efficacy of IL-2. As discussed above, different forms of the IL-2 receptor consist of different subunits and exhibit different affinities for IL-2. The intermediate-affinity IL-2 receptor, consisting of the β and γ receptor subunits, is expressed on resting effector cells and is sufficient for IL-2 signaling. The high-affinity IL-2 receptor, additionally comprising the α-subunit of the receptor, is mainly expressed on regulatory T ($T_{reg}$) cells as well as on activated effector cells where its engagement by IL-2 can promote $T_{reg}$ cell-mediated immunosuppression or activation-induced cell death (AICD), respectively. Thus, without wishing to be bound by theory, reducing or abolishing the affinity of IL-2 to the α-subunit of the IL-2 receptor should reduce IL-2 induced downregulation of effector cell function by regulatory T cells and development of tumor tolerance by the process of AICD. On the other hand, maintaining the affinity to the intermediate-affinity IL-2 receptor should preserve the induction of proliferation and activation of effector cells like NK and T cells by IL-2.

Several IL-2 mutants already exist in the art, however, the inventors have found novel amino acid mutations of the IL-2 polypeptide and combinations thereof that are particularly suitable to confer to IL-2 the desired characteristics for immunotherapy.

In a first aspect the invention provides a mutant interleukin-2 (IL-2) polypeptide comprising an amino acid mutation that abolishes or reduces affinity of the mutant IL-2 polypeptide to the α-subunit of the IL-2 receptor and preserves affinity of the mutant IL-2 polypeptide to the intermediate-affinity IL-2 receptor each compared to a wild-type IL-2 polypeptide. Mutants of human IL-2 (hIL-2) with decreased affinity to CD25 may for example be generated by amino acid substitution at amino acid position 35, 38, 42, 43, 45 or 72 or combinations thereof. Exemplary amino acid substitutions include K35E, K35A, R38A, R38E, R38N, R38F, R38S, R38L, R38G, R38Y, R38W, F42L, F42A, F42G, F42S, F42T, F42Q, F42E, F42N, F42D, F42R, F42K, K43E, Y45A, Y45G, Y45S, Y45T, Y45Q, Y45E, Y45N, Y45D, Y45R, Y45K, L72G, L72A, L72S, L72T, L72Q, L72E, L72N, L72D, L72R, and L72K. Particular IL-2 mutants according to the invention comprise a mutation at an amino acid position corresponding to residue 42, 45, or 72 of human IL-2, or a combination thereof. These mutants exhibit substantially similar binding affinity to the intermediate-affinity IL-2 receptor, and have substantially reduced affinity to the α-subunit of the IL-2 receptor and the high-affinity IL-2 receptor compared to a wild-type form of the IL-2 mutant.

Other characteristics of useful mutants may include the ability to induce proliferation of IL-2 receptor-bearing T and/or NK cells, the ability to induce IL-2 signaling in IL-2 receptor-bearing T and/or NK cells, the ability to generate interferon (IFN)-γ as a secondary cytokine by NK cells, a reduced ability to induce elaboration of secondary cytokines—particularly IL-10 and TNF-α—by peripheral blood mononuclear cells (PBMCs), a reduced ability to activate regulatory T cells, a reduced ability to induce apoptosis in T cells, and a reduced toxicity profile in vivo.

In one embodiment according to the invention, the amino acid mutation that abolishes or reduces affinity of the mutant IL-2 polypeptide to the high-affinity IL-2 receptor and preserves affinity of the mutant IL-2 polypeptide to the intermediate-affinity IL-2 receptor is at a position corresponding to residue 72 of human IL-2. In one embodiment said amino acid mutation is an amino acid substitution. In one embodiment said amino acid substitution is selected from the group of L72G, L72A, L72S, L72T, L72Q, L72E, L72N, L72D, L72R, and L72K. In a more specific embodiment said amino acid mutation is the amino acid substitution L72G.

In a particular aspect the invention provides a mutant IL-2 polypeptide comprising a first and a second amino acid mutation that abolishes or reduces affinity of the mutant IL-2 polypeptide to the α-subunit of the IL-2 receptor and preserves affinity of the mutant IL-2 polypeptide to the intermediate affinity IL-2 receptor. In one embodiment said first amino acid mutation is at a position corresponding to residue 72 of human IL-2. In one embodiment said first amino acid mutation is an amino acid substitution. In a specific embodiment said first amino acid mutation is an amino acid substitution selected from the group of L72G, L72A, L72S, L72T, L72Q, L72E, L72N, L72D, L72R, and L72K. In an even more specific embodiment said amino acid substitution is L72G. Said second amino acid mutation is at a different position than said first amino acid mutation. In one embodiment said second amino acid mutation is at a position selected from a position corresponding to residue 35, 38, 42, 43 and 45 of human IL-2. In one embodiment said second amino acid mutation is an amino acid substitution. In a specific embodiment said amino acid substitution is selected from the group of K35E, K35A, R38A, R38E, R38N, R38F, R38S, R38L, R38G, R38Y, R38W, F42L, F42A, F42G, F42S, F42T, F42Q, F42E, F42N, F42D, F42R, F42K, K43E, Y45A, Y45G, Y45S, Y45T, Y45Q, Y45E, Y45N, Y45D, Y45R, and Y45K. In a particular embodiment said second amino acid mutation is at a position corresponding to residue 42 or 45 of human IL-2. In a specific embodiment said second amino acid mutation is an amino acid substitution, selected from the group of F42A, F42G, F42S, F42T, F42Q, F42E, F42N, F42D, F42R, F42K, Y45A, Y45G, Y45S, Y45T, Y45Q, Y45E, Y45N, Y45D, Y45R, and Y45K. In a more specific embodiment said second amino acid mutation is the amino acid substitution F42A or Y45A. In a more particular embodiment said second amino acid mutation is at the position corresponding to residue 42 of human IL-2. In a specific embodiment said second amino acid mutation is an amino acid substitution, selected from the group of F42A, F42G, F42S, F42T, F42Q, F42E, F42N, F42D, F42R, and F42K. In a more specific embodiment said amino acid substitution is F42A. In another embodiment said second amino acid mutation is at the position corresponding to residue 45 of human IL-2. In a specific embodiment said second amino acid mutation is an amino acid substitution, selected from the group of Y45A, Y45G, Y45S, Y45T, Y45Q, Y45E, Y45N, Y45D, Y45R, and Y45K. In a more specific embodiment said amino acid substitution is Y45A. In certain embodiments the mutant IL-2 polypeptide comprises a third amino acid mutation that abolishes or reduces affinity of the mutant IL-2 polypeptide to the α-subunit of the IL-2 receptor and preserves affinity of the mutant IL-2 polypeptide to the intermediate-affinity IL-2 receptor, each compared to a wild-type IL-2 polypeptide. Said third amino acid mutation is at a different position than said first and second amino acid mutations. In one embodiment said third amino acid mutation is at a position selected from a position corresponding to residue 35, 38, 42, 43 and 45 of human IL-2. In a preferred embodiment said third amino acid mutation is at a position corresponding to residue 42 or 45 of human IL-2. In one embodiment said third amino acid mutation is at a position corresponding to residue 42 of human IL-2. In another embodiment said third amino acid mutation is at a position corresponding to residue 45 of human IL-2. In one embodiment said third amino acid mutation is an amino acid substitution. In a specific embodiment said amino acid substitution is selected from the group of K35E, K35A, R38A, R38E, R38N, R38F, R38S, R38L, R38G, R38Y, R38W, F42L, F42A, F42G, F42S, F42T, F42Q, F42E, F42N, F42D, F42R, F42K, K43E, Y45A, Y45G, Y45S, Y45T, Y45Q, Y45E, Y45N, Y45D, Y45R, and Y45K. In a more specific embodiment said amino acid substitution is selected from the group of F42A, F42G, F42S, F42T, F42Q, F42E, F42N, F42D, F42R, F42K, Y45A, Y45G, Y45S, Y45T, Y45Q, Y45E, Y45N, Y45D, Y45R, and Y45K. In an even more specific embodiment said amino acid substitution is F42A or Y45A. In one embodiment said amino acid substitution is F42A. In another embodiment said amino acid substitution is Y45A. In certain embodiments the mutant IL-2 polypeptide does not comprise an amino acid mutation at the position corresponding to residue 38 of human IL-2.

In an even more particular aspect of the invention is provided a mutant IL-2 polypeptide comprising three amino acid mutations that abolish or reduce affinity of the mutant IL-2 polypeptide to the α-subunit of the IL-2 receptor but preserve affinity of the mutant IL-2 polypeptide to the intermediate affinity IL-2 receptor. In one embodiment said three amino acid mutations are at positions corresponding to residue 42, 45 and 72 of human IL-2. In one embodiment said three amino acid mutations are amino acid substitutions. In one embodiment said three amino acid mutations are amino acid substitutions selected from the group of F42A, F42G, F42S, F42T, F42Q, F42E, F42N, F42D, F42R, F42K, Y45A, Y45G, Y45S, Y45T, Y45Q, Y45E, Y45N, Y45D, Y45R, Y45K, L72G, L72A, L72S, L72T, L72Q, L72E, L72N, L72D, L72R, and L72K. In a specific embodiment said three amino acid mutations are amino acid substitutions F42A, Y45A and L72G.

In certain embodiments said amino acid mutation reduces the affinity of the mutant IL-2 polypeptide to the α-subunit of the IL-2 receptor by at least 5-fold, specifically at least 10-fold, more specifically at least 25-fold. In embodiments where there is more than one amino acid mutation that reduces the affinity of the mutant IL-2 polypeptide to the α-subunit of the IL-2 receptor, the combination of these amino acid mutations may reduce the affinity of the mutant IL-2 polypeptide to the α-subunit of the IL-2 receptor by at least 30-fold, at least 50-fold, or even at least 100-fold. In one embodiment said amino acid mutation or combination of amino acid mutations abolishes the affinity of the mutant IL-2 polypeptide to the α-subunit of the IL-2 receptor so that no binding is detectable by surface plasmon resonance as described hereinbelow.

Substantially similar binding to the intermediate-affinity receptor, i.e. preservation of the affinity of the mutant IL-2 polypeptide to said receptor, is achieved when the IL-2 mutant exhibits greater than about 70% of the affinity of a wild-type form of the IL-2 mutant to the intermediate-affinity IL-2 receptor. IL-2 mutants of the invention may exhibit greater than about 80% and even greater than about 90% of such affinity.

The inventors have found that a reduction of the affinity of IL-2 for the α-subunit of the IL-2 receptor in combination with elimination of the O-glycosylation of IL-2 results in an IL-2 protein with improved properties. For example, elimination of the O-glycosylation site results in a more homogenous product when the mutant IL-2 polypeptide is expressed in mammalian cells such as CHO or HEK cells.

Thus, in certain embodiments the mutant IL-2 polypeptide according to the invention comprises an additional amino acid mutation which eliminates the O-glycosylation site of IL-2 at a position corresponding to residue 3 of human IL-2. In one embodiment said additional amino acid mutation which eliminates the O-glycosylation site of IL-2 at a position corresponding to residue 3 of human IL-2 is an amino acid substitution. Exemplary amino acid substitutions include T3A, T3G, T3Q, T3E, T3N, T3D, T3R, T3K, and T3P. In a specific embodiment, said additional amino acid mutation is the amino acid substitution T3A.

In certain embodiments the mutant IL-2 polypeptide is essentially a full-length IL-2 molecule. In certain embodiments the mutant IL-2 polypeptide is a human IL-2 molecule. In one embodiment the mutant IL-2 polypeptide comprises the sequence of SEQ ID NO: 1 with at least one amino acid mutation that abolishes or reduces affinity of the mutant IL-2 polypeptide to the α-subunit of the IL-2 receptor but preserve affinity of the mutant IL-2 polypeptide to the intermediate affinity IL-2 receptor, compared to an IL-2 polypeptide comprising SEQ ID NO: 1 without said mutation. In another embodiment, the mutant IL-2 polypeptide comprises the sequence of SEQ ID NO: 3 with at least one amino acid mutation that abolishes or reduces affinity of the mutant IL-2 polypeptide to the α-subunit of the IL-2 receptor but preserve affinity of the mutant IL-2 polypeptide to the intermediate affinity IL-2 receptor, compared to an IL-2 polypeptide comprising SEQ ID NO: 3 without said mutation.

In a specific embodiment, the mutant IL-2 polypeptide can elicit one or more of the cellular responses selected from the group consisting of: proliferation in an activated T lymphocyte cell, differentiation in an activated T lymphocyte cell, cytotoxic T cell (CTL) activity, proliferation in an activated, B cell, differentiation in an activated B cell, proliferation in a natural killer (NK) cell, differentiation in a NK cell, cytokine secretion by an activated T cell or an NK cell, and NK/lymphocyte activated killer (LAK) antitumor cytotoxicity.

In one embodiment the mutant IL-2 polypeptide has a reduced ability to induce IL-2 signaling in regulatory T cells, compared to a wild-type IL-2 polypeptide. In one embodiment the mutant IL-2 polypeptide induces less activation-induced cell death (AICD) in T cells, compared to a wild-type IL-2 polypeptide. In one embodiment the mutant IL-2 polypeptide has a reduced toxicity profile in vivo, compared to a wild-type IL-2 polypeptide. In one embodiment the mutant IL-2 polypeptide has a prolonged serum half-life, compared to a wild-type IL-2 polypeptide.

A particular mutant IL-2 polypeptide according to the invention comprises four amino acid substitutions at positions corresponding to residues 3, 42, 45 and 72 of human IL-2. Specific amino acid substitutions are T3A, F42A, Y45A and L72G. As demonstrated in the appended Examples, said quadruple mutant IL-2 polypeptide exhibits no detectable binding to CD25, reduced ability to induce apoptosis in T cells, reduced ability to induce IL-2 signaling in $T_{reg}$ cells, and a reduced toxicity profile in vivo. However, it retains ability to activate IL-2 signaling in effector cells, to induce proliferation of effector cells, and to generate IFN-γ as a secondary cytokine by NK cells.

Moreover, said mutant IL-2 polypeptide has further advantageous properties, such as reduced surface hydrophobicity, good stability, and good expression yield, as described in the Examples. Unexpectedly, said mutant IL-2 polypeptide also provides a prolonged serum half-life, compared to wild-type IL-2.

IL-2 mutants of the invention, in addition to having mutations in the region of IL-2 that forms the interface of IL-2 with CD25 or the glycosylation site, also may have one or more mutations in the amino acid sequence outside these regions. Such additional mutations in human IL-2 may provide additional advantages such as increased expression or stability. For example, the cysteine at position 125 may be replaced with a neutral amino acid such as serine, alanine, threonine or valine, yielding C125S IL-2, C125A IL-2, C125T IL-2 or C125V IL-2 respectively, as described in U.S. Pat. No. 4,518,584. As described therein, one may also delete the N-terminal alanine residue of IL-2 yielding such mutants as des-A1 C125S or des-A1 C125A. Alternatively or conjunctively, the IL-2 mutant may include a mutation whereby methionine normally occurring at position 104 of wild-type human IL-2 is replaced by a neutral amino acid such as alanine (see U.S. Pat. No. 5,206,344). The resulting mutants, e.g., des-A1 M104A IL-2, des-A1 M104A C125S IL-2, M104A IL-2, M104A C125A IL-2, des-A1 M104A C125A IL-2, or M104A C125S IL-2 (these and other mutants may be found in U.S. Pat. No. 5,116,943 and in Weiger et al., Eur J Biochem 180, 295-300 (1989)) may be used in conjunction with the particular IL-2 mutations of the invention.

Thus, in certain embodiments the mutant IL-2 polypeptide according to the invention comprises an additional amino acid mutation at a position corresponding to residue 125 of human IL-2. In one embodiment said additional amino acid mutation is the amino acid substitution C125A.

The skilled person will be able to determine which additional mutations may provide additional advantages for the purpose of the invention. For example, he will appreciate that amino acid mutations in the IL-2 sequence that reduce or abolish the affinity of IL-2 to the intermediate-affinity IL-2 receptor, such as D20T, N88R or Q126D (see e.g. US 2007/0036752), may not be suitable to include in the mutant IL-2 polypeptide according to the invention.

In one embodiment the mutant IL-2 polypeptide of the invention comprises a sequence selected from the group of SEQ ID NO: 7, SEQ ID NO: 11, SEQ ID NO: 15, and SEQ ID NO: 19. In a specific embodiment the mutant IL-2 polypeptide of the invention comprises a sequence of SEQ ID NO: 15 or SEQ ID NO: 19. In an even more specific embodiment the mutant IL-2 polypeptide comprises a sequence of SEQ ID NO: 19.

Mutant IL-2 polypeptides of the invention are particularly useful in the context of IL-2 fusion proteins such as IL-2 bearing immunoconjugates. Such fusion proteins comprise a mutant IL-2 polypeptide of the invention fused to a non-IL-2 moiety. The non-IL-2 moiety can be a synthetic or natural protein or a portion or variant thereof. Exemplary non-IL-2 moieties include albumin, or antibody domains such as Fc domains or antigen binding domains of immunoglobulins.

IL-2 bearing immunoconjugates are fusion proteins comprising an antigen binding moiety and an IL-2 moiety. They significantly increase the efficacy of IL-2 therapy by directly targeting IL-2 e.g. into a tumor microenvironment. According to the invention, an antigen binding moiety can be a whole antibody or immunoglobulin, or a portion or variant thereof that has a biological function such as antigen specific binding affinity.

The benefits of immunoconjugate therapy are readily apparent. For example, an antigen binding moiety of an immunoconjugate recognizes a tumor-specific epitope and results in targeting of the immunoconjugate molecule to the tumor site. Therefore, high concentrations of IL-2 can be delivered into the tumor microenvironment, thereby resulting in activation and proliferation of a variety of immune effector cells mentioned herein using a much lower dose of the immunoconjugate than would be required for unconjugated IL-2. Moreover, since application of IL-2 in form of immunoconjugates allows lower doses of the cytokine itself, the potential for undesirable side effects of IL-2 is restricted, and targeting the IL-2 to a specific site in the body by means of an immunoconjugate may also result in a reduction of systemic exposure and thus less side effects than obtained with unconjugated IL-2. In addition, the increased circulating half-life of an immunoconjugate compared to unconjugated IL-2 contributes to the efficacy of the immunoconjugate. However, this characteristic of IL-2 immunoconjugates may again aggravate potential side effects of the IL-2 molecule: Because of the significantly longer circulating half-life of IL-2 immunoconjugate in the bloodstream relative to unconjugated IL-2, the probability for IL-2 or other portions of the fusion protein molecule to activate components generally present in the vasculature is increased. The same concern applies to other fusion proteins that contain IL-2 fused to another moiety such as Fc or albumin, resulting in an extended half-life of IL-2 in the circulation. Therefore an immunoconjugate comprising a mutant IL-2 polypeptide according to the invention, with reduced toxicity compared to wild-type forms of IL-2, is particularly advantageous.

Accordingly, the invention further provides a mutant IL-2 polypeptide as described hereinbefore, linked to at least one non-IL-2 moiety. In one embodiment the mutant IL-2 polypeptide and the non-IL-2 moiety form a fusion protein, i.e. the mutant IL-2 polypeptide shares a peptide bond with the non-IL-2 moiety. In one embodiment the mutant IL-2 polypeptide is linked to a first and a second non-IL-2 moiety. In one embodiment the mutant IL-2 polypeptide shares an amino- or carboxy-terminal peptide bond with the first antigen binding moiety, and the second antigen binding moiety shares an amino- or carboxy-terminal peptide bond with either i) the mutant IL-2 polypeptide or ii) the first antigen binding moiety. In a specific embodiment the mutant IL-2 polypeptide shares a carboxy-terminal peptide bond with said first non-IL-2 moiety and an amino-terminal peptide bond with said second non-IL-2 moiety. In one embodiment said non-IL-2 moiety is a targeting moiety. In a particular embodiment said non-IL-2 moiety is an antigen binding moiety (thus forming an immunoconjugate with the mutant IL-2 polypeptide, as described in more detail hereinbelow). In certain embodiments the antigen binding moiety is an antibody or an antibody fragment. In one embodiment the antigen binding moiety is a full-length antibody. In one embodiment the antigen binding moiety is an immunoglobulin molecule, particularly an IgG class immunoglobulin molecule, more particularly an $IgG_1$ subclass immunoglobulin molecule. In one such embodiment, the mutant IL-2 polypeptide shares an amino-terminal peptide bond with one of the immunoglobulin heavy chains. In another embodiment the antigen binding moiety is an antibody fragment. In some embodiments said antigen binding moiety comprises an antigen binding domain of an antibody comprising an antibody heavy chain variable region and an antibody light chain variable region. In a more specific embodiment the antigen binding moiety is a Fab molecule or a scFv molecule. In a particular embodiment the antigen binding moiety is a Fab molecule. In another embodiment the antigen binding moiety is a scFv molecule. In one embodiment said antigen binding moiety is directed to an antigen presented on a tumor cell or in a tumor cell environment. In a preferred embodiment said antigen is selected from the group of Fibroblast Activation Protein (FAP), the A1 domain of Tenascin-C (TNC A1), the A2 domain of Tenascin-C (TNC A2), the Extra Domain B of Fibronectin (EDB), Carcinoembryonic Antigen (CEA) and the Melanoma-associated Chondroitin Sulfate Proteoglycan (MCSP). Where the mutant IL-2 polypeptide is linked to more than one antigen binding moiety, e.g. a first and a second antigen binding moiety, each antigen binding moiety can be independently selected from various forms of antibodies and antibody fragments. For example, the first antigen binding moiety can be a Fab molecule and the second antigen binding moiety can be a scFv molecule. In a specific embodiment each of said first and said second antigen binding moieties is a scFv molecule or each of said first and said second antigen binding moieties is a Fab molecule. In a particular embodiment each of said first and said second antigen binding moieties is a Fab molecule. Likewise, where the mutant IL-2 polypeptide is linked to more than one antigen binding moiety, e.g. a first and a second antigen binding moiety, the antigen to which each of the antigen binding moieties is directed can be independently selected. In one embodiment said first and said second antigen binding moieties are directed to different antigens. In another embodiment said first and said second antigen binding moieties are directed to the same antigen. As described above, the antigen is particularly an antigen presented on a tumor cell or in a tumor cell environment, more particularly an antigen selected from the group of Fibroblast Activation Protein (FAP), the A1 domain of Tenascin-C (TNC A1), the A2 domain of Tenascin-C (TNC A2), the Extra Domain B of Fibronectin (EDB), Carcinoembryonic Antigen (CEA) and the Melanoma-associated Chondroitin Sulfate Proteoglycan (MCSP). The antigen binding region may further incorporate any of the features, singly or in combination, described herein in relation to antigen binding domains of immunoconjugates.

Immunoconjugates

In a particular aspect the invention provides an immunoconjugate comprising a mutant IL-2 polypeptide comprising one or more amino acid mutation that abolishes or reduces affinity of the mutant IL-2 polypeptide to the α-subunit of the IL-2 receptor and preserves affinity of the mutant IL-2 polypeptide to the intermediate-affinity IL-2 receptor, and at least one antigen binding moiety. In one embodiment according to the invention, the amino acid mutation that abolishes or reduces affinity of the mutant IL-2 polypeptide to the α-subunit of the IL-2 receptor and preserves affinity of the mutant IL-2 polypeptide to the intermediate affinity IL-2 receptor is at a position selected from a position corresponding to residue 42, 45 and 72 of human IL-2. In one embodiment said amino acid mutation is an amino acid substitution. In one embodiment said amino acid mutation is an amino acid substitution selected from the group of F42A, F42G, F42S, F42T, F42Q, F42E, F42N, F42D, F42R, F42K, Y45A, Y45G, Y45S, Y45T, Y45Q, Y45E, Y45N, Y45D, Y45R, Y45K, L72G, L72A, L72S, L72T, L72Q, L72E, L72N, L72D, L72R, and L72K, more specifically an amino acid substitution selected from the group of F42A, Y45A and L72G. In one embodiment the amino acid mutation is at a position corresponding to residue 42 of human IL-2. In a specific embodiment said amino acid mutation is an amino acid substitution selected from the group of F42A, F42G, F42S, F42T, F42Q, F42E, F42N, F42D, F42R, and F42. In an even more specific embodiment said amino acid substitution is F42A. In another embodiment the amino acid mutation is at a position corresponding to residue 45 of human IL-2. In a specific embodiment said amino acid mutation is an amino acid substitution selected from the group of Y45A, Y45G, Y45S, Y45T, Y45Q, Y45E, Y45N, Y45D, Y45R, and Y45K. In an even more specific embodiment said amino acid substitution is Y45A. In yet another embodiment the amino acid mutation is at a position corresponding to residue 72 of human IL-2. In a specific embodiment said amino acid mutation is an amino acid substitution selected from the group of L72G, L72A, L72S, L72T, L72Q, L72E, L72N, L72D, L72R, and L72K. In an even more specific embodiment said amino acid substitution is L72G. In certain embodiments, the mutant IL-2 polypeptide according to the invention does not comprise an amino acid mutation at a position corresponding to residue 38 of human IL-2. In a particular embodiment, the mutant IL-2 polypeptide comprised in the immunoconjugate of the invention comprises at least a first and a second amino acid mutation that abolishes or reduces affinity of the mutant IL-2 polypeptide to the α-subunit of the IL-2 receptor and preserves affinity of the mutant IL-2 polypeptide to the intermediate affinity IL-2 receptor. In one embodiment said first and second amino acid mutations are at two positions selected from the positions corresponding to residue 42, 45 and 72 of human IL-2. In one embodiment said first and second amino acid mutations are amino acid substitutions. In one embodiment said first and second amino acid mutations are amino acid substitutions selected from the group of F42A, F42G, F42S, F42T, F42Q, F42E, F42N, F42D, F42R, F42K, Y45A, Y45G, Y45S, Y45T, Y45Q, Y45E, Y45N, Y45D, Y45R, Y45K, L72G, L72A, L72S, L72T, L72Q, L72E, L72N, L72D, L72R, and L72K. In a particular embodiment said first and second amino acid mutations are amino acid substitutions selected from the group of F42A, Y45A and L72G. The mutant IL-2 polypeptide may further incorporate any of the features, singly or in combination, described in the preceding paragraphs in relation to the mutant IL-2 polypeptides of the invention. In one embodiment said mutant IL-2 polypeptide shares an amino- or carboxy-terminal peptide bond with said antigen binding moiety comprised in the immunoconjugate, i.e. the immunoconjugate is a fusion protein. In certain embodiments said antigen binding moiety is an antibody or an antibody fragment. In some embodiments said antigen binding moiety comprises an antigen binding domain of an antibody comprising an antibody heavy chain variable region and an antibody light chain variable region. The antigen binding region may incorporate any of the features, singly or in combination, described hereinabove or below in relation to antigen binding domains.

Immunoconjugate Formats

Particularly suitable immunoconjugate formats are described in PCT publication no. WO 2011/020783, which is incorporated herein by reference in its entirety. These immunoconjugates comprise at least two antigen binding domains. Thus, in one embodiment, the immunoconjugate according to the present invention comprises at least a first mutant IL-2 polypeptide as described herein, and at least a first and a second antigen binding moiety. In a particular embodiment, said first and second antigen binding moiety are independently selected from the group consisting of an Fv molecule, particularly a scFv molecule, and a Fab molecule. In a specific embodiment, said first mutant IL-2 polypeptide shares an amino- or carboxy-terminal peptide bond with said first antigen binding moiety and said second antigen binding moiety shares an amino- or carboxy-terminal peptide bond with either i) the first mutant IL-2 polypeptide or ii) the first antigen binding moiety. In a particular embodiment, the immunoconjugate consists essentially of a first mutant IL-2 polypeptide and first and second antigen binding moieties, joined by one or more linker sequences. Such formats have the advantage that they bind with high affinity to the target antigen (such as a tumor antigen), but only monomeric binding to the IL-2 receptor, thus avoiding targeting the immunoconjugate to IL-2 receptor bearing immune cells at other locations than the target site. In a particular embodiment, a first mutant IL-2 polypeptide shares a carboxy-terminal peptide bond with a first antigen binding moiety and further shares an amino-terminal peptide bond with a second antigen binding moiety. In another embodiment, a first antigen binding moiety shares a carboxy-terminal peptide bond with a first mutant IL-2 polypeptide, and further shares an amino-terminal peptide bond with a second antigen binding moiety. In another embodiment, a first antigen binding moiety shares an amino-terminal peptide bond with a first mutant IL-2 polypeptide, and further shares a carboxy-terminal peptide with a second antigen binding moiety. In a particular embodiment, a mutant IL-2 polypeptide shares a carboxy-terminal peptide bond with a first heavy chain variable region and further shares an amino-terminal peptide bond with a second heavy chain variable region. In another embodiment a mutant IL-2 polypeptide shares a carboxy-terminal peptide bond with a first light chain variable region and further shares an amino-terminal peptide bond with a second light chain variable region. In another embodiment, a first heavy or light chain variable region is joined by a carboxy-terminal peptide bond to a first mutant IL-2 polypeptide and is further joined by an amino-terminal peptide bond to a second heavy or light chain variable region. In another embodiment, a first heavy or light chain variable region is joined by an amino-terminal peptide bond to a first mutant IL-2 polypeptide and is further joined by a carboxy-terminal peptide bond to a second heavy or light chain variable region. In one embodiment, a mutant IL-2 polypeptide shares a carboxy-terminal peptide bond with a first Fab heavy or light chain and further shares an amino-terminal peptide bond with a second Fab heavy or light chain. In another embodiment, a first Fab heavy or light chain shares a carboxy-terminal peptide bond with a first mutant IL-2 polypeptide and further shares an amino-terminal peptide bond with a second Fab heavy or light chain. In other embodiments, a first Fab heavy or light chain shares an amino-terminal peptide bond with a first mutant IL-2 polypeptide and further shares a carboxy-terminal peptide bond with a second Fab heavy or light chain. In one embodiment, the immunoconjugate comprises at least a first mutant IL-2 polypeptide sharing an amino-terminal peptide bond with one or more scFv molecules and further sharing a carboxy-terminal peptide bond with one or more scFv molecules.

Other particularly suitable immunoconjugate formats comprise an immunoglobulin molecule as antigen binding moiety. In one such embodiment, the immunoconjugate comprises at least one mutant IL-2 polypeptide as described herein and an immunoglobulin molecule, particularly an IgG molecule, more particularly an IgG$_1$ molecule. In one embodiment the immunoconjugate comprises not more than one mutant IL-2 polypeptide. In one embodiment the immunoglobulin molecule is human. In one embodiment the mutant IL-2 polypeptide shares an amino- or carboxy-terminal peptide bond with the immunoglobulin molecule. In one embodiment, the immunoconjugate essentially consists of a mutant IL-2 polypeptide and an immunoglobulin molecule, particularly an IgG molecule, more particularly an IgG$_1$ molecule, joined by one or more linker sequences. In a specific embodiment the mutant IL-2 polypeptide is joined at its amino-terminal amino acid to the carboxy-terminal amino acid of one of the immunoglobulin heavy chains. In certain embodiments, the immunoglobulin molecule comprises in the Fc domain a modification promoting heterodimerization of two non-identical immunoglobulin heavy chains. The site of most extensive protein-protein interaction between the two polypeptide chains of a human IgG Fc domain is in the CH3 domain of the Fc domain. Thus, in one embodiment said modification is in the CH3 domain of the Fc domain. In a specific embodiment said modification is a knob-into-hole modification, comprising a knob modification in one of the immunoglobulin heavy chains and a hole modification in the other one of the immunoglobulin heavy chains. The knob-into-hole technology is described e.g. in U.S. Pat. No. 5,731,168; U.S. Pat. No. 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two immunoglobulin heavy chains, and the hole modification comprises the amino acid substitutions T366S, L368A and Y407V in the other one of the two immunoglobulin heavy chains. In a further specific embodiment, immunoglobulin heavy chain comprising the knob modification additionally comprises the amino acid substitution S354C, and the immunoglobulin heavy chain comprising the hole modification additionally comprises the amino acid substitution Y349C. Introduction of these two cysteine residues results in formation of a disulfide bridge between the two heavy chains, further stabilizing the dimer (Carter, J Immunol Methods 248, 7-15 (2001)).

In a particular embodiment the mutant IL-2 polypeptide is joined to the carboxy-terminal amino acid of the immunoglobulin heavy chain comprising the knob modification.

In an alternative embodiment a modification promoting heterodimerization of two non-identical polypeptide chains comprises a modification mediating electrostatic steering effects, e.g. as described in PCT publication WO 2009/089004. Generally, this method involves replacement of one or more amino acid residues at the interface of the two polypeptide chains by charged amino acid residues so that homodimer formation becomes electrostatically unfavorable but heterodimerization electrostatically favorable.

An Fc domain confers to the immunoconjugate favorable pharmacokinetic properties, including a long serum half-life which contributes to good accumulation in the target tissue and a favorable tissue-blood distribution ratio. At the same time it may, however, lead to undesirable targeting of the immunoconjugate to cells expressing Fc receptors rather than to the preferred antigen-bearing cells. Moreover, the co-activation of Fc receptor signaling pathways may lead to cytokine release which, in combination with the IL-2 polypeptide and the long half-life of the immunoconjugate, results in excessive activation of cytokine receptors and severe side effects upon systemic administration. In line with this, conventional IgG-IL-2 immunoconjugates have been described to be associated with infusion reactions (see e.g. King et al., J Clin Oncol 22, 4463-4473 (2004)).

Accordingly, in certain embodiments the immunoglobulin molecule comprised in the immunoconjugate according to the invention is engineered to have reduced binding affinity to an Fc receptor. In one such embodiment the immunoglobulin comprises in its Fc domain one or more amino acid mutation that reduces the binding affinity of the immunoconjugate to an Fc receptor. Typically, the same one or more amino acid mutation is present in each of the two immunoglobulin heavy chains. In one embodiment said amino acid mutation reduces the binding affinity of the immunoconjugate to the Fc receptor by at least 2-fold, at least 5-fold, or at least 10-fold. In embodiments where there is more than one amino acid mutation that reduces the binding affinity of the immunoconjugate to the Fc receptor, the combination of these amino acid mutations may reduce the binding affinity of the Fc domain to the Fc receptor by at least 10-fold, at least 20-fold, or even at least 50-fold. In one embodiment the immunoconjugate comprising an engineered immunoglobulin molecule exhibits less than 20%, particularly less than 10%, more particularly less than 5% of the binding affinity to an Fc receptor as compared to an immunoconjugate comprising a non-engineered immunoglobulin molecule. In one embodiment the Fc receptor is an activating Fc receptor. In a specific embodiment the Fc receptor is an Fcγ receptor, more specifically an FcγRIIIa, FcγRI or FcγRIIa receptor. Preferably, binding to each of these receptors is reduced. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the immunoglobulin to said receptor, is achieved when the immunoglobulin (or the immunoconjugate comprising said immunoglobulin) exhibits greater than about 70% of the binding affinity of a non-engineered form of the immunoglobulin (or the immunoconjugate comprising said non-engineered form of the immunoglobulin) to FcRn. Immunoglobulins, or immunoconjugates comprising said immunoglobulins, may exhibit greater than about 80% and even greater than about 90% of such affinity. In one embodiment the amino acid mutation is an amino acid substitution. In one embodiment the immunoglobulin comprises an amino acid substitution at position P329 of the immunoglobulin heavy chain (Kabat numbering). In a more specific embodiment the amino acid substitution is P329A or P329G, particularly P329G. In one embodiment the immunoglobulin comprises a further amino acid substitution at a position selected from S228, E233, L234, L235, N297 and P331 of the immunoglobulin heavy chain. In a more specific embodiment the further amino acid substitution is S228P, E233P, L234A, L235A, L235E, N297A, N297D or P331S. In a particular embodiment the immunoglobulin comprises amino acid substitutions at positions P329, L234 and L235 of the immunoglobulin heavy chain. In a more particular embodiment the immunoglobulin comprises the amino acid mutations L234A, L235A and P329G (LALA P329G). This combination of amino acid substitutions almost completely abolishes Fcγ receptor binding of a human IgG molecule, and hence decreases effector function including antibody-dependent cell-mediated cytotoxicity (ADCC).

In certain embodiments, the immunoconjugate comprises one or more proteolytic cleavage sites located between mutant IL-2 polypeptide and antigen binding moieties.

Components of the immunoconjugate (e.g. antigen binding moieties and/or mutant IL-2 polypeptide) may be linked directly or through various linkers, particularly peptide linkers comprising one or more amino acids, typically about 2-20 amino acids, that are described herein or are known in the art. Suitable, non-immunogenic linker peptides include, for example, $(G4S)_n$, $(SG_4)_n$ or $G_4(SG_4)_n$ linker peptides, wherein n is generally a number between 1 and 10, typically between 2 and 4:

Antigen Binding Moieties

The antigen binding moiety of the immunoconjugate of the invention is generally a polypeptide molecule that binds to a specific antigenic determinant and is able to direct the entity to which it is attached (e.g. a mutant IL-2 polypeptide or a second antigen binding moiety) to a target site, for example to a specific type of tumor cell or tumor stroma that bears the antigenic determinant. The immunoconjugate can bind to antigenic determinants found, for example, on the surfaces of tumor cells, on the surfaces of virus-infected cells, on the surfaces of other diseased cells, free in blood serum, and/or in the extracellular matrix (ECM).

Non-limiting examples of tumor antigens include MAGE, MART-1/Melan-A, gp100, Dipeptidyl peptidase IV (DPPIV), adenosine deaminase-binding protein (ADAbp), cyclophilin b, Colorectal associated antigen (CRC)-C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100 Pme1117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2.

Non-limiting examples of viral antigens include influenza virus hemagglutinin, Epstein-Barr virus LMP-1, hepatitis C virus E2 glycoprotein, HIV gp160, and HIV gp120.

Non-limiting examples of ECM antigens include syndecan, heparanase, integrins, osteopontin, link, cadherins, laminin; laminin type EGF, lectin, fibronectin, notch, tenascin, and matrixin.

The immunoconjugates of the invention can bind to the following specific non-limiting examples of cell surface antigens: FAP, Her2, EGFR, IGF-1R, CD2 (T-cell surface antigen), CD3 (heteromultimer associated with the TCR), CD22 (B-cell receptor), CD23 (low affinity IgE receptor), CD30 (cytokine receptor), CD33 (myeloid cell surface antigen), CD40 (tumor necrosis factor receptor), IL-6R-(IL6 receptor), CD20, MCSP, and PDGFβR (β platelet-derived growth factor receptor).

In one embodiment, the immunoconjugate of the invention comprises two or more antigen binding moieties, wherein each of these antigen binding moieties specifically binds to the same antigenic determinant. In another embodiment, the immunoconjugate of the invention comprises two or more antigen binding moieties, wherein each of these antigen binding moieties specifically binds to different antigenic determinants.

The antigen binding moiety can be any type of antibody or fragment thereof that retains specific binding to an antigenic determinant. Antibody fragments include, but are not limited to, $V_H$ fragments, $V_L$ fragments, Fab fragments, $F(ab')_2$ fragments, scFv fragments, Fv fragments, minibodies, diabodies, triabodies, and tetrabodies (see e.g. Hudson and Souriau, Nature Med 9, 129-134 (2003)).

Particularly suitable antigen binding moieties are described in PCT publication no. WO 2011/020783, which is incorporated herein by reference in its entirety.

In one embodiment, the immunoconjugate comprises at least one, typically two or more antigen binding moieties that are specific for the Extra Domain B of fibronectin (EDB). In another embodiment, the immunoconjugate comprises at least one, typically two or more antigen binding moieties that can compete with monoclonal antibody L19 for binding to an epitope of EDB. See, e.g., PCT publication WO 2007/128563 A1 (incorporated herein by reference in its entirety). In yet another embodiment, the immunoconjugate comprises a polypeptide sequence wherein a first Fab heavy chain derived from the L19 monoclonal antibody shares a carboxy-terminal peptide bond with a mutant IL-2 polypeptide which in turn shares a carboxy-terminal peptide bond with a second Fab heavy chain derived from the L19 monoclonal antibody. In yet another embodiment, the immunoconjugate comprises a polypeptide sequence wherein a first Fab light chain derived from the L19 monoclonal antibody shares a carboxy-terminal peptide bond with a mutant IL-2 polypeptide which in turn shares a carboxy-terminal peptide bond with a second Fab light chain derived from the L19 monoclonal antibody. In a further embodiment, the immunoconjugate comprises a polypeptide sequence wherein a first scFv derived from the L19 monoclonal antibody shares a carboxy-terminal peptide bond with a mutant IL-2 polypeptide which in turn shares a carboxy-terminal peptide bond with a second scFv derived from the L19 monoclonal antibody.

In a more specific embodiment, the immunoconjugate comprises the polypeptide sequence of SEQ ID NO: 199 or a variant thereof that retains functionality. In another embodiment, the immunoconjugate comprises a Fab light chain derived from the L19 monoclonal antibody. In a more specific embodiment, the immunoconjugate comprises a polypeptide sequence that is at least about 80%, 85%, 90%, 95%, 96%, 97%, 98%, 99% or 100% identical to SEQ ID NO: 201 or a variant thereof that retains functionality. In yet another embodiment, the immunoconjugate comprises two polypeptide sequences that are at least about 80%, 85%, 90%, 95%, 96%, 97%, 98%, 99% or 100% identical to SEQ ID NO: 199 and SEQ ID NO: 201, or variants thereof that retain functionality. In another specific embodiment, the polypeptides are covalently linked, e.g., by a disulfide bond.

In one embodiment, the immunoconjugate of the invention comprises at least one, typically two or more antigen binding moieties that are specific for the A1 domain of Tenascin (TNC-A1). In another embodiment, the immunoconjugate comprises at least one, typically two or more antigen binding moieties that can compete with monoclonal antibody F16 for binding to an epitope of TNC-A1. See, e.g., PCT Publication WO 2007/128563 A1 (incorporated herein by reference in its entirety). In one embodiment, the immunoconjugate comprises at least one, typically two or more antigen binding moieties that are specific for the A1 and/or the A4 domain of Tenascin (TNC-A1 or TNC-A4 or TNC-A1/A4). In another embodiment, the immunoconjugate comprises a polypeptide sequence wherein a first Fab heavy chain specific for the A1 domain of Tenascin shares a carboxy-terminal peptide bond with a mutant IL-2 polypeptide, which in turn shares a carboxy-terminal peptide bond with a second Fab heavy chain specific for the A1 domain of Tenascin. In yet another embodiment, the immunoconjugate comprises a polypeptide sequence wherein a first Fab light chain specific for the A1 domain of Tenascin shares a carboxy-terminal peptide bond with a mutant IL-2 polypeptide which in turn shares a carboxy-terminal peptide bond with a second Fab light chain specific for the A1 domain of Tenascin. In a further embodiment, the immunoconjugate comprises a polypeptide sequence wherein a first scFv specific for the A1 domain of Tenascin shares a carboxy-terminal peptide bond with a mutant IL-2 polypeptide which in turn shares a carboxy-terminal peptide bond with a second scFv specific for the A1 domain of Tenascin. In another embodiment, the immunoconjugate comprises a polypeptide sequence wherein an immunoglobulin heavy chain specific for TNC-A1 shares a carboxy-terminal peptide bond with a mutant IL-2 polypeptide.

In a specific embodiment, the antigen binding moieties of the immunoconjugate comprise a heavy chain variable region sequence that is at least about 80%, 85%, 90%, 95%, 96%, 97%, 98%, 99% or 100% identical to either SEQ ID NO: 33 or SEQ ID NO: 35, or variants thereof that retain functionality. In another specific embodiment, the antigen binding moieties of the immunoconjugate comprise a light chain variable region sequence that is at least about 80%, 85%, 90%, 95%, 96%, 97%; 98%, 99% or 100% identical to either SEQ ID NO: 29 or SEQ ID NO: 31, or variants thereof that retain functionality. In a more specific embodiment, the antigen binding moieties of the immunoconjugate comprise a heavy chain variable region sequence that is at least about 80%, 85%; 90%, 95%, 96%, 97%, 98%, 99% or 100% identical to either SEQ ID NO: 33 or SEQ ID NO: 35 or variants thereof that retain functionality, and a light chain variable region sequence that is at least about 80%, 85%, 90%, 95%, 96%, 97%, 98%, 99% or 100% identical to either SEQ ID NO: 29 or SEQ ID NO: 31 or variants thereof that retain functionality.

In another specific embodiment, the heavy chain variable region sequence of the antigen binding moieties of the immunoconjugate is encoded by a polynucleotide sequence that is at least about 80%, 85%, 90%, 95%, 96%, 97%, 98%, or 99% identical to either SEQ ID NO: 34 or SEQ ID NO: 36. In yet another specific embodiment, the heavy chain variable region sequence of the antigen-binding moieties of the immunoconjugate is encoded by the polynucleotide sequence of either SEQ ID NO: 34 or SEQ ID NO: 36. In another specific embodiment, the light chain variable region sequence of the antigen binding moieties of the immunoconjugate is encoded by a polynucleotide sequence that is at least about 80%, 85%, 90%, 95%, 96%, 97%, 98%, or 99% identical to either SEQ ID NO: 30 or SEQ ID NO: 32. In yet another specific embodiment, the light chain variable region sequence of the antigen binding moieties of the immunoconjugate is encoded by the polynucleotide sequence of either SEQ ID NO: 30 or SEQ ID NO: 32.

In a specific embodiment, the immunoconjugate comprises a polypeptide sequence that is at least about 80%, 85%, 90%, 95%, 96%, 97%, 98%, 99% or 100% identical to SEQ ID NO: 203 or variants thereof that retain functionality. In another specific embodiment, the immunoconjugate of the invention comprises a polypeptide sequence that is at least about 80%, 85%, 90%, 95%, 96%, 97%, 98%, 99% or 100% identical to either SEQ ID NO: 205 or SEQ ID NO: 215, or variants thereof that retain functionality. In yet another specific embodiment, the immunoconjugate of the invention comprises a polypeptide sequence that is at least about 80%, 85%, 90%, 95%, 96%, 97%, 98%, 99% or 100% identical to either SEQ ID NO: 207 or SEQ ID NO: 237 or variants thereof that retain functionality. In a more specific embodiment, the immunoconjugate of the present invention comprises two polypeptide sequences that are at least about 80%, 85%, 90%, 95%, 96%, 97%, 98%, 99% or 100% identical to SEQ ID NO: 205 and SEQ ID NO: 207 or variants thereof that retain functionality. In another specific embodiment, the immunoconjugate of the present invention comprises two polypeptide sequences that are at least about 80%, 85%, 90%, 95%, 96%, 97%, 98%, 99% or 100% identical to SEQ ID NO: 215 and SEQ ID NO. 237 or variants thereof that retain functionality.

In a specific embodiment, the immunoconjugate comprises a polypeptide sequence encoded by a polynucleotide sequence that is at least about 80%, 85%, 90%, 95%, 96%, 97%, 98%, or 99% identical to SEQ ID NO: 204. In another specific embodiment, the immunoconjugate comprises a polypeptide sequence encoded by the polynucleotide sequence of SEQ ID NO: 204. In another specific embodiment, the immunoconjugate comprises a polypeptide sequence encoded by a polynucleotide sequence that is at least about 80%, 85%, 90%, 95%, 96%, 97%, 98%, or 99% identical to either SEQ ID NO: 206 or SEQ ID NO: 216. In yet another specific embodiment, the immunoconjugate comprises a polypeptide sequence encoded by the polynucleotide sequence of either SEQ ID NO: 206 or SEQ ID NO: 216. In another specific embodiment, the immunoconjugate comprises a polypeptide sequence encoded by a polynucleotide sequence that is at least about 80%, 85%, 90%, 95%, 96%, 97%, 98%, or 99% identical to either SEQ ID NO: 208 or SEQ ID NO: 238. In yet another embodiment, the immunoconjugate comprises a polypeptide sequence encoded by the polynucleotide sequence of either SEQ ID NO: 208 or SEQ ID NO: 238.

In one embodiment, the immunoconjugate comprises at least one, typically two or more antigen binding moieties that are specific for the A2 domain of Tenascin (TNC-A2). In another embodiment, the immunoconjugate comprises a polypeptide sequence wherein a first Fab heavy chain specific for the A2 domain of Tenascin shares a carboxy-terminal peptide bond with a IL mutant IL-2 polypeptide, which in turn shares a carboxy-terminal peptide bond with a second Fab heavy chain specific for the A2 domain of Tenascin. In yet another embodiment, the immunoconjugate comprises a polypeptide sequence wherein a first Fab light chain specific for the A2 domain of Tenascin shares a carboxy-terminal peptide bond with a mutant IL-2 polypeptide, which in turn shares a carboxy-terminal peptide bond with a second Fab light chain specific for the A2 domain of Tenascin. In another embodiment, the immunoconjugate comprises a polypeptide sequence wherein an immunoglobulin heavy chain specific for TNC-A2 shares a carboxy-terminal peptide bond with a mutant IL-2 polypeptide.

In a specific embodiment, the antigen binding moieties of the immunoconjugate comprise a heavy chain variable region sequence that is at least about 80%, 85%, 90%, 95%, 96%, 97%, 98%, 99% or 100% identical to a sequence selected from the group of SEQ ID NO: 27, SEQ ID NO: 159, SEQ ID NO: 163, SEQ ID NO: 167, SEQ ID NO: 171, SEQ ID NO:175, SEQ ID NO: 179, SEQ ID NO: 183 and SEQ ID NO: 187, or variants thereof that retain functionality. In another specific embodiment, the antigen binding moieties of the immunoconjugate comprise a light chain variable region sequence that is at least about 80%, 85%, 90%, 95%, 96%, 97%, 98%, 99% or 100% identical to a sequence selected from the group of SEQ ID NO: 23, SEQ ID NO: 25; SEQ ID NO: 157, SEQ ID NO: 161, SEQ ID NO:165, SEQ ID NO: 169, SEQ ID NO: 173, SEQ ID NO: 177, SEQ ID NO: 181 and SEQ ID NO: 185, or variants thereof that retain functionality.

In a specific embodiment, the immunoconjugate comprises a heavy chain variable region sequence that is at least about 80%, 85%, 90%, 95%, 96%, 97%, 98%, 99% or 100% identical to a sequence selected from the group of SEQ ID NO: 27, SEQ ID NO: 159, SEQ ID NO: 163, SEQ ID NO: 167, SEQ ID NO: 171, SEQ ID NO:175, SEQ ID NO: 179, SEQ ID NO: 183 and SEQ ID NO: 187, or variants thereof that retain functionality. In another specific embodiment, the antigen binding moieties of the immunoconjugate comprise a light chain variable region sequence that is at least about 80%, 85%, 90%, 95%, 96%, 97%, 98%, 99% or 100% identical to a sequence selected from the group of SEQ ID NO: 23, SEQ ID NO: 25; SEQ ID NO: 157, SEQ ID NO: 161, SEQ ID NO:165, SEQ ID NO: 169, SEQ ID NO: 173, SEQ ID NO: 177, SEQ ID NO: 181 and SEQ ID NO: 185, or variants thereof that retain functionality.

In another specific embodiment, the heavy chain variable region sequence of the antigen binding moieties of the immunoconjugate is encoded by a polynucleotide sequence that is at least about 80%, 85%, 90%, 95%, 96%, 97%, 98%, or 99% identical to a sequence selected from the group of SEQ ID NO: 28, SEQ ID NO: 160, SEQ ID NO: 164, SEQ ID NO: 168, SEQ ID NO: 172, SEQ ID NO: 176, SEQ ID NO: 180, SEQ ID NO: 184 and SEQ ID NO: 188. In yet another specific embodiment, the heavy chain variable region sequence of the antigen binding moieties of the immunoconjugate is encoded by a polynucleotide sequence selected from the group of SEQ ID NO: 28, SEQ ID NO: 160, SEQ ID NO: 164, SEQ ID NO: 168, SEQ ID NO: 172, SEQ ID NO: 176, SEQ ID NO: 180, SEQ ID NO: 184 and SEQ ID NO: 188. In another specific embodiment, the light chain variable region sequence of the antigen binding moieties of the immunoconjugate is encoded by a polynucleotide sequence that is at least about 80%, 85%, 90%, 95%, 96%, 97%, 98%, or 99% identical to a sequence selected from the group of SEQ ID NO: 24, SEQ ID NO: 26, SEQ ID NO: 158, SEQ ID NO: 162, SEQ ID NO: 166, SEQ ID NO: 170, SEQ ID NO: 174, SEQ ID NO: 178, SEQ ID NO: 182 and SEQ ID NO: 186. In yet another specific embodiment, the light chain variable region sequence of the antigen binding moieties of the immunoconjugate is encoded by a polynucleotide sequence selected from the group of SEQ ID NO: 24, SEQ ID NO: 26, SEQ ID NO: 158, SEQ ID NO: 162, SEQ ID NO: 166, SEQ ID NO: 170, SEQ ID NO: 174, SEQ ID NO: 178, SEQ ID NO: 182 and SEQ ID NO: 186.

In a specific embodiment, the immunoconjugate of the invention comprises a polypeptide sequence that is at least about 80%, 85%, 90%, 95%, 96%, 97%, 98%, 99% or 100% identical to a sequence selected from the group of SEQ ID NO: 241, SEQ ID NO: 243 and SEQ ID NO: 245, or variants thereof that retain functionality. In another specific embodiment, the immunoconjugate of the invention comprises a polypeptide sequence that is at least about 80%, 85%, 90%, 95%, 96%, 97%, 98%, 99% or 100% identical to a sequence selected from the group of SEQ ID NO: 247, SEQ ID NO: 249 and SEQ ID NO: 251, or variants thereof that retain functionality. In a more specific embodiment, the immunoconjugate of the present invention comprises a polypeptide sequence that is at least about 80%, 85%, 90%, 95%, 96%, 97%, 98%, 99% or 100% identical to a sequence selected from the group of SEQ ID NO: 241, SEQ ID NO: 243, and SEQ ID NO: 245 or variants thereof that retain functionality, and a polypeptide sequence that is at least about 80%, 85%, 90%, 95%, 96%, 97%, 98%, 99% or 100% identical to a sequence selected from the group of SEQ ID NO: 247, SEQ ID NO: 249 and SEQ ID NO: 251 or variants thereof that retain functionality. In another specific embodiment, the immunoconjugate of the present invention comprises two polypeptide sequences that are at least about 80%, 85%, 90%, 95%, 96%, 97%, 98%, 99% or 100% identical to SEQ ID NO: 241 and either SEQ ID NO: 249 or SEQ ID NO: 251, or variants thereof that retain functionality. In yet another specific embodiment, the immunoconjugate of the present invention comprises two polypeptide sequences that are at least about 80%, 85%, 90%, 95%, 96%, 97%, 98%, 99% or 100% identical to SEQ ID NO: 243 and either SEQ ID NO: 247 or SEQ ID NO: 249, or variants thereof that retain functionality. In another specific embodiment, the immunoconjugate of the present invention comprises two polypeptide sequences that are at least about 80%, 85%, 90%, 95%, 96%, 97%, 98%, 99% or 100% identical to SEQ ID NO: 245 and SEQ ID NO: 247, or variants thereof that retain functionality.

In a specific embodiment, the immunoconjugate comprises a polypeptide sequence encoded by a polynucleotide sequence that is at least about 80%, 85%, 90%, 95%, 96%, 97%, 98%, or 99% identical to a sequence selected from the group of SEQ ID NO: 242, SEQ ID NO: 244 and SEQ ID NO: 246. In another specific embodiment, the immunoconjugate comprises a polypeptide sequence encoded by a polynucleotide sequence selected from the group of SEQ ID NO: 242, SEQ ID NO: 244 and SEQ ID NO: 246. In another specific embodiment, the immunoconjugate comprises a polypeptide sequence encoded by a polynucleotide sequence that is at least about 80%, 85%, 90%, 95%, 96%, 97%, 98%, or 99% identical to a sequence selected from the group of SEQ ID NO: 248, SEQ ID NO: 250 and SEQ ID NO: 252. In yet another specific embodiment, the immunoconjugate comprises a polypeptide sequence encoded by a polynucleotide sequence selected from the group of SEQ ID NO: 248, SEQ ID NO: 250 and SEQ ID NO: 252.

In one embodiment, the immunoconjugate comprises at least one, typically two or more antigen binding moieties that are specific for the Fibroblast Activated Protein (FAP). In another embodiment, the immunoconjugate comprises a polypeptide sequence wherein a first Fab heavy chain specific for FAP shares a carboxy-terminal peptide bond with a mutant IL-2 polypeptide, which in turn shares a carboxy-terminal peptide bond with a second Fab heavy chain specific for FAP. In yet another embodiment, the immunoconjugate comprises a polypeptide sequence wherein a first Fab light chain specific for FAP shares a carboxy-terminal peptide bond with a mutant IL-2 polypeptide, which in turn shares a carboxy-terminal peptide bond with a second Fab light chain specific for FAP. In another embodiment, the immunoconjugate comprises a polypeptide sequence wherein an immunoglobulin heavy chain specific for FAP shares a carboxy-terminal peptide bond with a mutant IL-2 polypeptide.

In a specific embodiment, the antigen binding moieties of the immunoconjugate comprise a heavy chain variable region sequence that is at least about 80%, 85%, 90%, 95%, 96%, 97%, 98%, 99% or 100% identical to a sequence selected from the group consisting of SEQ ID NO: 41, SEQ ID NO: 45, SEQ ID NO: 47, SEQ ID NO: 51, SEQ ID NO: 55, SEQ ID NO: 59, SEQ ID NO: 63, SEQ ID NO: 67, SEQ ID NO: 71, SEQ ID NO: 75, SEQ ID NO: 79, SEQ ID NO: 83, SEQ ID NO: 87, SEQ ID NO: 91, SEQ ID NO: 95, SEQ ID NO: 99, SEQ ID NO: 103, SEQ ID NO: 107, SEQ ID NO: 111, SEQ ID NO: 115, SEQ ID NO: 119, SEQ ID NO: 123, SEQ ID NO: 127, SEQ ID NO: 131, SEQ ID NO: 135, SEQ ID NO: 139, SEQ ID NO: 143, SEQ ID NO: 147, SEQ ID NO: 151 and SEQ ID NO: 155, or variants thereof that retain functionality. In another specific embodiment, the antigen binding moieties of the immunoconjugate comprise a light chain variable region sequence that is at least about 80%, 85%, 90%, 95%, 96%, 97%, 98%, 99% or 100% identical to a sequence selected from the group consisting of: SEQ ID NO: 37, SEQ ID NO: 39, SEQ ID NO: 43, SEQ ID NO: 49, SEQ ID NO: 53, SEQ ID NO: 57, SEQ ID NO: 61, SEQ ID NO: 65, SEQ ID NO: 69, SEQ ID NO: 73, SEQ ID NO: 77, SEQ ID NO: 81, SEQ ID NO: 85, SEQ ID NO: 89, SEQ ID NO: 93, SEQ ID NO: 97, SEQ ID NO: 101, SEQ ID NO: 105, SEQ ID NO: 109, SEQ ID NO: 113, SEQ ID NO: 117, SEQ ID NO: 121, SEQ ID NO: 125, SEQ ID NO: 129, SEQ ID NO: 133, SEQ ID NO: 137, SEQ ID NO: 141, SEQ ID NO: 145, SEQ ID NO: 149 and SEQ ID NO: 153, or variants thereof that retain functionality. In a more specific embodiment, the antigen binding moieties of the immunoconjugate comprise a heavy chain variable region sequence that is at least about 80%, 85%, 90%, 95%, 96%, 97%, 98%, 99% or 100% identical to a sequence selected from the group consisting of SEQ ID NO: 41, SEQ ID NO: 45, SEQ ID NO: 47, SEQ ID NO: 51, SEQ ID NO: 55, SEQ ID NO: 59, SEQ ID NO: 63, SEQ ID NO: 67, SEQ ID NO: 71, SEQ ID NO: 75, SEQ ID NO: 79, SEQ ID NO: 83, SEQ ID NO: 87, SEQ ID NO: 91, SEQ ID NO: 95, SEQ ID NO: 99, SEQ ID NO: 103, SEQ ID NO: 107, SEQ ID NO: 111, SEQ ID NO: 115, SEQ ID NO: 119, SEQ ID NO: 123, SEQ ID NO: 127, SEQ ID NO: 131, SEQ ID NO: 135, SEQ ID NO: 139, SEQ ID NO: 143, SEQ ID NO: 147, SEQ ID NO: 151 and SEQ ID NO: 155, or variants thereof that retain functionality, and a light chain variable region sequence that is at least about 80%, 85%, 90%, 95%, 96%, 97%, 98%, 99% or 100% identical to a sequence selected from the group consisting of: SEQ ID NO: 37, SEQ ID NO: 39, SEQ ID NO: 43, SEQ ID NO: 49, SEQ ID NO: 53, SEQ ID NO: 57, SEQ ID NO: 61, SEQ ID NO: 65, SEQ ID NO: 69, SEQ ID NO: 73, SEQ ID NO: 77, SEQ ID NO: 81, SEQ ID NO: 85, SEQ ID NO: 89, SEQ ID NO: 93, SEQ ID NO: 97, SEQ ID NO: 101, SEQ ID NO: 105, SEQ ID NO: 109, SEQ ID NO: 113, SEQ ID NO: 117, SEQ ID NO: 121, SEQ ID NO: 125, SEQ ID NO: 129, SEQ ID NO: 133, SEQ ID NO: 137, SEQ ID NO: 141, SEQ ID NO: 145, SEQ ID NO: 149 and SEQ ID NO: 153, or variants thereof that retain functionality. In one embodiment, antigen binding moieties of the immunoconjugate comprise the heavy chain variable region sequence of SEQ ID NO: 41 and the light chain variable region sequence of SEQ ID NO: 39. In one embodiment, antigen binding moieties of the immunoconjugate comprise the heavy chain variable region sequence of SEQ ID NO: 51 and the light chain variable region sequence of SEQ ID NO: 49. In one embodiment, antigen binding moieties of the immunoconjugate comprise the heavy chain variable region sequence of SEQ ID NO: 111 and the light chain variable region sequence of SEQ ID. NO: 109. In one embodiment, antigen binding moieties of the immunoconjugate comprise the heavy chain variable region sequence of SEQ ID NO: 143 and the light chain variable region sequence of SEQ ID NO: 141. In one embodiment, antigen binding moieties of the immunoconjugate comprise the heavy chain variable region sequence of SEQ ID NO: 151 and the light chain variable region sequence of SEQ ID NO: 149.

In another specific embodiment, the heavy chain variable region sequence of the antigen binding moieties of the immunoconjugate is encoded by a polynucleotide sequence that is at least about 80%, 85%, 90%, 95%, 96%, 97%, 98%, or 99% identical to a sequence selected from the group consisting of: SEQ ID NO: 42, SEQ ID NO: 46, SEQ ID NO: 48, SEQ ID NO: 52, SEQ ID NO: 56, SEQ ID NO: 60, SEQ ID NO: 64, SEQ ID NO: 68, SEQ ID NO: 72, SEQ ID NO: 76, SEQ ID NO: 80, SEQ ID NO: 84, SEQ ID NO: 88, SEQ ID NO: 92, SEQ ID NO: 96, SEQ ID NO: 100, SEQ ID NO: 104, SEQ ID NO: 108, SEQ ID NO: 112, SEQ ID NO: 116, SEQ ID NO: 120, SEQ ID NO: 124, SEQ ID NO: 128, SEQ ID NO: 132, SEQ ID NO: 136, SEQ ID NO: 140, SEQ ID NO: 144, SEQ ID NO: 148, SEQ ID NO: 152, and SEQ ID NO: 156. In yet another specific embodiment, the heavy chain variable region sequence of the antigen binding moieties of the immunoconjugate is encoded by a polynucleotide sequence selected from the group consisting of: SEQ ID NO: 42, SEQ ID NO: 46, SEQ ID NO: 48, SEQ ID NO: 52, SEQ ID NO: 56, SEQ ID NO: 60, SEQ ID NO: 64, SEQ ID NO: 68, SEQ ID NO: 72, SEQ ID NO: 76, SEQ ID NO: 80, SEQ ID NO: 84, SEQ ID NO: 88, SEQ ID NO: 92, SEQ ID NO: 96, SEQ ID NO: 100, SEQ ID NO: 104, SEQ ID NO: 108, SEQ ID NO: 112, SEQ ID NO: 116, SEQ ID NO: 120, SEQ ID NO: 124, SEQ ID NO: 128, SEQ ID NO: 132, SEQ ID NO: 136, SEQ ID NO: 140, SEQ ID NO: 144, SEQ ID NO: 148, SEQ ID NO: 152, and SEQ ID NO: 156. In another specific embodiment, the light chain variable region sequence of the antigen binding moieties of the immunoconjugate is encoded by a polynucleotide sequence that is at least about 80%, 85%, 90%, 95%, 96%, 97%, 98%, of 99% identical to sequence selected from the group consisting of: SEQ ID NO: 38, SEQ ID NO: 40, SEQ ID NO: 44, SEQ ID NO: 50, SEQ ID NO: 54, SEQ ID NO: 58, SEQ ID NO: 62, SEQ ID NO: 66, SEQ ID NO: 70, SEQ ID NO: 74, SEQ ID NO: 78, SEQ ID NO: 82, SEQ ID NO: 86, SEQ ID NO: 90, SEQ ID NO: 94, SEQ ID NO: 98, SEQ ID NO: 102, SEQ ID NO: 106, SEQ ID NO: 110, SEQ ID NO: 114, SEQ ID NO: 118, SEQ ID NO: 122, SEQ ID NO: 126, SEQ ID NO: 130, SEQ ID NO: 134, SEQ ID NO: 138, SEQ ID NO: 142, SEQ ID NO: 146, SEQ ID NO: 150, and SEQ ID NO: 154. In yet another specific embodiment, the light chain variable region sequence of the antigen binding moieties of the immunoconjugate is encoded by a polynucleotide sequence selected from the group consisting of: SEQ ID NO: 38, SEQ ID NO: 40, SEQ ID NO: 44, SEQ ID NO: 50, SEQ ID NO: 54, SEQ ID NO: 58, SEQ ID NO: 62, SEQ ID NO: 66, SEQ ID NO: 70, SEQ ID NO: 74, SEQ ID NO: 78, SEQ ID NO: 82, SEQ ID NO: 86, SEQ ID NO: 90, SEQ ID NO: 94, SEQ ID NO: 98, SEQ ID NO: 102, SEQ ID NO: 106, SEQ ID NO: 110, SEQ ID NO: 114, SEQ ID NO: 118, SEQ ID NO: 122, SEQ ID NO: 126, SEQ ID NO: 130, SEQ ID NO: 134, SEQ ID NO: 138, SEQ ID NO: 142, SEQ ID NO: 146, SEQ ID NO: 150, and SEQ ID NO: 134.

In another specific embodiment, the immunoconjugate of the invention comprises a polypeptide sequence that is at least about 80%, 85%, 90%, 95%, 96%, 97%, 98%, 99% or 100% identical to a sequence selected from the group of SEQ ID NO: 209, SEQ ID NO: 211, SEQ ID NO: 213, SEQ ID NO: 217, SEQ ID NO: 219, SEQ ID NO: 221, SEQ ID NO: 223, SEQ ID NO: 225, SEQ ID NO: 227, and SEQ ID NO: 229, or variants thereof that retain functionality. In yet another specific embodiment, the immunoconjugate of the invention comprises a polypeptide sequence that is at least about 80%, 85%, 90%, 95%, 96%, 97%, 98%, 99% or 100% identical to a sequence selected from the group of SEQ ID NO: 231, SEQ ID NO: 233, SEQ ID NO: 235 and SEQ ID NO: 239 or variants thereof that retain functionality. In a more specific embodiment, the immunoconjugate of the present invention comprises a polypeptide sequence that is at least about 80%, 85%, 90%, 95%, 96%, 97%, 98%, 99% or 100% identical to SEQ ID NO: 211 or SEQ ID NO: 219 or variants thereof that retain functionality, and a polypeptide sequence that is at least-about 80%, 85%, 90%, 95%, 96%, 97%, 98%, 99% or 100% identical to SEQ ID NO: 233 or variants thereof that retain functionality. In another specific embodiment, the immunoconjugate of the present invention comprises a polypeptide sequence that is at least about 80%, 85%, 90%, 95%, 96%, 97%, 98%, 99% or 100% identical to a sequence selected from the group of SEQ ID NO: 209, SEQ ID NO: 221, SEQ ID NO: 223, SEQ ID NO: 225, SEQ ID NO: 227 and SEQ ID NO: 229, or variants thereof that retain functionality, and a polypeptide sequence that is at least about 80%, 85%, 90%, 95%, 96%, 97%, 98%, 99% or 100% identical to SEQ ID NO: 231 or variants thereof that retain functionality. In a further specific embodiment, the immunoconjugate of the present invention comprises two polypeptide sequences that are at least about 80%, 85%, 90%, 95%, 96%, 97%, 98%, 99% or 100% identical to SEQ ID NO: 213 and SEQ ID NO: 235 or variants thereof that retain functionality. In yet another specific embodiment, the immunoconjugate of the present invention comprises two polypeptide sequences that are at least about 80%, 85%, 90%, 95%, 96%, 97%, 98%, 99% or 100% identical to SEQ ID NO: 217 and SEQ ID NO: 239 or variants thereof that retain functionality. In yet another specific embodiment, the immunoconjugate of the present invention comprises two polypeptide sequences that are at least about 80%, 85%, 90%, 95%, 96%, 97%, 98%, 99% or 100% identical to SEQ ID NO: 219 and SEQ ID NO: 233 or variants thereof that retain functionality. In yet another specific embodiment, the immunoconjugate of the present invention comprises two polypeptide sequences that are at least about 80%, 85%, 90%, 95%, 96%, 97%, 98%, 99% or 100% identical to SEQ ID NO: 221 and SEQ ID NO: 231 or variants thereof that retain functionality. In yet another specific embodiment, the immunoconjugate of the present invention comprises two polypeptide sequences that are at least about 80%, 85%, 90%, 95%, 96%, 97%, 98%, 99% or 100% identical to SEQ ID NO: 223 and SEQ ID NO: 231 or variants thereof that retain functionality. In yet another specific embodiment, the immunoconjugate of the present invention comprises two polypeptide sequences that are at least about 80%, 85%, 90%, 95%, 96%, 97%, 98%, 99% or 100% identical to SEQ ID NO: 225 and SEQ ID NO: 231 or variants thereof that retain functionality. In yet another specific embodiment, the immunoconjugate of the present invention comprises two polypeptide sequences that are at least about 80%, 85%, 90%, 95%, 96%, 97%, 98%, 99% or 100% identical to SEQ ID NO: 227 and SEQ ID NO: 231 or variants thereof that retain functionality. In yet another specific embodiment, the immunoconjugate of the present invention comprises two polypeptide sequences that are at least about 80%, 85%, 90%, 95%, 96%, 97%, 98%, 99% or 100% identical to SEQ ID NO: 229 and SEQ ID NO: 231 or variants thereof that retain functionality. In yet another specific embodiment, the immunoconjugate of the present invention comprises two polypeptide sequences that are at least about 80%, 85%, 90%, 95%, 96%, 97%, 98%, 99% or 100% identical to SEQ ID NO: 211 and SEQ ID NO: 233 or variants thereof that retain functionality.

In another specific embodiment, the immunoconjugate of the invention comprises a polypeptide sequence that is at least about 80%, 85%, 90%, 95%, 96%, 97%, 98%, 99% or 100% identical to a sequence selected from the group of SEQ ID NO: 297, SEQ ID NO: 301 and SEQ ID NO: 315, or variants thereof that retain functionality. In yet another specific embodiment, the immunoconjugate of the invention comprises a polypeptide sequence that is at least about 80%, 85%, 90%, 95%, 96%, 97%, 98%, 99% or 100% identical to a sequence selected from the group of SEQ ID NO: 299, SEQ ID NO: 303 and SEQ ID NO: 317, or variants thereof that retain functionality. In a more specific embodiment, the immunoconjugate of the present invention comprises a polypeptide sequence that is at least about 80%, 85%, 90%, 95%, 96%, 97%, 98%, 99% or 100% identical to SEQ ID NO: 297 or a variant thereof that retains functionality, a polypeptide sequence that is at least about 80%, 85%, 90%, 95%, 96%, 97%, 98%, 99% or 100% identical to SEQ ID NO: 299 or a variant thereof that retains functionality, and a polypeptide sequence that is at least about 80%, 85%, 90%, 95%, 96%, 97%, 98%, 99% or 100% identical to SEQ ID NO: 233 or a variant thereof that retains functionality. In another specific embodiment, the immunoconjugate of the present invention comprises a polypeptide sequence that is at least about 80%, 85%, 90%, 95%, 96%, 97%, 98%, 99% or 100% identical to SEQ ID NO: 301 or a variant thereof that retains functionality, a polypeptide sequence that is at least about 80%, 85%, 90%, 95%, 96%, 97%, 98%, 99% or 100% identical to SEQ ID NO: 303 or a variant thereof that retains functionality, and a polypeptide sequence that is at least about 80%, 85%, 90%, 95%, 96%, 97%, 98%, 99% or 100% identical to SEQ ID NO: 231 or a variant thereof that retains functionality. In yet another specific embodiment, the immunoconjugate of the present invention comprises a polypeptide sequence that is at least about 80%, 85%, 90%, 95%, 96%, 97%, 98%, 99% or 100% identical to SEQ ID NO: 315 or a variant thereof that retains functionality, a polypeptide sequence that is at least about 80%, 85%, 90%, 95%, 96%, 97%, 98%, 99% or 100% identical to SEQ ID NO: 317 or a variant thereof that retains functionality, and a polypeptide sequence that is at least about 80%, 85%, 90%, 95%, 96%, 97%, 98%, 99% or 100% identical to SEQ ID NO: 233 or a variant thereof that retains functionality.

In another specific embodiment, the immunoconjugate comprises a polypeptide sequence encoded by a polynucleotide sequence that is at least about 80%, 85%, 90%, 95%, 96%, 97%, 98%, or 99% identical to a sequence selected from the group of SEQ ID NO: 210, SEQ ID NO: 212, SEQ ID NO: 214, SEQ ID NO: 218, SEQ ID NO: 220, SEQ ID NO: 222, SEQ ID NO: 224, SEQ ID NO: 226, SEQ ID NO: 228, and SEQ ID NO: 230. In yet another specific embodiment, the immunoconjugate comprises a polypeptide sequence encoded by a polynucleotide sequence selected from the group of SEQ ID NO: 210, SEQ ID NO: 212, SEQ ID NO: 214, SEQ ID NO: 218, SEQ ID NO: 220, SEQ ID NO: 222, SEQ ID NO: 224, SEQ ID NO: 226, SEQ ID NO: 228, and SEQ ID NO: 230. In another specific embodiment, the immunoconjugate comprises a polypeptide sequence encoded by a polynucleotide sequence that is at least about 80%, 85%, 90%, 95%, 96%, 97%, 98%, or 99% identical to a sequence selected from the group of SEQ ID NO: 232, SEQ ID NO: 234, SEQ ID NO: 236, and SEQ ID NO: 240. In yet another specific embodiment, the immunoconjugate comprises a polypeptide sequence encoded by a polynucleotide sequence selected from the group of SEQ ID NO: 232, SEQ ID NO: 234, SEQ ID NO: 236, and SEQ ID NO: 240.

In another specific embodiment, the immunoconjugate comprises a polypeptide sequence encoded by a polynucleotide sequence that is at least about 80%, 85%, 90%, 95%, 96%, 97%, 98%, or 99% identical to a sequence selected from the group of SEQ ID NO: 298, SEQ ID NO: 302 and SEQ ID NO: 316. In yet another specific embodiment, the immunoconjugate comprises a polypeptide sequence encoded by a polynucleotide sequence selected from the group of SEQ ID NO: 298, SEQ ID NO: 302 and SEQ ID NO: 316. In another specific embodiment, the immunoconjugate comprises a polypeptide sequence encoded by a polynucleotide sequence that is at least about 80%, 85%, 90%, 95%, 96%, 97%, 98%, or 99% identical to a sequence selected from the group of SEQ ID NO: 300, SEQ ID NO: 304 and SEQ ID NO: 318. In yet another specific embodiment, the immunoconjugate comprises a polypeptide sequence encoded by a polynucleotide sequence selected from the group of SEQ ID NO: 300, SEQ ID NO: 304 and SEQ ID NO: 318.

In one embodiment, the immunoconjugate comprises at least one, typically two or more antigen binding moieties that are specific for the Melanoma Chondroitin Sulfate Proteoglycan (MCSP). In another embodiment, the immunoconjugate comprises a polypeptide sequence wherein a first Fab heavy chain specific for MCSP shares a carboxy-terminal peptide bond with a mutant IL-2 polypeptide, which in turn shares a carboxy-terminal peptide bond with a second Fab heavy chain specific for MCSP. In yet another embodiment, the immunoconjugate comprises a polypeptide sequence wherein a first Fab light chain specific for MCSP shares a carboxy-terminal peptide bond with an IL-2 molecule, which in turn shares a carboxy-terminal peptide bond with a second Fab light chain specific for MCSP. In another embodiment, the immunoconjugate comprises a polypeptide sequence wherein an immunoglobulin heavy chain specific for MCSP shares a carboxy-terminal peptide bond with a mutant IL-2 polypeptide.

In a specific embodiment, the antigen binding moieties of the immunoconjugate comprise a heavy chain variable region sequence that is at least about 80%, 85%, 90%, 95%, 96%, 97%, 98%, 99% or 100% identical to the sequence of either SEQ ID NO: 189 or SEQ ID NO: 193 or variants thereof that retain functionality. In another specific embodiment, the antigen binding moieties of the immunoconjugate comprise a light chain variable region sequence that is at least about 80%, 85%, 90%, 95%, 96%, 97%, 98%, 99% or 100% identical to the sequence of either SEQ ID NO: 191 or SEQ ID NO: 197 or variants thereof that retain functionality. In a more specific embodiment, the antigen binding moieties of the immunoconjugate comprise a heavy chain variable region sequence that is at least about 80%, 85%, 90%, 95%, 96%, 97%, 98%, 99% or 100% identical to the sequence of either SEQ ID NO: 189 or SEQ ID NO: 193, or variants thereof that retain functionality, and a light chain variable region sequence that is at least about 80%, 85%, 90%, 95%, 96%, 97%, 98%, 99% or 100% identical to the sequence of either SEQ ID NO: 191 or SEQ ID NO: 197, or variants thereof that retain functionality. In a more specific embodiment, the antigen binding moieties of the immunoconjugate comprise a heavy chain variable region sequence that is at least about 80%, 85%, 90%, 95%, 96%, 97%, 98%, 99% or 100% identical to the sequence of SEQ ID NO: 189, and a light chain variable region sequence that is at least about 80%, 85%, 90%, 95%, 96%, 97%, 98%, 99% or 100% identical to the sequence of SEQ ID NO: 191. In another specific embodiment, the antigen binding moieties of the immunoconjugate comprise a heavy chain variable region sequence that is at least about 80%, 85%, 90%, 95%, 96%, 97%, 98%, 99% or 100% identical to the sequence of SEQ ID NO: 193, and a light chain variable region sequence that is at least about 80%, 85%, 90%, 95%, 96%, 97%, 98%, 99% or 100% identical to the sequence of SEQ ID NO: 191.

In another specific embodiment, the heavy chain variable region sequence of the antigen binding moieties of the immunoconjugate is encoded by a polynucleotide sequence that is at least about 80%, 85%, 90%, 95%, 96%, 97%, 98%, or 99% identical to the sequence of either SEQ ID NO: 190 or SEQ ID NO: 194. In yet another specific embodiment, the heavy chain variable region sequence of the antigen binding moieties of the immunoconjugate is encoded by the polynucleotide sequence of either SEQ ID NO: 190 or SEQ ID NO: 194. In another specific embodiment, the light chain variable region sequence of the antigen binding moieties of the immunoconjugate is encoded by a polynucleotide sequence that is at least about 80%, 85%, 90%, 95%, 96%, 97%, 98%, or 99% identical to the sequence of either SEQ ID NO: 192 or SEQ ID NO: 198. In yet another specific embodiment, the light chain variable region sequence of the antigen binding moieties of the immunoconjugate is encoded by the polynucleotide sequence of either SEQ ID NO: 192 or SEQ ID NO: 198.

In a specific embodiment, the immunoconjugate of the invention comprises a polypeptide sequence that is at least about 80%, 85%, 90%, 95%, 96%, 97%, 98%, 99% or 100% identical to either SEQ ID NO: 253 or SEQ ID NO: 257, or variants thereof that retain functionality. In another specific embodiment, the immunoconjugate of the invention comprises a polypeptide sequence that is at least about 80%, 85%, 90%, 95%, 96%, 97%, 98%, 99% or 100% identical to either SEQ ID NO: 255 or SEQ ID NO: 261, or variants thereof that retain functionality. In a more specific embodiment, the immunoconjugate of the present invention comprises a polypeptide sequence that is at least about 80%, 85%, 90%, 95%, 96%, 97%, 98%, 99% or 100% identical to either SEQ ID NO: 253 or SEQ ID NO: 257 or variants thereof that retain functionality, and a polypeptide sequence that is at least about 80%, 85%, 90%, 95%, 96%, 97%, 98%, 99% or 100% identical to either SEQ ID NO: 255 or SEQ ID NO: 261, or variants thereof that retain functionality. In another specific embodiment, the immunoconjugate of the present invention comprises a polypeptide sequence that is at least about 80%, 85%, 90%, 95%, 96%, 97%, 98%, 99% or 100% identical to SEQ ID NO: 253 or variants thereof that retain functionality, and a polypeptide sequence that is at least about 80%, 85%, 90%, 95%, 96%, 97%, 98%, 99% or 100% identical to SEQ ID NO: 255 or variants thereof that retain functionality. In another specific embodiment, the immunoconjugate of the present invention comprises a polypeptide sequence that is at least about 80%, 85%, 90%, 95%, 96%, 97%, 98%, 99% or 100% identical to SEQ ID NO: 257 or variants thereof that retain functionality, and a polypeptide sequence that is at least about 80%, 85%, 90%, 95%, 96%, 97%, 98%, 99% or 100% identical to SEQ ID NO: 255 or variants thereof that retain functionality.

In another specific embodiment, the immunoconjugate comprises a polypeptide sequence encoded by a polynucleotide sequence that is at least about 80%, 85%, 90%, 95%, 96%, 97%, 98%, or 99% identical to the sequence of either SEQ ID NO: 254 or SEQ ID NO: 258. In yet another specific embodiment, the immunoconjugate comprises a polypeptide sequence encoded by the polynucleotide sequence of either SEQ ID NO: 254 or SEQ ID NO: 258. In another specific embodiment, the immunoconjugate comprises a polypeptide sequence encoded by a polynucleotide sequence that is at least about 80%, 85%, 90%, 95%, 96%, 97%, 98%, or 99% identical to the sequence of either SEQ ID NO: 256 or SEQ ID NO: 262. In yet another specific embodiment, the immunoconjugate comprises a polypeptide sequence encoded by the polynucleotide sequence of either SEQ ID NO: 256 or SEQ ID NO: 262.

In one embodiment, the immunoconjugate comprises at least one, typically two or more antigen binding moieties that are specific for the Carcinoembryonic Antigen (CEA).

In another embodiment, the immunoconjugate comprises a polypeptide sequence wherein a first Fab heavy chain specific for CEA shares a carboxy-terminal peptide bond with a mutant IL-2 polypeptide, which in turn shares a carboxy-terminal peptide bond with a second Fab heavy chain specific for CEA. In yet another embodiment, the immunoconjugate comprises a polypeptide sequence wherein a first Fab heavy chain specific for CEA shares a carboxy-terminal peptide bond with a mutant IL-2 polypeptide, which in turn shares a carboxy-terminal peptide bond with a second Fab heavy chain specific for CEA. In one embodiment, the immunoconjugate comprises a polypeptide sequence wherein an immunoglobulin heavy chain specific for CEA shares a carboxy-terminal peptide bond with a mutant IL-2 polypeptide. In a specific embodiment, the antigen binding moieties of the immunoconjugate comprise a heavy chain variable region sequence that is at least about 80%, 85%, 90%, 95%, 96%, 97%, 98%, 99% or 100% identical to the sequence of SEQ ID NO: 313 or a variant thereof that retains functionality. In another specific embodiment, the antigen binding moieties of the immunoconjugate comprise a light chain variable region sequence that is at least about 80%, 85%, 90%, 95%, 96%, 97%, 98%, 99% or 100% identical to the sequence of SEQ ID NO: 311 or a variant thereof that retains functionality. In a more specific embodiment, the antigen binding moieties of the immunoconjugate comprise a heavy chain variable region sequence that is at least about 80%, 85%, 90%, 95%, 96%, 97%, 98%, 99% or 100% identical to the sequence of SEQ ID NO: 313, or a variant thereof that retains functionality, and a light chain variable region sequence that is at least about 80%, 85%, 90%, 95%, 96%, 97%, 98%, 99% or 100% identical to the sequence of SEQ ID NO: 311, or a variant thereof that retains functionality.

In another specific embodiment, the heavy chain variable region sequence of the antigen binding moieties of the immunoconjugate is encoded by a polynucleotide sequence that is at least about 80%, 85%, 90%, 95%, 96%, 97%, 98%, or 99% identical to the sequence of SEQ ID NO: 314. In yet another specific embodiment, the heavy chain variable region sequence of the antigen binding moieties of the immunoconjugate is encoded by the polynucleotide sequence of SEQ ID NO: 314. In another specific embodiment, the light chain variable region sequence of the antigen binding moieties of the immunoconjugate is encoded by a polynucleotide sequence that is at least about 80%, 85%, 90%, 95%, 96%, 97%, 98%, or 99% identical to the sequence of SEQ ID NO: 312. In yet another specific embodiment, the light chain variable region sequence of the antigen binding moieties of the immunoconjugate is encoded by the polynucleotide sequence of SEQ ID NO: 312.

In another specific embodiment, the immunoconjugate of the invention comprises a polypeptide sequence that is at least about 80%, 85%, 90%, 95%, 96%, 97%, 98%, 99% or 100% identical to the sequence of SEQ ID NO: 319, or variants thereof that retain functionality. In yet another specific embodiment, the immunoconjugate of the invention comprises a polypeptide sequence that is at least about 80%, 85%, 90%, 95%, 96%, 97%, 98%, 99% or 100% identical to the sequence of SEQ ID NO: 321, or variants thereof that retain functionality. In yet another specific embodiment, the immunoconjugate of the invention comprises a polypeptide sequence that is at least about 80%, 85%, 90%, 95%, 96%, 97%, 98%, 99% or 100% identical to the sequence of SEQ ID NO: 323, or variants thereof that retain functionality. In a more specific embodiment, the immunoconjugate of the present invention comprises a polypeptide sequence that is at least about 80%, 85%, 90%, 95%, 96%, 97%, 98%, 99% or 100% identical to SEQ ID NO: 319 or a variant thereof that retains functionality, a polypeptide sequence that is at least about 80%, 85%, 90%, 95%, 96%, 97%, 98%, 99% or 100% identical to SEQ ID NO: 321 or a variant thereof that retains functionality, and a polypeptide sequence that is at least about 80%, 85%, 90%, 95%, 96%, 97%, 98%, 99% or 100% identical to SEQ ID NO: 323 or a variant thereof that retains functionality.

In another specific embodiment, the immunoconjugate comprises a polypeptide sequence encoded by a polynucleotide sequence that is at least about 80%, 85%, 90%, 95%, 96%, 97%, 98%, or 99% identical to the sequence of SEQ ID NO: 320. In yet another specific embodiment, the immunoconjugate comprises a polypeptide sequence encoded by the polynucleotide sequence of SEQ ID NO: 320. In another specific embodiment, the immunoconjugate comprises a polypeptide sequence encoded by a polynucleotide sequence that is at least about 80%, 85%, 90%, 95%, 96%, 97%, 98%, or 99% identical to the sequence of SEQ ID NO: 322. In yet another specific embodiment, the immunoconjugate comprises a polypeptide sequence encoded by the polynucleotide sequence of SEQ ID NO: 322. In another specific embodiment, the immunoconjugate comprises a polypeptide sequence encoded by a polynucleotide sequence that is at least about 80%, 85%, 90%, 95%, 96%, 97%, 98%, or 99% identical to the sequence of SEQ ID NO: 324. In yet another specific embodiment, the immunoconjugate comprises a polypeptide sequence encoded by the polynucleotide sequence of SEQ ID NO: 324.

Antigen binding moieties of the invention include those that have sequences that are at least about 80%, 85%, 90%, 95%, 96%, 97%, 98%, 99%, or 100% identical to the peptide sequences set forth in SEQ ID NOs 23-261 (uneven numbers), 297-303 (uneven numbers), 311 and 313, including functional fragments or variants thereof. The invention also encompasses antigen binding moieties comprising sequences of SEQ ID NOs 23-261 (uneven numbers), 297-303 (uneven numbers), 311 and 313 with conservative amino acid substitutions.

Polynucleotides

The invention further provides isolated polynucleotides encoding a mutant IL-2 polypeptide or an immunoconjugate comprising a mutant IL-2 polypeptide as described herein.

Polynucleotides of the invention include those that are at least about 80%, 85%, 90%, 95%, 96%, 97%, 98%, 99%, or 100% identical to the sequences set forth in SEQ ID NOs 2, 4, 5, 6, 8, 9, 10, 12, 13, 14, 16, 17, 18, 20, 21, 22, 24-262 (even numbers), 293-296, and 298-324 (even numbers) including functional fragments or variants thereof.

The polynucleotides encoding mutant IL-2 polypeptides not linked to a non-IL-2 moiety are generally expressed as single polynucleotide that encodes the entire polypeptide.

In one embodiment, the present invention is directed to an isolated polynucleotide encoding a mutant IL-2 polypeptide, wherein the polynucleotide comprises a sequence that encodes a mutant IL-2 sequence of SEQ ID NO: 7, 11, 15 or 19. The invention also encompasses an isolated polynucleotide encoding a mutant IL-2 polypeptide, wherein the polynucleotide comprises a sequence that encodes a mutant IL-2 polypeptide of SEQ ID NO: 7, 11, 15 or 19 with conservative amino acid substitutions.

In another embodiment, the invention is directed to an isolated polynucleotide encoding a mutant IL-2 polypeptide, wherein the polynucleotide comprises a sequence that is at least about 80%, 85%, 90%, 95%, 96%, 97%, 98%, or 99% identical to a nucleotide sequence selected from the group of SEQ ID NO: 8, SEQ ID NO: 9, SEQ ID NO: 10, SEQ ID NO: 12, SEQ ID NO: 13, SEQ ID NO: 14, SEQ ID NO: 16, SEQ ID NO: 17, SEQ ID NO: 18, SEQ ID NO: 20, SEQ ID NO: 21, SEQ ID NO: 22, SEQ ID NO: 293, SEQ ID NO: 294, SEQ ID NO: 295 and SEQ ID NO: 296. In another embodiment, the invention is directed to an isolated polynucleotide encoding a mutant IL-2 polypeptide, wherein the polynucleotide comprises a nucleotide sequence selected from the group of SEQ ID NO: 8, SEQ ID NO: 9, SEQ ID NO: 10, SEQ ID NO: 12, SEQ ID NO: 13, SEQ ID NO: 14, SEQ ID NO: 16, SEQ ID NO: 17, SEQ ID NO: 18, SEQ ID NO: 20, SEQ ID NO: 21, SEQ ID NO: 22, SEQ ID NO: 293, SEQ ID NO: 294, SEQ ID NO: 295 and SEQ ID NO: 296. In another embodiment, the invention is directed to an isolated polynucleotide encoding an immunoconjugate or fragment thereof, wherein the polynucleotide comprises a nucleic acid sequence that is at least about 80%, 85%, 90%, 95%, 96%, 97%, 98%, or 99% identical to a nucleotide sequence selected from the group of SEQ ID NO: 8, SEQ ID NO: 9, SEQ ID NO: 10, SEQ ID NO: 12, SEQ ID NO: 13, SEQ ID NO: 14, SEQ ID NO: 16, SEQ ID NO: 17, SEQ ID NO: 18, SEQ ID NO: 20, SEQ ID NO: 21, SEQ ID NO: 22, SEQ ID NO: 293, SEQ ID NO: 294, SEQ ID NO: 295 and SEQ ID NO: 296. In another embodiment, the invention is directed to an isolated polynucleotide encoding an immunoconjugate or fragment thereof, wherein the polynucleotide comprises a nucleic acid sequence selected from the group of SEQ ID NO: 8, SEQ ID NO: 9, SEQ ID NO: 10, SEQ ID NO: 12, SEQ ID NO: 13, SEQ ID NO: 14, SEQ ID NO: 16, SEQ ID NO: 17, SEQ ID NO: 18, SEQ ID NO: 20, SEQ ID NO: 21, SEQ ID NO: 22, SEQ ID NO: 293, SEQ ID NO: 294, SEQ ID NO: 295 and SEQ ID NO: 296.

The polynucleotides encoding immunoconjugates of the invention may be expressed as a single polynucleotide that encodes the entire immunoconjugate or as multiple (e.g., two or more) polynucleotides that are co-expressed. Polypeptides encoded by polynucleotides that are co-expressed may associate through, e.g., disulfide bonds or other means to form a functional immunoconjugate. For example, the heavy chain portion of an antigen binding moiety may be encoded by a separate polynucleotide from the portion of the immunoconjugate comprising the light chain portion of the antigen binding moiety and the mutant IL-2 polypeptide. When co-expressed, the heavy chain polypeptides will associate with the light chain polypeptides to form the antigen binding moiety. Alternatively, in another example, the light chain portion of the antigen binding moiety could be encoded by a separate polynucleotide from the portion of the immunoconjugate comprising the heavy chain portion of the antigen binding moiety and the mutant IL-2 polypeptide. In one embodiment, an isolated polynucleotide of the invention encodes a fragment of an immunoconjugate comprising a mutant IL-2 polypeptide and an antigen binding moiety. In one embodiment, an isolated polynucleotide of the invention encodes the heavy chain of an antigen binding moiety and a mutant IL-2 polypeptide. In another embodiment, an isolated polynucleotide of the invention encodes the light chain of an antigen binding moiety and a mutant IL-2 polypeptide.

In a specific embodiment, an isolated polynucleotide of the invention encodes a fragment of an immunoconjugate comprising at least one mutant IL-2 polypeptide, and at least one, preferably two or more antigen binding moieties, wherein a first mutant IL-2 polypeptide shares an amino- or carboxy-terminal peptide bond with a first antigen binding moiety and a second antigen binding moiety shares an amino- or carboxy-terminal peptide bond with either the first mutant IL-2 polypeptide or the first antigen binding moiety. In a one embodiment, the antigen binding moieties are independently selected from the group consisting of a Fv molecule, particularly a scFv molecule, and a Fab molecule.

In another specific embodiment, the polynucleotide encodes the heavy chains of two of the antigen binding moieties and one mutant IL-2 polypeptide. In another specific embodiment, the polynucleotide encodes the light chains of two of the antigen binding moieties and one mutant IL-2 polypeptide. In another specific embodiment, the polynucleotide encodes one light chain of one of the antigen binding moieties, one heavy chain of a second antigen binding moiety and one mutant IL-2 polypeptide.

In another specific embodiment, an isolated polynucleotide of the invention encodes a fragment of an immunoconjugate, wherein the polynucleotide encodes the heavy chains of two Fab molecules and a mutant IL-2 polypeptide. In another specific embodiment, an isolated polynucleotide of the invention encodes a fragment of an immunoconjugate, wherein the polynucleotide encodes the light chains of two Fab molecules and a mutant IL-2 polypeptide. In another specific embodiment an isolated polynucleotide of the invention encodes a fragment of an immunoconjugate, wherein the polynucleotide encodes the heavy chain of one Fab molecule, the light chain of second Fab molecule and a mutant IL-2 polypeptide.

In one embodiment, an isolated polynucleotide of the invention encodes an immunoconjugate comprising at least one mutant IL-2 polypeptide, joined at its amino- and carboxy-terminal amino acids to one or more scFv molecules.

In one embodiment, an isolated polynucleotide of the invention encodes a fragment of an immunoconjugate, wherein the polynucleotide encodes the heavy chain of an immunoglobulin molecule, particularly an IgG molecule, more particularly an IgG$_1$ molecule, and a mutant IL-2 polypeptide. In a more specific embodiment, the isolated polynucleotide encodes a the heavy chain of an immunoglobulin molecule and a mutant IL-2 polypeptide, wherein the mutant IL-2 polypeptide shares a amino-terminal peptide bond with the immunoglobulin heavy chain.

In another embodiment, the present invention is directed to an isolated polynucleotide encoding an immunoconjugate or fragment thereof, wherein the polynucleotide comprises a sequence that encodes a variable region sequence as shown in SEQ ID NO: 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 231, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 311 or 313. In another embodiment, the present invention is directed to an isolated polynucleotide encoding an immunoconjugate or fragment thereof, wherein the polynucleotide comprises a sequence that encodes a polypeptide sequence as shown in SEQ ID NO: 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 297, 299, 301, 303, 315, 317, 319, 321 or 323. In another embodiment, the invention is further directed to an isolated polynucleotide encoding an immunoconjugate or fragment thereof, wherein the polynucleotide comprises a sequence that is at least about 80%, 85%, 90%, 95%, 96%, 97%, 98%, or 99% identical to a nucleotide sequence shown in SEQ ID NO: 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 298, 300, 302, 304, 312, 314, 316, 318, 320, 322 or 324. In another embodiment, the invention is directed to an isolated polynucleotide encoding an immunoconjugate or fragment thereof, wherein the polynucleotide comprises a nucleic acid sequence shown in SEQ ID NO: 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 298, 300, 302, 304, 312, 314, 316, 318, 320, 322 or 324. In another embodiment, the invention is directed to an isolated polynucleotide encoding an immunoconjugate or fragment thereof, wherein the polynucleotide comprises a sequence that encodes a variable region sequence that is at least about 80%, 85%, 90%, 95%, 96%, 97%, 98%, or 99% identical to an amino acid sequence of SEQ ID NO: 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 231, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 311 or 313. In another embodiment, the invention is directed to an isolated polynucleotide encoding an immunoconjugate or fragment thereof, wherein the polynucleotide comprises a sequence that encodes a polypeptide sequence that is at least 80%, 85%, 90%, 95%, 96%, 97%, 98%, or 99% identical to an amino acid sequence of SEQ ID NO: 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 297, 299, 301, 303, 315, 317, 319, 321 or 323. The invention encompasses an isolated polynucleotide encoding an immunoconjugate or fragment thereof, wherein the polynucleotide comprises a sequence that encodes the variable region sequences of SEQ ID NO: 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 231, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 311 or 313 with conservative amino acid substitutions. The invention also encompasses an isolated polynucleotide encoding an immunoconjugate of the invention or fragment thereof, wherein the polynucleotide comprises a sequence that encodes the polypeptide sequences of SEQ ID NO: 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 297, 299, 301, 303, 315, 317; 319, 321 or 323 with conservative amino acid substitutions.

In certain embodiments the polynucleotide or nucleic acid is DNA. In other embodiments, a polynucleotide of, the present invention is RNA, for example, in the form of messenger RNA (mRNA). RNA of the present invention may be single stranded or double stranded.

Recombinant Methods

Mutant-IL-2 polypeptides of the invention can be prepared by deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing. In this regard, the nucleotide sequence of native IL-2 has been described by Taniguchi et al. (Nature 302, 305-10 (1983)) and nucleic acid encoding human IL-2 is available from public depositories such as the American Type Culture Collection (Rockville Md.). The sequence of native human IL-2 is shown in SEQ ID NO: 1. Substitution or insertion may involve natural as well as non-natural amino acid residues. Amino acid modification includes well known methods of chemical modification such as the addition of glycosylation sites or carbohydrate attachments, and the like.

Mutant IL-2 polypeptides and immunoconjugates of the invention may be obtained, for example, by solid-state peptide synthesis or recombinant production. For recombinant production one or more polynucleotide encoding said mutant IL-2 polypeptide or immunoconjugate (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of a mutant IL-2 polypeptide or immunoconjugate (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989). The expression vector can be part of a plasmid, virus, or may be a nucleic acid fragment. The expression vector includes an expression cassette into which the polynucleotide encoding the IL-2 mutant or the immunoconjugate (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or-more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polyproteins, which are post- or co-translationally separated into the final proteins via proteolytic cleavage. In addition, a vector, polynucleotide, or nucleic acid of the invention may encode heterologous coding regions, either fused or unfused to a first or second polynucleotide encoding the polypeptides of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the mutant IL-2 polypeptide is desired, DNA encoding a signal sequence may be placed upstream of the nucleic acid encoding the mature amino acids of the mutant IL-2. The same applies to immunoconjugates of the invention or fragments thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. For example, human IL-2 is translated with a 20 amino acid signal sequence at the N-terminus of the polypeptide, which is subsequently cleaved off to produce the mature, 133 amino acid human IL-2. In certain embodiments, the native signal peptide, e.g. the IL-2 signal peptide or an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase. Exemplary amino acid and polynucleotide sequences of secretory signal peptides are shown in SEQ ID NOs 236-273.

DNA encoding a short protein sequence that could be used to facilitate later purification (e.g. a histidine tag) or assist in labeling the IL-2 mutant or immunoconjugate may be included within or at the ends of the IL-2 mutant or immunoconjugate (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes an amino acid sequence comprising the mutant IL-2 polypeptide of the invention. As used herein, the term "host cell" refers to any kind of cellular system which can be engineered to generate the mutant IL-2 polypeptides or immunoconjugates of the invention or fragments thereof. Host cells suitable for replicating and for supporting expression of mutant IL-2 polypeptides or immunoconjugates are well known in the art. Such cells may be transfected or transduced as appropriate with the particular expression vector and large quantities of vector containing cells can be grown for seeding large scale fermenters to obtain sufficient quantities of the IL-2 mutant or immunoconjugate for clinical applications. Suitable host cells include prokaryotic microorganisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized," resulting in the production of a polypeptide with a partially or fully human glycosylation pattern. See Gemgross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr$^-$ CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or lymphoid cell (e.g., Y0, NS0, Sp20 cell).

Standard technologies are known in the art to express foreign genes in these systems. Cells expressing a mutant-IL-2 polypeptide fused to either the heavy or the light chain of an antigen binding domain such as an antibody, may be engineered so as to also express the other of the antibody chains such that the expressed mutant IL-2 fusion product is an antibody that has both a heavy and a light chain.

In one embodiment, a method of producing a mutant IL-2 polypeptide or an immunoconjugate according to the invention is provided, wherein the method comprises culturing a host cell comprising a polynucleotide encoding the mutant IL-2 polypeptide or immunoconjugate, as provided herein, under conditions suitable for expression of the mutant IL-2 polypeptide or immunoconjugate, and optionally recovering the mutant IL-2 polypeptide or immunoconjugate from the host cell (or host cell culture medium).

In certain embodiments according to the invention the mutant IL-2 polypeptide is linked to at least one non-IL-2 moiety. An IL-2 mutant can be prepared where the mutant IL-2 polypeptide segment is linked to one or more molecules such as a polypeptide, protein, carbohydrate, lipid, nucleic acid, polynucleotide or molecules that are combinations of these molecules (e.g. glycoproteins, glycolipids etc.). The mutant IL-2 polypeptide also may be linked to an organic moiety, inorganic moiety or pharmaceutical drug. As used herein, a pharmaceutical drug is an organic containing compound of about 5,000 daltons or less. The mutant IL-2 polypeptide also may be linked to any biological agent including therapeutic compounds such as anti-neoplastic agents, anti-microbial agents, hormones, immunomodulators, anti-inflammatory agents and the like. Also included are radioisotopes such as those useful for imaging as well as for therapy.

The mutant IL-2 polypeptide may also be linked to multiple molecules of the same type or to more than one type of molecule. In certain embodiments, the molecule that is linked to IL-2 can confer the ability to target the IL-2 to specific tissues or cells in an animal, and is referred to herein as a "targeting moiety". In these embodiments, the targeting moiety may have affinity for a ligand or receptor in the target tissue or cell, thereby directing the IL-2 to the target tissue or cell. In a particular embodiment the targeting moiety directs the IL-2 to a tumor. Targeting moieties include, for example, antigen binding moieties (e.g. antibodies and fragments thereof) specific for cell surface or intracellular proteins, ligands of biological receptors, and the like. Such antigen binding moieties may be specific for tumor associated antigens such as the ones described herein.

A mutant IL-2 polypeptide may be genetically fused to another polypeptide, e.g. a single chain antibody, or (part of) an antibody heavy or light chains, or may be chemically conjugated to another molecule. Fusion of a mutant IL-2 polypeptide to part of an antibody heavy chain is described in the Examples. An IL-2 mutant which is a fusion between a mutant IL-2 polypeptide and another polypeptide can be designed such that the IL-2 sequence is fused directly to the polypeptide or indirectly through a linker sequence. The composition and length of the linker may be determined in accordance with methods well known in the art and may be tested for efficacy. An example of a linker sequence between IL-2 and an antibody heavy chain is found in the sequences shown e.g. in SEQ ID NOs 209, 211, 213 etc. Additional sequences may also be included to incorporate a cleavage site to separate the individual components of the fusion if desired, for example an endopeptidase recognition sequence. In addition, an IL-2 mutant or fusion protein thereof may also be synthesized chemically using methods of polypeptide synthesis as is well known in the art (e.g. Merrifield solid phase synthesis). Mutant IL-2 polypeptides may be chemically conjugated to other molecules, e.g. another polypeptide, using well known chemical conjugation methods. Bi-functional cross-linking reagents such as homofunctional and heterofunctional cross-linking reagents well known in the art can be used for this purpose. The type of cross-linking reagent to use depends on the nature of the molecule to be coupled to IL-2 and can readily be identified by those skilled in the art. Alternatively, or in addition, mutant IL-2 and/or the molecule to which it is intended to be conjugated may be chemically derivatized such that the two can be conjugated in a separate reaction as is also well known in the art.

In certain embodiment the mutant IL-2 polypeptide is linked to one or more antigen binding moieties (i.e. is part of an immunoconjugate) comprising at least an antibody variable region capable of binding an antigenic determinant. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty). Immunoconjugates, antigen binding moieties and methods for producing the same are also described in detail in PCT publication no. WO 2011/020783, the entire content of which is incorporated herein by reference.

Any animal species of antibody, antibody fragment, antigen binding domain or variable region can be linked to a mutant IL-2 polypeptide. Non-limiting antibodies, antibody fragments, antigen binding-domains or variable regions useful in the present invention can be of murine, primate, of human origin. If the mutant IL-2/antibody conjugate or fusion is intended for human use, a chimeric form of the antibody may be used wherein the constant regions of the antibody are from a human. A humanized or fully human form of the antibody can also be prepared in accordance with methods well known in the art (see e g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments. A detailed description of the preparation of antigen binding moieties for immunoconjugates by phage display can be found in the Examples appended to PCT publication no. WO 2011/020783.

In certain embodiments, the antigen binding moieties useful in the present invention are engineered to have enhanced binding affinity according to, for example, the methods disclosed in PCT publication no. WO 2011/020783 (see Examples relating to affinity maturation) or U.S. Pat. Appl. Publ. No. 2004/0132066, the entire contents of which are hereby incorporated by reference. The ability of the immunoconjugate of the invention to bind to a specific antigenic determinant can be measured either through an enzyme-linked immunosorbent assay (ELISA) or other techniques familiar to one of skill in the art, e.g. surface plasmon resonance technique (analyzed on a BIACORE T100 system) (Liljeblad, et al., Glyco J 17, 323-329 (2000)), and traditional binding assays (Heeley, Endocr Res 28, 217-229 (2002)). Competition assays may be used to identify an antibody, antibody fragment, antigen binding domain or variable domain that competes with a reference antibody for binding to a particular antigen, e.g. an antibody that competes with the L19 antibody for binding to the Extra Domain B of fibronectin (EDB). In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols," in Methods in Molecular Biology vol. 66 (Humana Press, Totowa, N.J.). In an exemplary competition assay, immobilized antigen (e.g. EDB) is incubated in a solution comprising a first labeled antibody that binds to the antigen (e.g. L19 antibody) and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch. 14 (Cold Spring Harbor Laboratory, Cold Spring Harbor, N.Y.).

Further chemical modification of the mutant IL-2 mutant or immunoconjugate of the invention may be desirable. For example, problems of immunogenicity and short half-life may be improved by conjugation to substantially straight chain polymers such as polyethylene glycol (PEG) or polypropylene glycol (PPG) (see e.g. WO 87/00056).

IL-2 mutants and immunoconjugates prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the mutant IL-2 polypeptide or immunoconjugate binds. For example, an antibody which specifically binds the mutant IL-2 polypeptide may be used. For affinity chromatography purification of immunoconjugates of the invention, a matrix with protein A or protein G may be used. For example, sequential Protein A or G affinity chromatography and size exclusion chromatography can be used to isolate an immunoconjugate essentially as described in the Examples. The purity of the mutant IL-2 polypeptides and fusion proteins thereof can be determined by any of a variety of well known analytical methods including gel electrophoresis, high pressure liquid chromatography, and the like. For example, the heavy chain fusion proteins expressed as described in the Examples were shown to be intact and properly assembled as demonstrated by reducing SDS-PAGE (see e.g. FIG. 14). Two bands were resolved at approximately Mr 25,000 and Mr 60,000, corresponding to the predicted molecular weights of the immunoglobulin light chain and heavy chain/IL-2 fusion protein.

Assays

Mutant IL-2 polypeptides and immunoconjugates provided herein may be identified, screened for, or characterized for their physical/chemical properties and/or biological activities by various assays known in the art.

Affinity Assays

The affinity of the mutant or wild-type IL-2 polypeptide for various forms of the Il-2 receptor can be determined in accordance with the method set forth in the Examples by surface plasmon resonance (SPR), using standard instrumentation such as a BIAcore instrument (GE Healthcare), and receptor subunits such as may be obtained by recombinant expression (see e.g. Shanafelt et al., Nature Biotechnol 18, 1197-1202 (2000)). A recombinant IL-2 receptor β/γ-subunit heterodimer can be generated by fusing each of the subunits to an antibody Fc domain monomer modified by the knobs-into-holes technology (see e.g. U.S. Pat. No. 5,731,168) to promote heterodimerization of the appropriate receptor subunit/Fc fusion proteins (see SEQ ID NOs 102 and 103). Alternatively, binding affinity of IL-2 mutants for different forms of the IL-2 receptor may be evaluated using cell lines known to express one or the other such form of the receptor. A specific illustrative and exemplary embodiment for measuring binding affinity is described in the following and in the Examples below. According to one embodiment, $K_D$ is measured by surface plasmon resonance using a BIACORE® T100 machine (GE Healthcare) at 25° C. with IL-2 receptors immobilized on CM5 chips. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Recombinant IL-2 receptor is diluted with 10 mM sodium acetate, pH 5.5, to 0.5-30 µg/ml before injection at a flow rate of 10 µl/minute to achieve approximately 200-1000 (for IL-2R α-subunit) or 500-3000 (for IL-2R βγ knobs-into-holes heterodimer) response units (RU) of coupled protein. Following the injection of IL-2 receptor, 1 M ethanolamine is injected to block unreacted groups. For kinetics measurements, three-fold serial dilutions of mutant IL-2 polypeptide or immunoconjugate (range between ~0.3 nM to 300 nM) are injected in HBS-EP+ (GE Healthcare, 10 mM HEPES, 150 mM NaCl, 3 mM EDTA, 0.05% Surfactant P20, pH 7.4) at 25° C. at a flow rate of approximately 30 µl/min. Association rates ($k_{on}$) and dissociation rates ($k_{off}$) are calculated using a simple one-to-one Langmuir binding model (BIACORE T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

Binding of immunoconjugates of the invention to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. Alternatively, binding affinity of Fc domains or immunoconjugates comprising an Fc domain for Fc receptors may be evaluated using cell lines known to express particular Fc receptors, such as NK cells expressing FcγIIIa receptor. According to one embodiment, $K_D$ is measured by surface plasmon resonance using a BIACORE® T100 machine (GE Healthcare) at 25° C. with Fc receptors immobilized on CM5 chips. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Recombinant Fc receptor is diluted with 10 mM sodium acetate, pH 5.5, to 0.5-30 µg/ml before injection at a flow rate of 10 µl/minute to achieve approximately 100-5000 response units (RU) of coupled protein. Following the injection of the Fc receptor, 1 M ethanolamine is injected to block unreacted groups. For kinetics measurements, three- to five-fold serial dilutions of immunoconjugate (range between ~0.01 nM to 300 nM) are injected in HBS-EP+ (GE Healthcare, 10 mM HEPES, 150 mM NaCl, 3 mM EDTA, 0.05% Surfactant P20, pH 7.4) at 25° C. at a flow rate of approximately 30-50 µl/min. Association rates ($k_{on}$) and dissociation rates ($k_{off}$) are calculated using a simple one-to-one Langmuir binding model (BIACORE T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

Activity Assays:

The ability of an IL-2 mutant to bind to IL-2 receptors may be indirectly measured by assaying the effects of immune activation that occur downstream of receptor binding.

In one aspect, assays are provided for identifying mutant IL-2 polypeptides having biological activity. Biological activities may include, e.g., the ability to induce proliferation of IL-2 receptor-bearing T and/or NK cells, the ability to induce IL-2 signaling in IL-2 receptor-bearing T and/or NK cells, the ability to generate interferon (IFN)-γ as a secondary cytokine by NK cells, a reduced ability to induce elaboration of secondary cytokines, particularly IL-10 and TNF-α, by peripheral blood mononuclear cells (PBMCs), a reduced ability to induce apoptosis in T cells, the ability to induce tumor regression and/or improve survival, and a reduced toxicity profile, particularly reduced vasopermeability, in vivo. Mutant IL-2 polypeptides having such biological activity in vivo and/or in vitro are also provided.

In certain embodiments, a mutant IL-2 polypeptide of the invention is tested for such biological activity. A variety of methods are well known the art for determining biological activities of IL-2, and also details for many of these methods are disclosed in the Examples appended herewith. The Examples provide a suitable assay for testing IL-2 mutants of the invention for their ability to generate IFN-γ by NK cells. Cultured NK cells are incubated with the mutant IL-2 polypeptide or immunoconjugates of the invention, and IFN-γ concentration in the culture medium is subsequently measured by ELISA.

IL-2 induced signaling induces several signaling pathways, and involves JAK (Janus kinase) and STAT (signal transducer and activator of transcription) signaling molecules. The interaction of IL-2 with the receptor β- and γ-subunits leads to phosphorylation of the receptor and of JAK1 and JAK3, which are associated with the β- and γ-subunit, respectively. STAT5 then associates with the phosphorylated receptor and is phosphorylated itself on a crucial tyrosin residue. This results in the dissociation of STAT5 from the receptor, dimerization of STAT5 and translocation of the STAT5 dimers to the nucleus where they promote the transcription of target genes. The ability of mutant IL-2 polypeptides to induce signaling through the IL-2 receptor can thus be assessed, for example, by measuring phosphorylation of STAT5. Details of this method are disclosed in the Examples. PBMCs are treated with mutant IL-2 polypeptides or immunoconjugates of the invention and levels of phosphorylated STAT5 are determined by flow cytometry.

Proliferation of T cells or NK cells in response to IL-2 may be measured by incubating T cells or NK cells isolated from blood with mutant IL-2 polypeptides or immunoconjugates of the invention, followed by determination of the ATP content in lysates of the treated cells. Before treatment, T cells may be pre-stimulated with phytohemagglutinin (PHA-M). This assay, described in the Examples, allows sensitive quantitation of the number of viable cells, however there are numerous suitable alternative assays known in the art (e.g. [$^3$H]-thymidine incorporation assay, Cell Titer Glo ATP assays, Alamar Blue assay, WST-1 assay, MTT assay).

An assay for determination of apoptosis of T cells and AICD is also provided in the Examples, wherein T cells are treated with an apoptosis-inducing antibody after the incubation with the mutant IL-2 polypeptides or immunoconjugates of the invention and apoptotic cells are quantified by flow cytometric detection of phosphatidyl serine/annexin exposure. Other assays are known in the art.

The effects of mutant IL-2 on tumor growth and survival can be assessed in a variety of animal tumor models known in the art. For example, xenografts of human cancer cell lines can be implanted to immunodeficient mice, and treated with mutant IL-2 polypeptides or immunoconjugates of the invention, as described in the Examples.

Toxicity of mutant IL-2 polypeptides and immunoconjugates of the invention in vivo can be determined based on mortality, in-life observations (visible symptoms of adverse effects, e.g. behaviour, body weight, body temperature) and clinical and anatomical pathology (e.g. measurements of blood chemistry values and/or histopathological analyses).

Vasopermeability induced by treatment with IL-2 can be examined in a pretreatment vasopermeability animal model. In general, the IL-2 mutant or immunoconjugate of the invention is administered to a suitable animal, e.g. a mouse, and at a later time the animal is injected with a vascular leak reporter molecule whose dissemination from the vasculature reflects the extent of vascular permeability. The vascular leak reporter molecule is preferably large enough to reveal permeability with the wild-type form of IL-2 used for pretreatment. An example of a vascular leak reporter molecule can be a serum protein such as albumin or an immunoglobulin. The vascular leak reporter molecule preferably is detectably labeled such as with a radioisotope to facilitate quantitative determination of the molecule's tissue distribution. Vascular permeability may be measured for vessels present in any of a variety of internal body organs such as liver, lung, and the like, as well as a tumor, including a tumor that is xenografted. Lung is a preferred organ for measuring vasopermeability of full-length IL-2 mutants.

Compositions, Formulations, and Routes of Administration

In a further aspect, the invention provides pharmaceutical compositions comprising any of the mutant IL-2 polypeptides or immunoconjugates provided herein, e.g., for use in any of the below therapeutic methods. In one embodiment, a pharmaceutical composition comprises any of the mutant IL-2 polypeptides or immunoconjugates provided herein and a pharmaceutically acceptable carrier. In another embodiment, a pharmaceutical composition comprises any of the mutant IL-2 polypeptides or immunoconjugates provided herein and at least one additional therapeutic agent, e.g., as described below.

Further provided is a method of producing a mutant IL-2 polypeptide or an immunoconjugate of the invention in a form suitable for administration in vivo, the method comprising (a) obtaining a mutant IL-2 polypeptide or immunoconjugate according to the invention, and (b) formulating the mutant IL-2 polypeptide or immunoconjugate with at least one pharmaceutically acceptable carrier, whereby a preparation of mutant IL-2 polypeptide or immunoconjugate is formulated for administration in vivo.

Pharmaceutical compositions of the present invention comprise a therapeutically effective amount of one or more mutant IL-2 polypeptide or immunoconjugate dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one mutant IL-2 polypeptide or immunoconjugate and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. Exemplary IL-2 compositions are described in U.S. Pat. Nos. 4,604,377 and 4,766,106. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition may comprise different types of carriers depending on whether it is to be administered in solid, liquid or aerosol form, and whether it need to be sterile for such routes of administration as injection. Mutant IL-2 polypeptides or immunoconjugates of the present invention (and any additional therapeutic agent) can be administered intravenously, intradermally, intraarterially, intraperitoneally, intralesionally, intracranially, intraarticularly, intraprostatically, intrasplenically, intrarenally, intrapleurally, intratracheally, intranasally, intravitreally, intravaginally, intrarectally, intratumorally, intramuscularly, intraperitoneally, subcutaneously, subconjunctivally, intravesicularlly, mucosally, intrapericardially, intraumbilically, intraocularally, orally, topically, locally, by inhalation (e.g. aerosol inhalation), injection, infusion, continuous infusion, localized perfusion bathing target cells directly, via a catheter, via a lavage, in cremes, in lipid compositions (e.g. liposomes), or by other method or any combination of the forgoing as would be known to one of ordinary skill in the art (see, for example, Remington's Pharmaceutical Sciences, 18th Ed. Mack Printing Company, 1990, incorporated herein by reference). Parenteral administration, in particular intravenous injection, is most commonly used for administering polypeptide molecules such as the mutant IL-2 polypeptides and immunoconjugates of the invention.

Parenteral compositions include those designed for administration by injection, e.g. subcutaneous, intradermal, intralesional, intravenous, intraarterial intramuscular, intrathecal or intraperitoneal injection. For injection, the mutant IL-2 polypeptides and immunoconjugates of the invention may be formulated in aqueous solutions, preferably in physiologically compatible buffers such as Hanks'- solution, Ringer's solution, or physiological saline buffer. The solution may contain formulatory agents such as suspending, stabilizing and/or dispersing agents. Alternatively, the mutant IL-2 polypeptides and immunoconjugates may be in powder form for constitution with a suitable vehicle, e.g., sterile pyrogen-free water, before use. Sterile injectable solutions are prepared by incorporating the IL-2 polypeptides or immunoconjugates of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

In addition to the compositions described previously, the immunoconjugates may also be formulated as a depot preparation. Such long acting formulations may be administered by implantation (for example subcutaneously or intramuscularly) or by intramuscular injection.

Thus, for example, the mutant IL-2 polypeptides and immunoconjugates may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the mutant IL-2 polypeptides and immunoconjugates of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The mutant IL-2 polypeptides and immunoconjugates may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

Therapeutic Methods and Compositions

Any of the mutant IL-2 polypeptides and immunoconjugates provided herein may be used in therapeutic methods. Mutant IL-2 polypeptides and immunoconjugates of the invention can be used as immunotherapeutic agents, for example in the treatment of cancers.

For use in therapeutic methods, mutant IL-2 polypeptides and immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

Mutant IL-2 polypeptides and immunoconjugates of the invention are useful in treating disease states where stimulation of the immune system of the host is beneficial, in particular conditions where an enhanced cellular immune response is desirable. These may include disease states where the host immune response is insufficient or deficient. Disease states for which the mutant IL-2 polypeptides or immunoconjugates of the invention can be administered comprise, for example, a tumor or infection where a cellular immune response would be a critical mechanism for specific immunity. Specific disease states for which IL-2 mutants of the present invention can be employed include cancer, for example renal cell carcinoma or melanoma; immune deficiency, specifically in HIV-positive patients, immunosuppressed patients, chronic infection and the like. The mutant IL-2 polypeptides or immunoconjugates of the invention may be administered per se or in any suitable pharmaceutical composition.

In one aspect, mutant IL-2 polypeptides and immunoconjugates of the invention for use as a medicament are provided. In further aspects, mutant IL-2 polypeptides and immunoconjugates of the invention for use in treating a disease are provided. In certain embodiments, mutant IL-2 polypeptides and immunoconjugates of the invention for use in a method of treatment are provided. In one embodiment, the invention provides a mutant IL-2 polypeptide or an immunoconjugate as described herein for use in the treatment of a disease in an individual in need thereof. In certain embodiments, the invention provides a mutant IL-2 polypeptide or an immunoconjugate for use in a method of treating an individual having a disease comprising administering to the individual a therapeutically effective amount of the mutant IL-2 polypeptide or the immunoconjugate. In certain embodiments the disease to be treated is a proliferative disorder. In a preferred embodiment the disease is cancer. In certain embodiments the method further comprises administering to the individual a therapeutically effective amount of at least one additional therapeutic agent, e.g., an anti-cancer agent if the disease to be treated is cancer. In further embodiments, the invention provides a mutant IL-2 polypeptide or an immunoconjugate for use in stimulating the immune system. In certain embodiments, the invention provides a mutant IL-2 polypeptide or an immunoconjugate for use in a method of stimulating the immune system in an individual comprising administering to the individual an effective amount of the mutant IL-2 polypeptide or immunoconjugate to stimulate the immune system. An "individual" according to any of the above embodiments is a mammal, preferably a human. "Stimulation of the immune system" according to any of the above embodiments may include any one or more of a general increase in immune function, an increase in T cell function, an increase in B cell function, a restoration of lymphocyte function, an increase in the expression of IL-2 receptors, an increase in T cell responsiveness, an increase in natural killer cell activity or lymphokine-activated killer (LAK) cell activity, and the like.

In a further aspect, the invention provides for the use of a mutant, IL-2 polypeptide or an immunoconjugate of the invention in the manufacture or preparation of a medicament for the treatment of a disease in an individual in need thereof. In one embodiment, the medicament is for use in a method of treating a disease comprising administering to an individual having the disease a therapeutically effective amount of the medicament. In certain embodiments the disease to be treated is a proliferative disorder. In a preferred embodiment the disease is cancer. In one such embodiment, the method further comprises administering to the individual a therapeutically effective amount of at least one additional therapeutic agent, e.g., an anti-cancer agent if the disease to be treated is cancer. In a further embodiment, the medicament is for stimulating the immune system. In a further embodiment, the medicament is for use in a method of stimulating the immune system in an individual comprising administering to the individual an amount effective of the medicament to stimulate the immune system. An "individual" according to any of the above embodiments may be a mammal, preferably a human. "Stimulation of the immune system" according to any of the above embodiments may include any one or more of a general increase in immune function, an increase in T cell function, an increase in B cell function, a restoration of lymphocyte function, an increase in the expression of IL-2 receptors, an increase in T cell responsiveness, an increase in natural killer cell activity or lymphokine-activated killer (LAK) cell activity, and the like.

In a further aspect, the invention provides a method for treating a disease in an individual, comprising administering to said individual a therapeutically effective amount of a mutant IL-2 polypeptide or an immunoconjugate of the invention. In one embodiment a composition is administered to said individual, comprising the mutant IL-2 polypeptide or the immunoconjugate of the invention in a pharmaceutically acceptable form. In certain embodiments the disease to be treated is a proliferative disorder. In a preferred embodiment the disease is cancer. In certain embodiments the method further comprises administering to the individual a therapeutically effective amount of at-least one additional therapeutic agent, e.g., an anti-cancer agent if the disease to be treated is cancer. In a further aspect, the invention provides a method for stimulating the immune system in an individual, comprising administering to the individual an effective amount of a mutant IL-2 polypeptide or an immunoconjugate to stimulate the immune system. An "individual" according to any of the above embodiments may be a mammal, preferably a human. "Stimulation of the immune system" according to any of the above embodiments may include any one or more of a general increase in immune function, an increase in T cell function, an increase in B cell function, a restoration of lymphocyte function, an increase in the expression of IL-2 receptors, an increase in T cell responsiveness, an increase in natural killer cell activity or lymphokine-activated killer (LAK) cell activity, and the like.

It is understood that any of the above therapeutic methods may be carried out using an immunoconjugate of the invention in place of or in addition to a mutant IL-2 polypeptide.

In certain embodiments the disease to be treated is a proliferative disorder, preferably cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using a mutant IL-2 polypeptide or an immunoconjugate of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. Similarly, other cell proliferation disorders can also be treated by the mutant IL-2 polypeptides and immunoconjugates of the present invention. Examples of such cell proliferation disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other cell proliferation disease, besides neoplasia, located in an organ system listed above. In another embodiment, the disease is related to autoimmunity, transplantation rejection, post-traumatic immune responses and infectious diseases (e.g. HIV). More specifically, the mutant IL-2 polypeptides and immunoconjugates may be used in eliminating cells involved in immune cell-mediated disorders, including lymphoma; autoimmunity, transplantation rejection, graft-versus-host disease, ischemia and stroke. A skilled artisan readily recognizes that in many cases the mutant IL-2 polypeptides or immunoconjugates may not provide a cure but may only provide partial benefit. In some embodiments, a physiological change having some benefit is also considered therapeutically beneficial. Thus, in some embodiments, an amount of mutant IL-2 polypeptide or immunoconjugate that provides a physiological change is considered an "effective amount" or a "therapeutically effective amount". The subject, patient, or individual in need of treatment is typically a mammal, more specifically a human.

The immunoconjugates of the invention are also useful as diagnostic reagents. The binding of an immunoconjugate to an antigenic determinant can be readily detected by using a secondary antibody specific for the IL-2 polypeptide. In one embodiment, the secondary antibody and the immunoconjugate facilitate the detection of binding of the immunoconjugate to an antigenic determinant located on a cell or tissue surface.

In some embodiments, an effective amount of the mutant IL-2 polypeptides or immunoconjugates of the invention is administered to a cell. In other embodiments, a therapeutically effective amount of the mutant IL-2 polypeptides or immunoconjugates of the invention is administered to an individual for the treatment of disease.

For the prevention or treatment of disease, the appropriate dosage of a mutant IL-2 polypeptide or immunoconjugate of the invention (when used alone or in combination with one or more other additional therapeutic agents) will depend on the type of disease to be treated, the route of administration, the body weight of the patient, the type of polypeptide (e.g. unconjugated IL-2 or immunoconjugate), the severity and course of the disease, whether the antibody is administered for preventive or therapeutic purposes, previous or concurrent therapeutic interventions, the patient's clinical history and response to the mutant IL-2 polypeptide or immunoconjugate, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

A single administration of unconjugated IL-2 can range from about 50,000 IU/kg to about 1,000,000 IU/kg or more, more typically about 600,000 IU/kg of IL-2. This may be repeated several times a day (e.g. 2-3×), for several days (e.g. about 3-5 consecutive days) and then may be repeated one or more times following a period of rest (e.g., about 7-14 days). Thus, a therapeutically effective amount may comprise only a single administration or many administrations over a period of time (e.g. about 20-30 individual administrations of about 600,000 IU/kg of IL-2 each given over about a 10-20 day period). When administered in the form of an immunconjugate, a therapeutically effective of the mutant IL-2 polypeptide may be lower than for unconjugated mutant IL-2 polypeptide.

Similarly, the immunoconjugate is suitably administered to the patient at one time or over a series of treatments. Depending on the type and severity of the disease, about 1 μg/kg to 15 mg/kg (e.g. 0.1 mg/kg-10 mg/kg) of immunoconjugate can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the immunoconjugate would be in the range from about 0.005 mg/kg to about 10 mg/kg. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the immunoconjugate). An initial higher loading dose, followed by one or more lower doses may be administered. However, other dosage regimens may be useful. The progress of this therapy is easily monitored by conventional techniques and assays.

The mutant IL-2 polypeptides and immunoconjugates of the invention will generally be used in an amount effective to achieve the intended purpose. For use to treat or prevent a disease condition, the mutant IL-2 polypeptides and immunoconjugates of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the mutant IL-2 polypeptides or immunoconjugates which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the immunoconjugates may not be related to plasma concentration. One having skill in the art will be able to optimize therapeutically effective local dosages without undue experimentation.

A therapeutically effective dose of the mutant IL-2 polypeptides or immunoconjugates described herein will generally provide therapeutic benefit without causing substantial toxicity. Toxicity and therapeutic efficacy of an IL-2 mutant or immunoconjugate can be determined by standard pharmaceutical procedures in cell culture or experimental animals (see, e.g. Examples 8 and 9). Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. IL-2 mutants and immunoconjugates that exhibit large therapeutic indices are preferred. In one embodiment, the mutant IL-2 polypeptide or the immunoconjugate according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition. (See, e.g., Fingl et al., 1975, In: The Pharmacological Basis of Therapeutics, Ch. 1, p. 1, incorporated herein by reference in its entirety).

The attending physician for patients treated with IL-2 mutants or immunoconjugates of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

The maximum therapeutic dose of a mutant IL-2 polypeptide or immunoconjugate comprising said polypeptide may be increased from those used for wild-type IL-2 or an immunoconjugate comprising wild-type IL-2, respectively.

Other Agents and Treatments

The mutant IL-2 polypeptides and the immunoconjugates according to the invention may be administered in combination with one or more other agents in therapy. For instance, a mutant IL-2 polypeptide or immunoconjugate of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a particular embodiment, the additional therapeutic agent is an anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent.

Such other agents are suitably present in combination in amounts that are effective for the purpose intended. The effective amount of such other agents depends on the amount of mutant IL-2 polypeptide or immunoconjugate used, the type of disorder or treatment, and other factors discussed above. The mutant IL-2 polypeptides and immunoconjugates are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the mutant IL-2 polypeptide or immunoconjugate of the invention can occur prior to, simultaneously, and/or following, administration of the additional therapeutic agent and/or adjuvant. Mutant IL-2 polypeptides and immunoconjugates of the invention can also be used in combination with radiation therapy.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a mutant IL-2 polypeptide of the invention. The label or package insert indicates that the composition is used for treating the condition of choice. Moreover, the article of manufacture may comprise (a) a first container with a composition contained therein, wherein the composition comprises a mutant IL-2 polypeptide of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to a mutant IL-2 polypeptide.

SHORT DESCRIPTION OF THE FIGURES

FIG. 1. Schematic representation of the Fab-IL-2-Fab (A) and IgG-IL-2 (B) immunoconjugate formats, comprising mutant IL-2 polypeptide.

Figure 2:
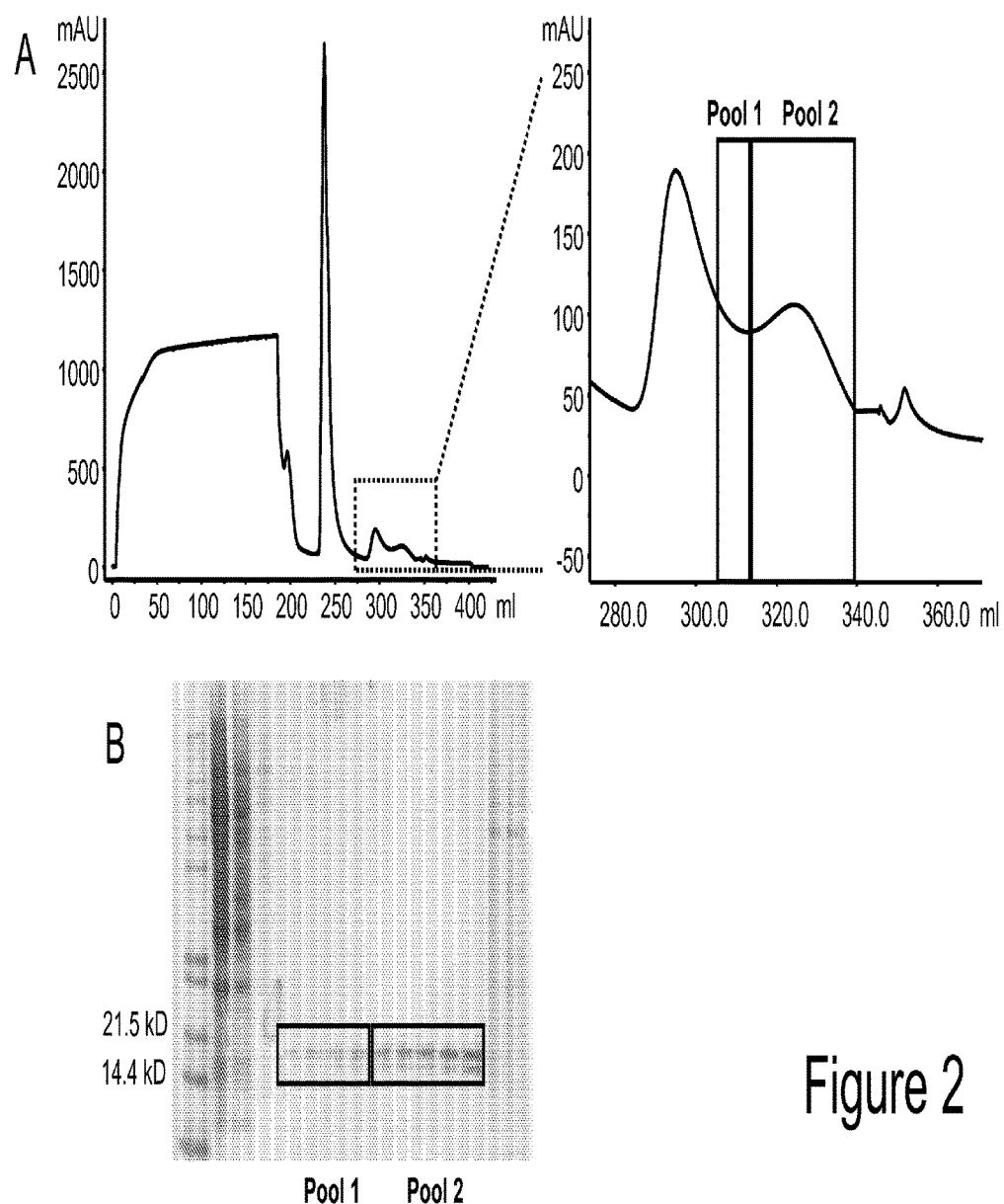

FIG. 2. Purification of the naked IL-2 wild-type construct. (A) Chromatogram of the His tag purification for the wild-type naked IL-2; (B) SDS PAGE of purified protein (8-12% Bis-Tris (NuPage, Invitrogen), MES running buffer).

Figure 3:
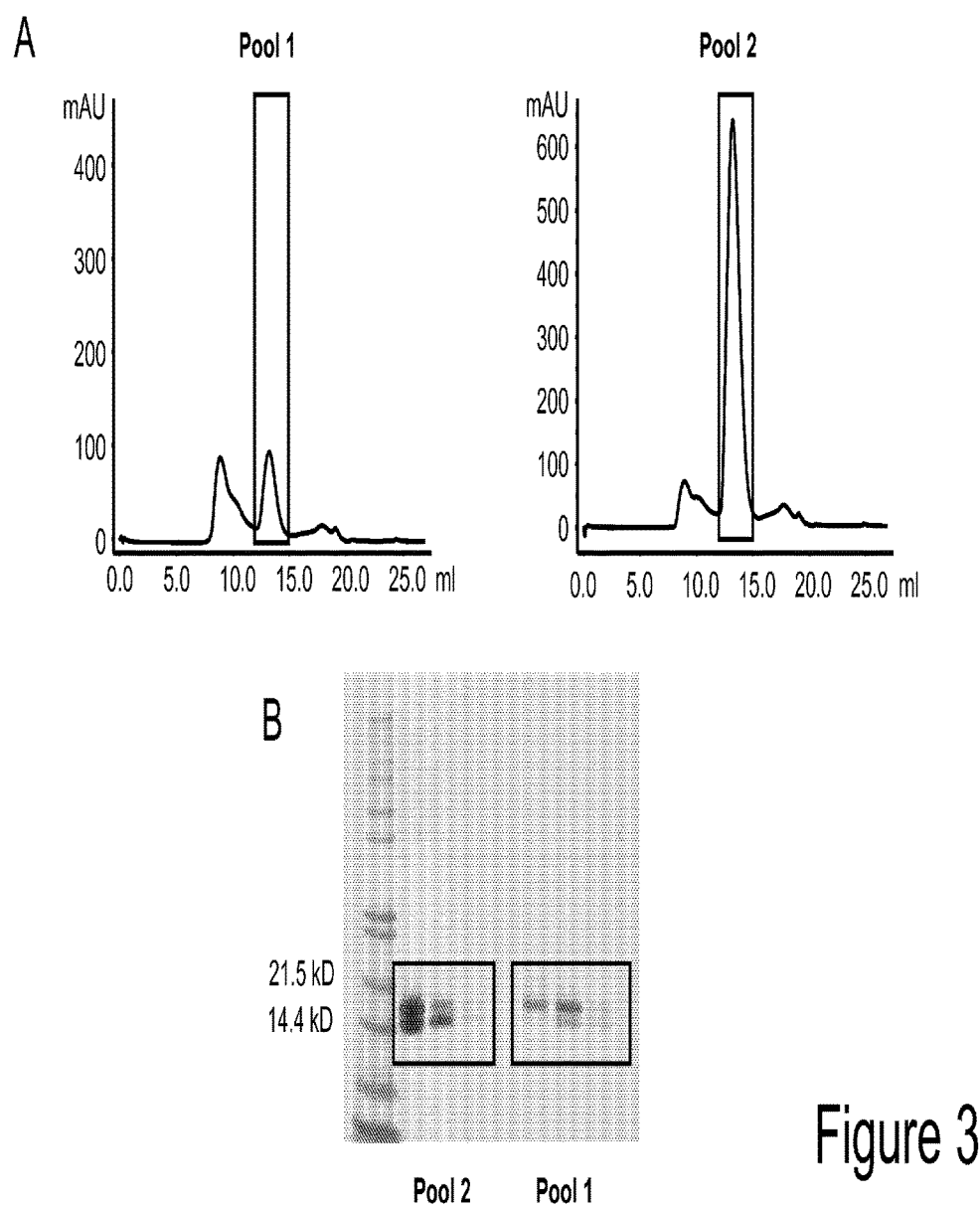

FIG. 3. Purification of the naked IL-2 wild-type construct. (A) Chromatogram of the size exclusion chromatography for the wild-type IL-2; (B) SDS PAGE of purified protein (8-12% Bis-Tris (NuPage, Invitrogen), MES running buffer).

FIG. 4. Analytical size exclusion chromatography for the wild-type IL-2 as determined on a Superdex 75, 10/300 GL. Pool 1 comprises 74% of the 23 kDa species and 26% of the 20 kDa species, Pool 2 comprises 40% of the 22 kDa species and 60% of the 20 kDa species.

Figure 5:
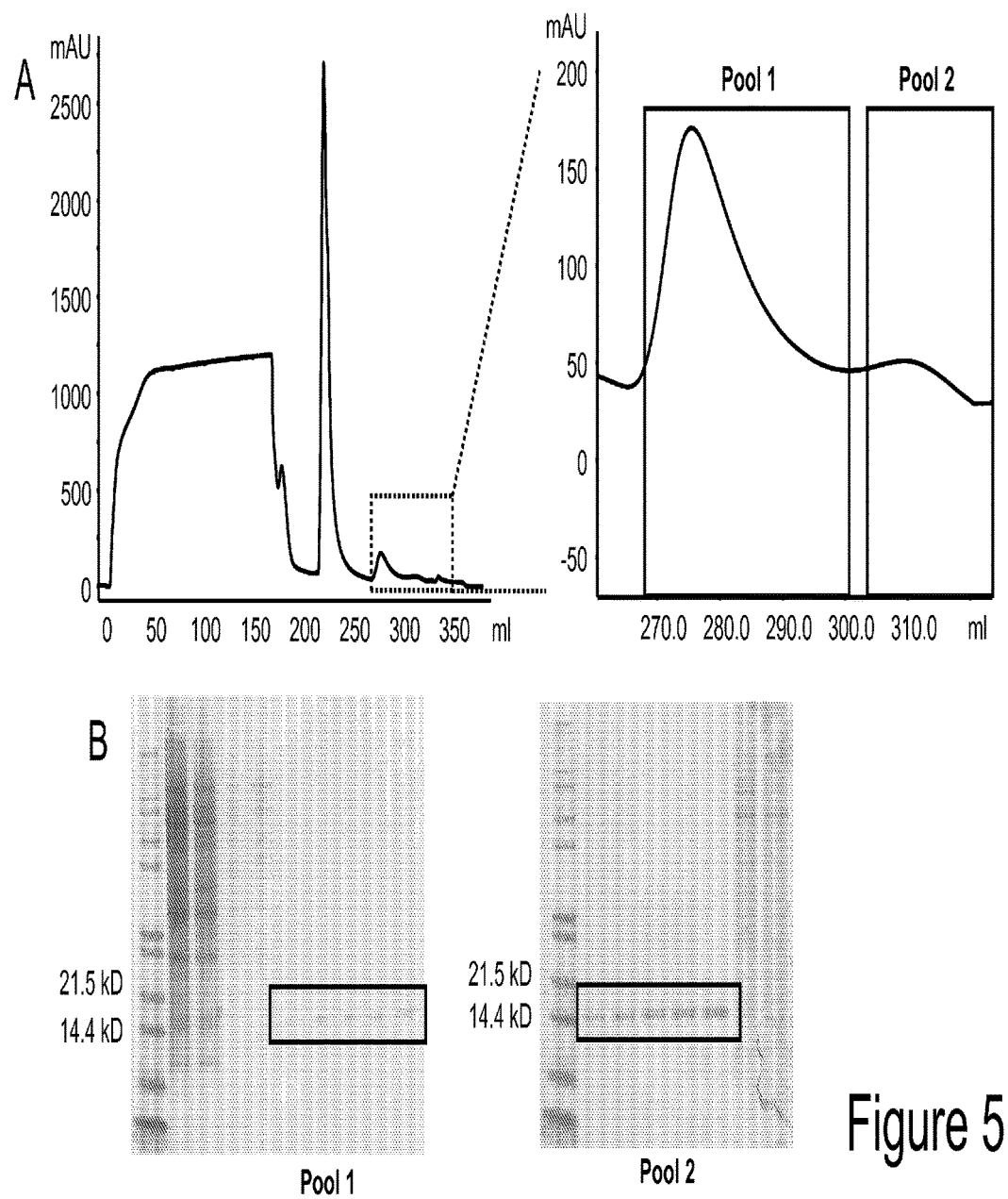

FIG. 5. Purification of the naked IL-2 quadruple mutant construct. (A) Chromatogram of the His tag purification for the IL-2 quadruple mutant; (B) SDS PAGE of purified protein (8-12% Bis-Tris (NuPage, Invitrogen), MES running buffer).

Figure 6:
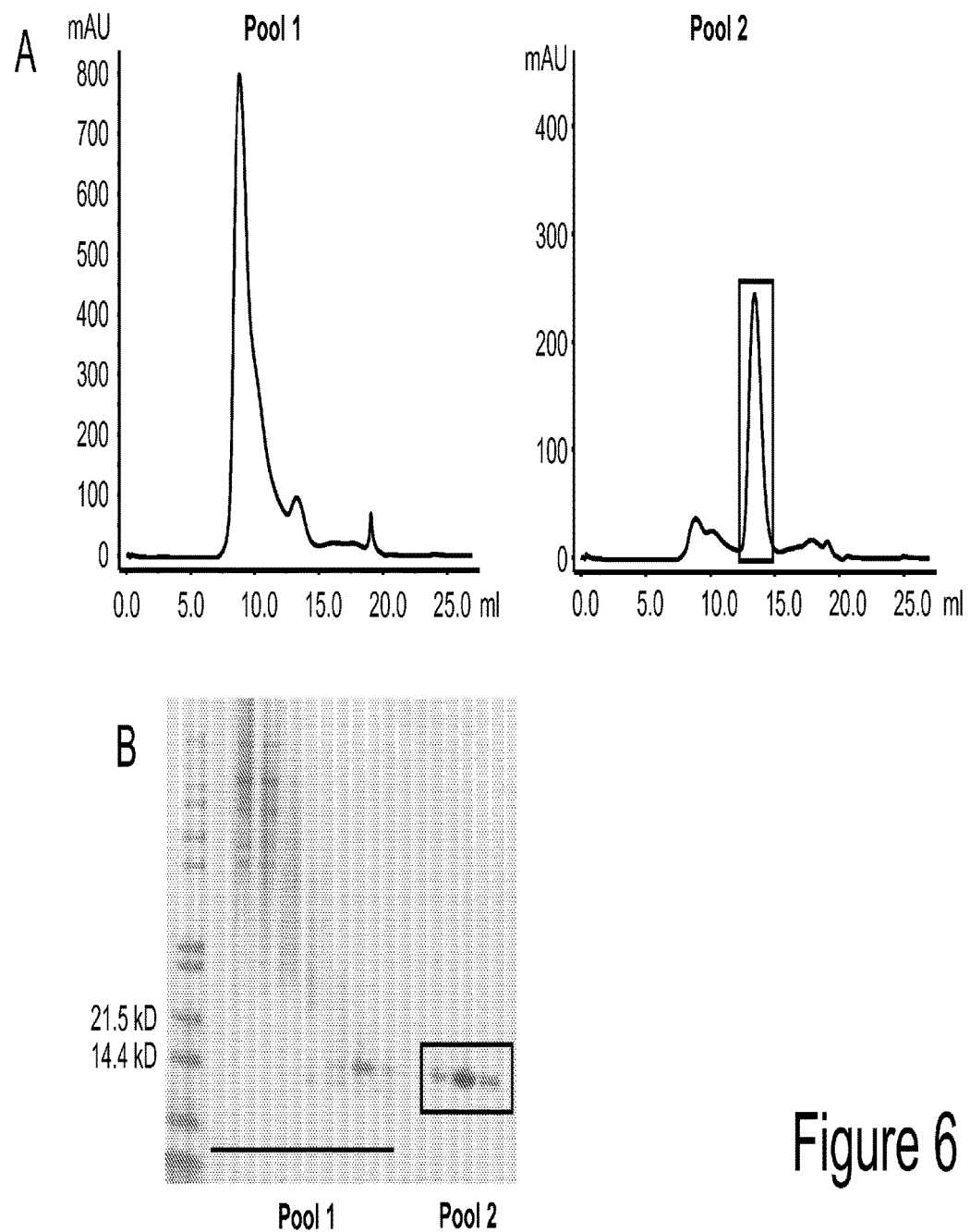

FIG. 6. Purification of the naked IL-2 quadruple mutant construct. (A) Chromatogram of the size exclusion chromatography for the IL-2 quadruple mutant; (B) SDS PAGE of purified protein (8-12% Bis-Tris (NuPage, Invitrogen), MES running buffer).

Figure 7:
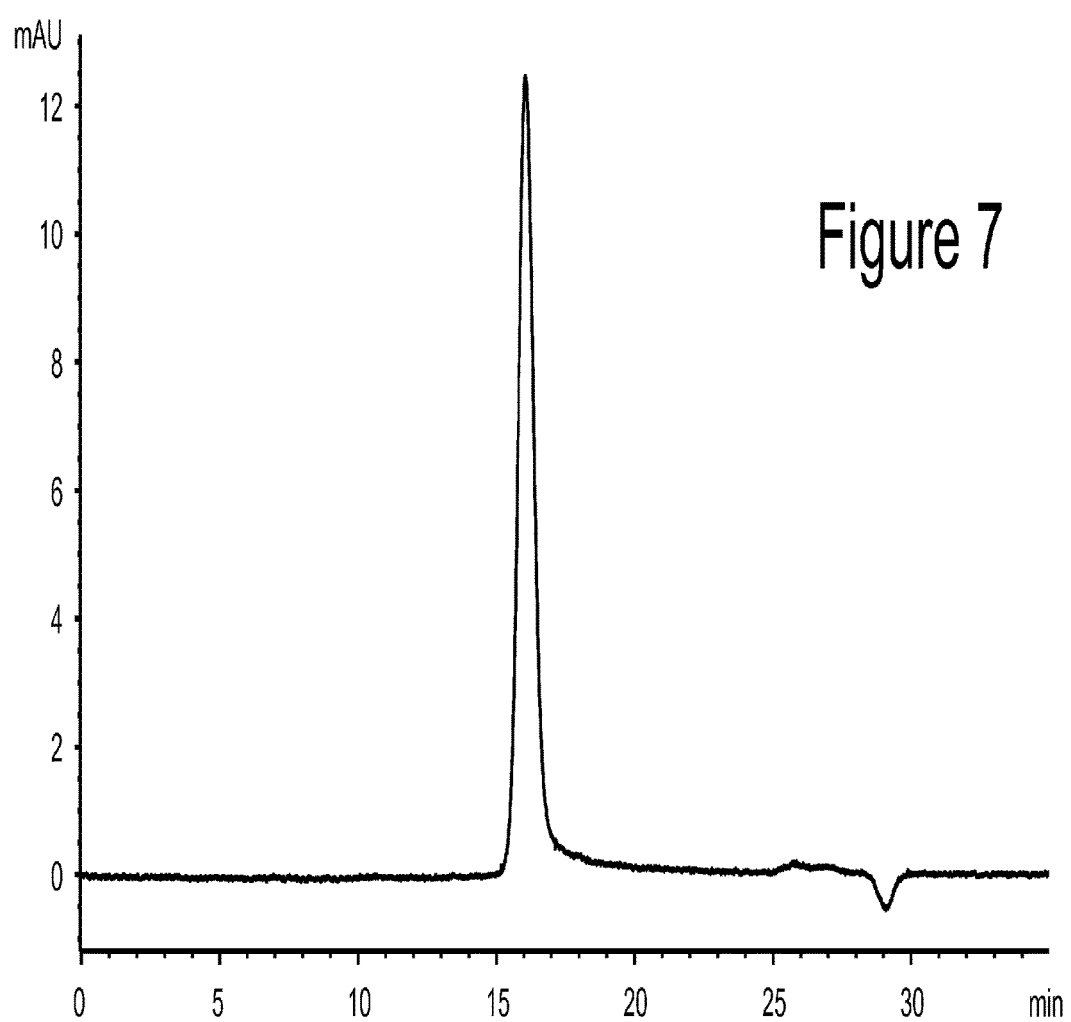

FIG. 7. Analytical size exclusion chromatography for the IL-2 quadruple mutant as determined on a Superdex 75, 10/300 GL (Pool 2, 20 kDa).

FIG. 8. Simultaneous binding to IL-2R and human FAP by FAP-targeted 29B11-based Fab-IL-2-Fab comprising wild-type or quadruple mutant IL-2. (A) Setup of the SPR assay; (B) SPR sensorgram.

Figure 9:
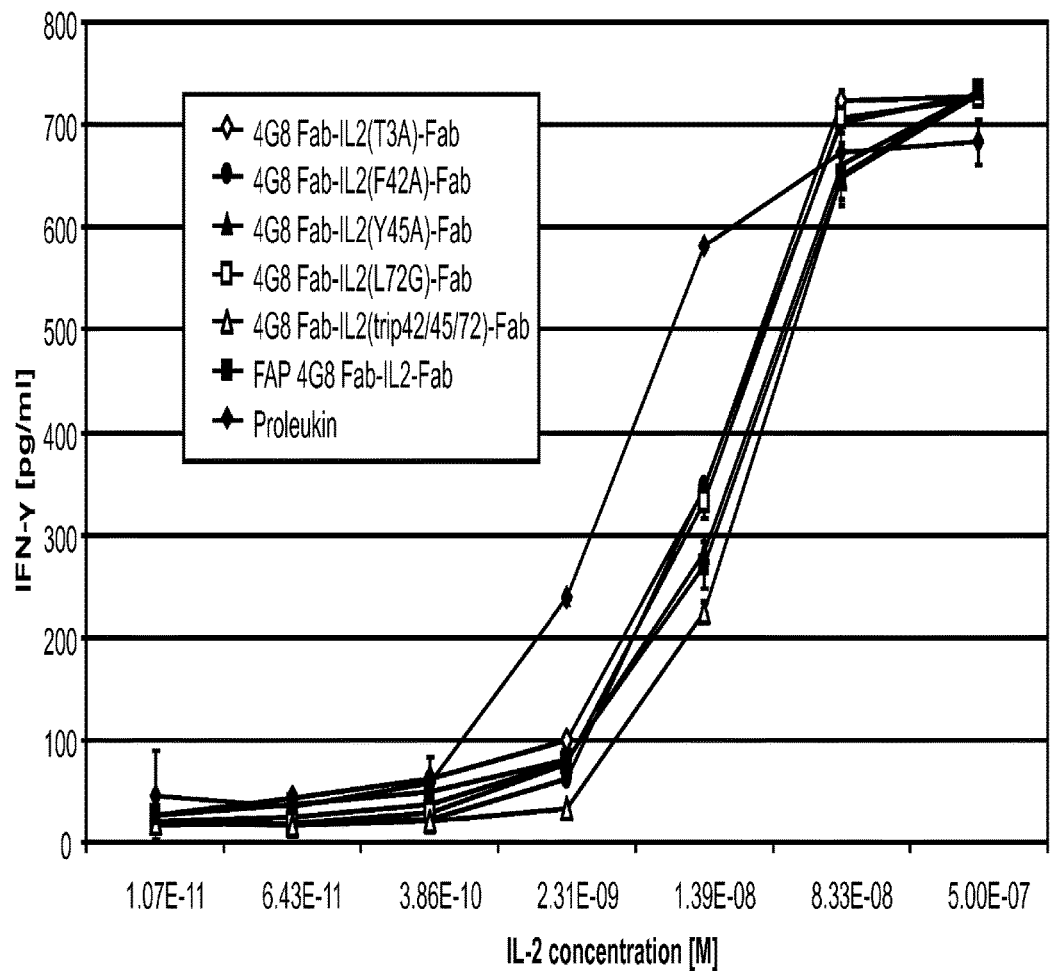

FIG. 9. Induction of IFN-γ release by NK92 cells by FAP-targeted 4G8-based Fab-IL-2-Fab comprising wild-type or mutant IL-2, compared to Proleukin, in solution.

Figure 10:
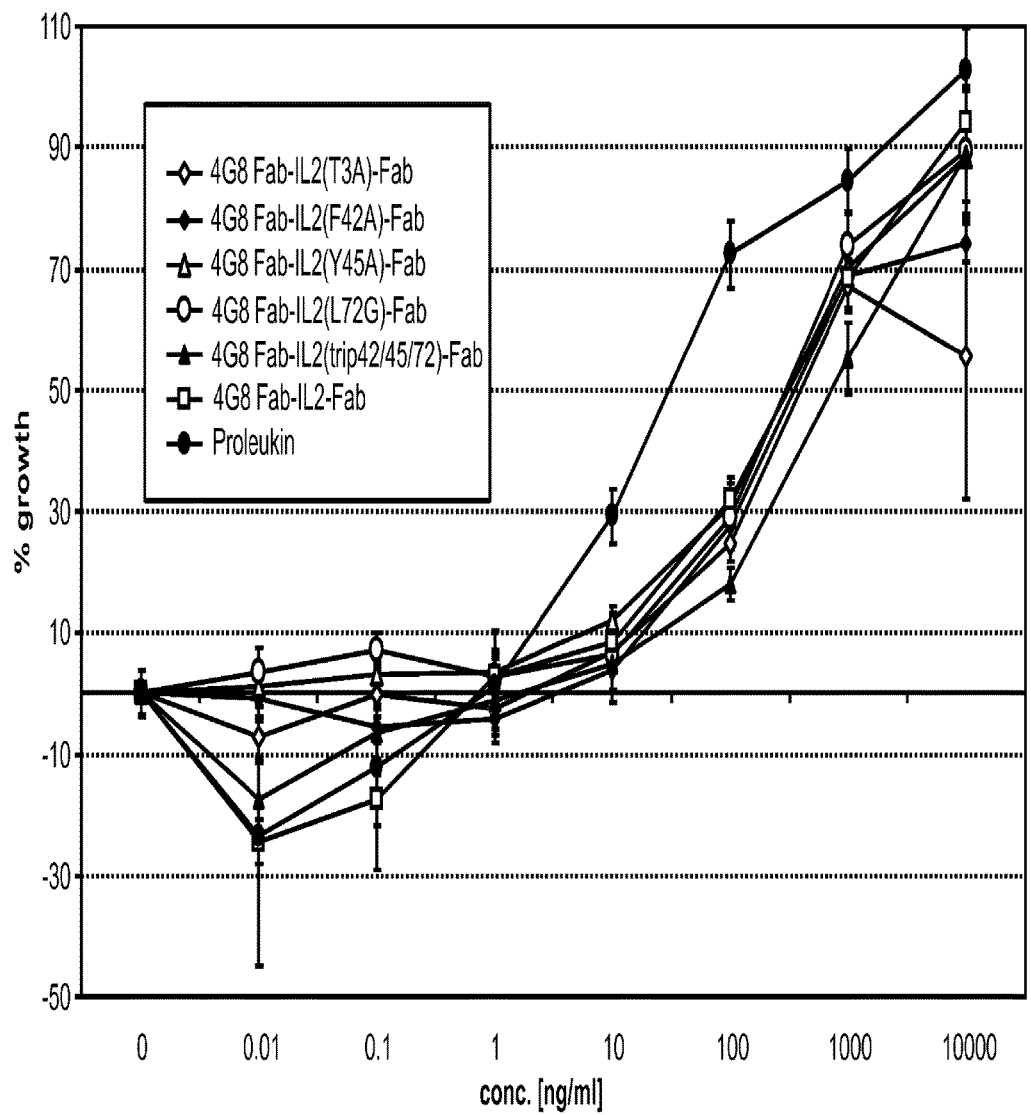

FIG. 10. Induction of proliferation of isolated NK cells (bottom) by FAP-targeted 4G8-based Fab-IL-2-Fab comprising wild-type or mutant IL-2, compared to Proleukin, in solution.

Figure 11:
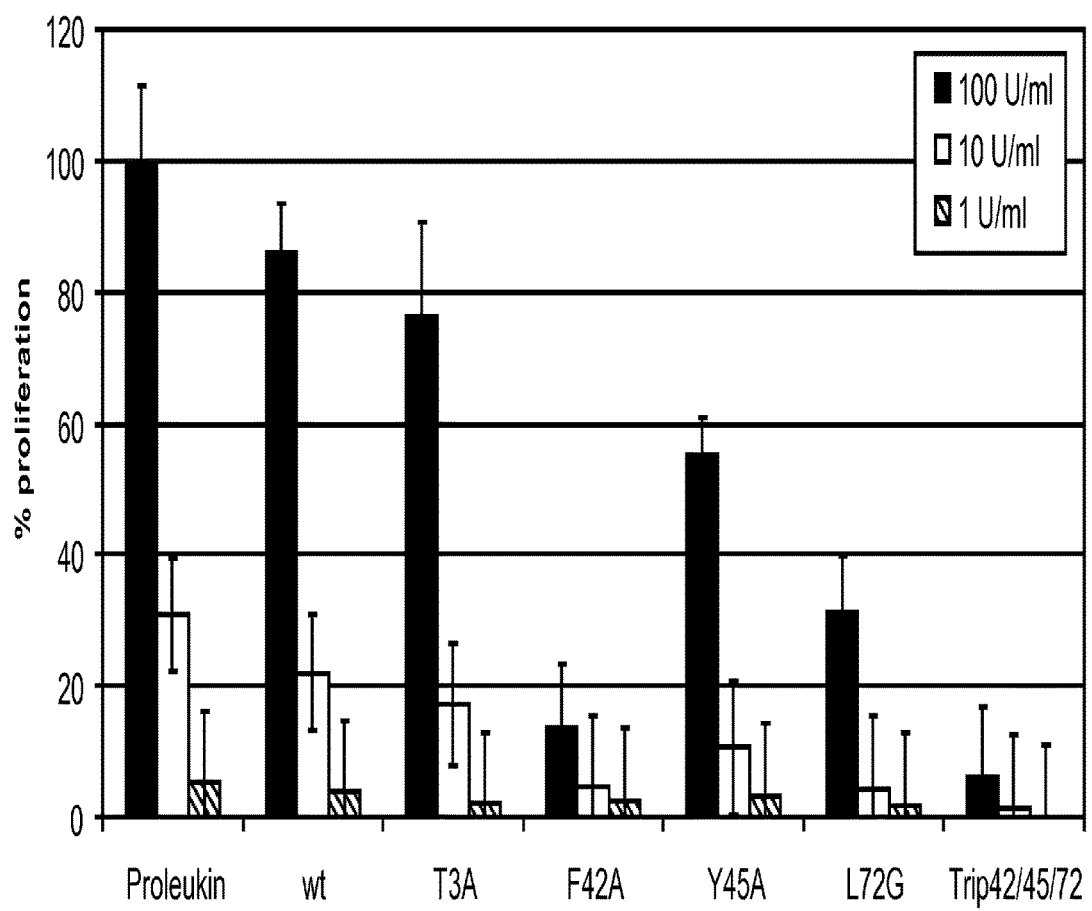

FIG. 11. Induction of proliferation of activated CD3$^+$ T cells by FAP-targeted 4G8-based Fab-IL-2-Fab comprising wild-type of mutant IL-2, compared, to Proleukin, in solution.

Figure 12:
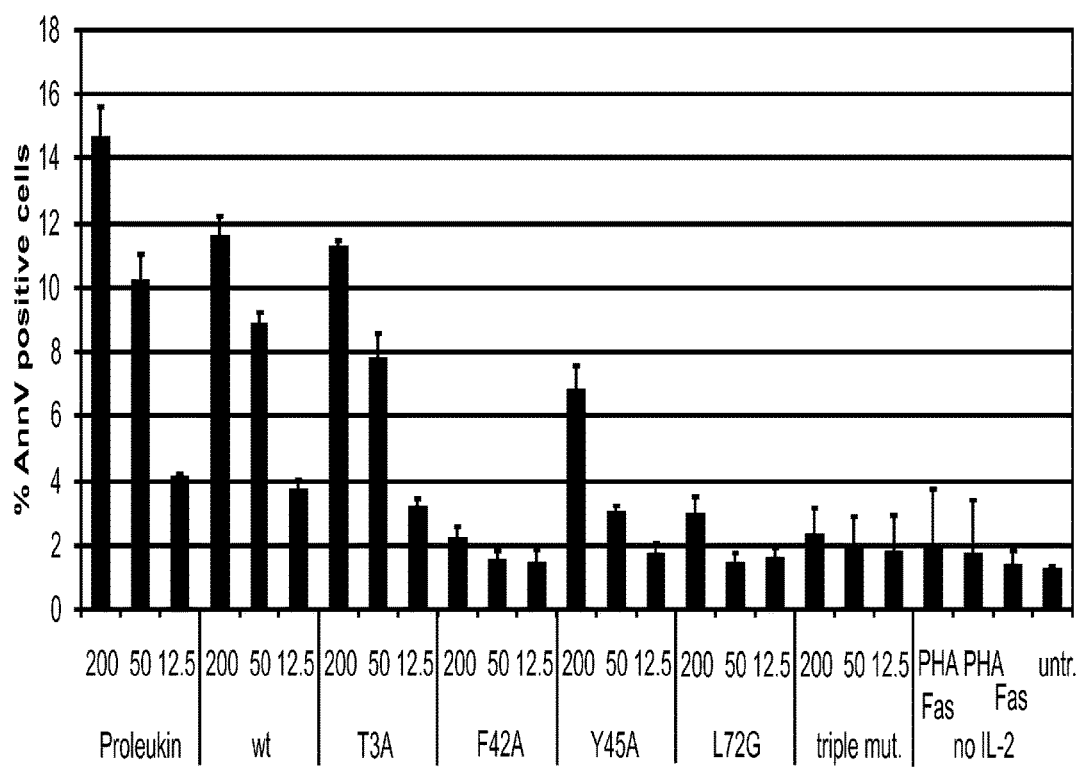

FIG. 12. Induction of activation induced cell death (AICD) of over-stimulated T cells by FAP-targeted 4G8-based Fab-IL-2-Fab comprising wild-type or mutant IL-2, compared to Proleukin, in solution.

Figure 13:
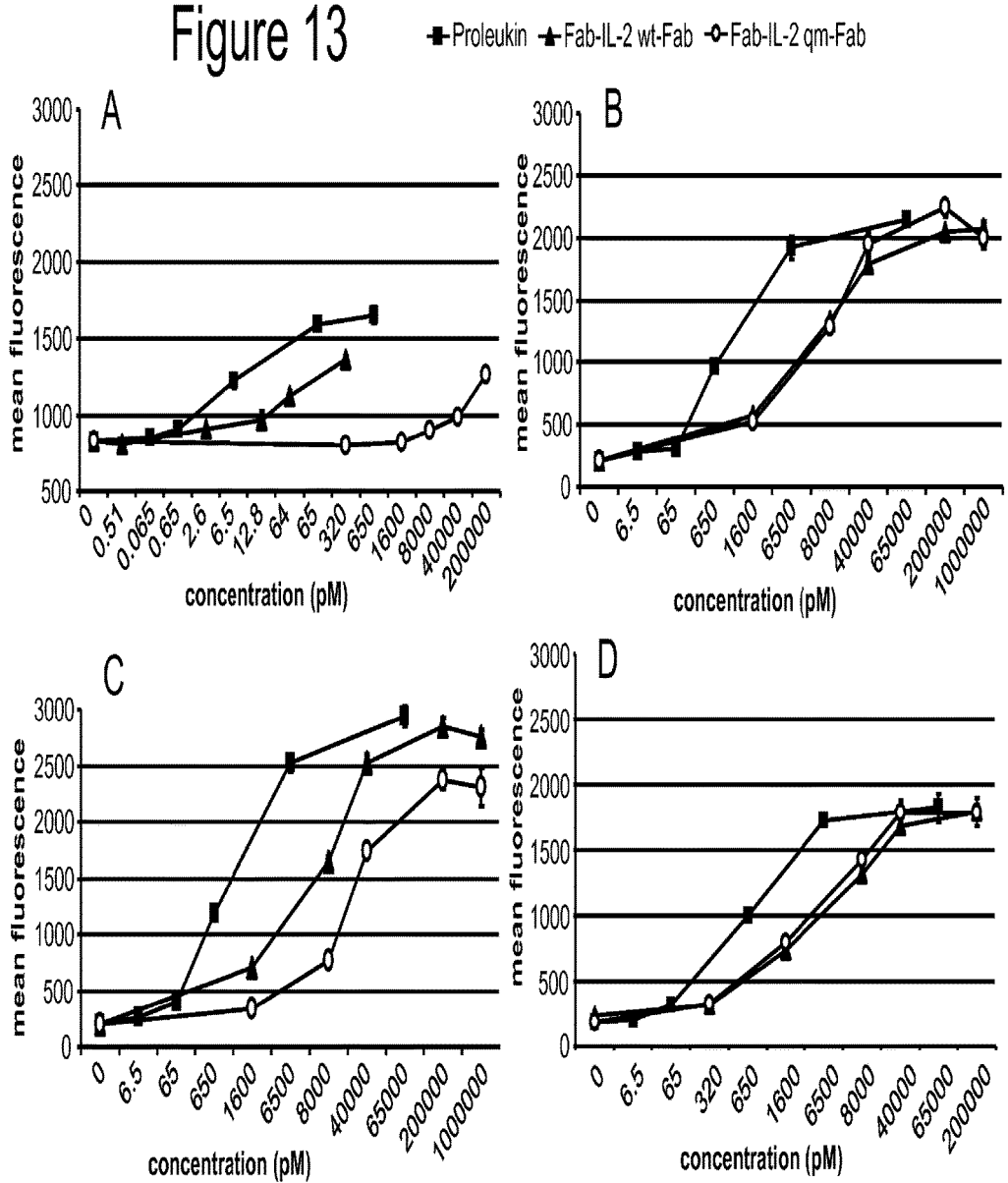

FIG. 13. Phospho-STAT5 FACS assay in solution with FAP-targeted 4G8-based Fab-IL-2-Fab comprising wild-type or quadruple mutant IL-2, compared to Proleukin, in solution. (A) regulatory T cells (CD4$^+$CD25$^+$FOXP3$^+$); (B) CD8$^+$ T cells (CD3$^+$CD8$^+$); (C) CD4$^+$ T cells (CD4$^+$CD25$^-$CD127$^+$); (D) NK cells (CD3$^+$CD56$^+$).

Figure 14:
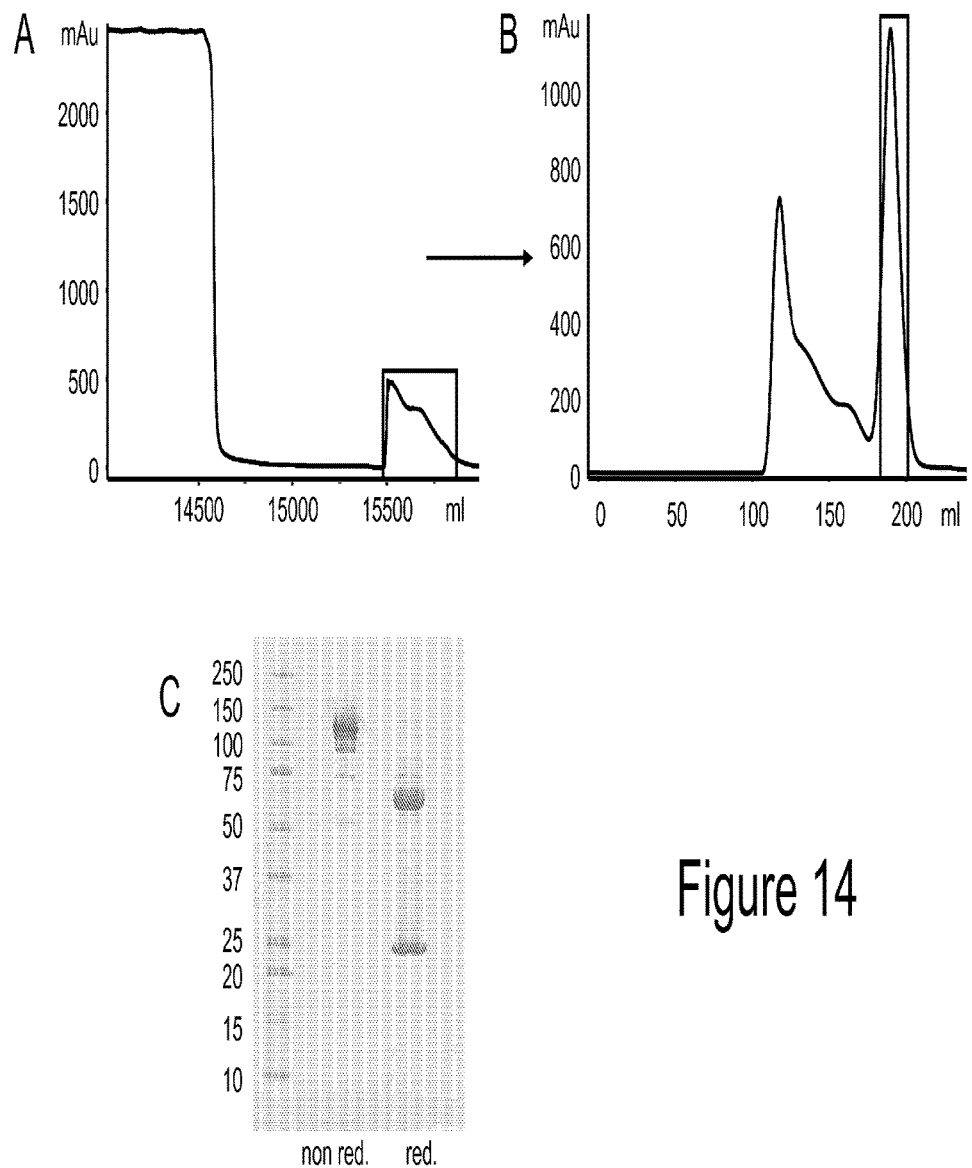

FIG. 14. Purification of the FAP-targeted 28H1-based Fab-IL-2 qm-Fab immunoconjugate. (A) Elution profile of Protein G column. (B) Elution profile of Superdex 200 size exclusion column. (C) Novex Tris-Glycine 4-20% SDS-PAGE of the end-product with non-reduced and reduced sample.

Figure 15:
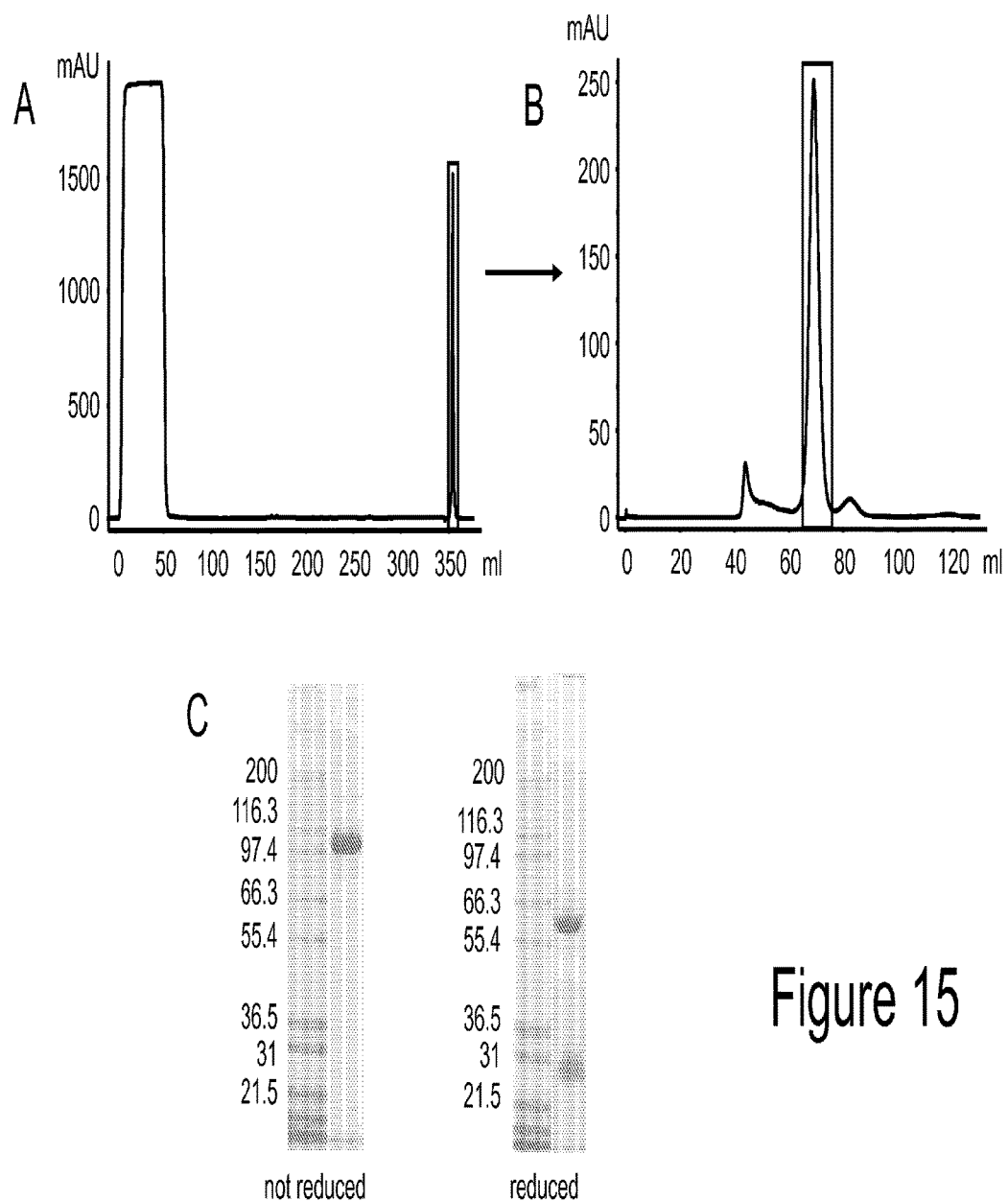

FIG. 15. Purification of the 4G8-based FAP-targeted Fab-IL-2 qm-Fab immunoconjugate. (A) Elution profile of Protein A column. (B) Elution profile of Superdex 200 size exclusion column. (C) NuPAGE Novex Bis-Tris Mini Gel (Invitrogen), MOPS running buffer of the end-product with non-reduced and reduced sample.

Figure 16:
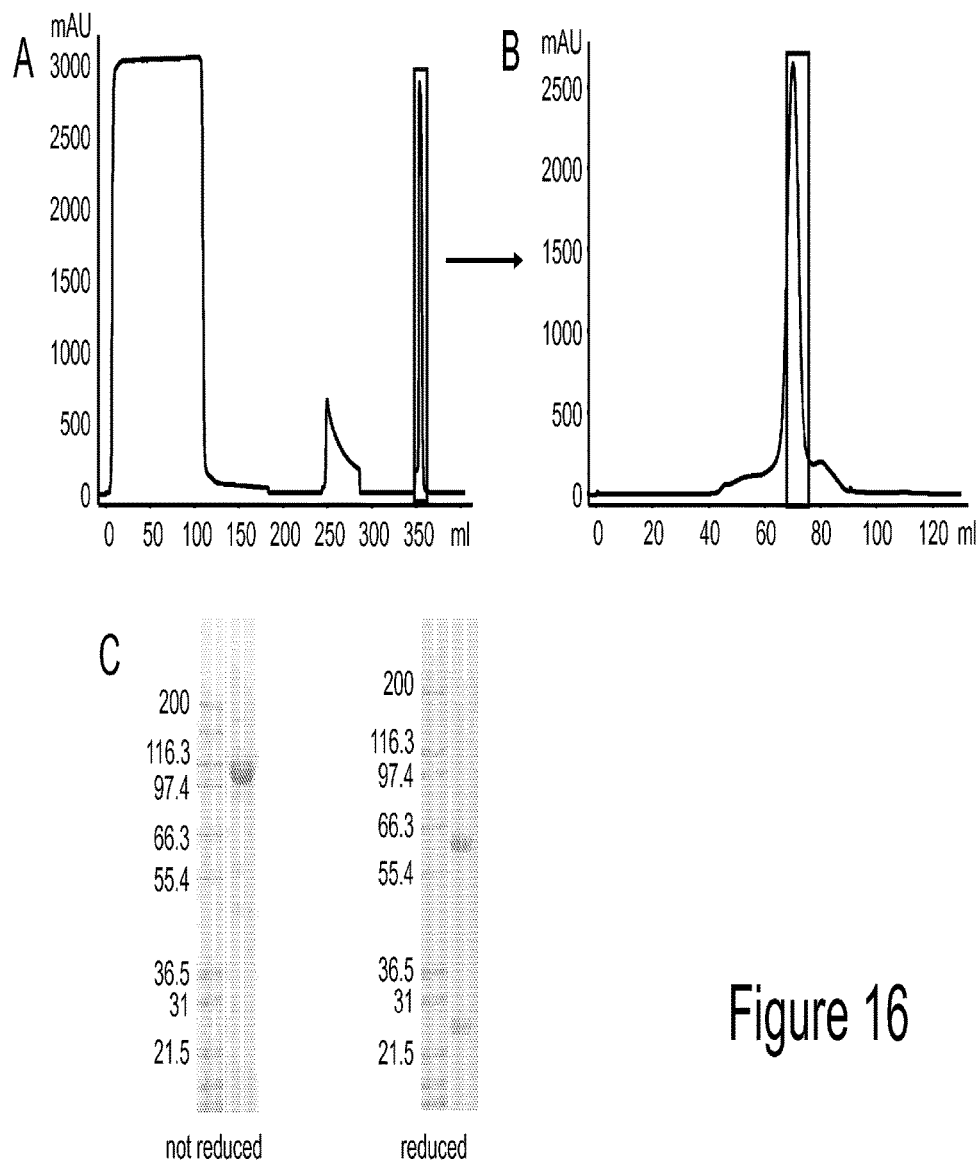

FIG. 16. Purification of the MHLG1 KV9 MCSP-targeted Fab-IL2QM-Fab immunoconjugate. (A) Elution profile of Protein A column, B) Elution profile of Superdex 200 size exclusion column. C) NuPAGE Novex Bis-Tris Mini Gel, Invitrogen, MOPS running buffer of the end-product with non-reduced and reduced sample.

Figure 17:
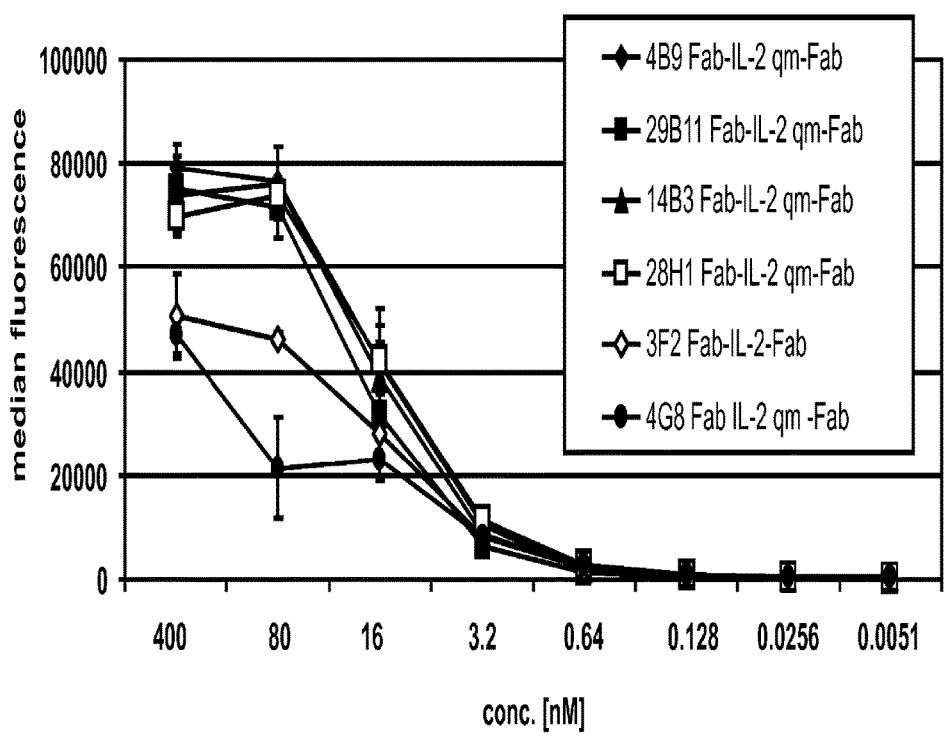

FIG. 17. Target binding of Fab-IL-2-Fab constructs on HEK 293-human FAP cells.

Figure 18:
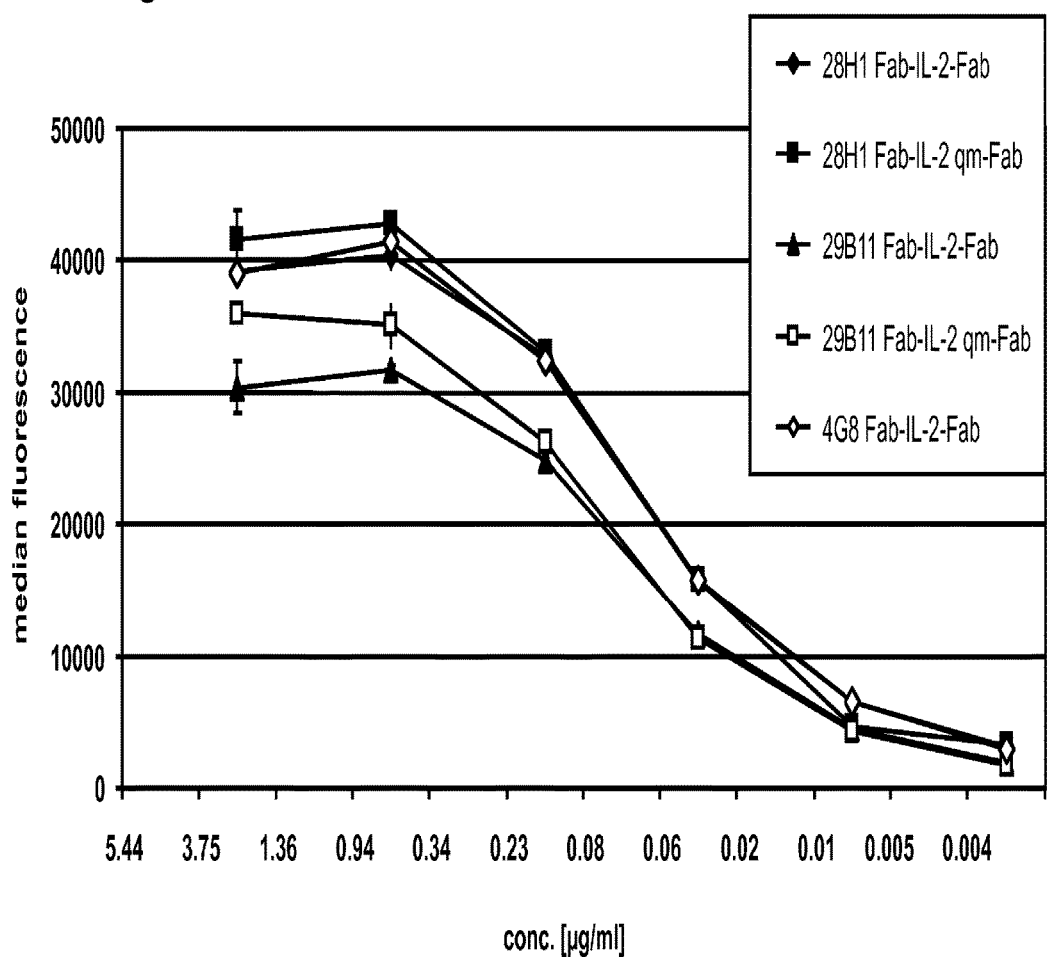

FIG. 18. Target binding of Fab-IL-2-Fab constructs on HEK 293-human FAP cells.

Figure 19:
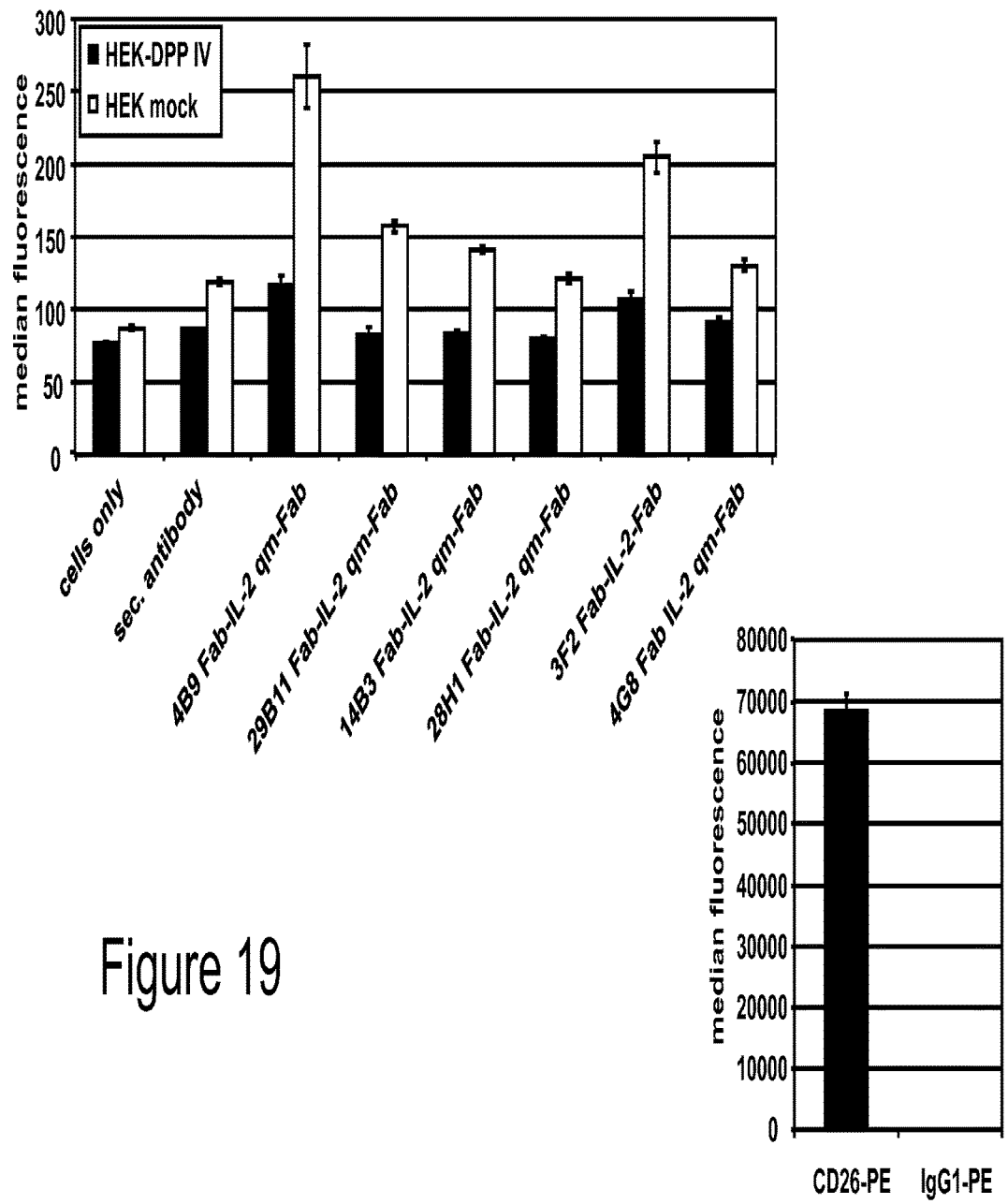

FIG. 19. Binding specificity of Fab-IL-2-Fab constructs as determined on HEK 293-human DPPIV and HEK 293 mock-transfected cells. Binding of a specific DPPIV (CD26) antibody is shown on the right.

Figure 20:
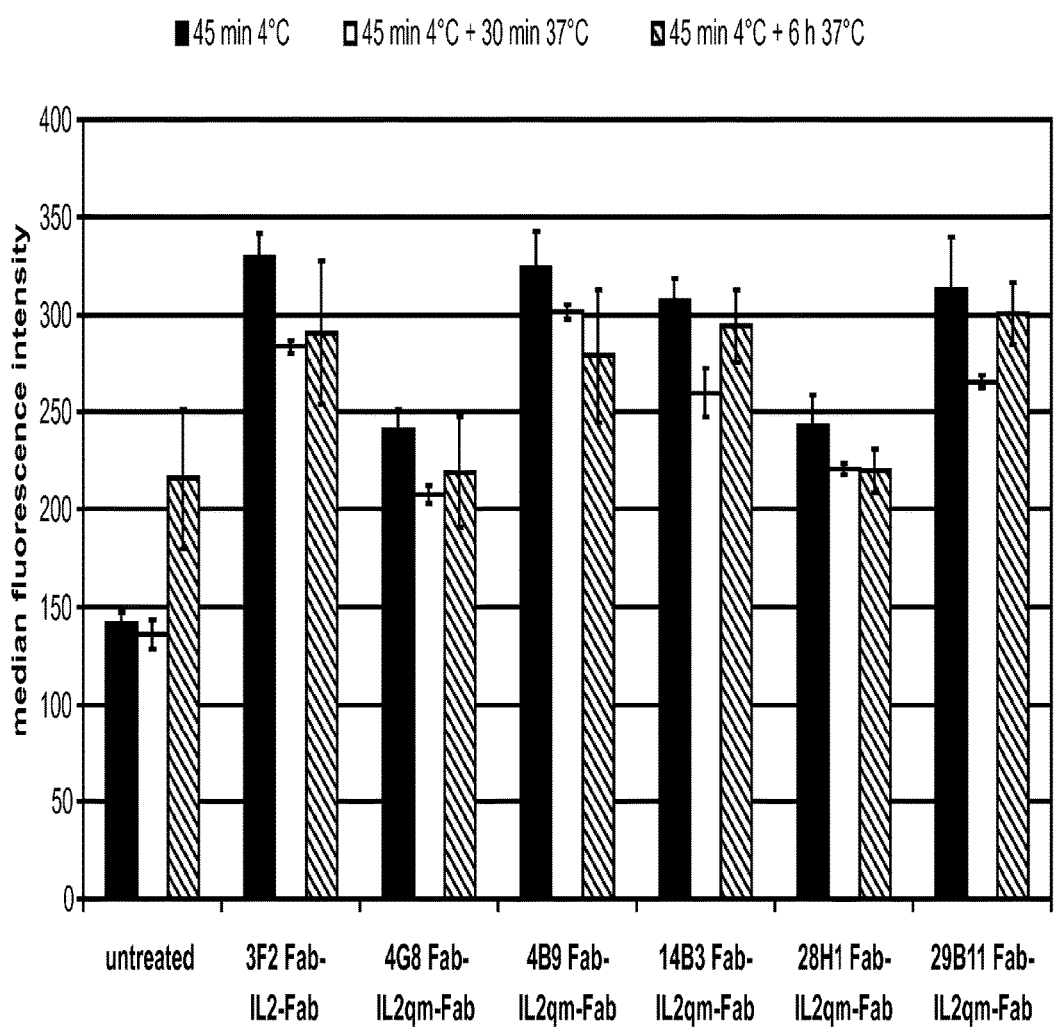

FIG. 20. Analysis of FAP internalization upon binding of Fab-IL-2-Fab constructs to FAP on GM05389 fibroblasts.

Figure 21:
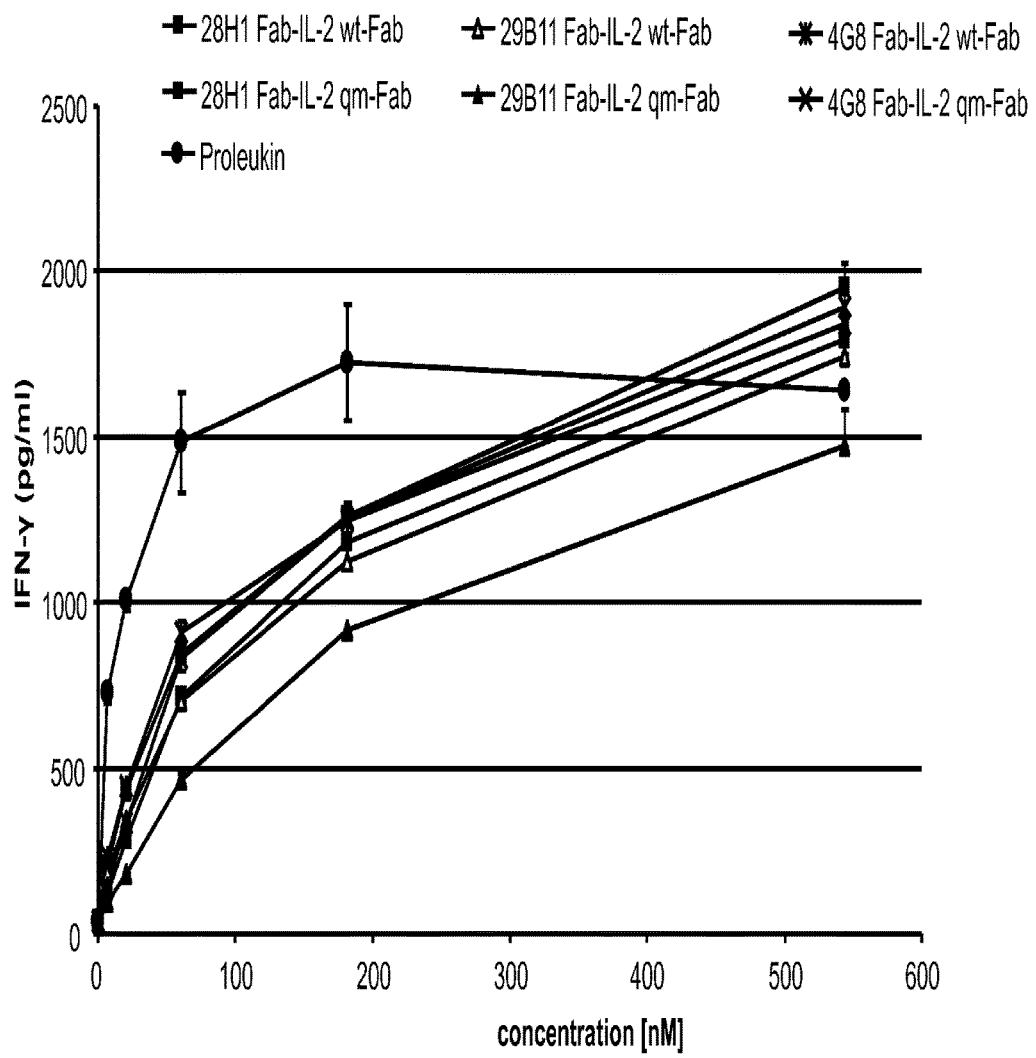

FIG. 21. IL-2 induced IFN-γ release by NK92 cells in solution.

Figure 22:
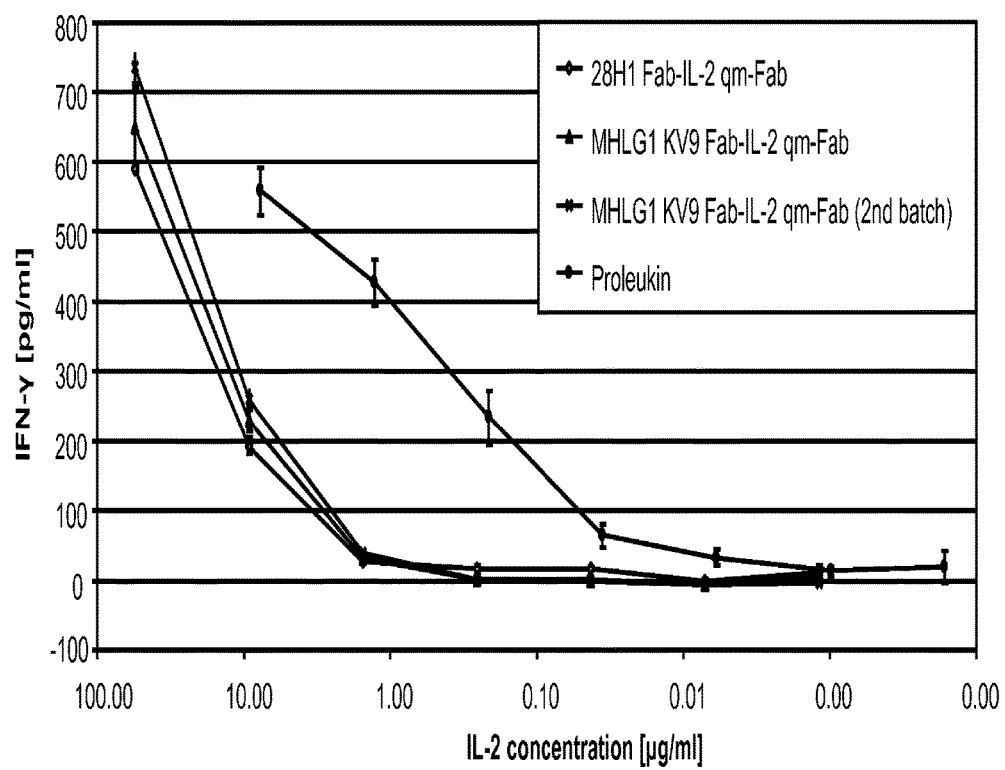

FIG. 22. IL-2 induced IFN-γ release by NK92 cells in solution.

Figure 23:
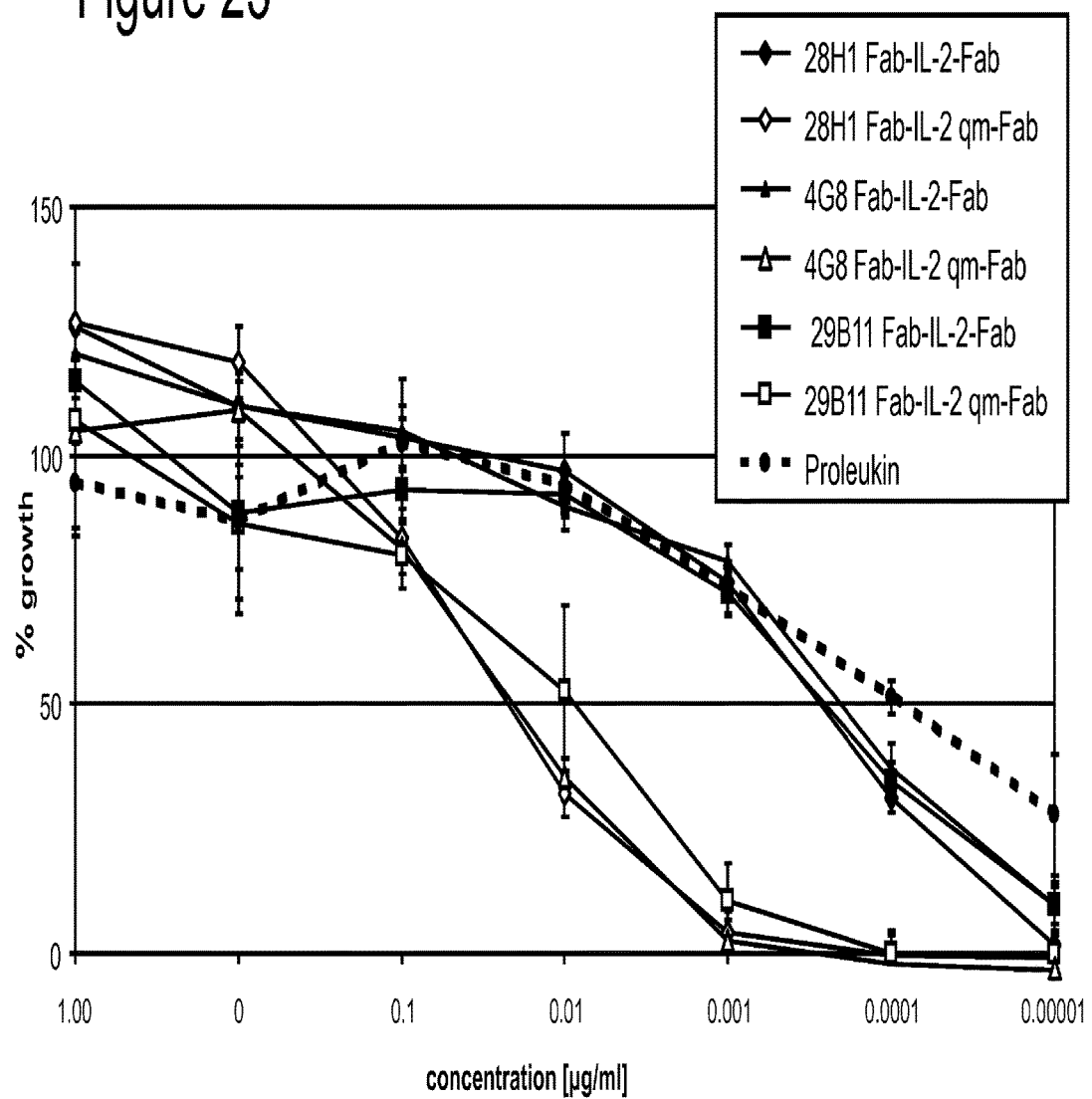

FIG. 23. IL-2 induced proliferation of NK92 cells in solution.

Figure 24:
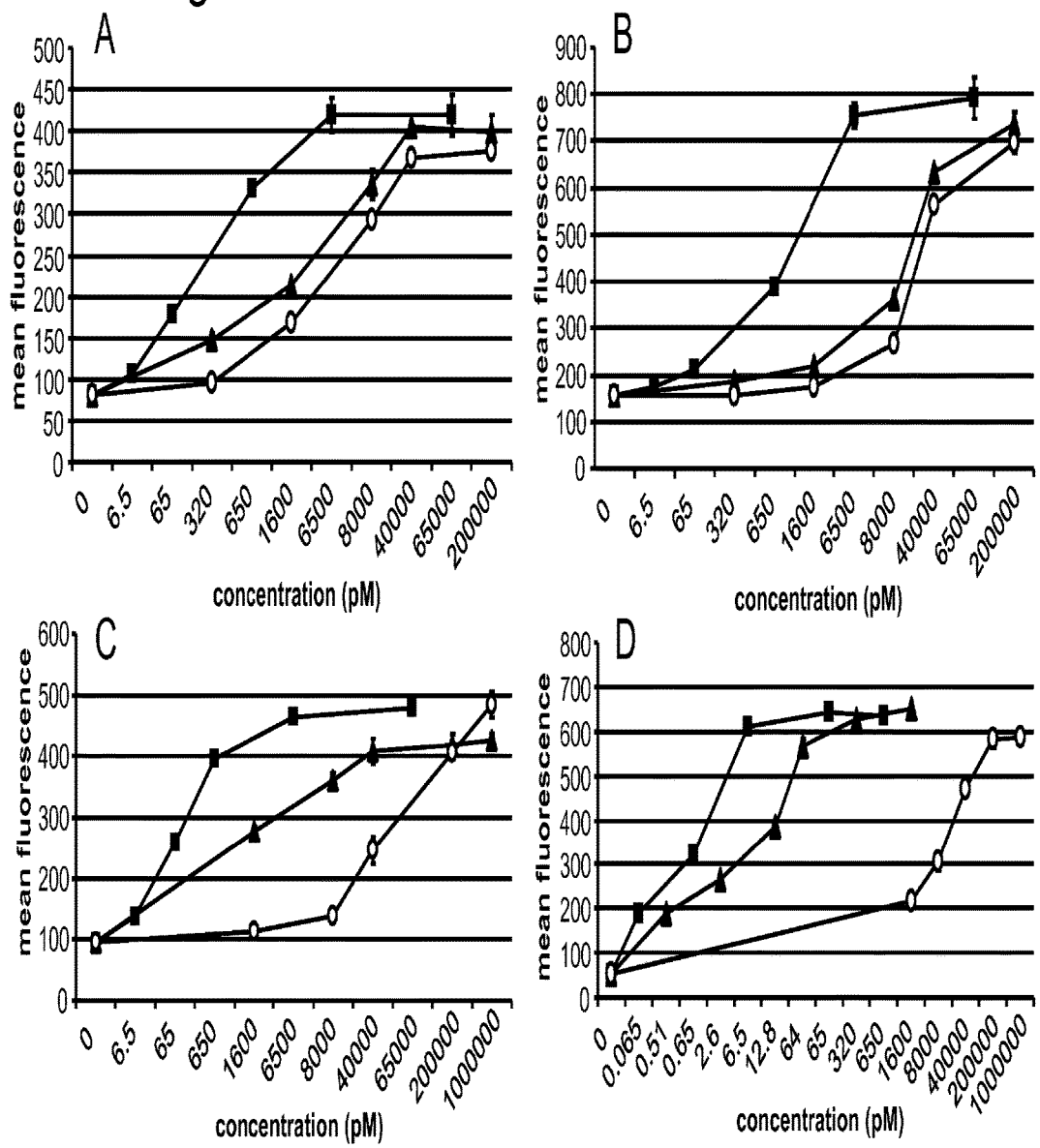

FIG. 24. Assessment of Fab-IL-2-Fab clones 28H1 vs. 29B11 vs. 4G8 in STAT5 phosphorylation assay with PBMCs in solution. (A) NK cells (CD3$^-$CD56$^+$); (B) CD8$^+$ T cells (CD3$^+$CD8$^+$); (C) CD4$^+$ T cells (CD3$^+$CD4$^+$CD25$^-$CD127$^+$); (D) regulatory T cells (CD4+CD25±FOXP3+).

Figure 25:
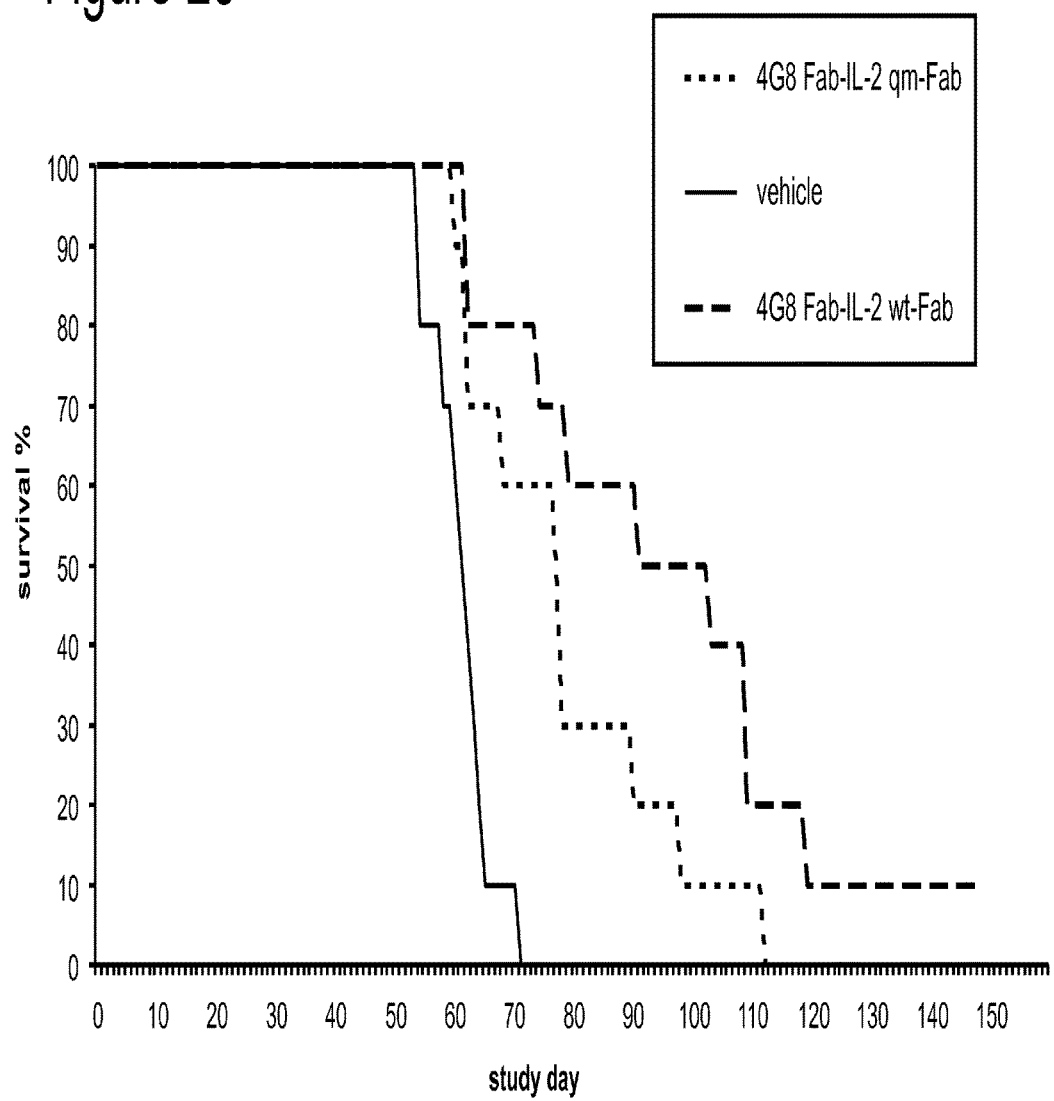

FIG. 25. Efficacy of the FAP-targeted 4G8 Fab-IL-2 wt-Fab and 4G8 Fab-IL-2 qm-Fab immunoconjugates in the human renal cell adenocarcinoma cell line ACHN.

Figure 26:
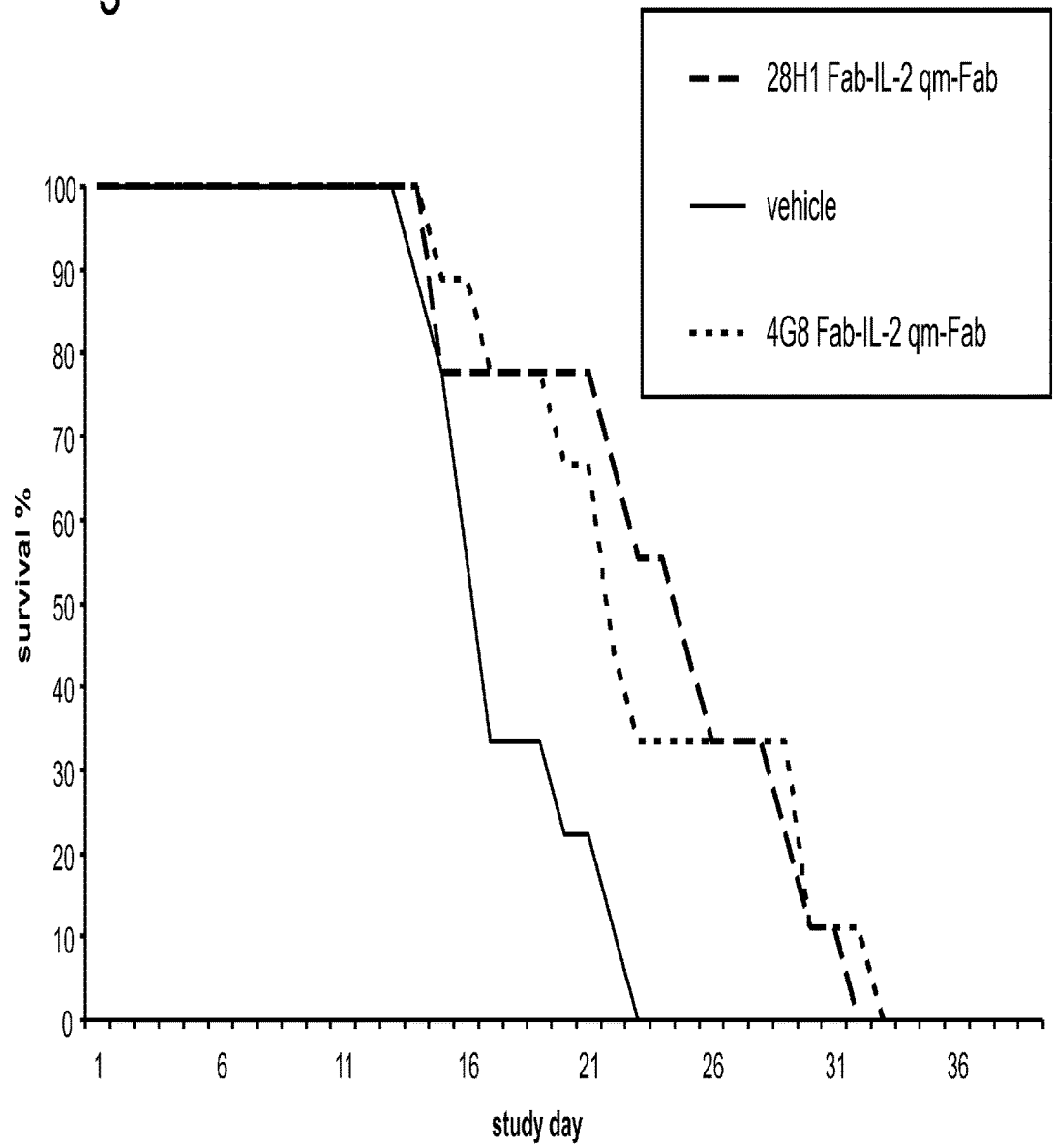

FIG. 26. Efficacy of the FM-targeted 4G8 FAP-IL-2 qm-Fab and 28H1 Fab-IL-2 qm-Fab immunoconjugates in the mouse Lewis lung carcinoma cell line LLC1.

Figure 27:
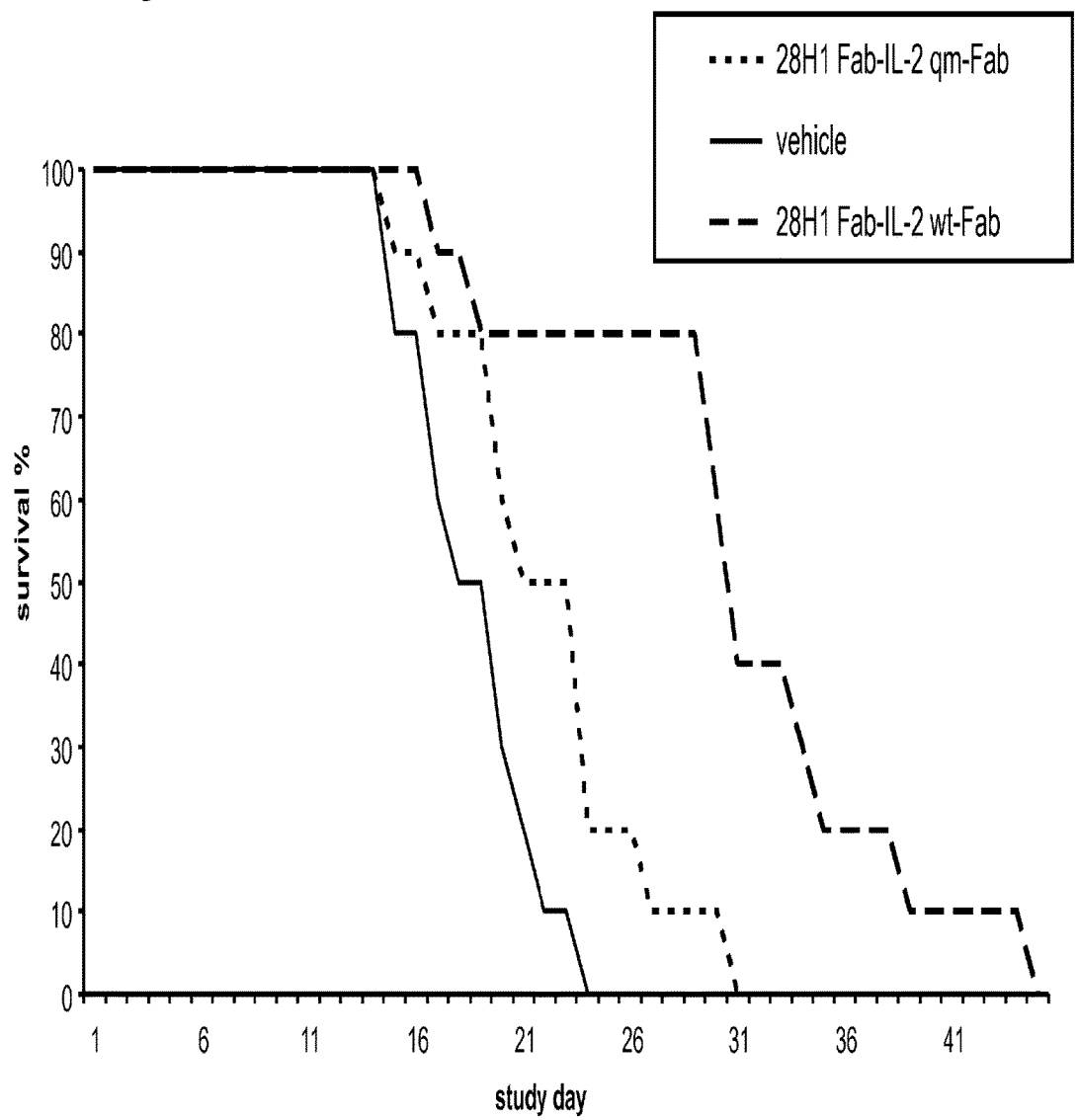

FIG. 27. Efficacy of the FAP-targeted 28H1 Fab-IL-2 wt-Fab and 28H1 Fab-IL-2 qm-Fab immunoconjugates in the mouse Lewis lung carcinoma cell line LLC1.

Figure 28:
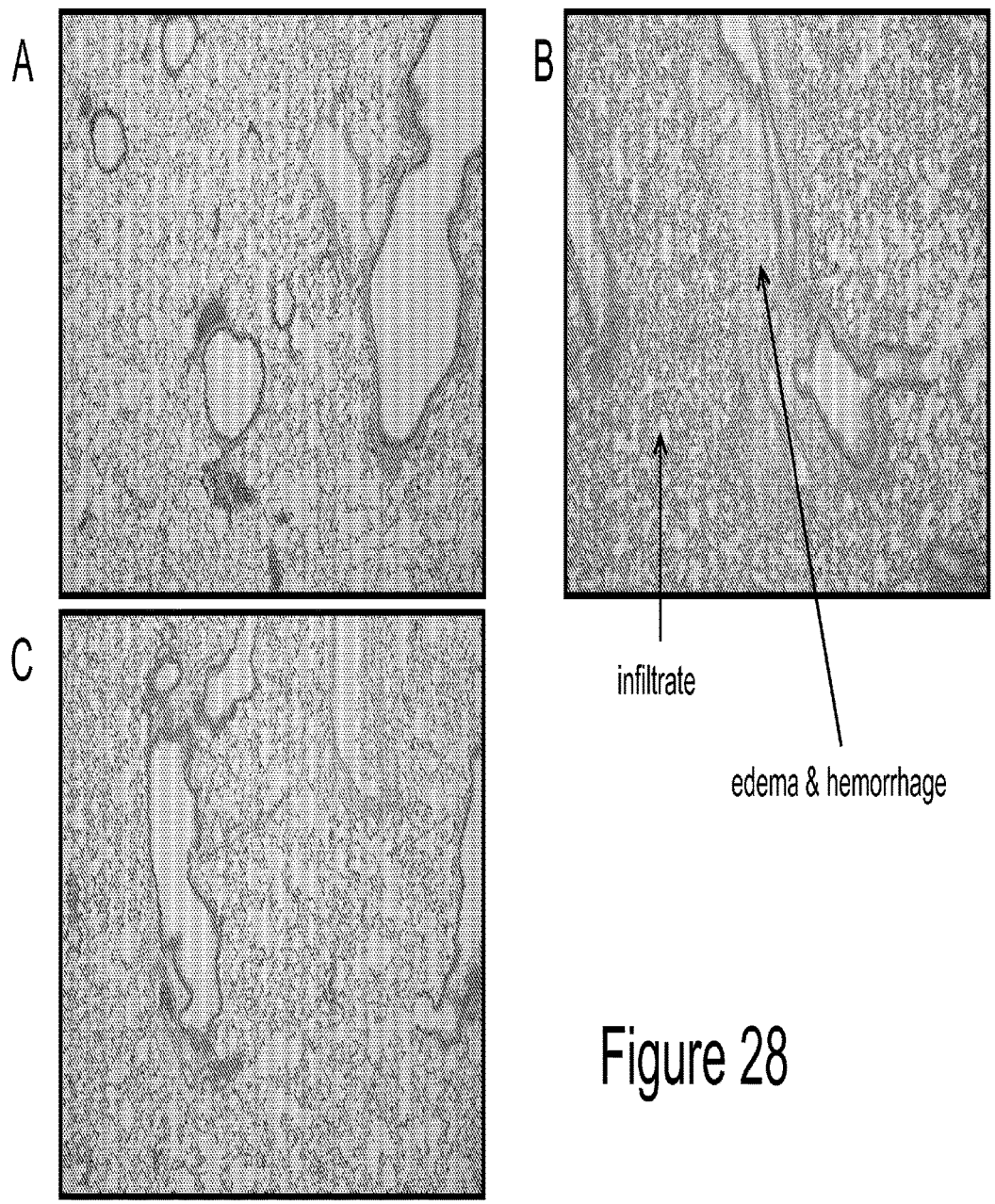

FIG. 28. Low magnification (100×) of lungs of mice treated with vehicle control (A) or 9 μg/g wt IL-2 (B) or qm IL-2 (C). Lungs of mice treated with 9 μg/g wt IL-2 show vasocentric mononuclear infiltrate that has moved into the alveolar spaces. Edema and hemorrhage is also present. Marginal infiltrate is noted in the mice treated with qm IL-2 around few vessels.

Figure 29:
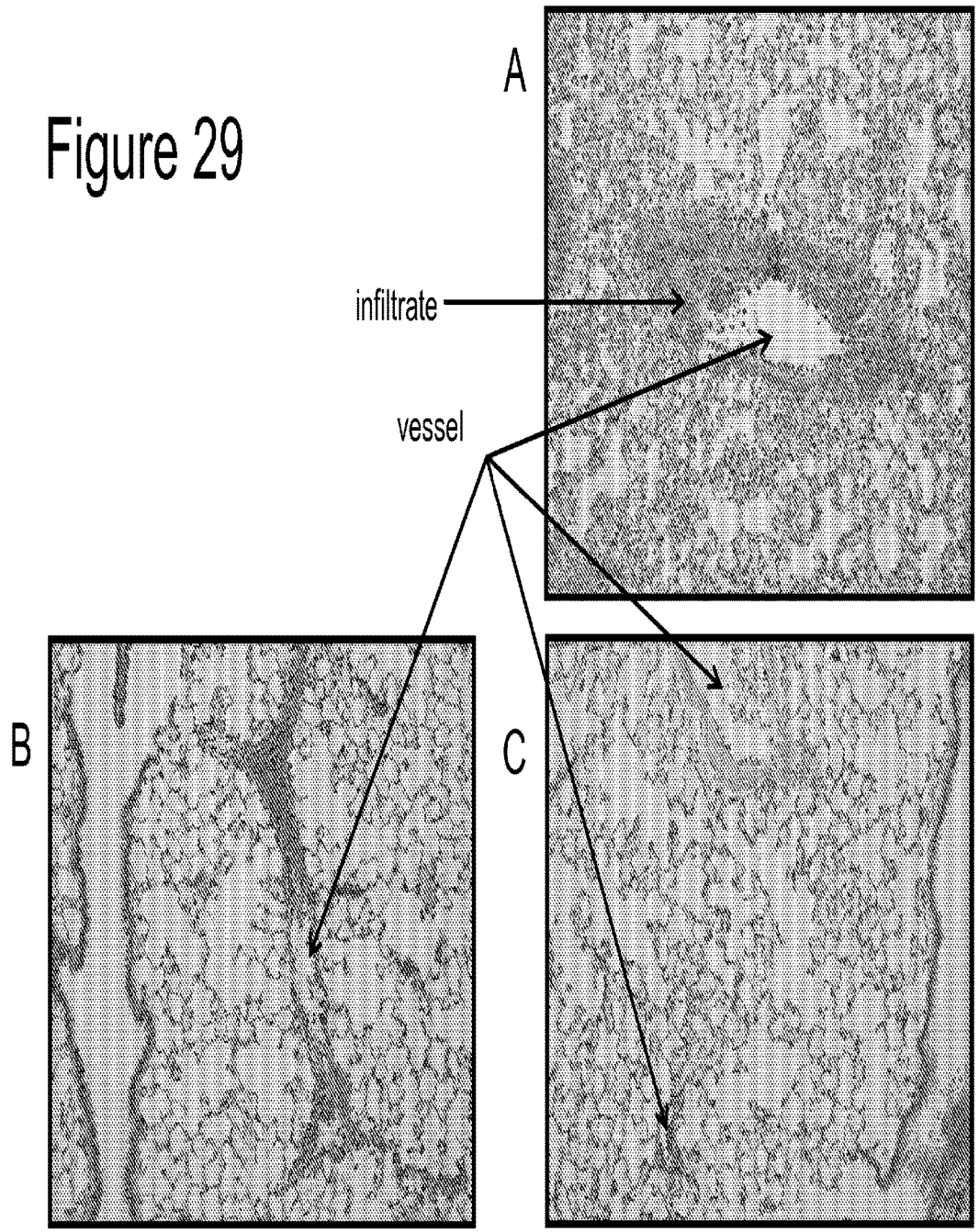

FIG. 29. Higher magnification (200×) of lungs shown in FIG. 28. Margination and infiltration of mononuclear cells in and around blood vessels is more severe in mice treated with wt IL-2 (A) than in mice treated with qm IL-2 (B and C).

Figure 30:
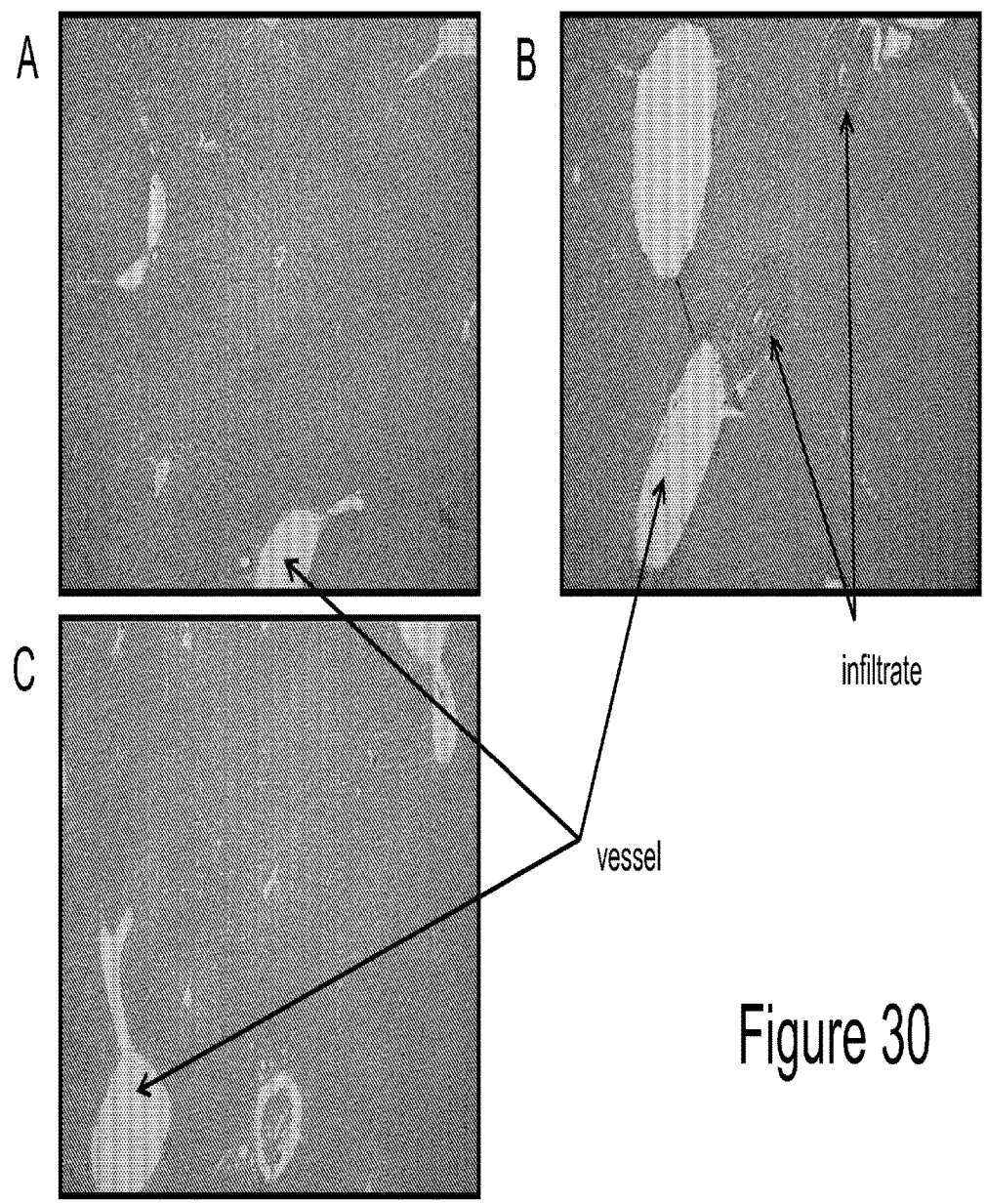

FIG. 30. Low magnification (100×) of livers of mice treated with vehicle control (A) or 9 μg/g wt IL-2 (B) or qm IL-2 (C). Vasocentric infiltration is seen in mice treated with wt IL-2.

Figure 31:
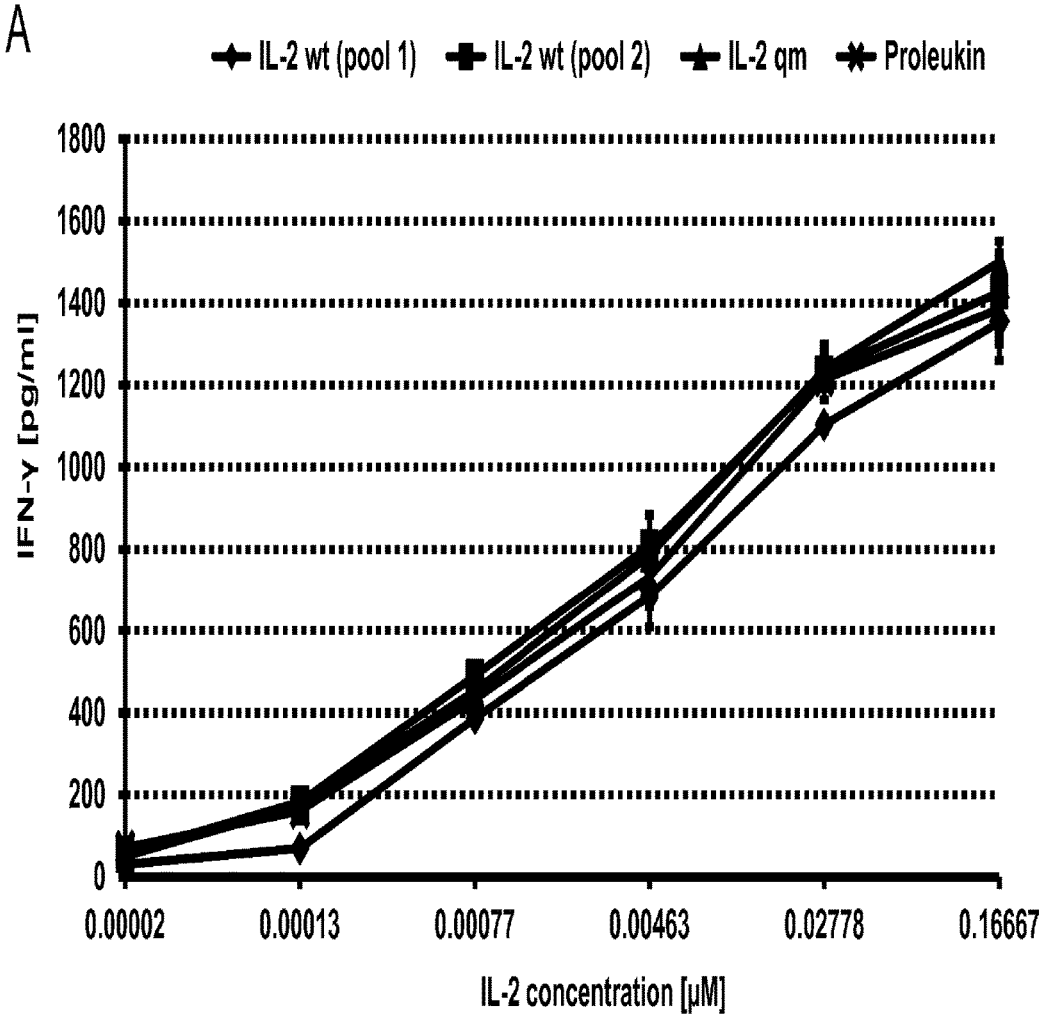
Figure 31:
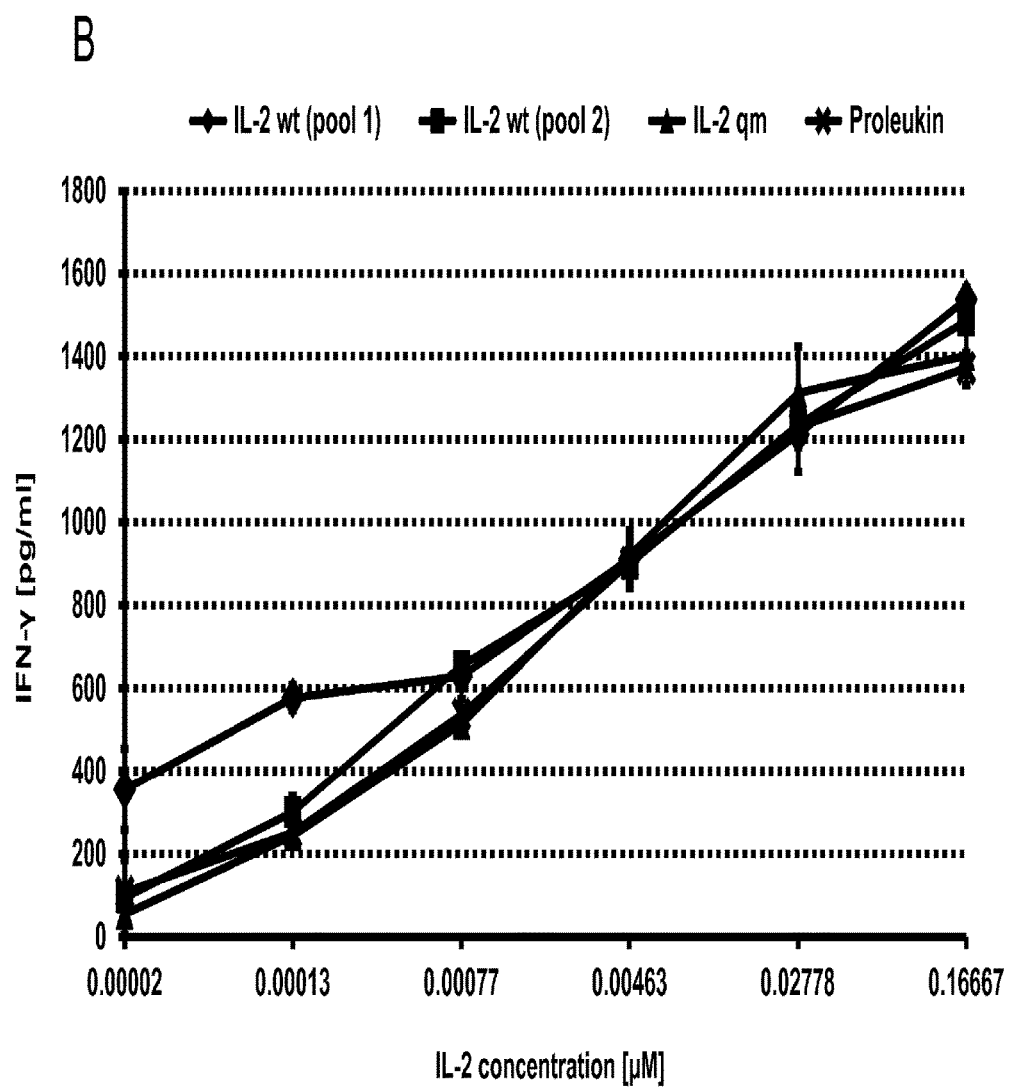

FIG. 31. IFN-γ secretion by NK92 cells upon incubation with different IL-2 wild-type (wt) and quadruple mutant (qm) preparations for 24 (A) or 48 hours (B).

Figure 32:
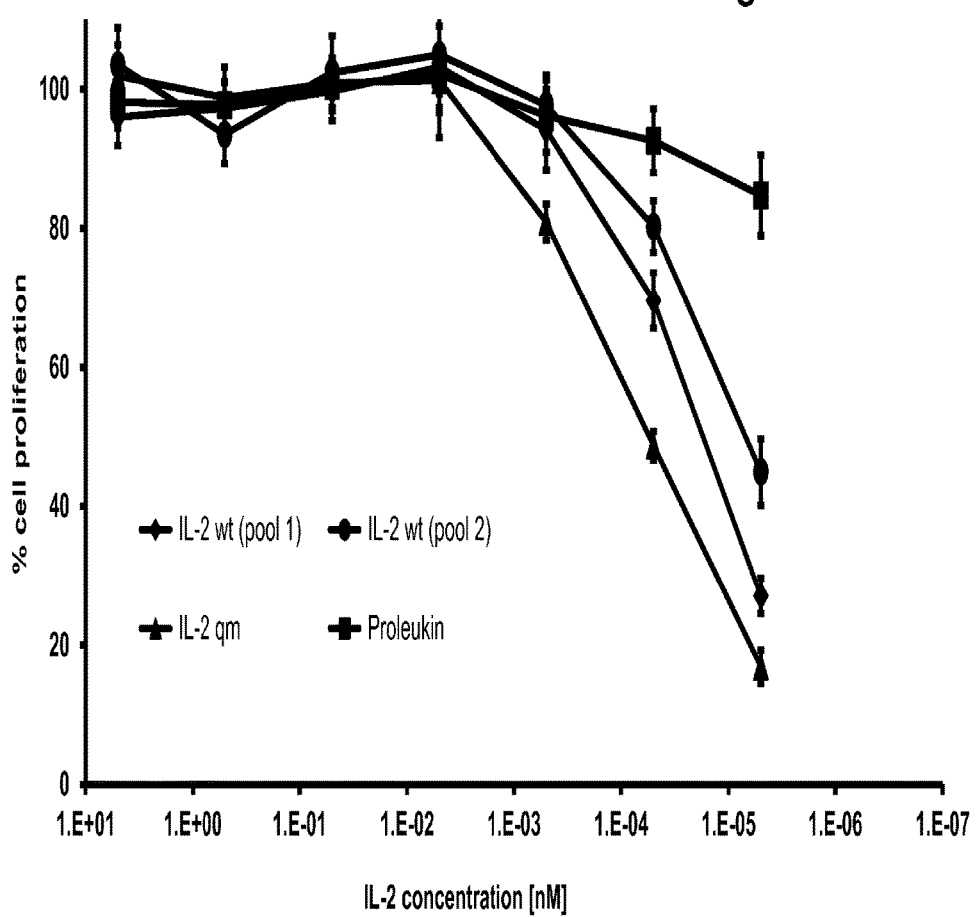

FIG. 32. Proliferation of NK92 cells upon incubation with different IL-2 wild-type (wt) and quadruple mutant (qm) preparations for 48 hours.

Figure 33:
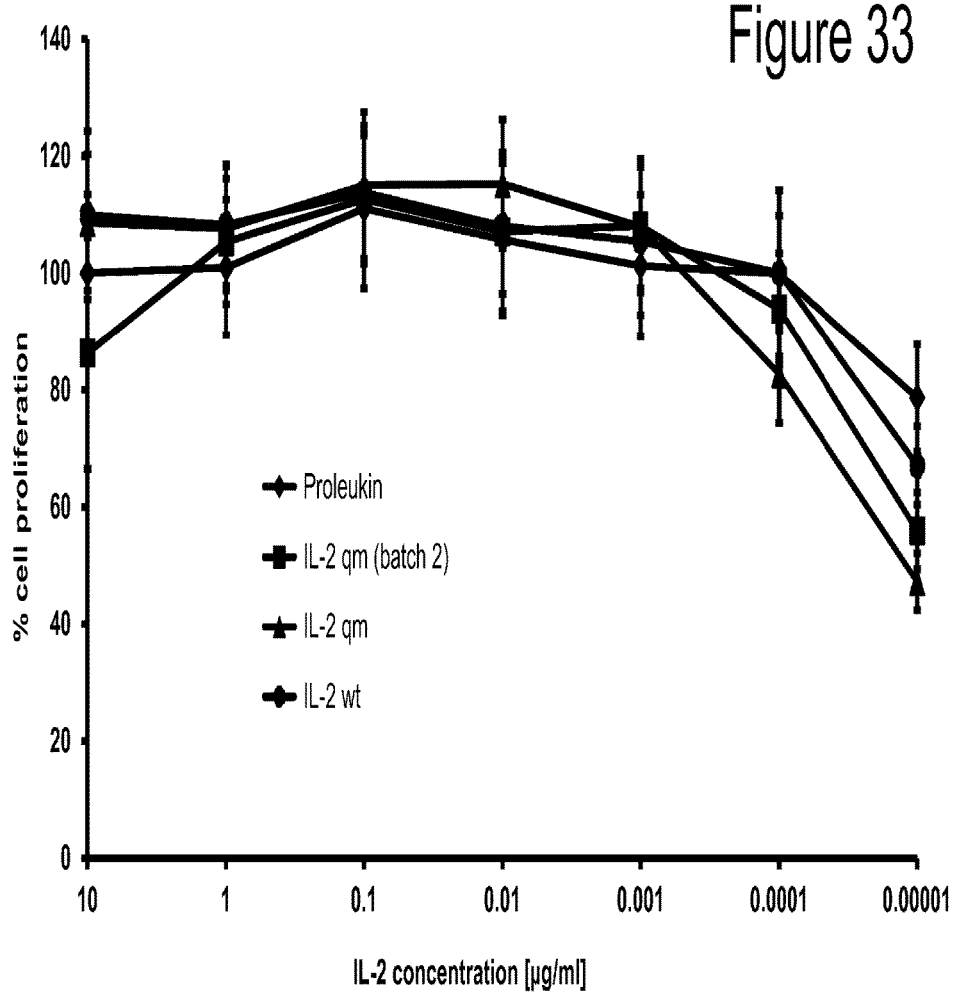

FIG. 33. Proliferation of NK92 cells upon incubation with different IL-2 wild-type (wt) and quadruple mutant (qm) preparations for 48 hours.

Figure 34:
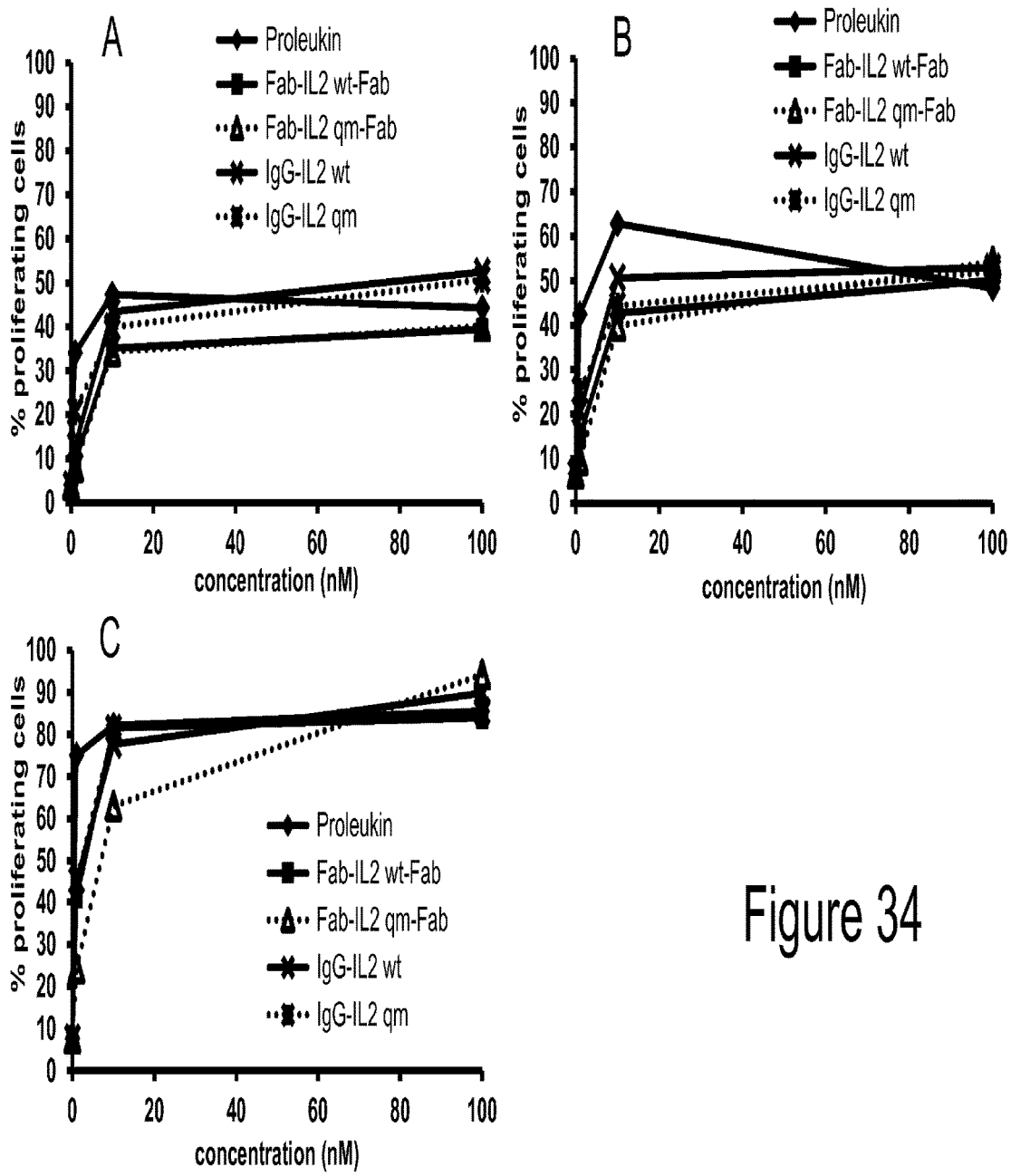

FIG. 34. Proliferation of NK cells upon incubation with different FAP-targeted 28H1 IL-2 immunoconjugates or Proleukin for 4 (A), 5 (B) or 6 (C) days.

Figure 35:
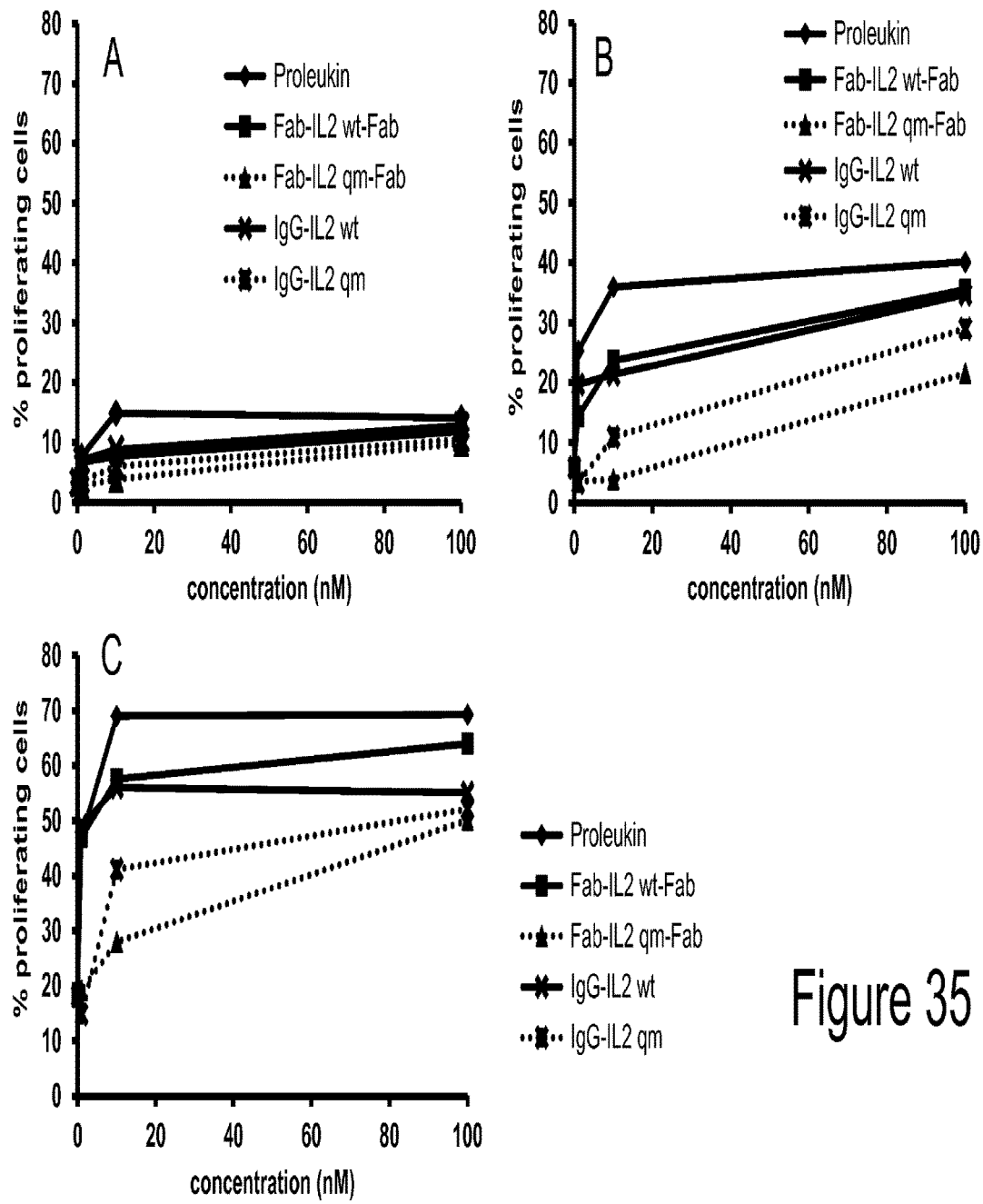

FIG. 35. Proliferation of CD4 T-cells upon incubation with different FAP-targeted 28H1 IL-2 immunoconjugates or Proleukin for 4 (A), 5 (B) or 6 (C) days.

Figure 36:
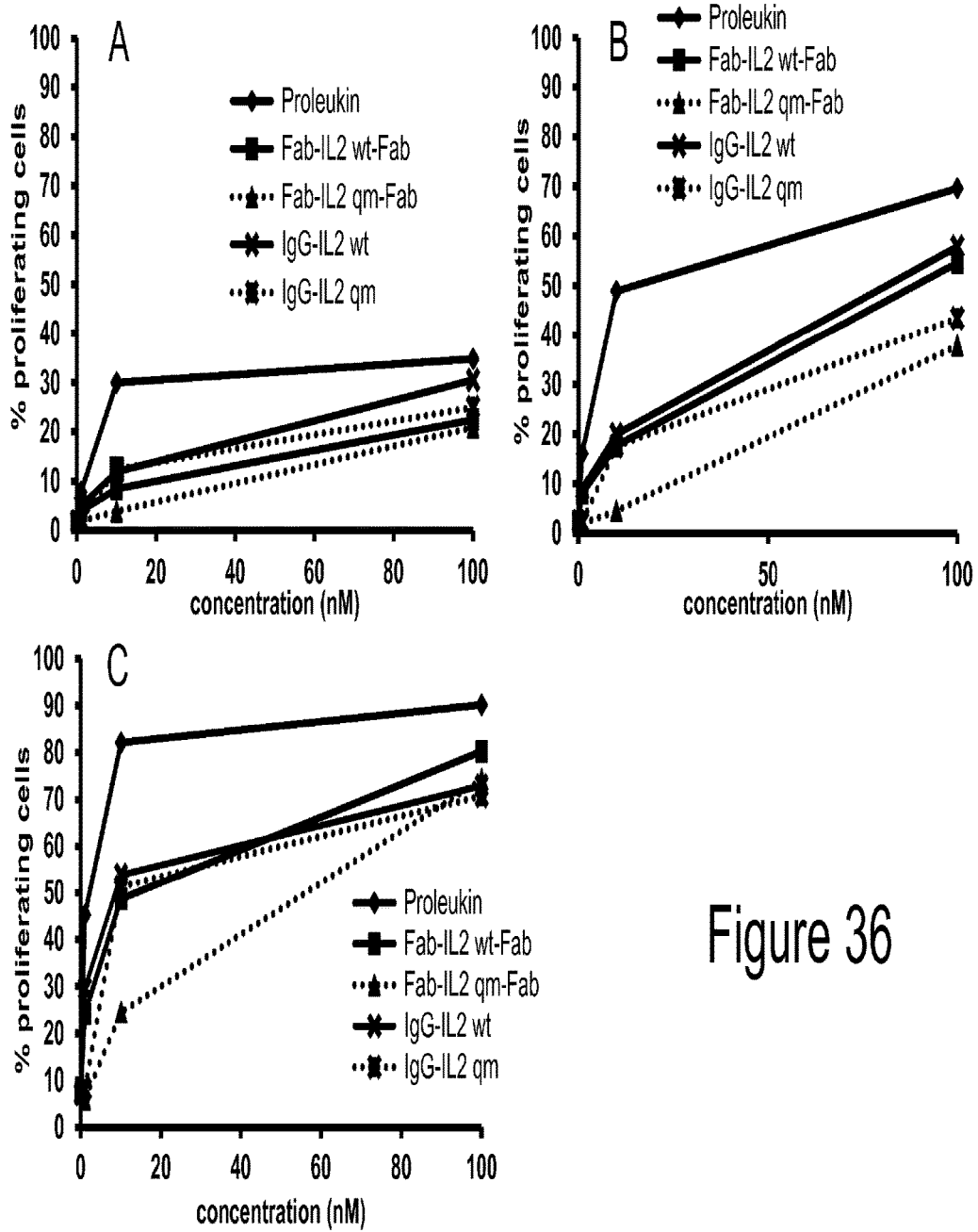

FIG. 36. Proliferation of CD8 T-cells upon incubation with different FAP-targeted 28H1 IL-2 immunoconjugates or Proleukin for 4 (A), 5 (B) or 6 (C) days.

Figure 37:
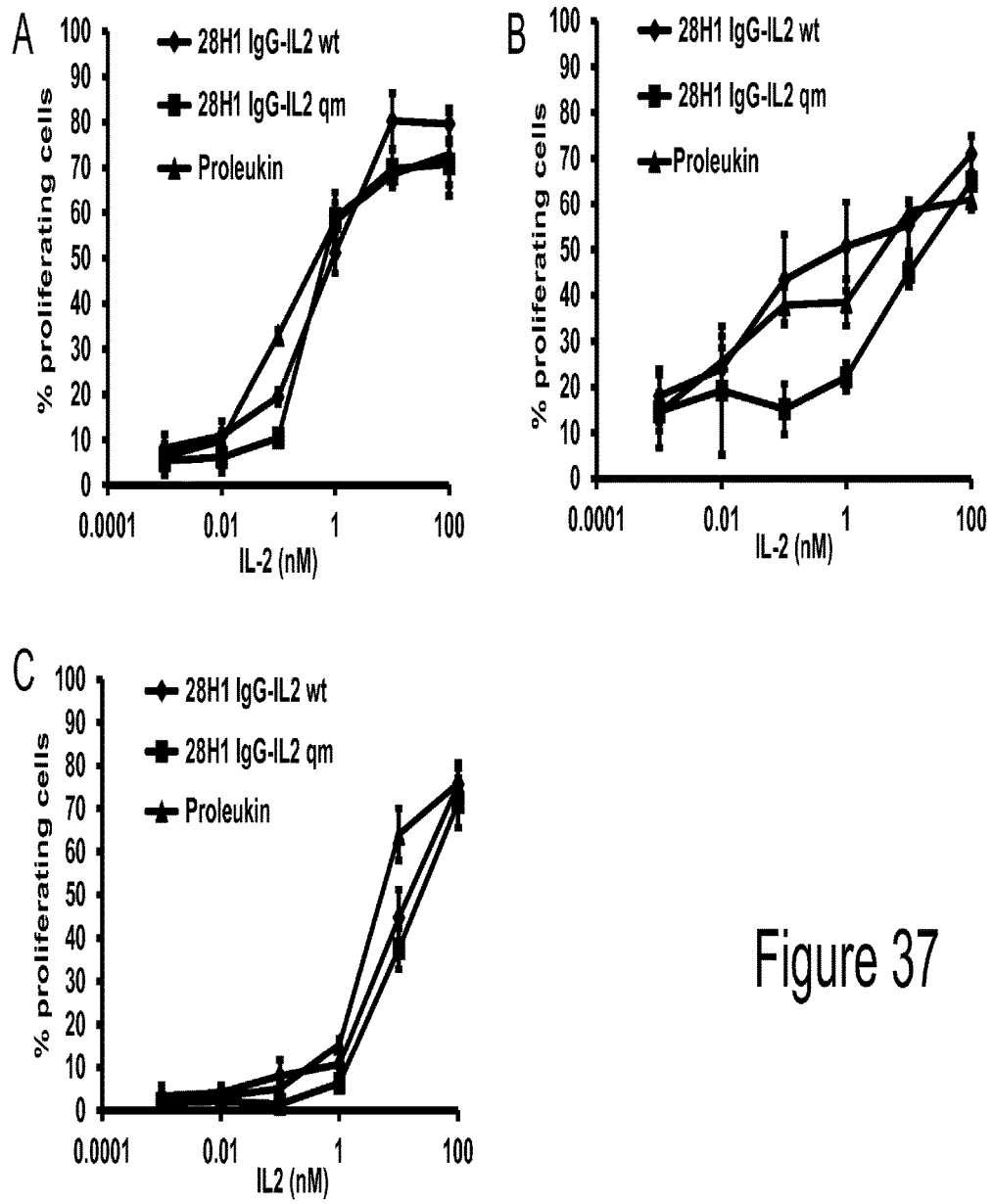

FIG. 37. Proliferation of NK cells (A), CD4 T-cells (B) and CD8 T-cells (C) upon incubation with different IL-2 immunoconjugates or Proleukin for 6 days.

FIG. 38. STAT phosphorylation in NK cells (A), CD8 T-cells (B), CD4 T-cells (C) and regulatory T-cells (D) after 30 min incubation with Proleukin, in-house produced wild-type IL-2 and quadruple mutant IL-2.

FIG. 39. STAT phosphorylation in NK cells (A), CD8 T-cells (B), CD4 T-cells (C) and regulatory T-cells (D) after 30 min incubation with Proleukin, IgG-IL-2 comprising wild-type IL-2 or IgG-IL-2 comprising quadruple mutant IL-2.

Figure 40:
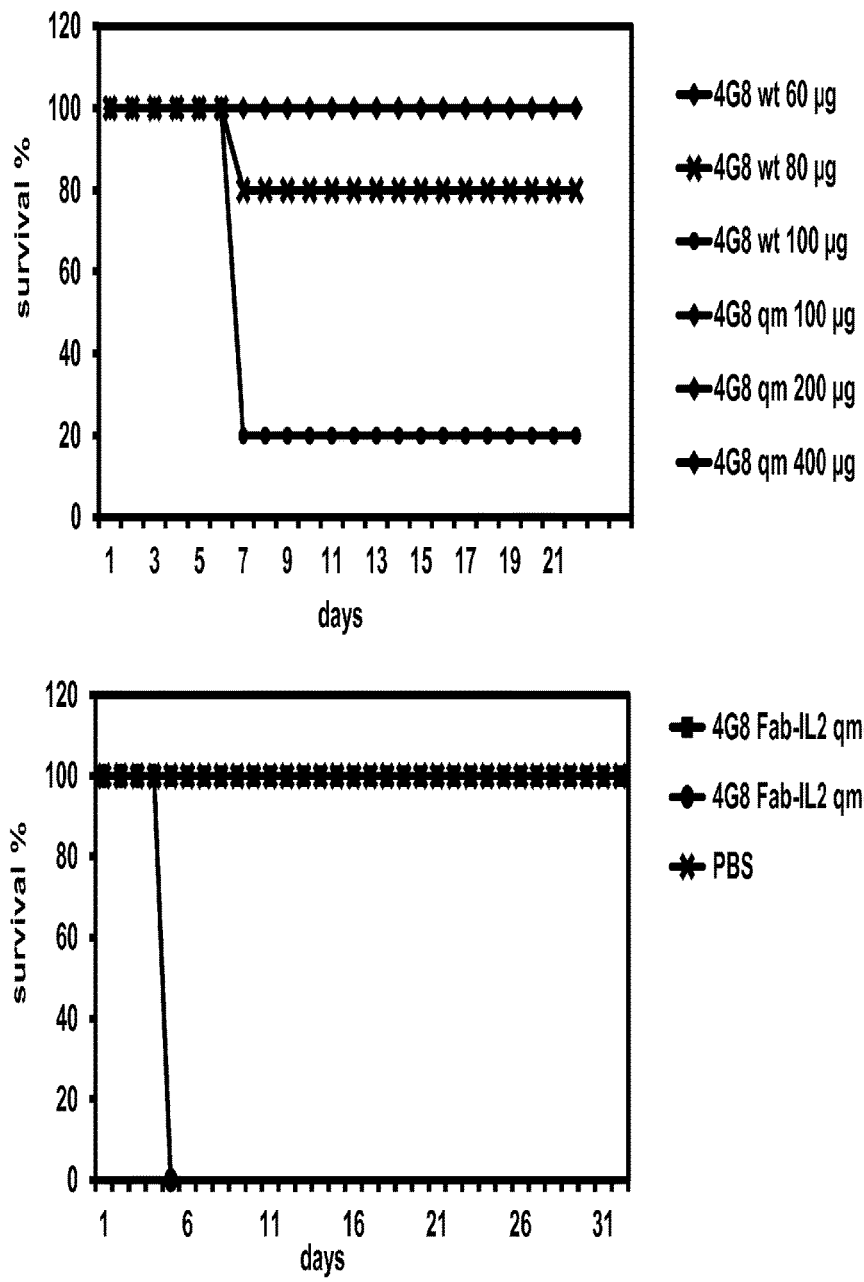

FIG. 40. Survival of Black 6 mice after administration (once daily for seven days) of different doses of IL-2 immunoconjugates comprising wild-type or quadruple mutant IL-2.

Figure 41:
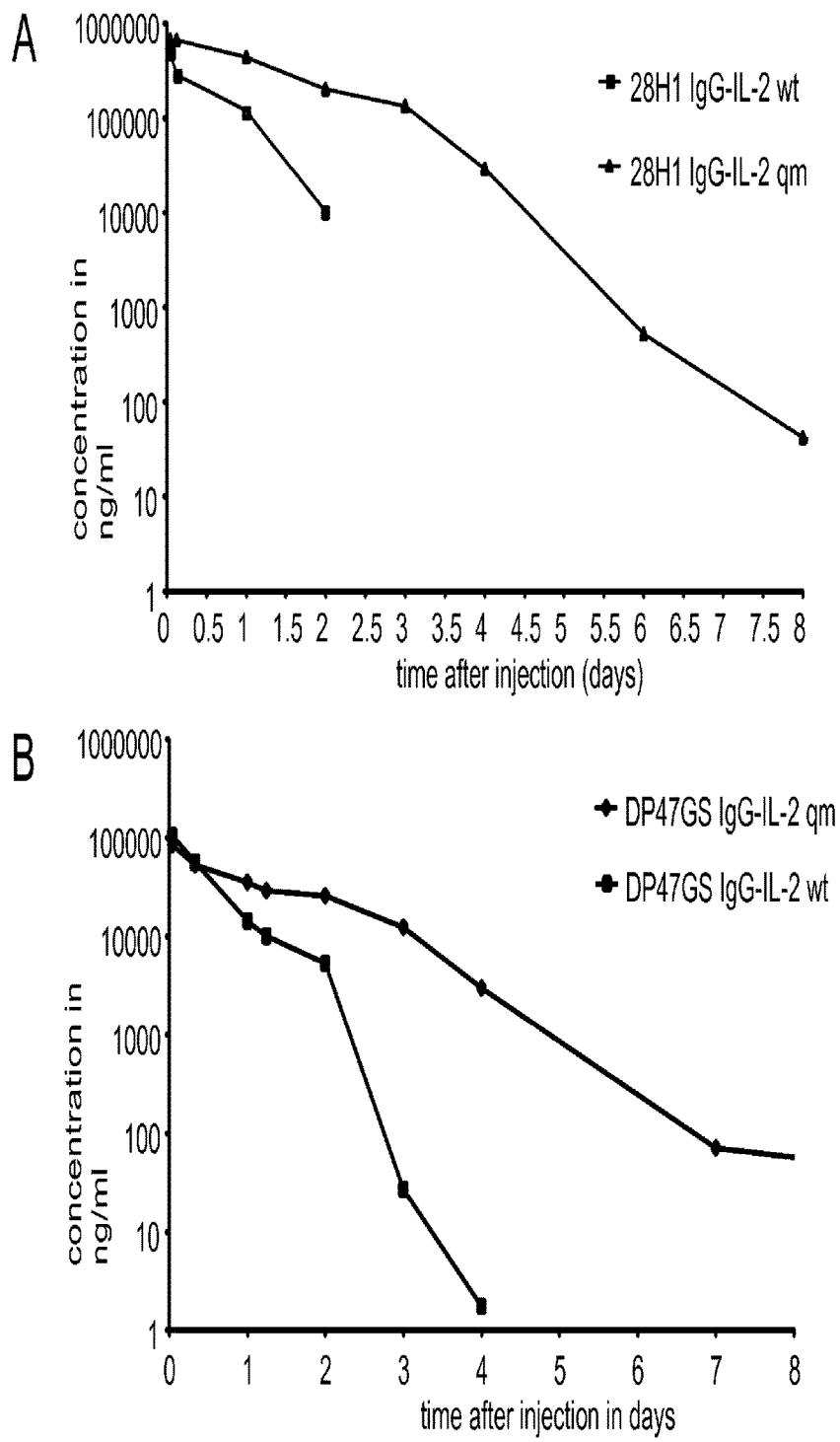

FIG. 41. Serum concentrations of IL-2 immunoconjugates after a single i.v. administration of FAP-targeted (A) and untargeted (B) IgG-IL-2 constructs comprising either wild-type (wt) or quadruple mutant (qm) IL-2.

Figure 42:
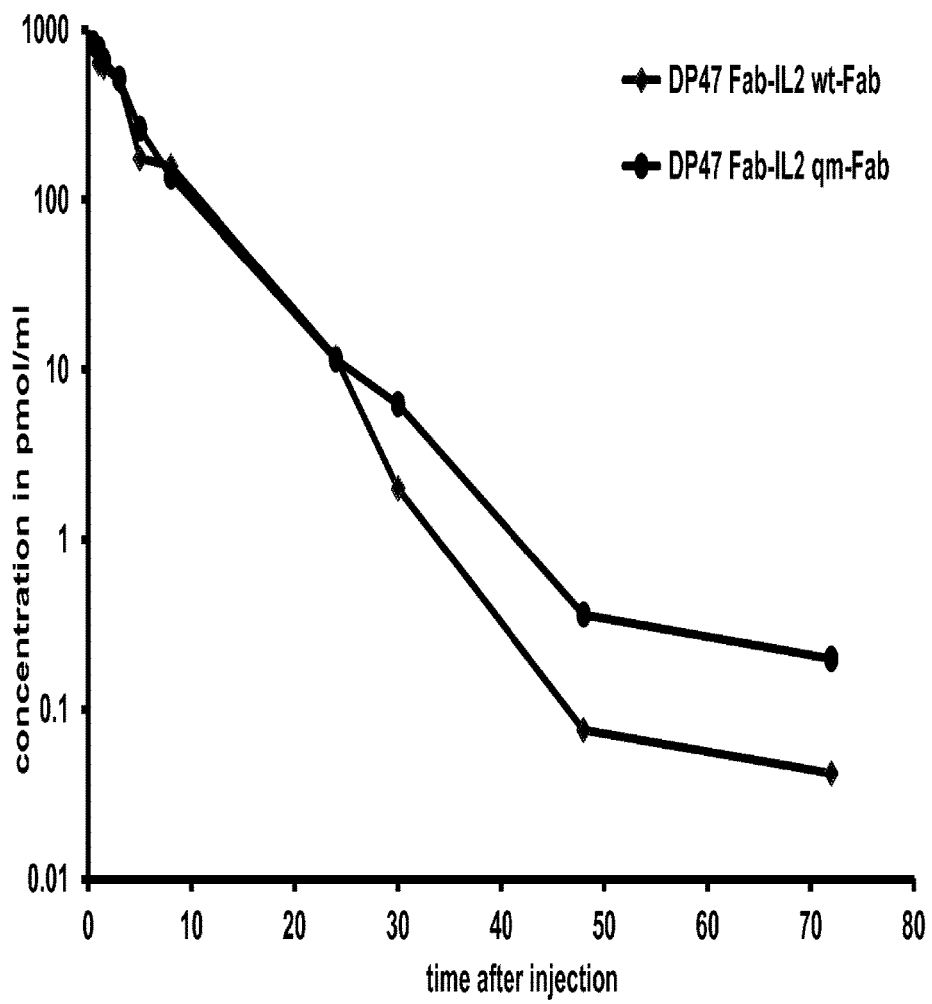

FIG. 42. Serum concentrations of IL-2 immunoconjugates after a single i.v. administration of untargeted Fab-IL-2-Fab constructs comprising either wild-type (wt) or quadruple mutant (qm) IL-2.

Figure 43:
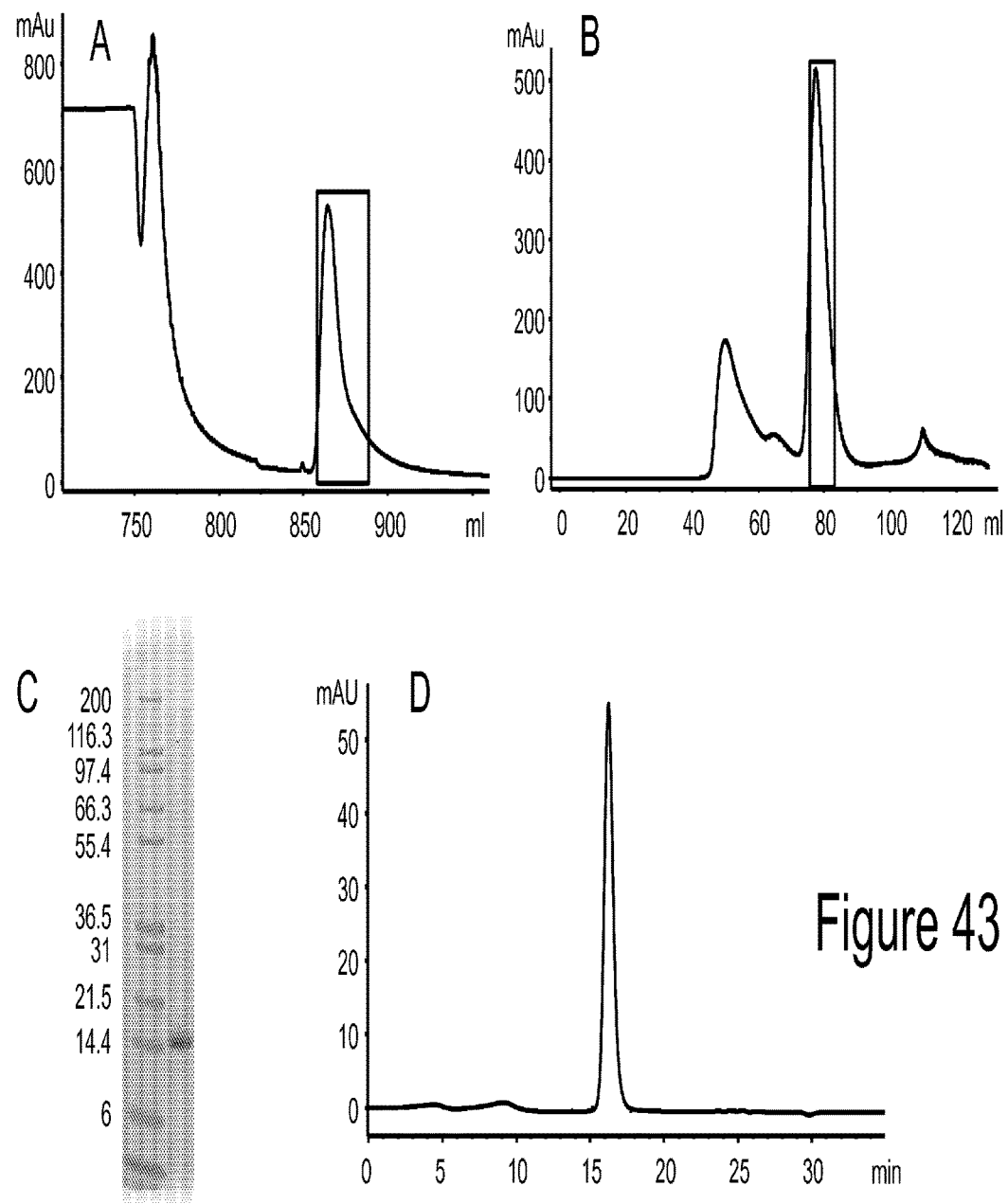

FIG. 43. Purification of quadruple mutant IL-2. (A) Immobilized metal ion chromatography; (B) size exclusion chromatography; (C) SDS PAGE under non-reducing conditions (NuPAGE Novex Bis-Tris gel (Invitrogen), MES running buffer); (D) analytical size exclusion chromatography (Superdex 75 10/300 GL).

Figure 44:
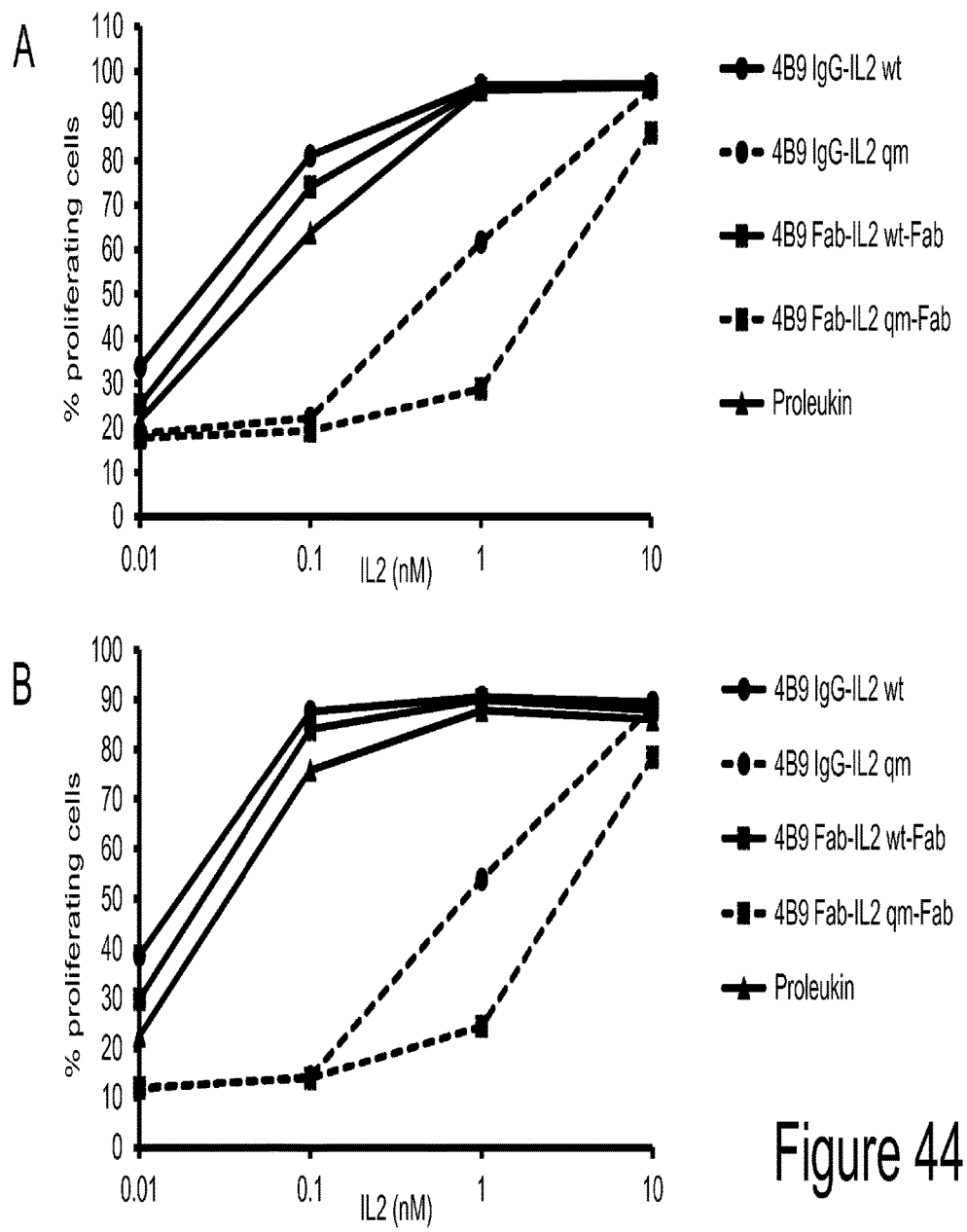

FIG. 44. Proliferation of pre-activated CD8 (A) and CD4 (B) T cells after six days incubation with different IL-2 immunoconjugates.

Figure 45:
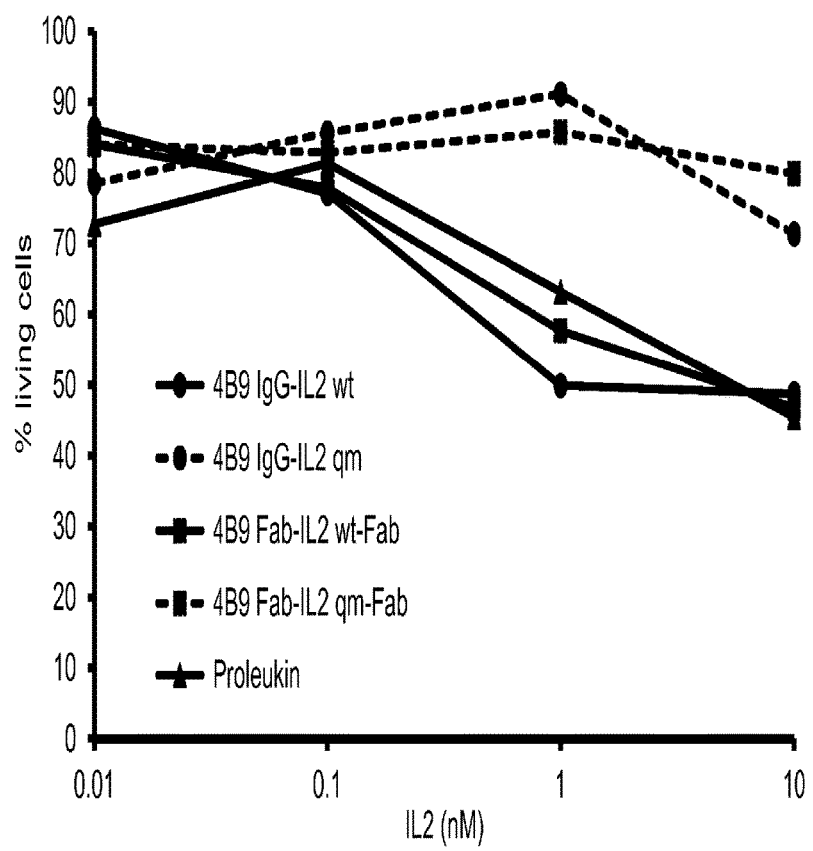

FIG. 45. Activation induced cell death of CD3+ T cells after six days incubation with different IL-2 immunoconjugates and overnight treatment with anti-Fas antibody.

Figure 46:
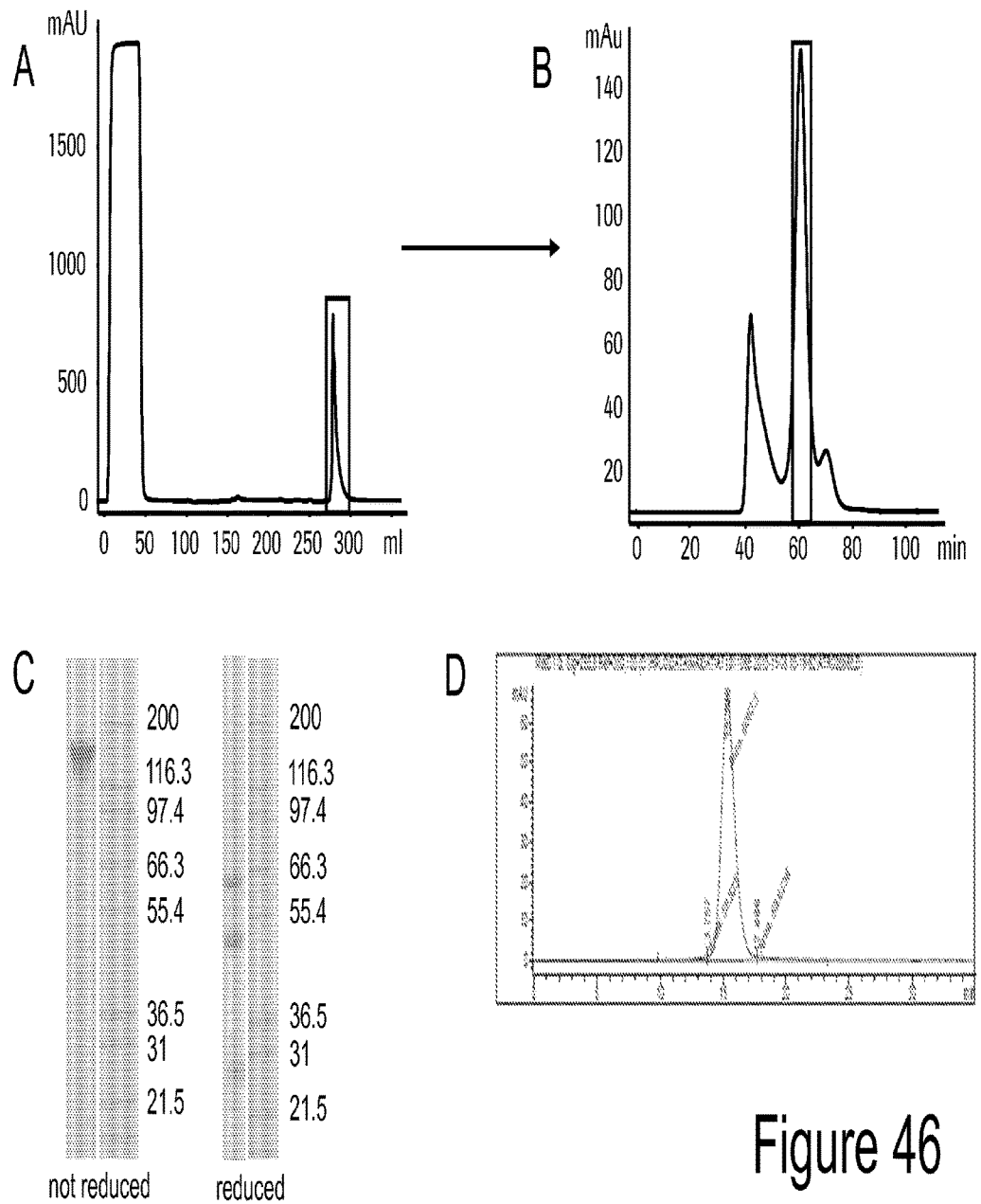

FIG. 46. Purification of FAP-targeted 4G8-based IgG-IL-2 quadruple mutant (qm) immunoconjugate. A) Elution profile of the Protein A affinity chromatography step. B) Elution profile of the size exclusion chromatography step. C) Analytical SDS-PAGE (NuPAGE Novex Bis-Tris Mini Gel, Invitrogen, MOPS running buffer) of the final product. D) Analytical size exclusion chromatography of the final product on a Superdex 200 column (97% monomer content).

Figure 47:
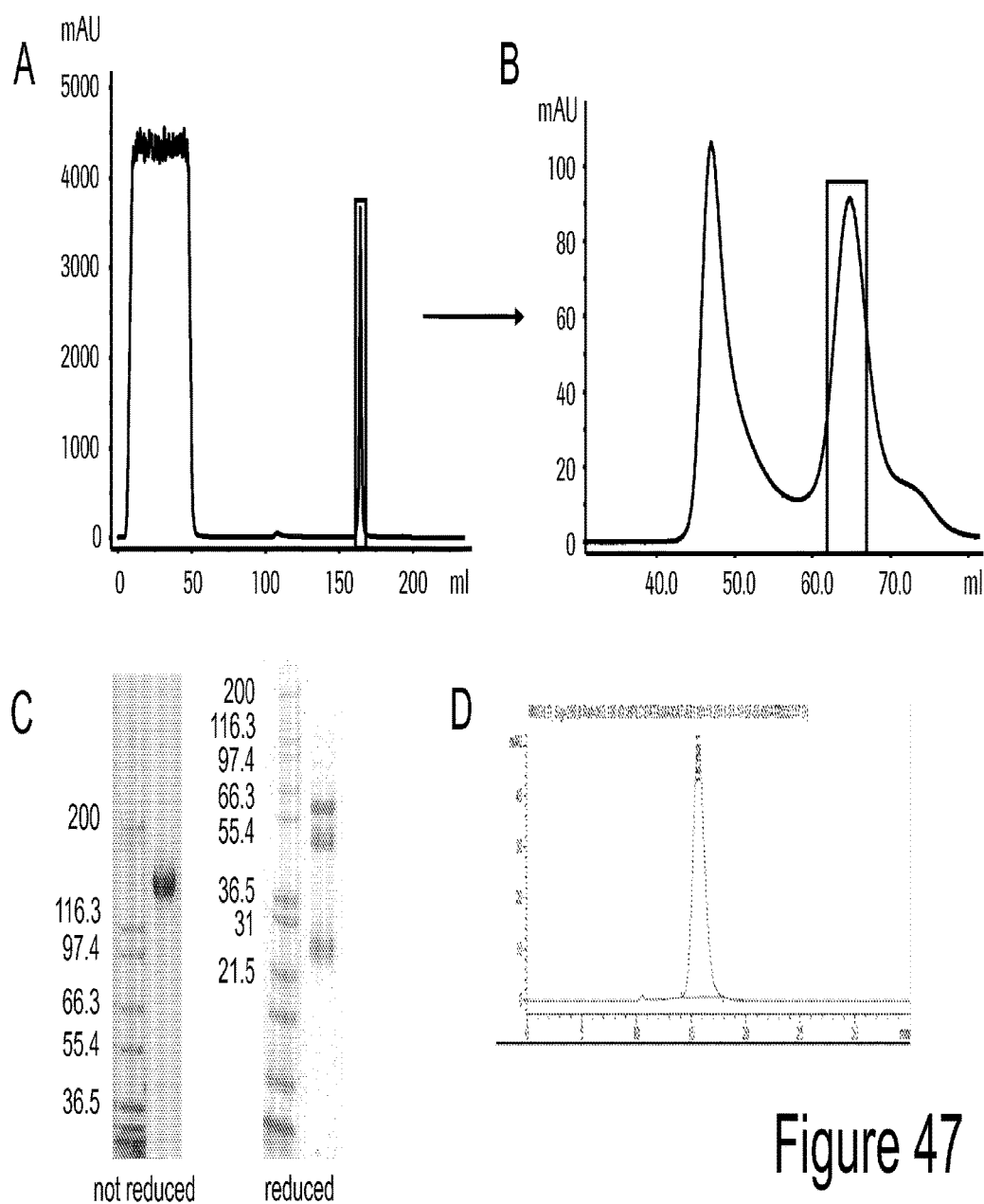

FIG. 47. Purification of FAP-targeted 28H1-based IgG-IL-2 qm immunoconjugate. A) Elution profile of the Protein A affinity chromatography step. B) Elution profile of the size exclusion chromatography step. C) Analytical SDS-PAGE (reduced: NuPAGE Novex Bis-Tris Mini Gel, Invitrogen, MOPS running buffer; non-reduced: NuPAGE Tris-Acetate, Invitrogen, Tris-Acetate running buffer) of the final product. D) Analytical size exclusion chromatography of the final product on a Superdex 200 column (100% monomer content).

Figure 48:
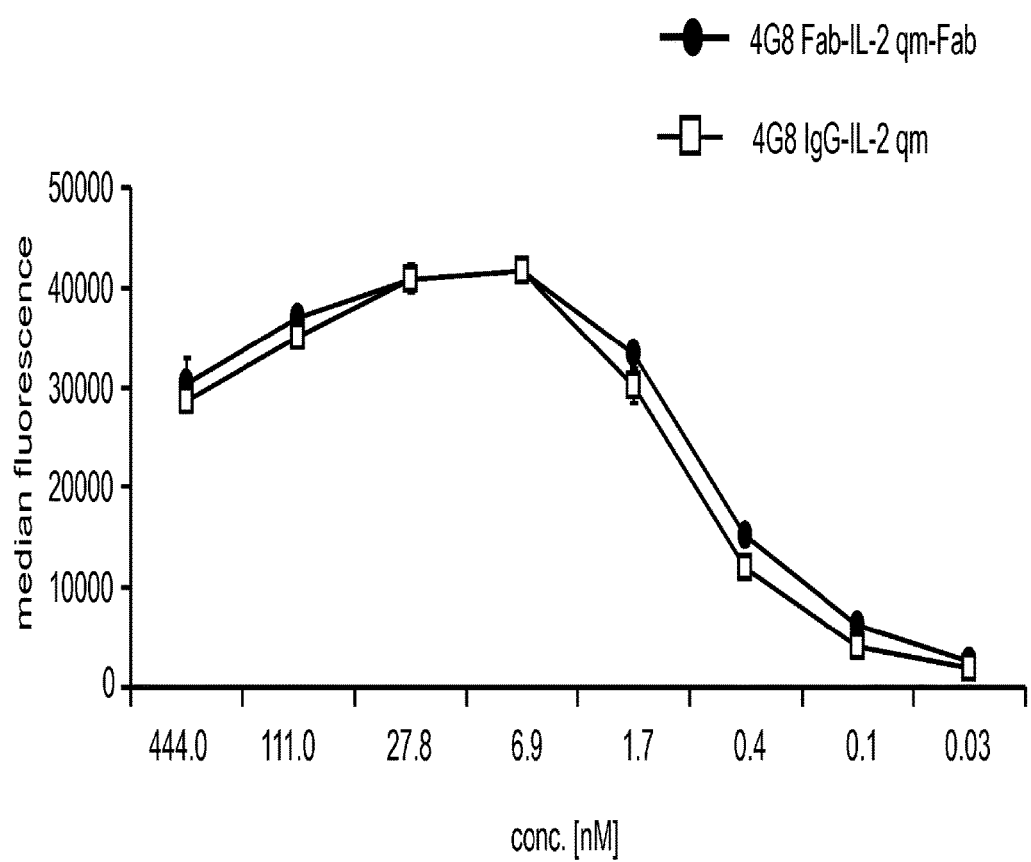

FIG. 48. Binding of FAP-targeted 4G8-based IgG-IL-2 qm immunoconjugate to human FAP expressed on stably transfected HEK 293 cells as measured by FACS, compared to the corresponding Fab-IL-2 qm-Fab construct.

FIG. 49. Interferon (IFN)-γ release on NK92 cells induced by FAP-targeted 4G8-based IgG-IL-2 qm immunoconjugate in solution, compared to the 28H1-based Fab-IL-2 qm-Fab construct.

FIG. 50. Detection of phosphorylated STAT5 by FACS in different cell types after stimulation for 20 min with FAP-targeted 4G8-based IgG-IL-2 qm immunoconjugate in solution, compared to the 28H1-based Fab-IL-2-Fab and Fab-IL-2 qm-Fab constructs as well as Proleukin. A) NK cells (CD3−CD56); B) CD8+ T cells (CD3+CD8+); C) CD4+ T cells (CD3+CD4+CD25−CD127+); D) regulatory T cells (CD4+CD25+FOXP3+).

EXAMPLES

The following are examples of methods and compositions of the invention. It is understood that various other embodiments may be practiced, given the general description provided above.

Example 1

General Methods
Recombinant DNA Techniques

Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturer's instructions. General information regarding the nucleotide sequences of human immunoglobulins light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments where required were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells. SEQ ID NOs 263-273 give exemplary leader peptides and polynucleotide sequences encoding them.

Preparation of IL-2R βγ Subunit-Fc Fusions and IL-2R α Subunit Fc Fusion

To study IL-2 receptor binding affinity, a tool was generated that allowed for the expression of a heterodimeric IL-2 receptor; the β-subunit of the IL-2 receptor was fused to an Fc molecule that was engineered to heterodimerize (Fc(hole)) (see SEQ ID NOs 274 and 275) using the "knobs-into-holes" technology (Merchant et al., Nat Biotech. 16, 677-681 (1998)). The γ-subunit of the IL-2 receptor was then fused to the Fc(knob) variant (see SEQ ID NOs 276 and 277), which heterodimerized with Fc(hole). This heterodimeric Fc-fusion protein was then used as a substrate for analyzing the IL-2/IL-2 receptor interaction. The IL-2R α-subunit was expressed as monomeric chain with an AcTev cleavage site and an Avi His tag (SEQ ID NOs 278 and 279). The respective IL-2R subunits were transiently expressed in HEK EBNA 293 with serum for the IL-2R βγ subunit construct and without serum for the α-subunit construct. The IL-2R βγ subunit construct was purified on protein A (GE Healthcare), followed by size exclusion chromatography (GE Healthcare, Superdex 200). The IL-2R α-subunit was purified via His tag on a NiNTA column (Qiagen) followed by size exclusion chromatography (GE Healthcare, Superdex 75).

Preparation of Immunoconjugates

Details about the preparation and purification of Fab-IL-2-Fab immunoconjugates, including generation and affinity maturation of antigen binding moieties can be found in the Examples appended to PCT publication no. WO 2011/020783, which is incorporated herein by reference in its entirety. As described therein, various antigen binding domains directed to FAP have been generated by phage display, including the ones designated 4G8, 3F2, 28H1, 29B11, 14B3, and 4B9 used in the following examples. Clone 28H1 is an affinity matured antibody based on parental clone 4G8, while clones 29B11, 14B3 and 4B9 are affinity matured antibodies based on parental clone 3F2. The antigen binding domain designated MHLG1 KV9 used herein is directed to MCSP.

The sequences of immunoconjugates comprising wild-type IL-2 that were used in the following examples can also be found in PCT publication no. WO 2011/020783. The sequences corresponding to the immunoconjugates comprising quadruple mutant IL-2 that were used in the following examples are: 4G8: SEQ ID NOs 211 and 233; 3F2: SEQ ID NOs 209 and 231; 28H1: SEQ ID NOs 219 and 233; 29B11: SEQ ID NOs 221 and 231; 14B3: SEQ ID NOs 229 and 231; 4B9: SEQ ID NOs 227 and 231; MHLG1-KV9: SEQ ID NOs 253 and 255. The DNA sequences were generated by gene synthesis and/or classical molecular biology techniques and subcloned into mammalian expression vectors (one for the light chain and one for the heavy chain/IL-2 fusion protein) under the control of an MPSV promoter and upstream of a synthetic polyA site, each vector carrying an EBV OriP sequence. Immunoconjugates as applied in the examples below were produced by co-transfecting exponentially growing HEK293-EBNA cells with the mammalian expression vectors using calcium phosphate-transfection. Alternatively, HEK293 cells growing in suspension were transfected by polyethylenimine (PEI) with the respective expression vectors. Alternatively, stably transfected CHO cell pools or CHO cell clones were used for production in serum-free media. While 4G8-based FAP-targeted Fab-IL-2-Fab constructs comprising wild-type or (quadruple) mutant IL-2 can be purified by affinity chromatography using a protein A matrix, affinity matured 28H1-based FAP-targeted Fab-IL-2-Fab constructs were purified by affinity chromatography on a protein G matrix in small scale.

Briefly, FAP-targeted 28H1 Fab-IL-2-Fab, comprising wild-type or (quadruple) mutant IL-2, was purified from cell supernatants by one affinity step (protein G) followed by size exclusion chromatography (Superdex 200, GE Healthcare). The protein G column was equilibrated in 20 mM sodium phosphate, 20 mM sodium citrate pH 7.5, supernatant was loaded, and the column was washed with 20 mM sodium phosphate, 20 mM sodium citrate pH 7.5. Fab-IL-2-Fab was eluted with 8.8 mM formic acid pH 3. The eluted fractions were pooled and polished by size exclusion chromatography in the final formulation buffer: 25 mM potassium phosphate, 125 mM sodium chloride, 100 mM glycine pH 6.7. Exemplary results from purification and analytics are given below.

FAP-targeted 3F2 Fab-IL-2-Fab or 4G8 Fab-IL-2-Fab, comprising wild-type or (quadruple) mutant IL-2, were purified by a similar method composed of one affinity step using protein A followed by size exclusion chromatography (Superdex 200, GE Healthcare). The protein A column was equilibrated in 20 mM sodium phosphate, 20 mM sodium citrate pH 7.5, supernatant was loaded, and the column was washed with 20 mM sodium phosphate, 20 mM sodium citrate, 500 mM sodium chloride pH 7.5, followed by a wash with 13.3 mM sodium phosphate, 20 mM sodium citrate, 500 mM sodium chloride pH 5.45. A third wash with 10 mM MES, 50 mM sodium chloride pH 5 was optionally performed. Fab-IL-2-Fab was eluted with 20 mM sodium citrate, 100 mM sodium chloride, 100 mM glycine, pH 3. The eluted fractions were pooled and polished by size exclusion chromatography in the final formulation buffer: 25 mM potassium phosphate, 125 mM sodium chloride, 100 mM glycine pH 6.7. Exemplary detailed purification procedures and results are given for selected constructs below.

FAP-targeted IgG-IL-2 qm fusion proteins were generated based on the FAP-antibodies 4G8, 4B9 and 28H1, wherein one single IL-2 quadruple mutant (qm) was fused to the C-terminus of one heterodimeric heavy chain as shown in FIG. 1B. Targeting to the tumor stroma where FAP is selectively expressed is achieved via the bivalent antibody Fab region (avidity effect). Heterodimerization resulting in the presence of a single IL-2 quadruple mutant is achieved by application of the knob-into-hole technology. In order to minimize the generation of homodimeric IgG-cytokine fusions the cytokine was fused to the C-terminus (with deletion of the C-terminal Lys residue) of the knob-containing IgG heavy chain via a $G_4$-$(SG_4)_2$- or $(G_4S)_3$-linker. The antibody-cytokine fusion has IgG-like properties. To reduce FcγR binding/effector function and prevent FcR co-activation, P329G L234A L235A (LALA) mutations were introduced in the Fc domain. The sequences of these immuno- conjugates are given in SEQ ID NOs 297, 299 and 233 (28H1), SEQ ID NOs 301, 303 and 231 (4B9), and SEQ ID NOs 315, 317 and 233 (4G8)). In addition, a CEA-targeted IgG-IL-2 qm fusion protein and a control DP47GS non-targeted IgG-IL-2 qm fusion protein wherein the IgG does not bind to a specified target was generated. The sequences of these immunoconjugates are given in SEQ ID NOs 305, 307 and 309 (DP47GS), and SEQ ID NOs 319, 321 and 323 (CH1A1A).

The IgG-IL-2 constructs were generated by transient expression in HEK293 EBNA cells and purified essentially as described above for the Fab-IL-2-Fab constructs. Briefly, IgG-IL-2 fusion proteins were purified by one affinity step with protein A (HiTrap ProtA, GE Healthcare) equilibrated in 20 mM sodium phosphate, 20 mM sodium citrate pH 7.5. After loading of the supernatant, the column was first washed with 20 mM sodium phosphate, 20 mM sodium citrate, pH 7.5 and subsequently washed with 13.3 mM sodium phosphate, 20 mM sodium citrate, 500 mM sodium chloride, pH 5.45. The IgG-cytokine fusion protein was eluted with 20 mM sodium citrate, 100 mM sodium chloride, 100 mM glycine, pH 3. Fractions were neutralized and pooled and purified by size exclusion chromatography (HiLoad 16/60 Superdex 200, GE Healthcare) in final formulation buffer: 25 mM potassium phosphate, 125 mM sodium chloride, 100 mM glycine pH 6.7. Exemplary detailed purification procedures and results are given for selected constructs below. The protein concentration of purified protein samples was determined by measuring the optical density (OD) at 280 nm, using the molar extinction coefficient calculated on the basis of the amino acid sequence. Purity and molecular weight of immunoconjugates were analyzed by SDS-PAGE in the presence and absence of a reducing agent (5 mM 1,4-dithiotreitol) and stained with Coomassie blue (SimpleBlue™ SafeStain, Invitrogen). The NuPAGE® Pre-Cast gel system (Invitrogen) was used according to the manufacturer's instructions (4-20% Tris-glycine-gels or 3-12% Bis-Tris). The aggregate content of immunoconjugate samples was analyzed using a Superdex 200 10/300GL analytical size-exclusion column (GE Healthcare) in 2 mM MOPS, 150 mM NaCl, 0.02% $NaN_3$, pH 7.3 running buffer at 25° C.

FAP Binding Affinity

The FAP binding activity of the cleaved Fab fragments used in these examples as antigen binding, moieties was determined by surface plasmon resonance (SPR) on a Biacore machine. Briefly, an anti-His antibody (Penta-His, Qiagen 34660) was immobilized on CM5 chips to capture 10 nM human, murine or cynomolgus FAP-His (20 s). Temperature was 25° C. and HBS-EP was used as buffer. Fab analyte concentration was 100 nM down to 0.41 nM (duplicates) at a flow rate of 50 µl/min (association: 300 s, dissociation: 600 s (4B9, 14B3, 29B11, 3F2) or 1200 s (28H1, 4G8), regeneration: 60 s 10 mM glycine pH 2). Fitting was performed based on a 1:1 binding model, RI=0, Rmax=local (because of capture format). Table 2 gives the monovalent affinities as determined by SPR.

TABLE 2

Affinity ($K_D$) of FAP-targeted Fab fragments to FAP as determined by SPR.

| $K_D$ in nM | Human FAP | Cynomolgus FAP | Murine FAP |
| --- | --- | --- | --- |
| 4B9 Fab | 0.3 | 0.23 | 5 |
| | 0.31 | 0.24 | 5.2 |

TABLE 2-continued

Affinity ($K_D$) of FAP-targeted Fab fragments to FAP as determined by SPR.

| $K_D$ in nM | Human FAP | Cynomolgus FAP | Murine FAP |
|---|---|---|---|
| 14B3 Fab | 0.47 | 0.61 | 4.7 |
|  | 0.47 | 0.59 | 4.7 |
| 29B11 Fab | 0.19 | 0.21 | 1.3 |
|  | 0.19 | 0.2 | 1.2 |
| 3F2 Fab | 6 | 4.7 | 8.9 |
|  | 6 | 5.3 | 9.5 |
| 28H1 Fab | 2.6 | 3.7 | 0.13 |
|  | 2.6 | 3.7 | 0.18 |
| 4G8 Fab | 53 (48 steady state) | 33 (33 steady state) | 0.07 |
|  | 51 (48 steady state) | 35 (34 steady state) | 0.07 |

Biological Activity Assays with Targeted IL-2 Immunoconjugates

The biological activity of FAP- or MCSP-targeted Fab-IL-2-Fab immunoconjugates and of FAP-targeted IgG-IL-2 immunoconjugates, comprising wild-type or (quadruple) mutant IL-2, was investigated in several cellular assays in comparison to commercially available IL-2 (Proleukin, Novartis, Chiron).

IFN-γ Release by NK Cells (in Solution)

IL-2 starved NK92 cells (100000 cells/well in 96-U-well plate) were incubated with different concentrations of IL-2 immunoconjugates, comprising wild-type or (quadruple) mutant IL-2, for 24 h in NK medium (MEM alpha from Invitrogen (#22561-021) supplemented with 10% FCS, 10% horse serum, 0.1 mM 2-mercaptoethanol, 0.2 mM inositol and 0.02 mM folic acid). Supernatants were harvested and the IFN-γ release was analysed using the anti-human IFN-γ ELISA Kit II from Becton Dickinson (#550612). Proleukin (Novartis) served as positive control for IL-2-mediated activation of the cells.

NK Cell Proliferation

Blood from healthy volunteers was taken in heparin-containing syringes and PBMCs were isolated. Untouched human NK cells were isolated from the PBMCs using the Human NK Cell Isolation Kit II from Miltenyi Biotec (#130-091-152). The CD25 expression of the cells was checked by flow cytometry. For proliferation assays, 20000 isolated human NK cells were incubated for 2 days in a humidified incubator at 37° C., 5% $CO_2$ in the presence of different IL-2 immunoconjugates, comprising wild-type or (quadruple) mutant IL-2. Proleukin (Novartis) served as control. After 2 days, the ATP content of the cell lysates was measured using the CellTiter-Glo Luminescent Cell Viability Assay from Promega (#G7571/2/3). The percentage of growth was calculated setting the highest Proleukin concentration to 100% proliferation and untreated cells without IL-2 stimulus to 0% proliferation.

STAT5 Phosphorylation Assay

Blood from healthy volunteers was taken in heparin-containing syringes and PBMCs were isolated. PBMCs were treated with IL-2 immunoconjugates, comprising wild-type or (quadruple) mutant IL-2, at the indicated concentrations or with Proleukin (Novartis) as control. After 20 min incubation at 37° C., PBMCs were fixed with pre-warmed Cytofix buffer (Becton Dickinson #554655) for 10 min at 37° C., followed by permeabilization with Phosflow Perm Buffer III (Becton Dickinson #558050) for 30 min at 4° C. Cells were washed twice with PBS containing 0.1% BSA before FACS staining was performed using mixtures of flow cytometry antibodies for detection of different cell populations and phosphorylation of STAT5. Samples were analysed using a FACSCantoII with HTS from Becton Dickinson.

NK cells were defined as $CD3^-CD56^+$, CD8 positive T cells were defined as $CD3^+CD8^+$, CD4 positive T cells were defined as $CD4^+CD25^-CD127^+$ and $T_{reg}$ cells were defined as $CD4^+CD25^+FoxP3^+$.

Proliferation and AICD of T Cells

Blood from healthy volunteers was taken in heparin-containing syringes and PBMCs were isolated. Untouched T cells were isolated using the Pan T Cell Isolation Kit II from Miltenyi Biotec (#130-091-156). T cells were pre-stimulated with 1 µg/ml PHA-M (Sigma Aldrich #L8902) for 16 h before adding Proleukin or Fab-IL-2-Fab immunoconjugates, comprising wild-type or (quadruple) mutant IL-2, to the washed cells for another 5 days. After 5 days, the ATP content of the cell lysates was measured using the CellTiter-Glo Luminescent Cell Viability Assay from Promega (#G7571/2/3). The relative proliferation was calculated setting the highest Proleukin concentration to 100% proliferation.

Phosphatidylserine (PS) exposure and cell death of T cells were assayed by flow cytometric analysis (FACSCantoII, BD Biosciences) of annexin V (Annexin-V-FLUOS Staining Kit, Roche Applied Science) and propidium iodide (PI)-stained cells. To induce activation-induced cell death (AICD); the T cells were treated with an apoptosis-inducing anti-Fas antibody (Millipore clone Ch11) for 16 h after the 16 h PHA-M and 5 days treatment with Fab-IL-2-Fab immunoconjugates. Annexin V staining was performed according to the manufacturer's instructions. Briefly, cells were washed with Ann-V Binding Buffer (lx stock: 0.01 M Hepes/NaOH pH7.4, 0.14 M NaCl, 2.5 mM $CaCl_2$) and stained for 15 mM at RT in the dark with Annexin V FITC (Roche). Cells were washed again in Ann-V-Binding buffer before addition of 200 µl/well Ann-V-Binding Buffer containing PI (0.3 µg/ml). The cells were analysed immediately by flow cytometry.

Binding to FAP Expressing Cells

Binding of FAP-targeted IgG-IL-2 qm and Fab-IL-2 qm-Fab immunoconjugates to human FAP expressed on stably transfected HEK293 cells was measured by FACS. Briefly, 250 000 cells per well were incubated with the indicated concentration of the immunoconjugates in a round-bottom 96-well plate, incubated for 30 min at 4° C., and washed once with PBS/0.1% BSA. Bound immunoconjugates were detected after incubation for 30 mM at 4° C. with FITC-conjugated AffiniPure F(ab')2 Fragment goat anti-human F(ab')2 Specific (Jackson Immuno Research Lab #109-096-097, working solution: 1:20 diluted in PBS/0.1% BSA, freshly prepared) using a FACS CantoII (Software FACS Diva).

Analysis of FAP Internalization Upon Binding by FACS

For several FAP antibodies known in the art it is described that they induce FAP internalization upon binding (described e.g. in Baum et al., J Drug Target 15, 399-406 (2007); Bauer et al., Journal of Clinical Oncology, 2010 ASCO Annual Meeting Proceedings (Post-Meeting Edition), vol. 28 (May 20 Supplement), abstract no. 13062 (2010); Ostermann et al., Clin Cancer Res 14, 4584-4592 (2008)). Thus, we analyzed the internalization properties of our Fab-IL-2-Fab immunoconjugates. Briefly, GM05389 cells (human lung fibroblasts) cultured in EMEM medium with 15% FCS, were detached, washed, counted, checked for viability and seeded at a density of $2\times10^5$ cells/well in 12-well plates. The next day, FAP-targeted Fab-IL-2-Fab immunoconjugates were diluted in cold medium and allowed to bind to cell surface for 30 min on ice. The excess of unbound antibody was washed away using cold PBS and cells were further incubated in 0.5 ml complete pre-warmed medium at 37° C. for the indicated time periods. When the different time points were reached, cells were transferred on ice, washed once with cold PBS and incubated with the secondary antibody (FITC-conjugated AffiniPure F(ab')2 Fragment goat anti-human F(ab')2 specific, Jackson Immuno Research Lab #109-096-097, 1:20 dilution) for 30 min at 4° C. Cells were then washed twice with PBS/0.1% BSA, transferred to a 96-well plate, centrifuged for 4 min at 4° C., 400×g and cell pellets were resuspended by vortexing. Cells were fixed using 100 μl 2% PFA. For FACS measurement, cells were re-suspended in 200 al/sample PBS/0.1% BSA and measured with the plate protocol in FACS CantoII (Software FACS Diva).

Example 2

We designed mutated versions of IL-2 that comprised one or more of the following mutations (compared to the wild-type IL-2 sequence shown in SEQ ID NO: 1):
1. T3A—knockout of predicted O-glycosylation site
2. F42A—knockout of IL-2/IL-2R α interaction
3. Y45A—knockout of IL-2/IL-2R α interaction
4. L72G—knockout of IL-2/IL-2R α interaction
5. C125A—previously described mutation to avoid disulfide-bridged IL-2 dimers A mutant IL-2 polypeptide comprising all of mutations 1-4 is denoted herein as IL-2 quadruple mutant (qm). It may further comprise mutation 5 (see SEQ ID NO: 19).

In addition to the three mutations F42A, Y45A and L72G designed to interfere with the binding to CD25, the T3A mutation was chosen to eliminate the O-glycosylation site and obtain a protein product with higher homogeneity and purity when the IL-2 qm polypeptide or immunoconjugate is expressed in eukaryotic cells such as CHO or HEK293 cells.

For purification purposes a His6 tag was introduced at the C-terminus linked via a VD sequence. For comparison a non-mutated analogous version of IL-2 was generated that only contained the C145A mutation to avoid undesired inter-molecular disulfide bridges (SEQ ID NO: 3). The respective molecular weights without signal sequence were 16423 D for naked IL-2 and 16169 D for the naked IL-2 qm. The wild-type and quadruple mutant IL-2 with His tag were transfected in HEK EBNA cells in serum-free medium (F17 medium) The filtered supernatant was buffer exchanged over a cross-flow, before loading it on a NiNTA Superflow Cartridge (5 ml, Qiagen). The column was washed with wash buffer: 20 mM sodium phosphate, 0.5 M sodium chloride pH 7.4 and eluted with elution buffer: 20 mM sodium phosphate, 0.5 M sodium chloride 0.5 M imidazole pH 7.4. After loading the column was washed with 8 column volumes (CV) wash buffer, 10 CV 5% elution buffer (corresponds to 25 mM imidazole), then eluted with a gradient to 0.5 M imidazole. The pooled eluate was polished by size exclusion chromatography on a HiLoad 16/60 Superdex75 (GE Healthcare) column in 2 mM MOPS, 150 mM sodium chloride, 0.02% sodium azide pH 7.3. FIG. 2 shows the chromatogram of the His tag purification for the wild-type naked IL-2. Pool 1 was made from fractions 78-85, pool 2 from fractions 86-111. FIG. 3 shows the chromatogram of the size exclusion chromatography for the wild-type IL-2, for each pool the fractions 12 to 14 were pooled. FIG. 4 shows the analytical size exclusion chromatography for wild-type IL-2 as determined on a Superdex 75, 10/300 GL (GE Healthcare) column in 2 mM MOPS, 150 mM sodium chloride, 0.02% sodium azide pH 7.3. Pool 1 and 2 contained 2 proteins of ca. 22 and 20 kDa. Pool 1 had more of the large protein, and pool 2 had more of the small protein, putatively this difference is due to differences in O-glycosylation. Yields were ca. 0.5 mg/L supernatant for pool 1 and ca. 1.6 mg/L supernatant for pool 2. FIG. 5 shows the chromatogram of the His tag purification for the quadruple mutant IL-2. Pool 1 was made from fractions 59-91, pool 2 from fractions 92-111. FIG. 6 shows the chromatogram of the size exclusion chromatography for the quadruple mutant IL-2, here only pool 2 fractions 12 to 14 were kept. FIG. 7 shows the analytical size exclusion chromatography for the quadruple mutant IL-2 as determined on a Superdex 75, 10/300 GL (GE Healthcare) column in 2 mM MOPS, 150 mM sodium chloride, 0.02% sodium azide pH 7.3. The preparation for the naked quadruple mutant IL-2 contained only one protein of 20 kD. This protein has the O-glycosylation site knocked out. Aliquots of the naked IL-2 wild-type and quadruple mutant were stored frozen at −80° C. Yields were ca 0.9 mg/L supernatant.

A second batch of His-tagged quadruple mutant IL-2 was purified as described above by immobilized metal ion affinity chromatography (IMAC) and followed by size exclusion chromatography (SEC). The buffers used for IMAC were 50 mM Tris, 20 mM imidazole, 0.5M NaCl pH 8 for column equilibration and washing, and 50 mM Tris, 0.5 M imidazole, 0.5 M NaCl pH 8 for elution. The buffer used for SEC and final formulation buffer was 20 mM histidine, 140 mM NaCl pH 6. FIG. 43 shows the result of that purification. The yield was 2.3 ml/L supernatant.

Subsequently, affinity for the IL-2R βγ heterodimer and the IL-2R α-subunit were determined by surface plasmon resonance (SPR). Briefly, the ligand—either human IL-2R α-subunit (Fc2) or human IL2-R β knob γ hole heterodimer (Fc3)—was immobilized on a CM5 chip. Subsequently, naked wild-type (pool 1 and 2) or quadruple mutant IL-2, and Proleukin (Novartis/Chiron) were applied to the chip as analytes at 25° C. in HBS-EP buffer in concentrations ranging from 300 nM down to 1.2 nM (1:3 dil.). Flow rate was 30 μl/min and the following conditions were applied for association: 180 s, dissociation: 300 s, and regeneration: 2×30 s 3M MgCl$_2$ for IL2-R β knob γ hole heterodimer, 10 s-50 mM NaOH for IL-2R α-subunit. 1:1 binding was applied for fitting (1:1 binding RI≠0, Rmax=local for IL-2R βγ, apparent K$_D$, 1:1 binding RI=0, Rmax=local for IL-2R α). Table 3 shows the respective K$_D$ values for binding of human wild-type and quadruple mutant IL-2 as well as of Proleukin to IL-2R βγ and α-subunit.

TABLE 3

Affinity of mutant IL-2 polypeptides to the intermediate affinity IL-2R and the IL-2R α-subunit.

| K$_D$ in nM T = 25° C. | Hu IL-2R βγ (kinetic) | Hu IL-2R α (kinetic) | Hu IL-2R α (steady state) |
|---|---|---|---|
| Naked IL-2 wt, pool 1 | 5.6 | 17.4 | 30.3 |
|  | 5 | 16.6 | 23.9 |
| Naked IL-2 wt, pool 2 | 2.8 | 10.6 | 19.7 |
|  | 1.8 | 10 | 17.6 |
| Naked IL-2 qm | 2.7 | no binding | no binding |
|  | 2 |  |  |
| Proleukin | 2.4 | 7.5 | 19 |
|  | 2.8 | 12.5 | 17.8 |

The data show that the naked IL-2 quadruple mutant shows the desired behaviour and has lost binding for the IL-2R α-subunit whereas binding to IL-2R βγ is retained and comparable to the respective wild type IL-2 construct and Proleukin. Differences between pools 1 and 2 of the wild-type IL-2 can probably be attributed to differences in O-glycosylation. This variability and heterogeneity has been overcome in the IL-2 quadruple mutant by introduction of the T23A mutation.

Example 3

The three mutations F42A, Y45A and L72G and the mutation T3A were introduced in the Fab-IL-2-Fab format (FIG. 1A) using the anti-FAP antibody 4G8 as model targeting domain either as single mutants: 1) 4G8 IL-2 T3A, 2) 4G8 IL-2 F42A, 3) 4G8 IL-2 Y45A, 4) 4G8 IL-2 L72G, or they were combined in Fab-IL-2 wt-Fab constructs as: 5) triple mutant F42A/Y45A/L72G, or as: 6) quadruple mutant T3A/F42A/Y45A/L72G to inactivate the O-glycosylation site as well. The 4G8-based Fab-IL-2 wt-Fab served for comparison. All constructs contained the C145A mutation to avoid disulfide-bridged IL-2 dimers. The different Fab-IL 2-Fab constructs were expressed in HEK 293 cells and purified as described above via protein A and size exclusion chromatography as specified above. Subsequently, the affinity of the selected IL 2 variants for the human and murine IL 2R $\beta\gamma$ heterodimer and for the human and murine IL-2R $\alpha$-subunit was determined by surface plasmon resonance (SPR) (Biacore) using recombinant IL-2R $\beta\gamma$ heterodimer and monomeric IL-2R $\alpha$-subunit under the following conditions: The IL-2R $\alpha$-subunit was immobilized in two densities and the flow cell with higher immobilization was used for the mutants that have lost CD25 binding. The following conditions were used: chemical immobilization: human IL-2R $\beta\gamma$ heterodimer 1675 RU; mouse IL-2R $\beta\gamma$ heterodimer 5094 RU; human IL-2R $\alpha$-subunit 1019 RU; human IL-2R $\alpha$-subunit 385 RU, murine IL-2R $\alpha$-subunit 1182 RU; murine IL-2R $\alpha$-subunit 378 RU, temperature: 25° C., analytes: 4G8 Fab-IL 2 variants-Fab constructs 3.1 nM to 200 nM, flow 40 μl/min, association: 180 s, dissociation: 180 s, regeneration: 10 mM glycine pH 1.5, 60 s, 40 μl/min. Fitting: two state reaction model (conformational change), RI=0 Rmax=local. Results of the kinetic analysis are given in Table 4.

TABLE 4

Affinity of FAP-targeted immunoconjugates comprising mutant IL-2 polypeptides to the intermediate affinity IL-2R and the IL-2R $\alpha$-subunit ($K_D$).

| Construct Fab-IL-2-Fab | Hu IL-2R $\beta\gamma$ | Hu IL-2R $\alpha$ | Mu IL-2R $\beta\gamma$ | Mu IL-2R $\alpha$ |
|---|---|---|---|---|
| 4G8 IL-2 wt | 3.8 nM | 4.5 nM | 45.6 nM | 29 nM |
| 4G8 IL-2 T3A | 1.6 nM | 4.9 nM | 15.6 nM | 15 nM |
| 4G8 IL-2 F42A | 4.7 nM | 149 nM | 57 nM | 363 nM |
| 4G8 IL-2 Y45A | 3.9 nM | 22.5 nM | 41.8 nM | 369 nM |
| 4G8 IL-2 L72G | ND | 45.3 nM | ND | ND |
| 4G8 IL-2 triple mutant F42A/Y45A/L72G | 5.6 nM | no binding | 68.8 nM | ND |
| 4G8 IL-2 quadruple mutant T3A/F42A/Y45A/L72G | 5.2 nM | no binding | 56.2 nM | no binding |

Simultaneous binding to the IL 2R heterodimer and FAP was shown by SPR. Briefly, the human IL 2R $\beta\gamma$ knob-into-hole construct was immobilized on a CM5 chip chemically and 10 nM Fab-IL-2=Fab constructs were captured for 90 s. Human FAP served as analyte at concentrations of 200 nM down to 0.2 nM. Conditions were: temperature: 25° C., buffer: HBS-EP, flow: 30 μl/min, association: 90 s, dissociation: 120 s. Regeneration was done for 60 s with 10 mM glycine pH 2. Fitting was performed with a model for 1:1 binding, RI≠0, Rmax=global. The SPR bridging assay showed that the Fab-IL-2-Fab constructs, both as wild-type and as quadruple mutant, as well as based on the affinity matured FAP binder 28H1 or the parental 3F2 or 4G8 antibodies, was able to bind at a concentration of 10 nM simultaneously to the IL 2R $\beta\gamma$ heterodimer immobilized on the chip as well as to human FAP used as analyte (FIG. 8). The determined affinities are shown in Table 5.

TABLE 5

Affinity of FAP-targeted immunoconjugates, comprising mutant IL-2 polypeptides and bound to the intermediate affinity IL-2R, to FAP ($K_D$).

| Construct Fab-IL-2-Fab | $K_D$ |
|---|---|
| 4G8 Fab-IL-2 wt-Fab | 5.0 nM |
| 4G8 Fab-IL-2 qm-Fab | 5.6 nM |
| 29B11 Fab-IL-2 wt-Fab | 0.32 nM |
| 29B11 Fab-IL-2 qm-Fab | 0.89 nM |
| 3F2 Fab-IL-2 wt-Fab | 1.2 nM |

Taken together the SPR data showed that i) the T3A mutation does not influence binding to CD25, ii) the three mutations F42A, Y45A and L72G do not influence the affinity for the IL 2R $\beta\gamma$ heterodimer while they reduce the affinity for CD25 in this order: wt=T3A>Y45A (ca. 5× lower)>L72G (ca. 10× lower)>F42A (ca. 33× lower); iii) the combination of the three mutations F42A, Y45A and L72G with or without the O-glycosylation site mutant BA results in a complete loss of CD25 binding as determined under SPR conditions, iv) although affinity of human IL-2 for murine IL-2R $\beta\gamma$ heterodimer and IL-2R $\alpha$-subunit is reduced approximately by a factor of 10 compared to human IL-2 receptors the selected mutations do not influence affinity for the murine IL-2R $\beta\gamma$ heterodimer, but abolish binding to murine IL-2R $\alpha$-subunit accordingly. This indicates that the mouse represents a valid model for the study of pharmacological and toxicological effects of IL-2 mutants, although overall IL-2 exhibits less toxicity in rodents than in humans.

Apart from the loss of O-glycosylation one additional advantage of the combination of the four mutations T3A, F42A, Y45A, L72G is a lower surface hydrophobicity of the IL-2 quadruple mutant due to the exchange of surface exposed hydrophobic residues such as phenylalanine, tyrosine or leucine by alanine. An analysis of the aggregation temperature by dynamic light scattering showed that the aggregation temperature for the FAP-targeted Fab-IL-2-Fab immunoconjugates comprising wild-type or quadruple mutant IL-2 were in the same range: ca. 57-58° C. for the 3F2 parental Fab-IL-2-Fab and for the affinity matured 29B11 3F2-derivative; and in the range of 62-63° C. for the 4G8 parental Fab-IL-2-Fab and the affinity matured 28111, 4B9 and 14B3 4G8-derivatives, indicating that the combination of the four mutations had no negative impact on protein stability. In support of the favorable properties of the selected IL-2 quadruple mutant, transient expression yields indicated that the quadruple mutant in the Fab-IL-2 qm-Fab format may even result in higher expression yields than those observed for the respective Fab-IL-2 wt-Fab constructs. Finally, pharmacokinetic analysis shows that both 4G8-based Fab-IL-2 qm-Fab and Fab-IL-2 wt-Fab have comparable PK properties (see example 9 below). Based on these data and the cellular data described in example 4 below the quadruple mutant T3A, F42A, Y45A, L72G was selected as ideal combination of mutations to abolish CD25 binding of IL-2 in the targeted Fab-IL-2-Fab immunoconjugate.

Example 4

The 4G8-based FAP-targeted Fab-IL 2-Fab immunoconjugates, comprising wild-type IL-2 or the single mutants 4G8 IL-2 T3A, 4G8 IL-2 F42A, 4G8 IL-2 Y45A, 4G8 IL-2 L72G or the respective triple (F42A/Y45A/L72G) or quadruple mutant (T3A/F42A/Y45A/L72G) IL-2, were subsequently tested in cellular assays in comparison to Proleukin as described above.

IL-2 induced IFN-γ release was measured following incubation of the NK cell line NK92 with the constructs (FIG. 9). NK92 cells express CD25 on their surface. The results show that the Fab-IL-2-Fab immunoconjugate comprising wild-type IL-2 was less potent in inducing IFN-γ release Than Proleukin as could be expected from the ca. 10-fold lower affinity of the Fab-IL-2 wt-Fab for the IL-2R βγ heterodimer. The introduction of single mutations interfering with CD25 binding as well as the combination of the three mutations interfering with CD25 binding in the IL-2 triple mutant resulted in Fab-IL-2-Fab constructs that were comparable to the wild-type IL-2 construct in terms of potency and absolute induction of IFN-γ release within the error of the method.

TABLE 6

Induction of IFN-γ release from NK cells by Fab-IL-2-Fab immunoconjugates comprising mutant IL-2 polypeptides.

| Construct | $EC_{50}$ [nM] |
| --- | --- |
| Proleukin | 4.1 |
| 4G8 Fab-IL 2 wt-Fab | 23.0 |
| 4G8Fab-IL-2 (T3A)-Fab | 16.2 |
| 4G8 Fab-IL-2 (F42A)-Fab | 15.4 |
| 4G8 Fab-IL-2(Y45A)-Fab | 20.9 |
| 4G8 Fab-IL-2 (L72G)-Fab | 16.3 |
| 4G8 Fab-IL-2 (triple mutant 42/45/72)-Fab | 24.4 |

Subsequently, induction of proliferation of isolated human NK cells by Fab-IL-2-Fab immunoconjugates was assessed in a proliferation assay (Cell Titer Glo, Promega) (FIG. 10). In contrast to NK92 cells, freshly isolated NK cells do not express CD25 (or only very low amounts). The results show that the Fab-IL-2-Fab immunoconjugate comprising wild-type IL-2 was ca. 10-fold less potent in inducing NK cell proliferation than Proleukin, as could be expected from the ca. 10-fold lower affinity of the Fab-IL-2 wt-Fab immunoconjugate for the IL-2R βγ heterodimer. The introduction of single mutations interfering with CD25 binding as well as the combination of the three mutations interfering with CD25 in the IL-2 triple mutant resulted in Fab-IL-2-Fab constructs that were comparable to the wild-type IL-2 construct in terms of potency and absolute induction of proliferation; there was only a very small shift in potency observed for the Fab-IL-2-Fab triple mutant. In a second experiment the induction of proliferation of PHA-activated T cells was assessed following incubation with different amounts of Proleukin and Fab-IL-2-Fab immunoconjugates (FIG. 11). As activated T cells express CD25, a clear reduction in T cell proliferation could be observed upon incubation with the immunoconjugates comprising IL-2 single mutants F42A, L72G or Y45A; with F42A showing the strongest reduction followed by L72G and Y45A, whereas when using Fab-IL-2 wt-Fab or Fab-IL-2 (T3A)-Fab the activation was almost retained compared to Proleukin. These data reflect the reduction in affinity for CD25 as determined by SPR (example above). The combination of the three mutations interfering with CD25 binding in the IL-2 triple mutant resulted in an immunoconjugate that mediated significantly reduced induction of T cell proliferation in solution. In line with these findings we measured cell death of T cells as determined by Annexin V/PI staining following over-stimulation induced by a first stimulation for 16 h with 1 μg/ml PHA, a second stimulation for 5 days with Proleukin or the respective Fab-IL-2-Fab immunoconjugates, followed by a third stimulation with 1 μg/ml PHA. In this setting we observed that activation induced cell death (AICD) in over-stimulated T cells was strongly reduced with the Fab-IL-2-Fab immunoconjugates comprising the IL-2 single mutants F42A, L72G and Y45A interfering with CD25 binding, with F42A and L72G showing the strongest reduction, which was similar to the reduction achieved by the combination of the three mutations in the immunoconjugate comprising the IL-2 triple mutant (FIG. 12). In a last set of experiments we studied the effects of the Fab-IL-2 qm-Fab on the induction of STAT5 phosphorylation compared to Fab-IL-2 wt-Fab and Proleukin on human NK cells, CD4+ T cells, CD8+ T cells and $T_{reg}$ cells from human PBMCs (FIG. 13). For NK cells and CDC T cells that show no or very low CD25 expression (meaning that IL-2R signaling is mediated via the IL-2R fry heterodimer) the results show that the Fab-IL-2-Fab format comprising wildtype IL-2 was ca. 10-fold less potent in inducing STAT5 phosphorylation than Proleukin, and that the Fab-IL-2 qm-Fab was comparable to the Fab-IL-2 wt-Fab construct. On CD4+ T cells, that show a rapid up-regulation of CD25 upon stimulation, the Fab-IL-2 qm-Fab was less potent then the Fab-IL-2 wt-Fab immunoconjugate, but still showed comparable induction of IL-2R signaling at saturating concentrations. This is in contrast to $T_{reg}$ cells where the potency of the Fab-IL-2 qm-Fab was significantly reduced compared to the Fab-IL-2 wt-Fab immunoconjugate due to the high CD25 expression on $T_{reg}$ cells and the subsequent high binding affinity of the Fab-IL-2 wt-Fab immunoconjugate to CD25 on $T_{reg}$ cells. As a consequence of the abolishment of CD25 binding in the Fab-IL-2 qm-Fab immunoconjugate, IL-2 signaling in $T_{reg}$ cells is only activated via the IL-2R βγ heterodimer at concentrations where IL-2R signaling is activated on CD25-negative effector cells through the IL-2R βγ heterodimer. Taken together the IL-2 quadruple mutant described here is able to activate IL-2R signaling through the IL-2R βγ heterodimer, but does neither result in AICD nor in a preferential stimulation of $T_{reg}$ cells over other effector cells.

Example 5

Based on the data described in examples 2 and 3 affinity matured FAP-targeted Fab-IL-2 qm-Fab immunoconjugates based on clones 28H1 or 29B11 were generated and purified as described above in the general methods section. In more detail, the FAP-targeted 28H1 targeted Fab-IL-2 qm-Fab was purified by one affinity step (protein G) followed by size exclusion chromatography (Superdex 200). Column equilibration was performed in PBS and supernatant from a stable CHO pool (CDCHO medium) was loaded onto a protein G column (GE Healthcare), the column was washed with PBS and samples were subsequently eluted with 2.5 mM HCl and fractions were immediately neutralized with 10×PBS. Size exclusion chromatography was performed in the final formulation buffer: 25 mM sodium phosphate, 125 mM sodium chloride, 100 mM glycine pH 6.7 on a Superdex 200 column. FIG. 14 shows the elution profiles from the purification and the results from the analytical characterization of the product by SDS-PAGE (NuPAGE Novex Bis-Tris Mini Gel 4-20%, Invitrogen, MOPS running buffer, reduced and non-reduced). Given the low binding capacity of the 28H1 Fab fragment to protein 0.0 and protein A additional capture steps may result in higher yields.

FAP-targeted 4G8, 3F2 and 29B11 Fab-IL-2 qm-Fab and MCSP-targeted MHLG1 KV9 Fab-IL-2 qm-Fab immunoconjugates were purified by one affinity step (protein A) followed by size exclusion chromatography (Superdex 200). Column equilibration was performed in 20 mM sodium phosphate, 20 mM sodium citrate pH 7.5 and supernatant was loaded onto the protein A column. A first wash was performed in 20 mM sodium phosphate, 20 mM sodium citrate, pH 7.5 followed by a second wash: 13.3 mM sodium phosphate, 20 mM sodium citrate, 500 mM sodium chloride, pH 5.45. The Fab-IL-2 qm-Fab immunoconjugates were eluted in 20 mM sodium citrate, 100 mM sodium chloride, 100 mM glycine pH 3. Size exclusion chromatography was performed in the final formulation buffer: 25 mM potassium phosphate, 125 mM sodium chloride, 100 mM glycine pH 6.7. FIG. 15 shows the elution profiles from the purification and the results from the analytical characterization of the product by SDS-PAGE (NuPAGE Novex Bis-Tris Mini Gel 4-20%, Invitrogen, MOPS running buffer, reduced and non-reduced) for the 4G8 Fab-IL-2 qm-Fab and FIG. 16 for the MHLG1 KV9 Fab-IL-2 qm-Fab immunoconjugate.

FAP-targeted IgG-IL-2 qm fusion proteins based on the FAP-antibodies 4G8, 4B9 and 28H1, and a control DP47GS non-targeted IgG-IL-2 qm fusion protein were generated as described above in the general methods section. FIGS. 46 and 47 show the respective chromatograms and elution profiles of the purification (A, B) as well as the analytical SDS-PAGE and size exclusion chromatographies of the final purified constructs (C, D) for the 4G8- and 28H1-based constructs. Transient expression yields were 42 mg/L for the 4G8-based and 20 mg/L for the 28H1-based IgG-IL-2 qm immunoconjugate.

The FAP binding activity of the IgG-IL-2 qm immunoconjugates based on 4G8 and 28H1 anti-FAP antibodies were determined by surface plasmon resonance (SPR) on a Biacore machine in comparison to the corresponding unmodified IgG antibodies. Briefly, an anti-His antibody (Penta-His, Qiagen 34660) was immobilized on CM5 chips to capture 10 nM His-tagged human FAP (20 s). Temperature was 25° C. and HBS-EP was used as buffer. Analyte concentration was 50 nM down to 0.05 nM at a flow rate of 50 μl/min (association: 300 s, dissociation: 900 s, regeneration: 60 s, with 10 mM glycine pH 2). Fitting was performed based on a 1:1 binding model, RI=0, Rmax=local (because of capture format). Table 7 gives the estimated apparent bivalent affinities (pM avidity) as determined by SPR fitted with 1:1 binding RI=0, Rmax=local.

TABLE 7

| $K_D$ [pM] | Hu FAP |
|---|---|
| 4G8 IgG-IL-2 qm | 100 |
| 4G8 IgG | 50 |
| 28H1 IgG-IL-2 qm | 175 |
| 28H1 IgG | 200 |

The data show that within the error of the method affinity for human FAP is retained for the 28H1-based immunoconjugate or only slightly decreased for the 4G8-based immunoconjugate as compared to the corresponding unmodified antibodies.

Example 6

The affinity of the FAP-targeted, affinity matured 28H1 and 29B11-based Fab-IL-2-Fab immunoconjugates, each comprising wild-type or quadruple mutant IL-2, and of the 3F2-based Fab-IL-2 wt-Fab were determined by surface plasmon resonance (SPR) for the human, murine and cynomolgus IL-2R βγ heterodimer using recombinant IL-2R βγ heterodimer under the following conditions: ligand: human, murine and cynomolgus IL-2R β knob γ hole heterodimer immobilized on CM5 chip, analyte: 28H1 or 29B11 Fab-IL-2-Fab (comprising wild-type or quadruple mutant IL-2), 3F2 Fab-IL-2-Fab (comprising wild-type IL-2), temperature: 25° C. or 37° C., buffer: HBS-EP, analyte concentration: 200 nM down to 2.5 nM, flow: 30 μl/min, association: 300 s, dissociation: 300 s, regeneration: 60 s 3M $MgCl_2$, fitting: 1:1 binding, RIO, Rmax=global. The affinity of the FAP-targeted affinity matured 28H1 and 29B11-based Fab-IL-2-Fab immunoconjugate, each containing wildtype or quadruple mutant IL-2, and of the 3F2-based Fab-IL-2 wt-Fab were determined by surface plasmon resonance (SPR) for the human, murine and cynomolgus IL-2R α-subunit using recombinant monomeric IL-2R α-subunit under the following conditions: ligand: human, murine and cynomolgus IL-2R α-subunit immobilized on a CM5 chip, analyte: 28H1 or 29B11 Fab-IL-2-Fab (comprising wild-type or mutant IL-2), 3F2 Fab-IL-2-Fab (comprising wild-type IL-2), temperature: 25° C. or 37° C., buffer: HBS-EP, analyte concentration 25 nM down to 0.3 nM, flow: 30 μl/min, association: 120 s, dissociation: 600 s, regeneration: none, fitting: 1:1 binding, RI=0, Rmax=global.

Results of the kinetic analysis with the IL-2R βγ heterodimer are given in Table 8.

TABLE 8

Binding of Fab-IL-2-Fab immunoconjugates comprising affinity matured Fab and mutant IL-2 to IL-2R βγ heterodimers.

| $K_D$ in nM | Hu IL-2R βγ (25° C.) | Hu IL-2R βγ (37° C.) | Cyno IL-2R βγ (25° C.) | Cyno IL-2R βγ (37° C.) | Mu IL-2R βγ (25° C.) | Mu IL-2R βγ (37° C.) |
|---|---|---|---|---|---|---|
| 28H1 Fab-IL-2 wt-Fab | 9.7 | 19 | 11.5 | 29.2 | 112 | 186 |
| | 9 | 22 | 11.6 | 30.4 | 79 | 219 |
| 28H1 Fab-IL-2 qm-Fab | 7.5 | 14.3 | 8.9 | 21.3 | 66 | 142 |
| | 6.9 | 14.7 | 8.4 | 21.2 | 54 | 106 |
| 29B11 Fab-IL-2 wt-Fab | 6.5 | 9.5 | 6.9 | 14 | 93 | 71 |
| | 5.7 | 12.4 | 6.7 | 19 | 74 | 74 |
| 29B11 Fab-IL-2 qm-Fab | 7.2 | 13.1 | 7.8 | 16.7 | 60 | 44 |
| | 7.4 | 13 | 8.4 | 18.1 | 63 | 42 |

TABLE 8-continued

Binding of Fab-IL-2-Fab immunoconjugates comprising affinity matured Fab and mutant IL-2 to IL-2R βγ heterodimers.

| $K_D$ in nM | Hu IL-2R βγ (25° C.) | Hu IL-2R βγ (37° C.) | Cyno IL-2R βγ (25° C.) | Cyno IL-2R βγ (37° C.) | Mu IL-2R βγ (25° C.) | Mu IL-2R βγ (37° C.) |
|---|---|---|---|---|---|---|
| 3F2 Fab-IL-2 wt-Fab | 5 4.8 | ND | 6.4 6.1 | ND | 40 40 | ND |

Whereas the affinity of human IL-2 to the human IL 2R βγ heterodimer is described to be around 1 nM, the Fab-IL-2-Fab immunoconjugates (comprising wild-type or quadruple mutant IL-2) both have a reduced affinity between 6 and 10 nM, and as shown for the naked IL-2 above the affinity to the murine IL-2R is around 10 times weaker than for the human and cynomolgous IL-2R.

Results of the kinetic analysis with the IL-2R α-subunit are given in Table 9. Under the chosen conditions there is no binding detectable of the immunoconjugates comprising the IL-2 quadruple mutant to the human, murine or cyno IL-2R α-subunit.

TABLE 9

Binding of Fab-IL-2-Fab immunoconjugates comprising affinity matured Fab and mutant IL-2 to IL-2R α-subunits.

| $K_D$ in nM | Hu IL-2R α (25° C.) | Hu IL-2R α (37° C.) | Cyno IL-2R α (25° C.) | Cyno IL-2R α (37° C.) | Mu IL-2R α (25° C.) | Mu IL-2R α (37° C.) |
|---|---|---|---|---|---|---|
| 28H1 Fab-IL-2 wt-Fab | 16 16.2 | 28.8 28.2 | 16 16.2 | 36.5 35.6 | 43.3 44 | 67.5 61.1 |
| 28H1 Fab-IL-2 qm-Fab | no binding | no binding | no binding | no binding | no binding | no binding |
| 29B11 Fab-IL-2 wt-Fab | 5 4.6 | 7.6 7.7 | 4.8 4.3 | 7.3 7.4 | 11.4 9.6 | 13.3 13.8 |
| 29B11 Fab-IL-2 qm-Fab | no binding | no binding | no binding | no binding | no binding | no binding |
| 3F2 Fab-IL-2 wt-Fab | 5.7 6.1 | ND | 5 5.4 | ND | 12.3 12.1 | ND |

The affinity of the MCSP-targeted MHLG1-KV9 Fab-IL-2-Fab immunoconjugates, comprising the wild-type or quadruple mutant IL-2, were determined by surface plasmon resonance (SPR) for the human IL-2R βγ heterodimer using recombinant IL-2R βγ heterodimer under the following conditions: human IL-2R β knob γ hole heterodimer was immobilized on a CM5 chip (1600 RU). MHLG1-KV9 Fab-IL-2 wt-Fab and Fab-IL-2 qm-Fab were used as analyte at 25° C. in HBS-P buffer. Analyte concentration was 300 nM down to 0.4 nM (1:3 dil.) for IL-2R βγ at a flow of 30 µl/min (association time 180 s, dissociation time 300 s). Regeneration was done for 2×30 s with 3M MgCl₂ for IL-2R βγ. Data were fitted using a 1:1 binding, RI≠0, Rmax=local for IL-2R βγ.

The affinity of the MCSP-targeted MHLG1-KV9 Fab-IL-2-Fab immunoconjugates, comprising the wild-type or quadruple mutant IL-2, were determined by surface plasmon resonance (SPR) for the human IL-2R α-subunit using recombinant monomeric IL-2R α-subunit under the following conditions: human IL-2R α-subunit was immobilized on a CM5 chip (190 RU). MHLG1-KV9 Fab-IL-2 wt-Fab and Fab-IL-2 qm-Fab were used as analyte at 25° C. in HBS-P buffer. Analyte concentration was 33.3 nM down to 0.4 nM (1:3 dil.) for IL-2R α at a flow of 30 td/min (association time 180 s, dissociation time 300 s). Regeneration was done for 10 s with 50 mM NaOH for IL-2R α. Data were fitted using a 1:1 binding, RI=0, Rmax=global for IL-2R α.

Results of the kinetic analysis with the IL-2R βγ heterodimer are given in Table 10.

TABLE 10

| $K_D$ in nM T = 25° C. | Hu IL 2R βγ (kinetic) | Hu IL 2R α (kinetic) | Hu IL 2R α (steady state) |
|---|---|---|---|
| MHLG1-KV9 Fab-IL-2 wt-Fab | 8.6 9.8 | 8.8 10.1 | 6.8 10.9 |
| MHLG1-KV9 Fab-IL 2 qm-Fab | 7.3 10.7 | No binding | No binding |

The data confirm that the MCSP-targeted MHLG1-KV9 Fab-IL-2 qm-Fab immunoconjugate has retained affinity for the IL-2R βγ receptor, whereas binding affinity to CD25 is abolished compared to the immunoconjugate comprising wild-type IL-2.

Subsequently, the affinity of the 4G8- and 28H1-based IgG-IL-2 qm immunoconjugates to the IL-2R βγ heterodimer and the IL-2R α-subunit were determined by surface plasmon resonance (SPR) in direct comparison to the Fab-IL-2 qm-Fab immunoconjugate format. Briefly, the ligands—either the human IL-2R α-subunit or the human IL-2R βγ heterodimer—were immobilized on a CM5 chip. Subsequently, the 4G8- and 28H1-based IgG-IL-2 qm immunoconjugates or the 4G8- and 28H1-based Fab-IL-2 qm-Fab immunoconjugates were applied to the chip as analytes at 25° C. in HBS-EP buffer in concentrations ranging from 300 nM down to 1.2 nM (1:3 dil.). Flow rate was 30 µl/min and the following conditions were applied for association: 180 s, dissociation: 300 s, and regeneration:

2×30 s with 3 M MgCl$_2$ for IL-2R βγ heterodimer, 10 s with 50 mM NaOH for IL-2R α-subunit. 1:1 binding was applied for fitting (1:1 binding RI≠0, Rmax=local for IL-2R βγ, apparent K$_D$, 1:1 binding RI=0, Rmax=local for IL-2R α). The respective K$_D$ values are given in Table 11.

TABLE 11

| Apparent K$_D$ [nM] | Hu IL-2R βγ | Hu IL-2R α |
|---|---|---|
| 4G8 IgG-IL-2 qm | 5.9 | No binding |
| 4G8 Fab-IL-2 qm-Fab | 10.4 | No binding |
| 28H1 IgG-IL-2 qm | 6.2 | No binding |
| 28H1 Fab-IL-2 qm-Fab | 11.4 | No binding |

The data show that the 4G8- and 28H1-based IgG-IL-2 qm immunoconjugates bind with at least as good affinity as the Fab-IL-2 qm-Fab immunoconjugates to the IL-2R βγ heterodimer, whereas they do not bind to the IL-2R α-subunit due to the introduction of the mutations interfering with CD25 binding. Compared to the corresponding Fab-IL-2 qm-Fab immunoconjugates the affinity of the IgG-IL-2 qm fusion proteins appears to be slightly enhanced within the error of the method.

Example 7

In a first set of experiments we confirmed that the FAP-targeted Fab-IL-2-Fab immunoconjugates comprising either wild-type or mutant IL-2 were able to bind to human FAP-expressing HEK 293-FAP cells by FACS (FIG. 17) and that the IL-2 quadruple mutation did not impact binding to FAP-expressing cells (FIG. 18).

TABLE 12

Binding of Fab-IL-2-Fab immunoconjugates to FAP-expressing HEK cells.

| EC$_{50}$ values | nM |
|---|---|
| 28H1 Fab-IL-2-Fab | 0.64 |
| 28H1 Fab-IL-2 qm-Fab | 0.70 |
| 29B11 Fab-IL-2-Fab | 0.66 |
| 29B11 Fab-IL-2 qm-Fab | 0.85 |
| 4G8 Fab-IL-2-Fab | 0.65 |

In particular, these binding experiments showed that the affinity matured FAP binders 28H1, 29B11, 14B3 and 4B9 as Fab-IL-2 qm-Fab showed superior absolute binding to the HEK 293-FAP target cells compared to the Fab-IL-2-Fab immunoconjugates based on the parental FAP binders 3F2 (29B11, 14B3, 4B9) and 4G8 (28H1) (FIG. 17), while retaining high specificity and no binding to HEK 293 cells transfected with DPPIV, a close homologue of FAP, or HEK 293 mock-transfected cells. For comparison the mouse anti-human CD26-PE DPPIV antibody clone M-A261 (BD Biosciences, #555437) was used as a positive control (FIG. 19). Analysis of the internalization properties showed that the binding of Fab-IL-2-Fab immunoconjugates do not result in the induction of FAP internalization (FIG. 20).

In a further experiment, binding of FAP-targeted 4G8-based IgG-IL-2 qm and Fab-IL-2 qm-Fab immunoconjugates to human FAP expressed on stably transfected HEK293 cells was measured by FACS. The results are shown in FIG. 48. The data show that the IgG-IL-2 qm immunoconjugate binds to FAP-expressing cells with an EC50 value of 0.9 nM, comparable to that of the corresponding 4G8-based Fab-IL-2 qm-Fab construct (0.7 nM).

The affinity matured anti-FAP Fab-IL-2-Fab immunoconjugates comprising wildtype IL-2 or the quadruple mutant were subsequently tested in cellular assays in comparison to Proleukin as described in the examples above.

IL-2 induced IFN-γ release was measured in the supernatant by ELISA following incubation of the NK-cell line NK92 with these immunoconjugates (FIG. 21) for 24 h. NK92 cells express CD25 on their surface. The results show that the Fab-IL-2-Fab immunoconjugate comprising wild-type IL-2 was less potent in inducing IFN-γ release than Proleukin as could be expected from the ca. 10-fold lower affinity of the Fab-IL-2 wt-Fab immunoconjugate for the IL-2R βγ heterodimer. The Fab-IL-2 qm-Fab immunoconjugates were quite comparable to the respective wild-type construct for a selected clone in terms of potency and absolute induction of IFN-γ release despite the fact that NK92 cells express some CD25. It could, however, be observed that the 29B11 Fab-IL-2 qm-Fab induced less cytokine release compared to the 29B11 Fab-IL-2 wt-Fab as well as the 28H1 and 4G8 constructs, for which there was only a small shift in potency observed for Fab-IL-2 qm-Fab over Fab-IL-2 wt-Fab.

In addition, the MCSP-targeted MHLG1-KV9-based Fab-IL-2 qm-Fab immunoconjugate was compared to the 28H1 and 29B11 based Fab-IL-2 qm-Fab immunoconjugates in the IFN-γ release assay on NK92 cells. FIG. 22 shows that the MCSP-targeted MHLG1-KV9-based Fab-IL-2 qm-Fab is quite comparable in inducing IFN-γ release to the FAP-targeted Fab-IL-2 qm-Fab immunoconjugates.

Subsequently, induction of proliferation of NK92 cells by IL-2 over a period of 3 days was assessed in a proliferation assay by ATP measurement using CellTiter Glo (Promega) (FIG. 23). Given that NK92 cells express low amounts of CD25, a difference between Fab-IL-2-Fab immunoconjugates comprising wild-type IL-2 and immunoconjugates comprising quadruple mutant IL-2 could be detected in the proliferation assay, however, under saturating conditions both achieved similar absolute induction of proliferation.

In a further experiment we studied the effects of the 28H1 affinity matured FAP-directed Fab-IL-2 qm-Fab immunoconjugate on induction of STAT5 phosphorylation compared to 28H1 Fab-IL-2 wt-Fab and Proleukin on human NK cells, CD4$^+$ T cells, CD8$^+$ T cells and T$_{reg}$ cells from human PBMCs (FIG. 24). For NK cells and CD8$^+$ T cells, that show no or very low CD25 expression (meaning that IL-2R signaling is mediated via the IL-2R βγ heterodimer), the results showed that the Fab-IL-2-Fab immunoconjugate comprising wild-type IL-2 was ca. >10-fold less potent in inducing IFN-γ release than Proleukin, and that the Fab-IL-2 qm-Fab immunoconjugate was only very slightly less potent than the Fab-IL-2 wt-Fab construct. On CD4$^+$ T cells that show a rapid up-regulation of CD25 upon stimulation, the Fab-IL-2 qm-Fab was significantly less potent than the Fab-IL-2 wt-Fab immunoconjugate, but still showed comparable induction of IL-2R signaling at saturating concentrations. This is in contrast to T$_{reg}$ cells, where the potency of the Fab-IL-2 qm-Fab was significantly reduced compared to the Fab-IL-2 wt-Fab construct due to the high CD25 expression on T$_{reg}$ cells and the subsequent high binding affinity of the Fab-IL-2 wt-Fab construct to CD25 on T$_{reg}$ cells. As a consequence of the abolishment of CD25 binding in the Fab-IL-2 qm-Fab immunoconjugate, IL-2 signaling in T$_{reg}$ cells is only activated via the IL-2R βγ heterodimer at concentrations where IL-2R signaling is activated on CD25 negative effector cells through the IL-2R βγ heterodimer. The respective pM EC50 values are given in Table 13.

TABLE 13

Induction of IFN-γ release from NK cells by 28H1 FAP-targeted
Fab-IL-2-Fab immunoconjugates comprising mutant IL-2 polypeptides.

| $EC_{50}$ [pM] | NK cells | $CD8^+$ T cells | $CD4^+$ T cells | $T_{reg}$ cells |
|---|---|---|---|---|
| Proleukin | 222 | 1071 | 92 | 1 |
| 28H1 Fab-IL-2 wt-Fab | 3319 | 14458 | 3626 | 15 |
| 28H1 Fab-IL-2 qm-Fab | 3474 | 20583 | 70712 | 19719 |

In another set of experiments, the biological activity of FAP-targeted 4G8-based IgG-IL-2 qm and Fab-IL-2 qm-Fab immunoconjugates was investigated in several cellular assays.

FAP-targeted 4G8-based IgG-IL-2 qm and 28H1-based Fab-IL-2 qm-Fab immunoconjugates were studied for the induction of IFN-γ release by NK92 cells as induced by activation of IL-2R βγ signaling. FIG. 49 shows that the FAP-targeted 4G8-based IgG-IL-2 qm immunoconjugate was equally efficacious in inducing IFN-γ release as the affinity matured 28H1-based Fab-IL-2 qm-Fab immunoconjugate.

We also studied the effects of the FAP-targeted 4G8-based IgG-IL-2 qm immunoconjugate on the induction of STAT5 phosphorylation compared to the 28H1 based Fab-IL-2 wt-Fab and Fab-IL-2 qm-Fab immunoconjugates as well as Proleukin on human NK cells, $CD4^+$ T cells, $CD8^+$ T cells and $T_{reg}$ cells from human PBMCs. The results of these experiments are shown in FIG. 50. For NK cells and CDC T cells the 4G8-based IgG-IL-2 qm immunoconjugate was <10-fold less potent in inducing STAT5 phosphorylation than Proleukin, but slightly more potent than 28H1-based Fab-IL-2 wt-Fab and Fab-IL-2 qm-Fab immunoconjugates. On $CD4^+$ T cells the 4G8-based IgG-IL-2: qm immunoconjugate was less potent than the 28H1 Fab-IL-2 wt-Fab immunoconjugate, but slightly more potent than the 28H1 Fab-IL-2 qm-Fab immunoconjugate, and still showed induction of IL-2R signaling at saturating concentrations comparable to Proleukin and 28H1 Fab-IL-2 wt-Fab. This is in contrast to $T_{reg}$ cells where the potency of the 4G8-based IgG-IL-2 qm and 28H1 Fab-IL-2 qm-Fab immunoconjugates was significantly reduced compared to the Fab-IL-2 wt-Fab immunoconjugate.

Taken together the IL-2 quadruple mutant described here is able to activate IL-2R signaling through the IL-2R βγ heterodimer similar to wild-type IL-2, but does not result in a preferential stimulation of $T_{reg}$ cells over other effector cells.

Example 8

The anti-tumoral effects of FAP-targeted Fab-IL-2 qm-Fab immonoconjugates were evaluated in vivo in comparison to FAP-targeted Fab-IL-2 wt-Fab immunoconjugates in ACHN xenograft and LLC1 syngeneic models: All FAP-targeted Fab-IL-2-Fab immunoconjugates (comprising wild-type or quadruple mutant IL-2) recognize murine FAP as well as the murine IL-2R. While the ACHN xenograft model in SCID-human FcγRIII transgenic mice is strongly positive for FAP in IHC, it is an immunocompromised model and can only reflect immune effector mechanisms mediated by NK cells and/or macrophages/monocytes, but lacks T cell mediated immunity and thus cannot reflect AICD or effects mediated through $T_{reg}$ cells. The syngeneic LLC1 model in contrast in fully immunocompetent mice can reflect adaptive T cell mediated immune effector mechanisms as well, but shows fairly low expression of FAP in the murine stroma. Each of these models thus partially reflects the situation as encountered in human tumors.

ACHN Renal Cell Carcinoma Xenograft Model

The FAP-targeted 4G8 Fab-IL-2 wt-Fab and 4G8 Fab-IL-2 qm-Fab immunoconjugates were tested using the human renal cell adenocarinoma cell line ACHN, intrarenally injected into SCID-human FcγRIII transgenic mice. ACHN cells were originally obtained from ATCC (American Type Culture Collection) and after expansion deposited in the Glycart internal cell bank. ACHN cells were cultured in DMEM containing 10% FCS, at 37° C. in a water-saturated atmosphere at 5% $CO_2$. In vitro passage 18 was used for intrarenal injection, at a viability of 98.4%. A small incision (2 cm) was made at the right flank and peritoneal wall of anesthetized SCID mice. Fifty μl cell suspension ($1\times10^6$ ACHN cells in AimV medium) was injected 2 mm subcapsularly in the kidney. Skin wounds and peritoneal wall were closed using clamps. Female SCID-FcγRIII mice (GLYCART-RCC), aged 8-9 weeks at the beginning of the experiment (bred at RCC, Switzerland) were maintained under specific-pathogen-free conditions with daily cycles of 12 h light/12 h darkness according to committed guidelines (GV-Solas; Felasa; TierschG). The experimental study protocol was reviewed and approved by local government (P 2008016). After arrival, animals were maintained for one week to get accustomed to new environment and for observation. Continuous health monitoring was carried out on a regular basis. Mice were injected intrarenally on study day 0 with $1\times10^6$ ACHN cells, randomized and weighed. One week after the tumor cell injection, mice were injected i.v. with 4G8 Fab-IL-2 wt-Fab and 4G8 Fab-IL-2 qm-Fab three times a week for three weeks. All mice were injected i.v. with 200 μl of the appropriate solution. The mice in the vehicle group were injected with PBS and the treatment groups with 4G8 Fab-IL-2 wt-Fab or 4G8 Fab-IL-2 qm-Fab immunoconjugate. To obtain the proper amount of immunoconjugate per 200 μl, the stock solutions were diluted with PBS when necessary. FIG. 25 shows that both 4G8 Fab-IL-2 wt-Fab and 4G8 Fab-IL-2 qm-Fab immunoconjugates mediated superior efficacy in terms of enhanced median survival compared to vehicle group with an advantage for the 4G8 Fab-IL-2 wt-Fab over the 4G8 Fab-IL-2 qm-Fab immunoconjugate in terms of efficacy.

TABLE 14-A

| Compound | Dose | Formulation buffer | Concentration (mg/mL) |
|---|---|---|---|
| 4G8 Fab-IL-2-Fab wild type = FAP 4G8 wt | 20 μg | 25 mM potassium phosphate, 125 mM NaCl, 100 mM glycine, pH 6.7 | 1.45 |
| 4G8 Fab-IL-2-Fab quadruple mutant = FAP 4G8 qm | 20 μg | 25 mM potassium phosphate, 125 mM NaCl, 100 mM glycine, pH 6.7 | 4.25 |

LLC1 Lewis Lung Carcinoma Syngeneic Model

The FAP-targeted 4G8 Fab-IL-2 qm-Fab and 28H1 Fab-IL-2 qm-Fab immunoconjugates were tested using the mouse Lewis lung carcinoma cell line LLC1, i.v. injected into Black 6 mice. The LLC1 Lewis lung carcinoma cells were originally obtained from ATCC and after expansion deposited in the Glycart internal cell bank. The tumor cell line was routinely cultured in DMEM containing 10% FCS (Gibco) at 37° C. in a water-saturated atmosphere at 5% $CO_2$. Passage 10 was used for transplantation, at a viability of 97.9%. $2\times10^5$ cells per animal were injected i.v. into the tail vein in 200 µl of Aim V cell culture medium (Gibco). Black 6 mice (Charles River, Germany), aged 8-9 weeks at the start of the experiment, were maintained under specific-pathogen-free conditions with daily cycles of 12 h light/12 h darkness according to committed guidelines (GV-Solas; Felasa; TierschG). The experimental study protocol was reviewed and approved by local government (P 2008016). After arrival, animals were maintained for one week to get accustomed to the new environment and for observation. Continuous health monitoring was carried out on a regular basis. Mice were injected i.v. on study day 0 with $2\times10^5$ of LLC1 cells, randomized and weighed. One week after the tumor cell injection, mice were injected i.v. with 4G8 Fab-IL-2 qm-Fab or 28H1 Fab-IL-2 qm-Fab, three times a week for three weeks. All mice were injected i.v. with 200 µl of the appropriate solution. The mice in the vehicle group were injected with PBS and the treatment group with the 4G8 Fab-IL-2 qm-Fab or 28H1 Fab-IL-2 qm-Fab constructs. To obtain the proper amount of immunoconjugate per 200 µl, the stock solutions were diluted with PBS when necessary. FIG. 26 shows that the 4G8 Fab-IL-2 qm-Fab or the affinity matured 28H1 Fab-IL-2 qm-Fab constructs mediated superior efficacy in terms of enhanced median survival compared to the vehicle group.

TABLE 14-B

| Compound | Dose | Formulation buffer | Concentration (mg/mL) |
|---|---|---|---|
| 28H1 Fab-IL-2-Fab quadruple mutant = FAP 28H1 qm | 30 µg | 25 mM potassium phosphate, 125 mM NaCl, 100 mM glycine, pH 6.7 | 2.74 |
| 4G8 Fab-IL-2-Fab quadruple mutant = FAP 4G8 qm | 30 µg | 25 mM potassium phosphate, 125 mM NaCl, 100 mM glycine, pH 6.7 | 4.25 |

In another experiment, the FAP-targeted 28H1 Fab-IL-2 wt-Fab and 28H1 Fab-IL-2 qm-Fab immunoconjugates were tested in the same mouse Lewis lung carcinoma cell line LLC1, i.v. injected into Black 6 mice. Passage 9 was used for transplantation, at a viability of 94.5%. $2\times10^5$ cells per animal were injected i.v. into the tail vein in 200 µl of Aim V cell culture medium (Gibco). Mice were injected i.v. on study day 0 with $2\times10^5$ of LLC1 cells, randomized and weighed. One week after the tumor cell injection, mice were injected i.v. with 28H1 Fab-IL-2 wt-Fab or 28H1 Fab-IL-2 qm-Fab, three times a week for three weeks. All mice were injected i.v. with 200 µl of the appropriate solution. The mice in the vehicle group were injected with PBS and the treatment group with the 28H1 Fab-IL-2 wt-Fab or 28H1 Fab-IL-2 qm-Fab constructs. To obtain the proper amount of immunoconjugate per 200 the stock solutions were diluted with PBS when necessary. FIG. 27 shows that the 28H1 Fab-IL-2 wt-Fab and 28H1 Fab-IL-2 qm-Fab immunoconjugates mediated superior efficacy in terms of enhanced median survival compared to the vehicle group with a slight advantage for the 28H1 Fab-IL-2 wt-Fab over the 28H1 Fab-IL-2 qm-Fab immunoconjugate in terms of efficacy.

TABLE 14-C

| Compound | Dose | Formulation buffer | Concentration (mg/mL) |
|---|---|---|---|
| 28H1 Fab-IL-2-Fab quadruple mutant = FAP 28H1 qm | 45 µg | 25 mM potassium phosphate, 125 mM NaCl, 100 mM glycine, pH 6.7 | 2.74 |
| 28H1 Fab-IL-2-Fab wild-type = FAP 28H1 wt | 45 µg | 25 mM potassium phosphate, 125 mM NaCl, 100 mM glycine, pH 6.7 | 1.66 |

Example 9

The 4G8 based FAP-targeted Fab-IL-2 qm-Fab was subsequently compared to the 4G8 based FAP-targeted Fab-IL-2 wt-Fab immunoconjugate in a seven-day intravenous toxicity and toxicokinetic study in Black 6 mice. Table 15 shows the study design of the toxicity and toxikokinetic studies.

TABLE 15

Study design.

| Group | Type | Dose [µg/g] | Purpose |
|---|---|---|---|
| 1 | DPBS | 0 | Control |
| 2 | 4G8 Fab-IL-2 wt-Fab | 4.5 | Toxicity titration |
| 3 | | 9.0 | |
| 4 | 4G8 Fab-IL-2 qm-Fab | 4.5 | |
| 5 | | 9.0 | |
| 6 | 4G8 Fab-IL-2 wt-Fab | 4.5 | Toxicokinetic study |
| 7 | | 9.0 | |
| 8 | 4G8 Fab-IL-2 qm-Fab | 4.5 | |
| 9 | | 9.0 | |

The purpose of this study was to characterize and compare the toxicity and toxicokinetic profiles of FAP-targeted 4G8 Fab-IL2-Fab wild type (wt) interleukin-2 (IL-2) and FAP-targeted G48 Fab-IL-2-Fab quadruple mutant IL-2 (qm) after once daily intravenous administration to non-tumor-hearing male mice for 7 days. For this study, 5 groups of 5 male mice/group were administered intravenously 0 (vehicle control), 4.5 or 9 µg/g/day wt IL-2, or 4.5 or 9 µg/g/day qm IL-2. An additional 4 groups of 6 male mice/group were administered 4.5 or 9 µg/g/day wt IL-2, or 4.5 or 9 µg/g/day qm IL-2 in order to assess toxicokinetics. The study duration was changed from 7 days to 5 days due to clinical signs observed in animals given 4.5 and 9 µg/g/day wt IL-2. Assessment of toxicity was based upon mortality, in-life observations, body weight, and clinical and anatomic pathology. Blood was collected at various time points from animals in the toxicokinetic groups for toxicokinetic analysis. The toxicokinetic data showed that the mice treated with wt IL-2 or qm IL-2 had measurable plasma levels up to the last bleeding time, indicating that the mice were exposed to the respective compounds throughout the duration of treatment. Day 1 AUC0-inf values suggest comparable exposure of wt IL-2 and qm IL-2 at both dose levels. Sparse samples were taken on Day 5 and showed equivalent plasma concentrations to Day 1, suggesting no accumulation occurred after 5 days of dosing either compound. In more details the following findings were observed.

Toxikokinetics

Table 16 summarizes the mean plasma toxicokinetic parameters for the FAP-targeted 4G8 Fab-IL-2 qm-Fab and the FAP-targeted 4G8 Fab-IL-2 wt-Fab as determined by WinNonLin Version 5.2.1 and a commercial kappa-specific ELISA (Human Kappa ELISA Quantitation Set, Bethyl Laboratories).

TABLE 16

| Parameter | Units | Group 6 4G8-FAP-Wild Type IL-2 | Group 7 4G8-FAP-Wild Type IL-2 | Group 8 4G8-FAP-Mutant IL-2 | Group 9 4G8-FAP-Mutant IL-2 |
|---|---|---|---|---|---|
| Cmax | ng/ml | 47198 | 97986 | 60639 | 146416 |
| Cmax/Dose | (ng/ml)/(ug/g) | 0.011 | 0.011 | 0.0135 | 0.016 |
| AUC | ng * h/ml | 331747 | 747449 | 355030 | 926683 |
| AUC/Dose | (ng * h/ml)/(ug/g) | 0.074 | 0.083 | 0.079 | 0.103 |
| T½z | h | 3.6 | 3.11 | 4.3 | 3.12 |
| Original Dose | ug/g | 4.5 | 9 | 4.5 | 9 |
| Route | | IV | IV | IV | IV |

*TK Parameters were calculated in WinNonlin Version 5.2.1 using noncompartmental analysis The individual serum concentrations are given in the following:

| Group (dose) | Bleed Day | Time (h) | Animal | Serum conc. (ng/ml) | Mean conc (ng/ml) |
|---|---|---|---|---|---|
| Group 6 (4.5 µg/g) 4G8 Fab-Il2-Fab WT | 1 | 1 | 26 | 64241 | 47198 |
| | | | 27 | 30155 | |
| | 1 | 5.5 | 28 | 14693 | 15784 |
| | | | 29 | 16875 | |
| | 1 | 24 | 30 | 318 | 419 |
| | | | 31 | 520 | |
| | 5 | 5.5 | 29 | 13061 | 13335 |
| | | | 30 | 13620 | |
| | | | 31 | 13325 | |
| Group 7 (9 µg/g) 4G8 Fab-Il2-Fab WT | 1 | 1 | 32 | 101208 | 97986 |
| | | | 33 | 94764 | |
| | 1 | 5.5 | 34 | 35766 | 34062 |
| | | | 35 | 32359 | |
| | 1 | 24 | 36 | 573 | 580 |
| | | | 37 | 588 | |
| | 5 | 5.5 | 32 | 31779 | 37473 |
| | | | 33 | 51143 | |
| | | | 35 | 53409 | |
| | | | 36 | 13562 | |
| Group 8 (4.5 µg/g) 4G8 Fab-Il2-Fab Mutant | 1 | 1 | 38 | 73326 | 60639 |
| | | | 39 | 47953 | |
| | 1 | 5.5 | 40 | 12168 | 13269 |
| | | | 41 | 14371 | |
| | 1 | 24 | 42 | 494 | 490 |
| | | | 43 | 487 | |
| | 5 | 5.5 | 40 | 6561 | 10957 |
| | | | 41 | 15352 | |
| | 5 | 24 | 38 | 608 | 721 |
| | | | 39 | 543 | |
| | | | 42 | 1298 | |
| | | | 43 | 437 | |
| Group 9 (9 µg/g) 4G8 Fab-Il2-Fab Mutant | 1 | 1 | 44 | 162970 | 146416 |
| | | | 45 | 129862 | |
| | 1 | 5.5 | 46 | 20475 | 24800 |
| | | | 47 | 29125 | |
| | 1 | 24 | 48 | 478 | 493 |
| | | | 49 | 509 | |
| | 5 | 5.5 | 46 | 20504 | 48031 |
| | | | 47 | 75557 | |
| | 5 | 24 | 44 | 634 | 703 |
| | | | 45 | 796 | |
| | | | 48 | 661 | |
| | | | 49 | 719 | |

These data show that both, the 4G8 Fab-IL-2 qm-Fab and the 4G8 Fab-IL-2 wt-Fab show comparable pharmacokinetic properties with slightly higher exposure for the 4G8 Fab-IL-2 qm-Fab.

Mortality

In the 9 µg/g FAP-targeted 4G8 Fab-IL-2 wt-Fab group, treatment-related mortality occurred in one animal prior to necropsy on Day 5. Hypoactivity, cold skin, and hunched posture were noted prior to death. This animal likely died due to a combination of cellular infiltration in the lung that was accompanied with edema and hemorrhage and marked bone marrow necrosis. Mortality is summarized in Table 17.

TABLE 17

Mortality day 5.

| Group | Type | Dose [µg/g] | Found dead | Severe toxicity Sacrifice** | Total |
|---|---|---|---|---|---|
| 1 | DPBS | 0 | 0/5 | 0/5 | 0/5 |
| 2 | 4G8 Fab-IL-2 wt-Fab | 4.5 | 0/5 | 5/5 | 5/5 |
| 3 | | 9 | 1/5* | 4/5 | 4/5 |
| 4 | 4G8 Fab-IL-2 qm- | 4.5 | 0/5 | 0/5 | 0/5 |

TABLE 17-continued

Mortality day 5.

| Group | Type | Dose [μg/g] | Found dead | Severe toxicity Sacrifice** | Total |
|---|---|---|---|---|---|
| 5 | Fab | 9 | 0/5 | 0/5 | 0/5 |
| 6 | 4G8 Fab-IL-2 wt-Fab | 4.5 | 1/6 | 5/6 | 6/6 |
| 7 | | 9 | 2/6 | 4/6 | 6/6 |
| 8 | 4G8 Fab-IL-2 qm-Fab | 4.5 | 0/6 | 0/6 | 0/6 |
| 9 | | 9 | 0/6 | 0/6 | 0/6 |

*in route to necropsy
**study was planned for seven days but all mice treated with the wild-type IL-2 immunoconjugate were markedly affected by Day 5 and were sacrificed as they were not expected to survive.

Clinical Observations

Observations of hypoactivity, cold skin, and hunched posture were noted in animals given 4.5 and 9 μg/g/day wt IL-2. Clinical observations are summarized in Table 18.

TABLE 18

Clinical observations day 5.

| Group | Type | Dose [μg/g] | Hunched posture | Hypoactive | Cool to touch |
|---|---|---|---|---|---|
| 1 | DPBS | 0 | 0/5 | 0/5 | 0/5 |
| 2 | 4G8 Fab-IL-2 wt-Fab | 4.5 | 4/5 | 4/5 | 5/5 |
| 3 | | 9 | 5/5 | 5/5 | 5/5 |
| 4 | 4G8 Fab-IL-2 qm-Fab | 4.5 | 0/5 | 0/5 | 0/5 |
| 5 | | 9 | 0/5 | 0/5 | 0/5 |
| 6 | 4G8 Fab-IL-2 wt-Fab | 4.5 | 6/6 | 2/6 | 2/6 |
| 7 | | 9 | 6/6 | 5/6 | 6/6 |
| 8 | 4G8 Fab-IL-2 qm-Fab | 4.5 | 0/6 | 0/6 | 0/6 |
| 9 | | 9 | 0/6 | 0/6 | 0/6 |

Body Weight

A moderate decrease in body weight was observed after 5 days of treatment in animals given 4.5 and 9 (9% and 11%, respectively) μg/g/day wt IL-2. A slight decrease in body weight was observed after 5 days of treatment in animals given 4.5 or 9 (2% and 1%, respectively) μg/g/day qm IL-2. A moderate (9%) decrease in body weight was also observed in vehicle controls after 5 days of treatment. However, the percent decrease would have been 5% if a potential outlier (Animal #3) was excluded. The body weight loss in the vehicle group may have been attributed to stress.

Hematology

A reduced platelet count was observed in animals given 4.5 (~4.5 fold) and 9 μg/g/day (~11 fold) 4G8 Fab-IL-2 wt-Fab, which correlated with reduced megakaryocytes in the bone marrow as well as systemic consumptive effects (fibrin) in spleen and lung of these animals (see Histopathology section below) These findings indicated that reduced platelets were likely due to combined effects of consumption and decrease in production/bone marrow crowding due to increase in lymphocyte/myeloid cell production as a direct or indirect effect of IL-2.

Hematologic findings of uncertain relationship to compound administration consisted of absolute lymphocyte count decreases with 4G8 Fab-IL-2 wt-Fab at 4.5 (~5-fold) and 9 μg/g (~3-fold) compared to the mean value of the vehicle control group. These findings lacked clear dose-dependency, but could be considered secondary to effects associated with stress noted in in-life observations or exagerated pharmacology of the compound (lymphocytes migrating into tissues). There were no treatment-related hematological changes attributed to the administration of 4G8-Fab-IL-2 qm-Fab. A few isolated hematologic findings were statistically different from their respective controls. However, these findings were of insufficient magnitude to suggest pathological relevance.

Gross Pathology and Histopathology

Treatment-related gross findings included enlarged spleen found in 5/5 and 4/5 mice of 4.5 and 9 μg/g 4G8 Fab-IL-2 wt-Fab groups, respectively, and in 1/5 in both 4.5 and 9 μg/g 4G8 Fab-IL-2 qm-Fab treatment groups.

Treatment-related histopathology findings were present in groups given 4.5 and 9 μg/g 4G8 Fab-IL-2 wt-Fab and 4.5 and 9 μg/g 4G8 Fab-IL-2 qm-Fab in lung, bone marrow, liver, spleen, and thymus, with differences in incidence, severity grading or nature of the changes, as reported below.

Treatment-related histopathology findings in the lung consisted of mononuclear infiltration found mild to marked in 5/5 mice of the 4.5 and 9 μg/g 4G8 Fab-IL-2 wt-Fab groups and marginally in 5/5 mice of the 4.5 and 9 μg/g 4G8 Fab-IL-2 qm-Fab groups. Mononuclear infiltration consisted of lymphocytes (some of which were noted as having cytoplasmic granules) as well as reactive macrophages. These cells were most often noted to have vasocentric patterns, often with margination noted within the vessels in the lung. These cells were also noted surrounding the vessels, but in more severe cases, the pattern was more diffuse. Hemorrhage was seen marginal to mild in 5/5 mice of the 4.5 and 9 μg/g 4G8 Fab-IL-2 wt-Fab groups and marginally in 2/5 mice in the 9 μg/g 4G8 Fab-IL-2 qm-Fab group. Though the hemorrhage was most often noted perivascularly, in more severe cases, it was noted in alveolar spaces. Edema was noted mild to moderate in 5/5 mice in the 4.5 and 9 μg/g 4G8 Fab-IL-2 wt-Fab groups and marginally in 5/5 mice in the 9 μg/g 4 G8 Fab-IL-2$_q$m-Fab group. Though the edema was frequently seen perivascularly, in more severe cases, it was noted in alveolar spaces as well. Marginal cellular degeneration and karyorrhexis was noted in 2/5 and 5/5 mice in the 4.5 and 9 μg/g 4G8 Fab-IL-2 wt-Fab groups, respectively and consisted of degeneration of infiltrative or reactive leukocytes. Selected animals with MSB stains were positive for fibrin found within the lungs of animals in both 4.5 and 9 μg/g 4G8 Fab-IL-2 wt-Fab groups which correlates in part with the reduced platelets noted in these animals.

Treatment-related changes in the bone marrow included marginal to mild increased overall marrow cellularity in 5/5 mice and 2/5 mice of both 4.5 and 5/5 mice and 2/5 mice of both 9 μg/g 4G8 Fab-IL-2 wt-Fab and 4G8 Fab-IL-2 qm-Fab groups, respectively. This was characterized by increased marginal to moderate lymphocyte-myelocyte hyperplasia in these groups that was supported, in part, by increased numbers of CD3 positive T cells within the marrow and sinuses (specifically T-lymphocytes, confirmed by immunohistochemistry with the pan-T-cell marker CD3 done on selected animals). CD3 positive T cell increase was moderate in both 4G8 Fab-IL-2 wt-Fab groups and marginal to mild in both 4G8 Fab-IL-2 qm-Fab groups Marginal to mild decreases in megakaryocytes were observed in 2/5 mice in the 4.5 and 5/5 mice in the 9 μg/g 4G8 Fab-IL-2 wt-Fab groups and marginal to moderate decreases in erythroid precursors were noted in 3/5 mice in the 4.5 and 5/5 mice in the 9 peg 4G8 Fab-IL-2 wt-Fab groups. Bone marrow necrosis was noted in 1/5 mice in 4.5 (minimal) and 5/5 mice in 9 (mild to marked) μg/g 4G8 Fab-IL-2 wt-Fab groups. The reduced number of megakaryocytes in the bone marrow correlated with decreased platelets which could be due to direct crowding of the bone marrow by increased lymphocytes/myeloid precursors and/or the bone marrow necrosis, and/or consumption of platelets due to inflammation in various tissues (see spleen and lung). The decreased erythroid precursors noted in the bone marrow, did not correlate with the peripheral blood hematology findings likely due to temporal effects (seen in bone marrow before peripheral blood) and the longer half-life of peripheral erythrocytes (compared to platelets). The mechanism of bone marrow necrosis in the bone marrow may be secondary due to overt overcrowding of the marrow cavity (due to production and growth of lymphocytes/myeloid cells), systemic or local release of cytokines from the proliferating cell types, possibly related to local affects of hypoxia or other pharmacologic effects of the compound.

Treatment-related findings in the liver consisted of mild to moderate primarily vasocentric mononuclear cell infiltrate and marginal to mild single cell necrosis in 5/5 mice of the 4.5 and 9 µg/g 4G8 Fab-IL-2 wt-Fab groups. Marginal single cell necrosis was seen in 2/5 and 4/5 mice in the 4.5 and 9 µg/g 4G8 Fab-IL-2 qm-Fab groups, respectively. The mononuclear infiltrate consisted primarily of lymphocytes (specifically T-lymphocytes, confirmed by immunohistochemistry with the pan-T cell marker CD3 done on selected animals) that were most often noted vasocentrically as well as marginating within the central and portal vessels. Selected animals for immunohistochemistry staining for F4/80 showed increased numbers and size (activated) of macrophages/Kupffer cells throughout the hepatic sinusoids in 9 µg/g 4G8 Fab-IL-2 wt-Fab and 4G8 Fab-IL-2 qm-Fab groups.

Treatment-related findings in the spleen consisted of moderate to marked lymphoid hyperplasia/infiltration and mild to moderate macrophage hyperplasia/infiltration in 5/5 mice in 4.5 and 9 µg/g 4G8 Fab-IL-2 wt-Fab groups and mild to moderate lymphoid hyperplasia/infiltration with marginal to mild macrophage hyperplasia/infiltration in 5/5 mice in 4.5 and 9 µg/g 4G8 Fab-IL-2 qm-Fab groups. Immunohistochemistry for 9 µg/g 4G8 Fab-IL-2 wt-Fab and 4G8 Fab-IL-2 qm-Fab showed different patterns using the pan-T cell marker CD3, as well as the macrophage marker F4/80. For 9 µg/g 4G8 Fab-IL-2 wt-Fab, the pattern of T-cell and macrophage immunoreactivity remained primarily within the red pulp areas, as the architecture of the primary follicles had been altered by lymphocytolysis and necrosis (described below). For 9 µg/g 4G8 Fab-IL-2 qm-Fab, special stains showed a pattern similar to that of the vehicle control, but with periarteriolar lymphoid sheath (PALS) white pulp expansion, by a T-cell population and a larger, expanded red pulp area. T-cell and macrophage positivity was also evident within the red pulp, with a similar pattern to the vehicle control group, but expanded. These findings correlate with the gross findings of enlarged spleen. Necrosis was noted marginally in 3/5 mice and marginally to mildly in 5/5 mice in 4.5 and 9 µg/g 4G8 Fab-IL-2 wt-Fab groups, respectively. Necrosis was usually located around the area of the primary follicles and selected animals using MSB stain were positive for fibrin in both 4.5 and 9 µg/g 4G8 Fab-IL-2 wt-Fab groups which correlates in part with the reduced platelets noted in these animals. Lymphocytolysis was seen in the 4.5 µg/g (minimal to mild) and 9 µg/g (moderate to marked) 4G8 Fab-IL-2 wt-Fab groups.

Treatment-related findings in the thymus included minimal to mild increases in lymphocytes in both 4.5 and 9 µg/g 4G8 Fab-IL-2 wt-Fab and in 4.5 ug/g 4G8 Fab-IL-2 qm-Fab groups. The cortex and medulla were not individually evident, in 4G8 Fab-IL-2 wt-Fab groups, but immunohistochemistry for the pan T cell marker (CD3) on selected animals in 9 µg/g 4G8 Fab-IL-2 wt-Fab and 9 µg/g 4G8 Fab-IL-2 qm-Fab groups showed strong positivity for the majority of the cells within the thymus. Increased lymphocytes in the thymus was considered to be a direct pharmacologic effect of both compounds where IL-2 induced proliferation of lymphocytes migrating to the thymus (T cells) from the bone marrow for further differentiation and clonal expansion. This occurred in all groups except 9 µg/g 4G8 Fab-IL-2 qm-Fab, which is likely a temporal effect. Lymphocytolysis was mild in 4.5 µg/g 4G8 Fab-IL-2 wt-Fab group, and was moderate to marked in the 9 µg/g 4G8 Fab-IL-2 wt-Fab group. Moderate lymphoid depletion was noted in both 4.5 and 9 µg/g 4G8 Fab-IL-2 wt-Fab groups. While these findings appear more robust in the 4.5 and 9 µg/g 4G8 Fab-IL-2 wt-Fab groups, these animals were described as moribund on Day 5, and the mild to marked lymphocytolysis as well as moderate lymphoid depletion may be related to this in-life observation (stress-related effects due to poor physical condition).

Histopathology findings of uncertain relationship to compound administration in the liver consisted of a marginal mixed cell (lymphocytes and macrophages) infiltrate/activation noted as small foci/microgranulomas scattered randomly throughout the liver in 5/5 mice in both 4.5 and 9 µg/g 4G8 Fab-IL-2 qm-Fab groups. This marginal change was also seen in the vehicle control group but with fewer incidence and severity. Stomach glandular dilation and atrophy was seen marginally to mildly in 5/5 mice and ileal villous atrophy was seen marginally in 3/5 mice in the 9 µg/g 4G8 Fab-IL-2 wt-Fab group. This finding is most likely attributed to poor physical condition seen in these mice such as reduced body weight, especially in the 9 µg/g 4G8 Fab-IL-2 wt-Fab group noted in the in-life observations.

Injection site findings included mixed cell infiltrate, perivascular edema, and myodegeneration that was noted equally in vehicle control, 9 µg/g 4G8 Fab-IL-2 wt-Fab and 9 µg/g 4G8 Fab-IL-2 qm-Fab groups. One animal had epidermal necrosis. These findings were not attributed to the treatment(s) itself, but to the daily i.v. injection and handling of the tail. Another animal had macrophage infiltration of the skeletal muscle (noted on the lung tissue histology section) associated with myodegeneration and myoregeneration likely due to a chronic lesion and was not attributed to the treatment. Marginal lymphoid depletion was noted in 3/5 and 4/5 mice in the 4.5 and 9 µg/g 4G8 Fab-IL-2 qm-Fab groups, respectively and was most likely attributed to normal physiologic changes seen in the thymus as mice get older (also seen in similar incidence, 4/5 mice, and severity in vehicle control animals).

In conclusion, the daily intravenous administration of 4G8 Fab-IL-2 wt-Fab or 4G8 Fab-IL-2 qm-Fab at doses of 4.5 or 9 µg/g/day for up to 5 days in male mice resulted in similar treatment-related histologic findings with both compounds. However, the findings were generally more prevalent and more severe with FAP-targeted 4G8 Fab-IL-2 wt-Fab in the lung (FIGS. 28 and 29) (mononuclear infiltration consisting of lymphocytes and reactive macrophages, hemorrhage, and edema), bone marrow (lympho-myelo hyperplasia and increased cellularity), liver (FIG. 30) (single cell necrosis, Kupffer cell/macrophage increase in number and activation), spleen (grossly enlarged, macrophage and lymphocyte infiltration/hyperplasia) and thymus (increased lymphocytes). In addition, mortality, lymphocytolysis, necrosis or cellular degeneration in the lung, spleen, bone marrow, and thymus, as well as reduced megakaryocytes and erythrocytes in bone marrow and reduced platelets in peripheral blood were seen only in animals given wt IL-2. Based on the clinical and anatomic pathologic findings, as well as clinical observations, and the comparable systemic exposure of both compounds, the qm IL-2 under conditions of this study exhibited markedly less systemic toxicity following 5 doses than wt IL-2.

Example 10

Induction of NK Cell IFN-γ Secretion by Wild Type and Quadruple Mutant IL-2

NK-92 cells were starved for 2 h before seeding 100000 cells/well into a 96 well-F-bottom plate. IL-2 constructs were titrated onto the seeded NK-92 cells. After 24 h or 48 h, plates were centrifuged before collecting the supernatants to determine the amount of human IFN-γ using a commercial IFN-γ ELISA (BD #550612).

Two different in-house preparations of wild type IL-2 (probably differing slightly in their 0-glycosylation profiles, see Example 2), a commercially available wild-type IL-2 (Proleukin) and in-house prepared quadruple mutant IL-2 (first batch) were tested.

FIG. 31 shows that the quadruple mutant IL-2 is equally potent as commercially obtained (Proleukin) or in-house produced wild-type IL-2 in inducing IFN-γ secretion by NK cells for 24 (A) or 48 hours (B).

Example 11

Induction of NK Cell Proliferation by Wild Type and Quadruple Mutant IL-2

NK-92-cells were starved for 2 h before seeding 10000 cells/well into 96-well-black-F-clear bottom plates. IL-2 constructs were titrated onto the seeded NK-92 cells. After 48 h the ATP content was measured to determine the number of viable cells using the "CellTiter-Glo Luminescent Cell Viability Assay" Kit from Promega according to the manufacturer's instructions.

The same IL-2 preparations as in Example 10 were tested.

FIG. 32 shows that all tested molecules were able to induce proliferation of NK cells. At low concentrations (<0.01 nM) the quadruple mutant IL-2 was slightly less active than the in-house produced wild-type IL-2, and all in-house preparations were less active than the commercially obtained wild-type IL-2 (Proleukin).

In a second experiment, the following IL-2 preparations were tested: wild-type IL-2 (pool 2), quadruple mutant IL-2 (first and second batch).

FIG. 33 shows that all tested molecules were about similarly active in inducing proliferation of NK cells, with the two mutant IL-2 preparations being only minimally less active than the wild-type IL-2 preparations at the lowest concentrations.

Example 12

Induction of Human PBMC Proliferation by Immunoconjugates Comprising Wild Type or Quadruple Mutant IL-2

Peripheral blood mononuclear cells (PBMC) were prepared using Histopaque-1077 (Sigma Diagnostics Inc., St. Louis, Mo., USA). In brief, venous blood from healthy volunteers was drawn into heparinized syringes. The blood was diluted 2:1 with calcium- and magnesium-free PBS, and layered on Histopaque-1077. The gradient was centrifuged at 450×g for 30 min at room temperature (RT) without breaks. The interphase containing the PBMCs was collected and washed three times with PBS (350×g followed by 300×g for 10 min at RT).

Subsequently, PBMCs were labeled with 40 nM CFSE (carboxyfluorescein succinimidyl ester) for 15 min at 37° C. Cells were washed with 20 ml medium before recovering the labeled PBMCs for 30 min at 37° C. The cells were washed, counted, and 100000 cells were seeded into 96-well-U-bottom plates. Pre-diluted Proleukin (commercially available wild-type IL-2) or IL2-immunoconjugates were titrated onto the seeded cells which were incubated for the indicated time points. After 4-6 days, cells were washed, stained for appropriate cell surface markers, and analyzed by FACS using a BD FACSCantoII. NK cells were defined as CD3$^-$/CD56$^+$, CD4 T cells as CD3$^+$/CD8$^-$, and CD8 T cells as CD3$^+$/CD8$^+$.

FIG. 34 shows proliferation of NK cells after incubation with different FAP-targeted 28H1 IL-2 immunoconjugates for 4 (A), 5 (B) or 6 (C) days. All tested constructs induced NK cell proliferation in a concentration-dependent manner. Proleukin was more efficacious than the immunoconjugates at lower concentrations, this difference no longer existed at higher concentrations, however. At earlier time points (day 4), the IgG-IL2 constructs appeared slightly more potent than the Fab-IL2-Fab constructs. At later time points (day 6), all constructs had comparable efficacy, with the Fab-IL2 qm-Fab construct being least potent at the low concentrations.

FIG. 35 shows proliferation of CD4 T-cells after incubation with different FAP-targeted 28H1 IL-2 immunoconjugates for 4 (A), 5 (B) or 6 (C) days. All tested constructs induced CD4 T cell proliferation in a concentration-dependent manner. Proleukin had a higher activity than the immunoconjugates, and the immunoconjugates comprising wild-type IL-2 were slightly more potent than the ones comprising quadruple mutant IL-2. As for the NK cells, the Fab-IL2 qm-Fab construct had the lowest activity. Most likely the proliferating CD4 T cells are partly regulatory T cells, at least for the wild-type IL-2 constructs.

FIG. 36 shows proliferation of CD8 T-cells after incubation with different FAP-targeted 28H1 IL-2 immunoconjugates for 4 (A), 5 (B) or 6 (C) days. All tested constructs induced CD8 T cell proliferation in a concentration-dependent manner. Proleukin had a higher activity than the immunoconjugates, and the immunoconjugates comprising wild-type IL-2 were slightly more potent than the ones comprising quadruple mutant IL-2. As for the NK and CD4 T cells, the Fab-IL2 qm-Fab construct had the lowest activity.

FIG. 37 depicts the results of another experiment, wherein FAP-targeted 28H1 IgG-IL-2, comprising either wild-type or quadruple mutant IL-2, and Proleukin were compared. Incubation time was 6 days. As shown in the figure, all three IL-2 constructs induce NK (A) and CD8 T-cell (C) proliferation in a dose-dependent manner with similar potency. For CD4 T-cells (B), the IgG-IL2 qm immunoconjugate has a lower activity, particularly at medium concentrations, which might be due to its lack of activity on CD25-positive (including regulatory) T cells which are a subset of CD4 T cells.

Example 13

Effector Cell Activation by Wild-Type and Quadruple Mutant IL-2 (pSTAT5 Assay) PBMCs were prepared as described above. 500000 PBMCs/well were seeded into 96-well-U-bottom plates and rested 45 min at 37° C. in RPMI medium containing 10% FCS and 1% Glutamax (Gibco). Afterwards, PBMCs were incubated with Proleukin, in-house produced wild-type IL-2 or quadruple mutant IL-2 at the indicated concentrations for 20 min at 37° C. to induce phosphorylation of STAT5. Subsequently, cells were immediately fixed (BD Cytofix Buffer) for 10 min at 37° C. and washed once, followed by a permeabilization step (BD Phosflow Perm Buffer III) for 30 min at 4° C. Afterwards, cells were washed with PBS/0.1% BSA and stained with mixtures of FACS antibodies for detection of NK cells (CD37CD56$^+$), CD8$^+$ T cells (CD3$^+$/CD8$^+$), CD4$^+$ T cells (CD3$^+$/CD4$^+$/CD257CD127$^+$) or $T_{1n}$ cells (CD4$^+$/CD25$^+$/CD127$^-$/FoxP3$^+$), as well as pSTAT5 for 30 min at RT in the dark. Cells were washed twice with PBS/0.1% BSA and resuspended in 2% PFA before flow cytometric analysis (BD FACSCantoII). FIG. 38 shows STAT phosphorylation in NK cells (A), CD8 T-cells (B), CD4 T-cells (C) and regulatory T-cells (D) after 30 min incubation with Proleukin, in-house produced wild-type IL-2 (pool 2) and quadruple mutant IL-2 (batch 1). All three IL-2 preparations were equally potent in inducing STAT phosphorylation in NK as well as CD8 T-cells. In CD4 T-cells and even more so in regulatory T-cells, the quadruple mutant IL-2 had a lower activity than the wild-type IL-2 preparations.

Example 14

Effector Cell Activation by Wild-Type and Quadruple Mutant IgG-IL-2 (pSTAT5 Assay)

Experimental conditions were as described above (see Example 13).

FIG. 39 shows STAT phosphorylation in NK cells (A), CD8 T-cells (B), CD4 T-cells (C) and regulatory T-cells (D) after 30 min incubation with Proleukin, IgG-IL-2 comprising wild-type IL-2 or IgG-IL-2 comprising quadruple mutant IL-2. On all cell types Proleukin was more potent in inducing STAT phosphorylation than the IgG-IL-2 immunoconjugates. The IgG-IL-2 wild-type and quadruple mutant constructs were equally potent in NK as well as CD8 T-cells. In CD4 T-cells and even more so in regulatory T-cells, the IgG-IL-2 quadruple mutant had a lower activity than the IgG-IL-2 wild-type immunoconjugate.

Example 15

Maximum Tolerated Dose (MTD) of FAP-Targeted Fab-IL2 wt-Fab and Fab-IL2 qm-Fab Immunoconjugates Escalating doses of FAP-targeted Fab-IL2-Fab immunoconjugates, comprising either wild type (wt) or quadruple mutant (qm) IL-2, were tested in tumor free immunocompetent Black 6 mice. Female Black 6 mice (Charles River, Germany), aged 8-9 weeks at the start of the experiment, were maintained under specific-pathogen-free conditions with daily cycles of 12 h light/12 h darkness according to committed guidelines (GV-Solas; Felasa; TierschG). The experimental study protocol was reviewed and approved by local government (P 2008016). After arrival, animals were maintained for one week to get accustomed to the new environment and for observation. Continuous health monitoring was carried out on a regular basis.

Mice were injected i.v. once a day for 7 days with 4G8 Fab-IL2 wt-Fab at doses of 60, 80 and 100 µg/mouse or 4G8 Fab-IL2 qm-Fab at doses of 100, 200, 400, 600 and 1000 µg/mouse. All mice were injected i.v. with 200 µl of the appropriate solution. To obtain the proper amount of immunoconjugate per 200 µl, the stock solutions were diluted with PBS as necessary. FIG. 40 shows that the MTD (maximum tolerated dose) for Fab-IL2 qm-Fab is 10-fold higher than for Fab-IL2 wt-Fab, namely 600 µg/mouse daily for 7 days for the Fab-IL2 qm-Fab vs. 60 µg/mouse daily for 7 days for the Fab-IL2 wt-Fab.

TABLE 19

| Compound | Dose | Formulation buffer | Concentration (mg/mL) |
| --- | --- | --- | --- |
| 4G8 Fab-IL2 wt-Fab | 60, 80, 100 µg | 25 mM potassium phosphate, 125 mM NaCl, 100 mM glycine, pH 6.7 | 3.32 (=stock solution) |
| 4G8 Fab-IL2 qm-Fab | 100, 200, 400, 600, 1000 µg | 25 mM potassium phosphate, 125 mM NaCl, 100 mM glycine, pH 6.7 | 4.25 (=stock solution) |

Example 16

Pharmacokinetics of a Single Dose of FAP-Targeted and Untargeted IgG-IL2 wt and Qm A single dose pharmacokinetics (PK) study was performed in tumor-free immunocompetent 129 mice for FAP-targeted-IgG-IL2 immunoconjugates comprising either wild type or quadruple mutant IL-2, and untargeted IgG-IL2 immunoconjugates comprising either wild type or quadruple mutant IL-2.

Female_129 mice (Harlan, United Kingdom), aged 8-9 weeks at the start of the experiment, were maintained under specific-pathogen-free conditions with daily cycles of 12 h light/12 h darkness according to committed guidelines (GV-Solas; Felasa; TierschG). The experimental study protocol was reviewed and approved by local government (P 2008016). After arrival, animals were maintained for one week to get accustomed to the new environment and for observation. Continuous health monitoring was carried out on a regular basis.

Mice were injected i.v. once with FAP-targeted 28H1 IgG-IL2 wt (2.5 mg/kg) or 28H1 IgG-IL2 qm (5 mg/kg), or untargeted DP47GS IgG-IL2 wt (5 mg/kg) or DP47GS IgG-IL2 qm (5 mg/kg). All mice were injected i.v. with 200 µl of the appropriate solution. To obtain the proper amount of immunoconjugate per 200 the stock solutions were diluted with PBS as necessary. Mice were bled at 1, 8, 24, 48, 72, 96 h; and every 2 days thereafter for 3 weeks. Sera were extracted and stored at −20° C. until ELISA analysis. Immunoconjugate concentrations in serum were determined using an ELISA for quantification of the IL2-immunoconjugate antibody (Roche-Penzberg). Absorption was measured using a measuring wavelength of 405 nm and a reference wavelength of 492 nm (VersaMax tunable microplate reader, Molecular Devices). FIG. 41 shows the pharmacokinetics of these IL-2 immunoconjugates. Both the FAP-targeted (A) and untargeted (B) IgG-IL2 qm constructs have a longer serum half-life (approx. 30 h) than the corresponding IgG-IL2 wt constructs (approx. 15 h).

TABLE 20

| Compound | Dose | Formulation buffer | Concentration (mg/mL) |
| --- | --- | --- | --- |
| 28H1-IgG-IL2 wt | 2.5 mg/kg | 20 mM Histidine, 140 mM NaCl, pH 6.0 | 3.84 (=stock solution) |

TABLE 20-continued

| Compound | Dose | Formulation buffer | Concentration (mg/mL) |
|---|---|---|---|
| 28H1-IgG-IL2 qm | 5 mg/kg | 20 mM Histidine, 140 mM NaCl, pH 6.0 | 2.42 (=stock solution) |
| DP47GS-IgG-IL2wt | 5 mg/kg | 20 mM Histidine, 140 mM NaCl, pH 6.0 | 3.74 (=stock solution) |
| DP47GS-IgG-IL2QM | 5 mg/kg | 20 mM Histidine, 140 mM NaCl, pH 6.0 | 5.87 (=stock solution) |

TABLE 21

| Compound | Dose | Formulation buffer | Concentration (mg/mL) |
|---|---|---|---|
| DP47GS Fab-IL2 wt-Fab | 65 nM/kg | 100 mM glycine, 125 mM NaCl, 25 mM $KH_2PO_4$, pH 6.7 | 3.84 (=stock solution) |
| DP47GS Fab-IL2 qm-Fab | 65 nM/kg | 100 mM glycine, 125 mM NaCl, 25 mM $KH_2PO_4$, pH 6.7 | 2.42 (=stock solution) |

Example 17

Pharmacokinetics of a Single Dose of Untargeted Fab-IL2 wt-Fab and Fab-IL2 qm-Fab A single dose pharmacokinetics (PK) study was performed in tumor-free immunocompetent 129 mice for untargeted Fab-IL2-Fab immunoconjugates comprising either wild type or quadruple mutant IL-2.

Female 129 mice (Harlan, United Kingdom), aged 8-9 weeks at the start of the experiment, were maintained under specific-pathogen-free conditions with daily cycles of 12 h light/12 h darkness according to committed guidelines (GV-Solas; Felasa; TierschG). The experimental study protocol was reviewed and approved by local government (P 2008016). After arrival, animals were maintained for one week to get accustomed to the new environment and for observation. Continuous health monitoring was carried out on a regular basis.

Mice were injected i.v. once with DP47GS Fab-IL2 wt-Fab at a dose of 65 nmol/kg or DP47GS Fab-IL2 qm-Fab at a dose of 65 nM/kg. All mice were injected i.v. with 200 µl of the appropriate solution. To obtain the proper amount of immunoconjugate per 200 µl, the stock solutions were diluted with PBS as necessary.

Mice were bled at 0.5, 1, 3, 8, 24, 48, 72, 96 hours and thereafter every 2 days for 3 weeks. Sera were extracted and stored at −20° C. until ELISA analysis. Immunoconjugate concentrations in serum were determined using an ELISA for quantification of IL2-immunoconjugate antibody (Roche-Penzberg). Absorption was measured using a measuring wavelength of 405 nm and a reference wavelength of 492 nm (VersaMax tunable microplate reader, Molecular Devices).

FIG. 42 shows the pharmacokinetics of these IL-2 immunoconjugates. Fab-IL2-Fab wt and qm constructs have an approx. serum half-life of 3-4 h. The difference in serum half-life between constructs comprising wild-type or quadruple mutant IL-2 is less pronounced for the Fab-IL2-Fab constructs than for IgG-like immunoconjugates, which per se have longer half-lives.

Example 18

Activation Induced Cell Death of IL-2 Activated PBMCs

Freshly isolated PBMCs from healthy donors were pre-activated overnight with PHA-M at 1 Ξg/ml in RPMI1640 with 10% FCS and 1% Glutamine. After pre-activation PBMCs were harvested, labeled with 40 nM CFSE in PBS, and seeded in 96-well plates at 100 000 cells/well. Pre-activated PBMCs were stimulated with different concentrations of IL-2 immunoconjugates (4B9 IgG-IL-2 wt, 4B9 IgG-IL-2 qm, 4B9 Fab-IL-2 wt-Fab, and 4B9 Fab-IL-2 qm-Fab). After six days of IL-2 treatment PBMCs were treated with 0.5 µg/ml activating anti-Fas antibody overnight. Proliferation of CD4 ($CD3^+CD8^-$) and CD8 ($CD3^+CD8^+$) T cells was analyzed after six days by CFSE dilution. The percentage of living T cells after anti-Fas treatment was determined by gating on $CD3^+$ Annexin V negative living cells.

As shown in FIG. 44, all constructs induced proliferation of pre-activated T cells. At low concentrations the constructs comprising wild-type IL-2 wt were more active than the IL-2 qm-comprising constructs. IgG-IL-2 wt, Fab-IL-2 wt-Fab and Proleukin had similar activity. Fab-IL-2 qm-Fab was slightly less active than IgG-IL-2 qm. The constructs comprising wild-type IL-2 were more active on CD4 T cells than on CD8 T cells, most probably because of the activation of regulatory T cells. The constructs comprising quadruple mutant IL-2 were similarly active on CD8 and CD4 T cells.

As shown in FIG. 45, T cells stimulated with high concentrations of wild-type IL-2 are more sensitive to anti-Fas induced apoptosis than T cells treated with quadruple mutant IL-2.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. An immunoconjugate comprising a mutant interleukin-2 (IL-2) polypeptide and an immunoglobulin molecule that specifically binds Fibroblast Activation Protein (FAP), wherein said mutant IL-2 polypeptide comprises a mutant form of SEQ ID NO: 1, wherein said mutant form of SEQ ID NO: 1 comprises up to five amino acid substitutions of SEQ ID NO: 1, wherein said up to five amino acid substitutions comprise: alanine at amino acid residue 42 of SEQ ID NO: 1, alanine at amino acid residue 45 of SEQ ID NO: 1, and glycine at amino acid residue 72 of SEQ ID NO: 1; and
wherein said immunoglobulin molecule comprises a heavy chain variable region sequence of SEQ ID NO: 111 and a light chain variable region sequence of SEQ ID NO: 109.

2. The immunoconjugate of claim 1, wherein said up to five amino acid substitutions further comprise:
   (a) zero additional amino acid substitution;
   (b) one additional amino acid substitution at amino acid residue 3 or 125 of SEQ ID NO: 1; or
   (c) two additional amino acid substitutions at amino acid residues 3 and 125 of SEQ ID NO: 1.

3. The immunoconjugate of claim 1, wherein said up to five amino acid substitutions comprise: alanine at amino acid residue 42 of SEQ ID NO: 1, alanine at amino acid residue 45 of SEQ ID NO: 1, glycine at amino acid residue 72 of SEQ ID NO: 1, and alanine at amino acid residue 3 of SEQ ID NO: 1.

4. The immunoconjugate of claim 1, wherein said up to five amino acid substitutions comprise:
   (a) alanine at amino acid residue 42 of SEQ ID NO: 1, alanine at amino acid residue 45 of SEQ ID NO: 1, glycine at amino acid residue 72 of SEQ ID NO: 1, and alanine, glycine, glutamine, glutamic acid, asparagine, aspartic acid, arginine, lysine, or proline at amino acid residue 3 of SEQ ID NO: 1, or
   (b) alanine at amino acid residue 42 of SEQ ID NO: 1, alanine at amino acid residue 45 of SEQ ID NO: 1, glycine at amino acid residue 72 of SEQ ID NO: 1, and serine, alanine, threonine, or valine at amino acid residue 125 of SEQ ID NO: 1.

5. The immunoconjugate of claim 1, wherein said up to five amino acid substitutions comprise: alanine at amino acid residue 42 of SEQ ID NO: 1, alanine at amino acid residue 45 of SEQ ID NO: 1, glycine at amino acid residue 72 of SEQ ID NO: 1; and two additional amino acid substitutions, wherein
one of said two additional amino acid substitutions is alanine, glycine, glutamine, glutamic acid, asparagine, aspartic acid, arginine, lysine, or proline at amino acid residue 3 of SEQ ID NO: 1; and
the other one of said two additional amino acid substitutions is serine, alanine, threonine, or valine at amino acid residue 125 of SEQ ID NO: 1.

6. The immunoconjugate of claim 1, wherein said immunoglobulin molecule is an IgG class immunoglobulin molecule.

7. The immunoconjugate of claim 1, wherein said immunoglobulin molecule is an IgG$_1$ subclass immunoglobulin molecule.

8. The immunoconjugate of claim 1, wherein said mutant IL-2 polypeptide is joined at its amino-terminal amino acid to the carboxy-terminal amino acid of one of the heavy chains of said immunoglobulin molecule.

9. The immunoconjugate of claim 8, wherein the immunoconjugate comprises not more than one mutant IL-2 polypeptide.

10. The immunoconjugate of claim 1, wherein the immunoconjugate comprises not more than one mutant IL-2 polypeptide.

11. The immunoconjugate of claim 10, consisting of the one mutant IL-2 polypeptide and the immunoglobulin molecule, joined by a linker sequence.

12. The immunoconjugate of claim 1, wherein said immunoglobulin molecule comprises a modification in the Fc domain promoting heterodimerization of the two immunoglobulin heavy chains.

13. The immunoconjugate of claim 12, wherein the modification is a knob-into-hole modification, comprising a knob modification in one of the immunoglobulin heavy chains and a hole modification in the other one of the immunoglobulin heavy chains.

14. The immunoconjugate of claim 13, wherein said immunoglobulin molecule is an IgG$_1$ subclass immunoglobulin molecule and wherein the knob modification comprises the amino acid substitution T366W in one of the two immunoglobulin heavy chains, and the hole modification comprises the amino acid substitutions T366S, L368A and Y407V in the other one of the two immunoglobulin heavy chains, according to the EU numbering of Kabat.

15. The immunoconjugate of claim 14, wherein the immunoglobulin heavy chain comprising the knob modification further comprises the amino acid substitution S354C, and the immunoglobulin heavy chain comprising the hole modification further comprises the amino acid substitution Y349C, according to the EU numbering of Kabat.

16. The immunoconjugate of claim 1, wherein the immunoglobulin molecule comprises one or more amino acid mutations in its Fc domain that reduces the binding affinity of the immunoconjugate to an FcγRIIIa, FcγRI or FcγRIIa receptor.

17. The immunoconjugate of claim 16, wherein said immunoglobulin molecule is an IgG$_1$ subclass immunoglobulin molecule and wherein the immunoglobulin molecule comprises the amino acid mutations L234A, L235A and P329G according to the EU numbering of Kabat.

18. A pharmaceutical composition comprising the immunoconjugate of claim 1 and a pharmaceutically acceptable carrier.

19. An immunoconjugate comprising a mutant interleukin-2 (IL-2) polypeptide and an immunoglobulin molecule that specifically binds Fibroblast Activation Protein (FAP),
wherein said mutant IL-2 polypeptide comprises the sequence of SEQ ID NO: 19; and
wherein said immunoglobulin molecule comprises a heavy chain variable region sequence of SEQ ID NO: 111 and a light chain variable region sequence of SEQ ID NO: 109.

20. The immunoconjugate of claim 19, wherein said mutant IL-2 polypeptide is joined at its amino-terminal amino acid to the carboxy-terminal amino acid of one of the heavy chains of said immunoglobulin molecule.

21. The immunoconjugate of claim 19, wherein the immunoconjugate comprises not more than one mutant IL-2 polypeptide.

22. The immunoconjugate of claim 21, wherein the immunoglobulin molecule comprises a modification in the Fc domain promoting heterodimerization of the two immunoglobulin heavy chains.

23. The immunoconjugate of claim 22, wherein the modification is a knob-into-hole modification, comprising a knob modification in one of the immunoglobulin heavy chains and a hole modification in the other one of the immunoglobulin heavy chains.

24. The immunoconjugate of claim 23, wherein said immunoglobulin molecule is an IgG$_1$ subclass immunoglobulin molecule and wherein the knob modification comprises the amino acid substitution T366W in one of the two immunoglobulin heavy chains, and the hole modification comprises the amino acid substitutions T366S, L368A and Y407V in the other one of the two immunoglobulin heavy chains, according to the EU numbering of Kabat.

25. The immunoconjugate of claim 24, wherein the immunoglobulin heavy chain comprising the knob modification further comprises the amino acid substitution S354C, and the immunoglobulin heavy chain comprising the hole modification further comprises the amino acid substitution Y349C, according to the EU numbering of Kabat.

26. The immunoconjugate of claim 19, wherein the immunoglobulin molecule comprises one or more amino acid mutations in its Fc domain that reduces the binding affinity of the immunoconjugate to an FcγRIIIa, FcγRI or FcγRIIa receptor.

27. The immunoconjugate of claim 26, wherein said immunoglobulin molecule is an IgG$_1$ subclass immunoglobulin molecule and wherein the immunoglobulin molecule comprises the amino acid mutations L234A, L235A and P329G according to the EU numbering of Kabat.

28. A pharmaceutical composition comprising the immunoconjugate of claim 19 and a pharmaceutically acceptable carrier.

29. An immunoconjugate comprising a mutant interleukin-2 (IL-2) polypeptide and an immunoglobulin molecule that specifically binds Fibroblast Activation Protein (FAP), wherein the immunoconjugate comprises a polypeptide sequence of SEQ ID NO: 301, a polypeptide sequence of SEQ ID NO: 303, and a polypeptide sequence of SEQ ID NO: 231.

30. A pharmaceutical composition comprising the immunoconjugate of claim 29 and a pharmaceutically acceptable carrier.

* * * * *

SEQUENCE LISTING

<160> NUMBER OF SEQ ID NOS: 324

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His

```
                1               5                  10                 15
            Leu Leu Leu Asp Leu Gln Met Ile Leu Asn Gly Ile Asn Asn Tyr Lys
                            20                  25                 30

Asn Pro Lys Leu Thr Arg Met Leu Thr Phe Lys Phe Tyr Met Pro Lys
                        35                  40                 45

Lys Ala Thr Glu Leu Lys His Leu Gln Cys Leu Glu Glu Glu Leu Lys
                    50                  55                 60

Pro Leu Glu Glu Val Leu Asn Leu Ala Gln Ser Lys Asn Phe His Leu
            65                  70                  75                 80

Arg Pro Arg Asp Leu Ile Ser Asn Ile Asn Val Ile Val Leu Glu Leu
                            85                  90                 95

Lys Gly Ser Glu Thr Thr Phe Met Cys Glu Tyr Ala Asp Glu Thr Ala
                        100                 105                110

Thr Ile Val Glu Phe Leu Asn Arg Trp Ile Thr Phe Cys Gln Ser Ile
                        115                 120                125

Ile Ser Thr Leu Thr
                        130

<210> SEQ ID NO 2
<211> LENGTH: 399
<212> TYPE: DNA
<213> ORGANISM: Artificial Sequence
<220> FEATURE:
<223> OTHER INFORMATION: Wild-type human IL-2

<400> SEQUENCE: 2
gcacctactt caagttctac aaagaaaaca cagctacaac tggagcattt actgctggat      60
ttacagatga ttttgaatgg aattaataat tacaagaatc ccaaactcac caggatgctc     120
acatttaagt tttacatgcc caagaaggcc acagaactga acatcttca gtgtctagaa      180 gaagaactca aacctctgga ggaagtgcta aatttagctc aaagcaaaaa ctttcactta     240
agacccaggg acttaatcag caatatcaac gtaatagttc tggaactaaa gggatctgaa     300
acaacattca gtgtgaata tgctgatgag acagcaacca ttgtagaatt tctgaacaga     360
tggattacct tttgtcaaag catcatctca acactgact                            399

<210> SEQ ID NO 3
<211> LENGTH: 133
<212> TYPE: PRT
<213> ORGANISM: Artificial Sequence
<220> FEATURE:
<223> OTHER INFORMATION: Wild-type human IL-2 (C125A)

<400> SEQUENCE: 3

Ala Pro Thr Ser Ser Ser Thr Lys Lys Thr Gln Leu Gln Leu Glu His
            1               5                  10                 15

Leu Leu Leu Asp Leu Gln Met Ile Leu Asn Gly Ile Asn Asn Tyr Lys
                            20                  25                 30

Asn Pro Lys Leu Thr Arg Met Leu Thr Phe Lys Phe Tyr Met Pro Lys
                        35                  40                 45

Lys Ala Thr Glu Leu Lys His Leu Gln Cys Leu Glu Glu Glu Leu Lys
                    50                  55                 60

Pro Leu Glu Glu Val Leu Asn Leu Ala Gln Ser Lys Asn Phe His Leu
            65                  70                  75                 80

Arg Pro Arg Asp Leu Ile Ser Asn Ile Asn Val Ile Val Leu Glu Leu
                            85                  90                 95

Lys Gly Ser Glu Thr Thr Phe Met Cys Glu Tyr Ala Asp Glu Thr Ala
```

```
                100                 105                 110
Thr Ile Val Glu Phe Leu Asn Arg Trp Ile Thr Phe Ala Gln Ser Ile
            115                 120                 125

Ile Ser Thr Leu Thr
    130

<210> SEQ ID NO 4
<211> LENGTH: 399
<212> TYPE: DNA
<213> ORGANISM: Artificial Sequence
<220> FEATURE:
<223> OTHER INFORMATION: Wild-type human IL-2 (C125A) (1)

<400> SEQUENCE: 4
gctcctacat cctccagcac caagaaaacc cagctccagc tggaacatct cctgctggat      60
ctgcagatga tcctgaacgg catcaacaac tacaagaacc ccaagctgac ccggatgctg     120
accttcaagt tctacatgcc caagaaggcc accgagctga acatctgca gtgcctggaa      180 gaggaactga agcctctgga agaggtgctg aacctggccc agtccaagaa cttccacctg     240
aggcctcggg acctgatctc caacatcaac gtgatcgtgc tggaactgaa gggctccgag     300
acaaccttca tgtgcgagta cgccgacgag acagctacca tcgtggaatt tctgaaccgg     360
tggatcacct tcgcccagtc catcatctcc accctgacc                            399

<210> SEQ ID NO 5
<211> LENGTH: 399
<212> TYPE: DNA
<213> ORGANISM: Artificial Sequence
<220> FEATURE:
<223> OTHER INFORMATION: Wild-type human IL-2 (C125A) (2)

<400> SEQUENCE: 5
gcacctactt caagttctac aaagaaaaca cagctacaac tggagcattt actgctggat      60
ttacagatga ttttgaatgg aattaataat tacaagaatc ccaaactcac caggatgctc     120
acatttaagt tttacatgcc caagaaggcc acagaactga acatcttca gtgtctagaa      180 gaagaactca aacctctgga ggaagtgcta aatttagctc aaagcaaaaa ctttcactta     240
agacccaggg acttaatcag caatatcaac gtaatagttc tggaactaaa gggatctgaa     300
acaacattca tgtgtgaata tgctgatgag acagcaacca ttgtagaatt tctgaacaga     360
tggattacct tgcccaaag catcatctca acactgact                             399

<210> SEQ ID NO 6
<211> LENGTH: 399
<212> TYPE: DNA
<213> ORGANISM: Artificial Sequence
<220> FEATURE:
<223> OTHER INFORMATION: Wild-type human IL-2 (C125A) (3)

<400> SEQUENCE: 6
gctcctacta gcagctccac caagaaaacc cagctccagc tggaacatct gctgctggat      60
ctgcagatga tcctgaacgg catcaacaac tacaagaacc ccaagctgac ccggatgctg     120
accttcaagt tctacatgcc caagaaggcc accgaactga acatctgca gtgcctggaa      180 gaggaactga agcctctgga agaggtgctg aacctggccc agagcaagaa cttccacctg     240
aggcccaggg acctgatcag caacatcaac gtgatcgtgc tggaactgaa gggcagcgag     300
acaaccttca tgtgcgagta cgccgacgag acagccacca tcgtggaatt tctgaaccgg     360
tggatcacct tcgcccagag catcatcagc accctgaca                            399
```

<210> SEQ ID NO 7
<211> LENGTH: 133
<212> TYPE: PRT
<213> ORGANISM: Artificial Sequence
<220> FEATURE:
<223> OTHER INFORMATION: IL-2 mutant L72G (C125A)

<400> SEQUENCE: 7

```
Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Gly Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ala Gln Ser Ile
        115                 120                 125
Ile Ser Thr Leu Thr
    130
```

<210> SEQ ID NO 8
<211> LENGTH: 399
<212> TYPE: DNA
<213> ORGANISM: Artificial Sequence
<220> FEATURE:
<223> OTHER INFORMATION: IL-2 mutant L72G (C125A) (1)

<400> SEQUENCE: 8

```
gctcctacat cctccagcac caagaaaacc cagctccagc tggaacatct cctgctggat      60
ctgcagatga tcctgaacgg catcaacaac tacaagaacc ccaagctgac ccggatgctg     120
accttcaagt tctacatgcc caagaaggcc accgagctga acatctgca gtgcctggaa     180
gaggaactga agcctctgga agaggtgctg aacggcgccc agtccaagaa cttccacctg     240
aggcctcggg acctgatctc caacatcaac gtgatcgtgc tggaactgaa gggctccgag     300
acaaccttca tgtgcgagta cgccgacgag acagctacca tcgtggaatt tctgaaccgg     360
tggatcacct tcgcccagtc catcatctcc accctgacc                            399
```

<210> SEQ ID NO 9
<211> LENGTH: 399
<212> TYPE: DNA
<213> ORGANISM: Artificial Sequence
<220> FEATURE:
<223> OTHER INFORMATION: IL-2 mutant L72G (C125A) (2)

<400> SEQUENCE: 9

```
gcacctactt caagttctac aaagaaaaca cagctacaac tggagcattt actgctggat      60
ttacagatga ttttgaatgg aattaataat tacaagaatc ccaaactcac caggatgctc     120
acatttaagt tttacatgcc caagaaggcc acagaactga acatcttca gtgtctagaa      180
gaagaactca aacctctgga ggaagtgcta aatggcgctc aaagcaaaaa ctttcactta     240
```

```
agacccaggg acttaatcag caatatcaac gtaatagttc tggaactaaa gggatctgaa      300
acaacattca tgtgtgaata tgctgatgag acagcaacca ttgtagaatt tctgaacaga      360
tggattacct ttgcccaaag catcatctca acactgact                             399
```

<210> SEQ ID NO 10
<211> LENGTH: 399
<212> TYPE: DNA
<213> ORGANISM: Artificial Sequence
<220> FEATURE:
<223> OTHER INFORMATION: IL-2 mutant L72G (C125A) (3)

<400> SEQUENCE: 10

```
gctcctacta gcagctccac caagaaaacc cagctccagc tggaacatct gctgctggat      60
ctgcagatga tcctgaacgg catcaacaac tacaagaacc ccaagctgac ccggatgctg      120
accttcaagt tctacatgcc caagaaggcc accgaactga acatctgca gtgcctggaa       180 gaggaactga agcctctgga agaggtgctg aacggcgccc agagcaagaa cttccacctg      240
aggcccaggg acctgatcag caacatcaac gtgatcgtgc tggaactgaa gggcagcgag      300
acaaccttca gtgcgagta cgccgacgag acagccacca tcgtggaatt tctgaaccgg      360
tggatcacct tcgcccagag catcatcagc accctgaca                             399
```

<210> SEQ ID NO 11
<211> LENGTH: 133
<212> TYPE: PRT
<213> ORGANISM: Artificial Sequence
<220> FEATURE:
<223> OTHER INFORMATION: IL-2 mutant L72G / F42A (C125A)

<400> SEQUENCE: 11

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130
```

<210> SEQ ID NO 12
<211> LENGTH: 399
<212> TYPE: DNA
<213> ORGANISM: Artificial Sequence
<220> FEATURE:
<223> OTHER INFORMATION: IL-2 mutant F42A / L72G (C125A) (1)

<400> SEQUENCE: 12

```
gctcctacat cctccagcac caagaaaacc cagctccagc tggaacatct cctgctggat      60
```

```
ctgcagatga tcctgaacgg catcaacaac tacaagaacc ccaagctgac ccggatgctg      120
accgccaagt tctacatgcc caagaaggcc accgagctga acatctgca gtgcctggaa      180 gaggaactga agcctctgga agaggtgctg aacggcgccc agtccaagaa cttccacctg      240
aggcctcggg acctgatctc caacatcaac gtgatcgtgc tggaactgaa gggctccgag      300
acaaccttca tgtgcgagta cgccgacgag acagctacca tcgtggaatt tctgaaccgg      360
tggatcacct tcgcccagtc catcatctcc accctgacc                             399

<210> SEQ ID NO 13
<211> LENGTH: 399
<212> TYPE: DNA
<213> ORGANISM: Artificial Sequence
<220> FEATURE:
<223> OTHER INFORMATION: IL-2 mutant F42A / L72G (C125A) (2)

<400> SEQUENCE: 13
gcacctactt caagttctac aaagaaaaca cagctacaac tggagcattt actgctggat       60
ttacagatga ttttgaatgg aattaataat tacaagaatc ccaaactcac caggatgctc      120
acagccaagt tttacatgcc caagaaggcc acagaactga acatcttca gtgtctagaa       180 gaagaactca aacctctgga ggaagtgcta aatggcgctc aaagcaaaaa ctttcactta      240
agacccaggg acttaatcag caatatcaac gtaatagttc tggaactaaa gggatctgaa      300
acaacattca tgtgtgaata cgctgatgag acagcaacca ttgtagaatt tctgaacaga      360
tggattacct ttgcccaaag catcatctca cactgact                              399

<210> SEQ ID NO 14
<211> LENGTH: 399
<212> TYPE: DNA
<213> ORGANISM: Artificial Sequence
<220> FEATURE:
<223> OTHER INFORMATION: IL-2 mutant F42A / L72G (C125A) (3)

<400> SEQUENCE: 14
gctcctacta gcagctccac caagaaaacc cagctccagc tggaacatct gctgctggat       60
ctgcagatga tcctgaacgg catcaacaac tacaagaacc ccaagctgac ccggatgctg      120
accgccaagt tctacatgcc caagaaggcc accgaactga acatctgca gtgcctggaa       180 gaggaactga agcctctgga agaggtgctg aacggcgccc agagcaagaa cttccacctg      240
aggcccaggg acctgatcag caacatcaac gtgatcgtgc tggaactgaa gggcagcgag      300
acaaccttca tgtgcgagta cgccgacgag acagccacca tcgtggaatt tctgaaccgg      360
tggatcacct tcgcccagag catcatcagc accctgaca                             399

<210> SEQ ID NO 15
<211> LENGTH: 133
<212> TYPE: PRT
<213> ORGANISM: Artificial Sequence
<220> FEATURE:
<223> OTHER INFORMATION: IL-2 triple mutant F42A / Y45A / L72G (C125A)

<400> SEQUENCE: 15

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Ala Met Pro Lys
            35                  40                  45
```

```
Lys Ala Thr Glu Leu Lys His Leu Gln Cys Leu Glu Glu Glu Leu Lys
 50                  55                  60

Pro Leu Glu Glu Val Leu Asn Gly Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
             100                 105                 110

Thr Ile Val Glu Phe Leu Asn Arg Trp Ile Thr Phe Ala Gln Ser Ile
         115                 120                 125

Ile Ser Thr Leu Thr
        130
```

<210> SEQ ID NO 16
<211> LENGTH: 399
<212> TYPE: DNA
<213> ORGANISM: Artificial Sequence
<220> FEATURE:
<223> OTHER INFORMATION: IL-2 triple mutant F42A / Y45A / L72G (C125A)
      (1)

<400> SEQUENCE: 16

```
gctcctacat cctccagcac caagaaaacc cagctccagc tggaacatct cctgctggat    60
ctgcagatga tcctgaacgg catcaacaac tacaagaacc ccaagctgac ccggatgctg   120
accgccaagt cgccatgcc caagaaggcc accgagctga acatctgca gtgcctggaa    180
gaggaactga agcctctgga agaggtgctg aacggcgccc agtccaagaa cttccacctg   240
aggcctcggg acctgatctc caacatcaac gtgatcgtgc tggaactgaa gggctccgag   300
acaaccttca tgtgcgagta cgccgacgag acagctacca tcgtggaatt ctgaaccgg   360
tggatcacct tcgcccagtc catcatctcc accctgacc                          399
```

<210> SEQ ID NO 17
<211> LENGTH: 399
<212> TYPE: DNA
<213> ORGANISM: Artificial Sequence
<220> FEATURE:
<223> OTHER INFORMATION: IL-2 triple mutant F42A / Y45A / L72G (C125A)
      (2)

<400> SEQUENCE: 17

```
gcacctactt caagttctac aaagaaaaca cagctacaac tggagcattt actgctggat    60
ttacagatga ttttgaatgg aattaataat tacaagaatc ccaaactcac caggatgctc   120
acagccaagt ttgccatgcc caagaaggcc acagaactga acatcttca gtgtctagaa    180
gaagaactca aacctctgga ggaagtgcta aatggcgctc aaagcaaaaa ctttcactta   240
agacccaggg acttaatcag caatatcaac gtaatagttc tggaactaaa gggatctgaa   300
acaacattca tgtgtgaata tgctgatgag acagcaacca ttgtagaatt ctgaacaga   360
tggattacct ttgcccaaag catcatctca acactgact                          399
```

<210> SEQ ID NO 18
<211> LENGTH: 399
<212> TYPE: DNA
<213> ORGANISM: Artificial Sequence
<220> FEATURE:
<223> OTHER INFORMATION: IL-2 triple mutant F42A / Y45A / L72G (C125A)
      (3)

<400> SEQUENCE: 18

```
gctcctacta gcagctccac caagaaaacc cagctccagc tggaacatct gctgctggat        60
ctgcagatga tcctgaacgg catcaacaac tacaagaacc ccaagctgac ccggatgctg       120
accgccaagt tcgccatgcc caagaaggcc accgaactga acatctgca gtgcctggaa       180 gaggaactga agcctctgga agaggtgctg aacggcgccc agagcaagaa cttccacctg       240
aggcccaggg acctgatcag caacatcaac gtgatcgtgc tggaactgaa gggcagcgag       300
acaaccttca tgtgcgagta cgccgacgag acagccacca tcgtggaatt tctgaaccgg       360
tggatcacct tcgcccagag catcatcagc accctgaca                              399
```

<210> SEQ ID NO 19
<211> LENGTH: 133
<212> TYPE: PRT
<213> ORGANISM: Artificial Sequence
<220> FEATURE:
<223> OTHER INFORMATION: IL-2 quadruple mutant T3A / F42A / Y45A / L72G (C125A)

<400> SEQUENCE: 19

```
Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Ala Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130
```

<210> SEQ ID NO 20
<211> LENGTH: 399
<212> TYPE: DNA
<213> ORGANISM: Artificial Sequence
<220> FEATURE:
<223> OTHER INFORMATION: IL-2 quadruple mutant T3A / F42A / Y45A / L72G (C125A) (1)

<400> SEQUENCE: 20

```
gctcctgcct cctccagcac caagaaaacc cagctccagc tggaacatct cctgctggat        60
ctgcagatga tcctgaacgg catcaacaac tacaagaacc ccaagctgac ccggatgctg       120
accgccaagt tcgccatgcc caagaaggcc accgagctga acatctgca gtgcctggaa       180 gaggaactga agcctctgga agaggtgctg aacggcgccc agtccaagaa cttccacctg       240
aggcctcggg acctgatctc caacatcaac gtgatcgtgc tggaactgaa gggctccgag       300
acaaccttca tgtgcgagta cgccgacgag acagctacca tcgtggaatt tctgaaccgg       360
tggatcacct tcgcccagtc catcatctcc accctgacc                              399
```

<210> SEQ ID NO 21
<211> LENGTH: 399
<212> TYPE: DNA
<213> ORGANISM: Artificial Sequence
<220> FEATURE:
<223> OTHER INFORMATION: IL-2 quadruple mutant T3A / F42A / Y45A / L72G (C125A) (2)

<400> SEQUENCE: 21

```
gcacctgcct caagttctac aaagaaaaca cagctacaac tggagcattt actgctggat    60
ttacagatga ttttgaatgg aattaataat acaagaatc ccaaactcac caggatgctc   120
acagccaagt tgccatgcc caagaaggcc acagaactga acatcttca gtgtctagaa    180
gaagaactca aacctctgga ggaagtgcta aatggcgctc aaagcaaaaa ctttcactta   240
agacccaggg acttaatcag caatatcaac gtaatagttc tggaactaaa gggatctgaa   300
acaacattca tgtgtgaata tgctgatgag acagcaacca ttgtagaatt tctgaacaga   360
tggattacct tgcccaaag catcatctca acactgact                           399
```

<210> SEQ ID NO 22
<211> LENGTH: 399
<212> TYPE: DNA
<213> ORGANISM: Artificial Sequence
<220> FEATURE:
<223> OTHER INFORMATION: IL-2 quadruple mutant T3A / F42A / Y45A / L72G (C125A) (3)

<400> SEQUENCE: 22

```
gctcctgcca gcagctccac caagaaaacc cagctccagc tggaacatct gctgctggat    60
ctgcagatga tcctgaacgg catcaacaac tacaagaacc ccaagctgac ccggatgctg   120
accgccaagt cgccatgcc caagaaggcc accgaactga acatctgca gtgcctggaa    180
gaggaactga agcctctgga agaggtgctg aacggcgccc agagcaagaa cttccacctg   240
aggcccaggg acctgatcag caacatcaac gtgatcgtgc tggaactgaa gggcagcgag   300
acaaccttca tgtgcgagta cgccgacgag acagccacca tcgtggaatt tctgaaccgg   360
tggatcacct tcgcccagag catcatcagc accctgaca                          399
```

<210> SEQ ID NO 23
<211> LENGTH: 107
<212> TYPE: PRT
<213> ORGANISM: Artificial Sequence
<220> FEATURE:
<223> OTHER INFORMATION: 2B10; VL

<400> SEQUENCE: 23

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105
```

<210> SEQ ID NO 24
<211> LENGTH: 321
<212> TYPE: DNA
<213> ORGANISM: Artificial Sequence
<220> FEATURE:
<223> OTHER INFORMATION: 2B10; VL

<400> SEQUENCE: 24

```
gatatccaga tgacccagtc tccatcctcc ctgtctgcat ctgtcggaga ccgggtcacc      60
atcacctgcc gggcaagtca gggcattaga aatgatttag ctggtacca gcagaagcca     120 gggaaagccc ctaagcgcct gatctatgct gcatccagtt tgcagagtgg cgtcccatca    180
aggttcagcg gcggtggatc cgggacagag ttcactctca ccatcagcag cttgcagcct    240
gaagattttg ccacctatta ctgcttgcag aatggtctgc agcccgcgac gtttggccag    300
ggcaccaaag tcgagatcaa g                                              321
```

<210> SEQ ID NO 25
<211> LENGTH: 107
<212> TYPE: PRT
<213> ORGANISM: Artificial Sequence
<220> FEATURE:
<223> OTHER INFORMATION: 2B10(GS); VL

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105
```

<210> SEQ ID NO 26
<211> LENGTH: 321
<212> TYPE: DNA
<213> ORGANISM: Artificial Sequence
<220> FEATURE:
<223> OTHER INFORMATION: 2B10(GS); VL

<400> SEQUENCE: 26

```
gatatccaga tgacccagtc tccatcctcc ctgtctgcat ctgtcggaga ccgggtcacc      60
atcacctgcc gggcaagtca gggcattaga aatgatttag ctggtacca gcagaagcca     120 gggaaagccc ctaagcgcct gatctatgct gcatccagtt tgcagagtgg cgtcccatca    180
aggttcagcg gcagtggatc cgggacagag ttcactctca ccatcagcag cttgcagcct    240
gaagattttg ccacctatta ctgcttgcag aatggtctgc agcccgcgac gtttggccag    300
ggcaccaaag tcgagatcaa g                                              321
```

<210> SEQ ID NO 27
<211> LENGTH: 121

```
<212> TYPE: PRT
<213> ORGANISM: Artificial Sequence
<220> FEATURE:
<223> OTHER INFORMATION: 2B10; VH

<400> SEQUENCE: 27
```

| Gln | Val | Gln | Leu | Val | Gln | Ser | Gly | Ala | Glu | Val | Lys | Lys | Pro | Gly | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Val | Lys | Val | Ser | Cys | Lys | Ala | Ser | Gly | Gly | Thr | Phe | Ser | Ser | Tyr |
|     |     |     | 20  |     |     |     |     | 25  |     |     |     |     | 30  |     |     |

| Ala | Ile | Ser | Trp | Val | Arg | Gln | Ala | Pro | Gly | Gln | Gly | Leu | Glu | Trp | Met |
|     |     |     | 35  |     |     |     |     | 40  |     |     |     |     | 45  |     |     |

| Gly | Gly | Ile | Ile | Pro | Ile | Phe | Gly | Thr | Ala | Asn | Tyr | Ala | Gln | Lys | Phe |
|     | 50  |     |     |     |     | 55  |     |     |     |     | 60  |     |     |     |     |

| Gln | Gly | Arg | Val | Thr | Ile | Thr | Ala | Asp | Lys | Ser | Thr | Ser | Thr | Ala | Tyr |
| 65  |     |     |     |     | 70  |     |     |     |     | 75  |     |     |     |     | 80  |

| Met | Glu | Leu | Ser | Ser | Leu | Arg | Ser | Glu | Asp | Thr | Ala | Val | Tyr | Tyr | Cys |
|     |     |     |     | 85  |     |     |     |     | 90  |     |     |     |     | 95  |     |

| Ala | Arg | Leu | Tyr | Gly | Tyr | Ala | Tyr | Tyr | Gly | Ala | Phe | Asp | Tyr | Trp | Gly |
|     |     |     |     | 100 |     |     |     |     | 105 |     |     |     |     | 110 |     |

| Gln | Gly | Thr | Thr | Val | Thr | Val | Ser | Ser |
|     |     |     | 115 |     |     |     |     | 120 |

```
<210> SEQ ID NO 28
<211> LENGTH: 363
<212> TYPE: DNA
<213> ORGANISM: Artificial Sequence
<220> FEATURE:
<223> OTHER INFORMATION: 2B10; VH

<400> SEQUENCE: 28
caggtgcaat tggtgcagtc tggggctgag gtgaagaagc ctgggtcctc ggtgaaggtc      60
tcctgcaagg cctccggagg cacattcagc agctacgcta taagctgggt gcgacaggcc     120
cctggacaag gctcgagtg gatgggaggg atcatcccta tctttggtac agcaaactac     180
gcacagaagt tccagggcag ggtcaccatt actgcagaca atccacgag cacagcctac     240
atggagctga gcagcctgag atctgaggac accgccgtgt attactgtgc gagactgtac     300
ggttacgctt actacggtgc ttttgactac tggggccaag gaccaccgt gaccgtctcc     360
tca                                                                    363

<210> SEQ ID NO 29
<211> LENGTH: 108
<212> TYPE: PRT
<213> ORGANISM: Artificial Sequence
<220> FEATURE:
<223> OTHER INFORMATION: 2F11; VL

<400> SEQUENCE: 29
```

| Glu | Ile | Val | Leu | Thr | Gln | Ser | Pro | Gly | Thr | Leu | Ser | Leu | Ser | Pro | Gly |
| 1   |     |     |     | 5   |     |     |     |     | 10  |     |     |     |     | 15  |     |

| Glu | Arg | Ala | Thr | Leu | Ser | Cys | Arg | Ala | Ser | Gln | Ser | Val | Ser | Ser | Ser |
|     |     |     | 20  |     |     |     |     | 25  |     |     |     |     | 30  |     |     |

| Tyr | Leu | Ala | Trp | Tyr | Gln | Gln | Lys | Pro | Gly | Gln | Ala | Pro | Arg | Leu | Leu |
|     |     |     | 35  |     |     |     |     | 40  |     |     |     |     | 45  |     |     |

| Ile | Tyr | Gly | Ala | Ser | Ser | Arg | Ala | Thr | Gly | Val | Pro | Asp | Arg | Phe | Ser |
|     |     |     | 50  |     |     |     |     | 55  |     |     |     |     | 60  |     |     |

| Gly | Ser | Gly | Ser | Gly | Thr | Asp | Phe | Thr | Leu | Thr | Ile | Ser | Arg | Leu | Glu |
| 65  |     |     |     |     | 70  |     |     |     |     | 75  |     |     |     |     | 80  |

```
Pro Glu Asp Phe Ala Val Tyr Tyr Cys Gln Gln Gly Gln Tyr Thr Pro
                85                  90                  95
Pro Thr Phe Gly Gln Gly Thr Lys Val Glu Ile Lys
            100                 105
```

<210> SEQ ID NO 30
<211> LENGTH: 324
<212> TYPE: DNA
<213> ORGANISM: Artificial Sequence
<220> FEATURE:
<223> OTHER INFORMATION: 2F11; VL

<400> SEQUENCE: 30

```
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcgtccca     180
gacaggttca gtggcagtgg atccgggaca gacttcactc tcaccatcag cagactggag     240
cctgaagatt ttgcagtgta ttactgtcag cagggtcagt atactccccc cacgttcggc     300
caggggacca agtggaaat caaa                                             324
```

<210> SEQ ID NO 31
<211> LENGTH: 108
<212> TYPE: PRT
<213> ORGANISM: Artificial Sequence
<220> FEATURE:
<223> OTHER INFORMATION: 2F11(VI); VL

<400> SEQUENCE: 31

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Gly Gln Tyr Thr Pro
                85                  90                  95
Pro Thr Phe Gly Gln Gly Thr Lys Val Glu Ile Lys
            100                 105
```

<210> SEQ ID NO 32
<211> LENGTH: 324
<212> TYPE: DNA
<213> ORGANISM: Artificial Sequence
<220> FEATURE:
<223> OTHER INFORMATION: 2F11(VI); VL

<400> SEQUENCE: 32

```
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcagtgta ttactgtcag cagggtcagt atactccccc cacgttcggc     300
``` cagggggacca aagtggaaat caaa                                          324

<210> SEQ ID NO 33
<211> LENGTH: 117
<212> TYPE: PRT
<213> ORGANISM: Artificial Sequence
<220> FEATURE:
<223> OTHER INFORMATION: 2F11; VH

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Met Ala Val Tyr Tyr Cys
                85                  90                  95

Ala Lys Trp Arg Trp Met Met Phe Asp Tyr Trp Gly Gln Gly Thr Leu
            100                 105                 110

Val Thr Val Ser Ser
        115

<210> SEQ ID NO 34
<211> LENGTH: 351
<212> TYPE: DNA
<213> ORGANISM: Artificial Sequence
<220> FEATURE:
<223> OTHER INFORMATION: 2F11; VH

<400> SEQUENCE: 34
gaggtgcaat tgttggagtc tgggggaggc ttggtacagc ctggggggtc cctgagactc    60
tcctgtgcag cctccggatt cacctttagc agttatgcca tgagctgggt ccgccaggct   120
ccagggaagg gcctgagtg gtctcagct attagtggta gtggtggtag cacatactac    180
gcagactccg tgaagggccg gttcaccatc tccagagaca attccaagaa cacgctgtat   240
ctgcagatga acagcctgag agccgaggac atggccgtat attactgtgc gaaatggaga   300
tggatgatgt ttgactactg gggccaagga accctggtca ccgtctcgag t            351

<210> SEQ ID NO 35
<211> LENGTH: 117
<212> TYPE: PRT
<213> ORGANISM: Artificial Sequence
<220> FEATURE:
<223> OTHER INFORMATION: 2F11(MT); VH

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Trp Arg Trp Met Met Phe Asp Tyr Trp Gly Gln Gly Thr Leu
                100                 105                 110

Val Thr Val Ser Ser
            115
```

<210> SEQ ID NO 36
<211> LENGTH: 351
<212> TYPE: DNA
<213> ORGANISM: Artificial Sequence
<220> FEATURE:
<223> OTHER INFORMATION: 2F11(MT); VH

<400> SEQUENCE: 36

```
gaggtgcaat tgttggagtc tgggggaggc ttggtacagc ctgggggtc cctgagactc      60 tcctgtgcag cctccggatt cacctttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac accgccgtat attactgtgc gaaatggaga    300
tggatgatgt ttgactactg gggccaagga accctggtca ccgtctcgag t             351
```

<210> SEQ ID NO 37
<211> LENGTH: 108
<212> TYPE: PRT
<213> ORGANISM: Artificial Sequence
<220> FEATURE:
<223> OTHER INFORMATION: 3F2; VL

<400> SEQUENCE: 37

```
Glu Ile Val Leu Thr Gln Ser Pro Gly Thr Leu Ser Leu Tyr Pro Gly
  1               5                  10                  15

Glu Arg Ala Thr Leu Ser Cys Arg Ala Ser Gln Ser Val Thr Ser Ser
                 20                  25                  30

Tyr Leu Ala Trp Tyr Gln Gln Lys Pro Gly Gln Ala Pro Arg Leu Leu
             35                  40                  45

Ile Asn Val Gly Ser Arg Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Ile Met Leu Pro
                 85                  90                  95

Pro Thr Phe Gly Gln Gly Thr Lys Val Glu Ile Lys
                100                 105
```

<210> SEQ ID NO 38
<211> LENGTH: 324
<212> TYPE: DNA
<213> ORGANISM: Artificial Sequence
<220> FEATURE:
<223> OTHER INFORMATION: 3F2; VL

<400> SEQUENCE: 38

```
gaaatcgtgt taacgcagtc tccaggcacc ctgtctttgt atccagggga aagagccacc      60
```

```
ctctcttgca gggccagtca gagtgttacc agtagctact tagcctggta ccagcagaaa    120
cctggccagg ctcccaggct cctcatcaat gtgggctccc gtagggccac tggcatccca    180
gacaggttca gtggcagtgg atccgggaca gacttcactc tcaccatcag cagactggag    240
cctgaagatt ttgcagtgta ttactgtcag cagggtatta tgcttccccc gacgttcggc    300
caggggacca agtggaaat caaa                                            324
```

<210> SEQ ID NO 39
<211> LENGTH: 108
<212> TYPE: PRT
<213> ORGANISM: Artificial Sequence
<220> FEATURE:
<223> OTHER INFORMATION: 3F2(YS); VL

<400> SEQUENCE: 39

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105
```

<210> SEQ ID NO 40
<211> LENGTH: 324
<212> TYPE: DNA
<213> ORGANISM: Artificial Sequence
<220> FEATURE:
<223> OTHER INFORMATION: 3F2(YS); VL

<400> SEQUENCE: 40

```
gaaatcgtgt taacgcagtc tccaggcacc ctgtctttgt ctccagggga aagagccacc     60
ctctcttgca gggccagtca gagtgttacc agtagctact tagcctggta ccagcagaaa    120
cctggccagg ctcccaggct cctcatcaat gtgggctccc gtagggccac tggcatccca    180
gacaggttca gtggcagtgg atccgggaca gacttcactc tcaccatcag cagactggag    240
cctgaagatt ttgcagtgta ttactgtcag cagggtatta tgcttccccc gacgttcggc    300
caggggacca agtggaaat caaa                                            324
```

<210> SEQ ID NO 41
<211> LENGTH: 117
<212> TYPE: PRT
<213> ORGANISM: Artificial Sequence
<220> FEATURE:
<223> OTHER INFORMATION: 3F2; VH

<400> SEQUENCE: 41

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
            115

<210> SEQ ID NO 42
<211> LENGTH: 351
<212> TYPE: DNA
<213> ORGANISM: Artificial Sequence
<220> FEATURE:
<223> OTHER INFORMATION: 3F2; VH

<400> SEQUENCE: 42
gaggtgcaat tgttggagtc tgggggaggc ttggtacagc ctgggggtc cctgagactc      60 tcctgtgcag cctccggatt cacctttagc agttatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcagatga acagcctgag agccgaggac acggccgtat attactgtgc gaaagggtgg    300
tttggtggtt ttaactactg gggccaagga accctggtca ccgtctcgag t             351

<210> SEQ ID NO 43
<211> LENGTH: 108
<212> TYPE: PRT
<213> ORGANISM: Artificial Sequence
<220> FEATURE:
<223> OTHER INFORMATION: 3D9, VL

<400> SEQUENCE: 43

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Gln Leu Ile Pro
                85                  90                  95

Pro Thr Phe Gly Gln Gly Thr Lys Val Glu Ile Lys
            100                 105

<210> SEQ ID NO 44
<211> LENGTH: 324
<212> TYPE: DNA
<213> ORGANISM: Artificial Sequence
<220> FEATURE:
<223> OTHER INFORMATION: 3D9, VL
```

```
<400> SEQUENCE: 44
gaaatcgtgt taacgcagtc tccaggcacc ctgtctttgt ctccagggga aagagccacc    60
ctctcttgca gggccagtca gagtgttagc agcagctact tagcctggta ccagcagaaa   120
cctggccagg ctcccaggct cctcatctat ggagcatcca gcagggccac tggcatccca   180
gacaggttca gtggcagtgg atccgggaca gacttcactc tcaccatcag cagactggag   240
cctgaagatt ttgcagtgta ttactgtcag cagggtcagc ttattccccc tacgttcggc   300
caggggacca agtggaaat caaa                                           324

<210> SEQ ID NO 45
<211> LENGTH: 117
<212> TYPE: PRT
<213> ORGANISM: Artificial Sequence
<220> FEATURE:
<223> OTHER INFORMATION: 3D9, VH

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Thr Pro Gly Lys Gly Leu Glu Trp Val
        35                  40                  45

Ser Ala Ile Gly Val Ser Thr Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Pro Phe Asp Tyr Trp Gly Gln Gly Thr Leu
            100                 105                 110

Val Thr Val Ser Ser
        115

<210> SEQ ID NO 46
<211> LENGTH: 351
<212> TYPE: DNA
<213> ORGANISM: Artificial Sequence
<220> FEATURE:
<223> OTHER INFORMATION: 3D9, VH

<400> SEQUENCE: 46
gaggtgcaat tgttggagtc tgggggaggc ttggtacagc ctggggggtc cctgagactc    60
tcctgtgcag cctccggatt cacctttagc agttatgcta tgagctgggt ccgccagact   120
ccagggaagg ggctggagtg ggtctcagct attggtgtta gtactggtag cacatactac   180
gcagactccg tgaagggccg gttcaccatc tccagagaca attccaagaa cacgctgtat   240
ctgcagatga acagcctgag agccgaggac acggccgtat attactgtgc gaaaggttgg   300
ctgggtcctt ttgactactg gggccaagga accctggtca ccgtctcgag t           351

<210> SEQ ID NO 47
<211> LENGTH: 117
<212> TYPE: PRT
<213> ORGANISM: Artificial Sequence
<220> FEATURE:
<223> OTHER INFORMATION: 3D9(TA); VH

<400> SEQUENCE: 47
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Val Ser Thr Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Pro Phe Asp Tyr Trp Gly Gln Gly Thr Leu
            100                 105                 110

Val Thr Val Ser Ser
            115
```

<210> SEQ ID NO 48
<211> LENGTH: 351
<212> TYPE: DNA
<213> ORGANISM: Artificial Sequence
<220> FEATURE:
<223> OTHER INFORMATION: 3D9(TA); VH

<400> SEQUENCE: 48

```
gaggtgcaat tgttggagtc tgggggaggc ttggtacagc ctgggggtc cctgagactc      60 tcctgtgcag cctccggatt cacctttagc agttatgcta tgagctgggt ccgccaggct    120
ccagggaagg gctggagtg gtctcagct attggtgtta gtactggtag cacatactac      180
gcagactccg tgaagggccg gttcaccatc tccagagaca attccaagaa cacgctgtat    240
ctgcagatga acagcctgag agccgaggac acggccgtat attactgtgc gaaaggttgg    300
ctgggtcctt ttgactactg gggccaagga accctggtca ccgtctcgag t             351
```

<210> SEQ ID NO 49
<211> LENGTH: 108
<212> TYPE: PRT
<213> ORGANISM: Artificial Sequence
<220> FEATURE:
<223> OTHER INFORMATION: 4G8; VL

<400> SEQUENCE: 49

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105
```

<210> SEQ ID NO 50
<211> LENGTH: 324
<212> TYPE: DNA
<213> ORGANISM: Artificial Sequence
<220> FEATURE:
<223> OTHER INFORMATION: 4G8; VL

<400> SEQUENCE: 50

```
gaaatcgtgt taacgcagtc tccaggcacc ctgtctttgt ctccagggga aagagccacc      60
ctctcttgca gggccagtca gagtgttagc cgcagctact tagcctggta ccagcagaaa     120
cctggccagg ctcccaggct cctcatcatt ggggcctcca ccagggccac tggcatccca     180
gacaggttca gtggcagtgg atccgggacg gacttcactc tcaccatcag cagactggag     240
cctgaagatt ttgcagtgta ttactgtcag cagggtcagg ttattccccc tacgttcggc     300
caggggacca agtggaaat caaa                                              324
```

<210> SEQ ID NO 51
<211> LENGTH: 117
<212> TYPE: PRT
<213> ORGANISM: Artificial Sequence
<220> FEATURE:
<223> OTHER INFORMATION: 4G8; VH

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser
        115

<210> SEQ ID NO 52
<211> LENGTH: 351
<212> TYPE: DNA
<213> ORGANISM: Artificial Sequence
<220> FEATURE:
<223> OTHER INFORMATION: 4G8; VH

<400> SEQUENCE: 52

```
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg ggctggagtg gtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaaggtgg     300 ctgggtaatt ttgactactg gggccaagga accctggtca ccgtctcgag t              351
```

<210> SEQ ID NO 53

```
<211> LENGTH: 108
<212> TYPE: PRT
<213> ORGANISM: Artificial Sequence
<220> FEATURE:
<223> OTHER INFORMATION: 4B3; VL

<400> SEQUENCE: 53

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Tyr Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105

<210> SEQ ID NO 54
<211> LENGTH: 324
<212> TYPE: DNA
<213> ORGANISM: Artificial Sequence
<220> FEATURE:
<223> OTHER INFORMATION: 4B3; VL

<400> SEQUENCE: 54
gaaatcgtgt taacgcagtc tccaggcacc ctgtctttgt ctccagggga aagagccacc      60
ctctcttgca gggccagtca gagtgttagc agcaattact tagcctggta ccagcagaaa     120
cctggccagg ctcccaggct cctcatctat ggcgcctaca tcagggccac tggcatccca     180
gacaggttca gtggcagtgg atccgggaca gacttcactc tcaccatcag cagactggag     240
cctgaagatt ttgcagtgta ttactgtcag cagggtcagg ttattccccc tacgttcggc     300
caggggacca agtggaaat caaa                                              324

<210> SEQ ID NO 55
<211> LENGTH: 117
<212> TYPE: PRT
<213> ORGANISM: Artificial Sequence
<220> FEATURE:
<223> OTHER INFORMATION: 4B3; VH

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys Gly Trp Leu Gly Asn Phe Asp Tyr Trp Gly Gln Gly Thr Leu
            100                 105                 110

Val Thr Val Ser Ser
        115

<210> SEQ ID NO 56
<211> LENGTH: 351
<212> TYPE: DNA
<213> ORGANISM: Artificial Sequence
<220> FEATURE:
<223> OTHER INFORMATION: 4B3; VH

<400> SEQUENCE: 56
gaggtgcaat tgttggagtc tgggggaggc ttggtacagc ctgggggtc cctgagactc     60 tcctgtgcag cctccggatt caccttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaagggtgg    300
ctgggtaatt ttgactactg gggccaagga accctggtca ccgtctcgag t            351

<210> SEQ ID NO 57
<211> LENGTH: 108
<212> TYPE: PRT
<213> ORGANISM: Artificial Sequence
<220> FEATURE:
<223> OTHER INFORMATION: 4D6; VL

<400> SEQUENCE: 57

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Gln Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105

<210> SEQ ID NO 58
<211> LENGTH: 324
<212> TYPE: DNA
<213> ORGANISM: Artificial Sequence
<220> FEATURE:
<223> OTHER INFORMATION: 4D6; VL

<400> SEQUENCE: 58
gaaatcgtgt taacgcagtc tccaggcacc ctgtctttgt ctccagggga aagagccacc     60
ctctcttgca gggccagtca gagtgttagc agcaactact tagcctggta ccagcagaaa    120
cctggccagg ctcccaggct cctcatccag ggcgcctcca gcagggccac tggcatccca    180
gacaggttca gtggcagtgg atccgggaca gacttcactc tcaccatcag cagactggag    240
cctgaagatt ttgcagtgta ttactgtcag cagggtcagg ttattccccc tacgttcggc    300 cagggggacca aagtggaaat caaa                                          324

<210> SEQ ID NO 59
<211> LENGTH: 117
<212> TYPE: PRT
<213> ORGANISM: Artificial Sequence
<220> FEATURE:
<223> OTHER INFORMATION: 4D6; VH

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser
        115

<210> SEQ ID NO 60
<211> LENGTH: 351
<212> TYPE: DNA
<213> ORGANISM: Artificial Sequence
<220> FEATURE:
<223> OTHER INFORMATION: 4D6; VH

<400> SEQUENCE: 60
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaaggtgg     300
ctgggtaatt ttgactactg gggccaagga accctggtca ccgtctcgag t             351

<210> SEQ ID NO 61
<211> LENGTH: 108
<212> TYPE: PRT
<213> ORGANISM: Artificial Sequence
<220> FEATURE:
<223> OTHER INFORMATION: 2C6; VL

<400> SEQUENCE: 61

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

```
Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Gln Ile Pro
                85                  90                  95

Pro Thr Phe Gly Gln Gly Thr Lys Val Glu Ile Lys
            100                 105
```

<210> SEQ ID NO 62
<211> LENGTH: 324
<212> TYPE: DNA
<213> ORGANISM: Artificial Sequence
<220> FEATURE:
<223> OTHER INFORMATION: 2C6; VL

<400> SEQUENCE: 62

```
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag caggctggag     240
cctgaagatt ttgcagtgta ttactgtcag cagggtcagc agattccccc tacgttcggc     300
caggggacca agtggaaat caaa                                             324
```

<210> SEQ ID NO 63
<211> LENGTH: 117
<212> TYPE: PRT
<213> ORGANISM: Artificial Sequence
<220> FEATURE:
<223> OTHER INFORMATION: 2C6; VH

<400> SEQUENCE: 63

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Ala Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Asn Phe Asp Tyr Trp Gly Gln Gly Thr Leu
            100                 105                 110

Val Thr Val Ser Ser
        115
```

<210> SEQ ID NO 64
<211> LENGTH: 351
<212> TYPE: DNA
<213> ORGANISM: Artificial Sequence
<220> FEATURE:
<223> OTHER INFORMATION: 2C6; VH

<400> SEQUENCE: 64

```
gaggtgcaat tgttggagtc tgggggaggc ttggtacagc ctggggggtc cctgagactc      60
tcctgtgcag cctccggatc cacctttagc agttatgcca tgagctgggt ccgccaggct     120
```

-continued

```
ccagggaagg ggctggagtg ggtctcagct attagtggga gtgctggtta tacatactac    180
gcagactccg tgaagggccg gttcaccatc tccagagaca attccaagaa cacgctgtat    240
ctgcagatga acagcctgag agccgaggac acggccgtat attactgtgc gaaaggttgg    300
tttgggaatt ttgactactg gggccaagga accctggtca ccgtctcgag t             351
```

<210> SEQ ID NO 65
<211> LENGTH: 108
<212> TYPE: PRT
<213> ORGANISM: Artificial Sequence
<220> FEATURE:
<223> OTHER INFORMATION: 5H5; VL

<400> SEQUENCE: 65

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Asn Gln Ile Pro
                85                  90                  95

Pro Thr Phe Gly Gln Gly Thr Lys Val Glu Ile Lys
            100                 105

<210> SEQ ID NO 66
<211> LENGTH: 324
<212> TYPE: DNA
<213> ORGANISM: Artificial Sequence
<220> FEATURE:
<223> OTHER INFORMATION: 5H5; VL

<400> SEQUENCE: 66

```
gaaatcgtgt taacgcagtc tccaggcacc ctgtctttgt ctccagggga agagccacc    60 ctctcttgca gggccagtca gagtgttagc agcagctact tagcctggta ccagcagaaa    120
cctggccagg ctcccaggct cctcatctat ggagcatcca gcagggccac tggcatccca    180
gacaggttca gtggcagtgg atccgggaca gacttcactc tcaccatcag cagactggag    240
cctgaagatt ttgcagtgta ttactgtcag cagggtaatc agattccccc tacgttcggt    300
caggggacca agtggaaat caaa                                             324
```

<210> SEQ ID NO 67
<211> LENGTH: 116
<212> TYPE: PRT
<213> ORGANISM: Artificial Sequence
<220> FEATURE:
<223> OTHER INFORMATION: 5H5; VH

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Arg Ser Pro Gly Lys Gly Leu Glu Trp Val

```
                35                  40                  45
Ser Ala Ile Ser Gly Gly Gly Arg Thr Tyr Tyr Ala Asp Ser Val Lys
        50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys Gly Trp Phe Thr Pro Phe Asp Tyr Trp Gly Gln Gly Thr Leu Val
            100                 105                 110

Thr Val Ser Ser
        115

<210> SEQ ID NO 68
<211> LENGTH: 348
<212> TYPE: DNA
<213> ORGANISM: Artificial Sequence
<220> FEATURE:
<223> OTHER INFORMATION: 5H5; VH

<400> SEQUENCE: 68
gaggtgcaat tgttggagtc tgggggaggc ttggtacagc ctgggggtc cctgagactc      60 tcctgtgcag cctccggatt cacctttagc agttatacca tgagctgggt ccgccggtct    120
ccagggaagg ggctggagtg ggtctcagct attagtggtg gtggtaggac atactacgca    180
gactccgtga agggccggtt caccatctcc agagacaatt ccaagaacac gctgtatctg    240
cagatgaaca gcctgagagc cgaggacacg gccgtatatt actgtgcgaa aggttggttt    300
acgccttttg actactgggg ccaaggaacc ctggtcaccg tctcgagt              348

<210> SEQ ID NO 69
<211> LENGTH: 108
<212> TYPE: PRT
<213> ORGANISM: Artificial Sequence
<220> FEATURE:
<223> OTHER INFORMATION: 2C4; VL

<400> SEQUENCE: 69

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Asn
             20                  25                  30

Tyr Leu Ala Trp Tyr Gln Gln Lys Pro Gly Gln Ala Pro Arg Leu Leu
         35                  40                  45

Ile Tyr Gly Ala Ser Ile Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Asn Gln Ile Pro
                 85                  90                  95

Pro Thr Phe Gly Gln Gly Thr Lys Val Glu Ile Lys
            100                 105

<210> SEQ ID NO 70
<211> LENGTH: 324
<212> TYPE: DNA
<213> ORGANISM: Artificial Sequence
<220> FEATURE:
<223> OTHER INFORMATION: 2C4; VL

<400> SEQUENCE: 70
```

```
gaaatcgtgt taacgcagtc tccaggcacc ctgtctttgt ctccagggga aagagccacc      60
ctctcttgca gggccagtca gagtgttagc agtaactact tagcctggta ccagcagaaa     120
cctggccagg ctcccaggct cctcatctat ggtgcctcca ttagggccac tggcatccca     180
gacaggttca gtggcagtgg atccgggaca gacttcactc tcaccatcag cagactggag     240
cctgaagatt ttgcagtgta ttactgtcag cagggtaatc agattccccc tacgttcggt     300
caggggacca agtggaaat caaa                                             324
```

<210> SEQ ID NO 71
<211> LENGTH: 117
<212> TYPE: PRT
<213> ORGANISM: Artificial Sequence
<220> FEATURE:
<223> OTHER INFORMATION: 2C4; VH

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Thr Pro Phe Asp Tyr Trp Gly Gln Gly Thr Leu
            100                 105                 110

Val Thr Val Ser Ser
        115

<210> SEQ ID NO 72
<211> LENGTH: 351
<212> TYPE: DNA
<213> ORGANISM: Artificial Sequence
<220> FEATURE:
<223> OTHER INFORMATION: 2C4; VH

<400> SEQUENCE: 72

```
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg gctggagtg gtctcagct attagcggta gtggtggtag cacatactac       180
gcagactccg tgaagggccg gttcaccatc tccagagaca attccaagaa cacgctgtat     240
ctgcagatga acagcctgag agccgaggac acggccgtat attactgtgc gaaaggttgg     300
tttacgcctt ttgactactg gggccaagga accctggtca ccgtctcgag t              351
```

<210> SEQ ID NO 73
<211> LENGTH: 108
<212> TYPE: PRT
<213> ORGANISM: Artificial Sequence
<220> FEATURE:
<223> OTHER INFORMATION: 2D9; VL

<400> SEQUENCE: 73

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Asn Gln Ile Pro
                85                  90                  95

Pro Thr Phe Gly Gln Gly Thr Lys Val Glu Ile Lys
            100                 105
```

<210> SEQ ID NO 74
<211> LENGTH: 324
<212> TYPE: DNA
<213> ORGANISM: Artificial Sequence
<220> FEATURE:
<223> OTHER INFORMATION: 2D9; VL

<400> SEQUENCE: 74

```
gaaatcgtgt taacgcagtc tccaggcacc ctgtctttgt ctccagggga aagagccacc     60
ctctcttgca gggccagtca gagtgttagc agcagctact tagcctggta ccagcagaaa   120
cctggccagg ctcccaggct cctcatctat ggagcatcca gcagggccac tggcatccca   180
gacaggttca gtggcagtgg atccgggaca gacttcactc tcaccatcag cagactggag   240
cctgaagatt ttgcagtgta ttactgtcag cagggtaatc agattccccc tacgttcggt   300
caggggacca aagtggaaat caaa                                          324
```

<210> SEQ ID NO 75
<211> LENGTH: 117
<212> TYPE: PRT
<213> ORGANISM: Artificial Sequence
<220> FEATURE:
<223> OTHER INFORMATION: 2D9; VH

<400> SEQUENCE: 75

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Thr Pro Phe Asp Tyr Trp Gly Gln Gly Thr Leu
            100                 105                 110

Val Thr Val Ser Ser
        115
```

<210> SEQ ID NO 76

```
<211> LENGTH: 351
<212> TYPE: DNA
<213> ORGANISM: Artificial Sequence
<220> FEATURE:
<223> OTHER INFORMATION: 2D9; VH

<400> SEQUENCE: 76
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg ggctggagtg ggtctcagct attagcggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaaggttgg     300
tttacgcctt tgactactg gggccaagga accctggtca ccgtctcgag t               351

<210> SEQ ID NO 77
<211> LENGTH: 108
<212> TYPE: PRT
<213> ORGANISM: Artificial Sequence
<220> FEATURE:
<223> OTHER INFORMATION: 4B8; VL

<400> SEQUENCE: 77

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105

<210> SEQ ID NO 78
<211> LENGTH: 324
<212> TYPE: DNA
<213> ORGANISM: Artificial Sequence
<220> FEATURE:
<223> OTHER INFORMATION: 4B8; VL

<400> SEQUENCE: 78
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcagtgta ttactgtcag cagggtcagg ttattccccc tacgttcggc     300
caggggacca aagtggaaat caaa                                             324

<210> SEQ ID NO 79
<211> LENGTH: 117
<212> TYPE: PRT
<213> ORGANISM: Artificial Sequence
<220> FEATURE:
```

<223> OTHER INFORMATION: 4B8; VH

<400> SEQUENCE: 79

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Gly Trp Leu Gly Asn Phe Asp Tyr Trp Gly Gln Gly Thr Leu
            100                 105                 110
Val Thr Val Ser Ser
        115
```

<210> SEQ ID NO 80
<211> LENGTH: 351
<212> TYPE: DNA
<213> ORGANISM: Artificial Sequence
<220> FEATURE:
<223> OTHER INFORMATION: 4B8; VH

<400> SEQUENCE: 80

```
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaaggtgg     300
ctgggtaatt ttgactactg gggccaagga accctggtca ccgtctcgag t             351
```

<210> SEQ ID NO 81
<211> LENGTH: 108
<212> TYPE: PRT
<213> ORGANISM: Artificial Sequence
<220> FEATURE:
<223> OTHER INFORMATION: 7A1; VL

<400> SEQUENCE: 81

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Gly Gln Gln Ile Pro
                85                  90                  95
Pro Thr Phe Gly Gln Gly Thr Lys Val Glu Ile Lys
```

-continued

```
                100                 105
```

<210> SEQ ID NO 82
<211> LENGTH: 324
<212> TYPE: DNA
<213> ORGANISM: Artificial Sequence
<220> FEATURE:
<223> OTHER INFORMATION: 7A1; VL

<400> SEQUENCE: 82

```
gaaatcgtgt taacgcagtc tccaggcacc ctgtctttgt ctccagggga aagagccacc    60
ctctcttgca gggccagtca gagtgttagc agcagctact tagcctggta ccagcagaaa   120
cctggccagg ctcccaggct cctcatctat ggagcatcca gcagggccac tggcatccca   180
gacaggttca gtggcagtgg atccgggaca gacttcactc tcaccatcag cagactggag   240
cctgaagatt ttgcagtgta ttactgtcag cagggtcagc agattccccc tacgttcggc   300
caggggacca agtggaaat caaa                                            324
```

<210> SEQ ID NO 83
<211> LENGTH: 117
<212> TYPE: PRT
<213> ORGANISM: Artificial Sequence
<220> FEATURE:
<223> OTHER INFORMATION: 7A1; VH

<400> SEQUENCE: 83

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Asn Phe Asp Tyr Trp Gly Gln Gly Thr Leu
            100                 105                 110

Val Thr Val Ser Ser
        115
```

<210> SEQ ID NO 84
<211> LENGTH: 351
<212> TYPE: DNA
<213> ORGANISM: Artificial Sequence
<220> FEATURE:
<223> OTHER INFORMATION: 7A1; VH

<400> SEQUENCE: 84

```
gaggtgcaat tgttggagtc tgggggaggc ttggtacagc ctgggggtc cctgagactc     60
tcctgtgcag cctccggatt cacctttagc agttatgcca tgagctggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcagatga acagcctgag agccgaggac acggccgtat attactgtgc gaaaggttgg   300
tttgggaatt ttgactactg gggccaagga accctggtca ccgtctcgag t            351
```

<210> SEQ ID NO 85
<211> LENGTH: 108
<212> TYPE: PRT
<213> ORGANISM: Artificial Sequence
<220> FEATURE:
<223> OTHER INFORMATION: 13C2; VL

<400> SEQUENCE: 85

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Leu Ile Pro
                85                  90                  95

Pro Thr Phe Gly Gln Gly Thr Lys Val Glu Ile Lys
            100                 105
```

<210> SEQ ID NO 86
<211> LENGTH: 324
<212> TYPE: DNA
<213> ORGANISM: Artificial Sequence
<220> FEATURE:
<223> OTHER INFORMATION: 13C2; VL

<400> SEQUENCE: 86

```
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcagtgta ttactgtcag cagggtcagc ttattccccc tacgttcggc     300
caggggacca agtggaaat caaa                                             324
```

<210> SEQ ID NO 87
<211> LENGTH: 117
<212> TYPE: PRT
<213> ORGANISM: Artificial Sequence
<220> FEATURE:
<223> OTHER INFORMATION: 13C2; VH

<400> SEQUENCE: 87

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
            85                  90                  95

Ala Lys Gly Trp Leu Gly Pro Phe Asp Tyr Trp Gly Gln Gly Thr Leu
        100                 105                 110

Val Thr Val Ser Ser
        115

<210> SEQ ID NO 88
<211> LENGTH: 351
<212> TYPE: DNA
<213> ORGANISM: Artificial Sequence
<220> FEATURE:
<223> OTHER INFORMATION: 13C2; VH

<400> SEQUENCE: 88

```
gaggtgcaat tgttggagtc tgggggaggc ttggtacagc ctgggggtc cctgagactc    60 tcctgtgcag cctccggatt cacctttagc agttatgcca tgagctgggt ccgccaggct   120
ccagggaagg gctggagtg gtctcagct attagtggta gtggtggtag cacatactac     180
gcagactccg tgaagggccg gttcaccatc tccagagaca attccaagaa cacgctgtat   240
ctgcagatga acagcctgag agccgaggac acggccgtat attactgtgc gaaaggttgg   300
ctgggtcctt ttgactactg gggccaagga accctggtca ccgtctcgag t           351
```

<210> SEQ ID NO 89
<211> LENGTH: 108
<212> TYPE: PRT
<213> ORGANISM: Artificial Sequence
<220> FEATURE:
<223> OTHER INFORMATION: 13E8; VL

<400> SEQUENCE: 89

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Leu Asn Ile Pro
                85                  90                  95

Ser Thr Phe Gly Gln Gly Thr Lys Val Glu Ile Lys
            100                 105

<210> SEQ ID NO 90
<211> LENGTH: 324
<212> TYPE: DNA
<213> ORGANISM: Artificial Sequence
<220> FEATURE:
<223> OTHER INFORMATION: 13E8; VL

<400> SEQUENCE: 90

```
gaaatcgtgt taacgcagtc tccaggcacc ctgtctttgt ctccagggga aagagccacc    60
ctctcttgca gggccagtca gagtgttagc agcagctact tagcctggta ccagcagaaa   120
cctggccagg ctcccaggct cctcatctat ggagcatcca gcagggccac tggcatccca   180
gacaggttca gtggcagtgg atccgggaca gacttcactc tcaccatcag cagactggag   240
```

```
cctgaagatt tgcagtgta ttactgtcag cagggtctga atattccctc gacgttcggc    300
caggggacca aagtggaaat caaa                                          324
```

<210> SEQ ID NO 91
<211> LENGTH: 117
<212> TYPE: PRT
<213> ORGANISM: Artificial Sequence
<220> FEATURE:
<223> OTHER INFORMATION: 13E8; VH

<400> SEQUENCE: 91

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Pro Phe Asp Tyr Trp Gly Gln Gly Thr Leu
            100                 105                 110

Val Thr Val Ser Ser
        115

<210> SEQ ID NO 92
<211> LENGTH: 351
<212> TYPE: DNA
<213> ORGANISM: Artificial Sequence
<220> FEATURE:
<223> OTHER INFORMATION: 13E8; VH

<400> SEQUENCE: 92

```
gaggtgcaat tgttggagtc tgggggaggc ttggtacagc ctggggggtc cctgagactc    60
tcctgtgcag cctccggatt cacctttagc agttatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcagatga acagcctgag agccgaggac acggccgtat attactgtgc gaaaggttgg   300
ttgggtccgt ttgactactg gggccaagga accctggtca ccgtctcgag t            351
```

<210> SEQ ID NO 93
<211> LENGTH: 108
<212> TYPE: PRT
<213> ORGANISM: Artificial Sequence
<220> FEATURE:
<223> OTHER INFORMATION: 14C10; VL

<400> SEQUENCE: 93

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly His Ile Ile Pro
                85                  90                  95

Pro Thr Phe Gly Gln Gly Thr Lys Val Glu Ile Lys
            100                 105

<210> SEQ ID NO 94
<211> LENGTH: 324
<212> TYPE: DNA
<213> ORGANISM: Artificial Sequence
<220> FEATURE:
<223> OTHER INFORMATION: 14C10; VL

<400> SEQUENCE: 94
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcagtgta ttactgtcag cagggtcata ttattccccc gacgttcggc     300
caggggacca agtggaaat caaa                                             324

<210> SEQ ID NO 95
<211> LENGTH: 117
<212> TYPE: PRT
<213> ORGANISM: Artificial Sequence
<220> FEATURE:
<223> OTHER INFORMATION: 14C10; VH

<400> SEQUENCE: 95

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ala Trp Met Gly Pro Phe Asp Tyr Trp Gly Gln Gly Thr Leu
            100                 105                 110

Val Thr Val Ser Ser
        115

<210> SEQ ID NO 96
<211> LENGTH: 351
<212> TYPE: DNA
<213> ORGANISM: Artificial Sequence
<220> FEATURE:
<223> OTHER INFORMATION: 14C10; VH

<400> SEQUENCE: 96

```
gaggtgcaat tgttggagtc tgggggaggc ttggtacagc ctgggggtc cctgagactc    60 tcctgtgcag cctccggatt caccttagc agttatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcagatga acagcctgag agccgaggac acggccgtat attactgtgc gaaagcttgg   300
atggggcctt tgactactg gggccaagga accctggtca ccgtctcgag t             351
```

<210> SEQ ID NO 97
<211> LENGTH: 108
<212> TYPE: PRT
<213> ORGANISM: Artificial Sequence
<220> FEATURE:
<223> OTHER INFORMATION: 17A11; VL

<400> SEQUENCE: 97

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Leu Asn Ile Pro
                85                  90                  95

Ser Thr Phe Gly Gln Gly Thr Lys Val Glu Ile Lys
            100                 105
```

<210> SEQ ID NO 98
<211> LENGTH: 324
<212> TYPE: DNA
<213> ORGANISM: Artificial Sequence
<220> FEATURE:
<223> OTHER INFORMATION: 17A11; VL

<400> SEQUENCE: 98

```
gaaatcgtgt taacgcagtc tccaggcacc ctgtctttgt ctccagggga aagagccacc    60
ctctcttgca gggccagtca gagtgttagc agcagctact tagcctggta ccagcagaaa   120
cctggccagg ctcccaggct cctcatctat ggagcatcca gcagggccac tggcatccca   180
gacaggttca gtggcagtgg atccgggaca gacttcactc tcaccatcag cagactggag   240
cctgaagatt ttgcagtgta ttactgtcag cagggtctga atattccctc gacgttcggc   300
caggggacca agtggaaat caaa                                            324
```

<210> SEQ ID NO 99
<211> LENGTH: 117
<212> TYPE: PRT
<213> ORGANISM: Artificial Sequence
<220> FEATURE:
<223> OTHER INFORMATION: 17A11; VH

<400> SEQUENCE: 99

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                    20                  25                  30
Ala Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Lys Gly Trp Leu Gly Pro Phe Asp Tyr Trp Gly Gln Gly Thr Leu
            100                 105                 110

Val Thr Val Ser Ser
            115

<210> SEQ ID NO 100
<211> LENGTH: 351
<212> TYPE: DNA
<213> ORGANISM: Artificial Sequence
<220> FEATURE:
<223> OTHER INFORMATION: 17A11; VH

<400> SEQUENCE: 100
gaggtgcaat tgttggagtc tgggggaggc ttggtacagc ctgggggtc cctgagactc      60 tcctgtgcag cctccggatt caccttagc agttatgcca tgagctgggt ccgccaggct     120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaaggttgg    300
ttgggtccgt ttgactactg gggccaagga accctggtca ccgtctcgag t            351

<210> SEQ ID NO 101
<211> LENGTH: 108
<212> TYPE: PRT
<213> ORGANISM: Artificial Sequence
<220> FEATURE:
<223> OTHER INFORMATION: 19G1; VL

<400> SEQUENCE: 101

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Thr Ser Ser
                20                  25                  30

Tyr Leu Ala Trp Tyr Gln Gln Lys Pro Gly Gln Ala Pro Arg Leu Leu
            35                  40                  45

Ile Asn Val Gly Ser Arg Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                 70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 102
<211> LENGTH: 324
<212> TYPE: DNA
<213> ORGANISM: Artificial Sequence
<220> FEATURE:
```

<223> OTHER INFORMATION: 19G1; VL

<400> SEQUENCE: 102

```
gaaatcgtgt taacgcagtc tccaggcacc ctgtctttgt ctccagggga agagccacc      60 ctctcttgca gggccagtca gagtgttacc agtagctact tagcctggta ccagcagaaa    120
cctggccagg ctcccaggct cctcatcaat gtgggctccc gtagggccac tggcatccca    180
gacaggttca gtggcagtgg atccgggaca gacttcactc tcaccatcag cagactggag    240
cctgaagatt ttgcagtgta ttactgtcag cagggtatta tgcttccccc gacgttcggc    300
caggggacca agtggaaat caaa                                            324
```

<210> SEQ ID NO 103
<211> LENGTH: 117
<212> TYPE: PRT
<213> ORGANISM: Artificial Sequence
<220> FEATURE:
<223> OTHER INFORMATION: 19G1; VH

<400> SEQUENCE: 103

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Ser Ser Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115
```

<210> SEQ ID NO 104
<211> LENGTH: 351
<212> TYPE: DNA
<213> ORGANISM: Artificial Sequence
<220> FEATURE:
<223> OTHER INFORMATION: 19G1; VH

<400> SEQUENCE: 104

```
gaggtgcaat gttggagtc tgggggaggc ttggtacagc ctgggggtc cctgagactc       60 tcctgtgcag cctccggatt cacctttagc agttatgcga tgagctgggt ccgccaggct   120
ccagggaagg ggctggagtg gtctcagcg attattagta gtggtggtct cacatactac    180
gcagactccg tgaagggccg gttcaccatc tccagagaca attccaagaa cacgctgtat   240
ctgcagatga acagcctgag agccgaggac acggccgtat attactgtgc gaaaggtgg    300 tttggtggtt ttaactactg gggccaagga accctggtca ccgtctcgtc c            351
```

<210> SEQ ID NO 105
<211> LENGTH: 108
<212> TYPE: PRT
<213> ORGANISM: Artificial Sequence
<220> FEATURE:
<223> OTHER INFORMATION: 20G8; VL

<400> SEQUENCE: 105

| Glu | Ile | Val | Leu | Thr | Gln | Ser | Pro | Gly | Thr | Leu | Ser | Leu | Ser | Pro | Gly |
|---|---|---|---|---|---|---|---|---|---|---|---|---|---|---|---|
| 1 | | | | 5 | | | | | 10 | | | | | 15 | |

| Glu | Arg | Ala | Thr | Leu | Ser | Cys | Arg | Ala | Ser | Gln | Ser | Val | Thr | Ser | Ser |
|---|---|---|---|---|---|---|---|---|---|---|---|---|---|---|---|
| | | | 20 | | | | | 25 | | | | | 30 | | |

| Tyr | Leu | Ala | Trp | Tyr | Gln | Gln | Lys | Pro | Gly | Gln | Ala | Pro | Arg | Leu | Leu |
|---|---|---|---|---|---|---|---|---|---|---|---|---|---|---|---|
| | | 35 | | | | | 40 | | | | | 45 | | | |

| Ile | Asn | Val | Gly | Ser | Arg | Arg | Ala | Thr | Gly | Ile | Pro | Asp | Arg | Phe | Ser |
|---|---|---|---|---|---|---|---|---|---|---|---|---|---|---|---|
| 50 | | | | | 55 | | | | | 60 | | | | | |

| Gly | Ser | Gly | Ser | Gly | Thr | Asp | Phe | Thr | Leu | Thr | Ile | Ser | Arg | Leu | Glu |
|---|---|---|---|---|---|---|---|---|---|---|---|---|---|---|---|
| 65 | | | | | 70 | | | | | 75 | | | | | 80 |

| Pro | Glu | Asp | Phe | Ala | Val | Tyr | Tyr | Cys | Gln | Gln | Gly | Ile | Met | Leu | Pro |
|---|---|---|---|---|---|---|---|---|---|---|---|---|---|---|---|
| | | | | 85 | | | | | 90 | | | | | 95 | |

| Pro | Thr | Phe | Gly | Gln | Gly | Thr | Lys | Val | Glu | Ile | Lys |
|---|---|---|---|---|---|---|---|---|---|---|---|
| | | | 100 | | | | | 105 | | | |

<210> SEQ ID NO 106
<211> LENGTH: 324
<212> TYPE: DNA
<213> ORGANISM: Artificial Sequence
<220> FEATURE:
<223> OTHER INFORMATION: 20G8; VL

<400> SEQUENCE: 106

```
gaaatcgtgt taacgcagtc tccaggcacc ctgtctttgt ctccagggga aagagccacc      60
ctctcttgca gggccagtca gagtgttacc agtagctact tagcctggta ccagcagaaa     120
cctggccagg ctcccaggct cctcatcaat gtgggctccc gtagggccac tggcatccca     180
gacaggttca gtggcagtgg atccgggaca gacttcactc tcaccatcag cagactggag     240
cctgaagatt ttgcagtgta ttactgtcag cagggtatta tgcttccccc gacgttcggc     300
caggggacca agtggaaat caaa                                             324
```

<210> SEQ ID NO 107
<211> LENGTH: 117
<212> TYPE: PRT
<213> ORGANISM: Artificial Sequence
<220> FEATURE:
<223> OTHER INFORMATION: 20G8; VH

<400> SEQUENCE: 107

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Ala | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Ala | Ile | Ile | Gly | Ser | Gly | Ser | Arg | Thr | Tyr | Tyr | Ala | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Lys | Gly | Trp | Phe | Gly | Gly | Phe | Asn | Tyr | Trp | Gly | Gln | Gly | Thr | Leu |
|---|---|---|---|---|---|---|---|---|---|---|---|---|---|---|---|
| | | | 100 | | | | | 105 | | | | | 110 | | |

| Val | Thr | Val | Ser | Ser |
|---|---|---|---|---|
| | | | 115 | |

<210> SEQ ID NO 108
<211> LENGTH: 351
<212> TYPE: DNA
<213> ORGANISM: Artificial Sequence
<220> FEATURE:
<223> OTHER INFORMATION: 20G8; VH

<400> SEQUENCE: 108

```
gaggtgcaat tgttggagtc tgggggaggc ttggtacagc ctgggggtc cctgagactc      60
tcctgtgcag cctccggatt cacctttagc agttatgcaa tgagctgggt ccgccaggct    120
ccagggaagg gctggagtg gtctcagct attattggga gtggtagtcg tacatactac     180
gcagactccg tgaagggccg gttcaccatc tccagagaca attccaagaa cacgctgtat    240
ctgcagatga acagcctgag agccgaggac acggccgtat attactgtgc gaaagggtgg    300
tttggtggtt ttaactactg ggccaagga accctggtca ccgtctcgtc c             351
```

<210> SEQ ID NO 109
<211> LENGTH: 108
<212> TYPE: PRT
<213> ORGANISM: Artificial Sequence
<220> FEATURE:
<223> OTHER INFORMATION: 4B9; VL

<400> SEQUENCE: 109

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Thr Ser Ser
             20                  25                  30

Tyr Leu Ala Trp Tyr Gln Gln Lys Pro Gly Gln Ala Pro Arg Leu Leu
         35                  40                  45

Ile Asn Val Gly Ser Arg Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Ile Met Leu Pro
                 85                  90                  95

Pro Thr Phe Gly Gln Gly Thr Lys Val Glu Ile Lys
            100                 105
```

<210> SEQ ID NO 110
<211> LENGTH: 324
<212> TYPE: DNA
<213> ORGANISM: Artificial Sequence
<220> FEATURE:
<223> OTHER INFORMATION: 4B9; VL

<400> SEQUENCE: 110

```
gaaatcgtgt taacgcagtc tccaggcacc ctgtctttgt ctccagggga aagagccacc     60
ctctcttgca gggccagtca gagtgttacc agtagctact tagcctggta ccagcagaaa    120
cctggccagg ctcccaggct cctcatcaat gtgggctccc gtagggccac tggcatccca    180
gacaggttca gtggcagtgg atccgggaca gacttcactc tcaccatcag cagactggag    240
cctgaagatt ttgcagtgta ttactgtcag cagggtatta tgcttccccc gacgttcggc    300
caggggacca agtggaaat caaa                                            324
```

<210> SEQ ID NO 111
<211> LENGTH: 117

```
<212> TYPE: PRT
<213> ORGANISM: Artificial Sequence
<220> FEATURE:
<223> OTHER INFORMATION: 4B9; VH

<400> SEQUENCE: 111
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

```
<210> SEQ ID NO 112
<211> LENGTH: 351
<212> TYPE: DNA
<213> ORGANISM: Artificial Sequence
<220> FEATURE:
<223> OTHER INFORMATION: 4B9; VH

<400> SEQUENCE: 112
```

| | | | | | |
|---|---|---|---|---|---|
| gaggtgcaat | tgttggagtc | tgggggaggc | ttggtacagc | ctggggggtc | cctgagactc | 60 |
| tcctgtgcag | cctccggatt | cacctttagc | agttatgcta | tgagctgggt | ccgccaggct | 120 |
| ccagggaagg | ggctggagtg | ggtctcagct | attattggta | gtggtgctag | cacatactac | 180 |
| gcagactccg | tgaagggccg | gttcaccatc | tccagagaca | attccaagaa | cacgctgtat | 240 |
| ctgcagatga | acagcctgag | agccgaggac | acggccgtat | attactgtgc | gaaagggtgg | 300 |
| tttggtggtt | ttaactactg | gggccaagga | accctggtca | ccgtctcgtc | c | 351 |

```
<210> SEQ ID NO 113
<211> LENGTH: 108
<212> TYPE: PRT
<213> ORGANISM: Artificial Sequence
<220> FEATURE:
<223> OTHER INFORMATION: 5B8; VL

<400> SEQUENCE: 113
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro

```
                    85                  90                  95
Pro Thr Phe Gly Gln Gly Thr Lys Val Glu Ile Lys
            100                 105

<210> SEQ ID NO 114
<211> LENGTH: 324
<212> TYPE: DNA
<213> ORGANISM: Artificial Sequence
<220> FEATURE:
<223> OTHER INFORMATION: 5B8; VL

<400> SEQUENCE: 114
gaaatcgtgt taacgcagtc tccaggcacc ctgtctttgt ctccagggga aagagccacc      60
ctctcttgca gggccagtca gagtgttacc agtagctact tagcctggta ccagcagaaa     120
cctggccagg ctcccaggct cctcatcaat gtgggctccc gtagggccac tggcatccca     180
gacaggttca gtggcagtgg atccgggaca gacttcactc tcaccatcag cagactggag     240
cctgaagatt ttgcagtgta ttactgtcag cagggtatta tgcttccccc gacgttcggc     300
caggggacca agtggaaat caaa                                             324

<210> SEQ ID NO 115
<211> LENGTH: 117
<212> TYPE: PRT
<213> ORGANISM: Artificial Sequence
<220> FEATURE:
<223> OTHER INFORMATION: 5B8; VH

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Trp Gly Gly Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 116
<211> LENGTH: 351
<212> TYPE: DNA
<213> ORGANISM: Artificial Sequence
<220> FEATURE:
<223> OTHER INFORMATION: 5B8; VH

<400> SEQUENCE: 116
gaggtgcaat tgttggagtc tgggggaggc ttggtacagc ctggggggtc cctgagactc      60
tcctgtgcag cctccggatt cacctttagc agttatgcta tgagctgggt ccgccaggct     120
ccagggaagg gctggagtg gtctcagct atttggggtg tggtcgtag cacatactac        180 gcagactccg tgaagggccg gttcaccatc tccagagaca attccaagaa cacgctgtat     240
```

```
ctgcagatga acagcctgag agccgaggac acggccgtat attactgtgc gaaaggtgg      300 tttggtggtt ttaactactg gggccaagga accctggtca ccgtctcgtc c              351
```

<210> SEQ ID NO 117
<211> LENGTH: 108
<212> TYPE: PRT
<213> ORGANISM: Artificial Sequence
<220> FEATURE:
<223> OTHER INFORMATION: 5F1; VL

<400> SEQUENCE: 117

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105
```

<210> SEQ ID NO 118
<211> LENGTH: 324
<212> TYPE: DNA
<213> ORGANISM: Artificial Sequence
<220> FEATURE:
<223> OTHER INFORMATION: 5F1; VL

<400> SEQUENCE: 118

```
gaaatcgtgt taacgcagtc tccaggcacc ctgtctttgt ctccagggga agagccacc     60 ctctcttgca gggccagtca gagtgttacc agtagctact tagcctggta ccagcagaaa    120
cctggccagg ctcccaggct cctcatcaat gtgggctccc gtagggccac tggcatccca    180
gacaggttca gtggcagtgg atccgggaca gacttcactc tcaccatcag cagactggag    240
cctgaagatt ttgcagtgta ttactgtcag cagggtatta tgcttccccc gacgttcggc    300
caggggacca agtggaaat caaa                                              324
```

<210> SEQ ID NO 119
<211> LENGTH: 117
<212> TYPE: PRT
<213> ORGANISM: Artificial Sequence
<220> FEATURE:
<223> OTHER INFORMATION: 5F1; VH

<400> SEQUENCE: 119

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Ser Ser Gly Ala Ser Thr Tyr Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
            115

<210> SEQ ID NO 120
<211> LENGTH: 351
<212> TYPE: DNA
<213> ORGANISM: Artificial Sequence
<220> FEATURE:
<223> OTHER INFORMATION: 5F1; VH

<400> SEQUENCE: 120
gaggtgcaat tgttggagtc tgggggaggc ttggtacagc ctggggggtc cctgagactc    60
tcctgtgcag cctccggatt cacctttagc agttatgcta tgagctgggt ccgccaggct   120
ccagggaagg ggctggagtg ggtctcagct attattagta gtgggctag cacatactac   180 gcagactccg tgaagggccg gttcaccatc tccagagaca attccaagaa cacgctgtat   240
ctgcagatga acagcctgag agccgaggac acggccgtat attactgtgc gaaagggtgg   300
tttggtggtt ttaactactg gggccaagga accctggtca ccgtctcgtc c            351

<210> SEQ ID NO 121
<211> LENGTH: 108
<212> TYPE: PRT
<213> ORGANISM: Artificial Sequence
<220> FEATURE:
<223> OTHER INFORMATION: 14B3; VL

<400> SEQUENCE: 121

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 122
<211> LENGTH: 324
<212> TYPE: DNA
<213> ORGANISM: Artificial Sequence
<220> FEATURE:
<223> OTHER INFORMATION: 14B3; VL

<400> SEQUENCE: 122
gaaatcgtgt taacgcagtc tccaggcacc ctgtctttgt ctccagggga aagagccacc    60
ctctcttgca gggccagtca gagtgttacc agtagctact tagcctggta ccagcagaaa   120

```
cctggccagg ctcccaggct cctcatcaat gtgggctccc gtagggccac tggcatccca    180
gacaggttca gtggcagtgg atccgggaca gacttcactc tcaccatcag cagactggag    240
cctgaagatt ttgcagtgta ttactgtcag cagggtatta tgcttccccc gacgttcggc    300
caggggacca agtggaaat caaa                                            324
```

<210> SEQ ID NO 123
<211> LENGTH: 117
<212> TYPE: PRT
<213> ORGANISM: Artificial Sequence
<220> FEATURE:
<223> OTHER INFORMATION: 14B3; VH

<400> SEQUENCE: 123

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Leu Ala Ser Gly Ala Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115
```

<210> SEQ ID NO 124
<211> LENGTH: 351
<212> TYPE: DNA
<213> ORGANISM: Artificial Sequence
<220> FEATURE:
<223> OTHER INFORMATION: 14B3; VH

<400> SEQUENCE: 124

```
gaggtgcaat gttggagtc tggggggaggc ttggtacagc ctgggggggtc cctgagactc    60 tcctgtgcag cctccggatt cacctttagc agttatgcta tgagctgggt ccgccaggct    120
ccagggaagg ggctggagtg ggtctcagct attttggcta gtggtgcgat cacatactac    180
gcagactccg tgaagggccg gttcaccatc tccagagaca attccaagaa cacgctgtat    240
ctgcagatga acagcctgag agccgaggac acggccgtat attactgtgc gaaagggtgg    300
tttggtggtt ttaactactg ggccaagga accctggtca ccgtctcgtc c              351
```

<210> SEQ ID NO 125
<211> LENGTH: 108
<212> TYPE: PRT
<213> ORGANISM: Artificial Sequence
<220> FEATURE:
<223> OTHER INFORMATION: 16F1; VL

<400> SEQUENCE: 125

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30
```

```
        Tyr Leu Ala Trp Tyr Gln Gln Lys Pro Gly Gln Ala Pro Arg Leu Leu
                    35                  40                  45

Ile Asn Val Gly Ser Arg Arg Ala Thr Gly Ile Pro Asp Arg Phe Ser
         50                  55                  60

Gly Ser Gly Ser Gly Thr Asp Phe Thr Leu Thr Ile Ser Arg Leu Glu
         65                  70                  75                  80

Pro Glu Asp Phe Ala Val Tyr Tyr Cys Gln Gln Gly Ile Met Leu Pro
                            85                  90                  95

Pro Thr Phe Gly Gln Gly Thr Lys Val Glu Ile Lys
                        100                 105

<210> SEQ ID NO 126
<211> LENGTH: 324
<212> TYPE: DNA
<213> ORGANISM: Artificial Sequence
<220> FEATURE:
<223> OTHER INFORMATION: 16F1; VL

<400> SEQUENCE: 126
gaaatcgtgt taacgcagtc tccaggcacc ctgtctttgt ctccagggga aagagccacc     60
ctctcttgca gggccagtca gagtgttacc agtagctact tagcctggta ccagcagaaa    120
cctggccagg ctcccaggct cctcatcaat gtgggctccc gtagggccac tggcatccca    180
gacaggttca gtggcagtgg atccgggaca gacttcactc tcaccatcag cagactggag    240
cctgaagatt ttgcagtgta ttactgtcag cagggtatta tgcttccccc gacgttcggc    300
caggggacca agtggaaat caaa                                            324

<210> SEQ ID NO 127
<211> LENGTH: 117
<212> TYPE: PRT
<213> ORGANISM: Artificial Sequence
<220> FEATURE:
<223> OTHER INFORMATION: 16F1; VH

<400> SEQUENCE: 127

Glu Val Gln Leu Leu Glu Ser Gly Gly Gly Leu Val Gln Pro Gly Gly
         1               5                   10                  15

Ser Leu Arg Leu Ser Cys Ala Ala Ser Gly Phe Thr Phe Ser Ser Tyr
                        20                  25                  30

Ala Met Ser Trp Val Arg Gln Ala Pro Gly Lys Gly Leu Glu Trp Val
                    35                  40                  45

Ser Gly Ile Ile Gly Ser Gly Ile Thr Tyr Tyr Ala Asp Ser Val
         50                  55                  60

Lys Gly Arg Phe Thr Ile Ser Arg Asp Asn Ser Lys Asn Thr Leu Tyr
         65                  70                  75                  80

Leu Gln Met Asn Ser Leu Arg Ala Glu Asp Thr Ala Val Tyr Tyr Cys
                            85                  90                  95

Ala Lys Gly Trp Phe Gly Gly Phe Asn Tyr Trp Gly Gln Gly Thr Leu
                        100                 105                 110

Val Thr Val Ser Ser
                115

<210> SEQ ID NO 128
<211> LENGTH: 351
<212> TYPE: DNA
<213> ORGANISM: Artificial Sequence
<220> FEATURE:
<223> OTHER INFORMATION: 16F1; VH
```

<400> SEQUENCE: 128

```
gaggtgcaat tgttggagtc tgggggaggc ttggtacagc ctggggggtc cctgagactc        60
tcctgtgcag cctccggatt cacctttagc agttatgcta tgagctgggt ccgccaggct       120
ccagggaagg gctggagtg gtctcaggt attattggta gtggtggtat cacatactac         180
gcagactccg tgaagggccg gttcaccatc tccagagaca attccaagaa cacgctgtat       240
ctgcagatga acagcctgag agccgaggac acggccgtat attactgtgc gaaagggtgg       300
tttggtggtt ttaactactg gggccaagga accctggtca ccgtctcgtc c               351
```

<210> SEQ ID NO 129
<211> LENGTH: 108
<212> TYPE: PRT
<213> ORGANISM: Artificial Sequence
<220> FEATURE:
<223> OTHER INFORMATION: 16F8; VL

<400> SEQUENCE: 129

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Thr Ser Ser
            20                  25                  30
Tyr Leu Ala Trp Tyr Gln Gln Lys Pro Gly Gln Ala Pro Arg Leu Leu
        35                  40                  45
Ile Asn Val Gly Ser Arg Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Gly Ile Met Leu Pro
                85                  90                  95
Pro Thr Phe Gly Gln Gly Thr Lys Val Glu Ile Lys
            100                 105
```

<210> SEQ ID NO 130
<211> LENGTH: 324
<212> TYPE: DNA
<213> ORGANISM: Artificial Sequence
<220> FEATURE:
<223> OTHER INFORMATION: 16F8; VL

<400> SEQUENCE: 130

```
gaaatcgtgt taacgcagtc tccaggcacc ctgtctttgt ctccagggga aagagccacc        60
ctctcttgca gggccagtca gagtgttacc agtagctact tagcctggta ccagcagaaa       120
cctggccagg ctcccaggct cctcatcaat gtgggctccc gtagggccac tggcatccca       180
gacaggttca gtggcagtgg atccgggaca gacttcactc tcaccatcag cagactggag       240
cctgaagatt ttgcagtgta ttactgtcag cagggtatta tgcttccccc gacgttcggc       300
caggggacca aagtggaaat caaa                                               324
```

<210> SEQ ID NO 131
<211> LENGTH: 117
<212> TYPE: PRT
<213> ORGANISM: Artificial Sequence
<220> FEATURE:
<223> OTHER INFORMATION: 16F8; VH

<400> SEQUENCE: 131

```
Glu Val Gln Leu Leu Glu Ser Gly Gly Gly Leu Val Gln Pro Gly Gly
```

```
                1               5                  10                 15
              Ser Leu Arg Leu Ser Cys Ala Ala Ser Gly Phe Thr Phe Ser Ser Tyr
                              20                  25                 30

Ala Met Ser Trp Val Arg Gln Ala Pro Gly Lys Gly Leu Glu Trp Val
                              35                  40                 45

Ser Ala Ile Leu Gly Ser Gly Ser Thr Tyr Tyr Ala Asp Ser Val
                              50                  55                 60

Lys Gly Arg Phe Thr Ile Ser Arg Asp Asn Ser Lys Asn Thr Leu Tyr
               65                              70                 75                       80

Leu Gln Met Asn Ser Leu Arg Ala Glu Asp Thr Ala Val Tyr Tyr Cys
                                      85                  90                 95

Ala Lys Gly Trp Phe Gly Gly Phe Asn Tyr Trp Gly Gln Gly Thr Leu
                                      100                 105                110

Val Thr Val Ser Ser
                              115

<210> SEQ ID NO 132
<211> LENGTH: 351
<212> TYPE: DNA
<213> ORGANISM: Artificial Sequence
<220> FEATURE:
<223> OTHER INFORMATION: 16F8; VH

<400> SEQUENCE: 132
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg ggctggagtg ggtctcagct attcttggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaagggtgg     300
tttggtggtt ttaactactg ggccaaggaa accctggtca ccgtctcgtc c              351

<210> SEQ ID NO 133
<211> LENGTH: 108
<212> TYPE: PRT
<213> ORGANISM: Artificial Sequence
<220> FEATURE:
<223> OTHER INFORMATION: O3C9; VL

<400> SEQUENCE: 133

Glu Ile Val Leu Thr Gln Ser Pro Gly Thr Leu Ser Leu Ser Pro Gly
               1               5                  10                 15

Glu Arg Ala Thr Leu Ser Cys Arg Ala Ser Gln Ser Val Thr Ser Ser
                              20                  25                 30

Tyr Leu Ala Trp Tyr Gln Gln Lys Pro Gly Gln Ala Pro Arg Leu Leu
                              35                  40                 45

Ile Asn Val Gly Ser Arg Arg Ala Thr Gly Ile Pro Asp Arg Phe Ser
                              50                  55                 60

Gly Ser Gly Ser Gly Thr Asp Phe Thr Leu Thr Ile Ser Arg Leu Glu
               65                              70                 75                       80

Pro Glu Asp Phe Ala Val Tyr Tyr Cys Gln Gln Gly Ile Met Leu Pro
                                      85                  90                 95

Pro Thr Phe Gly Gln Gly Thr Lys Val Glu Ile Lys
                                      100                 105

<210> SEQ ID NO 134
<211> LENGTH: 324
```

<212> TYPE: DNA
<213> ORGANISM: Artificial Sequence
<220> FEATURE:
<223> OTHER INFORMATION: O3C9; VL

<400> SEQUENCE: 134

```
gaaatcgtgt taacgcagtc tccaggcacc ctgtctttgt ctccagggga aagagccacc      60
ctctcttgca gggccagtca gagtgttacc agtagctact tagcctggta ccagcagaaa     120
cctggccagg ctcccaggct cctcatcaat gtgggctccc gtagggccac tggcatccca     180
gacaggttca gtggcagtgg atccgggaca gacttcactc tcaccatcag cagactggag     240
cctgaagatt ttgcagtgta ttactgtcag cagggtatta tgcttccccc gacgttcggc     300
caggggacca agtggaaat caaa                                             324
```

<210> SEQ ID NO 135
<211> LENGTH: 117
<212> TYPE: PRT
<213> ORGANISM: Artificial Sequence
<220> FEATURE:
<223> OTHER INFORMATION: O3C9; VH

<400> SEQUENCE: 135

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Phe
            20                  25                  30

Ala Met Ser Trp Val Arg Gln Ser Pro Gly Lys Gly Leu Glu Trp Val
        35                  40                  45

Ser Ala Ile Ile Gly Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115
```

<210> SEQ ID NO 136
<211> LENGTH: 351
<212> TYPE: DNA
<213> ORGANISM: Artificial Sequence
<220> FEATURE:
<223> OTHER INFORMATION: O3C9; VH

<400> SEQUENCE: 136

```
gaggtgcaat tgttggagtc tgggggaggc ttggtacagc ctggggggtc cctgagactc      60
tcctgtgcag cctccggatt cacctttagc agttttgcca tgagctgggt ccgtcagtct     120
ccagggaagg ggctggagtg gtctcagct attattggta gtggtagtaa cacatactac     180
gcagactccg tgaagggccg gttcaccatc tccagacaca attccaagaa cacgctgtat     240
ctgcagatga acagcctgag agccgaggac acggccgtat attactgtgc gaaagggtgg     300
tttggtggtt ttaactactg gggccaagga accctggtca ccgtctcgtc c              351
```

<210> SEQ ID NO 137
<211> LENGTH: 108
<212> TYPE: PRT

<213> ORGANISM: Artificial Sequence
<220> FEATURE:
<223> OTHER INFORMATION: O2D7; VL

<400> SEQUENCE: 137

| | | | | | | | | | | | | | | |
|---|---|---|---|---|---|---|---|---|---|---|---|---|---|---|
| Glu | Ile | Val | Leu | Thr | Gln | Ser | Pro | Gly | Thr | Leu | Ser | Leu | Ser | Pro | Gly |
| 1 | | | | 5 | | | | | 10 | | | | | 15 | |
| Glu | Arg | Ala | Thr | Leu | Ser | Cys | Arg | Ala | Ser | Gln | Ser | Val | Thr | Ser | Ser |
| | | | 20 | | | | | 25 | | | | | 30 | | |
| Tyr | Leu | Ala | Trp | Tyr | Gln | Gln | Lys | Pro | Gly | Gln | Ala | Pro | Arg | Leu | Leu |
| | | 35 | | | | | 40 | | | | | 45 | | | |
| Ile | Asn | Val | Gly | Ser | Arg | Arg | Ala | Thr | Gly | Thr | Pro | Asp | Arg | Phe | Ser |
| 50 | | | | | 55 | | | | | 60 | | | | | |
| Gly | Ser | Gly | Ser | Gly | Thr | Asp | Phe | Thr | Leu | Thr | Ile | Ser | Arg | Leu | Glu |
| 65 | | | | | 70 | | | | 75 | | | | | | 80 |
| Pro | Glu | Asp | Phe | Ala | Val | Tyr | Tyr | Cys | Gln | Gln | Ala | Ile | Met | Leu | Pro |
| | | | | 85 | | | | | 90 | | | | | 95 | |
| Pro | Thr | Phe | Gly | Gln | Gly | Thr | Lys | Val | Glu | Ile | Lys | | | | |
| | | | 100 | | | | | 105 | | | | | | | |

<210> SEQ ID NO 138
<211> LENGTH: 324
<212> TYPE: DNA
<213> ORGANISM: Artificial Sequence
<220> FEATURE:
<223> OTHER INFORMATION: O2D7; VL

<400> SEQUENCE: 138

```
gaaatcgtgt taacgcagtc tccaggcacc ctgtctttgt ctccagggga agagccacc    60
ctctcttgca gggccagtca gagtgttacc agtagctact tagcctggta ccagcagaaa  120
cctggccagg ctcccaggct cctcatcaat gtgggctccc gtagggccac tggcacccca  180
gacaggttca gtggcagtgg atccgggaca gacttcactc tcaccatcag cagactggag  240
cctgaagatt ttgcagtgta ttactgtcag caggctatta tgcttcctcc gacgttcggc  300
caggggacca agtggaaat caaa                                           324
```

<210> SEQ ID NO 139
<211> LENGTH: 117
<212> TYPE: PRT
<213> ORGANISM: Artificial Sequence
<220> FEATURE:
<223> OTHER INFORMATION: O2D7; VH

<400> SEQUENCE: 139

| | | | | | | | | | | | | | | | |
|---|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |
| Ala | Met | Ser | Trp | Val | Arg | Gln | Ala | Pro | Gly | Lys | Gly | Leu | Glu | Trp | Val |
| | | | 35 | | | | | 40 | | | | | 45 | | |
| Ser | Ala | Ile | Ser | Gly | Ser | Gly | Gly | Ser | Thr | Tyr | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Lys | Gly | Trp | Phe | Gly | Gly | Phe | Asn | Tyr | Trp | Gly | Gln | Gly | Thr | Leu |
| | | | 100 | | | | | 105 | | | | | 110 | | |

Val Thr Val Ser Ser
        115

<210> SEQ ID NO 140
<211> LENGTH: 351
<212> TYPE: DNA
<213> ORGANISM: Artificial Sequence
<220> FEATURE:
<223> OTHER INFORMATION: O2D7; VH

<400> SEQUENCE: 140

```
gaggtgcaat tgttggagtc tgggggaggc ttggtacagc ctgggggtc cctgagactc      60
tcctgtgcag cctccggatt cacctttagc agttatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcagatga acagcctgag agccgaggac acggccgtat attactgtgc gaaagggtgg    300
tttggtggtt taactactg gggccaagga accctggtca ccgtctcgtc c              351
```

<210> SEQ ID NO 141
<211> LENGTH: 108
<212> TYPE: PRT
<213> ORGANISM: Artificial Sequence
<220> FEATURE:
<223> OTHER INFORMATION: 28H1; VL

<400> SEQUENCE: 141

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105

<210> SEQ ID NO 142
<211> LENGTH: 324
<212> TYPE: DNA
<213> ORGANISM: Artificial Sequence
<220> FEATURE:
<223> OTHER INFORMATION: 28H1; VL

<400> SEQUENCE: 142

```
gaaatcgtgt taacgcagtc tccaggcacc ctgtctttgt ctccagggga agagccacc     60
ctctcttgca gggccagtca gagtgttagc cgcagctact tagcctggta ccagcagaaa   120
cctggccagg ctcccaggct cctcatcatt ggggcctcca ccaggccac tggcatccca    180
gacaggttca gtggcagtgg atccgggaca gacttcactc tcaccatcag cagactggag   240
cctgaagatt ttgcagtgta ttactgtcag cagggtcagg ttattccccc tacgttcggc   300
caggggacca aagtggaaat caaa                                          324
```

<210> SEQ ID NO 143
<211> LENGTH: 116
<212> TYPE: PRT
<213> ORGANISM: Artificial Sequence
<220> FEATURE:
<223> OTHER INFORMATION: 28H1; VH

<400> SEQUENCE: 143

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser
        115

<210> SEQ ID NO 144
<211> LENGTH: 348
<212> TYPE: DNA
<213> ORGANISM: Artificial Sequence
<220> FEATURE:
<223> OTHER INFORMATION: 28H1; VH

<400> SEQUENCE: 144
gaggtgcaat tgttggagtc tgggggaggc ttggtacagc ctggggggtc cctgagactc      60
tcctgtgcag cctccggatt cacctttagc agtcatgcta tgagctgggt ccgccaggct     120
ccagggaagg gctggagtg gtctcagct atttgggcta gtgggagca atactacgca        180 gactccgtga agggccggtt caccatctcc agagacaatt ccaagaacac gctgtatctg     240
cagatgaaca gcctgagagc cgaggacacg gccgtatatt actgtgcgaa agggtggctg     300
ggtaattttg actactgggg ccaaggaacc ctggtcaccg tctcgagt                 348

<210> SEQ ID NO 145
<211> LENGTH: 108
<212> TYPE: PRT
<213> ORGANISM: Artificial Sequence
<220> FEATURE:
<223> OTHER INFORMATION: 22A3; VL

<400> SEQUENCE: 145

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu

```
                65                  70                  75                  80
Pro Glu Asp Phe Ala Val Tyr Tyr Cys Gln Gln Gly Ile Met Leu Pro
                    85                  90                  95

Pro Thr Phe Gly Gln Gly Thr Lys Val Glu Ile Lys
                100                 105

<210> SEQ ID NO 146
<211> LENGTH: 324
<212> TYPE: DNA
<213> ORGANISM: Artificial Sequence
<220> FEATURE:
<223> OTHER INFORMATION: 22A3; VL

<400> SEQUENCE: 146
gaaatcgtgt taacgcagtc tccaggcacc ctgtctttgt ctccagggga aagagccacc     60
ctctcttgca gggccagtca gagtgttacc agtagctact tagcctggta ccagcagaaa    120
cctggccagg ctcccaggct cctcatcaat gtgggctccc gtaggccact ggcatccca    180 gacaggttca gtggcagtgg atccgggaca gacttcactc tcaccatcag cagactggag    240
cctgaagatt ttgcagtgta ttactgtcag cagggtatta tgcttccccc gacgttcggc    300
caggggacca agtggaaat caaa                                             324

<210> SEQ ID NO 147
<211> LENGTH: 117
<212> TYPE: PRT
<213> ORGANISM: Artificial Sequence
<220> FEATURE:
<223> OTHER INFORMATION: 22A3; VH

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ile Gly Ser Gly Ser Ile Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
                100                 105                 110

Val Thr Val Ser Ser
        115

<210> SEQ ID NO 148
<211> LENGTH: 351
<212> TYPE: DNA
<213> ORGANISM: Artificial Sequence
<220> FEATURE:
<223> OTHER INFORMATION: 22A3; VH

<400> SEQUENCE: 148
gaggtgcaat tgttggagtc tgggggaggc ttggtacagc ctggggggtc cctgagactc     60
tcctgtgcag cctccggatt cacctttagc agttatgcca tgagctgggt ccgccaggct    120
ccagggaagg ggctggagtg ggtctcagct attattggta gtggtagtat cacatactac    180
```

```
gcagactccg tgaagggccg gttcaccatc tccagagaca attccaagaa cacgctgtat      240
ctgcagatga acagcctgag agccgaggac acggccgtat attactgtgc gaaagggtgg      300
tttggtggtt ttaactactg gggccaagga accctggtca ccgtctcgag t               351
```

<210> SEQ ID NO 149
<211> LENGTH: 108
<212> TYPE: PRT
<213> ORGANISM: Artificial Sequence
<220> FEATURE:
<223> OTHER INFORMATION: 29B11; VL

<400> SEQUENCE: 149

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105
```

<210> SEQ ID NO 150
<211> LENGTH: 324
<212> TYPE: DNA
<213> ORGANISM: Artificial Sequence
<220> FEATURE:
<223> OTHER INFORMATION: 29B11; VL

<400> SEQUENCE: 150

```
gaaatcgtgt taacgcagtc tccaggcacc ctgtctttgt ctccagggga aagagccacc      60
ctctcttgca gggccagtca gagtgttacc agtagctact tagcctggta ccagcagaaa     120
cctggccagg ctcccaggct cctcatcaat gtgggctccc gtaggccac tggcatccca     180 gacaggttca gtggcagtgg atccgggaca gacttcactc tcaccatcag cagactggag     240
cctgaagatt ttgcagtgta ttactgtcag cagggtatta tgcttccccc gacgttcggc     300
caggggacca agtggaaat caaa                                              324
```

<210> SEQ ID NO 151
<211> LENGTH: 117
<212> TYPE: PRT
<213> ORGANISM: Artificial Sequence
<220> FEATURE:
<223> OTHER INFORMATION: 29B11; VH

<400> SEQUENCE: 151

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

-continued

Ser Ala Ile Ile Gly Ser Gly Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 152
<211> LENGTH: 351
<212> TYPE: DNA
<213> ORGANISM: Artificial Sequence
<220> FEATURE:
<223> OTHER INFORMATION: 29B11; VH

<400> SEQUENCE: 152
gaggtgcaat tgttggagtc tgggggaggc ttggtacagc ctggggggtc cctgagactc     60
tcctgtgcag cctccggatt caccttagc agttatgcta tgagctgggt ccgccaggct     120
ccagggaagg ggctggagtg ggtctcagct attattggta gtggtggtat cacatactac    180
gcagactccg tgaagggccg gttcaccatc tccagagaca attccaagaa cacgctgtat    240
ctgcagatga acagcctgag agccgaggac acggccgtat attactgtgc gaaagggtgg    300
tttggtggtt ttaactactg ggccaagga accctggtca ccgtctcgag t              351

<210> SEQ ID NO 153
<211> LENGTH: 108
<212> TYPE: PRT
<213> ORGANISM: Artificial Sequence
<220> FEATURE:
<223> OTHER INFORMATION: 23C10; VL

<400> SEQUENCE: 153

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105

<210> SEQ ID NO 154
<211> LENGTH: 324
<212> TYPE: DNA
<213> ORGANISM: Artificial Sequence
<220> FEATURE:
<223> OTHER INFORMATION: 23C10; VL

<400> SEQUENCE: 154
gaaatcgtgt taacgcagtc tccaggcacc ctgtctttgt ctccagggga aagagccacc    60

```
ctctcttgca gggccagtca gagtgttagc cgcagctact tagcctggta ccagcagaaa    120
cctggccagg ctcccaggct cctcatcatt ggggcctcca ccagggccac tggcatccca    180
gacaggttca gtggcagtgg atccgggaca gacttcactc tcaccatcag cagactggag    240
cctgaagatt ttgcagtgta ttactgtcag cagggtcagg ttattccccc tacgttcggc    300
caggggacca agtggaaat caaa                                            324
```

<210> SEQ ID NO 155
<211> LENGTH: 117
<212> TYPE: PRT
<213> ORGANISM: Artificial Sequence
<220> FEATURE:
<223> OTHER INFORMATION: 23C10; VH

<400> SEQUENCE: 155

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Ala Pro Gly Lys Gly Leu Glu Trp Val
        35                  40                  45

Ser Ala Ile Ser Thr Asn Gly Asn Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser
        115
```

<210> SEQ ID NO 156
<211> LENGTH: 351
<212> TYPE: DNA
<213> ORGANISM: Artificial Sequence
<220> FEATURE:
<223> OTHER INFORMATION: 23C10; VH

<400> SEQUENCE: 156

```
gaggtgcaat tgttggagtc tgggggaggc ttggtacagc ctgggggtc cctgagactc      60 tcctgtgcag cctccggatt caccttagc agttctgcca tgagctgggt ccgccaggct     120
ccagggaagg ggctggagtg gtctcagct attagtacta atggtaatta cacatactac     180
gcagactccg tgaagggccg gttcaccatc tccagagaca attccaagaa cacgctgtat    240
ctgcagatga acagcctgag agccgaggac acggccgtat attactgtgc gaaaggtgg     300 ctgggtaatt ttgactactg gggccaagga accctggtca ccgtctcgag t             351
```

<210> SEQ ID NO 157
<211> LENGTH: 107
<212> TYPE: PRT
<213> ORGANISM: Artificial Sequence
<220> FEATURE:
<223> OTHER INFORMATION: 2B10_C3B6; VL

<400> SEQUENCE: 157

```
Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105

<210> SEQ ID NO 158
<211> LENGTH: 321
<212> TYPE: DNA
<213> ORGANISM: Artificial Sequence
<220> FEATURE:
<223> OTHER INFORMATION: 2B10_C3B6; VL

<400> SEQUENCE: 158
gatatccaga tgacccagtc tccatcctcc ctgtctgcat ctgtcggaga ccgggtcacc     60
atcacctgcc gggcaagtca gggcattaga aatgatttag ctggtacca gcagaagcca    120 gggaaagccc ctaagcgcct gatctatgct gcatccagtt tgcagagtgg cgtcccatca    180
aggttcagcg gcagtggatc cgggacagag ttcactctca ccatcagcag cttgcagcct    240
gaagattttg ccacctatta ctgcttgcag aatggtctgc agcccgcgac gtttggccag    300
ggcaccaaag tcgagatcaa g                                              321

<210> SEQ ID NO 159
<211> LENGTH: 121
<212> TYPE: PRT
<213> ORGANISM: Artificial Sequence
<220> FEATURE:
<223> OTHER INFORMATION: 2B10_C3B6; VH

<400> SEQUENCE: 159

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ala Ile Ile Pro Ile Leu Gly Ile Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120

<210> SEQ ID NO 160
<211> LENGTH: 363
<212> TYPE: DNA

<213> ORGANISM: Artificial Sequence
<220> FEATURE:
<223> OTHER INFORMATION: 2B10_C3B6; VH

<400> SEQUENCE: 160

```
caggtgcaat tggtgcagtc tggggctgag gtgaagaagc ctgggtcctc ggtgaaggtc      60
tcctgcaagg cctccggagg cacattcagc agctacgcta taagctgggt gcgacaggcc     120
cctggacaag gctcgagtg gatgggagct atcatcccga tccttggtat cgcaaactac     180
gcacagaagt tccagggcag ggtcaccatt actgcagaca atccacgag cacagcctac     240
atggagctga gcagcctgag atctgaggac accgccgtgt attactgtgc gagactgtac     300
ggttacgctt actacggtgc ttttgactac tggggccaag gaccaccgt gaccgtctcc     360
tca                                                                   363
```

<210> SEQ ID NO 161
<211> LENGTH: 107
<212> TYPE: PRT
<213> ORGANISM: Artificial Sequence
<220> FEATURE:
<223> OTHER INFORMATION: 2B10_6A12; VL

<400> SEQUENCE: 161

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105
```

<210> SEQ ID NO 162
<211> LENGTH: 321
<212> TYPE: DNA
<213> ORGANISM: Artificial Sequence
<220> FEATURE:
<223> OTHER INFORMATION: 2B10_6A12; VL

<400> SEQUENCE: 162

```
gatatccaga tgacccagtc tccatcctcc ctgtctgcat ctgtcggaga ccgggtcacc      60
atcacctgcc gggcaagtca gggcattaga aatgatttag ctggtaccag cagaagcca     120
gggaaagccc ctaagcgcct gatctatgct gcatccagtt tgcagagtgg cgtcccatca     180
aggttcagcg gcagtggatc cgggacagag ttcactctca ccatcagcag cttgcagcct     240
gaagattttg ccacctatta ctgcttgcag aatggtctgc agcccgcgac gtttggccag     300
ggcaccaaag tcgagatcaa g                                               321
```

<210> SEQ ID NO 163
<211> LENGTH: 121
<212> TYPE: PRT
<213> ORGANISM: Artificial Sequence
<220> FEATURE:

<223> OTHER INFORMATION: 2B10_6A12; VH

<400> SEQUENCE: 163

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Val Ile Ile Pro Ile Leu Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120

<210> SEQ ID NO 164
<211> LENGTH: 363
<212> TYPE: DNA
<213> ORGANISM: Artificial Sequence
<220> FEATURE:
<223> OTHER INFORMATION: 2B10_6A12; VH

<400> SEQUENCE: 164
caggtgcaat tggtgcagtc tgggctgag gtgaagaagc ctgggtcctc ggtgaaggtc     60
tcctgcaagg cctccggagg cacattcagc agctatgcta taagctgggt gcgacaggcc    120
cctggacaag ggctcgagtg gatgggagtg atcatccta tccttggtac cgcaaactac    180
gcacagaagt tccagggcag ggtcaccatt actgcagaca aatccacgag cacagcctac    240
atggagctga gcagcctgag atctgaggac accgccgtgt attactgtgc gagactgtac    300
ggttacgctt actacggtgc ttttgactac tggggccaag gaccaccgt gaccgtctcc    360
tca                                                                  363

<210> SEQ ID NO 165
<211> LENGTH: 107
<212> TYPE: PRT
<213> ORGANISM: Artificial Sequence
<220> FEATURE:
<223> OTHER INFORMATION: 2B10_C3A6; VL

<400> SEQUENCE: 165

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Val
            20                  25                  30

Leu Gly Trp Tyr Gln Gln Lys Pro Gly Lys Ala Pro Lys Arg Leu Ile
        35                  40                  45

Tyr Asp Ser Ser Ser Leu Gln Ser Gly Val Pro Ser Arg Phe Ser Gly
50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

-continued

```
Thr Phe Gly Gln Gly Thr Lys Val Glu Ile Lys
            100                 105
```

<210> SEQ ID NO 166
<211> LENGTH: 321
<212> TYPE: DNA
<213> ORGANISM: Artificial Sequence
<220> FEATURE:
<223> OTHER INFORMATION: 2B10_C3A6; VL

<400> SEQUENCE: 166

```
gacatccaga tgacccagtc tccttcctcc ctgtctgcat ctgtcggaga ccgggtcacc    60
atcacctgcc gggcaagtca gggcattcgt aatgttttag ctggtaccag cagaagcca   120
gggaaagccc ctaagcgcct gatctatgat tcgtccagtt tgcagagtgg cgtcccatca   180
aggttcagcg gcggtggatc cgggacagag ttcactctca ccatcagcag cttgcagcct   240
gaagattttg ccacctatta ctgcttgcag aatggtctgc agcccgcgac gtttggccag   300
ggcaccaaag tcgagatcaa g                                             321
```

<210> SEQ ID NO 167
<211> LENGTH: 121
<212> TYPE: PRT
<213> ORGANISM: Artificial Sequence
<220> FEATURE:
<223> OTHER INFORMATION: 2B10_C3A6; VH

<400> SEQUENCE: 167

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Leu Tyr Gly Tyr Ala Tyr Tyr Gly Ala Phe Asp Tyr Trp Gly
            100                 105                 110
Gln Gly Thr Thr Val Thr Val Ser Ser
        115                 120
```

<210> SEQ ID NO 168
<211> LENGTH: 363
<212> TYPE: DNA
<213> ORGANISM: Artificial Sequence
<220> FEATURE:
<223> OTHER INFORMATION: 2B10_C3A6; VH

<400> SEQUENCE: 168

```
caggtgcaat tggtgcagtc tggggctgag gtgaagaagc ctgggtcctc ggtgaaggtc    60
tcctgcaagg cctccggagg cacattcagc agctacgcta taagctgggt gcgacaggcc   120
cctggacaag gctcgagtg gatgggaggg atcatcccta tctttggtac agcaaactac   180
gcacagaagt tccagggcag ggtcaccatt actgcagaca aatccacgag cacagcctac   240
atggagctga gcagcctgag atctgaggac accgccgtgt attactgtgc gagactgtac   300
```

```
ggttacgctt actacggtgc ttttgactac tggggccaag ggaccaccgt gaccgtctcc    360
tca                                                                  363
```

<210> SEQ ID NO 169
<211> LENGTH: 107
<212> TYPE: PRT
<213> ORGANISM: Artificial Sequence
<220> FEATURE:
<223> OTHER INFORMATION: 2B10_D1A2_wt; VL

<400> SEQUENCE: 169

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Val
            20                  25                  30

Leu Gly Trp Tyr Gln Gln Lys Pro Gly Lys Ala Pro Lys Arg Leu Ile
        35                  40                  45

Tyr Asp Ala Tyr Ser Leu Gln Ser Gly Val Pro Ser Arg Phe Ser Gly
50                  55                  60

Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105
```

<210> SEQ ID NO 170
<211> LENGTH: 321
<212> TYPE: DNA
<213> ORGANISM: Artificial Sequence
<220> FEATURE:
<223> OTHER INFORMATION: 2B10_D1A2_wt; VL

<400> SEQUENCE: 170

```
gatatccaga tgacccagtc tccatcctcc ctgtctgcat ctgtcggaga ccgggtcacc    60
atcacctgcc gggcaagtca ggggattcgt aatgttttag ctggtaccag cagaagcca   120 gggaaagccc ctaagcgcct gatctatgat gcttacagct tgcagagtgg cgtcccatca   180
aggttcagcg gcgtggatc cgggacagag ttcactctca ccatcagcag cttgcagcct   240
gaagattttg ccacctatta ctgcttgcag aatggtctgc agcccgcgac gtttggccag   300
ggcaccaaag tcgagatcaa g                                             321
```

<210> SEQ ID NO 171
<211> LENGTH: 121
<212> TYPE: PRT
<213> ORGANISM: Artificial Sequence
<220> FEATURE:
<223> OTHER INFORMATION: 2B10_D1A2_wt; VH

<400> SEQUENCE: 171

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60
```

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Leu Tyr Gly Tyr Ala Tyr Gly Ala Phe Asp Tyr Trp Gly
        100                 105                 110

Gln Gly Thr Thr Val Thr Val Ser Ser
        115                 120

<210> SEQ ID NO 172
<211> LENGTH: 363
<212> TYPE: DNA
<213> ORGANISM: Artificial Sequence
<220> FEATURE:
<223> OTHER INFORMATION: 2B10_D1A2_wt; VH

<400> SEQUENCE: 172
caggtgcaat tggtgcagtc tggggctgag gtgaagaagc ctgggtcctc ggtgaaggtc      60
tcctgcaagg cctccggagg cacattcagc agctacgcta taagctgggt gcgacaggcc     120
cctggacaag gctcgagtg gatgggaggg atcatcccta tctttggtac agcaaactac     180
gcacagaagt tccagggcag ggtcaccatt actgcagaca atccacgag cacagcctac     240 atggagctga gcagcctgag atctgaggac accgccgtgt attactgtgc gagactgtac     300
ggttacgctt actacggtgc ttttgactac tggggccaag gaccaccgt gaccgtctcc     360 tca                                                                   363

<210> SEQ ID NO 173
<211> LENGTH: 107
<212> TYPE: PRT
<213> ORGANISM: Artificial Sequence
<220> FEATURE:
<223> OTHER INFORMATION: 2B10_D1A2_VD; VL

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Asp Ala Tyr Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
            85                  90                  95

Thr Phe Gly Gln Gly Thr Lys Val Glu Ile Lys
        100                 105

<210> SEQ ID NO 174
<211> LENGTH: 321
<212> TYPE: DNA
<213> ORGANISM: Artificial Sequence
<220> FEATURE:
<223> OTHER INFORMATION: 2B10_D1A2_VD; VL

<400> SEQUENCE: 174
gacatccaga tgacccagtc tccatcctcc ctgtctgcat ctgtcggaga ccgggtcacc      60

```
atcacctgcc gggcaagtca ggggattcgt aatgatttag ctggtacca gcagaagcca    120 gggaaagccc ctaagcgcct gatctatgat gcttacagct tgcagagtgg cgtcccatca    180
aggttcagcg gcggtggatc cgggacagag ttcactctca ccatcagcag cttgcagcct    240
gaagattttg ccacctatta ctgcttgcag aatggtctgc agcccgcgac gtttggccag    300
ggcaccaaag tcgagatcaa g                                              321
```

<210> SEQ ID NO 175
<211> LENGTH: 121
<212> TYPE: PRT
<213> ORGANISM: Artificial Sequence
<220> FEATURE:
<223> OTHER INFORMATION: 2B10_D1A2_VD; VH

<400> SEQUENCE: 175

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120

<210> SEQ ID NO 176
<211> LENGTH: 363
<212> TYPE: DNA
<213> ORGANISM: Artificial Sequence
<220> FEATURE:
<223> OTHER INFORMATION: 2B10_D1A2_VD; VH

<400> SEQUENCE: 176

```
caggtgcaat tggtgcagtc tggggctgag gtgaagaagc ctgggtcctc ggtgaaggtc    60
tcctgcaagg cctccggagg cacattcagc agctacgcta taagctgggt gcgacaggcc   120
cctggacaag gctcgagtg gatgggaggg atcatcccta tctttggtac agcaaactac    180
gcacagaagt tccagggcag ggtcaccatt actgcagaca aatccacgag cacagcctac    240
atggagctga gcagcctgag atctgaggac accgccgtgt attactgtgc gagactgtac    300
ggttacgctt actacggtgc ttttgactac tggggccaag gaccaccgt gaccgtctcc    360 tca                                                                  363
```

<210> SEQ ID NO 177
<211> LENGTH: 107
<212> TYPE: PRT
<213> ORGANISM: Artificial Sequence
<220> FEATURE:
<223> OTHER INFORMATION: 2B10_O7D8; VL

<400> SEQUENCE: 177

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Asn Val
            20                  25                  30

Leu Gly Trp Tyr Gln Gln Lys Pro Gly Lys Ala Pro Lys Arg Leu Ile
        35                  40                  45

Tyr Asp Val Ser Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105
```

<210> SEQ ID NO 178
<211> LENGTH: 321
<212> TYPE: DNA
<213> ORGANISM: Artificial Sequence
<220> FEATURE:
<223> OTHER INFORMATION: 2B10_O7D8; VL

<400> SEQUENCE: 178

```
gatatccaga tgacccagtc tccatcctcc ctgtctgcat ctgtcggaga ccgggtcacc      60
atcacctgcc gggcaagtca gagcattcgt aatgttttag ctggtacca gcagaagcca     120
gggaaagccc ctaagcgcct gatctatgat gtgtccagtt tgcagagtgg cgtcccatca    180
aggttcagcg gcggtggatc cgggacagag ttcactctca ccatcagcag cttgcagcct   240
gaagattttg ccacctatta ctgcttgcag aatggtctgc agcccgcgac gtttggccag   300
ggcaccaaag tcgagatcaa g                                              321
```

<210> SEQ ID NO 179
<211> LENGTH: 121
<212> TYPE: PRT
<213> ORGANISM: Artificial Sequence
<220> FEATURE:
<223> OTHER INFORMATION: 2B10_O7D8; VH

<400> SEQUENCE: 179

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Gly Ala Phe Asp Tyr Trp Gly
            100                 105                 110

Gln Gly Thr Thr Val Thr Val Ser Ser
            115                 120
```

<210> SEQ ID NO 180

```
<211> LENGTH: 363
<212> TYPE: DNA
<213> ORGANISM: Artificial Sequence
<220> FEATURE:
<223> OTHER INFORMATION: 2B10_O7D8; VH

<400> SEQUENCE: 180
caggtgcaat tggtgcagtc tggggctgag gtgaagaagc ctgggtcctc ggtgaaggtc      60
tcctgcaagg cctccggagg cacattcagc agctacgcta taagctgggt gcgacaggcc     120
cctggacaag ggctcgagtg gatgggaggg atcatccta tctttggtac agcaaactac      180
gcacagaagt tccagggcag ggtcaccatt actgcagaca atccacgag cacagcctac      240 atggagctga gcagcctgag atctgaggac accgccgtgt attactgtgc gagactgtac     300
ggttacgctt actacggtgc ttttgactac tggggccaag gaccaccgt gaccgtctcc      360 tca                                                                  363

<210> SEQ ID NO 181
<211> LENGTH: 107
<212> TYPE: PRT
<213> ORGANISM: Artificial Sequence
<220> FEATURE:
<223> OTHER INFORMATION: 2B10_O1F7; VL

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Val
            20                  25                  30

Leu Gly Trp Tyr Gln Gln Lys Pro Gly Lys Ala Pro Lys Arg Leu Ile
        35                  40                  45

Tyr Asp Ala Ser Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105

<210> SEQ ID NO 182
<211> LENGTH: 321
<212> TYPE: DNA
<213> ORGANISM: Artificial Sequence
<220> FEATURE:
<223> OTHER INFORMATION: 2B10_O1F7; VL

<400> SEQUENCE: 182
gatatccaga tgacccagtc tccatcctcc ctgtctgcat ctgtcggaga ccgggtcacc      60
atcacctgcc gggcaagtca gggcattcgt aatgttttag ctggtaccag cagaagcca     120 gggaaagccc ctaagcgcct gatctatgat gcgtccagtt tgcagagtgg cgtcccatca     180
aggttcagcg gcggtggatc cgggacagag ttcactctca ccatcagcag cttgcagcct     240
gaagattttg ccacctatta ctgcctgcag aatggtctgc agcccgcgac gtttggccag     300
ggcaccaaag tcgagatcaa g                                              321

<210> SEQ ID NO 183
<211> LENGTH: 121
<212> TYPE: PRT
```

<213> ORGANISM: Artificial Sequence
<220> FEATURE:
<223> OTHER INFORMATION: 2B10_O1F7; VH

<400> SEQUENCE: 183

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120

<210> SEQ ID NO 184
<211> LENGTH: 363
<212> TYPE: DNA
<213> ORGANISM: Artificial Sequence
<220> FEATURE:
<223> OTHER INFORMATION: 2B10_O1F7; VH

<400> SEQUENCE: 184
caggtgcaat tggtgcagtc tgggctgag gtgaagaagc ctgggtcctc ggtgaaggtc      60
tcctgcaagg cctccggagg cacattcagc agctacgcta taagctgggt gcgacaggcc    120
cctggacaag gctcgagtg gatgggaggg atcatcccta tctttggtac agcaaactac     180
gcacagaagt tccagggcag ggtcaccatt actgcagaca atccacgag cacagcctac     240 atggagctga gcagcctgag atctgaggac accgccgtgt attactgtgc gagactgtac    300
ggttacgctt actacggtgc ttttgactac tgggccaag ggaccaccgt gaccgtctcc     360
tca                                                                   363

<210> SEQ ID NO 185
<211> LENGTH: 107
<212> TYPE: PRT
<213> ORGANISM: Artificial Sequence
<220> FEATURE:
<223> OTHER INFORMATION: 2B10_6H10; VL

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Val
            20                  25                  30

Leu Gly Trp Tyr Gln Gln Lys Pro Gly Lys Ala Pro Lys Arg Leu Ile
        35                  40                  45

Gln Ala Ala Thr Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

```
Glu Asp Phe Ala Thr Tyr Tyr Cys Leu Gln Asn Gly Leu Gln Pro Ala
             85                  90                  95

Thr Phe Gly Gln Gly Thr Lys Val Glu Ile Lys
        100                 105
```

<210> SEQ ID NO 186
<211> LENGTH: 321
<212> TYPE: DNA
<213> ORGANISM: Artificial Sequence
<220> FEATURE:
<223> OTHER INFORMATION: 2B10_6H10; VL

<400> SEQUENCE: 186

```
gacatccaga tgacccagtc tccatcctcc ctgtctgcat ctgtcggaga ccgggtcacc      60
atcacctgcc gggcaagtca gggcattcgt aatgttttag ctggtacca gcagaagcca     120
gggaaagccc ctaagcgcct gatccaggct gctaccagtt tgcagagtgg cgtcccatca    180
aggttcagcg gcggtggatc cgggacagag ttcactctca ccatcagcag cttgcagcct    240
gaagattttg ccacctatta ctgcttgcag aatggtctgc agcccgcgac gtttggccag    300
ggcaccaaag tcgagatcaa g                                              321
```

<210> SEQ ID NO 187
<211> LENGTH: 121
<212> TYPE: PRT
<213> ORGANISM: Artificial Sequence
<220> FEATURE:
<223> OTHER INFORMATION: 2B10_6H10; VH

<400> SEQUENCE: 187

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120
```

<210> SEQ ID NO 188
<211> LENGTH: 363
<212> TYPE: DNA
<213> ORGANISM: Artificial Sequence
<220> FEATURE:
<223> OTHER INFORMATION: 2B10_6H10; VH

<400> SEQUENCE: 188

```
caggtgcaat tggtgcagtc tggggctgag gtgaagaagc ctgggtcctc ggtgaaggtc      60
tcctgcaagg cctccggagg cacattcagc agctacgcta taagctgggt gcgacaggcc    120
cctggacaag gctcgagtg gatgggaggg atcatcccta tctttggtac agcaaactac    180
gcacagaagt tccagggcag ggtcaccatt actgcagaca aatccacgag cacagcctac    240
```

```
atggagctga gcagcctgag atctgaggac accgccgtgt attactgtgc gagactgtac    300
ggttacgctt actacggtgc ttttgactac tggggccaag gaccaccgt gaccgtctcc    360 tca                                                                  363
```

<210> SEQ ID NO 189
<211> LENGTH: 122
<212> TYPE: PRT
<213> ORGANISM: Artificial Sequence
<220> FEATURE:
<223> OTHER INFORMATION: MHLG1; VH

<400> SEQUENCE: 189

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Asn Phe Gly Arg Tyr Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Tyr Gly Asn Tyr Val Gly His Tyr Phe Asp His Trp
            100                 105                 110

Gly Gln Gly Thr Thr Val Thr Val Ser Ser
        115                 120
```

<210> SEQ ID NO 190
<211> LENGTH: 366
<212> TYPE: DNA
<213> ORGANISM: Artificial Sequence
<220> FEATURE:
<223> OTHER INFORMATION: MHLG1; VH

<400> SEQUENCE: 190

```
gaagtgcagc tggtggagtc tggaggaggc ttggtcaagc ctggcgggtc cctgcggctc     60
tcctgtgcag cctccggatt cacatttagc aactattgga tgaactgggt gcggcaggct    120
cctggaaagg gcctcgagtg ggtggccgag atcagattga atccaataa cttcggaaga    180 tattacgctg caagcgtgaa gggccggttc accatcagca gagatgattc aagaacacg     240 ctgtacctgc agatgaacag cctgaagacc gaggatacgg ccgtgtatta ctgtaccaca    300
tacggcaact acgttgggca ctacttcgac cactgggcc aaggaccac cgtcaccgtc     360 tccagt                                                               366
```

<210> SEQ ID NO 191
<211> LENGTH: 109
<212> TYPE: PRT
<213> ORGANISM: Artificial Sequence
<220> FEATURE:
<223> OTHER INFORMATION: KV9; VL

<400> SEQUENCE: 191

```
Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
```

```
                20                  25                  30
Val Ala Trp Tyr Gln Gln Lys Pro Gly Gln Ala Pro Arg Pro Leu Ile
            35                  40                  45
Tyr Ser Ala Ser Tyr Arg Tyr Thr Gly Val Pro Ser Arg Phe Ser Gly
        50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Gln Gln Tyr Asn Ser Tyr Pro Leu
                85                  90                  95
Thr Phe Gly Gly Gly Thr Lys Val Glu Ile Lys Arg Thr
                100                 105

<210> SEQ ID NO 192
<211> LENGTH: 327
<212> TYPE: DNA
<213> ORGANISM: Artificial Sequence
<220> FEATURE:
<223> OTHER INFORMATION: KV9; VL

<400> SEQUENCE: 192
gatatccagt tgacccagtc tccatccttc ctgtctgcat ctgtgggcga ccgggtcacc      60
atcacctgca aggccagtca gaatgtggat actaacgtgg cttggtacca gcagaagcca    120
gggcaggcac ctaggcctct gatctattcg gcatcctacc ggtacactgg cgtcccatca    180
aggttcagcg gcagtggatc cgggacagag ttcactctca caatctcaag cctgcaacct    240
gaagatttcg caacttacta ctgtcaacag tacaatagtt accctctgac gttcggcgga    300
ggtaccaagg tggagatcaa gcgtacg                                        327

<210> SEQ ID NO 193
<211> LENGTH: 122
<212> TYPE: PRT
<213> ORGANISM: Artificial Sequence
<220> FEATURE:
<223> OTHER INFORMATION: MHLG; VH

<400> SEQUENCE: 193

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
            20                  25                  30
Trp Met Asn Trp Val Arg Gln Ala Pro Gly Lys Gly Leu Glu Trp Val
        35                  40                  45
Ala Glu Ile Arg Leu Lys Ser Asn Asn Phe Gly Arg Tyr Tyr Ala Ala
    50                  55                  60
Ser Val Lys Gly Arg Phe Thr Ile Ser Arg Asp Asp Ser Lys Asn Thr
65                  70                  75                  80
Leu Tyr Leu Gln Met Asn Ser Leu Lys Thr Glu Asp Thr Ala Val Tyr
                85                  90                  95
Tyr Cys Thr Thr Tyr Gly Asn Tyr Val Gly His Tyr Phe Asp His Trp
            100                 105                 110
Gly Gln Gly Thr Thr Val Thr Val Ser Ser
        115                 120

<210> SEQ ID NO 194
<211> LENGTH: 366
<212> TYPE: DNA
<213> ORGANISM: Artificial Sequence
<220> FEATURE:
```

<223> OTHER INFORMATION: MHLG; VH

<400> SEQUENCE: 194

```
gaagtgcagc tggtggagtc tggaggaggc ttggtccagc ctggcgggtc cctgcggctc    60
tcctgtgcag cctccggatt cacatttagc aactattgga tgaactgggt gcggcaggct   120
cctggaaagg gcctcgagtg ggtggccgag atcagattga atccaataa cttcggaaga    180
tattacgctg caagcgtgaa gggccggttc accatcagca gagatgattc caagaacacg   240
ctgtacctgc agatgaacag cctgaagacc gaggatacgg ccgtgtatta ctgtaccaca   300
tacggcaact acgttgggca ctacttcgac cactgggggcc aagggaccac cgtcaccgtc  360
tccagt                                                              366
```

<210> SEQ ID NO 195
<211> LENGTH: 109
<212> TYPE: PRT
<213> ORGANISM: Artificial Sequence
<220> FEATURE:
<223> OTHER INFORMATION: KV1; VL

<400> SEQUENCE: 195

```
Asp Ile Gln Leu Thr Gln Ser Pro Ser Phe Leu Ser Ala Ser Val Gly
 1               5                  10                  15
Asp Arg Val Thr Ile Thr Cys Arg Ala Ser Gln Asn Val Asp Thr Asn
            20                  25                  30
Leu Ala Trp Tyr Gln Gln Lys Pro Gly Lys Ala Pro Lys Leu Leu Ile
        35                  40                  45
Tyr Ser Ala Ser Tyr Arg Tyr Thr Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Gln Gln Tyr Asn Ser Tyr Pro Leu
                85                  90                  95
Thr Phe Gly Gly Gly Thr Lys Val Glu Ile Lys Arg Thr
            100                 105
```

<210> SEQ ID NO 196
<211> LENGTH: 330
<212> TYPE: DNA
<213> ORGANISM: Artificial Sequence
<220> FEATURE:
<223> OTHER INFORMATION: KV1; VL

<400> SEQUENCE: 196

```
gatatccagt tgacccagtc tccatccttc ctgtctgcat ctgtgggcga ccgggtcacc    60
atcacctgca gggccagtca gaatgtggat actaacttag cttggtacca gcagaagcca   120
gggaaagcac ctaagctcct gatctattcg gcatcctacc gttacactgg cgtcccatca   180
aggttcagcg gcagtggatc cgggacagag ttcactctca caatctcaag cctgcaacct   240
gaagatttcg caacttacta ctgtcaacag tacaatagtt accctctgac gttcggcgga   300
ggtaccaagg tggagatcaa gcgtacggtg                                     330
```

<210> SEQ ID NO 197
<211> LENGTH: 109
<212> TYPE: PRT
<213> ORGANISM: Artificial Sequence
<220> FEATURE:
<223> OTHER INFORMATION: KV7; VL -continued

<400> SEQUENCE: 197

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Pro Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr
            100                 105

<210> SEQ ID NO 198
<211> LENGTH: 330
<212> TYPE: DNA
<213> ORGANISM: Artificial Sequence
<220> FEATURE:
<223> OTHER INFORMATION: KV7; VL

<400> SEQUENCE: 198
gatatccagt tgacccagtc tccatccttc ctgtctgcat ctgtgggcga ccgggtcacc    60
atcacctgca aggccagtca gaatgtggat actaacgtgg cttggtacca gcagaagcca   120
gggaaagcac ctaagcctct gatctattcg gcatcctacc ggtacactgg cgtcccatca   180
aggttcagcg gcagtggatc cgggacagag ttcactctca caatctcaag cctgcaacct   240
gaagatttcg caacttacta ctgtcaacag tacaatagtt accctctgac gttcggcgga   300
ggtaccaagg tggagatcaa agcgtacggtg                                   330

<210> SEQ ID NO 199
<211> LENGTH: 603
<212> TYPE: PRT
<213> ORGANISM: Artificial Sequence
<220> FEATURE:
<223> OTHER INFORMATION: L19 Fab-IL2 qm-Fab (heavy chain cytokine fusion
      construct)

<400> SEQUENCE: 199

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

```
Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Ser Gly Gly Gly
210                 215                 220

Gly Ser Gly Gly Gly Gly Ser Gly Gly Gly Ala Pro Ala Ser Ser
225                 230                 235                 240

Ser Thr Lys Lys Thr Gln Leu Gln Leu Glu His Leu Leu Asp Leu
            245                 250                 255

Gln Met Ile Leu Asn Gly Ile Asn Asn Tyr Lys Asn Pro Lys Leu Thr
        260                 265                 270

Arg Met Leu Thr Ala Lys Phe Ala Met Pro Lys Lys Ala Thr Glu Leu
        275                 280                 285

Lys His Leu Gln Cys Leu Glu Glu Leu Lys Pro Leu Glu Glu Val
    290                 295                 300

Leu Asn Gly Ala Gln Ser Lys Asn Phe His Leu Arg Pro Arg Asp Leu
305                 310                 315                 320

Ile Ser Asn Ile Asn Val Ile Val Leu Glu Leu Lys Gly Ser Glu Thr
                325                 330                 335

Thr Phe Met Cys Glu Tyr Ala Asp Glu Thr Ala Thr Ile Val Glu Phe
            340                 345                 350

Leu Asn Arg Trp Ile Thr Phe Ala Gln Ser Ile Ile Ser Thr Leu Thr
        355                 360                 365

Ser Gly Gly Gly Gly Ser Gly Gly Gly Gly Ser Gly Gly Gly Gly Glu
    370                 375                 380

Val Gln Leu Leu Glu Ser Gly Gly Gly Leu Val Gln Pro Gly Gly Ser
385                 390                 395                 400

Leu Arg Leu Ser Cys Ala Ala Ser Gly Phe Thr Phe Ser Ser Phe Ser
                405                 410                 415

Met Ser Trp Val Arg Gln Ala Pro Gly Lys Gly Leu Glu Trp Val Ser
            420                 425                 430

Ser Ile Ser Gly Ser Ser Gly Thr Thr Tyr Tyr Ala Asp Ser Val Lys
        435                 440                 445

Gly Arg Phe Thr Ile Ser Arg Asp Asn Ser Lys Asn Thr Leu Tyr Leu
    450                 455                 460

Gln Met Asn Ser Leu Arg Ala Glu Asp Thr Ala Val Tyr Tyr Cys Ala
465                 470                 475                 480

Lys Pro Phe Pro Tyr Phe Asp Tyr Trp Gly Gln Gly Thr Leu Val Thr
                485                 490                 495

Val Ser Ser Ala Ser Thr Lys Gly Pro Ser Val Phe Pro Leu Ala Pro
            500                 505                 510

Ser Ser Lys Ser Thr Ser Gly Gly Thr Ala Ala Leu Gly Cys Leu Val
        515                 520                 525

Lys Asp Tyr Phe Pro Glu Pro Val Thr Val Ser Trp Asn Ser Gly Ala
    530                 535                 540
```

| Leu | Thr | Ser | Gly | Val | His | Thr | Phe | Pro | Ala | Val | Leu | Gln | Ser | Ser | Gly |
|---|---|---|---|---|---|---|---|---|---|---|---|---|---|---|---|
| 545 | | | | 550 | | | | | 555 | | | | | 560 | |

| Leu | Tyr | Ser | Leu | Ser | Ser | Val | Val | Thr | Val | Pro | Ser | Ser | Ser | Leu | Gly |
|---|---|---|---|---|---|---|---|---|---|---|---|---|---|---|---|
| | | | | 565 | | | | | 570 | | | | | 575 | |

| Thr | Gln | Thr | Tyr | Ile | Cys | Asn | Val | Asn | His | Lys | Pro | Ser | Asn | Thr | Lys |
|---|---|---|---|---|---|---|---|---|---|---|---|---|---|---|---|
| | | | 580 | | | | | 585 | | | | | 590 | | |

| Val | Asp | Lys | Lys | Val | Glu | Pro | Lys | Ser | Cys | Asp |
|---|---|---|---|---|---|---|---|---|---|---|
| | 595 | | | | | 600 | | | | |

<210> SEQ ID NO 200
<211> LENGTH: 1809
<212> TYPE: DNA
<213> ORGANISM: Artificial Sequence
<220> FEATURE:
<223> OTHER INFORMATION: L19 Fab-IL2 qm-Fab (heavy chain cytokine fusion construct)

<400> SEQUENCE: 200

```
gaggtgcagc tgttggagtc tgggggaggc ttggtacagc ctggggggtc cctgagactc      60
tcctgtgcag cctctggatt cacctttagc agttttcga tgagctgggt ccgccaggct     120
ccagggaagg gctggagtg gtctcatct atttccggta gttcgggtac acatactac     180
gcagactccg tgaagggccg gttcaccatc tccagagaca attccaagaa cacgctgtat     240
ctgcaaatga acagcctgag agccgaggac acggccgtat attactgtgc gaaaccgttt     300
ccgtattttg actactgggg ccagggaacc ctggtcaccg tctcgagtgc tagcaccaag     360
ggcccatcgg tcttcccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gataagaaag ttgagcccaa atcttgtgac     660
tccggcggag gagggagcgg cggaggtggc tccgaggtg gcggagcacc tgcctcaagt     720
tctacaaaga aaacacagct acaactggag catttactgc tggatttaca gatgattttg     780
aatggaatta ataattacaa gaatcccaaa ctcaccagga tgctcacagc caagtttgcc     840
atgcccaaga aggccacaga actgaaacat cttcagtgtc tagaagaaga actcaaacct     900
ctggaggaag tgctaaatgg cgctcaaagc aaaaactttc acttaagacc cagggactta     960
atcagcaata tcaacgtaat agttctggaa ctaaagggat ctgaaacaac attcatgtgt    1020
gaatatgctg atgagacagc aaccattgta gaatttctga acagatggat tacctttgcc    1080
caaagcatca tctcaacact gacttccggc ggaggaggat ccggcggagg tggctctggc    1140
ggtggcggaa aggtgcagct gttggagtct gggggaggct tggtacagcc tggggggtcc    1200
ctgagactct cctgtgcagc ctctggattc acctttagca gttttcgat gagctgggtc    1260
cgccaggctc cagggaaggg ctggagtgg gtctcatcta tttccggtag ttcgggtacc    1320
acatactacg cagactccgt gaagggccgg ttcaccatct ccagagacaa ttccaagaac    1380
acgctgtatc tgcaaatgaa cagcctgaga gccgaggaca cggccgtata ttactgtgcg    1440
aaaccgtttc cgtattttga ctactgggc agggaaccc tggtcaccgt ctcgagtgct    1500
agcaccaagg gcccatcggt cttcccctg caccctcct ccaagagcac ctctggggc    1560
acagcggccc tgggctgcct ggtcaaggac tacttcccg aaccggtgac ggtgtcgtgg    1620
aactcaggcg ccctgaccag cggcgtgcac accttcccgg ctgtcctaca gtcctcagga    1680
```

```
ctctactccc tcagcagcgt ggtgaccgtg ccctccagca gcttgggcac ccagacctac    1740
atctgcaacg tgaatcacaa gcccagcaac accaaggtgg ataagaaagt tgagcccaaa    1800
tcttgtgac                                                            1809
```

<210> SEQ ID NO 201
<211> LENGTH: 215
<212> TYPE: PRT
<213> ORGANISM: Artificial Sequence
<220> FEATURE:
<223> OTHER INFORMATION: L19 light chain

<400> SEQUENCE: 201

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 202
<211> LENGTH: 645
<212> TYPE: DNA
<213> ORGANISM: Artificial Sequence
<220> FEATURE:
<223> OTHER INFORMATION: L19 light chain

<400> SEQUENCE: 202

```
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat tatgcatcca gcagggccac tggcatccca    180
gacaggttca gtggcagtgg gtctgggaca gacttcactc tcaccatcag cagactggag    240
cctgaagatt ttgcagtgta ttactgtcag cagacgggtc gtattcctcc gacgttcggc    300
caagggacca aggtggaaat caaacgtacg gtggctgcac catctgtctt catcttcccg    360
```
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgt    645

```
<210> SEQ ID NO 203
<211> LENGTH: 641
<212> TYPE: PRT
<213> ORGANISM: Artificial Sequence
<220> FEATURE:
<223> OTHER INFORMATION: F16 scFv-IL2 qm-scFv

<400> SEQUENCE: 203
```

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly |
| 1 | | | | 5 | | | | | 10 | | | | | 15 |
| Gly Ser | Leu | Arg | Leu | Ser | Cys | Ala | Ala | Ser | Gly | Phe | Thr | Phe | Ser | Arg | Tyr |
| | | 20 | | | | | 25 | | | | | 30 | | |
| Gly | Met | Ser | Trp | Val | Arg | Gln | Ala | Pro | Gly | Lys | Gly | Leu | Glu | Trp | Val |
| | | 35 | | | | | 40 | | | | | 45 | | |
| Ser | Ala | Ile | Ser | Gly | Ser | Gly | Gly | Ser | Thr | Tyr | Tyr | Ala | Asp | Ser | Val |
| | 50 | | | | | 55 | | | | | 60 | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Lys | Ala | His | Asn | Ala | Phe | Asp | Tyr | Trp | Gly | Gln | Gly | Thr | Leu | Val |
| | | | 100 | | | | | 105 | | | | | 110 | | |
| Thr | Val | Ser | Arg | Gly | Gly | Gly | Gly | Ser | Gly | Gly | Gly | Gly | Ser | Gly | Gly |
| | | 115 | | | | | 120 | | | | | 125 | | | |
| Gly | Gly | Ser | Ser | Glu | Leu | Thr | Gln | Asp | Pro | Ala | Val | Ser | Val | Ala | Leu |
| 130 | | | | | 135 | | | | | 140 | | | | | |
| Gly | Gln | Thr | Val | Arg | Ile | Thr | Cys | Gln | Gly | Asp | Ser | Leu | Arg | Ser | Tyr |
| 145 | | | | 150 | | | | | 155 | | | | | 160 | |
| Tyr | Ala | Ser | Trp | Tyr | Gln | Gln | Lys | Pro | Gly | Gln | Ala | Pro | Val | Leu | Val |
| | | | | 165 | | | | | 170 | | | | | 175 | |
| Ile | Tyr | Gly | Lys | Asn | Asn | Arg | Pro | Ser | Gly | Ile | Pro | Asp | Arg | Phe | Ser |
| | | | 180 | | | | | 185 | | | | | 190 | | |
| Gly | Ser | Ser | Ser | Gly | Asn | Thr | Ala | Ser | Leu | Thr | Ile | Thr | Gly | Ala | Gln |
| | 195 | | | | | 200 | | | | | 205 | | | | |
| Ala | Glu | Asp | Glu | Ala | Asp | Tyr | Tyr | Cys | Asn | Ser | Ser | Val | Tyr | Thr | Met |
| | 210 | | | | | 215 | | | | | 220 | | | | |
| Pro | Pro | Val | Val | Phe | Gly | Gly | Thr | Lys | Leu | Thr | Val | Leu | Gly | Ser |
| 225 | | | | | 230 | | | | | 235 | | | | | 240 |
| Ser | Ser | Ser | Gly | Ser | Ser | Ser | Gly | Ser | Ser | Ser | Gly | Ala | Pro |
| | | | | 245 | | | | | 250 | | | | | 255 |
| Ala | Ser | Ser | Ser | Thr | Lys | Lys | Thr | Gln | Leu | Gln | Leu | Glu | His | Leu | Leu |
| | | | 260 | | | | | 265 | | | | | 270 | | |
| Leu | Asp | Leu | Gln | Met | Ile | Leu | Asn | Gly | Ile | Asn | Asn | Tyr | Lys | Asn | Pro |
| | 275 | | | | | 280 | | | | | 285 | | | | |
| Lys | Leu | Thr | Arg | Met | Leu | Thr | Ala | Lys | Phe | Ala | Met | Pro | Lys | Lys | Ala |
| 290 | | | | | 295 | | | | | 300 | | | | | |
| Thr | Glu | Leu | Lys | His | Leu | Gln | Cys | Leu | Glu | Glu | Glu | Leu | Lys | Pro | Leu |

```
          305                 310                 315                 320
Glu Glu Val Leu Asn Gly Ala Gln Ser Lys Asn Phe His Leu Arg Pro
                    325                 330                 335
Arg Asp Leu Ile Ser Asn Ile Asn Val Ile Val Leu Glu Leu Lys Gly
                340                 345                 350
Ser Glu Thr Thr Phe Met Cys Glu Tyr Ala Asp Glu Thr Ala Thr Ile
            355                 360                 365
Val Glu Phe Leu Asn Arg Trp Ile Thr Phe Ala Gln Ser Ile Ile Ser
370                 375                 380
Thr Leu Thr Ser Gly Gly Gly Ser Gly Gly Gly Ser Gly Gly
385                 390                 395                 400
Gly Gly Ser Ser Glu Leu Thr Gln Asp Pro Ala Val Ser Val Ala Leu
                405                 410                 415
Gly Gln Thr Val Arg Ile Thr Cys Gln Gly Asp Ser Leu Arg Ser Tyr
            420                 425                 430
Tyr Ala Ser Trp Tyr Gln Gln Lys Pro Gly Gln Ala Pro Val Leu Val
            435                 440                 445
Ile Tyr Gly Lys Asn Asn Arg Pro Ser Gly Ile Pro Asp Arg Phe Ser
450                 455                 460
Gly Ser Ser Ser Gly Asn Thr Ala Ser Leu Thr Ile Thr Gly Ala Gln
465                 470                 475                 480
Ala Glu Asp Glu Ala Asp Tyr Tyr Cys Asn Ser Ser Val Tyr Thr Met
                485                 490                 495
Pro Pro Val Val Phe Gly Gly Gly Thr Lys Leu Thr Val Leu Gly Ser
                500                 505                 510
Gly Gly Gly Ser Gly Gly Gly Ser Gly Gly Gly Ser Gly Ser Glu Val
            515                 520                 525
Gln Leu Leu Glu Ser Gly Gly Gly Leu Val Gln Pro Gly Gly Ser Leu
        530                 535                 540
Arg Leu Ser Cys Ala Ala Ser Gly Phe Thr Phe Ser Arg Tyr Gly Met
545                 550                 555                 560
Ser Trp Val Arg Gln Ala Pro Gly Lys Gly Leu Glu Trp Val Ser Ala
                565                 570                 575
Ile Ser Gly Ser Gly Gly Ser Thr Tyr Tyr Ala Asp Ser Val Lys Gly
            580                 585                 590
Arg Phe Thr Ile Ser Arg Asp Asn Ser Lys Thr Leu Tyr Leu Gln
            595                 600                 605
Met Asn Ser Leu Arg Ala Glu Asp Thr Ala Val Tyr Tyr Cys Ala Lys
        610                 615                 620
Ala His Asn Ala Phe Asp Tyr Trp Gly Gln Gly Thr Leu Val Thr Val
625                 630                 635                 640
Ser
```

<210> SEQ ID NO 204
<211> LENGTH: 1923
<212> TYPE: DNA
<213> ORGANISM: Artificial Sequence
<220> FEATURE:
<223> OTHER INFORMATION: F16 scFv-IL2 qm-scFv

<400> SEQUENCE: 204

```
gaggtgcagc tgttggagtc tgggggaggc ttggtacagc ctgggggtc cctgagactc        60 tcctgtgcag cctctggatt cacctttagc cggtatggta tgagctgggt ccgccaggct       120
ccagggaagg gcctggagtg gtctcagct attagtggta gtggtggtag cacatactac       180
```

```
gcagactccg tgaagggccg gttcaccatc tccagagaca attccaagaa cacgctgtat    240
ctgcaaatga acagcctgag agccgaggac acggccgtat attactgtgc gaaagcgcat    300
aatgcttttg actactgggg ccagggaacc ctggtcaccg tgtcgagagg tggaggcggt    360
tcaggcggag gtggctctgg cggtggcgga tcgtctgagc tgactcagga ccctgctgtg    420
tctgtggcct tgggacagac agtcaggatc acatgccaag agacagcct cagaagctat     480 tatgcaagct ggtaccagca gaagccagga caggcccctg tacttgtcat ctatggtaaa    540
aacaaccggc cctcagggat cccagaccga ttctctggct ccagctcagg aaacacagct    600
tccttgacca tcactggggc tcaggcgaa gatgaggctg actattactg taactcctct     660
gtttatacta tgccgcccgt ggtattcggc ggagggacca agctgaccgt cctaggctct    720
tcctcatcgg gtagtagctc ttccggctca tcgtcctccg agcacctgc ctcaagttct     780 acaaagaaaa cacagctaca actggagcat ttactgctgg atttacagat gattttgaat    840
ggaattaata attacaagaa tcccaaactc accaggatgc tcacagccaa gtttgccatg    900
cccaagaagg ccacagaact gaaacatctt cagtgtctag aagaagaact caaacctctg    960
gaggaagtgc taaatggcgc tcaaagcaaa aactttcact taagacccag ggacttaatc   1020
agcaatatca acgtaatagt tctggaacta aagggatctg aaacaacatt catgtgtgaa   1080
tatgctgatg agacagcaac cattgtagaa tttctgaaca atggattac ctttgcccaa    1140 agcatcatct caacactgac ttccggcgga ggagggagcg gcggaggtgg ctctggcggt   1200
ggcggatcgt ctgagctcac tcaggaccct gctgtgtctg tggccttggg acagacagtc   1260
aggatcacat gccaaggaga cagcctcaga agctattatg caagctggta ccagcagaag   1320
ccaggacagg cccctgtact tgtcatctat ggtaaaaaca accggccctc agggatccca   1380
gaccgattct ctggctccag ctcaggaaac acagcttcct tgaccatcac tggggctcag   1440
gcggaagatg aggctgacta ttactgtaac tcctctgttt atactatgcc gcccgtggta   1500
ttcggcggag ggaccaagct taccgtacta ggctcaggag gcggttcagg cggaggttct   1560
ggcggcggta gcggatcgga ggtgcagctg ttggagtctg ggggaggctt ggtacagcct   1620
ggggggtccc tgagactctc ctgtgcagcc tctggattca cctttagccg gtatggtatg   1680
agctgggtcc gccaggctcc agggaagggg ctggagtggg tctcagctat tagtggtagt   1740
ggtggtagca catactacgc agactccgtg aagggccggt tcaccatctc cagagacaat   1800
tccaagaaca cgctgtatct gcaaatgaac agcctgagag ccgaggacac ggccgtatat   1860
tactgtgcga aagcgcataa tgcttttgac tactggggcc agggaaccct ggtcaccgtg   1920
tcg                                                                 1923
```

<210> SEQ ID NO 205
<211> LENGTH: 603
<212> TYPE: PRT
<213> ORGANISM: Artificial Sequence
<220> FEATURE:
<223> OTHER INFORMATION: F16 Fab-IL2 qm-Fab (heavy chain cytokine fusion construct)

<400> SEQUENCE: 205

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val

```
                35                  40                  45
Ser Ala Ile Ser Gly Ser Gly Gly Ser Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Ala His Asn Ala Phe Asp Tyr Trp Gly Gln Gly Thr Leu Val
                100                 105                 110
Thr Val Ser Ser Ala Ser Thr Lys Gly Pro Ser Val Phe Pro Leu Ala
                115                 120                 125
Pro Ser Ser Lys Ser Thr Ser Gly Gly Thr Ala Ala Leu Gly Cys Leu
        130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                        165                 170                 175
Gly Leu Tyr Ser Leu Ser Ser Val Val Thr Val Pro Ser Ser Ser Leu
                180                 185                 190
Gly Thr Gln Thr Tyr Ile Cys Asn Val Asn His Lys Pro Ser Asn Thr
                195                 200                 205
Lys Val Asp Lys Lys Val Glu Pro Lys Ser Cys Asp Ser Ser Ser Ser
210                 215                 220
Gly Ser Ser Ser Ser Gly Ser Ser Ser Gly Ala Pro Ala Ser Ser
225                 230                 235                 240
Ser Thr Lys Lys Thr Gln Leu Gln Leu Glu His Leu Leu Asp Leu
                245                 250                 255
Gln Met Ile Leu Asn Gly Ile Asn Asn Tyr Lys Asn Pro Lys Leu Thr
                260                 265                 270
Arg Met Leu Thr Ala Lys Phe Ala Met Pro Lys Lys Ala Thr Glu Leu
                275                 280                 285
Lys His Leu Gln Cys Leu Glu Glu Glu Leu Lys Pro Leu Glu Glu Val
                290                 295                 300
Leu Asn Gly Ala Gln Ser Lys Asn Phe His Leu Arg Pro Arg Asp Leu
305                 310                 315                 320
Ile Ser Asn Ile Asn Val Ile Val Leu Glu Leu Lys Gly Ser Glu Thr
                        325                 330                 335
Thr Phe Met Cys Glu Tyr Ala Asp Glu Thr Ala Thr Ile Val Glu Phe
                340                 345                 350
Leu Asn Arg Trp Ile Thr Phe Ala Gln Ser Ile Ile Ser Thr Leu Thr
                355                 360                 365
Ser Gly Gly Gly Gly Ser Gly Gly Gly Ser Gly Gly Gly Gly Glu
        370                 375                 380
Val Gln Leu Leu Glu Ser Gly Gly Gly Leu Val Gln Pro Gly Gly Ser
385                 390                 395                 400
Leu Arg Leu Ser Cys Ala Ala Ser Gly Phe Thr Phe Ser Arg Tyr Gly
                        405                 410                 415
Met Ser Trp Val Arg Gln Ala Pro Gly Lys Gly Leu Glu Trp Val Ser
                420                 425                 430
Ala Ile Ser Gly Ser Gly Gly Ser Thr Tyr Tyr Ala Asp Ser Val Lys
                435                 440                 445
Gly Arg Phe Thr Ile Ser Arg Asp Asn Ser Lys Asn Thr Leu Tyr Leu
        450                 455                 460
```

```
Gln Met Asn Ser Leu Arg Ala Glu Asp Thr Ala Val Tyr Tyr Cys Ala
465                 470                 475                 480

Lys Ala His Asn Ala Phe Asp Tyr Trp Gly Gln Gly Thr Leu Val Thr
            485                 490                 495

Val Ser Ser Ala Ser Thr Lys Gly Pro Ser Val Phe Pro Leu Ala Pro
        500                 505                 510

Ser Ser Lys Ser Thr Ser Gly Gly Thr Ala Ala Leu Gly Cys Leu Val
        515                 520                 525

Lys Asp Tyr Phe Pro Glu Pro Val Thr Val Ser Trp Asn Ser Gly Ala
530                 535                 540

Leu Thr Ser Gly Val His Thr Phe Pro Ala Val Leu Gln Ser Ser Gly
545                 550                 555                 560

Leu Tyr Ser Leu Ser Ser Val Val Thr Val Pro Ser Ser Ser Leu Gly
                565                 570                 575

Thr Gln Thr Tyr Ile Cys Asn Val Asn His Lys Pro Ser Asn Thr Lys
            580                 585                 590

Val Asp Lys Lys Val Glu Pro Lys Ser Cys Asp
        595                 600

<210> SEQ ID NO 206
<211> LENGTH: 1809
<212> TYPE: DNA
<213> ORGANISM: Artificial Sequence
<220> FEATURE:
<223> OTHER INFORMATION: F16 Fab-IL2 qm-Fab (heavy chain cytokine fusion
      construct)

<400> SEQUENCE: 206
gaggtgcagc tgttggagtc tgggggaggc ttggtacagc ctgggggggtc cctgagactc      60 tcctgtgcag cctctggatt caccttagc cggtatggta tgagctgggt ccgccaggct      120
ccagggaagg gctggagtg gtctcagct attagtggta gtggtggtag cacatactac      180
gcagactccg tgaagggccg gttcaccatc tccagagaca attccaagaa cacgctgtat      240
ctgcaaatga acagcctgag agccgaggac acggccgtat attactgtgc gaaagcgcat      300
aatgcttttg actactgggg ccagggaacc ctggtcaccg tgtcgagtgc tagcaccaag      360
ggcccatcgg tcttcccccct ggcaccctcc tccaagagca cctctggggg cacagcggcc      420
ctgggctgcc tggtcaagga ctacttcccc gaaccggtga cggtgtcgtg gaactcaggc      480
gccctgacca gcggcgtgca ccttcccg gctgtcctac agtcctcagg actctactcc      540
ctcagcagcg tggtgaccgt gccctccagc agcttgggca cccagaccta catctgcaac      600
gtgaatcaca gcccagcaa caccaaggtg gataagaaag ttgagcccaa atcttgtgac      660
tcttcctcat cgggtagtag ctcttccggc tcatcgtcct ccggagcacc tgcctcaagt      720
tctacaaaga aaacacagct acaactggag catttactgc tggatttaca gatgattttg      780 aatgaatta ataattacaa gaatcccaaa ctcaccagga tgctcacagc caagtttgcc      840
atgcccaaga aggccacaga actgaaacat cttcagtgtc tagaagaaga actcaaacct      900
ctggaggaag tgctaaatgg cgctcaaagc aaaaactttc acttaagacc cagggactta      960
atcagcaata tcaacgtaat agttctggaa ctaaagggat ctgaaacaac attcatgtgt     1020
gaatatgctg atgagacagc aaccattgta gaatttctga acagatggat taccttgcc     1080 caaagcatca tctcaacact gacttccggc ggaggaggga gcggcggagg tggctctggc     1140
ggtggcggag aggtgcaatt gttggagtct gggggaggct tggtacagcc tggggggtcc     1200
```

-continued

```
ctgagactct cctgtgcagc ctctggattc acctttagcc ggtatggtat gagctgggtc    1260
cgccaggctc cagggaaggg gctggagtgg gtctcagcta ttagtggtag tggtggtagc    1320
acatactacg cagactccgt gaagggccgg ttcaccatct ccagagacaa ttccaagaac    1380
acgctgtatc tgcaaatgaa cagcctgaga gccgaggaca cggccgtata ttactgtgcg    1440
aaagcgcata atgcttttga ctactggggc cagggaaccc tggtcaccgt gtcgagtgct    1500
agcaccaagg gcccatcggt cttccccctg gcaccctcct ccaagagcac ctctgggggc    1560
acagcggccc tgggctgcct ggtcaaggac tacttccccg aaccggtgac ggtgtcgtgg    1620
aactcaggcg ccctgaccag cggcgtgcac accttcccgg ctgtcctaca gtcctcagga    1680
ctctactccc tcagcagcgt ggtgaccgtg ccctccagca gcttgggcac ccagacctac    1740
atctgcaacg tgaatcacaa gcccagcaac accaaggtgg acaagaaagt tgagcccaaa    1800
tcttgtgac                                                            1809
```

<210> SEQ ID NO 207
<211> LENGTH: 214
<212> TYPE: PRT
<213> ORGANISM: Artificial Sequence
<220> FEATURE:
<223> OTHER INFORMATION: F16 light chain

<400> SEQUENCE: 207

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Val Tyr Thr Met Pro Pro
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 208
<211> LENGTH: 642
<212> TYPE: DNA
<213> ORGANISM: Artificial Sequence
<220> FEATURE:
<223> OTHER INFORMATION: F16 light chain

<400> SEQUENCE: 208

```
tcttctgagc tgactcagga ccctgctgtg tctgtggcct tgggacagac agtcaggatc      60
acatgccaag agacagcct cagaagctat tatgcaagct ggtaccagca gaagccagga     120
caggcccctg tacttgtcat ctatggtaaa acaaccggc cctcagggat cccagaccga     180
ttctctggct ccagctcagg aaacacagct tccttgacca tcactgggc tcaggcggaa     240
gatgaggctg actattactg taactcctct gtttatacta tgccgccgt ggtattcggc     300
ggagggacca agctgaccgt cctaggtcaa cccaaggctg ccccagcgt gaccctgttc     360
cccccagca gcgaggaact gcaggccaac aaggccaccc tggtctgcct gatcagcgac     420
ttctacccag cgccgtgac cgtggcctgg aaggccgaca gcagcccgt gaaggccggc     480
gtggagacca ccaccccag caagcagagc aacaacaagt acgccgccag cagctacctg     540
agcctgaccc ccgagcagtg gaagagccac aggtcctaca gctgccaggt gacccacgag     600
ggcagcaccg tggagaaaac cgtggccccc accgagtgca gc                       642
```

<210> SEQ ID NO 209
<211> LENGTH: 605
<212> TYPE: PRT
<213> ORGANISM: Artificial Sequence
<220> FEATURE:
<223> OTHER INFORMATION: 3F2 Fab-IL2 qm-Fab (heavy chain cytokine fusion construct)

<400> SEQUENCE: 209

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Gly Trp Phe Gly Gly Phe Asn Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Ser Gly Gly
    210                 215                 220
```

Gly Gly Ser Gly Gly Gly Ser Gly Gly Gly Ala Pro Ala Ser
225                 230                 235             240

Ser Ser Thr Lys Lys Thr Gln Leu Gln Leu Glu His Leu Leu Leu Asp
            245                 250                 255

Leu Gln Met Ile Leu Asn Gly Ile Asn Asn Tyr Lys Asn Pro Lys Leu
        260                 265                 270

Thr Arg Met Leu Thr Ala Lys Phe Ala Met Pro Lys Lys Ala Thr Glu
        275                 280                 285

Leu Lys His Leu Gln Cys Leu Glu Glu Glu Leu Lys Pro Leu Glu Glu
    290                 295                 300

Val Leu Asn Gly Ala Gln Ser Lys Asn Phe His Leu Arg Pro Arg Asp
305                 310                 315                 320

Leu Ile Ser Asn Ile Asn Val Ile Val Leu Glu Leu Lys Gly Ser Glu
                325                 330                 335

Thr Thr Phe Met Cys Glu Tyr Ala Asp Glu Thr Ala Thr Ile Val Glu
            340                 345                 350

Phe Leu Asn Arg Trp Ile Thr Phe Ala Gln Ser Ile Ile Ser Thr Leu
        355                 360                 365

Thr Ser Gly Gly Gly Gly Ser Gly Gly Gly Gly Ser Gly Gly Gly Gly
    370                 375                 380

Glu Val Gln Leu Leu Glu Ser Gly Gly Gly Leu Val Gln Pro Gly Gly
385                 390                 395                 400

Ser Leu Arg Leu Ser Cys Ala Ala Ser Gly Phe Thr Phe Ser Ser Tyr
                405                 410                 415

Ala Met Ser Trp Val Arg Gln Ala Pro Gly Lys Gly Leu Glu Trp Val
            420                 425                 430

Ser Ala Ile Ser Gly Ser Gly Gly Ser Thr Tyr Tyr Ala Asp Ser Val
        435                 440                 445

Lys Gly Arg Phe Thr Ile Ser Arg Asp Asn Ser Lys Asn Thr Leu Tyr
450                 455                 460

Leu Gln Met Asn Ser Leu Arg Ala Glu Asp Thr Ala Val Tyr Tyr Cys
465                 470                 475                 480

Ala Lys Gly Trp Phe Gly Gly Phe Asn Tyr Trp Gly Gln Gly Thr Leu
                485                 490                 495

Val Thr Val Ser Ser Ala Ser Thr Lys Gly Pro Ser Val Phe Pro Leu
            500                 505                 510

Ala Pro Ser Ser Lys Ser Thr Ser Gly Gly Thr Ala Ala Leu Gly Cys
        515                 520                 525

Leu Val Lys Asp Tyr Phe Pro Glu Pro Val Thr Val Ser Trp Asn Ser
    530                 535                 540

Gly Ala Leu Thr Ser Gly Val His Thr Phe Pro Ala Val Leu Gln Ser
545                 550                 555                 560

Ser Gly Leu Tyr Ser Leu Ser Ser Val Val Thr Val Pro Ser Ser Ser
                565                 570                 575

Leu Gly Thr Gln Thr Tyr Ile Cys Asn Val Asn His Lys Pro Ser Asn
            580                 585                 590

Thr Lys Val Asp Lys Lys Val Glu Pro Lys Ser Cys Asp
        595                 600                 605

<210> SEQ ID NO 210
<211> LENGTH: 1815
<212> TYPE: DNA
<213> ORGANISM: Artificial Sequence
<220> FEATURE:

<223> OTHER INFORMATION: 3F2 Fab-IL2 qm-Fab (heavy chain cytokine fusion construct)

<400> SEQUENCE: 210

```
gaggtgcaat tgttggagtc tggggggaggc ttggtacagc ctggggggtc cctgagactc      60
tcctgtgcag cctccggatt cacctttagc agttatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaagggtgg     300
tttggtggtt ttaactactg gggccaagga accctggtca ccgtctcgag tgctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggataaga agttgagcc caaatcttgt     660
gactccggcg gaggagggag cggcggaggt ggctccggag gtggcggagc acctgcctca     720
agttctacaa agaaaacaca gctacaactg gagcatttac tgctggattt acagatgatt     780
ttgaatggaa ttaataatta caagaatccc aaactcacca gatgctcac agccaagttt     840
gccatgccca agaaggccac agaactgaaa catcttcagt gtctagaaga gaactcaaa     900
cctctggagg aagtgctaaa tggcgctcaa agcaaaaact tcacttaag acccagggac     960
ttaatcagca atatcaacgt aatagttctg gaactaaagg gatctgaaac aacattcatg    1020
tgtgaatatg ctgatgagac agcaaccatt gtagaatttc tgaacagatg gattaccttt    1080
gcccaaagca tcatctcaac actgacttcc ggcggaggag gatccggcgg aggtggctct    1140
ggcggtggcg gagaggtgca attgttggag tctggggggag gcttggtaca gcctgggggg    1200
tccctgagac tctcctgtgc agcctccgga ttcaccttta gcagttatgc catgagctgg    1260
gtccgccagg ctccagggaa ggggctggag tgggtctcag ctattagtgg tagtggtggt    1320
agcacatact acgcagactc cgtgaagggc cggttcacca tctccagaga caattccaag    1380
aacacgctgt atctgcagat gaacagcctg agagccgagg acacggccgt atattactgt    1440
gcgaaagggt ggtttggtgg ttttaactac tggggccaag gaaccctggt caccgtctcg    1500
agtgctagca ccaagggccc atcggtcttc cccctggcac cctcctccaa gagcacctct    1560
gggggcacag cggccctggg ctgcctggtc aaggactact tccccgaacc ggtgacggtg    1620
tcgtggaact caggcgccct gaccagcggc gtgcacacct tcccggctgt cctacagtcc    1680
tcaggactct actccctcag cagcgtggtg accgtgccct ccagcagctt gggcacccag    1740
acctacatct gcaacgtgaa tcacaagccc agcaacacca aggtggataa gaaagttgag    1800
cccaaatctt gtgac                                                     1815
```

<210> SEQ ID NO 211
<211> LENGTH: 605
<212> TYPE: PRT
<213> ORGANISM: Artificial Sequence
<220> FEATURE:
<223> OTHER INFORMATION: 4G8 Fab-IL2 qm-Fab (heavy chain cytokine fusion construct)

<400> SEQUENCE: 211

Glu Val Gln Leu Leu Glu Ser Gly Gly Gly Leu Val Gln Pro Gly Gly

```
            1               5                  10                 15
        Ser Leu Arg Leu Ser Cys Ala Ala Ser Gly Phe Thr Phe Ser Ser Tyr
                        20                  25                 30

Ala Met Ser Trp Val Arg Gln Ala Pro Gly Lys Gly Leu Glu Trp Val
                        35                  40                 45

Ser Ala Ile Ser Gly Ser Gly Gly Ser Thr Tyr Tyr Ala Asp Ser Val
                        50                  55                 60

Lys Gly Arg Phe Thr Ile Ser Arg Asp Asn Ser Lys Asn Thr Leu Tyr
         65                  70                  75                 80

Leu Gln Met Asn Ser Leu Arg Ala Glu Asp Thr Ala Val Tyr Tyr Cys
                        85                  90                 95

Ala Lys Gly Trp Leu Gly Asn Phe Asp Tyr Trp Gly Gln Gly Thr Leu
                        100                 105                110

Val Thr Val Ser Ser Ala Ser Thr Lys Gly Pro Ser Val Phe Pro Leu
                        115                 120                125

Ala Pro Ser Ser Lys Ser Thr Ser Gly Gly Thr Ala Ala Leu Gly Cys
                        130                 135                140

Leu Val Lys Asp Tyr Phe Pro Glu Pro Val Thr Val Ser Trp Asn Ser
        145                 150                 155                160

Gly Ala Leu Thr Ser Gly Val His Thr Phe Pro Ala Val Leu Gln Ser
                        165                 170                175

Ser Gly Leu Tyr Ser Leu Ser Ser Val Val Thr Val Pro Ser Ser Ser
                        180                 185                190

Leu Gly Thr Gln Thr Tyr Ile Cys Asn Val Asn His Lys Pro Ser Asn
                        195                 200                205

Thr Lys Val Asp Lys Lys Val Glu Pro Lys Ser Cys Asp Ser Gly Gly
        210                 215                 220

Gly Gly Ser Gly Gly Gly Ser Gly Gly Gly Ala Pro Ala Ser
        225                 230                 235                240

Ser Ser Thr Lys Lys Thr Gln Leu Gln Leu Glu His Leu Leu Leu Asp
                        245                 250                255

Leu Gln Met Ile Leu Asn Gly Ile Asn Asn Tyr Lys Asn Pro Lys Leu
                        260                 265                270

Thr Arg Met Leu Thr Ala Lys Phe Ala Met Pro Lys Lys Ala Thr Glu
                        275                 280                285

Leu Lys His Leu Gln Cys Leu Glu Glu Glu Leu Lys Pro Leu Glu Glu
                        290                 295                300

Val Leu Asn Gly Ala Gln Ser Lys Asn Phe His Leu Arg Pro Arg Asp
        305                 310                 315                320

Leu Ile Ser Asn Ile Asn Val Ile Val Leu Glu Leu Lys Gly Ser Glu
                        325                 330                335

Thr Thr Phe Met Cys Glu Tyr Ala Asp Glu Thr Ala Thr Ile Val Glu
                        340                 345                350

Phe Leu Asn Arg Trp Ile Thr Phe Ala Gln Ser Ile Ile Ser Thr Leu
                        355                 360                365

Thr Ser Gly Gly Gly Gly Ser Gly Gly Gly Gly Ser Gly Gly Gly Gly
                        370                 375                380

Glu Val Gln Leu Leu Glu Ser Gly Gly Gly Leu Val Gln Pro Gly Gly
        385                 390                 395                400

Ser Leu Arg Leu Ser Cys Ala Ala Ser Gly Phe Thr Phe Ser Ser Tyr
                        405                 410                415

Ala Met Ser Trp Val Arg Gln Ala Pro Gly Lys Gly Leu Glu Trp Val
                        420                 425                430
```

```
Ser Ala Ile Ser Gly Ser Gly Gly Ser Thr Tyr Tyr Ala Asp Ser Val
        435                 440                 445

Lys Gly Arg Phe Thr Ile Ser Arg Asp Asn Ser Lys Asn Thr Leu Tyr
    450                 455                 460

Leu Gln Met Asn Ser Leu Arg Ala Glu Asp Thr Ala Val Tyr Tyr Cys
465                 470                 475                 480

Ala Lys Gly Trp Leu Gly Asn Phe Asp Tyr Trp Gly Gln Gly Thr Leu
                485                 490                 495

Val Thr Val Ser Ser Ala Ser Thr Lys Gly Pro Ser Val Phe Pro Leu
            500                 505                 510

Ala Pro Ser Ser Lys Ser Thr Ser Gly Gly Thr Ala Ala Leu Gly Cys
        515                 520                 525

Leu Val Lys Asp Tyr Phe Pro Glu Pro Val Thr Val Ser Trp Asn Ser
    530                 535                 540

Gly Ala Leu Thr Ser Gly Val His Thr Phe Pro Ala Val Leu Gln Ser
545                 550                 555                 560

Ser Gly Leu Tyr Ser Leu Ser Ser Val Val Thr Val Pro Ser Ser Ser
                565                 570                 575

Leu Gly Thr Gln Thr Tyr Ile Cys Asn Val Asn His Lys Pro Ser Asn
            580                 585                 590

Thr Lys Val Asp Lys Lys Val Glu Pro Lys Ser Cys Asp
        595                 600                 605

<210> SEQ ID NO 212
<211> LENGTH: 1815
<212> TYPE: DNA
<213> ORGANISM: Artificial Sequence
<220> FEATURE:
<223> OTHER INFORMATION: 4G8 Fab-IL2 qm-Fab (heavy chain cytokine fusion
      construct)

<400> SEQUENCE: 212
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaagggtgg     300
ctgggtaatt ttgactactg gggccaagga accctggtca ccgtctcgag tgctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggataaga agttgagcc caaatcttgt     660 gactccggcg gaggagggag cggcggaggt ggctccggag gtggcggagc acctgcctca     720
agttctacaa agaaaacaca gctacaactg gagcatttac tgctggattt acagatgatt     780
ttgaatggaa ttaataatta caagaatccc aaactcacca ggatgctcac agccaagttt     840
gccatgccca gaaggccac agaactgaaa catcttcagt gtctagaaga gaactcaaa     900 cctctggagg aagtgctaaa tggcgctcaa agcaaaaact tcacttaag acccagggac     960 ttaatcagca atatcaacgt aatagttctg gaactaaagg gatctgaaac aacattcatg    1020
```

```
tgtgaatatg ctgatgagac agcaaccatt gtagaatttc tgaacagatg gattaccttt    1080
gcccaaagca tcatctcaac actgacttcc ggcggaggag gatccggcgg aggtggctct    1140
ggcggtggcg gagaggtgca attgttggag tctgggggag gcttggtaca gcctggggg    1200
tccctgagac tctcctgtgc agcctccgga ttcaccttta gcagttatgc catgagctgg    1260
gtccgccagg ctccagggaa ggggctggag tgggtctcag ctattagtgg tagtggtggt    1320
agcacatact acgcagactc cgtgaagggc cggttcacca tctccagaga caattccaag    1380
aacacgctgt atctgcagat gaacagcctg agagccgagg acacggccgt atattactgt    1440
gcgaaagggt ggctgggtaa ttttgactac tggggccaag gaaccctggt caccgtctcg    1500
agtgctagca ccaagggccc atcggtcttc cccctggcac cctcctccaa gagcacctct    1560
gggggcacag cggccctggg ctgcctggtc aaggactact tccccgaacc ggtgacggtg    1620
tcgtggaact caggcgccct gaccagcggc gtgcacacct tcccggctgt cctacagtcc    1680
tcaggactct actccctcag cagcgtggtg accgtgccct ccagcagctt gggcacccag    1740
acctacatct gcaacgtgaa tcacaagccc agcaacacca aggtggataa gaaagttgag    1800
cccaaatctt gtgac                                                     1815

<210> SEQ ID NO 213
<211> LENGTH: 605
<212> TYPE: PRT
<213> ORGANISM: Artificial Sequence
<220> FEATURE:
<223> OTHER INFORMATION: 3D9 Fab-IL2 qm-Fab (heavy chain cytokine fusion
      construct)

<400> SEQUENCE: 213

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Thr Pro Gly Lys Gly Leu Glu Trp Val
        35                  40                  45

Ser Ala Ile Gly Val Ser Thr Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Pro Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Ser Gly Gly
```

```
            210                 215                 220
Gly Gly Ser Gly Gly Gly Ser Gly Gly Gly Ala Pro Ala Ser
225                 230                 235                 240

Ser Ser Thr Lys Lys Thr Gln Leu Gln Leu Glu His Leu Leu Leu Asp
                245                 250                 255

Leu Gln Met Ile Leu Asn Gly Ile Asn Asn Tyr Lys Asn Pro Lys Leu
                260                 265                 270

Thr Arg Met Leu Thr Ala Lys Phe Ala Met Pro Lys Lys Ala Thr Glu
                275                 280                 285

Leu Lys His Leu Gln Cys Leu Glu Glu Glu Leu Lys Pro Leu Glu Glu
                290                 295                 300

Val Leu Asn Gly Ala Gln Ser Lys Asn Phe His Leu Arg Pro Arg Asp
305                 310                 315                 320

Leu Ile Ser Asn Ile Asn Val Ile Val Leu Glu Leu Lys Gly Ser Glu
                325                 330                 335

Thr Thr Phe Met Cys Glu Tyr Ala Asp Glu Thr Ala Thr Ile Val Glu
                340                 345                 350

Phe Leu Asn Arg Trp Ile Thr Phe Ala Gln Ser Ile Ile Ser Thr Leu
                355                 360                 365

Thr Ser Gly Gly Gly Gly Ser Gly Gly Gly Ser Gly Gly Gly Gly
                370                 375                 380

Glu Val Gln Leu Leu Glu Ser Gly Gly Gly Leu Val Gln Pro Gly Gly
385                 390                 395                 400

Ser Leu Arg Leu Ser Cys Ala Ala Ser Gly Phe Thr Phe Ser Ser Tyr
                405                 410                 415

Ala Met Ser Trp Val Arg Gln Thr Pro Gly Lys Gly Leu Glu Trp Val
                420                 425                 430

Ser Ala Ile Gly Val Ser Thr Gly Ser Thr Tyr Tyr Ala Asp Ser Val
                435                 440                 445

Lys Gly Arg Phe Thr Ile Ser Arg Asp Asn Ser Lys Asn Thr Leu Tyr
                450                 455                 460

Leu Gln Met Asn Ser Leu Arg Ala Glu Asp Thr Ala Val Tyr Tyr Cys
465                 470                 475                 480

Ala Lys Gly Trp Leu Gly Pro Phe Asp Tyr Trp Gly Gln Gly Thr Leu
                485                 490                 495

Val Thr Val Ser Ser Ala Ser Thr Lys Gly Pro Ser Val Phe Pro Leu
                500                 505                 510

Ala Pro Ser Ser Lys Ser Thr Ser Gly Gly Thr Ala Ala Leu Gly Cys
                515                 520                 525

Leu Val Lys Asp Tyr Phe Pro Glu Pro Val Thr Val Ser Trp Asn Ser
                530                 535                 540

Gly Ala Leu Thr Ser Gly Val His Thr Phe Pro Ala Val Leu Gln Ser
545                 550                 555                 560

Ser Gly Leu Tyr Ser Leu Ser Ser Val Val Thr Val Pro Ser Ser Ser
                565                 570                 575

Leu Gly Thr Gln Thr Tyr Ile Cys Asn Val Asn His Lys Pro Ser Asn
                580                 585                 590

Thr Lys Val Asp Lys Lys Val Glu Pro Lys Ser Cys Asp
                595                 600                 605

<210> SEQ ID NO 214
<211> LENGTH: 1815
<212> TYPE: DNA
<213> ORGANISM: Artificial Sequence
```

<220> FEATURE:
<223> OTHER INFORMATION: 3D9 Fab-IL2 qm-Fab (heavy chain cytokine fusion construct)

<400> SEQUENCE: 214

| | | | | | |
|---|---|---|---|---|---|
| gaggtgcaat | tgttggagtc | tgggggaggc | ttggtacagc | ctggggggtc | cctgagactc | 60 |
| tcctgtgcag | cctccggatt | cacctttagc | agttatgcta | tgagctgggt | ccgccagact | 120 |
| ccagggaagg | gctggagtg | gtctcagct | attggtgtta | gtactggtag | cacatactac | 180 |
| gcagactccg | tgaagggccg | gttcaccatc | tccagagaca | attccaagaa | cacgctgtat | 240 |
| ctgcagatga | acagcctgag | agccgaggac | acggccgtat | attactgtgc | gaaaggttgg | 300 |
| ctgggtcctt | ttgactactg | gggccaagga | accctggtca | ccgtctcgag | tgctagcacc | 360 |
| aagggcccat | cggtcttccc | cctggcaccc | tcctccaaga | gcacctctgg | gggcacagcg | 420 |
| gccctgggct | gcctggtcaa | ggactacttc | cccgaaccgg | tgacggtgtc | gtggaactca | 480 |
| ggcgccctga | ccagcggcgt | gcacaccttc | ccggctgtcc | tacagtcctc | aggactctac | 540 |
| tccctcagca | gcgtggtgac | cgtgccctcc | agcagcttgg | gcacccagac | ctacatctgc | 600 |
| aacgtgaatc | acaagcccag | caacaccaag | gtggataaga | aagttgagcc | caaatcttgt | 660 |
| gactccggcg | gaggagggag | cggcggaggt | ggctccggag | gtggcggagc | acctgcctca | 720 |
| agttctacaa | agaaaacaca | gctacaactg | gagcatttac | tgctggattt | acagatgatt | 780 |
| ttgaatggaa | ttaataatta | caagaatccc | aaactcacca | ggatgctcac | agccaagttt | 840 |
| gccatgccca | agaaggccac | agaactgaaa | catcttcagt | gtctagaaga | agaactcaaa | 900 |
| cctctggagg | aagtgctaaa | tggcgctcaa | agcaaaaact | tcacttaag | acccagggac | 960 |
| ttaatcagca | atatcaacgt | aatagttctg | gaactaaagg | atctgaaac | aacattcatg | 1020 |
| tgtgaatatg | ctgatgagac | agcaaccatt | gtagaatttc | tgaacagatg | gattaccttt | 1080 |
| gcccaaagca | tcatctcaac | actgacttcc | ggcggaggag | gatccggcgg | aggtggctct | 1140 |
| ggcggtggcg | gagaggtgca | attgttggag | tctgggggag | gcttggtaca | gcctgggggg | 1200 |
| tccctgagac | tctcctgtgc | agcctccgga | ttcacccttta | gcagttatgc | tatgagctgg | 1260 |
| gtccgccaga | ctccagggaa | ggggctggag | tgggtctcag | ctattggtgt | tagtactggt | 1320 |
| agcacatact | acgcagactc | cgtgaagggc | cggttcacca | tctccagaga | caattccaag | 1380 |
| aacacgctgt | atctgcagat | gaacagcctg | agagccgagg | acacggccgt | atattactgt | 1440 |
| gcgaaaggtt | ggctgggtcc | ttttgactac | tggggccaag | gaaccctggt | caccgtctcg | 1500 |
| agtgctagca | ccaagggccc | atcggtcttc | cccctggcac | cctcctccaa | gagcacctct | 1560 |
| gggggcacag | cggccctggg | ctgcctggtc | aaggactact | tccccgaacc | ggtgacggtg | 1620 |
| tcgtggaact | caggcgcccct | gaccagcggc | gtgcacacct | tcccggctgt | cctacagtcc | 1680 |
| tcaggactct | actccctcag | cagcgtggtg | accgtgccct | ccagcagctt | gggcacccag | 1740 |
| acctacatct | gcaacgtgaa | tcacaagccc | agcaacacca | aggtggataa | gaaagttgag | 1800 |
| cccaaatctt | gtgac | | | | | 1815 |

<210> SEQ ID NO 215
<211> LENGTH: 605
<212> TYPE: PRT
<213> ORGANISM: Artificial Sequence
<220> FEATURE:
<223> OTHER INFORMATION: 2F11 Fab-IL2 qm-Fab (heavy chain cytokine fusion construct)

<400> SEQUENCE: 215

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Arg Trp Met Met Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Ser Gly Gly
    210                 215                 220

Gly Gly Ser Gly Gly Gly Gly Ser Gly Gly Gly Gly Ala Pro Ala Ser
225                 230                 235                 240

Ser Ser Thr Lys Lys Thr Gln Leu Gln Leu Glu His Leu Leu Leu Asp
                245                 250                 255

Leu Gln Met Ile Leu Asn Gly Ile Asn Asn Tyr Lys Asn Pro Lys Leu
            260                 265                 270

Thr Arg Met Leu Thr Ala Lys Phe Ala Met Pro Lys Lys Ala Thr Glu
        275                 280                 285

Leu Lys His Leu Gln Cys Leu Glu Glu Glu Leu Lys Pro Leu Glu Glu
    290                 295                 300

Val Leu Asn Gly Ala Gln Ser Lys Asn Phe His Leu Arg Pro Arg Asp
305                 310                 315                 320

Leu Ile Ser Asn Ile Asn Val Ile Val Leu Glu Leu Lys Gly Ser Glu
                325                 330                 335

Thr Thr Phe Met Cys Glu Tyr Ala Asp Glu Thr Ala Thr Ile Val Glu
            340                 345                 350

Phe Leu Asn Arg Trp Ile Thr Phe Ala Gln Ser Ile Ile Ser Thr Leu
        355                 360                 365

Thr Ser Gly Gly Gly Gly Ser Gly Gly Gly Gly Ser Gly Gly Gly Gly
    370                 375                 380

Glu Val Gln Leu Leu Glu Ser Gly Gly Gly Leu Val Gln Pro Gly Gly
385                 390                 395                 400

Ser Leu Arg Leu Ser Cys Ala Ala Ser Gly Phe Thr Phe Ser Ser Tyr
                405                 410                 415

Ala Met Ser Trp Val Arg Gln Ala Pro Gly Lys Gly Leu Glu Trp Val
```

```
                420             425              430
Ser Ala Ile Ser Gly Ser Gly Ser Thr Tyr Tyr Ala Asp Ser Val
            435              440              445

Lys Gly Arg Phe Thr Ile Ser Arg Asp Asn Ser Lys Asn Thr Leu Tyr
            450              455             460

Leu Gln Met Asn Ser Leu Arg Ala Glu Asp Thr Ala Val Tyr Tyr Cys
465             470              475              480

Ala Lys Trp Arg Trp Met Met Phe Asp Tyr Trp Gly Gln Gly Thr Leu
                485              490             495

Val Thr Val Ser Ser Ala Ser Thr Lys Gly Pro Ser Val Phe Pro Leu
            500              505             510

Ala Pro Ser Ser Lys Ser Thr Ser Gly Gly Thr Ala Ala Leu Gly Cys
            515              520             525

Leu Val Lys Asp Tyr Phe Pro Glu Pro Val Thr Val Ser Trp Asn Ser
            530              535             540

Gly Ala Leu Thr Ser Gly Val His Thr Phe Pro Ala Val Leu Gln Ser
545             550              555              560

Ser Gly Leu Tyr Ser Leu Ser Ser Val Val Thr Val Pro Ser Ser Ser
            565              570             575

Leu Gly Thr Gln Thr Tyr Ile Cys Asn Val Asn His Lys Pro Ser Asn
            580              585             590

Thr Lys Val Asp Lys Lys Val Glu Pro Lys Ser Cys Asp
            595              600             605
```

<210> SEQ ID NO 216
<211> LENGTH: 1815
<212> TYPE: DNA
<213> ORGANISM: Artificial Sequence
<220> FEATURE:
<223> OTHER INFORMATION: 2F11 Fab-IL2 qm-Fab (heavy chain cytokine fusion construct)

<400> SEQUENCE: 216

```
gaggtgcaat tgttggagtc tgggggaggc ttggtacagc ctgggggtc cctgagactc       60
tcctgtgcag cctccggatt cacctttagc agttatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcagatga acagcctgag agccgaggac accgccgtat attactgtgc gaaatggaga     300
tggatgatgt ttgactactg gggccaagga accctggtca ccgtctcgag tgctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggataaga agttgagcc caaatcttgt     660
gactccggcg aggagggag cggcggaggt ggctccggag gtggcggagc acctgcctca     720
agttctacaa agaaaacaca gctacaactg gagcatttac tgctggattt acagatgatt     780
ttgaatggaa ttaataatta caagaatccc aaactcacca ggatgctcac agccaagttt     840
gccatgccca gaaggccac agaactgaaa catcttcagt gtctagaaga gaactcaaa     900
cctctggagg aagtgctaaa tggcgctcaa agcaaaaact tcacttaag acccagggac     960
ttaatcagca atatcaacgt aatagttctg gaactaaagg gatctgaaac aacattcatg    1020
```

```
tgtgaatatg ctgatgagac agcaaccatt gtagaatttc tgaacagatg gattaccttt    1080
gcccaaagca tcatctcaac actgacttcc ggcggaggag gatccggcgg aggtggctct    1140
ggcggtggcg gagaggtgca attgttggag tctgggggag gcttggtaca gcctgggggg    1200
tccctgagac tctcctgtgc agcctccgga ttcaccttta gcagttatgc catgagctgg    1260
gtccgccagg ctccagggaa ggggctggag tgggtctcag ctattagtgg tagtggtggt    1320
agcacatact acgcagactc cgtgaagggc cggttcacca tctccagaga caattccaag    1380
aacacgctgt atctgcagat gaacagcctg agagccgagg acaccgccgt atattactgt    1440
gcgaaatgga gatggatgat gtttgactac tggggccaag gaaccctggt caccgtctcg    1500
agtgctagca ccaagggccc atcggtcttc cccctggcac cctcctccaa gagcacctct    1560
gggggcacag cggccctggg ctgcctggtc aaggactact tccccgaacc ggtgacggtg    1620
tcgtggaact caggcgccct gaccagcggc gtgcacacct tcccggctgt cctacagtcc    1680
tcaggactct actccctcag cagcgtggtg accgtgccct ccagcagctt gggcacccag    1740
acctacatct gcaacgtgaa tcacaagccc agcaacacca aggtggataa gaaagttgag    1800
cccaaatctt gtgac                                                    1815
```

<210> SEQ ID NO 217
<211> LENGTH: 605
<212> TYPE: PRT
<213> ORGANISM: Artificial Sequence
<220> FEATURE:
<223> OTHER INFORMATION: 4B3 Fab-IL2 qm-Fab (heavy chain cytokine fusion construct)

<400> SEQUENCE: 217

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

Thr Lys Val Asp Lys Lys Val Glu Pro Lys Ser Cys Asp Ser Gly Gly
        210                 215                 220

Gly Gly Ser Gly Gly Gly Ser Gly Gly Gly Ala Pro Ala Ser
225                 230                 235                 240

Ser Ser Thr Lys Lys Thr Gln Leu Gln Leu Glu His Leu Leu Leu Asp
            245                 250                 255

Leu Gln Met Ile Leu Asn Gly Ile Asn Asn Tyr Lys Asn Pro Lys Leu
            260                 265                 270

Thr Arg Met Leu Thr Ala Lys Phe Ala Met Pro Lys Lys Ala Thr Glu
            275                 280                 285

Leu Lys His Leu Gln Cys Leu Glu Glu Glu Leu Lys Pro Leu Glu Glu
            290                 295                 300

Val Leu Asn Gly Ala Gln Ser Lys Asn Phe His Leu Arg Pro Arg Asp
305                 310                 315                 320

Leu Ile Ser Asn Ile Asn Val Ile Val Leu Glu Leu Lys Gly Ser Glu
                325                 330                 335

Thr Thr Phe Met Cys Glu Tyr Ala Asp Glu Thr Ala Thr Ile Val Glu
            340                 345                 350

Phe Leu Asn Arg Trp Ile Thr Phe Ala Gln Ser Ile Ile Ser Thr Leu
            355                 360                 365

Thr Ser Gly Gly Gly Gly Ser Gly Gly Gly Gly Ser Gly Gly Gly Gly
370                 375                 380

Glu Val Gln Leu Leu Glu Ser Gly Gly Gly Leu Val Gln Pro Gly Gly
385                 390                 395                 400

Ser Leu Arg Leu Ser Cys Ala Ala Ser Gly Phe Thr Phe Ser Ser Tyr
            405                 410                 415

Ala Met Ser Trp Val Arg Gln Ala Pro Gly Lys Gly Leu Glu Trp Val
            420                 425                 430

Ser Ala Ile Ser Gly Ser Gly Gly Ser Thr Tyr Tyr Ala Asp Ser Val
            435                 440                 445

Lys Gly Arg Phe Thr Ile Ser Arg Asp Asn Ser Lys Asn Thr Leu Tyr
            450                 455                 460

Leu Gln Met Asn Ser Leu Arg Ala Glu Asp Thr Ala Val Tyr Tyr Cys
465                 470                 475                 480

Ala Lys Gly Trp Leu Gly Asn Phe Asp Tyr Trp Gly Gln Gly Thr Leu
            485                 490                 495

Val Thr Val Ser Ser Ala Ser Thr Lys Gly Pro Ser Val Phe Pro Leu
            500                 505                 510

Ala Pro Ser Ser Lys Ser Thr Ser Gly Gly Thr Ala Ala Leu Gly Cys
            515                 520                 525

Leu Val Lys Asp Tyr Phe Pro Glu Pro Val Thr Val Ser Trp Asn Ser
530                 535                 540

Gly Ala Leu Thr Ser Gly Val His Thr Phe Pro Ala Val Leu Gln Ser
545                 550                 555                 560

Ser Gly Leu Tyr Ser Leu Ser Ser Val Val Thr Val Pro Ser Ser Ser
            565                 570                 575

Leu Gly Thr Gln Thr Tyr Ile Cys Asn Val Asn His Lys Pro Ser Asn
            580                 585                 590

Thr Lys Val Asp Lys Lys Val Glu Pro Lys Ser Cys Asp
            595                 600                 605

<210> SEQ ID NO 218
<211> LENGTH: 1815
<212> TYPE: DNA

<213> ORGANISM: Artificial Sequence
<220> FEATURE:
<223> OTHER INFORMATION: 4B3 Fab-IL2 qm-Fab (heavy chain cytokine fusion construct)

<400> SEQUENCE: 218

```
gaggtgcaat tgttggagtc tgggggaggc ttggtacagc ctgggggtc cctgagactc        60
tcctgtgcag cctccggatt cacctttagc agttatgcca tgagctgggt ccgccaggct      120
ccagggaagg ggctggagtg ggtctcagct attagtggta gtggtggtag cacatactac      180
gcagactccg tgaagggccg gttcaccatc tccagagaca attccaagaa cacgctgtat      240
ctgcagatga acagcctgag agccgaggac acggccgtat attactgtgc gaaagggtgg      300
ctgggtaatt ttgactactg gggccaagga accctggtca ccgtctcgag tgctagcacc      360
aagggcccat cggtcttccc cctggcaccc tcctccaaga gcacctctgg gggcacagcg      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggataaga agttgagcc caaatcttgt      660
gactccggcg aggagggag cggcggaggt ggctccggag gtggcggagc acctgcctca      720
agttctacaa agaaaacaca gctacaactg gagcatttac tgctggattt acagatgatt      780
ttgaatggaa ttaataatta caagaatccc aaactcacca ggatgctcac agccaagttt      840
gccatgccca gaaggccac agaactgaaa catcttcagt gtctagaaga gaactcaaa       900
cctctggagg aagtgctaaa tggcgctcaa agcaaaaact tcacttaag acccagggac       960
ttaatcagca atatcaacgt aatagttctg gaactaaagg gatctgaaac aacattcatg     1020
tgtgaatatg ctgatgagac agcaaccatt gtagaatttc tgaacagatg gattaccttt     1080
gcccaaagca tcatctcaac actgacttcc ggcggaggag gatccggcgg aggtggctct     1140
ggcggtggcg gagaggtgca attgttggag tctgggggag gcttggtaca gcctgggggg     1200
tccctgagac tctcctgtgc agcctccgga ttcaccttta gcagttatgc catgagctgg     1260
gtccgccagg ctccagggaa ggggctggag tgggtctcag ctattagtgg tagtggtggt     1320
agcacatact acgcagactc cgtgaagggc cggttcacca tctccagaga caattccaag     1380
aacacgctgt atctgcagat gaacagcctg agagccgagg acacggccgt atattactgt     1440
gcgaaagggt ggctgggtaa ttttgactac tggggccaag gaaccctggt caccgtctcg     1500
agtgctagca ccaagggccc atcggtcttc cccctggcac cctcctccaa gagcacctct     1560
gggggcacag cggccctggg ctgcctggtc aaggactact tccccgaacc ggtgacggtg     1620
tcgtggaact caggcgccct gaccagcggc gtgcacacct tcccggctgt cctacagtcc     1680
tcaggactct actccctcag cagcgtggtg accgtgccct ccagcagctt gggcacccag     1740
acctacatct gcaacgtgaa tcacaagccc agcaacacca aggtggataa gaaagttgag     1800
cccaaatctt gtgac                                                      1815
```

<210> SEQ ID NO 219
<211> LENGTH: 603
<212> TYPE: PRT
<213> ORGANISM: Artificial Sequence
<220> FEATURE:
<223> OTHER INFORMATION: 28H1 Fab-IL2 qm-Fab (heavy chain cytokine fusion construct)

<400> SEQUENCE: 219

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
50                  55                  60

Gly Arg Phe Thr Ile Ser Arg Asp Asn Ser Lys Asn Thr Leu Tyr Leu
65              70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Ser Gly Gly Gly
210                 215                 220

Gly Ser Gly Gly Gly Gly Ser Gly Gly Gly Gly Ala Pro Ala Ser Ser
225                 230                 235                 240

Ser Thr Lys Lys Thr Gln Leu Gln Leu Glu His Leu Leu Leu Asp Leu
                245                 250                 255

Gln Met Ile Leu Asn Gly Ile Asn Asn Tyr Lys Asn Pro Lys Leu Thr
            260                 265                 270

Arg Met Leu Thr Ala Lys Phe Ala Met Pro Lys Lys Ala Thr Glu Leu
        275                 280                 285

Lys His Leu Gln Cys Leu Glu Glu Glu Leu Lys Pro Leu Glu Glu Val
        290                 295                 300

Leu Asn Gly Ala Gln Ser Lys Asn Phe His Leu Arg Pro Arg Asp Leu
305                 310                 315                 320

Ile Ser Asn Ile Asn Val Ile Val Leu Glu Leu Lys Gly Ser Glu Thr
                325                 330                 335

Thr Phe Met Cys Glu Tyr Ala Asp Glu Thr Ala Thr Ile Val Glu Phe
            340                 345                 350

Leu Asn Arg Trp Ile Thr Phe Ala Gln Ser Ile Ile Ser Thr Leu Thr
        355                 360                 365

Ser Gly Gly Gly Gly Ser Gly Gly Gly Gly Ser Gly Gly Gly Gly Glu
        370                 375                 380

Val Gln Leu Leu Glu Ser Gly Gly Gly Leu Val Gln Pro Gly Gly Ser
385                 390                 395                 400

Leu Arg Leu Ser Cys Ala Ala Ser Gly Phe Thr Phe Ser Ser His Ala
            405                 410                 415
```

```
Met Ser Trp Val Arg Gln Ala Pro Gly Lys Gly Leu Glu Trp Val Ser
            420                 425                 430
Ala Ile Trp Ala Ser Gly Glu Gln Tyr Tyr Ala Asp Ser Val Lys Gly
        435                 440                 445
Arg Phe Thr Ile Ser Arg Asp Asn Ser Lys Asn Thr Leu Tyr Leu Gln
    450                 455                 460
Met Asn Ser Leu Arg Ala Glu Asp Thr Ala Val Tyr Tyr Cys Ala Lys
465                 470                 475                 480
Gly Trp Leu Gly Asn Phe Asp Tyr Trp Gly Gln Gly Thr Leu Val Thr
                485                 490                 495
Val Ser Ser Ala Ser Thr Lys Gly Pro Ser Val Phe Pro Leu Ala Pro
            500                 505                 510
Ser Ser Lys Ser Thr Ser Gly Gly Thr Ala Ala Leu Gly Cys Leu Val
        515                 520                 525
Lys Asp Tyr Phe Pro Glu Pro Val Thr Val Ser Trp Asn Ser Gly Ala
    530                 535                 540
Leu Thr Ser Gly Val His Thr Phe Pro Ala Val Leu Gln Ser Ser Gly
545                 550                 555                 560
Leu Tyr Ser Leu Ser Ser Val Val Thr Val Pro Ser Ser Ser Leu Gly
                565                 570                 575
Thr Gln Thr Tyr Ile Cys Asn Val Asn His Lys Pro Ser Asn Thr Lys
            580                 585                 590
Val Asp Lys Lys Val Glu Pro Lys Ser Cys Asp
        595                 600
```

<210> SEQ ID NO 220
<211> LENGTH: 1809
<212> TYPE: DNA
<213> ORGANISM: Artificial Sequence
<220> FEATURE:
<223> OTHER INFORMATION: 28H1 Fab-IL2 qm-Fab (heavy chain cytokine fusion construct)

<400> SEQUENCE: 220

```
gaagtgcagc tgctggaatc cggcggaggc ctggtgcagc ctggcggatc tctgagactg      60
tcctgcgccg cctccggctt caccttctcc tcccacgcca tgtcctgggt ccgacaggct     120
cctggcaaag cctggaatg gtgtccgca atctgggcct ccggcgagca gtactacgcc      180
gactctgtga agcgccggt caccatctcc cgggacaact ccaagaacac cctgtacctg     240
cagatgaact ccctgcgggc cgaggacacc gccgtgtact actgtgccaa gggctggctg     300
ggcaacttcg actactgggg acagggcacc ctggtcaccg tgtccagcgc tagcaccaag     360
ggaccctccg tgttcccct ggccccctcc agcaagtcta cctctggcgg caccgccgct     420
ctgggctgcc tggtcaagga ctacttcccc gagcccgtga ccgtgtcctg aactctggc     480
gccctgacca gcggcgtcca caccttttca gccgtgctgc agtcctccgg cctgtactcc     540
ctgtcctccg tcgtgaccgt gccctccagc tctctgggca cccagaccta catctgcaac     600
gtgaaccaca gccctccaa caccaaggtg gacaagaagg tggaacccaa gtcctgcgac     660
agtggtgggg gaggatctgg tggcggaggt tctggcggag gtggcgctcc tgcctcctcc     720
agcaccaaga aacccagct ccagctggaa catctcctgc tggatctgca gatgatcctg     780
aacggcatca acaactacaa gaaccccaag ctgacccgga tgctgaccgc caagttcgcc     840
atgcccaaga aggccaccga gctgaaacat ctgcagtgcc tggaagagga actgaagcct     900
ctggaagagg tgctgaacgg cgcccagtcc aagaacttcc acctgaggcc tcgggacctg     960
```

```
atctccaaca tcaacgtgat cgtgctggaa ctgaagggct ccgagacaac cttcatgtgc    1020
gagtacgccg acgagacagc taccatcgtg aatttctga accggtggat caccttcgcc    1080
cagtccatca tctccaccct gacctccggt ggtggcggat ccggggggagg gggttctggc    1140 ggaggcggag aagtgcagct gctggaatcc ggcggaggcc tggtgcagcc tggcggatct    1200
ctgagactgt cctgcgccgc ctccggcttc accttctcct cccacgccat gtcctgggtc    1260
cgacaggctc caggcaaggg cctggaatgg gtgtccgcca tctgggcctc cggcgagcag    1320
tactacgccg actctgtgaa gggccggttc accatctccc gggacaactc caagaacacc    1380
ctgtacctgc agatgaactc cctgcgggcc gaggacaccg ccgtgtacta ctgtgccaag    1440
ggctggctgg gcaacttcga ctactggggc cagggcaccc tggtcaccgt gtcctccgcc    1500
tctaccaagg gccccctccgt gttccctctg gccccctcca gcaagtctac ctctggcggc    1560
accgccgctc tgggctgcct ggtcaaggac tacttccccg agcccgtgac cgtgtcctgg    1620
aactctggcg ccctgaccag cggcgtgcac acctttccag ccgtgctgca gtcctccggc    1680
ctgtactccc tgtcctccgt cgtgaccgtg ccctccagct ctctgggcac ccagacctac    1740
atctgcaacg tgaaccacaa gccctccaac accaaggtgg acaagaaggt ggaacccaag    1800
tcctgcgac                                                             1809
```

<210> SEQ ID NO 221
<211> LENGTH: 605
<212> TYPE: PRT
<213> ORGANISM: Artificial Sequence
<220> FEATURE:
<223> OTHER INFORMATION: 29B11 Fab-IL2 qm-Fab (heavy chain cytokine fusion construct)

<400> SEQUENCE: 221

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

```
Thr Lys Val Asp Lys Val Glu Pro Lys Ser Cys Asp Ser Gly Gly
    210                 215                 220
Gly Gly Ser Gly Gly Gly Ser Gly Gly Gly Ala Pro Ala Ser
225                 230                 235                 240
Ser Ser Thr Lys Lys Thr Gln Leu Gln Leu Glu His Leu Leu Leu Asp
                245                 250                 255
Leu Gln Met Ile Leu Asn Gly Ile Asn Asn Tyr Lys Asn Pro Lys Leu
            260                 265                 270
Thr Arg Met Leu Thr Ala Lys Phe Ala Met Pro Lys Lys Ala Thr Glu
        275                 280                 285
Leu Lys His Leu Gln Cys Leu Glu Glu Glu Leu Lys Pro Leu Glu Glu
    290                 295                 300
Val Leu Asn Gly Ala Gln Ser Lys Asn Phe His Leu Arg Pro Arg Asp
305                 310                 315                 320
Leu Ile Ser Asn Ile Asn Val Ile Val Leu Glu Leu Lys Gly Ser Glu
                325                 330                 335
Thr Thr Phe Met Cys Glu Tyr Ala Asp Glu Thr Ala Thr Ile Val Glu
            340                 345                 350
Phe Leu Asn Arg Trp Ile Thr Phe Ala Gln Ser Ile Ile Ser Thr Leu
        355                 360                 365
Thr Ser Gly Gly Gly Gly Ser Gly Gly Gly Gly Ser Gly Gly Gly Gly
    370                 375                 380
Glu Val Gln Leu Leu Glu Ser Gly Gly Gly Leu Val Gln Pro Gly Gly
385                 390                 395                 400
Ser Leu Arg Leu Ser Cys Ala Ala Ser Gly Phe Thr Phe Ser Ser Tyr
                405                 410                 415
Ala Met Ser Trp Val Arg Gln Ala Pro Gly Lys Gly Leu Glu Trp Val
            420                 425                 430
Ser Ala Ile Ile Gly Ser Gly Gly Ile Thr Tyr Tyr Ala Asp Ser Val
        435                 440                 445
Lys Gly Arg Phe Thr Ile Ser Arg Asp Asn Ser Lys Asn Thr Leu Tyr
    450                 455                 460
Leu Gln Met Asn Ser Leu Arg Ala Glu Asp Thr Ala Val Tyr Tyr Cys
465                 470                 475                 480
Ala Lys Gly Trp Phe Gly Gly Phe Asn Tyr Trp Gly Gln Gly Thr Leu
                485                 490                 495
Val Thr Val Ser Ser Ala Ser Thr Lys Gly Pro Ser Val Phe Pro Leu
            500                 505                 510
Ala Pro Ser Ser Lys Ser Thr Ser Gly Gly Thr Ala Ala Leu Gly Cys
        515                 520                 525
Leu Val Lys Asp Tyr Phe Pro Glu Pro Val Thr Val Ser Trp Asn Ser
    530                 535                 540
Gly Ala Leu Thr Ser Gly Val His Thr Phe Pro Ala Val Leu Gln Ser
545                 550                 555                 560
Ser Gly Leu Tyr Ser Leu Ser Ser Val Val Thr Val Pro Ser Ser Ser
                565                 570                 575
Leu Gly Thr Gln Thr Tyr Ile Cys Asn Val Asn His Lys Pro Ser Asn
            580                 585                 590
Thr Lys Val Asp Lys Lys Val Glu Pro Lys Ser Cys Asp
        595                 600                 605

<210> SEQ ID NO 222
<211> LENGTH: 1815
```

<210> SEQ ID NO 222
<211> LENGTH: 1815
<212> TYPE: DNA
<213> ORGANISM: Artificial Sequence
<220> FEATURE:
<223> OTHER INFORMATION: 29B11 Fab-IL2 qm-Fab (heavy chain cytokine fusion construct)

<400> SEQUENCE: 222

```
gaagtgcagc tgctggaatc cggcggaggc ctggtgcagc ctggcggatc tctgagactg      60
tcctgcgccg cctccggctt caccttctcc tcctacgcca tgtcctgggt ccgacaggct     120
cctggcaaag gcctggaatg ggtgtccgcc atcatcggct ccggcggcat cacctactac     180
gccgactctg tgaagggccg gttcaccatc tccgggaca actccaagaa cacccctgtac    240
ctgcagatga actccctgcg ggccgaggac accgccgtgt actactgtgc caagggctgg    300
ttcggaggct caactactg ggacagggc accctggtca ccgtgtccag cgctagcacc      360
aagggaccct ccgtgttccc cctggccccc tccagcaagt ctacctctgg cggcaccgcc    420
gctctgggct gcctggtcaa ggactacttc cccgagcccg tgaccgtgtc ctggaactct    480
ggcgccctga ccagcggcgt ccacaccttt ccagccgtgc tgcagtcctc cggcctgtac    540
tccctgtcct ccgtcgtgac cgtgccctcc agctctctgg gcacccagac ctacatctgc    600
aacgtgaacc acaagccctc caacaccaag gtggacaaga aggtggaacc caagtcctgc    660
gacagtggtg ggggaggatc tggtggcgga ggttctggcg gaggtggcgc tcctgcctcc    720
tccagcacca agaaacccca gctccagctg aacatctcc tgctggatct gcagatgatc    780
ctgaacggca tcaacaacta caagaacccc aagctgaccc ggatgctgac cgccaagttc    840
gccatgccca gaaggccac cgagctgaaa catctgcagt gcctggaaga ggaactgaag    900
cctctggaag aggtgctgaa cggcgcccag tccaagaact tccacctgag gcctcgggac    960
ctgatctcca catcaacgt gatcgtgctg gaactgaagg gctccgagac aaccttcatg   1020
tgcgagtacg ccgacgagac agctaccatc gtggaatttc tgaaccggtg gatcaccttc   1080
gcccagtcca tcatctccac cctgaccctcc ggtggtggcg gatccggggg agggggttct   1140
ggcggaggcg gagaagtgca gctgctggaa tccggcggag gcctggtgca gcctggcgga   1200
tctctgagac tgtcctgcgc cgcctccggc ttcaccttct cctcctatgc catgtcctgg   1260
gtccgacagg ctccaggcaa gggcctggaa tgggtgtccg ccatcatcgg ctccggcggc   1320
atcacctact acgccgactc tgtgaagggc cggttcacca tctcccggga caactccaag   1380
aacaccctgt acctgcagat gaactccctg cgggccgagg acaccgccgt gtactactgt   1440
gccaagggct ggttcggagg cttcaactac tggggccagg gcaccctggt caccgtgtcc   1500
tccgcctcta ccaagggccc ctccgtgttc cctctggccc cctccagcaa gtctacctct   1560
ggcggcaccg ccgctctggg ctgcctggtc aaggactact ccccgagcc cgtgaccgtg   1620
tcctggaact ctggcgccct gaccagcggc gtgcacacct tccagccgt gctgcagtcc   1680
tccggcctgt actccctgtc ctccgtcgtg accgtgccct ccagctctct gggcacccag   1740
acctacatct gcaacgtgaa ccacaagccc tccaacacca aggtggacaa gaaggtggaa   1800
cccaagtcct gcgac                                                  1815
```

<210> SEQ ID NO 223
<211> LENGTH: 605
<212> TYPE: PRT
<213> ORGANISM: Artificial Sequence
<220> FEATURE:
<223> OTHER INFORMATION: 19G1 Fab-IL2 qm-Fab (heavy chain cytokine fusion construct)

```
<400> SEQUENCE: 223

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Ser Ser Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Ser Gly Gly
    210                 215                 220

Gly Gly Ser Gly Gly Gly Ser Gly Gly Gly Gly Ala Pro Ala Ser
225                 230                 235                 240

Ser Ser Thr Lys Lys Thr Gln Leu Gln Leu Glu His Leu Leu Leu Asp
                245                 250                 255

Leu Gln Met Ile Leu Asn Gly Ile Asn Asn Tyr Lys Asn Pro Lys Leu
            260                 265                 270

Thr Arg Met Leu Thr Ala Lys Phe Ala Met Pro Lys Lys Ala Thr Glu
        275                 280                 285

Leu Lys His Leu Gln Cys Leu Glu Glu Glu Leu Lys Pro Leu Glu Glu
    290                 295                 300

Val Leu Asn Gly Ala Gln Ser Lys Asn Phe His Leu Arg Pro Arg Asp
305                 310                 315                 320

Leu Ile Ser Asn Ile Asn Val Ile Val Leu Glu Leu Lys Gly Ser Glu
                325                 330                 335

Thr Thr Phe Met Cys Glu Tyr Ala Asp Glu Thr Ala Thr Ile Val Glu
            340                 345                 350

Phe Leu Asn Arg Trp Ile Thr Phe Ala Gln Ser Ile Ile Ser Thr Leu
        355                 360                 365

Thr Ser Gly Gly Gly Gly Ser Gly Gly Gly Gly Ser Gly Gly Gly Gly
    370                 375                 380

Glu Val Gln Leu Leu Glu Ser Gly Gly Gly Leu Val Gln Pro Gly Gly
385                 390                 395                 400

Ser Leu Arg Leu Ser Cys Ala Ala Ser Gly Phe Thr Phe Ser Ser Tyr
                405                 410                 415
```

Ala Met Ser Trp Val Arg Gln Ala Pro Gly Lys Gly Leu Glu Trp Val
            420                 425                 430

Ser Ala Ile Ile Ser Ser Gly Gly Leu Thr Tyr Tyr Ala Asp Ser Val
                435                 440                 445

Lys Gly Arg Phe Thr Ile Ser Arg Asp Asn Ser Lys Asn Thr Leu Tyr
    450                 455                 460

Leu Gln Met Asn Ser Leu Arg Ala Glu Asp Thr Ala Val Tyr Tyr Cys
465                 470                 475                 480

Ala Lys Gly Trp Phe Gly Phe Asn Tyr Trp Gly Gln Gly Thr Leu
                485                 490                 495

Val Thr Val Ser Ser Ala Ser Thr Lys Gly Pro Ser Val Phe Pro Leu
            500                 505                 510

Ala Pro Ser Ser Lys Ser Thr Ser Gly Gly Thr Ala Ala Leu Gly Cys
            515                 520                 525

Leu Val Lys Asp Tyr Phe Pro Glu Pro Val Thr Val Ser Trp Asn Ser
        530                 535                 540

Gly Ala Leu Thr Ser Gly Val His Thr Phe Pro Ala Val Leu Gln Ser
545                 550                 555                 560

Ser Gly Leu Tyr Ser Leu Ser Ser Val Val Thr Val Pro Ser Ser Ser
                565                 570                 575

Leu Gly Thr Gln Thr Tyr Ile Cys Asn Val Asn His Lys Pro Ser Asn
            580                 585                 590

Thr Lys Val Asp Lys Lys Val Glu Pro Lys Ser Cys Asp
            595                 600                 605

<210> SEQ ID NO 224
<211> LENGTH: 1815
<212> TYPE: DNA
<213> ORGANISM: Artificial Sequence
<220> FEATURE:
<223> OTHER INFORMATION: 19G1 Fab-IL2 qm-Fab (heavy chain cytokine
      fusion construct)

<400> SEQUENCE: 224
gaggtgcagc tgctcgaaag cggcggagga ctggtgcagc ctggcggcag cctgagactg     60
tcttgcgccg ccagcggctt caccttcagc agctacgcca tgagctgggt ccgccaggcc    120
cctggcaagg gactggaatg ggtgtccgcc atcatcagct ctggcggcct gacctactac    180
gccgacagcg tgaagggccg gttcaccatc agccgggaca acagcaagaa caccctgtac    240
ctgcagatga acagcctgcg ggccgaggac accgccgtgt actactgcgc caagggatgg    300
ttcggcggct tcaactactg gggacagggc accctggtca cagtgtccag cgctagcacc    360
aagggaccca cgctgttccc cctggccccc agcagcaaga gcacatctgg cggaacagcc    420
gccctgggct gcctggtcaa agactacttc cccgagcccg tgaccgtgtc ctggaacagc    480
ggagccctga ccagcggcgt gcacaccttt ccagccgtgc tgcagagcag cggcctgtac    540
agcctgagca gcgtggtcac cgtgcctagc tctagcctgg caccagac ctacatctgc    600 aacgtgaacc acaagcccag caacaccaag gtggacaaga aggtggaacc caagagctgc    660
gactccggcg gaggcggatc tggcggtgga ggctccggag gcgaggcgc tcctgccagc    720 agctccacca agaaaaccca gctccagctg aacatctgc tgctggatct gcagatgatc    780
ctgaacggca tcaacaacta caagaacccc aagctgaccc ggatgctgac cgccaagttc    840
gccatgccca agaggccac cgaactgaaa catctgcagt gcctggaaga ggaactgaag    900
cctctggaag aggtgctgaa cggcgcccag agcaagaact tccacctgag gccagggac    960

```
ctgatcagca acatcaacgt gatcgtgctg gaactgaagg gcagcgagac aaccttcatg    1020
tgcgagtacg ccgacgagac agccaccatc gtggaatttc tgaaccggtg gatcaccttc    1080
gcccagagca tcatcagcac cctgacaagc ggaggcggcg gatccggcgg aggcggatct    1140
ggcggaggag gcgaggtcca gctgctcgaa agcggcggag actggtgca gcctggcggc    1200 agcctgagac tgtcttgcgc cgccagcggc ttcaccttca gcagctacgc catgagctgg    1260
gtccgccagg cccctggcaa gggactgaa tgggtgtccg ccatcatcag ctctggcggc    1320
ctgacctact acgccgacag cgtgaagggc cggttcacca tcagccggga caacagcaag    1380
aacaccctgt acctgcagat gaacagcctg cgggccgagg acaccgccgt gtactactgc    1440
gccaagggat ggttcggcgg cttcaactac tggggacagg gcaccctggt cacagtgtcc    1500
agcgccagca ccaagggccc cagcgtgttc cccctggccc ccagcagcaa gagcacatct    1560
ggcggaacag ccgccctggg ctgcctggtc aaagactact ccccgagcc cgtgaccgtg    1620 tcctggaaca gcggagccct gaccagcggc gtgcacacct ttccagccgt gctgcagagc    1680
agcggcctgt acagcctgag cagcgtggtc accgtgccta gctctagcct gggcacccag    1740
acctacatct gcaacgtgaa ccacaagccc agcaacacca aggtggacaa gaaggtggaa    1800
cccaagagct gcgac                                                     1815
```

<210> SEQ ID NO 225
<211> LENGTH: 605
<212> TYPE: PRT
<213> ORGANISM: Artificial Sequence
<220> FEATURE:
<223> OTHER INFORMATION: 20G8 Fab-IL2 qm-Fab (heavy chain cytokine
      fusion construct)

<400> SEQUENCE: 225

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ser Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
```

|   |   |   |   |   |   |   |   |   |   |   |   |
|---|---|---|---|---|---|---|---|---|---|---|---|
|   |   | 195 |   |   |   | 200 |   |   |   | 205 |   |
| Thr | Lys | Val | Asp | Lys | Val | Glu | Pro | Lys | Ser | Cys | Asp | Ser | Gly | Gly |
|   |   | 210 |   |   |   | 215 |   |   |   | 220 |   |

Thr Lys Val Asp Lys Val Glu Pro Lys Ser Cys Asp Ser Gly Gly
   210              215              220

Gly Gly Ser Gly Gly Gly Ser Gly Gly Gly Ala Pro Ala Ser
225             230              235              240

Ser Ser Thr Lys Lys Thr Gln Leu Gln Leu Glu His Leu Leu Leu Asp
            245              250              255

Leu Gln Met Ile Leu Asn Gly Ile Asn Asn Tyr Lys Asn Pro Lys Leu
        260              265              270

Thr Arg Met Leu Thr Ala Lys Phe Ala Met Pro Lys Lys Ala Thr Glu
    275              280              285

Leu Lys His Leu Gln Cys Leu Glu Glu Glu Leu Lys Pro Leu Glu Glu
    290              295              300

Val Leu Asn Gly Ala Gln Ser Lys Asn Phe His Leu Arg Pro Arg Asp
305             310              315              320

Leu Ile Ser Asn Ile Asn Val Ile Val Leu Glu Leu Lys Gly Ser Glu
                325              330              335

Thr Thr Phe Met Cys Glu Tyr Ala Asp Glu Thr Ala Thr Ile Val Glu
            340              345              350

Phe Leu Asn Arg Trp Ile Thr Phe Ala Gln Ser Ile Ile Ser Thr Leu
        355              360              365

Thr Ser Gly Gly Gly Gly Ser Gly Gly Gly Ser Gly Gly Gly Gly
370             375              380

Glu Val Gln Leu Leu Glu Ser Gly Gly Gly Leu Val Gln Pro Gly Gly
385             390              395              400

Ser Leu Arg Leu Ser Cys Ala Ala Ser Gly Phe Thr Phe Ser Ser Tyr
                405              410              415

Ala Met Ser Trp Val Arg Gln Ala Pro Gly Lys Gly Leu Glu Trp Val
            420              425              430

Ser Ala Ile Ile Gly Ser Gly Ser Arg Thr Tyr Tyr Ala Asp Ser Val
        435              440              445

Lys Gly Arg Phe Thr Ile Ser Arg Asp Asn Ser Lys Asn Thr Leu Tyr
    450              455              460

Leu Gln Met Asn Ser Leu Arg Ala Glu Asp Thr Ala Val Tyr Tyr Cys
465             470              475              480

Ala Lys Gly Trp Phe Gly Gly Phe Asn Tyr Trp Gly Gln Gly Thr Leu
                485              490              495

Val Thr Val Ser Ser Ala Ser Thr Lys Gly Pro Ser Val Phe Pro Leu
            500              505              510

Ala Pro Ser Ser Lys Ser Thr Ser Gly Gly Thr Ala Ala Leu Gly Cys
        515              520              525

Leu Val Lys Asp Tyr Phe Pro Glu Pro Val Thr Val Ser Trp Asn Ser
    530              535              540

Gly Ala Leu Thr Ser Gly Val His Thr Phe Pro Ala Val Leu Gln Ser
545             550              555              560

Ser Gly Leu Tyr Ser Leu Ser Ser Val Val Thr Val Pro Ser Ser Ser
                565              570              575

Leu Gly Thr Gln Thr Tyr Ile Cys Asn Val Asn His Lys Pro Ser Asn
            580              585              590

Thr Lys Val Asp Lys Lys Val Glu Pro Lys Ser Cys Asp
        595              600              605

<210> SEQ ID NO 226

<211> LENGTH: 1815
<212> TYPE: DNA
<213> ORGANISM: Artificial Sequence
<220> FEATURE:
<223> OTHER INFORMATION: 20G8 Fab-IL2 qm-Fab (heavy chain cytokine fusion construct)

<400> SEQUENCE: 226

```
gaggtgcagc tgctcgaaag cggcggagga ctggtgcagc ctggcggcag cctgagactg      60
tcttgcgccg ccagcggctt caccttcagc agctacgcca tgagctgggt ccgccaggcc     120
cctggcaagg gactggaatg ggtgtccgcc atcatcggct ctggcagccg gacctactac     180
gccgacagcg tgaagggccg gttcaccatc agccgggaca cagcaagaa caccctgtac     240
ctgcagatga acagcctgcg ggccgaggac accgccgtgt actactgcgc caagggatgg     300
ttcggcggct tcaactactg gggacagggc accctggtca cagtgtccag cgctagcacc     360
aagggaccca cgtgttccc cctggccccc agcagcaaga gcacatctgg cggaacagcc     420
gccctgggct gcctggtcaa agactacttc cccgagcccg tgaccgtgtc ctggaacagc     480
ggagccctga ccagcggcgt gcacaccttt ccagccgtgc tgcagagcag cggcctgtac     540
agcctgagca gcgtggtcac cgtgcctagc tctagcctgg gcacccagac ctacatctgc     600
aacgtgaacc acaagcccag caacaccaag gtggacaaga aggtggaacc caagagctgc     660
gactccggcg gaggcggatc tggcggtgga ggctccggag gcggaggcgc tcctgccagc     720
agctccacca gaaaaaccca gctccagctg gaacatctgc tgctggatct gcagatgatc     780
ctgaacggca tcaacaacta caagaacccc aagctgaccc ggatgctgac cgccaagttc     840
gccatgccca agaaggccac cgaactgaaa catctgcagt gcctggaaga ggaactgaag     900
cctctggaag aggtgctgaa cggcgcccag agcaagaact ccacctgag gcccagggac     960
ctgatcagca acatcaacgt gatcgtgctg gaactgaagg gcagcgagac aaccttcatg    1020
tgcgagtacg ccgacgagac agccaccatc gtggaatttc tgaaccggtg gatcaccttc    1080
gcccagagca tcatcagcac cctgacaagc ggaggcggcg gatccggcgg aggcggatct    1140
ggcgggagga ggcgaggtcca gctgctcgaa agcggcggag gactggtgca gcctggcggc    1200
agcctgagac tgtcttgcgc cgccagcggc ttcaccttca gcagctacgc catgagctgg    1260
gtccgccagg cccctggcaa gggactggaa tgggtgtccg ccatcatcgg ctctggcagc    1320
cggacctact acgccgacag cgtgaagggc cggttcacca tcagccggga caacagcaag    1380
aacaccctgt acctgcagat gaacagcctg cgggccgagg acaccgccgt gtactactgc    1440
gccaagggat ggttcggcgg cttcaactac tggggacagg gcaccctggt cacagtgtcc    1500
agcgccagca ccaagggccc cagcgtgttc cccctggccc ccagcagcaa gagcacatct    1560
ggcggaacag ccgccctggg ctgcctggtc aaagactact ccccgagcc cgtgaccgtg    1620
tcctggaaca gcggagccct gaccagcggc gtgcacacct ttccagccgt gctgcagagc    1680
agcggcctgt acagcctgag cagcgtggtc accgtgccta gctctagcct gggcacccag    1740
acctacatct gcaacgtgaa ccacaagccc agcaacacca aggtggacaa gaaggtggaa    1800
cccaagagct gcgac                                                   1815
```

<210> SEQ ID NO 227
<211> LENGTH: 605
<212> TYPE: PRT
<213> ORGANISM: Artificial Sequence
<220> FEATURE:
<223> OTHER INFORMATION: 4B9 Fab-IL2 qm-Fab (heavy chain cytokine fusion construct)

<400> SEQUENCE: 227

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Ser Gly Gly
    210                 215                 220

Gly Gly Ser Gly Gly Gly Ser Gly Gly Gly Ala Pro Ala Ser
225                 230                 235                 240

Ser Ser Thr Lys Lys Thr Gln Leu Gln Leu Glu His Leu Leu Leu Asp
                245                 250                 255

Leu Gln Met Ile Leu Asn Gly Ile Asn Asn Tyr Lys Asn Pro Lys Leu
            260                 265                 270

Thr Arg Met Leu Thr Ala Lys Phe Ala Met Pro Lys Lys Ala Thr Glu
        275                 280                 285

Leu Lys His Leu Gln Cys Leu Glu Glu Glu Leu Lys Pro Leu Glu Glu
290                 295                 300

Val Leu Asn Gly Ala Gln Ser Lys Asn Phe His Leu Arg Pro Arg Asp
305                 310                 315                 320

Leu Ile Ser Asn Ile Asn Val Ile Val Leu Glu Leu Lys Gly Ser Glu
                325                 330                 335

Thr Thr Phe Met Cys Glu Tyr Ala Asp Glu Thr Ala Thr Ile Val Glu
            340                 345                 350

Phe Leu Asn Arg Trp Ile Thr Phe Ala Gln Ser Ile Ile Ser Thr Leu
        355                 360                 365

Thr Ser Gly Gly Gly Gly Ser Gly Gly Gly Gly Ser Gly Gly Gly Gly
    370                 375                 380

Glu Val Gln Leu Leu Glu Ser Gly Gly Gly Leu Val Gln Pro Gly Gly
385                 390                 395                 400

Ser Leu Arg Leu Ser Cys Ala Ala Ser Gly Phe Thr Phe Ser Ser Tyr
```

```
                    405                 410                 415
Ala Met Ser Trp Val Arg Gln Ala Pro Gly Lys Gly Leu Glu Trp Val
            420                 425                 430

Ser Ala Ile Ile Gly Ser Gly Ala Ser Thr Tyr Tyr Ala Asp Ser Val
            435                 440                 445

Lys Gly Arg Phe Thr Ile Ser Arg Asp Asn Ser Lys Asn Thr Leu Tyr
450                 455                 460

Leu Gln Met Asn Ser Leu Arg Ala Glu Asp Thr Ala Val Tyr Tyr Cys
465                 470                 475                 480

Ala Lys Gly Trp Phe Gly Gly Phe Asn Tyr Trp Gly Gln Gly Thr Leu
            485                 490                 495

Val Thr Val Ser Ser Ala Ser Thr Lys Gly Pro Ser Val Phe Pro Leu
            500                 505                 510

Ala Pro Ser Ser Lys Ser Thr Ser Gly Gly Thr Ala Ala Leu Gly Cys
            515                 520                 525

Leu Val Lys Asp Tyr Phe Pro Glu Pro Val Thr Val Ser Trp Asn Ser
530                 535                 540

Gly Ala Leu Thr Ser Gly Val His Thr Phe Pro Ala Val Leu Gln Ser
545                 550                 555                 560

Ser Gly Leu Tyr Ser Leu Ser Ser Val Val Thr Val Pro Ser Ser Ser
                565                 570                 575

Leu Gly Thr Gln Thr Tyr Ile Cys Asn Val Asn His Lys Pro Ser Asn
            580                 585                 590

Thr Lys Val Asp Lys Lys Val Glu Pro Lys Ser Cys Asp
            595                 600                 605

<210> SEQ ID NO 228
<211> LENGTH: 1815
<212> TYPE: DNA
<213> ORGANISM: Artificial Sequence
<220> FEATURE:
<223> OTHER INFORMATION: 4B9 Fab-IL2 qm-Fab (heavy chain cytokine fusion
      construct)

<400> SEQUENCE: 228
gaggtgcagc tgctcgaaag cggcggagga ctggtgcagc ctggcggcag cctgagactg     60
tcttgcgccg ccagcggctt caccttcagc agctacgcca tgagctgggt ccgccaggcc    120
cctggcaagg gactggaatg ggtgtccgcc atcatcggct ctggcgccag cacctactac    180
gccgacagcg tgaagggccg gttcaccatc agccgggaca acagcaagaa caccctgtac    240
ctgcagatga acagcctgcg ggccgaggac accgccgtgt actactgcgc caagggatgg    300
ttcggcggct tcaactactg gggacagggc accctggtca cagtgtccag cgctagcacc    360
aagggaccca gcgtgttccc cctggccccc agcagcaaga gcacatctgg cggaacagcc    420
gccctgggct gcctggtcaa agactacttc cccgagcccg tgaccgtgtc ctggaacagc    480
ggagccctga ccagcggcgt gcacaccttt ccagccgtgc tgcagagcag cggcctgtac    540
agcctgagca gcgtggtcac cgtgcctagc tctagcctgg gcacccagac ctacatctgc    600
aacgtgaacc acaagcccag caacaccaag gtggacaaga aggtggaacc caagagctgc    660
gactccggcg gaggcggatc tggcggtgga ggctccggag gcgaggcgc tcctgccagc    720 agctccacca gaaaaaccca gctccagctg gaacatctgc tgctggatct gcagatgatc    780
ctgaacggca tcaacaacta caagaacccc aagctgaccc ggatgctgac cgccaagttc    840
gccatgccca gaaggccac cgaactgaaa catctgcagt gcctggaaga ggaactgaag    900
```

```
cctctggaag aggtgctgaa cggcgcccag agcaagaact tccacctgag gcccagggac   960
ctgatcagca acatcaacgt gatcgtgctg gaactgaagg gcagcgagac aaccttcatg  1020
tgcgagtacg ccgacgagac agccaccatc gtggaatttc tgaaccggtg gatcaccttc  1080
gcccagagca tcatcagcac cctgacaagc ggaggcggcg gatccggcgg aggcggatct  1140
ggcggaggag gcgaggtcca gctgctcgaa agcggcggag gactggtgca gcctggcggc  1200
agcctgagac tgtcttgcgc cgccagcggc ttcaccttca gcagctacgc catgagctgg  1260
gtccgccagg cccctggcaa gggactggaa tgggtgtccg ccatcatcgg ctctggcgcc  1320
agcacctact acgccgacag cgtgaagggc cggttcacca tcagccggga caacagcaag  1380
aacaccctgt acctgcagat gaacagcctg cgggccgagg acaccgccgt gtactactgc  1440
gccaagggat ggttcggcgg cttcaactac tggggacagg gcaccctggt cacagtgtcc  1500
agcgccagca ccaagggccc cagcgtgttc cccctggccc cagcagcaa gagcacatct  1560
ggcggaacag ccgccctggg ctgcctggtc aaagactact cccccgagcc cgtgaccgtg  1620
tcctggaaca gcggagccct gaccagcggc gtgcacacct tccagccgt gctgcagagc  1680
agcggcctgt acagcctgag cagcgtggtc accgtgccta gctctagcct gggcacccag  1740
acctacatct gcaacgtgaa ccacaagccc agcaacacca aggtggacaa gaaggtggaa  1800
cccaagagct gcgac                                                   1815
```

```
<210> SEQ ID NO 229
<211> LENGTH: 605
<212> TYPE: PRT
<213> ORGANISM: Artificial Sequence
<220> FEATURE:
<223> OTHER INFORMATION: 14B3 Fab-IL2 qm-Fab (heavy chain cytokine
      fusion construct)

<400> SEQUENCE: 229

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Leu Ala Ser Gly Ala Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

-continued

```
Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Ser Gly Gly
    210                 215                 220

Gly Gly Ser Gly Gly Gly Gly Ser Gly Gly Gly Ala Pro Ala Ser
225                 230                 235                 240

Ser Ser Thr Lys Lys Thr Gln Leu Gln Leu Glu His Leu Leu Leu Asp
                245                 250                 255

Leu Gln Met Ile Leu Asn Gly Ile Asn Asn Tyr Lys Asn Pro Lys Leu
            260                 265                 270

Thr Arg Met Leu Thr Ala Lys Phe Ala Met Pro Lys Lys Ala Thr Glu
        275                 280                 285

Leu Lys His Leu Gln Cys Leu Glu Glu Glu Leu Lys Pro Leu Glu Glu
        290                 295                 300

Val Leu Asn Gly Ala Gln Ser Lys Asn Phe His Leu Arg Pro Arg Asp
305                 310                 315                 320

Leu Ile Ser Asn Ile Asn Val Ile Val Leu Glu Leu Lys Gly Ser Glu
                325                 330                 335

Thr Thr Phe Met Cys Glu Tyr Ala Asp Glu Thr Ala Thr Ile Val Glu
            340                 345                 350

Phe Leu Asn Arg Trp Ile Thr Phe Ala Gln Ser Ile Ile Ser Thr Leu
        355                 360                 365

Thr Ser Gly Gly Gly Gly Ser Gly Gly Gly Gly Ser Gly Gly Gly Gly
    370                 375                 380

Glu Val Gln Leu Leu Glu Ser Gly Gly Gly Leu Val Gln Pro Gly Gly
385                 390                 395                 400

Ser Leu Arg Leu Ser Cys Ala Ala Ser Gly Phe Thr Phe Ser Ser Tyr
                405                 410                 415

Ala Met Ser Trp Val Arg Gln Ala Pro Gly Lys Gly Leu Glu Trp Val
            420                 425                 430

Ser Ala Ile Leu Ala Ser Gly Ala Ile Thr Tyr Tyr Ala Asp Ser Val
        435                 440                 445

Lys Gly Arg Phe Thr Ile Ser Arg Asp Asn Ser Lys Asn Thr Leu Tyr
    450                 455                 460

Leu Gln Met Asn Ser Leu Arg Ala Glu Asp Thr Ala Val Tyr Tyr Cys
465                 470                 475                 480

Ala Lys Gly Trp Phe Gly Gly Phe Asn Tyr Trp Gly Gln Gly Thr Leu
                485                 490                 495

Val Thr Val Ser Ser Ala Ser Thr Lys Gly Pro Ser Val Phe Pro Leu
            500                 505                 510

Ala Pro Ser Ser Lys Ser Thr Ser Gly Gly Thr Ala Ala Leu Gly Cys
        515                 520                 525

Leu Val Lys Asp Tyr Phe Pro Glu Pro Val Thr Val Ser Trp Asn Ser
    530                 535                 540

Gly Ala Leu Thr Ser Gly Val His Thr Phe Pro Ala Val Leu Gln Ser
545                 550                 555                 560

Ser Gly Leu Tyr Ser Leu Ser Ser Val Val Thr Val Pro Ser Ser Ser
                565                 570                 575

Leu Gly Thr Gln Thr Tyr Ile Cys Asn Val Asn His Lys Pro Ser Asn
            580                 585                 590

Thr Lys Val Asp Lys Lys Val Glu Pro Lys Ser Cys Asp
        595                 600                 605
```

<210> SEQ ID NO 230
<211> LENGTH: 1815
<212> TYPE: DNA
<213> ORGANISM: Artificial Sequence
<220> FEATURE:
<223> OTHER INFORMATION: 14B3 Fab-IL2 qm-Fab (heavy chain cytokine fusion construct)

<400> SEQUENCE: 230

```
gaggtgcagc tgctcgaaag cggcggagga ctggtgcagc ctggcggcag cctgagactg      60
tcttgcgccg ccagcggctt caccttcagc agctacgcca tgagctgggt ccgccaggcc     120
cctggcaagg gactggaatg ggtgtccgcc atcctggcct ctggcgccat cacctactac     180
gccgacagcg tgaagggccg gttcaccatc agccgggaca cagcaagaa caccctgtac     240
ctgcagatga acagcctgcg ggccgaggac accgccgtgt actactgcgc aagggatgg     300
ttcggcggct caactactg gggacagggc acctggtca cagtgtccag cgctagcacc     360
aagggaccca cgtgttccc cctggccccc agcagcaaga gcacatctgg cggaacagcc     420
gccctgggct gcctggtcaa agactacttc cccgagcccg tgaccgtgtc ctggaacagc     480
ggagccctga ccagcggcgt gcacaccttt ccagccgtgc tgcagagcag cggcctgtac     540
agcctgagca gcgtggtcac cgtgcctagc tctagcctgg cacccagac ctacatctgc     600
aacgtgaacc acaagcccag caacaccaag gtggacaaga aggtggaacc caagagctgc     660
gactccggcg gaggcggatc tggcggtgga ggctccggag gcgaggcgc tcctgccagc     720
agctccacca gaaaacccca gctccagctg aacatctgc tgctggatct gcagatgatc     780
ctgaacggca tcaacaacta caagaacccc aagctgaccc ggatgctgac cgccaagttc     840
gccatgccca gaaggccac cgaactgaaa catctgcagt gcctggaaga ggaactgaag     900
cctctggaag aggtgctgaa cggcgcccag agcaagaact ccacctgag gccagggac     960
ctgatcagca acatcaacgt gatcgtgctg aactgaagg gcagcgagac aaccttcatg    1020
tgcgagtacg ccgacgagac agccaccatc gtggaatttc tgaaccggtg gatcaccttc    1080
gcccagagca tcatcagcac cctgacaagc ggaggcggcg gatccggcgg aggcggatct    1140
ggcggaggag gcgaggtcca gctgctcgaa agcggcggag gactggtgca gcctggcggc    1200
agcctgagac tgtcttgcgc cgccagcggc ttcaccttca gcagctacgc catgagctgg    1260
gtccgccagg cccctggcaa gggactggaa tgggtgtccg ccatcctggc ctctggcgcc    1320
atcacctact acgccgacag cgtgaagggc cggttcacca tcagccggga caacagcaag    1380
aacaccctgt acctgcagat gaacagcctg cgggccgagg acaccgccgt gtactactgc    1440
gccaagggat ggttcggcgg cttcaactac tggggacagg gcaccctggt cacagtgtcc    1500
agcgccagca ccaagggccc cagcgtgttc cccctggccc cagcagcaa gagcacatct    1560
ggcggaacag ccgccctggg ctgcctggtc aaagactact ccccgagcc cgtgaccgtg    1620
tcctggaaca gcggagccct gaccagcggc gtgcacacct tccagccgt gctgcagagc    1680
agcggcctgt acagcctgag cagcgtggtc accgtgccta gctctagcct gggcacccag    1740
acctacatct gcaacgtgaa ccacaagccc agcaacacca aggtggacaa gaaggtggaa    1800
cccaagagct gcgac                                                     1815
```

<210> SEQ ID NO 231
<211> LENGTH: 215
<212> TYPE: PRT
<213> ORGANISM: Artificial Sequence
<220> FEATURE:
<223> OTHER INFORMATION: 3F2 light chain

<400> SEQUENCE: 231

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 232
<211> LENGTH: 645
<212> TYPE: DNA
<213> ORGANISM: Artificial Sequence
<220> FEATURE:
<223> OTHER INFORMATION: 3F2 light chain

<400> SEQUENCE: 232

```
gagatcgtgc tgacccagtc ccccggcacc ctgtctctga gccctggcga gagagccacc    60
ctgtcctgca gagcctccca gtccgtgacc tcctcctacc tcgcctggta tcagcagaag   120
cccggccagg cccctcggct gctgatcaac gtgggcagtc ggagagccac cggcatccct   180
gaccggttct ccggctctgg ctccggcacc gacttcaccc tgaccatctc ccggctggaa   240
cccgaggact tcgccgtgta ctactgccag cagggcatca tgctgccccc cacctttggc   300
cagggcacca aggtggaaat caagcgtacg gtggccgctc cctccgtgtt catcttccca   360
ccctccgacg agcagctgaa gtccggcacc gcctccgtcg tgtgcctgct gaacaacttc   420
taccccgcg aggccaaggt gcagtggaag gtggacaacg ccctgcagtc cggcaactcc   480
caggaatccg tcaccgagca ggactccaag gacagcacct actccctgtc ctccaccctg   540
accctgtcca aggccgacta cgagaagcac aaggtgtacg cctgcgaagt gacccaccag   600
ggcctgtcca gccccgtgac caagtccttc aaccggggcg agtgc                   645
```

<210> SEQ ID NO 233

```
<211> LENGTH: 215
<212> TYPE: PRT
<213> ORGANISM: Artificial Sequence
<220> FEATURE:
<223> OTHER INFORMATION: 4G8 light chain

<400> SEQUENCE: 233

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 234
<211> LENGTH: 645
<212> TYPE: DNA
<213> ORGANISM: Artificial Sequence
<220> FEATURE:
<223> OTHER INFORMATION: 4G8 light chain

<400> SEQUENCE: 234
gagatcgtgc tgacccagtc ccccggcacc ctgtctctga gccctggcga gagagccacc     60
ctgtcctgca gagcctccca gtccgtgtcc cggtcctacc tcgcctggta tcagcagaag    120
cccggccagg cccctcggct gctgatcatc ggcgcctcta ccagagccac cggcatccct    180
gaccggttct ccggctctgg ctccggcacc gacttcaccc tgaccatctc ccggctggaa    240
cccgaggact tcgccgtgta ctactgccag cagggccagg tcatccctcc cacctttggc    300
cagggcacca agtggaaat  caagcgtacg gtggccgctc cctccgtgtt catcttccca    360 cctccgacg  agcagctgaa gtccggcacc gcctccgtcg tgtgcctgct gaacaacttc    420 taccccgcg  aggccaaggt gcagtggaag gtggacaacg ccctgcagtc cggcaactcc    480
caggaatccg tcaccgagca ggactccaag gacagcacct actccctgtc ctccaccctg    540
accctgtcca aggccgacta cgagaagcac aaggtgtacg cctgcgaagt gacccaccag    600
```
ggcctgtcca gccccgtgac caagtccttc aaccggggcg agtgc    645

<210> SEQ ID NO 235
<211> LENGTH: 215
<212> TYPE: PRT
<213> ORGANISM: Artificial Sequence
<220> FEATURE:
<223> OTHER INFORMATION: 3D9 light chain

<400> SEQUENCE: 235

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Gly Gln Leu Ile Pro
                85                  90                  95
Pro Thr Phe Gly Gln Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215
```

<210> SEQ ID NO 236
<211> LENGTH: 645
<212> TYPE: DNA
<213> ORGANISM: Artificial Sequence
<220> FEATURE:
<223> OTHER INFORMATION: 3D9 light chain

<400> SEQUENCE: 236
gaaatcgtgt taacgcagtc tccaggcacc ctgtctttgt ctccagggga aagagccacc    60
ctctcttgca gggccagtca gagtgttagc agcagctact tagcctggta ccagcagaaa    120
cctggccagg ctcccaggct cctcatctat ggagcatcca gcagggccac tggcatccca    180
gacaggttca gtggcagtgg atccgggaca gacttcactc tcaccatcag cagactggag    240
cctgaagatt ttgcagtgta ttactgtcag cagggtcagc ttattccccc tacgttcggc    300
caggggacca aagtggaaat caaacgtacg gtggctgcac catctgtctt catcttcccg    360
ccatctgatg agcagttgaa atctggaact gcctctgttg tgtgcctgct gaataacttc    420

```
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca aagcagacta cgagaaacac aaagtctacg cctgcgaagt cacccatcag      600
ggcctgagct cgcccgtcac aaagagcttc aacaggggag agtgt                      645
```

<210> SEQ ID NO 237
<211> LENGTH: 215
<212> TYPE: PRT
<213> ORGANISM: Artificial Sequence
<220> FEATURE:
<223> OTHER INFORMATION: 2F11 light chain

<400> SEQUENCE: 237

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Tyr Thr Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 238
<211> LENGTH: 645
<212> TYPE: DNA
<213> ORGANISM: Artificial Sequence
<220> FEATURE:
<223> OTHER INFORMATION: 2F11 light chain

<400> SEQUENCE: 238

```
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcagtgta ttactgtcag cagggtcagt atactccccc cacgttcggc     300
```

```
cagggggacca aagtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgt    645
```

<210> SEQ ID NO 239
<211> LENGTH: 215
<212> TYPE: PRT
<213> ORGANISM: Artificial Sequence
<220> FEATURE:
<223> OTHER INFORMATION: 4B3 light chain

<400> SEQUENCE: 239

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Tyr Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 240
<211> LENGTH: 645
<212> TYPE: DNA
<213> ORGANISM: Artificial Sequence
<220> FEATURE:
<223> OTHER INFORMATION: 4B3 light chain

<400> SEQUENCE: 240

```
gaaatcgtgt taacgcagtc tccaggcacc ctgtctttgt ctccagggga aagagccacc    60
ctctcttgca gggccagtca gagtgttagc agcaattact tagcctggta ccagcagaaa    120
```

```
cctggccagg ctcccaggct cctcatctat ggcgcctaca tcagggccac tggcatccca    180
gacaggttca gtggcagtgg atccgggaca gacttcactc tcaccatcag cagactggag    240
cctgaagatt ttgcagtgta ttactgtcag cagggtcagg ttattccccc tacgttcggc    300
caggggacca aagtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgt               645
```

<210> SEQ ID NO 241
<211> LENGTH: 613
<212> TYPE: PRT
<213> ORGANISM: Artificial Sequence
<220> FEATURE:
<223> OTHER INFORMATION: 2B10 Fab-IL2 qm-Fab (heavy chain cytokine fusion construct)

<400> SEQUENCE: 241

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Ser Gly Gly Gly Gly Ser Gly Gly Gly Ser Gly Gly Gly Gly
225                 230                 235                 240

Ala Pro Ala Ser Ser Ser Thr Lys Lys Thr Gln Leu Gln Leu Glu His
                245                 250                 255

Leu Leu Leu Asp Leu Gln Met Ile Leu Asn Gly Ile Asn Asn Tyr Lys
            260                 265                 270
```

```
Asn Pro Lys Leu Thr Arg Met Leu Thr Ala Lys Phe Ala Met Pro Lys
        275                 280                 285
Lys Ala Thr Glu Leu Lys His Leu Gln Cys Leu Glu Glu Glu Leu Lys
    290                 295                 300
Pro Leu Glu Glu Val Leu Asn Gly Ala Gln Ser Lys Asn Phe His Leu
305                 310                 315                 320
Arg Pro Arg Asp Leu Ile Ser Asn Ile Asn Val Ile Val Leu Glu Leu
                325                 330                 335
Lys Gly Ser Glu Thr Thr Phe Met Cys Glu Tyr Ala Asp Glu Thr Ala
            340                 345                 350
Thr Ile Val Glu Phe Leu Asn Arg Trp Ile Thr Phe Ala Gln Ser Ile
        355                 360                 365
Ile Ser Thr Leu Thr Ser Gly Gly Gly Ser Gly Gly Gly Gly Ser
    370                 375                 380
Gly Gly Gly Gly Gln Val Gln Leu Val Gln Ser Gly Ala Glu Val Lys
385                 390                 395                 400
Lys Pro Gly Ser Ser Val Lys Val Ser Cys Lys Ala Ser Gly Gly Thr
                405                 410                 415
Phe Ser Ser Tyr Ala Ile Ser Trp Val Arg Gln Ala Pro Gly Gln Gly
            420                 425                 430
Leu Glu Trp Met Gly Gly Ile Ile Pro Ile Phe Gly Thr Ala Asn Tyr
        435                 440                 445
Ala Gln Lys Phe Gln Gly Arg Val Thr Ile Thr Ala Asp Lys Ser Thr
    450                 455                 460
Ser Thr Ala Tyr Met Glu Leu Ser Ser Leu Arg Ser Glu Asp Thr Ala
465                 470                 475                 480
Val Tyr Tyr Cys Ala Arg Leu Tyr Gly Tyr Ala Tyr Tyr Gly Ala Phe
                485                 490                 495
Asp Tyr Trp Gly Gln Gly Thr Thr Val Thr Val Ser Ser Ala Ser Thr
            500                 505                 510
Lys Gly Pro Ser Val Phe Pro Leu Ala Pro Ser Ser Lys Ser Thr Ser
        515                 520                 525
Gly Gly Thr Ala Ala Leu Gly Cys Leu Val Lys Asp Tyr Phe Pro Glu
    530                 535                 540
Pro Val Thr Val Ser Trp Asn Ser Gly Ala Leu Thr Ser Gly Val His
545                 550                 555                 560
Thr Phe Pro Ala Val Leu Gln Ser Ser Gly Leu Tyr Ser Leu Ser Ser
                565                 570                 575
Val Val Thr Val Pro Ser Ser Ser Leu Gly Thr Gln Thr Tyr Ile Cys
            580                 585                 590
Asn Val Asn His Lys Pro Ser Asn Thr Lys Val Asp Lys Lys Val Glu
        595                 600                 605
Pro Lys Ser Cys Asp
    610

<210> SEQ ID NO 242
<211> LENGTH: 1839
<212> TYPE: DNA
<213> ORGANISM: Artificial Sequence
<220> FEATURE:
<223> OTHER INFORMATION: 2B10 Fab-IL2 qm-Fab (heavy chain cytokine
      fusion construct)

<400> SEQUENCE: 242
caggtgcaat tggtgcagtc tggggctgag gtgaagaagc ctgggtcctc ggtgaaggtc      60
```

```
tcctgcaagg cctccggagg cacattcagc agctacgcta taagctgggt gcgacaggcc    120
cctggacaag ggctcgagtg gatgggaggg atcatccta  tctttggtac agcaaactac    180
gcacagaagt tccagggcag ggtcaccatt actgcagaca atccacgag  cacagcctac    240
atggagctga gcagcctgag atctgaggac accgccgtgt attactgtgc gagactgtac    300
ggttacgctt actacggtgc ttttgactac tggggccaag gaccaccgt  gaccgtctcc    360
tcagctagca ccaagggccc atcggtcttc cccctggcac cctcctccaa gagcacctct    420
gggggcacag cggccctggg ctgcctggtc aaggactact ccccgaacc  ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca ggtggataa  gaaagttgag    660
cccaaatctt gtgactccgg cggaggaggg agcggcggag gtggctccgg aggtggcgga    720
gcacctgcct caagttctac aaagaaaaca cagctacaac tggagcattt actgctggat    780
ttacagatga ttttgaatgg aattaataat tacaagaatc ccaaactcac caggatgctc    840
acagccaagt ttgccatgcc caagaaggcc acagaactga acatcttca  gtgtctagaa    900
gaagaactca acctctgga  ggaagtgcta atggcgctc  aaagcaaaaa ctttcactta    960
agacccaggg acttaatcag caatatcaac gtaatagttc tggaactaaa gggatctgaa   1020
acaacattca tgtgtgaata tgctgatgag acagcaacca ttgtagaatt tctgaacaga   1080
tggattacct ttgcccaaag catcatctca cactgactt  ccggcggagg aggatccggc   1140
ggaggtggct ctggcggtgg cggacaggtg caattggtgc agtctggggc tgaggtgaag   1200
aagcctgggt cctcggtgaa ggtctcctgc aaggcctccg gaggcacatt cagcagctac   1260
gctataagct gggtgcgaca ggcccctgga caagggctcg agtggatggg agggatcatc   1320
cctatctttg gtacagcaaa ctacgcacag aagttccagg gcagggtcac cattactgca   1380
gacaaatcca cgagcacagc ctacatggag ctgagcagcc tgagatctga ggacaccgcc   1440
gtgtattact gtgcgagact gtacggttac gcttactacg gtgctttga  ctactggggc   1500
caagggacca ccgtgaccgt ctcctcagct agcaccaagg gccatcggt  cttcccctg    1560
gcaccctcct ccaagagcac ctctggggc  acagcggccc tgggctgcct ggtcaaggac   1620
tacttccccg aaccggtgac ggtgtcgtgg aactcaggcg ccctgaccag cggcgtgcac   1680
accttcccgg ctgtcctaca gtcctcagga ctctactccc tcagcagcgt ggtgaccgtg   1740
ccctccagca gcttgggcac ccagacctac atctgcaacg tgaatcacaa gcccagcaac   1800
accaaggtgg ataagaaagt tgagcccaaa tcttgtgac                          1839
```

<210> SEQ ID NO 243
<211> LENGTH: 613
<212> TYPE: PRT
<213> ORGANISM: Artificial Sequence
<220> FEATURE:
<223> OTHER INFORMATION: C3B6 Fab-IL2 qm-Fab (heavy chain cytokine fusion construct)

<400> SEQUENCE: 243

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
```

-continued

```
                35                  40                  45
Gly Ala Ile Ile Pro Ile Leu Gly Ile Ala Asn Tyr Ala Gln Lys Phe
 50                  55                  60
Gln Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Leu Tyr Gly Tyr Ala Tyr Tyr Gly Ala Phe Asp Tyr Trp Gly
                100                 105                 110
Gln Gly Thr Thr Val Thr Val Ser Ser Ala Ser Thr Lys Gly Pro Ser
                115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Lys Val Glu Pro Lys Ser Cys
210                 215                 220
Asp Ser Gly Gly Gly Gly Ser Gly Gly Gly Gly Ser Gly Gly Gly Gly
225                 230                 235                 240
Ala Pro Ala Ser Ser Ser Thr Lys Lys Thr Gln Leu Gln Leu Glu His
                245                 250                 255
Leu Leu Leu Asp Leu Gln Met Ile Leu Asn Gly Ile Asn Asn Tyr Lys
                260                 265                 270
Asn Pro Lys Leu Thr Arg Met Leu Thr Ala Lys Phe Ala Met Pro Lys
                275                 280                 285
Lys Ala Thr Glu Leu Lys His Leu Gln Cys Leu Glu Glu Glu Leu Lys
290                 295                 300
Pro Leu Glu Glu Val Leu Asn Gly Ala Gln Ser Lys Asn Phe His Leu
305                 310                 315                 320
Arg Pro Arg Asp Leu Ile Ser Asn Ile Asn Val Ile Val Leu Glu Leu
                325                 330                 335
Lys Gly Ser Glu Thr Thr Phe Met Cys Glu Tyr Ala Asp Glu Thr Ala
                340                 345                 350
Thr Ile Val Glu Phe Leu Asn Arg Trp Ile Thr Phe Ala Gln Ser Ile
                355                 360                 365
Ile Ser Thr Leu Thr Ser Gly Gly Gly Ser Gly Gly Gly Gly Ser
                370                 375                 380
Gly Gly Gly Gly Gln Val Gln Leu Val Gln Ser Gly Ala Glu Val Lys
385                 390                 395                 400
Lys Pro Gly Ser Ser Val Lys Val Ser Cys Lys Ala Ser Gly Gly Thr
                405                 410                 415
Phe Ser Ser Tyr Ala Ile Ser Trp Val Arg Gln Ala Pro Gly Gln Gly
                420                 425                 430
Leu Glu Trp Met Gly Ala Ile Ile Pro Ile Leu Gly Ile Ala Asn Tyr
                435                 440                 445
Ala Gln Lys Phe Gln Gly Arg Val Thr Ile Thr Ala Asp Lys Ser Thr
                450                 455                 460
```

```
Ser Thr Ala Tyr Met Glu Leu Ser Ser Leu Arg Ser Glu Asp Thr Ala
465                 470                 475                 480

Val Tyr Tyr Cys Ala Arg Leu Tyr Gly Tyr Ala Tyr Tyr Gly Ala Phe
                485                 490                 495

Asp Tyr Trp Gly Gln Gly Thr Thr Val Thr Val Ser Ser Ala Ser Thr
            500                 505                 510

Lys Gly Pro Ser Val Phe Pro Leu Ala Pro Ser Ser Lys Ser Thr Ser
            515                 520                 525

Gly Gly Thr Ala Ala Leu Gly Cys Leu Val Lys Asp Tyr Phe Pro Glu
            530                 535                 540

Pro Val Thr Val Ser Trp Asn Ser Gly Ala Leu Thr Ser Gly Val His
545                 550                 555                 560

Thr Phe Pro Ala Val Leu Gln Ser Ser Gly Leu Tyr Ser Leu Ser Ser
                565                 570                 575

Val Val Thr Val Pro Ser Ser Ser Leu Gly Thr Gln Thr Tyr Ile Cys
            580                 585                 590

Asn Val Asn His Lys Pro Ser Asn Thr Lys Val Asp Lys Lys Val Glu
            595                 600                 605

Pro Lys Ser Cys Asp
    610
```

<210> SEQ ID NO 244
<211> LENGTH: 1839
<212> TYPE: DNA
<213> ORGANISM: Artificial Sequence
<220> FEATURE:
<223> OTHER INFORMATION: C3B6 Fab-IL2 qm-Fab (heavy chain cytokine fusion construct)

<400> SEQUENCE: 244

```
caggtgcaat tggtgcagtc tggggctgag gtgaagaagc ctgggtcctc ggtgaaggtc      60
tcctgcaagg cctccggagg cacattcagc agctacgcta taagctgggt gcgacaggcc     120
cctggacaag gctcgagtg atgggagct atcatcccga tccttggtat cgcaaactac       180
gcacagaagt tccagggcag ggtcaccatt actgcagaca atccacgag cacagcctac      240
atggagctga gcagcctgag atctgaggac accgccgtgt attactgtgc gagactgtac      300
ggttacgctt actacggtgc ttttgactac tggggccaag gaccaccgt gaccgtctcc       360
tcagctagca ccaagggccc atcggtcttc cccctggcac cctcctccaa gagcacctct     420
gggggcacag cggccctggg ctgcctggtc aaggactact cccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggataa gaaagttgag     660
cccaaatctt gtgactccgg cggaggaggg agcggcggag gtggctccgg aggtggcgga     720
gcacctgcct caagttctac aaagaaaaca cagctacaac tggagcattt actgctggat     780
ttacagatga ttttgaatgg aattaataat tacaagaatc ccaaactcac caggatgctc     840
acagccaagt ttgccatgcc caagaaggcc acagaactga acatcttca gtgtctagaa     900
gaagaactca aacctctgga ggaagtgcta atggcgctc aaagcaaaaa ctttcactta     960
agacccaggg acttaatcag caatatcaac gtaatagttc tggaactaaa gggatctgaa    1020
acaacattca tgtgtgaata tgctgatgag acagcaacca ttgtagaatt tctgaacaga    1080
tggattacct ttgcccaaag catcatctca acactgactt ccggcggagg aggatccggc    1140
```

```
ggaggtggct ctggcggtgg cggacaggtg caattggtgc agtctggggc tgaggtgaag    1200
aagcctgggt cctcggtgaa ggtctcctgc aaggcctccg gaggcacatt cagcagctac    1260
gctataagct gggtgcgaca ggcccctgga caagggctcg agtggatggg agctatcatc    1320
ccgatccttg gtatcgcaaa ctacgcacag aagttccagg gcagggtcac cattactgca    1380
gacaaatcca cgagcacagc ctacatggag ctgagcagcc tgagatctga ggacaccgcc    1440
gtgtattact gtgcgagact gtacggttac gcttactacg gtgcttttga ctactggggc    1500
caagggacca ccgtgaccgt ctcctcagct agcaccaagg gcccatcggt cttccccctg    1560
gcaccctcct ccaagagcac ctctgggggc acagcggccc tgggctgcct ggtcaaggac    1620
tacttccccg aaccggtgac ggtgtcgtgg aactcaggcg ccctgaccag cggcgtgcac    1680
accttcccgg ctgtcctaca gtcctcagga ctctactccc tcagcagcgt ggtgaccgtg    1740
ccctccagca gcttgggcac ccagacctac atctgcaacg tgaatcacaa gcccagcaac    1800
accaaggtgg ataagaaagt tgagcccaaa tcttgtgac                            1839
```

<210> SEQ ID NO 245
<211> LENGTH: 613
<212> TYPE: PRT
<213> ORGANISM: Artificial Sequence
<220> FEATURE:
<223> OTHER INFORMATION: 6A12 Fab-IL2 qm-Fab (heavy chain cytokine fusion construct)

<400> SEQUENCE: 245

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Val Ile Ile Pro Ile Leu Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Ser Gly Gly Gly Gly Ser Gly Gly Gly Gly Ser Gly Gly Gly Gly
```

```
            225                 230                 235                 240

Ala Pro Ala Ser Ser Thr Lys Lys Thr Gln Leu Gln Leu Glu His
                245                 250                 255

Leu Leu Leu Asp Leu Gln Met Ile Leu Asn Gly Ile Asn Asn Tyr Lys
                260                 265                 270

Asn Pro Lys Leu Thr Arg Met Leu Thr Ala Lys Phe Ala Met Pro Lys
                275                 280                 285

Lys Ala Thr Glu Leu Lys His Leu Gln Cys Leu Glu Glu Glu Leu Lys
            290                 295                 300

Pro Leu Glu Glu Val Leu Asn Gly Ala Gln Ser Lys Asn Phe His Leu
305                 310                 315                 320

Arg Pro Arg Asp Leu Ile Ser Asn Ile Asn Val Ile Val Leu Glu Leu
                325                 330                 335

Lys Gly Ser Glu Thr Thr Phe Met Cys Glu Tyr Ala Asp Glu Thr Ala
                340                 345                 350

Thr Ile Val Glu Phe Leu Asn Arg Trp Ile Thr Phe Ala Gln Ser Ile
                355                 360                 365

Ile Ser Thr Leu Thr Ser Gly Gly Gly Ser Gly Gly Gly Gly Ser
                370                 375                 380

Gly Gly Gly Gly Gln Val Gln Leu Val Gln Ser Gly Ala Glu Val Lys
385                 390                 395                 400

Lys Pro Gly Ser Ser Val Lys Val Ser Cys Lys Ala Ser Gly Gly Thr
                405                 410                 415

Phe Ser Ser Tyr Ala Ile Ser Trp Val Arg Gln Ala Pro Gly Gln Gly
                420                 425                 430

Leu Glu Trp Met Gly Val Ile Ile Pro Ile Leu Gly Thr Ala Asn Tyr
                435                 440                 445

Ala Gln Lys Phe Gln Gly Arg Val Thr Ile Thr Ala Asp Lys Ser Thr
                450                 455                 460

Ser Thr Ala Tyr Met Glu Leu Ser Ser Leu Arg Ser Glu Asp Thr Ala
465                 470                 475                 480

Val Tyr Tyr Cys Ala Arg Leu Tyr Gly Tyr Ala Tyr Tyr Gly Ala Phe
                485                 490                 495

Asp Tyr Trp Gly Gln Gly Thr Thr Val Thr Val Ser Ser Ala Ser Thr
                500                 505                 510

Lys Gly Pro Ser Val Phe Pro Leu Ala Pro Ser Ser Lys Ser Thr Ser
                515                 520                 525

Gly Gly Thr Ala Ala Leu Gly Cys Leu Val Lys Asp Tyr Phe Pro Glu
                530                 535                 540

Pro Val Thr Val Ser Trp Asn Ser Gly Ala Leu Thr Ser Gly Val His
545                 550                 555                 560

Thr Phe Pro Ala Val Leu Gln Ser Ser Gly Leu Tyr Ser Leu Ser Ser
                565                 570                 575

Val Val Thr Val Pro Ser Ser Ser Leu Gly Thr Gln Thr Tyr Ile Cys
                580                 585                 590

Asn Val Asn His Lys Pro Ser Asn Thr Lys Val Asp Lys Lys Val Glu
                595                 600                 605

Pro Lys Ser Cys Asp
        610

<210> SEQ ID NO 246
<211> LENGTH: 1839
<212> TYPE: DNA
<213> ORGANISM: Artificial Sequence
```

<220> FEATURE:
<223> OTHER INFORMATION: 6A12 Fab-IL2 qm-Fab (heavy chain cytokine fusion construct)

<400> SEQUENCE: 246

```
caggtgcaat tggtgcagtc tggggctgag gtgaagaagc ctgggtcctc ggtgaaggtc      60
tcctgcaagg cctccggagg cacattcagc agctatgcta taagctgggt gcgacaggcc     120
cctggacaag gctcgagtg gatgggagtg atcatcccta tccttggtac cgcaaactac     180
gcacagaagt tccagggcag ggtcaccatt actgcagaca atccacgag cacagcctac     240
atggagctga gcagcctgag atctgaggac accgccgtgt attactgtgc gagactgtac     300
ggttacgctt actacggtgc ttttgactac tggggccaag gaccaccgt gaccgtctcc     360
tcagctagca ccaagggccc atcggtcttc cccctggcac cctcctccaa gagcacctct     420
gggggcacag cggccctggg ctgcctggtc aaggactact tccccgaacc ggtgacggtg     480
tcgtggaact caggcgccct gaccagcggc gtgcacacct tcccggctgt cctacagtcc     540
tcaggactct actccctcag cagcgtgtg accgtgccct ccagcagctt gggcacccag     600
acctacatct gcaacgtgaa tcacaagccc agcaacacca aggtggataa gaaagttgag     660
cccaaatctt gtgactccgg cggaggaggg agcggcggag gtggctccgg aggtggcgga     720
gcacctgcct caagttctac aaagaaaaca cagctacaac tggagcattt actgctggat     780
ttacagatga ttttgaatgg aattaataat tacaagaatc ccaaactcac caggatgctc     840
acagccaagt ttgccatgcc caagaaggcc acagaactga acatcttca gtgtctagaa     900
gaagaactca aacctctgga ggaagtgcta aatggcgctc aaagcaaaaa ctttcactta     960
agacccaggg acttaatcag caatatcaac gtaatagttc tggaactaaa gggatctgaa    1020
acaacattca tgtgtgaata tgctgatgag acagcaacca ttgtagaatt tctgaacaga    1080
tggattacct ttgcccaaag catcatctca acactgactt ccggcggagg aggatccggc    1140
ggaggtggct ctggcggtgg cggacaggtg caattggtgc agtctggggc tgaggtgaag    1200
aagcctgggt cctcggtgaa ggtctcctgc aaggcctccg gaggcacatt cagcagctat    1260
gctataagct gggtgcgaca ggcccctgga caagggctcg agtggatggg agtgatcatc    1320
cctatccttg gtaccgcaaa ctacgcacag aagttccagg gcagggtcac cattactgca    1380
gacaaatcca cgagcacagc ctacatggag ctgagcagcc tgagatctga ggacaccgcc    1440
gtgtattact gtgcgagact gtacggttac gcttactacg gtgcttttga ctactggggc    1500
caagggacca ccgtgaccgt ctcctcagct agcaccaagg gcccatcggt cttccccctg    1560
gcaccctcct ccaagagcac ctctgggggc acagcggccc tgggctgcct ggtcaaggac    1620
tacttccccg aaccggtgac ggtgtcgtgg aactcaggcg ccctgaccag cggcgtgcac    1680
accttcccgg ctgtcctaca gtcctcagga ctctactccc tcagcagcgt ggtgaccgtg    1740
ccctccagca gcttgggcac ccagacctac atctgcaacg tgaatcacaa gcccagcaac    1800
accaaggtgg ataagaaagt tgagcccaaa tcttgtgac                            1839
```

<210> SEQ ID NO 247
<211> LENGTH: 214
<212> TYPE: PRT
<213> ORGANISM: Artificial Sequence
<220> FEATURE:
<223> OTHER INFORMATION: 2B10 light chain

<400> SEQUENCE: 247

Asp Ile Gln Met Thr Gln Ser Pro Ser Ser Leu Ser Ala Ser Val Gly

```
                1               5                  10                 15
           Asp Arg Val Thr Ile Thr Cys Arg Ala Ser Gln Gly Ile Arg Asn Asp
                           20                  25                  30
           Leu Gly Trp Tyr Gln Gln Lys Pro Gly Lys Ala Pro Lys Arg Leu Ile
                       35                  40                  45
           Tyr Ala Ala Ser Ser Leu Gln Ser Gly Val Pro Ser Arg Phe Ser Gly
                   50                  55                  60
           Ser Gly Ser Gly Thr Glu Phe Thr Leu Thr Ile Ser Ser Leu Gln Pro
           65                  70                  75                  80
           Glu Asp Phe Ala Thr Tyr Tyr Cys Leu Gln Asn Gly Leu Gln Pro Ala
                           85                  90                  95
           Thr Phe Gly Gln Gly Thr Lys Val Glu Ile Lys Arg Thr Val Ala Ala
                       100                 105                 110
           Pro Ser Val Phe Ile Phe Pro Pro Ser Asp Glu Gln Leu Lys Ser Gly
                   115                 120                 125
           Thr Ala Ser Val Val Cys Leu Leu Asn Asn Phe Tyr Pro Arg Glu Ala
                   130                 135                 140
           Lys Val Gln Trp Lys Val Asp Asn Ala Leu Gln Ser Gly Asn Ser Gln
           145                 150                 155                 160
           Glu Ser Val Thr Glu Gln Asp Ser Lys Asp Ser Thr Tyr Ser Leu Ser
                           165                 170                 175
           Ser Thr Leu Thr Leu Ser Lys Ala Asp Tyr Glu Lys His Lys Val Tyr
                       180                 185                 190
           Ala Cys Glu Val Thr His Gln Gly Leu Ser Ser Pro Val Thr Lys Ser
                   195                 200                 205
           Phe Asn Arg Gly Glu Cys
                   210
```

<210> SEQ ID NO 248
<211> LENGTH: 642
<212> TYPE: DNA
<213> ORGANISM: Artificial Sequence
<220> FEATURE:
<223> OTHER INFORMATION: 2B10 light chain

<400> SEQUENCE: 248

```
gatatccaga tgacccagtc tccatcctcc ctgtctgcat ctgtcggaga ccgggtcacc      60
atcacctgcc gggcaagtca gggcattaga aatgatttag ctggtaccca gcagaagcca     120
gggaaagccc ctaagcgcct gatctatgct gcatccagtt tgcagagtgg cgtcccatca     180
aggttcagcg gcagtggatc cgggacagag ttcactctca ccatcagcag cttgcagcct     240
gaagattttg ccacctatta ctgcttgcag aatggtctgc agcccgcgac gtttggccag     300
ggcaccaaag tcgagatcaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac agggagagt gt                         642
```

<210> SEQ ID NO 249
<211> LENGTH: 214
<212> TYPE: PRT
<213> ORGANISM: Artificial Sequence
<220> FEATURE:

<223> OTHER INFORMATION: D1A2 light chain

<400> SEQUENCE: 249

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
        35                  40                  45
Tyr Asp Ala Tyr Ser Leu Gln Ser Gly Val Pro Ser Arg Phe Ser Gly
 50                  55                  60
Gly Gly Ser Gly Thr Glu Phe Thr Leu Thr Ile Ser Ser Leu Gln Pro
 65                  70                  75                  80
Glu Asp Phe Ala Thr Tyr Tyr Cys Leu Gln Asn Gly Leu Gln Pro Ala
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 250
<211> LENGTH: 642
<212> TYPE: DNA
<213> ORGANISM: Artificial Sequence
<220> FEATURE:
<223> OTHER INFORMATION: D1A2 light chain

<400> SEQUENCE: 250

```
gacatccaga tgacccagtc tccatcctcc ctgtctgcat ctgtcggaga ccgggtcacc    60
atcacctgcc gggcaagtca ggggattcgt aatgatttag gctggtacca gcagaagcca   120
gggaaagccc ctaagcgcct gatctatgat gcttacagct tgcagagtgg cgtcccatca   180
aggttcagcg gcggtggatc cgggacagag ttcactctca ccatcagcag cttgcagcct   240
gaagattttg ccacctatta ctgcttgcag aatggtctgc agcccgcgac gtttggccag   300
ggcaccaaag tcgagatcaa gcgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac agggagagt gt                       642
```

<210> SEQ ID NO 251
<211> LENGTH: 214
<212> TYPE: PRT
<213> ORGANISM: Artificial Sequence
<220> FEATURE:
<223> OTHER INFORMATION: O7D8 light chain

<400> SEQUENCE: 251

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Asn Val
            20                  25                  30

Leu Gly Trp Tyr Gln Gln Lys Pro Gly Lys Ala Pro Lys Arg Leu Ile
        35                  40                  45

Tyr Asp Val Ser Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 252
<211> LENGTH: 642
<212> TYPE: DNA
<213> ORGANISM: Artificial Sequence
<220> FEATURE:
<223> OTHER INFORMATION: O7D8 light chain

<400> SEQUENCE: 252

```
gatatccaga tgacccagtc tccatcctcc ctgtctgcat ctgtcggaga ccgggtcacc      60
atcacctgcc gggcaagtca gagcattcgt aatgttttag ctggtaccag cagaagcca     120 gggaaagccc ctaagcgcct gatctatgat gtgtccagtt tgcagagtgg cgtcccatca    180
aggttcagcg gcggtggatc cgggacagag ttcactctca ccatcagcag cttgcagcct    240
gaagattttg ccacctatta ctgcttgcag aatggtctgc agcccgcgac gtttggccag    300
ggcaccaaag tcgagatcaa gcgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
```

-continued

```
ctgagcaaag cagactacga gaaacacaaa gtctacgcct gcgaagtcac ccatcagggc    600
ctgagctcgc ccgtcacaaa gagcttcaac aggggagagt gt                      642
```

<210> SEQ ID NO 253
<211> LENGTH: 615
<212> TYPE: PRT
<213> ORGANISM: Artificial Sequence
<220> FEATURE:
<223> OTHER INFORMATION: MHLG1 Fab-IL2 qm-Fab (heavy chain cytokine fusion construct)

<400> SEQUENCE: 253

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Asn Phe Gly Arg Tyr Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Tyr Gly Asn Tyr Val Gly His Tyr Phe Asp His Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Ser Gly Gly Gly Gly Ser Gly Gly Gly Ser Gly Gly Gly Gly
225                 230                 235                 240

Gly Ala Pro Ala Ser Ser Ser Thr Lys Lys Thr Gln Leu Gln Leu Glu
                245                 250                 255

His Leu Leu Leu Asp Leu Gln Met Ile Leu Asn Gly Ile Asn Asn Tyr
            260                 265                 270

Lys Asn Pro Lys Leu Thr Arg Met Leu Thr Ala Lys Phe Ala Met Pro
        275                 280                 285

Lys Lys Ala Thr Glu Leu Lys His Leu Gln Cys Leu Glu Glu Glu Leu
    290                 295                 300

Lys Pro Leu Glu Glu Val Leu Asn Gly Ala Gln Ser Lys Asn Phe His
305                 310                 315                 320

Leu Arg Pro Arg Asp Leu Ile Ser Asn Ile Asn Val Ile Val Leu Glu
                325                 330                 335

Leu Lys Gly Ser Glu Thr Thr Phe Met Cys Glu Tyr Ala Asp Glu Thr
```

```
            340                 345                 350
Ala Thr Ile Val Glu Phe Leu Asn Arg Trp Ile Thr Phe Ala Gln Ser
            355                 360                 365
Ile Ile Ser Thr Leu Thr Ser Gly Gly Gly Ser Gly Gly Gly Gly
        370                 375                 380
Ser Gly Gly Gly Gly Glu Val Gln Leu Val Glu Ser Gly Gly Gly Leu
385                 390                 395                 400
Val Lys Pro Gly Gly Ser Leu Arg Leu Ser Cys Ala Ala Ser Gly Phe
                405                 410                 415
Thr Phe Ser Asn Tyr Trp Met Asn Trp Val Arg Gln Ala Pro Gly Lys
                420                 425                 430
Gly Leu Glu Trp Val Ala Glu Ile Arg Leu Lys Ser Asn Asn Phe Gly
                435                 440                 445
Arg Tyr Tyr Ala Ala Ser Val Lys Gly Arg Phe Thr Ile Ser Arg Asp
                450                 455                 460
Asp Ser Lys Asn Thr Leu Tyr Leu Gln Met Asn Ser Leu Lys Thr Glu
465                 470                 475                 480
Asp Thr Ala Val Tyr Tyr Cys Thr Thr Tyr Gly Asn Tyr Val Gly His
                485                 490                 495
Tyr Phe Asp His Trp Gly Gln Gly Thr Thr Val Thr Val Ser Ser Ala
                500                 505                 510
Ser Thr Lys Gly Pro Ser Val Phe Pro Leu Ala Pro Ser Ser Lys Ser
                515                 520                 525
Thr Ser Gly Gly Thr Ala Ala Leu Gly Cys Leu Val Lys Asp Tyr Phe
            530                 535                 540
Pro Glu Pro Val Thr Val Ser Trp Asn Ser Gly Ala Leu Thr Ser Gly
545                 550                 555                 560
Val His Thr Phe Pro Ala Val Leu Gln Ser Ser Gly Leu Tyr Ser Leu
                565                 570                 575
Ser Ser Val Val Thr Val Pro Ser Ser Ser Leu Gly Thr Gln Thr Tyr
            580                 585                 590
Ile Cys Asn Val Asn His Lys Pro Ser Asn Thr Lys Val Asp Lys Lys
            595                 600                 605
Val Glu Pro Lys Ser Cys Asp
    610                 615

<210> SEQ ID NO 254
<211> LENGTH: 1845
<212> TYPE: DNA
<213> ORGANISM: Artificial Sequence
<220> FEATURE:
<223> OTHER INFORMATION: MHLG1 Fab-IL2 qm-Fab (heavy chain cytokine
      fusion construct)

<400> SEQUENCE: 254
gaagtgcagc tggtggagtc tggaggaggc ttggtcaagc ctggcgggtc cctgcggctc    60
tcctgtgcag cctccggatt cacatttagc aactattgga tgaactgggt gcggcaggct   120
cctggaaagg gcctcgagtg ggtggccgag atcagattga atccaataa cttcggaaga   180 tattacgctg caagcgtgaa gggccggttc accatcagca gagatgattc caagaacacg   240
ctgtacctgc agatgaacag cctgaagacc gaggatacgg ccgtgtatta ctgtaccaca   300
tacggcaact acgttgggca ctacttcgac cactggggcc aagggaccac cgtcaccgtc   360
tccagtgcta gcaccaaggg cccatcggtc ttccccctgg cacctcctc caagagcacc   420 tctgggggca gcggcccct gggctgcctg gtcaaggact acttccccga accggtgacg   480
```

-continued

```
gtgtcgtgga actcaggcgc cctgaccagc ggcgtgcaca ccttcccggc tgtcctacag      540
tcctcaggac tctactccct cagcagcgtg gtgaccgtgc cctccagcag cttgggcacc      600
cagacctaca tctgcaacgt gaatcacaag cccagcaaca ccaaggtgga taagaaagtt      660
gagcccaaat cttgtgactc cggcggagga gggagcggcg gaggtggctc cggaggtggc      720
ggagcacctg cctcaagttc tacaaagaaa acacagctac aactggagca tttactgctg      780
gatttacaga tgattttgaa tggaattaat aattacaaga tcccaaaact caccaggatg      840
ctcacagcca gtttgccat gcccaagaag ccacagaac tgaaacatct tcagtgtcta       900
gaagaagaac tcaaacctct ggaggaagtg ctaaatggcg ctcaaagcaa aactttcac       960 ttaagaccca gggacttaat cagcaatatc aacgtaatag ttctggaact aaagggatct     1020
gaaacaacat tcatgtgtga atatgctgat gagacagcaa ccattgtaga atttctgaac     1080
agatggatta cctttgccca aagcatcatc tcaacactga cttccggcgg aggaggatcc     1140
ggcggaggtg gctctggcgg tggcggagaa gtgcagctgg tggagtctgg aggaggcttg     1200
gtcaagcctg gcgggtccct gcggctctcc tgtgcagcct ccggattcac atttagcaac     1260
tattggatga ctgggtgcg gcaggctcct ggaaagggcc tcgagtgggt ggccgagatc     1320
agattgaaat ccaataactt cggaagatat acgctgcaa gcgtgaaggg ccggttcacc      1380
atcagcagag atgattccaa gaacacgctg tacctgcaga tgaacagcct gaagaccgag     1440
gatacggccg tgtattactg taccacatac ggcaactacg ttgggcacta cttcgaccac     1500
tggggccaag ggaccaccgt caccgtctcc agtgctagca ccaagggccc atcggtcttc     1560
cccctggcac cctcctccaa gagcacctct gggggcacag cggccctggg ctgcctggtc     1620
aaggactact ccccgaacc ggtgacggtg tcgtggaact caggcgccct gaccagcggc     1680
gtgcacacct tcccggctgt cctacagtcc tcaggactct actccctcag cagcgtggtg     1740
accgtgccct ccagcagctt gggcacccag acctacatct gcaacgtgaa tcacaagccc     1800
agcaacacca aggtggataa gaaagttgag cccaaatctt gtgac                     1845
```

<210> SEQ ID NO 255
<211> LENGTH: 214
<212> TYPE: PRT
<213> ORGANISM: Artificial Sequence
<220> FEATURE:
<223> OTHER INFORMATION: KV9 light chain

<400> SEQUENCE: 255

```
Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Gln Ala Pro Arg Pro Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
                115                 120                 125
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
210

<210> SEQ ID NO 256
<211> LENGTH: 642
<212> TYPE: DNA
<213> ORGANISM: Artificial Sequence
<220> FEATURE:
<223> OTHER INFORMATION: KV9 light chain

<400> SEQUENCE: 256
gatatccagt tgacccagtc tccatccttc ctgtctgcat ctgtgggcga ccgggtcacc      60
atcacctgca aggccagtca gaatgtggat actaacgtgg cttggtacca gcagaagcca     120
gggcaggcac ctaggcctct gatctattcg catcctaccg gtacactggc gtcccatca      180 aggttcagcg gcagtggatc cgggacagag ttcactctca aatctcaagc ctgcaacct      240 gaagatttcg caacttacta ctgtcaacag tacaatagtt accctctgac gttcggcgga     300
ggtaccaagg tggagatcaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                       642

<210> SEQ ID NO 257
<211> LENGTH: 615
<212> TYPE: PRT
<213> ORGANISM: Artificial Sequence
<220> FEATURE:
<223> OTHER INFORMATION: MHLG Fab-IL2 qm-Fab (heavy chain cytokine
      fusion construct)

<400> SEQUENCE: 257

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Asn Phe Gly Arg Tyr Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
```

```
                     85                  90                  95
Tyr Cys Thr Thr Tyr Gly Asn Tyr Val Gly His Tyr Phe Asp His Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys Asp Ser Gly Gly Gly Gly Ser Gly Gly Gly Gly Ser Gly Gly Gly
225                 230                 235                 240

Gly Ala Pro Ala Ser Ser Ser Thr Lys Lys Thr Gln Leu Gln Leu Glu
                245                 250                 255

His Leu Leu Leu Asp Leu Gln Met Ile Leu Asn Gly Ile Asn Asn Tyr
            260                 265                 270

Lys Asn Pro Lys Leu Thr Arg Met Leu Thr Ala Lys Phe Ala Met Pro
        275                 280                 285

Lys Lys Ala Thr Glu Leu Lys His Leu Gln Cys Leu Glu Glu Glu Leu
290                 295                 300

Lys Pro Leu Glu Glu Val Leu Asn Gly Ala Gln Ser Lys Asn Phe His
305                 310                 315                 320

Leu Arg Pro Arg Asp Leu Ile Ser Asn Ile Asn Val Ile Val Leu Glu
                325                 330                 335

Leu Lys Gly Ser Glu Thr Thr Phe Met Cys Glu Tyr Ala Asp Glu Thr
            340                 345                 350

Ala Thr Ile Val Glu Phe Leu Asn Arg Trp Ile Thr Phe Ala Gln Ser
            355                 360                 365

Ile Ile Ser Thr Leu Thr Ser Gly Gly Gly Gly Ser Gly Gly Gly Gly
        370                 375                 380

Ser Gly Gly Gly Gly Glu Val Gln Leu Val Glu Ser Gly Gly Gly Leu
385                 390                 395                 400

Val Gln Pro Gly Gly Ser Leu Arg Leu Ser Cys Ala Ala Ser Gly Phe
                405                 410                 415

Thr Phe Ser Asn Tyr Trp Met Asn Trp Val Arg Gln Ala Pro Gly Lys
            420                 425                 430

Gly Leu Glu Trp Val Ala Glu Ile Arg Leu Lys Ser Asn Asn Phe Gly
            435                 440                 445

Arg Tyr Tyr Ala Ala Ser Val Lys Gly Arg Phe Thr Ile Ser Arg Asp
        450                 455                 460

Asp Ser Lys Asn Thr Leu Tyr Leu Gln Met Asn Ser Leu Lys Thr Glu
465                 470                 475                 480

Asp Thr Ala Val Tyr Tyr Cys Thr Thr Tyr Gly Asn Tyr Val Gly His
                485                 490                 495

Tyr Phe Asp His Trp Gly Gln Gly Thr Thr Val Thr Val Ser Ser Ala
            500                 505                 510
```

```
Ser Thr Lys Gly Pro Ser Val Phe Pro Leu Ala Pro Ser Ser Lys Ser
        515                 520                 525

Thr Ser Gly Gly Thr Ala Ala Leu Gly Cys Leu Val Lys Asp Tyr Phe
        530                 535                 540

Pro Glu Pro Val Thr Val Ser Trp Asn Ser Gly Ala Leu Thr Ser Gly
545                 550                 555                 560

Val His Thr Phe Pro Ala Val Leu Gln Ser Ser Gly Leu Tyr Ser Leu
                565                 570                 575

Ser Ser Val Val Thr Val Pro Ser Ser Ser Leu Gly Thr Gln Thr Tyr
                580                 585                 590

Ile Cys Asn Val Asn His Lys Pro Ser Asn Thr Lys Val Asp Lys Lys
        595                 600                 605

Val Glu Pro Lys Ser Cys Asp
    610                 615
```

<210> SEQ ID NO 258
<211> LENGTH: 1845
<212> TYPE: DNA
<213> ORGANISM: Artificial Sequence
<220> FEATURE:
<223> OTHER INFORMATION: MHLG Fab-IL2 qm-Fab (heavy chain cytokine fusion construct)

<400> SEQUENCE: 258

```
gaagtgcagc tggtggagtc tggaggaggc ttggtccagc ctggcgggtc cctgcggctc      60
tcctgtgcag cctccggatt cacatttagc aactattgga tgaactgggt gcggcaggct     120
cctggaaagg gcctcgagtg ggtggccgag atcagattga atccaataac ttcggaaga     180
tattacgctg caagcgtgaa gggccggttc accatcagca gagatgattc caagaacacg     240
ctgtacctgc agatgaacag cctgaagacc gaggatacgg ccgtgtatta ctgtaccaca     300
tacggcaact acgttgggca ctacttcgac cactgggggc aagggaccac cgtcaccgtc     360
tccagtgcta gcaccaaggg cccatcggtc ttccccctgg caccctcctc caagagcacc     420
tctgggggca gcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga taagaaagtt     660
gagcccaaat cttgtgactc cggcggagga gggagcggcg aggtggctc cggaggtggc     720
ggagcacctg cctcaagttc tacaaagaaa acacagctac aactggagca tttactgctg     780
gatttacaga tgattttgaa tggaattaat aattacaaga atcccaaact caccaggatg     840
ctcacagcca agtttgccat gcccaagaag gccacagaac tgaaacatct tcagtgtcta     900
gaagaagaac tcaaacctct ggaggaagtg ctaaatggcg ctcaaagcaa aaactttcac     960
ttaagaccca gggacttaat cagcaatatc aacgtaatag ttctggaact aaagggatct    1020
gaaacaacat tcatgtgtga atatgctgat gagacagcaa ccattgtaga atttctgaac    1080
agatggatta ccttttgccca aagcatcatc tcaacactga cttccggcgg aggaggatcc    1140
ggcggaggtg gctctggcgg tggcggagaa gtgcagctgg tggagtctgg aggaggcttg    1200
gtccagcctg gcgggtccct gcggctctcc tgtgcagcct ccggattcac atttagcaac    1260
tattggatga actgggtgcg gcaggctcct ggaaagggcc tcgagtgggt ggccgagatc    1320
agattgaaat ccaataactt cggaagatat tacgctgcaa gcgtgaaggg ccggttcacc    1380
```

```
atcagcagag atgattccaa gaacacgctg tacctgcaga tgaacagcct gaagaccgag    1440
gatacggccg tgtattactg taccacatac ggcaactacg ttgggcacta cttcgaccac    1500
tggggccaag ggaccaccgt caccgtctcc agtgctagca ccaagggccc atcggtcttc    1560
cccctggcac cctcctccaa gagcacctct gggggcacag cggccctggg ctgcctggtc    1620
aaggactact cccccgaacc ggtgacggtg tcgtggaact caggcgccct gaccagcggc    1680
gtgcacacct tcccggctgt cctacagtcc tcaggactct actccctcag cagcgtggtg    1740
accgtgccct ccagcagctt gggcacccag acctacatct gcaacgtgaa tcacaagccc    1800
agcaacacca aggtggataa gaaagttgag cccaaatctt gtgac                   1845
```

<210> SEQ ID NO 259
<211> LENGTH: 214
<212> TYPE: PRT
<213> ORGANISM: Artificial Sequence
<220> FEATURE:
<223> OTHER INFORMATION: KV1 light chain

<400> SEQUENCE: 259

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Asn Val Asp Thr Asn
            20                  25                  30

Leu Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 260
<211> LENGTH: 642
<212> TYPE: DNA
<213> ORGANISM: Artificial Sequence
<220> FEATURE:
<223> OTHER INFORMATION: KV1 light chain

<400> SEQUENCE: 260

```
gatatccagt tgacccagtc tccatccttc ctgtctgcat ctgtgggcga ccgggtcacc    60
```

-continued

```
atcacctgca gggccagtca gaatgtggat actaacttag cttggtacca gcagaagcca    120
gggaaagcac ctaagctcct gatctattcg gcatcctacc gttacactgg cgtcccatca    180
aggttcagcg gcagtggatc cgggacagag ttcactctca caatctcaag cctgcaacct    240
gaagatttcg caacttacta ctgtcaacag tacaatagtt accctctgac gttcggcgga    300
ggtaccaagg tggagatcaa gcgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt    642
```

<210> SEQ ID NO 261
<211> LENGTH: 214
<212> TYPE: PRT
<213> ORGANISM: Artificial Sequence
<220> FEATURE:
<223> OTHER INFORMATION: KV7 light chain

<400> SEQUENCE: 261

```
Asp Ile Gln Leu Thr Gln Ser Pro Ser Phe Leu Ser Ala Ser Val Gly
 1               5                  10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Pro Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 262
<211> LENGTH: 642
<212> TYPE: DNA
<213> ORGANISM: Artificial Sequence
<220> FEATURE:

<223> OTHER INFORMATION: KV7 light chain

<400> SEQUENCE: 262

```
gatatccagt tgacccagtc tccatccttc ctgtctgcat ctgtgggcga ccgggtcacc      60
atcacctgca aggccagtca gaatgtggat actaacgtgg cttggtacca gcagaagcca     120
gggaaagcac ctaagcctct gatctattcg gcatcctacc ggtacactgg cgtcccatca     180
aggttcagcg gcagtggatc cgggacagag ttcactctca caatctcaag cctgcaacct     240
gaagatttcg caacttacta ctgtcaacag tacaatagtt accctctgac gttcggcgga     300
ggtaccaagg tggagatcaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642
```

<210> SEQ ID NO 263
<211> LENGTH: 19
<212> TYPE: PRT
<213> ORGANISM: Artificial Sequence
<220> FEATURE:
<223> OTHER INFORMATION: leader sequence

<400> SEQUENCE: 263

Met Asp Trp Thr Trp Arg Ile Leu Phe Leu Val Ala Ala Ala Thr Gly
1               5                   10                  15

Ala His Ser

<210> SEQ ID NO 264
<211> LENGTH: 57
<212> TYPE: DNA
<213> ORGANISM: Artificial Sequence
<220> FEATURE:
<223> OTHER INFORMATION: leader sequence

<400> SEQUENCE: 264

```
atggactgga cctggagaat cctcttcttg gtggcagcag ccacaggagc ccactcc         57
```

<210> SEQ ID NO 265
<211> LENGTH: 57
<212> TYPE: DNA
<213> ORGANISM: Artificial Sequence
<220> FEATURE:
<223> OTHER INFORMATION: leader sequence

<400> SEQUENCE: 265

```
atggactgga cctggaggat cctcttcttg gtggcagcag ccacaggagc ccactcc         57
```

<210> SEQ ID NO 266
<211> LENGTH: 22
<212> TYPE: PRT
<213> ORGANISM: Artificial Sequence
<220> FEATURE:
<223> OTHER INFORMATION: leader sequence

<400> SEQUENCE: 266

Met Asp Met Arg Val Pro Ala Gln Leu Leu Gly Leu Leu Leu Leu Trp
1               5                   10                  15

Phe Pro Gly Ala Arg Cys

<210> SEQ ID NO 267
<211> LENGTH: 66
<212> TYPE: DNA
<213> ORGANISM: Artificial Sequence
<220> FEATURE:
<223> OTHER INFORMATION: leader sequence

<400> SEQUENCE: 267
atggacatga gggtccccgc tcagctcctg ggcctcctgc tgctctggtt cccaggtgcc    60
aggtgt                                                                66

<210> SEQ ID NO 268
<211> LENGTH: 19
<212> TYPE: PRT
<213> ORGANISM: Artificial Sequence
<220> FEATURE:
<223> OTHER INFORMATION: leader sequence

<400> SEQUENCE: 268

Met Gly Trp Ser Cys Ile Ile Leu Phe Leu Val Ala Thr Ala Thr Gly
1               5                   10                  15

Val His Ser

<210> SEQ ID NO 269
<211> LENGTH: 57
<212> TYPE: DNA
<213> ORGANISM: Artificial Sequence
<220> FEATURE:
<223> OTHER INFORMATION: leader sequence

<400> SEQUENCE: 269
atgggatgga gctgtatcat cctcttcttg gtagcaacag ctaccggtgt gcattcc       57

<210> SEQ ID NO 270
<211> LENGTH: 57
<212> TYPE: DNA
<213> ORGANISM: Artificial Sequence
<220> FEATURE:
<223> OTHER INFORMATION: leader sequence

<400> SEQUENCE: 270
atgggctggt cctgcatcat cctgtttctg gtggctaccg ccactggagt gcattcc       57

<210> SEQ ID NO 271
<211> LENGTH: 57
<212> TYPE: DNA
<213> ORGANISM: Artificial Sequence
<220> FEATURE:
<223> OTHER INFORMATION: leader sequence

<400> SEQUENCE: 271
atgggctggt cctgcatcat cctgtttctg gtcgccacag ccaccggcgt gcactct       57

<210> SEQ ID NO 272
<211> LENGTH: 20
<212> TYPE: PRT
<213> ORGANISM: Artificial Sequence
<220> FEATURE:
<223> OTHER INFORMATION: leader sequence

<400> SEQUENCE: 272

Met Tyr Arg Met Gln Leu Leu Ser Cys Ile Ala Leu Ser Leu Ala Leu
1               5                   10                  15

Val Thr Asn Ser
         20

<210> SEQ ID NO 273
<211> LENGTH: 60
<212> TYPE: DNA
<213> ORGANISM: Artificial Sequence
<220> FEATURE:
<223> OTHER INFORMATION: leader sequence

<400> SEQUENCE: 273
atgtacagga tgcaactcct gtcttgcatt gcactaagtc ttgcacttgt cacaaacagt    60

<210> SEQ ID NO 274
<211> LENGTH: 466
<212> TYPE: PRT
<213> ORGANISM: Artificial Sequence
<220> FEATURE:
<223> OTHER INFORMATION: Human IL-2R-beta-Fc(hole) fusion protein

<400> SEQUENCE: 274

Met Asp Met Arg Val Pro Ala Gln Leu Leu Gly Leu Leu Leu Leu Trp
1               5                   10                  15

Phe Pro Gly Ala Arg Cys Ala Val Asn Gly Thr Ser Gln Phe Thr Cys
            20                  25                  30

Phe Tyr Asn Ser Arg Ala Asn Ile Ser Cys Val Trp Ser Gln Asp Gly
        35                  40                  45

Ala Leu Gln Asp Thr Ser Cys Gln Val His Ala Trp Pro Asp Arg Arg
    50                  55                  60

Arg Trp Asn Gln Thr Cys Glu Leu Leu Pro Val Ser Gln Ala Ser Trp
65                  70                  75                  80

Ala Cys Asn Leu Ile Leu Gly Ala Pro Asp Ser Gln Lys Leu Thr Thr
                85                  90                  95

Val Asp Ile Val Thr Leu Arg Val Leu Cys Arg Glu Gly Val Arg Trp
            100                 105                 110

Arg Val Met Ala Ile Gln Asp Phe Lys Pro Phe Glu Asn Leu Arg Leu
        115                 120                 125

Met Ala Pro Ile Ser Leu Gln Val Val His Val Glu Thr His Arg Cys
    130                 135                 140

Asn Ile Ser Trp Glu Ile Ser Gln Ala Ser His Tyr Phe Glu Arg His
145                 150                 155                 160

Leu Glu Phe Glu Ala Arg Thr Leu Ser Pro Gly His Thr Trp Glu Glu
                165                 170                 175

Ala Pro Leu Leu Thr Leu Lys Gln Lys Gln Glu Trp Ile Cys Leu Glu
            180                 185                 190

Thr Leu Thr Pro Asp Thr Gln Tyr Glu Phe Gln Val Arg Val Lys Pro
        195                 200                 205

Leu Gln Gly Glu Phe Thr Thr Trp Ser Pro Trp Ser Gln Pro Leu Ala
    210                 215                 220

Phe Arg Thr Lys Pro Ala Ala Leu Gly Lys Asp Thr Gly Ala Gln Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
            290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Cys
        355                 360                 365

Thr Leu Pro Pro Ser Arg Asp Glu Leu Thr Lys Asn Gln Val Ser Leu
    370                 375                 380

Ser Cys Ala Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Val Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 275
<211> LENGTH: 1401
<212> TYPE: DNA
<213> ORGANISM: Artificial Sequence
<220> FEATURE:
<223> OTHER INFORMATION: Human IL-2R-beta-Fc(hole) fusion protein

<400> SEQUENCE: 275
atggacatga gggtccccgc tcagctcctg ggcctcctgc tgctctggtt cccaggtgcc     60
aggtgtgcgg tgaatggcac ttcccagttc acatgcttct acaactcgag agccaacatc    120
tcctgtgtct ggagccaaga tgggctctg caggacactt cctgccaagt ccatgcctgg    180
ccggacagac ggcggtggaa ccaaacctgt gagctgctcc ccgtgagtca agcatcctgg    240
gcctgcaacc tgatcctcgg agccccagat tctcagaaac tgaccacagt tgacatcgtc    300
accctgaggg tgctgtgccg tgaggggtg cgatggaggg tgatggccat ccaggacttc    360 aagcccttg agaaccttcg cctgatggcc ccatctccc tccaagttgt ccacgtggag    420
acccacagat gcaacataag ctgggaaatc tcccaagcct ccactacttt gaaagacac    480 ctggagttcg aggcccggac gctgtcccca ggccacacct gggaggaggc ccccctgctg    540
actctcaagc agaagcagga atggatctgc tggagacgc tcaccccaga cacccagtat    600
gagtttcagg tgcgggtcaa gcctctgcaa ggcgagttca cgacctggag ccctggagc    660 cagcccctgg ccttcagaac aaagcctgca gcccttggga aggacaccgg agctcaggac    720
aaaactcaca catgcccacc gtgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtgacggc    900 gtggaggtgc ataatgccaa gacaaagccg cgggaggagc agtacaacag cacgtaccgt    960

-continued

```
gtggtcagcg tcctcaccgt cctgcaccag gactggctga atggcaagga gtacaagtgc    1020
aaggtctcca acaaagccct cccagccccc atcgagaaaa ccatctccaa agccaaaggg    1080
cagccccgag aaccacaggt gtgcaccctg cccccatccc gggatgagct gaccaagaac    1140
caggtcagcc tctcgtgcgc agtcaaaggc ttctatccca gcgacatcgc cgtggagtgg    1200
gagagcaatg ggcagccgga gaacaactac aagaccacgc ctcccgtgct ggactccgac    1260
ggctccttct tcctcgtgag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaatg a                                              1401
```

<210> SEQ ID NO 276
<211> LENGTH: 492
<212> TYPE: PRT
<213> ORGANISM: Artificial Sequence
<220> FEATURE:
<223> OTHER INFORMATION: Human IL-2R-gamma-Fc(knob) fusion protein

<400> SEQUENCE: 276

```
Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Gly Ala Gln Asp Lys Thr His Thr Cys Pro
            260                 265                 270

Pro Cys Pro Ala Pro Glu Leu Leu Gly Gly Pro Ser Val Phe Leu Phe
        275                 280                 285
```

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Cys Arg
385                 390                 395                 400

Asp Glu Leu Thr Lys Asn Gln Val Ser Leu Trp Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490

<210> SEQ ID NO 277
<211> LENGTH: 1479
<212> TYPE: DNA
<213> ORGANISM: Artificial Sequence
<220> FEATURE:
<223> OTHER INFORMATION: Human IL-2R-gamma-Fc(knob) fusion protein

<400> SEQUENCE: 277
atgttgaagc catcattacc attcacatcc ctcttattcc tgcagctgcc cctgctggga      60
gtggggctga acacgacaat tctgacgccc aatgggaatg aagacaccac agctgatttc    120
ttcctgacca ctatgcccac tgactccctc agtgttttcca ctctgcccct cccagaggtt    180
cagtgttttg tgttcaatgt cgagtacatg aattgcactt ggaacagcag ctctgagccc    240
cagcctacca acctcactct gcattattgg tacaagaact cggataatga taaagtccag    300
aagtgcagcc actatctatt ctctgaagaa atcacttctg ctgtcagtt gcaaaaaaag    360 gagatccacc tctaccaaac atttgttgtt cagctccagg acccacggga acccaggaga    420
caggccacac agatgctaaa actgcagaat ctggtgatcc cctgggctcc agagaaccta    480
acacttcaca aactgagtga atcccagcta gaactgaact ggaacaacag attcttgaac    540
cactgtttgg agcacttggt gcagtaccgg actgactggg accacagctg gactgaacaa    600
tcagtggatt atagacataa gttctccttg cctagtgtgg atgggcagaa acgctacacg    660
tttcgtgttc ggagccgctt taacccactc tgtggaagtg ctcagcattg gagtgaatgg    720
agccacccaa tccactgggg gagcaatact tcaaaagaga atccttttcct gtttgcattg    780 gaagccggag ctcaggacaa aactcacaca tgcccaccgt gcccagcacc tgaactcctg    840
gggggaccgt cagtcttcct cttccccccca aaacccaagg acaccctcat gatctcccgg    900

```
accccctgagg tcacatgcgt ggtggtggac gtgagccacg aagaccctga ggtcaagttc    960
aactggtacg tggacggcgt ggaggtgcat aatgccaaga caaagccgcg ggaggagcag   1020
tacaacagca cgtaccgtgt ggtcagcgtc ctcaccgtcc tgcaccagga ctggctgaat   1080
ggcaaggagt acaagtgcaa ggtctccaac aaagccctcc cagcccccat cgagaaaacc   1140
atctccaaag ccaaagggca gccccgagaa ccacaggtgt acaccctgcc cccatgccgg   1200
gatgagctga ccaagaacca ggtcagcctg tggtgcctgg tcaaaggctt ctatcccagc   1260
gacatcgccg tggagtggga gagcaatggg cagccggaga caactacaa gaccacgcct   1320 cccgtgctgg actccgacgg ctccttcttc ctctacagca agctcaccgt ggacaagagc   1380
aggtggcagc aggggaacgt cttctcatgc tccgtgatgc atgaggctct gcacaaccac   1440
tacacgcaga gagcctctc cctgtctccg ggtaaatga                           1479
```

<210> SEQ ID NO 278
<211> LENGTH: 219
<212> TYPE: PRT
<213> ORGANISM: Artificial Sequence
<220> FEATURE:
<223> OTHER INFORMATION: Human IL-2R alpha subunit + Avi-tag + His-tag

<400> SEQUENCE: 278

```
Met Gly Trp Ser Cys Ile Ile Leu Phe Leu Val Ala Thr Ala Thr Gly
1               5                   10                  15

Val His Ser Glu Leu Cys Asp Asp Pro Pro Glu Ile Pro His Ala
            20                  25                  30

Thr Phe Lys Ala Met Ala Tyr Lys Glu Gly Thr Met Leu Asn Cys Glu
        35                  40                  45

Cys Lys Arg Gly Phe Arg Arg Ile Lys Ser Gly Ser Leu Tyr Met Leu
    50                  55                  60

Cys Thr Gly Asn Ser Ser His Ser Ser Trp Asp Asn Gln Cys Gln Cys
65                  70                  75                  80

Thr Ser Ser Ala Thr Arg Asn Thr Thr Lys Gln Val Thr Pro Gln Pro
                85                  90                  95

Glu Glu Gln Lys Glu Arg Lys Thr Thr Glu Met Gln Ser Pro Met Gln
            100                 105                 110

Pro Val Asp Gln Ala Ser Leu Pro Gly His Cys Arg Glu Pro Pro Pro
        115                 120                 125

Trp Glu Asn Glu Ala Thr Glu Arg Ile Tyr His Phe Val Val Gly Gln
    130                 135                 140

Met Val Tyr Tyr Gln Cys Val Gln Gly Tyr Arg Ala Leu His Arg Gly
145                 150                 155                 160

Pro Ala Glu Ser Val Cys Lys Met Thr His Gly Lys Thr Arg Trp Thr
                165                 170                 175

Gln Pro Gln Leu Ile Cys Thr Gly Val Asp Glu Gln Leu Tyr Phe Gln
            180                 185                 190

Gly Gly Ser Gly Leu Asn Asp Ile Phe Glu Ala Gln Lys Ile Glu Trp
        195                 200                 205

His Glu Ala Arg Ala His His His His His His
    210                 215
```

<210> SEQ ID NO 279
<211> LENGTH: 660
<212> TYPE: DNA
<213> ORGANISM: Artificial Sequence
<220> FEATURE:

<223> OTHER INFORMATION: Human IL-2R alpha subunit + Avi-tag + His-tag

<400> SEQUENCE: 279

```
atgggatgga gctgtatcat cctcttcttg gtagcaacag ctaccggtgt gcattccgag      60
ctctgtgacg atgacccgcc agagatccca cacgccacat tcaaagccat ggcctacaag     120
gaaggaacca tgttgaactg tgaatgcaag agaggtttcc gcagaataaa aagcgggtca     180
ctctatatgc tctgtacagg aaactctagc cactcgtcct gggacaacca atgtcaatgc     240
acaagctctg ccactcggaa cacaacgaaa caagtgacac tcaacctga gaacagaaa      300
gaaaggaaaa ccacagaaat gcaaagtcca atgcagccag tggaccaagc gagccttcca     360
ggtcactgca gggaacctcc accatgggaa aatgaagcca cagagagaat ttatcatttc     420
gtggtggggc agatggttta ttatcagtgc gtccagggat acagggctct acacagaggt     480
cctgctgaga gcgtctgcaa aatgacccac gggaagacaa ggtggaccca gccccagctc     540
atatgcacag tgtcgacga acagttatat tttcagggcg gctcaggcct gaacgacatc      600
ttcgaggccc agaagatcga gtggcacgag gctcgagctc accaccatca ccatcactga    660
```

<210> SEQ ID NO 280
<211> LENGTH: 473
<212> TYPE: PRT
<213> ORGANISM: Artificial Sequence
<220> FEATURE:
<223> OTHER INFORMATION: Murine IL-2R-beta-Fc(hole) fusion protein

<400> SEQUENCE: 280

```
Met Asp Met Arg Val Pro Ala Gln Leu Leu Gly Leu Leu Leu Leu Trp
  1               5                  10                  15

Phe Pro Leu Leu Leu Leu Trp Phe Pro Gly Ala Arg Cys Ala Val Lys
                 20                  25                  30

Asn Cys Ser His Leu Glu Cys Phe Tyr Asn Ser Arg Ala Asn Val Ser
             35                  40                  45

Cys Met Trp Ser His Glu Glu Ala Leu Asn Val Thr Thr Cys His Val
         50                  55                  60

His Ala Lys Ser Asn Leu Arg His Trp Asn Lys Thr Cys Glu Leu Thr
 65                  70                  75                  80

Leu Val Arg Gln Ala Ser Trp Ala Cys Asn Leu Ile Leu Gly Ser Phe
                 85                  90                  95

Pro Glu Ser Gln Ser Leu Thr Ser Val Asp Leu Leu Asp Ile Asn Val
            100                 105                 110

Val Cys Trp Glu Glu Lys Gly Trp Arg Arg Val Lys Thr Cys Asp Phe
        115                 120                 125

His Pro Phe Asp Asn Leu Arg Leu Val Ala Pro His Ser Leu Gln Val
    130                 135                 140

Leu His Ile Asp Thr Gln Arg Cys Asn Ile Ser Trp Lys Val Ser Gln
145                 150                 155                 160

Val Ser His Tyr Ile Glu Pro Tyr Leu Glu Phe Glu Ala Arg Arg Arg
                165                 170                 175

Leu Leu Gly His Ser Trp Glu Asp Ala Ser Val Leu Ser Leu Lys Gln
            180                 185                 190

Arg Gln Gln Trp Leu Phe Leu Glu Met Leu Ile Pro Ser Thr Ser Tyr
        195                 200                 205

Glu Val Gln Val Arg Val Lys Ala Gln Arg Asn Asn Thr Gly Thr Trp
    210                 215                 220

Ser Pro Trp Ser Gln Pro Leu Thr Phe Arg Thr Arg Pro Ala Asp Pro
```

```
                225                 230                 235                 240
Met Lys Glu Gly Ala Gln Asp Lys Thr His Thr Cys Pro Pro Cys Pro
                    245                 250                 255

Ala Pro Glu Leu Leu Gly Gly Pro Ser Val Phe Leu Phe Pro Pro Lys
                260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
        290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
                340                 345                 350

Ala Leu Pro Ala Pro Ile Glu Lys Thr Ile Ser Lys Ala Lys Gly Gln
                355                 360                 365

Pro Arg Glu Pro Gln Val Cys Thr Leu Pro Pro Ser Arg Asp Glu Leu
            370                 375                 380

Thr Lys Asn Gln Val Ser Leu Ser Cys Ala Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
                420                 425                 430

Val Ser Lys Leu Thr Val Asp Lys Ser Arg Trp Gln Gln Gly Asn Val
                435                 440                 445

Phe Ser Cys Ser Val Met His Glu Ala Leu His Asn His Tyr Thr Gln
            450                 455                 460

Lys Ser Leu Ser Leu Ser Pro Gly Lys
465                 470

<210> SEQ ID NO 281
<211> LENGTH: 1422
<212> TYPE: DNA
<213> ORGANISM: Artificial Sequence
<220> FEATURE:
<223> OTHER INFORMATION: Murine IL-2R-beta-Fc(hole) fusion protein

<400> SEQUENCE: 281
atggacatga gggtccccgc tcagctcctg ggcctcctgc tgctctggtt cccctcctg     60 ctgctctggt tcccaggtgc caggtgtgca gtgaaaaact gttcccatct tgaatgcttc    120
tacaactcaa gagccaatgt ctcttgcatg tggagccatg aagaggctct gaatgtcaca    180
acctgccacg tccatgccaa gtcgaacctg cgacactgga acaaaaacctg tgagctaact    240 cttgtgaggc aggcatcctg ggcctgcaac ctgatcctcg gtcgttccc agagtcccag    300 tcactgacct ccgtggacct ccttgacata aatgtggtgt gctgggaaga aagggttgg    360 cgtagggtaa agacctgcga cttccatccc tttgacaacc ttcgcctggt ggcccctcat    420
tccctccaag ttctgcacat tgatacccag agatgtaaca taagctggaa ggtctcccag    480
gtctctcact acattgaacc atacttggaa tttgaggccc gtagacgtct tctgggccac    540
agctgggagg atgcatccgt attaagcctc aagcagagac agcagtggct tcttcttgag    600
atgctgatcc ctagtaccct catatgaggtc caggtgaggg tcaaagctca acgaaacaat    660
```

```
accgggacct ggagtccctg gagccagccc ctgacctttc ggacaaggcc agcagatccc    720
atgaaggagg gagctcagga caaaactcac acatgcccac cgtgcccagc acctgaactc    780
ctggggggac cgtcagtctt cctcttcccc ccaaaaccca aggacaccct catgatctcc    840
cggacccctg aggtcacatg cgtggtggtg gacgtgagcc acgaagaccc tgaggtcaag    900
ttcaactggt acgtggacgg cgtggaggtg cataatgcca agacaaagcc gcgggaggag    960
cagtacaaca gcacgtaccg tgtggtcagc gtcctcaccg tcctgcacca ggactggctg   1020
aatggcaagg agtacaagtg caaggtctcc aacaaagccc tcccagcccc catcgagaaa   1080
accatctcca aagccaaagg gcagcccga gaaccacagg tgtgcaccct gcccccatcc    1140
cgggatgagc tgaccaagaa ccaggtcagc ctctcgtgcg cagtcaaagg cttctatccc   1200
agcgacatcg ccgtggagtg ggagagcaat gggcagccgg agaacaacta caagaccacg   1260
cctcccgtgc tggactccga cggctccttc ttcctcgtga gcaagctcac cgtggacaag   1320
agcaggtggc agcaggggaa cgtcttctca tgctccgtga tgcatgaggc tctgcacaac   1380
cactacacgc agaagagcct ctccctgtct ccgggtaaat ga                      1422
```

<210> SEQ ID NO 282
<211> LENGTH: 500
<212> TYPE: PRT
<213> ORGANISM: Artificial Sequence
<220> FEATURE:
<223> OTHER INFORMATION: Murine IL-2R-gamma-Fc(knob) fusion protein

<400> SEQUENCE: 282

```
Met Asp Met Arg Val Pro Ala Gln Leu Leu Gly Leu Leu Leu Leu Trp
1               5                   10                  15

Phe Pro Leu Leu Leu Leu Trp Phe Pro Gly Ala Arg Cys Trp Ser Ser
                20                  25                  30

Lys Val Leu Met Ser Ser Ala Asn Glu Asp Ile Lys Ala Asp Leu Ile
            35                  40                  45

Leu Thr Ser Thr Ala Pro Glu His Leu Ser Ala Pro Thr Leu Pro Leu
        50                  55                  60

Pro Glu Val Gln Cys Phe Val Phe Asn Ile Glu Tyr Met Asn Cys Thr
65                  70                  75                  80

Trp Asn Ser Ser Ser Glu Pro Gln Ala Thr Asn Leu Thr Leu His Tyr
                85                  90                  95

Arg Tyr Lys Val Ser Asp Asn Asn Thr Phe Gln Glu Cys Ser His Tyr
            100                 105                 110

Leu Phe Ser Lys Glu Ile Thr Ser Gly Cys Gln Ile Gln Lys Glu Asp
        115                 120                 125

Ile Gln Leu Tyr Gln Thr Phe Val Val Gln Leu Gln Asp Pro Gln Lys
    130                 135                 140

Pro Gln Arg Arg Ala Val Gln Lys Leu Asn Leu Gln Asn Leu Val Ile
145                 150                 155                 160

Pro Arg Ala Pro Glu Asn Leu Thr Leu Ser Asn Leu Ser Glu Ser Gln
                165                 170                 175

Leu Glu Leu Arg Trp Lys Ser Arg His Ile Lys Glu Arg Cys Leu Gln
            180                 185                 190

Tyr Leu Val Gln Tyr Arg Ser Asn Arg Asp Arg Ser Trp Thr Glu Leu
        195                 200                 205

Ile Val Asn His Glu Pro Arg Phe Ser Leu Pro Ser Val Asp Glu Leu
    210                 215                 220

Lys Arg Tyr Thr Phe Arg Val Arg Ser Arg Tyr Asn Pro Ile Cys Gly
```

```
                225                 230                 235                 240
Ser Ser Gln Gln Trp Ser Lys Trp Ser Gln Pro Val His Trp Gly Ser
                245                 250                 255
His Thr Val Glu Glu Asn Pro Ser Leu Phe Ala Leu Glu Ala Gly Ala
                260                 265                 270
Gln Asp Lys Thr His Thr Cys Pro Cys Pro Ala Pro Glu Leu Leu
                275                 280                 285
Gly Gly Pro Ser Val Phe Leu Phe Pro Pro Lys Pro Lys Asp Thr Leu
                290                 295                 300
Met Ile Ser Arg Thr Pro Glu Val Thr Cys Val Val Val Asp Val Ser
305                 310                 315                 320
His Glu Asp Pro Glu Val Lys Phe Asn Trp Tyr Val Asp Gly Val Glu
                325                 330                 335
Val His Asn Ala Lys Thr Lys Pro Arg Glu Glu Gln Tyr Asn Ser Thr
                340                 345                 350
Tyr Arg Val Val Ser Val Leu Thr Val Leu His Gln Asp Trp Leu Asn
                355                 360                 365
Gly Lys Glu Tyr Lys Cys Lys Val Ser Asn Lys Ala Leu Pro Ala Pro
                370                 375                 380
Ile Glu Lys Thr Ile Ser Lys Ala Lys Gly Gln Pro Arg Glu Pro Gln
385                 390                 395                 400
Val Tyr Thr Leu Pro Pro Cys Arg Asp Glu Leu Thr Lys Asn Gln Val
                405                 410                 415
Ser Leu Trp Cys Leu Val Lys Gly Phe Tyr Pro Ser Asp Ile Ala Val
                420                 425                 430
Glu Trp Glu Ser Asn Gly Gln Pro Glu Asn Asn Tyr Lys Thr Thr Pro
                435                 440                 445
Pro Val Leu Asp Ser Asp Gly Ser Phe Phe Leu Tyr Ser Lys Leu Thr
                450                 455                 460
Val Asp Lys Ser Arg Trp Gln Gln Gly Asn Val Phe Ser Cys Ser Val
465                 470                 475                 480
Met His Glu Ala Leu His Asn His Tyr Thr Gln Lys Ser Leu Ser Leu
                485                 490                 495
Ser Pro Gly Lys
                500
```

<210> SEQ ID NO 283
<211> LENGTH: 1503
<212> TYPE: DNA
<213> ORGANISM: Artificial Sequence
<220> FEATURE:
<223> OTHER INFORMATION: Murine IL-2R-gamma-Fc(knob) fusion protein

<400> SEQUENCE: 283

```
atggacatga gggtccccgc tcagctcctg ggcctcctgc tgctctggtt ccccctcctg      60
ctgctctggt tcccaggtgc caggtgttgg agttccaagg tcctcatgtc cagtgcgaat     120
gaagacatca aagctgattt gatcctgact tctacagccc tgaacacctc agtgctcct     180
actctgcccc ttccagaggt tcagtgcttt gtgttcaaca tagagtacat gaattgcact     240
tggaatagca gttctgagcc tcaggcaacc aacctcacgc tgcactatag gtacaaggta     300
tctgataata atacattcca ggagtgcagt cactatttgt ctccaaagga gattacttct     360
ggctgtcaga tacaaaaaga agatatccag ctctaccaga catttgttgt ccagctccag     420
gaccccagaa accccagag gcgagctgta cagaagctaa acctacagaa tcttgtgatc     480
```

```
ccacgggctc cagaaaatct aacactcagc aatctgagtg aatcccagct agagctgaga    540
tggaaaagca gacatattaa agaacgctgt ttacaatact tggtgcagta ccggagcaac    600
agagatcgaa gctggacgga actaatagtg aatcatgaac ctagattctc cctgcctagt    660
gtggatgagc tgaaacggta cacatttcgg gttcggagcc gctataaccc aatctgtgga    720
agttctcaac agtggagtaa atggagccag cctgtccact gggggagtca tactgtagag    780
gagaatcctt ccttgtttgc actggaagct ggagctcagg acaaaactca cacatgccca    840
ccgtgcccag cacctgaact cctgggggga ccgtcagtct tcctcttccc cccaaaaccc    900
aaggacaccc tcatgatctc ccggacccct gaggtcacat gcgtggtggt ggacgtgagc    960
cacgaagacc ctgaggtcaa gttcaactgg tacgtggacg gcgtggaggt gcataatgcc   1020
aagacaaagc cgcgggagga gcagtacaac agcacgtacc gtgtggtcag cgtcctcacc   1080
gtcctgcacc aggactggct gaatggcaag gagtacaagt gcaaggtctc caacaaagcc   1140
ctcccagccc ccatcgagaa aaccatctcc aaagccaaag gcagccccg  agaaccacag   1200 gtgtacaccc tgcccccatg ccgggatgag ctgaccaaga accaggtcag cctgtggtgc   1260
ctggtcaaag gcttctatcc cagcgacatc gccgtggagt gggagagcaa tgggcagccg   1320
gagaacaact acaagaccac gcctcccgtg ctggactccg acggctcctt cttcctctac   1380
agcaagctca ccgtggacaa gagcaggtgg cagcagggga acgtcttctc atgctccgtg   1440
atgcatgagg ctctgcacaa ccactacacg cagaagagcc tctccctgtc tccgggtaaa   1500
tga                                                                 1503
```

<210> SEQ ID NO 284
<211> LENGTH: 213
<212> TYPE: PRT
<213> ORGANISM: Artificial Sequence
<220> FEATURE:
<223> OTHER INFORMATION: Murine IL-2R alpha subunit + Avi-tag + His-tag

<400> SEQUENCE: 284

```
Met Gly Trp Ser Cys Ile Ile Leu Phe Leu Val Ala Thr Ala Thr Gly
1               5                   10                  15

Val His Ser Glu Leu Cys Leu Tyr Asp Pro Pro Glu Val Pro Asn Ala
            20                  25                  30

Thr Phe Lys Ala Leu Ser Tyr Lys Asn Gly Thr Ile Leu Asn Cys Glu
        35                  40                  45

Cys Lys Arg Gly Phe Arg Arg Leu Lys Glu Leu Val Tyr Met Arg Cys
    50                  55                  60

Leu Gly Asn Ser Trp Ser Ser Asn Cys Gln Cys Thr Ser Asn Ser His
65                  70                  75                  80

Asp Lys Ser Arg Lys Gln Val Thr Ala Gln Leu Glu His Gln Lys Glu
                85                  90                  95

Gln Gln Thr Thr Thr Asp Met Gln Lys Pro Thr Gln Ser Met His Gln
            100                 105                 110

Glu Asn Leu Thr Gly His Cys Arg Glu Pro Pro Trp Lys His Glu
        115                 120                 125

Asp Ser Lys Arg Ile Tyr His Phe Val Glu Gly Gln Ser Val His Tyr
    130                 135                 140

Glu Cys Ile Pro Gly Tyr Lys Ala Leu Gln Arg Gly Pro Ala Ile Ser
145                 150                 155                 160

Ile Cys Lys Met Lys Cys Gly Lys Thr Gly Trp Thr Gln Pro Gln Leu
                165                 170                 175
```

Thr Cys Val Asp Glu Gln Leu Tyr Phe Gln Gly Gly Ser Gly Leu Asn
            180                 185                 190

Asp Ile Phe Glu Ala Gln Lys Ile Glu Trp His Glu Ala Arg Ala His
            195                 200                 205

His His His His His
        210

<210> SEQ ID NO 285
<211> LENGTH: 642
<212> TYPE: DNA
<213> ORGANISM: Artificial Sequence
<220> FEATURE:
<223> OTHER INFORMATION: Murine IL-2R alpha subunit + Avi-tag + His-tag

<400> SEQUENCE: 285

```
atgggatgga gctgtatcat cctcttcttg gtagcaacag ctaccggtgt gcattccgaa      60
ctgtgtctgt atgacccacc cgaggtcccc aatgccacat tcaaagccct ctcctacaag     120
aacggcacca tcctaaactg tgaatgcaag agaggtttcc gaagactaaa ggaattggtc     180
tatatgcgtt gcttaggaaa ctcctggagc agcaactgcc agtgcaccag caactcccat     240
gacaaatcga aaagcaagt tacagctcaa cttgaacacc agaaagagca acaaaccaca     300
acagacatgc agaagccaac acagtctatg caccaagaga accttacagg tcactgcagg     360
gagccacctc cttggaaaca tgaagattcc aagagaatct atcatttcgt ggaaggacag     420
agtgttcact acgagtgtat tccgggatac aaggctctac agagaggtcc tgctattagc     480
atctgcaaga tgaagtgtgg gaaaacgggg tggactcagc cccagctcac atgtgtcgac     540
gaacagttat attttcaggg cggctcaggc ctgaacgaca tcttcgaggc ccagaagatc     600
gagtggcacg aggctcgagc tcaccaccat caccatcact ga                        642
```

<210> SEQ ID NO 286
<211> LENGTH: 480
<212> TYPE: PRT
<213> ORGANISM: Artificial Sequence
<220> FEATURE:
<223> OTHER INFORMATION: Cynomolgous IL-2R-beta-Fc(knob) fusion protein
      + Avi-tag

<400> SEQUENCE: 286

Met Gly Trp Ser Cys Ile Ile Leu Phe Leu Val Ala Thr Ala Thr Gly
1               5                   10                  15

Val His Ser Ala Val Asn Gly Thr Ser Arg Phe Thr Cys Phe Tyr Asn
            20                  25                  30

Ser Arg Ala Asn Ile Ser Cys Val Trp Ser Gln Asp Gly Ala Leu Gln
        35                  40                  45

Asp Thr Ser Cys Gln Val His Ala Trp Pro Asp Arg Arg Arg Trp Asn
    50                  55                  60

Gln Thr Cys Glu Leu Leu Pro Val Ser Gln Ala Ser Trp Ala Cys Asn
65                  70                  75                  80

Leu Ile Leu Gly Thr Pro Asp Ser Gln Lys Leu Thr Ala Val Asp Ile
                85                  90                  95

Val Thr Leu Arg Val Met Cys Arg Glu Gly Val Arg Trp Arg Met Met
            100                 105                 110

Ala Ile Gln Asp Phe Lys Pro Phe Glu Asn Leu Arg Leu Met Ala Pro
        115                 120                 125

Ile Ser Leu Gln Val Val His Val Glu Thr His Arg Cys Asn Ile Ser
    130                 135                 140

Trp Lys Ile Ser Gln Ala Ser His Tyr Phe Arg His Leu Glu Phe
145                 150                 155                 160

Glu Ala Arg Thr Leu Ser Pro Gly His Thr Trp Glu Glu Ala Pro Leu
            165                 170                 175

Met Thr Leu Lys Gln Lys Gln Glu Trp Ile Cys Leu Glu Thr Leu Thr
                180                 185                 190

Pro Asp Thr Gln Tyr Glu Phe Gln Val Arg Val Lys Pro Leu Gln Gly
            195                 200                 205

Glu Phe Thr Thr Trp Ser Pro Trp Ser Gln Pro Leu Ala Phe Arg Thr
210                 215                 220

Lys Pro Ala Ala Leu Gly Lys Asp Thr Gly Ala Gln Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Val Asp Val Ser His Glu Asp Pro Glu
            275                 280                 285

Val Lys Phe Asn Trp Tyr Val Asp Gly Val Glu Val His Asn Ala Lys
290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
                340                 345                 350

Ser Lys Ala Lys Gly Gln Pro Arg Glu Pro Gln Val Tyr Thr Leu Pro
            355                 360                 365

Pro Cys Arg Asp Glu Leu Thr Lys Asn Gln Val Ser Leu Trp Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys Ser
450                 455                 460

Gly Gly Leu Asn Asp Ile Phe Glu Ala Gln Lys Ile Glu Trp His Glu
465                 470                 475                 480

<210> SEQ ID NO 287
<211> LENGTH: 1443
<212> TYPE: DNA
<213> ORGANISM: Artificial Sequence
<220> FEATURE:
<223> OTHER INFORMATION: Cynomolgous IL-2R-beta-Fc(knob) fusion protein
      + Avi-tag

<400> SEQUENCE: 287
atgggatgga gctgtatcat cctcttcttg gtagcaacag ctaccggtgt gcattccgcg      60
gtcaacggca cttccggtt cacatgcttc tacaactcga gagccaacat ctcctgtgtc     120
tggagccaag atgggctct gcaggacact tcctgccaag tccacgcctg ccggacagaa     180

```
cggcggtgga accaaacctg tgagctgctc cctgtgagtc aagcatcctg ggcctgcaac    240
ctgatcctcg gaaccccaga ttctcagaaa ctgaccgcag tggatatcgt caccctgagg    300
gtgatgtgcc gtgaagggt gcgatggagg atgatggcca tccaggactt caaacccttt    360
gagaaccttc gcctgatggc ccccatctcc ctccaagtcg tccacgtgga gacccacaga    420
tgcaacataa gctggaaaat ctcccaagcc tcccactact ttgaaagaca cctggagttt    480
gaggcccgga cgctgtcccc aggccacacc tgggaggagg ccccctgat gaccctcaag     540
cagaagcagg aatggatctg cctggagacg ctcaccccag acacccagta tgagtttcag    600
gtgcgggtca gcctctgca aggcgagttc acgacctgga gccccctggag ccagcccctg    660
gccttcagga caaagcctgc agccttggg aaggacaccg gagctcagga caaaactcac     720
acatgcccac cgtgcccagc acctgaactc ctggggggac cgtcagtctt cctcttcccc    780
ccaaaaccca aggacaccct catgatctcc cggacccctg aggtcacatg cgtggtggtg    840
gacgtgagcc acgaagaccc tgaggtcaag ttcaactggt acgtggacgg cgtggaggtg    900
cataatgcca agacaaagcc gcgggaggag cagtacaaca gcacgtaccg tgtggtcagc    960
gtcctcaccg tcctgcacca ggactggctg aatggcaagg agtacaagtg caaggtctcc   1020
aacaaagccc tcccagcccc catcgagaaa accatctcca agccaaagg gcagccccga    1080
gaaccacagg tgtacaccct gcccccatgc cgggatgagc tgaccaagaa ccaggtcagc   1140
ctgtggtgcc tggtcaaagg cttctatccc agcgacatcg ccgtggagtg ggagagcaat   1200
gggcagccgg agaacaacta caagaccacg cctcccgtgc tggactccga cggctccttc   1260
ttcctctaca gcaagctcac cgtggacaag agcaggtggc agcaggggaa cgtcttctca   1320
tgctccgtga tgcatgaggc tctgcacaac cactacacgc agaagagcct ctccctgtct   1380
ccgggtaaat ccggaggcct gaacgacatc ttcgaggccc agaagattga atggcacgag   1440
tga                                                                1443
```

<210> SEQ ID NO 288
<211> LENGTH: 489
<212> TYPE: PRT
<213> ORGANISM: Artificial Sequence
<220> FEATURE:
<223> OTHER INFORMATION: Cynomolgous IL-2R-gamma-Fc(hole) fusion protein

<400> SEQUENCE: 288

```
Met Gly Trp Ser Cys Ile Ile Leu Phe Leu Val Ala Thr Ala Thr Gly
1               5                   10                  15

Val His Ser Leu Asn Thr Thr Ile Leu Thr Pro Asn Gly Asn Glu Asp
            20                  25                  30

Ala Thr Thr Asp Phe Phe Leu Thr Ser Met Pro Thr Asp Ser Leu Ser
        35                  40                  45

Val Ser Thr Leu Pro Leu Pro Glu Val Gln Cys Phe Val Phe Asn Val
    50                  55                  60

Glu Tyr Met Asn Cys Thr Trp Asn Ser Ser Glu Pro Gln Pro Thr
65                  70                  75                  80

Asn Leu Thr Leu His Tyr Trp Tyr Lys Asn Ser Asp Asn Asp Lys Val
                85                  90                  95

Gln Lys Cys Ser His Tyr Leu Phe Ser Glu Glu Ile Thr Ser Gly Cys
            100                 105                 110

Gln Leu Gln Lys Lys Glu Ile His Leu Tyr Gln Thr Phe Val Val Gln
        115                 120                 125
```

Leu Gln Asp Pro Arg Glu Pro Arg Arg Gln Ala Thr Gln Met Leu Lys
130                 135                 140

Leu Gln Asn Leu Val Ile Pro Trp Ala Pro Glu Asn Leu Thr Leu Arg
145                 150                 155                 160

Lys Leu Ser Glu Ser Gln Leu Glu Leu Asn Trp Asn Asn Arg Phe Leu
                165                 170                 175

Asn His Cys Leu Glu His Leu Val Gln Tyr Arg Thr Asp Trp Asp His
            180                 185                 190

Ser Trp Thr Glu Gln Ser Val Asp Tyr Arg His Lys Phe Ser Leu Pro
        195                 200                 205

Ser Val Asp Gly Gln Lys Arg Tyr Thr Phe Arg Val Arg Ser Arg Phe
210                 215                 220

Asn Pro Leu Cys Gly Ser Ala Gln His Trp Ser Glu Trp Ser His Pro
225                 230                 235                 240

Ile His Trp Gly Ser Asn Ser Ser Lys Glu Asn Pro Phe Leu Phe Ala
                245                 250                 255

Leu Glu Ala Gly Ala Gln Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
        355                 360                 365

Ala Leu Pro Ala Pro Ile Glu Lys Thr Ile Ser Lys Ala Lys Gly Gln
370                 375                 380

Pro Arg Glu Pro Gln Val Cys Thr Leu Pro Pro Ser Arg Asp Glu Leu
385                 390                 395                 400

Thr Lys Asn Gln Val Ser Leu Ser Cys Ala Val Lys Gly Phe Tyr Pro
                405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
        435                 440                 445

Val Ser Lys Leu Thr Val Asp Lys Ser Arg Trp Gln Gln Gly Asn Val
450                 455                 460

Phe Ser Cys Ser Val Met His Glu Ala Leu His Asn His Tyr Thr Gln
465                 470                 475                 480

Lys Ser Leu Ser Leu Ser Pro Gly Lys
                485

<210> SEQ ID NO 289
<211> LENGTH: 1470
<212> TYPE: DNA
<213> ORGANISM: Artificial Sequence
<220> FEATURE:
<223> OTHER INFORMATION: Cynomolgous IL-2R-gamma-Fc(hole) fusion protein

<400> SEQUENCE: 289

```
atgggatgga gctgtatcat cctcttcttg gtagcaacag ctaccggtgt gcattccctg      60
aacacgacaa ttctgacgcc caatgggaat gaagacgcca caactgattt cttcctgacc     120
tctatgccca ctgactccct cagtgttttc actctgcccc tcccagaggt tcagtgtttt     180
gtgttcaatg tcgagtacat gaattgcact tggaacagca gctctgagcc ccagcctacc     240
aacctcactc tgcattattg gtacaagaat tcggataatg ataaagtcca gaagtgcagc     300
cactatctat tctctgaaga aatcacttct ggctgtcagt tgcaaaaaaa ggagatccac     360
ctctaccaaa cgtttgttgt tcagctccag gacccacggg aacccaggag acaggccaca     420
cagatgctaa aactgcagaa tctggtgatc ccctgggctc cggagaacct aacacttcgc     480
aaactgagtg aatcccagct agaactgaac tggaacaaca gattcttgaa ccactgtttg     540
gagcacttgg tgcagtaccg gactgactgg gaccacagct ggactgaaca atcagtggat     600
tatagacata agttctcctt gcctagtgtg gatgggcaga aacgctacac gtttcgtgtc     660
cggagccgct ttaacccact ctgtggaagt gctcagcatt ggagtgaatg gagccaccca     720
atccactggg ggagcaatag ttcaaaagag aatccttttcc tgtttgcatt ggaagccgga     780
gctcaggaca aaactcacac atgcccaccg tgcccagcac ctgaactcct ggggggaccg     840
tcagtcttcc tcttcccccc aaaacccaag gacaccctca tgatctcccg gacccctgag     900
gtcacatgcg tggtggtgga cgtgagccac gaagaccctg aggtcaagtt caactggtac     960
gtggacggcg tggaggtgca taatgccaag acaaagccgc gggaggagca gtacaacagc    1020
acgtaccgtg tggtcagcgt cctcaccgtc ctgcaccagg actggctgaa tggcaaggag    1080
tacaagtgca aggtctccaa caaagccctc ccagccccca tcgagaaaac catctccaaa    1140
gccaaagggc agccccgaga accacaggtg tgcaccctgc cccatcccg ggatgagctg      1200
accaagaacc aggtcagcct ctcgtgcgca gtcaaaggct tctatcccag cgacatcgcc    1260
gtggagtggg agagcaatgg gcagccggag aacaactaca agaccacgcc tcccgtgctg    1320
gactccgacg gctccttctt cctcgtgagc aagctcaccg tggacaagag caggtggcag    1380
caggggaacg tcttctcatg ctccgtgatg catgaggctc tgcacaacca ctacacgcag    1440
aagagcctct ccctgtctcc gggtaaatga                                    1470
```

<210> SEQ ID NO 290
<211> LENGTH: 217
<212> TYPE: PRT
<213> ORGANISM: Artificial Sequence
<220> FEATURE:
<223> OTHER INFORMATION: Cynomolgous IL-2R alpha subunit + Avi-tag + His-tag

<400> SEQUENCE: 290

```
Met Gly Trp Ser Cys Ile Ile Leu Phe Leu Val Ala Thr Ala Thr Gly
1               5                   10                  15

Glu Leu Cys Asp Asp Asp Pro Pro Lys Ile Thr His Ala Thr Phe Lys
            20                  25                  30

Ala Met Ala Tyr Lys Glu Gly Thr Met Leu Asn Cys Glu Cys Lys Arg
        35                  40                  45

Gly Phe Arg Arg Ile Lys Ser Gly Ser Pro Tyr Met Leu Cys Thr Gly
    50                  55                  60

Asn Ser Ser His Ser Ser Trp Asp Asn Gln Cys Gln Cys Thr Ser Ser
65                  70                  75                  80

Ala Ala Arg Asn Thr Thr Lys Gln Val Thr Pro Gln Pro Glu Glu Gln
                85                  90                  95
```

```
Lys Glu Arg Lys Thr Thr Glu Met Gln Ser Gln Met Gln Leu Ala Asp
                100                 105                 110
Gln Val Ser Leu Pro Gly His Cys Arg Glu Pro Pro Trp Glu Asn
        115                 120                 125
Glu Ala Thr Glu Arg Ile Tyr His Phe Val Val Gly Gln Thr Val Tyr
    130                 135                 140
Tyr Gln Cys Val Gln Gly Tyr Arg Ala Leu His Arg Gly Pro Ala Glu
145                 150                 155                 160
Ser Val Cys Lys Met Thr His Gly Lys Thr Arg Trp Thr Gln Pro Gln
                165                 170                 175
Leu Ile Cys Thr Gly Glu Val Asp Glu Gln Leu Tyr Phe Gln Gly Gly
            180                 185                 190
Ser Gly Leu Asn Asp Ile Phe Glu Ala Gln Lys Ile Glu Trp His Glu
        195                 200                 205
Ala Arg Ala His His His His His His
    210                 215
```

<210> SEQ ID NO 291
<211> LENGTH: 654
<212> TYPE: DNA
<213> ORGANISM: Artificial Sequence
<220> FEATURE:
<223> OTHER INFORMATION: Cynomolgous IL-2R alpha subunit + Avi-tag +
    His-tag

<400> SEQUENCE: 291

```
atgggatgga gctgtatcat cctcttcttg gtagcaacag ctaccggtga gctctgtgac    60
gatgacccgc caaaaatcac acatgccaca ttcaaagcca tggcctacaa ggaaggaacc   120
atgttgaact gtgaatgcaa gagaggtttc gcagaataa aaagcgggtc accctatatg    180
ctctgtacag gaaactctag ccactcgtcc tgggacaacc aatgtcaatg cacaagctct   240
gctgctcgga cacaacaaa acaagtgaca cctcaacctg aagaacagaa agaaagaaaa    300
accacagaaa tgcaaagtca aatgcagctg gcggaccaag tgagccttcc aggtcactgc   360
agggaacctc caccgtggga aaatgaagcc acagaaagaa tttatcattt cgtggtgggg   420
cagacggttt actaccagtg cgtccaggga tacagggctc tacacagagg tcctgctgag   480
agcgtctgca aaatgaccca cgggaagaca agatggaccc agccccagct catatgcaca   540
ggtgaagtcg acgaacagtt atattttcag ggcggctcag gcctgaacga catcttcgag   600
gcccagaaga tcgagtggca cgaggctcga gctcaccacc atcaccatca ctga         654
```

<210> SEQ ID NO 292
<211> LENGTH: 399
<212> TYPE: DNA
<213> ORGANISM: Artificial Sequence
<220> FEATURE:
<223> OTHER INFORMATION: Wild-type IL-2 (C125A) (4)

<400> SEQUENCE: 292

```
gcacctactt caagttctac aaagaaaaca cagctacaac tggagcattt actgctggat    60
ttacagatga ttttgaatgg aattaataat tacaagaatc ccaaactcac caggatgctc   120
acatttaagt tttacatgcc caagaaggcc acagaactga acatcttca gtgtctagaa    180
gaagaactca aacctctgga ggaagtgcta aatttagctc aaagcaaaaa cttcacttta   240
agacccaggg acttaatcag caatatcaac gtaatagttc tggaactaaa gggatctgaa   300
acaacattca tgtgtgaata tgctgatgag acagcaacca ttgtagaatt tctgaacaga   360
```

```
tggattacct ttgcccaaag catcatctca acactgact                    399
```

<210> SEQ ID NO 293
<211> LENGTH: 399
<212> TYPE: DNA
<213> ORGANISM: Artificial Sequence
<220> FEATURE:
<223> OTHER INFORMATION: IL-2 mutant L72G (C125A) (4)

<400> SEQUENCE: 293

```
gcacctactt caagttctac aaagaaaaca cagctacaac tggagcattt actgctggat    60
ttacagatga ttttgaatgg aattaataat tacaagaatc ccaaactcac caggatgctc   120
acatttaagt tttacatgcc caagaaggcc acagaactga acatcttca gtgtctagaa    180
gaagaactca aacctctgga ggaagtgcta aatggcgctc aaagcaaaaa ctttcactta   240
agacccaggg acttaatcag caatatcaac gtaatagttc tggaactaaa gggatctgaa   300
acaacattca tgtgtgaata tgctgatgag acagcaacca ttgtagaatt tctgaacaga   360
tggattacct ttgcccaaag catcatctca acactgact                          399
```

<210> SEQ ID NO 294
<211> LENGTH: 399
<212> TYPE: DNA
<213> ORGANISM: Artificial Sequence
<220> FEATURE:
<223> OTHER INFORMATION: IL-2 mutant L72G / F42A (C125A) (4)

<400> SEQUENCE: 294

```
gcacctactt caagttctac aaagaaaaca cagctacaac tggagcattt actgctggat    60
ttacagatga ttttgaatgg aattaataat tacaagaatc ccaaactcac caggatgctc   120
acagccaagt tttacatgcc caagaaggcc acagaactga acatcttca gtgtctagaa    180
gaagaactca aacctctgga ggaagtgcta aatggcgctc aaagcaaaaa ctttcactta   240
agacccaggg acttaatcag caatatcaac gtaatagttc tggaactaaa gggatctgaa   300
acaacattca tgtgtgaata tgctgatgag acagcaacca ttgtagaatt tctgaacaga   360
tggattacct ttgcccaaag catcatctca acactgact                          399
```

<210> SEQ ID NO 295
<211> LENGTH: 399
<212> TYPE: DNA
<213> ORGANISM: Artificial Sequence
<220> FEATURE:
<223> OTHER INFORMATION: IL-2 triple mutant F42A / Y45A / L72G (C125A)
      (4)

<400> SEQUENCE: 295

```
gcacctactt caagttctac aaagaaaaca cagctacaac tggagcattt actgctggat    60
ttacagatga ttttgaatgg aattaataat tacaagaatc ccaaactcac caggatgctc   120
acagccaagt tgccatgcc caagaaggcc acagaactga acatcttca gtgtctagaa     180
gaagaactca aacctctgga ggaagtgcta aatggcgctc aaagcaaaaa ctttcactta   240
agacccaggg acttaatcag caatatcaac gtaatagttc tggaactaaa gggatctgaa   300
acaacattca tgtgtgaata tgctgatgag acagcaacca ttgtagaatt tctgaacaga   360
tggattacct ttgcccaaag catcatctca acactgact                          399
```

<210> SEQ ID NO 296
<211> LENGTH: 399
<212> TYPE: DNA

<213> ORGANISM: Artificial Sequence
<220> FEATURE:
<223> OTHER INFORMATION: IL-2 quadruple mutant T3A / F42A /Y45A /L72G (C125A) (4)

<400> SEQUENCE: 296

```
gcacctgcct caagttctac aaagaaaaca cagctacaac tggagcattt actgctggat      60
ttacagatga ttttgaatgg aattaataat tacaagaatc ccaaactcac caggatgctc     120
acagccaagt ttgccatgcc caagaaggcc acagaactga acatcttca gtgtctagaa      180
gaagaactca aacctctgga ggaagtgcta atggcgctc aaagcaaaaa ctttcactta      240
agacccaggg acttaatcag caatatcaac gtaatagttc tggaactaaa gggatctgaa      300
acaacattca tgtgtgaata tgctgatgag acagcaacca ttgtagaatt tctgaacaga      360
tggattacct ttgcccaaag catcatctca acactgact                            399
```

<210> SEQ ID NO 297
<211> LENGTH: 593
<212> TYPE: PRT
<213> ORGANISM: Artificial Sequence
<220> FEATURE:
<223> OTHER INFORMATION: 28H1 Fab heavy chain-Fc (knob)-IL-2 qm

<400> SEQUENCE: 297

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255
```

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Cys Arg Asp Glu Leu Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Gly Gly Gly
        435                 440                 445

Gly Ser Gly Gly Gly Ser Gly Gly Gly Ser Ala Pro Ala Ser
    450                 455                 460

Ser Ser Thr Lys Lys Thr Gln Leu Gln Leu Glu His Leu Leu Leu Asp
465                 470                 475                 480

Leu Gln Met Ile Leu Asn Gly Ile Asn Asn Tyr Lys Asn Pro Lys Leu
                485                 490                 495

Thr Arg Met Leu Thr Ala Lys Phe Ala Met Pro Lys Lys Ala Thr Glu
            500                 505                 510

Leu Lys His Leu Gln Cys Leu Glu Glu Glu Leu Lys Pro Leu Glu Glu
        515                 520                 525

Val Leu Asn Gly Ala Gln Ser Lys Asn Phe His Leu Arg Pro Arg Asp
    530                 535                 540

Leu Ile Ser Asn Ile Asn Val Ile Val Leu Glu Leu Lys Gly Ser Glu
545                 550                 555                 560

Thr Thr Phe Met Cys Glu Tyr Ala Asp Glu Thr Ala Thr Ile Val Glu
                565                 570                 575

Phe Leu Asn Arg Trp Ile Thr Phe Ala Gln Ser Ile Ile Ser Thr Leu
            580                 585                 590

Thr

<210> SEQ ID NO 298
<211> LENGTH: 1779
<212> TYPE: DNA
<213> ORGANISM: Artificial Sequence
<220> FEATURE:
<223> OTHER INFORMATION: 28H1 Fab heavy chain-Fc (knob)-IL-2 qm

<400> SEQUENCE: 298
gaagtgcagc tgctggaatc cggcggaggc ctggtgcagc ctggcggatc tctgagactg      60
tcctgcgccg cctccggctt caccttctcc tcccacgcca tgtcctgggt ccgacaggct     120

```
cctggcaaag gcctggaatg ggtgtccgcc atctgggcct ccggcgagca gtactacgcc      180
gactctgtga agggccggtt caccatctcc cgggacaact ccaagaacac cctgtacctg      240
cagatgaact ccctgcgggc cgaggacacc gccgtgtact actgtgccaa gggctggctg      300
ggcaacttcg actactgggg cagggcacc ctggtcaccg tgtccagcgc tagcaccaag       360
ggcccatcgg tcttccccct ggcaccctcc tccaagagca cctctggggg cacagcggcc      420
ctgggctgcc tggtcaagga ctacttcccc gaaccggtga cggtgtcgtg gaactcaggc      480
gccctgacca gcggcgtgca caccttcccg gctgtcctac agtcctcagg actctactcc      540
ctcagcagcg tggtgaccgt gccctccagc agcttgggca cccagaccta catctgcaac      600
gtgaatcaca agcccagcaa caccaaggtg gacaagaaag ttgagcccaa atcttgtgac      660
aaaactcaca catgcccacc gtgcccagca cctgaagctg caggggggacc gtcagtcttc      720
ctcttccccc caaaacccaa ggacaccctc atgatctccc ggacccctga ggtcacatgc      780
gtggtggtgg acgtgagcca cgaagaccct gaggtcaagt tcaactggta cgtggacggc      840
gtggaggtgc ataatgccaa gacaaagccg cgggaggagc agtacaacag cacgtaccgt      900
gtggtcagcg tcctcaccgt cctgcaccag gactggctga atggcaagga gtacaagtgc      960
aaggtctcca acaaagccct cggcgccccc atcgagaaaa ccatctccaa agccaaaggg     1020
cagccccgag aaccacaggt gtacaccctg cccccatgcc gggatgagct gaccaagaac     1080
caggtcagcc tgtggtgcct ggtcaaaggc ttctatccca gcgacatcgc cgtggagtgg     1140
gagagcaatg ggcagccgga gaacaactac aagaccacgc ctcccgtgct ggactccgac     1200
ggctccttct cctctacag caagctcacc gtggacaaga gcaggtggca gcaggggaac      1260
gtcttctcat gctccgtgat gcatgaggct ctgcacaacc actacacgca gaagagcctc     1320
tccctgtctc cgggtggcgg cggaggctcc ggaggcggag gttctggcgg aggtggctcc     1380
gcacctgcct caagttctac aaagaaaaca cagctacaac tggagcattt actgctggat     1440
ttacagatga ttttgaatgg aattaataat tacaagaatc ccaaactcac caggatgctc     1500
acagccaagt ttgccatgcc caagaaggcc acagaactga acatcttca gtgtctagaa      1560
gaagaactca aacctctgga ggaagtgcta aatggcgctc aaagcaaaaa cttttcactta    1620
agacccaggg acttaatcag caatatcaac gtaatagttc tggaactaaa gggatctgaa     1680
acaacattca tgtgtgaata tgctgatgag acagcaacca ttgtagaatt tctgaacaga     1740
tggattacct tgcccaaag catcatctca acactgact                             1779
```

<210> SEQ ID NO 299
<211> LENGTH: 446
<212> TYPE: PRT
<213> ORGANISM: Artificial Sequence
<220> FEATURE:
<223> OTHER INFORMATION: 28H1 Fab heavy chain-Fc (hole)

<400> SEQUENCE: 299

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu

```
                65                  70                  75                  80
        Gln Met Asn Ser Leu Arg Ala Glu Asp Thr Ala Val Tyr Tyr Cys Ala
                            85                  90                  95

Lys Gly Trp Leu Gly Asn Phe Asp Tyr Trp Gly Gln Gly Thr Leu Val
                            100                 105                 110

Thr Val Ser Ser Ala Ser Thr Lys Gly Pro Ser Val Phe Pro Leu Ala
                            115                 120                 125

Pro Ser Ser Lys Ser Thr Ser Gly Gly Thr Ala Ala Leu Gly Cys Leu
                    130                 135                 140

Val Lys Asp Tyr Phe Pro Glu Pro Val Thr Val Ser Trp Asn Ser Gly
        145                 150                 155                 160

Ala Leu Thr Ser Gly Val His Thr Phe Pro Ala Val Leu Gln Ser Ser
                            165                 170                 175

Gly Leu Tyr Ser Leu Ser Ser Val Val Thr Val Pro Ser Ser Ser Leu
                            180                 185                 190

Gly Thr Gln Thr Tyr Ile Cys Asn Val Asn His Lys Pro Ser Asn Thr
                    195                 200                 205

Lys Val Asp Lys Lys Val Glu Pro Lys Ser Cys Asp Lys Thr His Thr
                    210                 215                 220

Cys Pro Pro Cys Pro Ala Pro Glu Ala Ala Gly Gly Pro Ser Val Phe
        225                 230                 235                 240

Leu Phe Pro Pro Lys Pro Lys Asp Thr Leu Met Ile Ser Arg Thr Pro
                            245                 250                 255

Glu Val Thr Cys Val Val Val Asp Val Ser His Glu Asp Pro Glu Val
                            260                 265                 270

Lys Phe Asn Trp Tyr Val Asp Gly Val Glu Val His Asn Ala Lys Thr
                    275                 280                 285

Lys Pro Arg Glu Glu Gln Tyr Asn Ser Thr Tyr Arg Val Val Ser Val
                    290                 295                 300

Leu Thr Val Leu His Gln Asp Trp Leu Asn Gly Lys Glu Tyr Lys Cys
        305                 310                 315                 320

Lys Val Ser Asn Lys Ala Leu Gly Ala Pro Ile Glu Lys Thr Ile Ser
                            325                 330                 335

Lys Ala Lys Gly Gln Pro Arg Glu Pro Gln Val Cys Thr Leu Pro Pro
                            340                 345                 350

Ser Arg Asp Glu Leu Thr Lys Asn Gln Val Ser Leu Ser Cys Ala Val
                    355                 360                 365

Lys Gly Phe Tyr Pro Ser Asp Ile Ala Val Glu Trp Glu Ser Asn Gly
                    370                 375                 380

Gln Pro Glu Asn Asn Tyr Lys Thr Thr Pro Pro Val Leu Asp Ser Asp
        385                 390                 395                 400

Gly Ser Phe Phe Leu Val Ser Lys Leu Thr Val Asp Lys Ser Arg Trp
                            405                 410                 415

Gln Gln Gly Asn Val Phe Ser Cys Ser Val Met His Glu Ala Leu His
                            420                 425                 430

Asn His Tyr Thr Gln Lys Ser Leu Ser Leu Ser Pro Gly Lys
                    435                 440                 445

<210> SEQ ID NO 300
<211> LENGTH: 1338
<212> TYPE: DNA
<213> ORGANISM: Artificial Sequence
<220> FEATURE:
<223> OTHER INFORMATION: 28H1 Fab heavy chain-Fc (hole)
```

<400> SEQUENCE: 300

```
gaagtgcagc tgctggaatc cggcggaggc ctggtgcagc ctggcggatc tctgagactg    60
tcctgcgccg cctccggctt caccttctcc tcccacgcca tgtcctgggt ccgacaggct   120
cctggcaaag gcctggaatg ggtgtccgcc atctgggcct ccggcgagca gtactacgcc   180
gactctgtga agggccggtt caccatctcc cgggacaact ccaagaacac cctgtacctg   240
cagatgaact ccctgcgggc cgaggacacc gccgtgtact actgtgccaa gggctggctg   300
ggcaacttcg actactgggg acagggcacc ctggtcaccg tgtccagcgc tagcaccaag   360
ggcccctccg tgttccccct ggccccccagc agcaagagca ccagcggcgg cacagccgct   420
ctgggctgcc tggtcaagga ctacttcccc gagcccgtga ccgtgtcctg aacagcgga   480
gccctgacct ccggcgtgca caccttcccc gccgtgctgc agagttctgg cctgtatagc   540
ctgagcagcg tggtcaccgt gccttctagc agcctgggca cccagaccta tctgcaac    600
gtgaaccaca gcccagcaa caccaaggtg gacaagaagg tggagcccaa gagctgcgac   660
aaaactcaca catgcccacc gtgcccagca cctgaagctg caggggaccc gtcagtcttc   720
ctcttccccc caaaacccaa ggacaccctc atgatctccc ggacccctga ggtcacatgc   780
gtggtggtgg acgtgagcca cgaagaccct gaggtcaagt tcaactggta cgtggacggc   840
gtggaggtgc ataatgccaa gacaaagccg cgggaggagc agtacaacag cacgtaccgt   900
gtggtcagcg tcctcaccgt cctgcaccag gactggctga atggcaagga gtacaagtgc   960
aaggtctcca acaaagccct cggcgccccc atcgagaaaa ccatctccaa agccaagggc  1020
cagccccgag aaccacaggt gtgcaccctg cccccatccc gggatgagct gaccaagaac  1080
caggtcagcc tctcgtgcgc agtcaaaggc ttctatccca gcgacatcgc cgtggagtgg  1140
gagagcaatg gcagccgga gaacaactac aagaccacgc tccccgtgct ggactccgac  1200
ggctccttct tcctcgtgag caagctcacc gtggacaaga gcaggtggca gcaggggaac  1260
gtcttctcat gctccgtgat gcatgaggct ctgcacaacc actacacgca gaagagcctc  1320
tccctgtctc cgggtaaa                                                1338
```

<210> SEQ ID NO 301
<211> LENGTH: 594
<212> TYPE: PRT
<213> ORGANISM: Artificial Sequence
<220> FEATURE:
<223> OTHER INFORMATION: 4B9 Fab heavy chain-Fc (knob)-IL-2 qm

<400> SEQUENCE: 301

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ile Gly Ser Gly Ala Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Gly Trp Phe Gly Gly Phe Asn Tyr Trp Gly Gln Gly Thr Leu
            100                 105                 110
```

```
Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Ser Gly Gly Gly Ser Ala Pro Ala
    450                 455                 460

Ser Ser Ser Thr Lys Lys Thr Gln Leu Gln Leu Glu His Leu Leu Leu
465                 470                 475                 480

Asp Leu Gln Met Ile Leu Asn Gly Ile Asn Asn Tyr Lys Asn Pro Lys
                485                 490                 495

Leu Thr Arg Met Leu Thr Ala Lys Phe Ala Met Pro Lys Lys Ala Thr
            500                 505                 510

Glu Leu Lys His Leu Gln Cys Leu Glu Glu Glu Leu Lys Pro Leu Glu
        515                 520                 525

Glu Val Leu Asn Gly Ala Gln Ser Lys Asn Phe His Leu Arg Pro Arg
```

```
            530                 535                 540
Asp Leu Ile Ser Asn Ile Asn Val Ile Val Leu Glu Leu Lys Gly Ser
545                 550                 555                 560

Glu Thr Thr Phe Met Cys Glu Tyr Ala Asp Glu Thr Ala Thr Ile Val
                565                 570                 575

Glu Phe Leu Asn Arg Trp Ile Thr Phe Ala Gln Ser Ile Ile Ser Thr
                580                 585                 590

Leu Thr
```

<210> SEQ ID NO 302
<211> LENGTH: 1782
<212> TYPE: DNA
<213> ORGANISM: Artificial Sequence
<220> FEATURE:
<223> OTHER INFORMATION: 4B9 Fab heavy chain-Fc (knob)-IL-2 qm

<400> SEQUENCE: 302

```
gaggtgcagc tgctcgaaag cggcggagga ctggtgcagc ctggcggcag cctgagactg       60
tcttgcgccg ccagcggctt caccttcagc agctacgcca tgagctgggt ccgccaggcc      120
cctggcaagg gactggaatg ggtgtccgcc atcatcggct ctggcgccag cacctactac      180
gccgacagcg tgaagggccg gttcaccatc agccgggaca cagcaagaa caccctgtac      240
ctgcagatga acagcctgcg ggccgaggac accgccgtgt actactgcgc caagggatgg      300
ttcggcggct tcaactactg gggacagggc accctggtca cagtgtccag cgctagcacc      360
aagggcccat cggtcttccc cctggcaccc tcctccaaga gcacctctgg gggcacagcg      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga agttgagcc caaatcttgt      660
gacaaaactc acacatgccc accgtgccca gcacctgaag ctgcagggg accgtcagtc      720
ttcctcttcc ccccaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcggcgcc cccatcgaga aaaccatctc caaagccaaa     1020
gggcagcccc gagaaccaca ggtgtacacc ctgcccccat gccgggatga gctgaccaag     1080
aaccaggtca gcctgtggtg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta cagcaagctc accgtggaca agagcaggtg gcagcagggg     1260
aacgtcttct catgctccgt gatgcatgag gctctgcaca accactacac gcagaagagc     1320
ctctccctgt ctccgggtgg cggcggaggc tccggaggcg aggttctgg cggaggtggc     1380
tccgcacctg cctcaagttc tacaaagaaa acacagctac aactggagca tttactgctg     1440
gatttacaga tgattttgaa tggaattaat aattacaaga atcccaaact caccaggatg     1500
ctcacagcca gtttgccat gcccaagaag gccacagaac tgaaacatct tcagtgtcta     1560
gaagaagaac tcaaacctct ggaggaagtg ctaaatggcg ctcaaagcaa aaactttcac     1620
ttaagaccca gggacttaat cagcaatatc aacgtaatag ttctggaact aaagggatct     1680
```

```
gaaacaacat tcatgtgtga atatgctgat gagacagcaa ccattgtaga atttctgaac    1740
agatggatta cctttgccca aagcatcatc tcaacactga ct                      1782
```

<210> SEQ ID NO 303
<211> LENGTH: 447
<212> TYPE: PRT
<213> ORGANISM: Artificial Sequence
<220> FEATURE:
<223> OTHER INFORMATION: 4B9 Fab heavy chain-Fc (hole)

<400> SEQUENCE: 303

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
            340                 345                 350
```

```
Pro Ser Arg Asp Glu Leu Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 304
<211> LENGTH: 1341
<212> TYPE: DNA
<213> ORGANISM: Artificial Sequence
<220> FEATURE:
<223> OTHER INFORMATION: 4B9 Fab heavy chain-Fc (hole)

<400> SEQUENCE: 304
gaggtgcagc tgctcgaaag cggcggagga ctggtgcagc ctggcggcag cctgagactg      60
tcttgcgccg ccagcggctt caccttcagc agctacgcca tgagctgggt ccgccaggcc     120
cctggcaagg gactggaatg ggtgtccgcc atcatcggct ctggcgccag cacctactac     180
gccgacagcg tgaagggccg gttcaccatc agccgggaca acagcaagaa caccctgtac     240
ctgcagatga acagcctgcg ggccgaggac accgccgtgt actactgcgc caagggatgg     300
ttcggcggct tcaactactg gggacagggc accctggtca cagtgtccag cgctagcacc     360
aagggcccct ccgtgttccc cctggccccc agcagcaaga gcaccagcgg cggcacagcc     420
gctctgggct gcctggtcaa ggactacttc cccgagcccg tgaccgtgtc ctggaacagc     480
ggagccctga cctccggcgt gcacaccttc cccgccgtgc tgcagagttc tggcctgtat     540
agcctgagca gcgtggtcac cgtgccttct agcagcctgg gcacccagac ctacatctgc     600
aacgtgaacc acaagcccag caacaccaag gtggacaaga aggtggagcc caagagctgc     660
gacaaaactc acacatgccc accgtgccca gcacctgaag ctgcagggg a ccgtcagtc     720 ttcctcttcc cccaaaaccc aaggacaccc tcatgatctc ccggacccc t gaggtcaca     780 tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcggcgcc cccatcgaga aaaccatctc caaagccaaa    1020 ggcagcccc gagaaccaca ggtgtgcacc ctgcccccat cccgggatga gctgaccaag    1080
aaccaggtca gcctctcgtg cgcagtcaaa ggcttctatc cagcgacat cgccgtggag    1140 tgggagagca atgggcagcc ggagaacaac tacaagacca cgcctcccgt gctggactcc    1200
gacggctcct tcttcctcgt gagcaagctc accgtggaca agagcaggtg gcagcagggg    1260
aacgtcttct catgctccgt gatgcatgag gctctgcaca accactacac gcagaagagc    1320
ctctccctgt ctccgggtaa a                                              1341

<210> SEQ ID NO 305
<211> LENGTH: 592
<212> TYPE: PRT
```

<213> ORGANISM: Artificial Sequence
<220> FEATURE:
<223> OTHER INFORMATION: DP47GS Fab heavy chain-Fc (knob)-IL-2 qm

<400> SEQUENCE: 305

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Cys
            340                 345                 350

Arg Asp Glu Leu Thr Lys Asn Gln Val Ser Leu Trp Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
```

```
            385                 390                 395                 400
        Ser Phe Phe Leu Tyr Ser Lys Leu Thr Val Asp Lys Ser Arg Trp Gln
                        405                 410                 415

Gln Gly Asn Val Phe Ser Cys Ser Val Met His Glu Ala Leu His Asn
                        420                 425                 430

His Tyr Thr Gln Lys Ser Leu Ser Leu Ser Pro Gly Gly Gly Gly
                        435                 440                 445

Ser Gly Gly Gly Gly Ser Gly Gly Gly Ser Ala Pro Ala Ser Ser
        450                 455                 460

Ser Thr Lys Lys Thr Gln Leu Gln Leu Glu His Leu Leu Asp Leu
        465                 470                 475                 480

Gln Met Ile Leu Asn Gly Ile Asn Asn Tyr Lys Asn Pro Lys Leu Thr
                        485                 490                 495

Arg Met Leu Thr Ala Lys Phe Ala Met Pro Lys Lys Ala Thr Glu Leu
                        500                 505                 510

Lys His Leu Gln Cys Leu Glu Glu Glu Leu Lys Pro Leu Glu Glu Val
                        515                 520                 525

Leu Asn Gly Ala Gln Ser Lys Asn Phe His Leu Arg Pro Arg Asp Leu
        530                 535                 540

Ile Ser Asn Ile Asn Val Ile Val Leu Glu Leu Lys Gly Ser Glu Thr
        545                 550                 555                 560

Thr Phe Met Cys Glu Tyr Ala Asp Glu Thr Ala Thr Ile Val Glu Phe
                        565                 570                 575

Leu Asn Arg Trp Ile Thr Phe Ala Gln Ser Ile Ile Ser Thr Leu Thr
                        580                 585                 590

<210> SEQ ID NO 306
<211> LENGTH: 1776
<212> TYPE: DNA
<213> ORGANISM: Artificial Sequence
<220> FEATURE:
<223> OTHER INFORMATION: DP47GS Fab heavy chain-Fc (knob)-IL-2 qm

<400> SEQUENCE: 306
gaggtgcaat gttggagtc tgggggaggc ttggtacagc ctgggggtc cctgagactc        60 tcctgtgcag cctccggatt cacctttagc agttatgcca tgagctgggt ccgccaggct       120
ccagggaagg gctgagtg gtctcagct attagtggta gtggtggtag cacatactac       180
gcagactccg tgaagggccg gttcaccatc tccagagaca attccaagaa cacgctgtat       240
ctgcagatga acagcctgag agccgaggac acggccgtat attactgtgc gaaaggcagc       300
ggatttgact actggggcca aggaaccctg gtcaccgtct cgagtgctag caccaagggc       360
ccatcggtct tccccctggc accctcctcc aagagcacct ctgggggcac agcggccctg       420
ggctgcctgg tcaaggacta cttccccgaa ccggtgacgg tgtcgtggaa ctcaggcgcc       480
ctgaccagcg gcgtgcacac cttcccggct gtcctacagt cctcaggact ctactccctc       540
agcagcgtgg tgaccgtgcc ctccagcagc ttgggcaccc agacctacat ctgcaacgtg       600
aatcacaagc ccagcaacac caaggtggac aagaaagttg agcccaaatc ttgtgacaaa       660
actcacacat gcccaccgtg cccagcacct gaagctgcag gggaccgtc agtcttcctc       720 ttccccccaa aacccaagga caccctcatg atctcccgga cccctgaggt cacatgcgtg       780
gtggtggacg tgagccacga agaccctgag gtcaagttca actggtacgt ggacggcgtg       840
gaggtgcata atgccaagac aaagccgcgg gaggagcagt acaacagcac gtaccgtgtg       900
gtcagcgtcc tcaccgtcct gcaccaggac tggctgaatg gcaaggagta caagtgcaag       960
```

-continued

```
gtctccaaca aagccctcgg cgcccccatc gagaaaacca tctccaaagc caaagggcag      1020
ccccgagaac acaggtgta cacctgccc ccatgccggg atgagctgac caagaaccag       1080
gtcagcctgt ggtgcctggt caaaggcttc tatcccagcg acatcgccgt ggagtgggag     1140
agcaatgggc agccggagaa caactacaag accacgcctc ccgtgctgga ctccgacggc     1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtggcggcgg aggctccgga ggcggaggtt ctggcggagg tggctccgca    1380
cctgcctcaa gttctacaaa gaaaacacag ctacaactgg agcatttact gctggattta    1440
cagatgattt tgaatggaat taataattac aagaatccca aactcaccag gatgctcaca    1500
gccaagtttg ccatgcccaa gaaggccaca gaactgaaac atcttcagtg tctagaagaa    1560
gaactcaaac ctctggagga agtgctaaat ggcgctcaaa gcaaaaactt tcacttaaga    1620
cccagggact taatcagcaa tatcaacgta atagttctgg aactaaaggg atctgaaaca    1680
acattcatgt gtgaatatgc tgatgagaca gcaaccattg tagaatttct gaacagatgg    1740
attacctttg cccaaagcat catctcaaca ctgact                              1776
```

<210> SEQ ID NO 307
<211> LENGTH: 445
<212> TYPE: PRT
<213> ORGANISM: Artificial Sequence
<220> FEATURE:
<223> OTHER INFORMATION: DP47GS Fab heavy chain-Fc (hole)

<400> SEQUENCE: 307

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
```

```
            210                 215                 220
Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Cys Thr Leu Pro Pro Ser
            340                 345                 350

Arg Asp Glu Leu Thr Lys Asn Gln Val Ser Leu Ser Cys Ala Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Val Leu Asp Ser Asp Gly
385                 390                 395                 400

Ser Phe Phe Leu Val Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 308
<211> LENGTH: 1335
<212> TYPE: DNA
<213> ORGANISM: Artificial Sequence
<220> FEATURE:
<223> OTHER INFORMATION: DP47GS Fab heavy chain-Fc (hole)

<400> SEQUENCE: 308
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaaggcagc     300
ggatttgact actggggcca aggaaccctg gtcaccgtct cgagtgctag caccaagggc     360
ccctccgtgt tccccctggc cccagcagc aagagcacca cggcggcac agccgctctg      420 ggctgcctgg tcaaggacta cttccccgag cccgtgaccg tgtcctggaa cagcggagcc     480
ctgacctccg gcgtgcacac cttccccgcc gtgctgcaga gttctggcct gtatagcctg     540
agcagcgtgg tcaccgtgcc ttctagcagc ctgggcaccc agacctacat ctgcaacgtg     600
aaccacaagc ccagcaacac caaggtggac aagaaggtgg agcccaagag ctgcgacaaa     660
actcacacat gcccaccgtg cccagcacct gaagctgcag gggaccgtc agtcttcctc       720 ttccccccaa aacccaagga caccctcatg atctcccgga cccctgaggt cacatgcgtg     780
```

```
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctcgg cgcccccatc gagaaaacca tctccaaagc caaagggcag   1020
ccccgagaac cacaggtgtg caccctgccc ccatcccggg atgagctgac caagaaccag   1080
gtcagcctct cgtgcgcagt caaaggcttc tatcccagcg acatcgccgt ggagtgggag   1140
agcaatgggc agccggagaa caactacaag accacgcctc ccgtgctgga ctccgacggc   1200
tccttcttcc tcgtgagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaa                                                   1335
```

<210> SEQ ID NO 309
<211> LENGTH: 215
<212> TYPE: PRT
<213> ORGANISM: Artificial Sequence
<220> FEATURE:
<223> OTHER INFORMATION: DP47GS light chain

<400> SEQUENCE: 309

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 310
<211> LENGTH: 645
<212> TYPE: DNA
<213> ORGANISM: Artificial Sequence
<220> FEATURE:

<223> OTHER INFORMATION: DP47GS light chain

<400> SEQUENCE: 310

```
gaaatcgtgt taacgcagtc tccaggcacc ctgtctttgt ctccagggga aagagccacc    60
ctctcttgca gggccagtca gagtgttagc agcagctact tagcctggta ccagcagaaa   120
cctggccagg ctcccaggct cctcatctat ggagcatcca gcagggccac tggcatccca   180
gacaggttca gtggcagtgg atccgggaca gacttcactc tcaccatcag cagactggag   240
cctgaagatt ttgcagtgta ttactgtcag cagtatggta gctcaccgct gacgttcggc   300
caggggacca agtgtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac gagaaacac aaagtctacg cctgcgaagt cacccatcag   600
ggcctgagct cgcccgtcac aaagagcttc aacaggggag agtgt               645
```

<210> SEQ ID NO 311
<211> LENGTH: 108
<212> TYPE: PRT
<213> ORGANISM: Artificial Sequence
<220> FEATURE:
<223> OTHER INFORMATION: CH1A1A; VL

<400> SEQUENCE: 311

```
Asp Ile Gln Met Thr Gln Ser Pro Ser Ser Leu Ser Ala Ser Val Gly
1               5                   10                  15
Asp Arg Val Thr Ile Thr Cys Lys Ala Ser Ala Ala Val Gly Thr Tyr
            20                  25                  30
Val Ala Trp Tyr Gln Gln Lys Pro Gly Lys Ala Pro Lys Leu Leu Ile
        35                  40                  45
Tyr Ser Ala Ser Tyr Arg Lys Arg Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys His Gln Tyr Tyr Thr Tyr Pro Leu
                85                  90                  95
Phe Thr Phe Gly Gln Gly Thr Lys Leu Glu Ile Lys
            100                 105
```

<210> SEQ ID NO 312
<211> LENGTH: 324
<212> TYPE: DNA
<213> ORGANISM: Artificial Sequence
<220> FEATURE:
<223> OTHER INFORMATION: CH1A1A; VL

<400> SEQUENCE: 312

```
gatatccaga tgacccagtc tccatcctcc ctgtctgcat ctgtgggaga cagagtcacc    60
atcacttgca aggccagtgc ggctgtgggt acgtatgttg cgtggtatca gcagaaacca   120
gggaaagcac ctaagctcct gatctattcg gcatcctacc gcaaaagggg agtcccatca   180
aggttcagtg gcagtggatc tgggacagat ttcactctca ccatcagcag tctgcaacct   240
gaagatttcg caacttacta ctgtcaccaa tattacacct atcctctatt cacgtttggc   300
cagggcacca agctcgagat caag                                          324
```

<210> SEQ ID NO 313
<211> LENGTH: 121
<212> TYPE: PRT
<213> ORGANISM: Artificial Sequence
<220> FEATURE:
<223> OTHER INFORMATION: CH1A1A; VH

<400> SEQUENCE: 313

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Glu Phe
            20                  25                  30
Gly Met Asn Trp Val Arg Gln Ala Pro Gly Gln Gly Leu Glu Trp Met
        35                  40                  45
Gly Trp Ile Asn Thr Lys Thr Gly Glu Ala Thr Tyr Val Glu Glu Phe
    50                  55                  60
Lys Gly Arg Val Thr Phe Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Trp Asp Phe Ala Tyr Tyr Val Glu Ala Met Asp Tyr Trp Gly
            100                 105                 110
Gln Gly Thr Thr Val Thr Val Ser Ser
        115                 120
```

<210> SEQ ID NO 314
<211> LENGTH: 363
<212> TYPE: DNA
<213> ORGANISM: Artificial Sequence
<220> FEATURE:
<223> OTHER INFORMATION: CH1A1A; VH

<400> SEQUENCE: 314

```
caggtgcagc tggtgcagtc tggcgccgaa gtgaagaaac ctggagctag tgtgaaggtg      60
tcctgcaagg ccagcggcta caccttcacc gagttcggca tgaactgggt ccgacaggct     120
ccaggccagg gcctcgaatg gatgggctgg atcaacacca agaccggcga ggccacctac     180
gtggaagagt tcaagggcag agtgaccttc accacggaca ccagcaccag caccgcctac     240
atggaactgc ggagcctgag aagcgacgac accgccgtgt actactgcgc cagatgggac     300
ttcgcctatt acgtggaagc catggactac tggggccagg gcaccaccgt gaccgtgtct     360
agc                                                                   363
```

<210> SEQ ID NO 315
<211> LENGTH: 594
<212> TYPE: PRT
<213> ORGANISM: Artificial Sequence
<220> FEATURE:
<223> OTHER INFORMATION: 4G8 Fab heavy chain-Fc (knob)-IL-2 qm

<400> SEQUENCE: 315

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Trp Leu Gly Asn Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Gly Ser Gly Gly Gly Gly Ser Ala Pro Ala
450                 455                 460

Ser Ser Ser Thr Lys Lys Thr Gln Leu Gln Leu Glu His Leu Leu Leu
465                 470                 475                 480
```

```
Asp Leu Gln Met Ile Leu Asn Gly Ile Asn Asn Tyr Lys Asn Pro Lys
            485                 490                 495
Leu Thr Arg Met Leu Thr Ala Lys Phe Ala Met Pro Lys Lys Ala Thr
        500                 505                 510
Glu Leu Lys His Leu Gln Cys Leu Glu Glu Glu Leu Lys Pro Leu Glu
        515                 520                 525
Glu Val Leu Asn Gly Ala Gln Ser Lys Asn Phe His Leu Arg Pro Arg
    530                 535                 540
Asp Leu Ile Ser Asn Ile Asn Val Ile Val Leu Glu Leu Lys Gly Ser
545                 550                 555                 560
Glu Thr Thr Phe Met Cys Glu Tyr Ala Asp Glu Thr Ala Thr Ile Val
                565                 570                 575
Glu Phe Leu Asn Arg Trp Ile Thr Phe Ala Gln Ser Ile Ile Ser Thr
            580                 585                 590
Leu Thr
```

<210> SEQ ID NO 316
<211> LENGTH: 1782
<212> TYPE: DNA
<213> ORGANISM: Artificial Sequence
<220> FEATURE:
<223> OTHER INFORMATION: 4G8 Fab heavy chain-Fc (knob)-IL-2 qm

<400> SEQUENCE: 316

```
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaagggtgg     300
ctgggtaatt ttgactactg gggccaagga accctggtca ccgtctcgag tgctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagccc aaatcttgt      660
gacaaaactc acacatgccc accgtgccca gcacctgaag ctgcagggg accgtcagtc      720
ttcctcttcc cccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcggcgcc cccatcgaga aaaccatctc caaagccaaa    1020
gggcagcccc gagaaccaca ggtgtacacc ctgcccccat gccgggatga gctgaccaag    1080
aaccaggtca gcctgtggtg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtgg cggcggaggc tccggaggcg gaggttctgg cggaggtggc    1380
```

```
tccgcacctg cctcaagttc tacaaagaaa acacagctac aactggagca tttactgctg    1440
gatttacaga tgattttgaa tggaattaat aattacaaga atcccaaact caccaggatg    1500
ctcacagcca agtttgccat gcccaagaag gccacagaac tgaaacatct tcagtgtcta    1560
gaagaagaac tcaaacctct ggaggaagtg ctaaatggcg ctcaaagcaa aaactttcac    1620
ttaagaccca gggacttaat cagcaatatc aacgtaatag ttctggaact aaagggatct    1680
gaaacaacat tcatgtgtga atatgctgat gagacagcaa ccattgtaga atttctgaac    1740
agatggatta cctttgccca agcatcatc tcaacactga ct    1782
```

<210> SEQ ID NO 317
<211> LENGTH: 447
<212> TYPE: PRT
<213> ORGANISM: Artificial Sequence
<220> FEATURE:
<223> OTHER INFORMATION: 4G8 Fab heavy chain-Fc (hole)

<400> SEQUENCE: 317

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
```

```
                290             295             300
Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 318
<211> LENGTH: 1341
<212> TYPE: DNA
<213> ORGANISM: Artificial Sequence
<220> FEATURE:
<223> OTHER INFORMATION: 4G8 Fab heavy chain-Fc (hole)

<400> SEQUENCE: 318
gaggtgcaat tgttggagtc tgggggaggc ttggtacagc ctggggggtc cctgagactc        60
tcctgtgcag cctccggatt cacctttagc agttatgcca tgagctgggt ccgccaggct       120
ccagggaagg gctgagtg gtctcagct attagtggta gtggtggtag cacatactac          180
gcagactccg tgaagggccg gttcaccatc tccagagaca attccaagaa cacgctgtat       240
ctgcagatga acagcctgag agccgaggac acggccgtat attactgtgc gaaagggtgg      300
ctgggtaatt ttgactactg gggccaagga accctggtca ccgtctcgag tgctagcacc      360
aagggcccct ccgtgttccc cctggcccccc agcagcaaga gcaccagcgg cggcacagcc    420
gctctgggct gcctggtcaa ggactacttc cccgagcccg tgaccgtgtc ctggaacagc     480
ggagccctga cctccggcgt gcacaccttc cccgccgtgc tgcagagttc tggcctgtat     540
agcctgagca gcgtggtcac cgtgccttct agcagcctgg gcacccagac ctacatctgc     600
aacgtgaacc acaagcccag caacaccaag gtggacaaga aggtggagcc caagagctgc    660
gacaaaactc acacatgccc accgtgccca gcacctgaag ctgcagggg accgtcagtc     720 ttcctcttcc cccaaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac   900
cgtgtggtca gcgtcctcac cgtcctgcac caggactggc tgaatggcaa ggagtacaag    960
tgcaaggtct ccaacaaagc cctcggcgcc ccatcgaga aaaccatctc caaagccaaa    1020
gggcagcccc gagaaccaca ggtgtgcacc ctgcccccat cccgggatga gctgaccaag  1080
aaccaggtca gcctctcgtg cgcagtcaaa ggcttctatc ccagcgacat cgccgtggag   1140
tgggagagca atgggcagcc ggagaacaac tacaagacca cgcctcccgt gctggactcc   1200
```

```
gacggctcct tcttcctcgt gagcaagctc accgtggaca gagcaggtg gcagcagggg    1260 aacgtcttct catgctccgt gatgcatgag gctctgcaca accactacac gcagaagagc    1320
ctctccctgt ctccgggtaa a                                              1341
```

<210> SEQ ID NO 319
<211> LENGTH: 600
<212> TYPE: PRT
<213> ORGANISM: Artificial Sequence
<220> FEATURE:
<223> OTHER INFORMATION: CH1A1A Fab heavy chain-Fc (knob)-IL-2 qm

<400> SEQUENCE: 319

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335
```

Glu Lys Thr Ile Ser Lys Ala Lys Gly Gln Pro Arg Glu Pro Gln Val
             340                 345                 350

Tyr Thr Leu Pro Pro Cys Arg Asp Glu Leu Thr Lys Asn Gln Val Ser
         355                 360                 365

Leu Trp Cys Leu Val Lys Gly Phe Tyr Pro Ser Asp Ile Ala Val Glu
     370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
             420                 425                 430

His Glu Ala Leu His Asn His Tyr Thr Gln Lys Ser Leu Ser Leu Ser
         435                 440                 445

Pro Gly Lys Ser Gly Gly Gly Ser Gly Gly Gly Ser Gly Gly
     450                 455                 460

Gly Gly Ser Ala Pro Ala Ser Ser Ser Thr Lys Lys Thr Gln Leu Gln
465                 470                 475                 480

Leu Glu His Leu Leu Leu Asp Leu Gln Met Ile Leu Asn Gly Ile Asn
                485                 490                 495

Asn Tyr Lys Asn Pro Lys Leu Thr Arg Met Leu Thr Ala Lys Phe Ala
             500                 505                 510

Met Pro Lys Lys Ala Thr Glu Leu Lys His Leu Gln Cys Leu Glu Glu
         515                 520                 525

Glu Leu Lys Pro Leu Glu Glu Val Leu Asn Gly Ala Gln Ser Lys Asn
     530                 535                 540

Phe His Leu Arg Pro Arg Asp Leu Ile Ser Asn Ile Asn Val Ile Val
545                 550                 555                 560

Leu Glu Leu Lys Gly Ser Glu Thr Thr Phe Met Cys Glu Tyr Ala Asp
                565                 570                 575

Glu Thr Ala Thr Ile Val Glu Phe Leu Asn Arg Trp Ile Thr Phe Ala
             580                 585                 590

Gln Ser Ile Ile Ser Thr Leu Thr
         595                 600

<210> SEQ ID NO 320
<211> LENGTH: 1800
<212> TYPE: DNA
<213> ORGANISM: Artificial Sequence
<220> FEATURE:
<223> OTHER INFORMATION: CH1A1A Fab heavy chain-Fc (knob)-IL-2 qm

<400> SEQUENCE: 320
caggtgcagc tggtgcagtc tggcgccgaa gtgaagaaac tggagctag tgtgaaggtg      60 tcctgcaagg ccagcggcta caccttcacc gagttcggca tgaactgggt ccgacaggct     120
ccaggccagg gctcgaatg gatgggctgg atcaacacca gaccggcga ggccacctac     180 gtggaagagt tcaagggcag agtgaccttc accacggaca ccagcaccag caccgcctac     240
atggaactgc ggagcctgag aagcgacgac accgccgtgt actactgcgc cagatgggac     300
ttcgcctatt acgtggaagc catggactac tggggccagg gcaccaccgt gaccgtgtct     360
agcgctagca ccaagggccc aagcgtgttc cctctggccc ccagcagcaa gagcacaagc     420
ggcggaacag ccgccctggg ctgcctggtc aaggactact cccccgagcc cgtgacagtg     480
tcctggaaca gcggagccct gaccagcggc gtgcacacct tccagccgt gctgcagagc     540

```
agcggcctgt acagcctgag cagcgtggtc acagtgccta gcagcagcct gggcacccag    600
acctacatct gcaacgtgaa ccacaagccc agcaacacca aggtggacaa gaaggtggag    660
cccaagagct gcgacaagac ccacacctgt cccccttgtc ctgcccctga gctgctgggc    720
ggacccagcg tgttcctgtt ccccccaaag cccaaggaca ccctgatgat cagccggacc    780
cccgaagtga cctgcgtggt ggtggacgtg tcccacgagg accctgaagt gaagttcaat    840
tggtacgtgg acggcgtgga ggtgcacaat gccaagacca gccccgggga ggaacagtac    900
aacagcacct accgggtggt gtccgtgctg accgtgctgc accaggactg gctgaacggc    960
aaagagtaca agtgcaaggt ctccaacaag gccctgcctg cccccatcga aaaaccatc    1020
agcaaggcca agggccagcc cagagaaccc aggtgtaca ccctgccccc ctgcagagat    1080
gagctgacca gaaccaggt gtccctgtgg tgtctggtca agggcttcta ccccagcgat    1140
atcgccgtgg agtgggagag caacggccag cctgagaaca actacaagac cacccccct    1200
gtgctggaca gcgacggcag cttcttcctg tactccaaac tgaccgtgga caagagccgg    1260
tggcagcagg gcaacgtgtt cagctgcagc gtgatgcacg aggccctgca caaccactac    1320
acccagaagt ccctgagcct gagccccggc aagtccggag gcggaggctc cggcggcgga    1380
ggttctggcg gaggtggctc cgcacctgcc tcaagttcta caagaaaac acagctacaa    1440
ctggagcatt tactgctgga tttacagatg attttgaatg aattaataa ttacaagaat    1500
cccaaactca ccaggatgct cacagccaag tttgccatgc caagaaggc cacagaactg    1560
aaacatcttc agtgtctaga agaagaactc aaacctctgg aggaagtgct aaatggcgct    1620
caaagcaaaa actttcactt aagacccagg gacttaatca gcaatatcaa cgtaatagtt    1680
ctggaactaa agggatctga acaacattc atgtgtgaat atgctgatga gacagcaacc    1740
attgtagaat ttctgaacag atggattacc tttgcccaaa gcatcatctc aacactgact    1800
```

<210> SEQ ID NO 321
<211> LENGTH: 451
<212> TYPE: PRT
<213> ORGANISM: Artificial Sequence
<220> FEATURE:
<223> OTHER INFORMATION: CH1A1A Fab heavy chain-Fc (hole)

<400> SEQUENCE: 321

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Glu Phe
            20                  25                  30
Gly Met Asn Trp Val Arg Gln Ala Pro Gly Gln Gly Leu Glu Trp Met
        35                  40                  45
Gly Trp Ile Asn Thr Lys Thr Gly Glu Ala Thr Tyr Val Glu Glu Phe
    50                  55                  60
Lys Gly Arg Val Thr Phe Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Trp Asp Phe Ala Tyr Tyr Val Glu Ala Met Asp Tyr Trp Gly
            100                 105                 110
Gln Gly Thr Thr Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Cys Thr Leu Pro Pro Ser Arg Asp Glu Leu Thr Lys Asn Gln Val Ser
    355                 360                 365

Leu Ser Cys Ala Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 322
<211> LENGTH: 1353
<212> TYPE: DNA
<213> ORGANISM: Artificial Sequence
<220> FEATURE:
<223> OTHER INFORMATION: CH1A1A Fab heavy chain-Fc (hole)

<400> SEQUENCE: 322
caggtgcagc tggtgcagtc tggcgccgaa gtgaagaaac tggagctag tgtgaaggtg      60 tcctgcaagg ccagcggcta caccttcacc gagttcggca tgaactgggt ccgacaggct     120
ccaggccagg gcctcgaatg gatgggctgg atcaacacca agaccggcga ggccacctac    180
gtggaagagt tcaagggcag agtgaccttc accacggaca ccagcaccag caccgcctac    240
atggaactgc ggagcctgag aagcgacgac accgccgtgt actactgcgc cagatgggac    300
```

```
ttcgcctatt acgtggaagc catggactac tggggccagg gcaccaccgt gaccgtgtct      360
agcgctagca ccaagggccc aagcgtgttc cctctggccc ccagcagcaa gagcacaagc      420
ggcggaacag ccgccctggg ctgcctggtc aaggactact ccccgagcc cgtgacagtg       480
tcctggaaca gcggagccct gaccagcggc gtgcacacct tccagccgt gctgcagagc       540
agcggcctgt acagcctgag cagcgtggtc acagtgccta gcagcagcct gggcacccag      600
acctacatct gcaacgtgaa ccacaagccc agcaacacca aggtggacaa gaaggtggag      660
cccaagagct gcgacaagac ccacacctgt cccccttgtc ctgcccctga gctgctgggc      720
ggacccagcg tgttcctgtt ccccccaaag cccaaggaca ccctgatgat cagccggacc      780
cccgaagtga cctgcgtggt ggtggacgtg tcccacgagg accctgaagt gaagttcaat      840
tggtacgtgg acggcgtgga ggtgcacaat gccaagacca gccccggga ggaacagtac      900
aacagcacct accgggtggt gtccgtgctg accgtgctgc accaggactg gctgaacggc      960
aaagagtaca agtgcaaggt ctccaacaag gccctgcctg cccccatcga gaaaaccatc     1020
agcaaggcca agggccagcc cagagaaccc caggtgtgca ccctgccccc agcagagat     1080
gagctgacca gaaccaggt gtccctgagc tgtgccgtca gggcttcta ccccagcgat      1140
atcgccgtgg agtgggagag caacggccag cctgagaaca actacaagac cacccccct     1200
gtgctggaca cgacggcag cttcttcctg gtgtccaaac tgaccgtgga caagagccgg     1260
tggcagcagg gcaacgtgtt cagctgcagc gtgatgcacg aggccctgca caaccactac     1320
acccagaagt ccctgagcct gagccccggc aag                                  1353
```

<210> SEQ ID NO 323
<211> LENGTH: 215
<212> TYPE: PRT
<213> ORGANISM: Artificial Sequence
<220> FEATURE:
<223> OTHER INFORMATION: CH1A1A light chain

<400> SEQUENCE: 323

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

```
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 324
<211> LENGTH: 645
<212> TYPE: DNA
<213> ORGANISM: Artificial Sequence
<220> FEATURE:
<223> OTHER INFORMATION: CH1A1A light chain

<400> SEQUENCE: 324
gatatccaga tgacccagtc tccatcctcc ctgtctgcat ctgtgggaga cagagtcacc      60
atcacttgca aggccagtgc ggctgtgggt acgtatgttg cgtggtatca gcagaaacca     120
gggaaagcac ctaagctcct gatctattcg gcatcctacc gcaaaagggg agtcccatca     180
aggttcagtg gcagtggatc tgggacagat ttcactctca ccatcagcag tctgcaacct     240
gaagatttcg caacttacta ctgtcaccaa tattacacct atcctctatt cacgtttggc     300
cagggcacca agctcgagat caagcgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac cgagaaacac aaagtctacg cctgcgaagt cacccatcag     600
ggcctgagct cgcccgtcac aaagagcttc aacaggggag agtgt                     645
```